US007888004B2

(12) United States Patent
Coit et al.

(10) Patent No.: US 7,888,004 B2
(45) Date of Patent: Feb. 15, 2011

(54) HCV NON-STRUCTURAL POLYPEPTIDE

(75) Inventors: Doris Coit, Petaluma, CA (US);
Angelica Medina-Selby, San Francisco, CA (US); Mark Selby, San Francisco, CA (US); Michael Houghton, Berkeley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/287,006

(22) Filed: Oct. 3, 2008

(65) Prior Publication Data

US 2009/0087447 A1   Apr. 2, 2009

Related U.S. Application Data

(63) Continuation of application No. 11/195,009, filed on Aug. 2, 2005, now Pat. No. 7,449,566, which is a continuation of application No. 09/721,479, filed on Nov. 22, 2000, now Pat. No. 6,986,892.

(60) Provisional application No. 60/167,502, filed on Nov. 24, 1999.

(51) Int. Cl.
*A61K 39/29* (2006.01)
*A61K 39/12* (2006.01)

(52) U.S. Cl. .................. 435/5; 424/228.1; 424/185.1; 424/186.1; 424/204.1

(58) Field of Classification Search .................. None
See application file for complete search history.

(56) References Cited

U.S. PATENT DOCUMENTS

| 5,371,017 A | 12/1994 | Houghton et al. |
| 5,683,864 A | 11/1997 | Cho et al. |
| 5,843,752 A | 12/1998 | Dasmahapatra et al. |
| 6,333,186 B1 | 12/2001 | Wittekind et al. |
| 6,800,456 B2 | 10/2004 | Weinheimer et al. |

FOREIGN PATENT DOCUMENTS

| EP | 0450931 A | 10/1991 |
| EP | 0696640 A | 2/1996 |
| WO | WO 90/09253 A | 5/1993 |
| WO | WO 95/25122 A | 9/1995 |
| WO | WO 99/07734 A | 2/1999 |
| WO | WO 99/28482 A | 6/1999 |
| WO | WO 99/38880 A | 8/1999 |
| WO | WO 00/66623 A | 11/2000 |

OTHER PUBLICATIONS

Choo et al. PNAS USA, 1991, 88:2452-2455.*
Bartenschlager, et al., "Nonstructural Protein 3 of the Hepatitis C Virus Encodes a Serine-Type Proteinase Required for Cleavage at the NS3/4 and NS4/5 Junctions," *J Virol* 67:3835-3844 (1993).
Botarelli, et al., "T-Lymphocyte Response to Hepatitis C Virus in Different Clinical Courses of Infection," *Gastroenterology* 104:580-587 (1993).
Chen, et al., "Human and Murine Antibody Recognition Is Focused on the ATPase/Helicase But Not on the Protease Domain of the Hepatitis C Virus Nonstructural 3 Protein," *Hepatology* 28(1):219-224 (1998).
Chien, et al., "Use of a Novel Hepatitus C Virus (HCV) Major-Epitope Chimeric Polypeptide for Diagnosis of HCV Infection," *J Clin Microbiol* 87:1393-1397 (1999).
Cho, et al., "Enhanced Cellular Immunity to Hepatitis C Virus Nonstructural Proteins by Codelivery of Granulocyte Macrophage-Colony Stimulating Factor Gene in Intramuscular DNA Immunization," *Vaccine* 17:9-10 (1999).
Clarke, "Molecular Virology of Hepatitis C Virus," *J Gen Virol* 78:2397-2410 (1997).
Cooper, et al., "Analysis of a Succesful Immune Response Against Hepatitis C Virus," *Immunity* 10:439-449 (1999).
Diepolder, et al., "Possible Mechanism Involving T-Lymphocyte Response to Non-Structural Protein 3 Viral Clearance in Acute Hepatitis C Virus Infection," *Lancet* 346:1006-1007 (1995) .
Diepolder, et al., "Immunodominant CD$+ T-Cell Epitope Within Nonstructural Protein 3 in Acute Hepatitis C Virus Infection," *J Virol* 71:6011-6019 (1997).
Eckart, et al., "The Hepatitis C Virus Encodes a Serine Protease Involved in Processing of the Putative Nonstructural Proteins From the Viral Polyprotein Precursor," *Biochem. Biophys. Res. Comm.* 192(2):399-406 (1993).
Farrari, et al., "T-Cell-Response to Structural and Nonstructuial Hepatitis C Virus Antigens in Persistant and Self-Limited Hepatitis C Virus Infections," *Hepatology* 19:286-295 (1994).
Hoffman, et al., "Mapping of Immunodominant CD$+ Lymphocyte Epitopes of Hepatitis C Virus Antigens and Their Relevance During the Course of Chronic Infection," *Hepatology* 21:632-638 (1995).
Iwata, et al., "Interferon Gamma Production by Peripheral Blood Lymphocytes to Hepatitis C Virus Core Protein in Chronic Hepatitis C Infection," *Hepatology* 22:1057-1064 (1995).
Minutello, et al., "Compartmentalization of T-Lymphocytes to the Site of Disease: Intrahepatic CD4+ T Cells Specific for the Protein NS4 of Hepatitis C Virus in Patients With Chronic Hepatitis C," *J Exp Med* 178:17-25 (1993).
Missale, et al., "Different Clinical Behaviors of Acute Hepatitis C Virus Infection Are Associated With Different Vigor of the Anti-Viral Cell-Mediated Immune Response," *J Clin Invest* 98:706-714 (1996).
Tsai, et al., "Detection of Type 2-Like T-Helper Cells in Hepatitis C Virus Infection: Implications for Hepatits C Virus Chronocity," *Hepatology* 25:449458 (1997).
Tsai, et al., "Cellular Immune Responses in Patients With Dual Infection of Hepatitis B and C Viruses: Dominant Role of Hepatitis C Virus," *Hepatology* 21:908-912 (1995).

* cited by examiner

*Primary Examiner*—Stacy B Chen
(74) *Attorney, Agent, or Firm*—Leonardo Rasile; Roberts Robins

(57) ABSTRACT

Polypeptides comprising a mutant non-structural Hepatitis C virus useful in diagnostic and/or immunogenic compositions are disclosed, in which the mutant is an N-terminal mutation that functionally disrupts the catalytic domain of NS3. Polynucleotides encoding these polypeptides, host cells transformed with polynucleotides and methods of using the polypeptides and polynucleotides are also disclosed.

13 Claims, 119 Drawing Sheets pCMV-NS35

```
  1  TCGCGCGTTT CGGTGATGAC GGTGAAAACC TCTGACACAT GCAGCTCCCG GAGACGGTCA CAGCTTGTCT GTAAGCGGAT
     AGCGCGCAAA GCCACTACTG CCACTTTTGG AGACTGTGTA CGTCGAGGGC CTCTGCCAGT GTCGAACAGA CATTCGCCTA

81  GCCGGGAGCA GACAAGCCCG TCAGGGGCGC TCAGCGGGTG TTGGCGGGTG TCGGGGGCTG CTTAACTATG CGGCATCAGA
     CGGCCCTCGT CTGTTCGGGC AGTCCCCGCG AGTCGCCCAC AACCGCCCAC AGCCCCCGAC GAATTGATAC GCCGTAGTCT

StuI
                                          ------
161  GCAGATTGTA CTGAGAGTGC ACCATATGAA GCTTTTTGCA AAAGCCTAGG CCTCCAAAAA AGCCTCCTCA CTACTTCTGG
     CGTCTAACAT GACTCTCACG TGGTATACTT CGAAAAACGT TTTCGGATCC GGAGGTTTTT TCGGAGGAGT GATGAAGACC

241  AATAGCTCAG AGGCCGAGGC GGCCTCGGCC TCTGCATAAA TAAAAAAAAT TAGTCAGCCA TGGGGCGGAG AATGGGCGGA
     TTATCGAGTC TCCGGCTCCG CCGGAGCCGG AGACGTATTT ATTTTTTTTA ATCAGTCGGT ACCCCGCCTC TTACCCGCCT

321  ACTGGGCGGG GAGGGAATTA TTGGCTATTG GCCATTGCAT ACGTTGTATC TATATCATAT TATGTACATT TATATATTGGCT
     TGACCCGCCC CTCCCTTAAT AACCGATAAC CGGTAACGTA TGCAACATAG ATATAGTATA ATACATGTAA ATATAACCGA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC ATTGACGTCA ATGGGTGGAG TATTTACGGT
     CTGCAGTTAT TACTGCATAC AAGGGTATCA TTGCGGTTAT CCCTGAAAGG TAACTGCAGT TACCCACCTC ATAAATGCCA

641  AAACTGCCCA CTTGGCAGTA CATCAAGTGT ATCATATGCC AAGTCCGCCC CCTATTGACG TCAATGACGG TAAATGGCCC
     TTTGACGGGT GAACCGTCAT GTAGTTCACA TAGTATACGG TTCAGGCGGG GGATAACTGC AGTTACTGCC ATTTACCGGG
```

FIG. 3-1 pCMV-NS35

```
 721  GCCTGGCATT ATGCCCAGTA CATGACCTTA CGGGACTTTC CTACTTGGCA GTACATCTAC GTATTAGTCA TCGCTATTAC
      CGGACCGTAA TACGGGTCAT GTACTGGAAT GCCCTGAAAG GATGAACCGT CATGTAGATG CATAATCAGT AGCGATAATG

801  CATGGTGATG CGGTTTTGGC AGTACACCAA TGGGCGTTTG TAGCCGTTTG ACTCACGGGG ATTTCCAAGT CTCCACCCCA
      GTACCACTAC GCCAAAACCG TCATGTGGTT ACCCGCACCT ATCGGCAAAC TGAGTGCCCC TAAAGGTTCA GAGGTGGGGT

881  TTGACCTCAA TGGGACTTTG TTTTGGCACC AAAATCAACG GGACTTTCCA AAATGTCGTA ATAACCCCGC CCCGTTGACG
      AACTGGAGTT ACCCTGAAAC AAAACCGTGG TTTTAGTTGC CCTGAAAGGT TTTACAGCAT TATTGGGGCG GGGCAACTGC

961  CAAATGGGCG GTAGGCCTGT ACGGTGGGAG GTCTATATAA GCAGAGCTCG TTTAGTGAAC CGTCAGATCG CCTGAGACG
      GTTTACCCGC CATCCGGACA TGCCACCCTC CAGATATATT CGTCTCGAGC AAATCACTTG GCAGTCTAGC GGACTCTGC

1041  CCATCCACGC TGTTTTGACC TCCATAGAAG ACACCGGGAC CGATCCAGCC TCCGGGGCCG GGAACGGTGC ATTGGAACGC
      GGTAGGTGCG ACAAAACTGG AGGTATCTTC TGTGGCCCTG GCTAGGTCGG AGGCCCCGGC CCTTGCCACG TAACCTTGCG

1121  GGATTCCCCG TGCCAAGAGT GACGTAAGTA CCGCCTATAG ACTCTATAGG CACACCCCTT TGGCTCTTAT GCATGCTATA
      CCTAAGGGGC ACGGTTCTCA CTGCATTCAT GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGGTGA TGGTATAGCT TAGCCTATAG GTGTGGGTTA
      GACAAAAACC GAACCCCGGA TATGTGGGGG CGAGGAATAC GATATCCACT ACCATATCGA ATCGGATATC CACACCCAAT

1281  TTGACCATTA TACTCTGTCC CCCTATTGGT GACGATACTT TCCATTACTA ATCCATAACA TGGCTCTTTG CCACAACTAT
      AACTGGTAAT ATGAGACAGG GGGATAACCA CTGCTATGAA AGGTAATGAT TAGGTATTGT ACCGAGAAAC GGTGTTGATA

1361  CTCTATTGGC TATATGCCAA TACTCTGTCC TTCAGAGACT GACACGGACT CTGTATTTTT ACAGGATGGG GTCCATTTAT
      GAGATAACCG ATATACGGTT ATGAGACAGG AAGTCTCTGA CTGTGCCTGA GACATAAAAA TGTCCTACCC CAGGTAAATA
```

FIG. 3-2 pCMV-NS35

```
1441  TATTTACAAA TTCACATATA CAACAACGCC GTCCCCCGTG CCCGCAGTTT TTATTAAACA TAGCCTGGGA TCTCCGACAT
      ATAAATGTTT AAGTGTATAT GTTGTTGCGG CAGGGGGCAC GGGCGTCAAA AATAATTTGT ATCGGACCCT AGAGGCTGTA

1521  CTCGGGTACG TGTTCCGGAC ATGGGCTCTT CTCCGGTAGC GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGGT

1601  GCGGCTCATG GTCCCTCGGC AGTCCTTGC TCCTAACAGT GGAGGCCAGA CTTAGGCACA GCACAATGCC CACCACCACC
      CGCCGAGTAC CAGGGAGCCG TCGAGAACG AGGATTGTCA CCTCCGGTCT GAATCCGTGT CGTGTTACGG GTGGTGGTGG

1681  AGTGTGCCGC ACAAGGCCCGT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CTCAGTCTCC ATTGAGGCA

1841  TGCGGTGCTG TTAACGGTGG AGGGCAGTGT AGTCTGAGCA GTACTCGTTG CTGCCGCCG CGCCACCAGA CATAATAGCT
      ACGCCACGAC AATTGCCACC TCCCGTCACA TCAGACTCGT CATGAGCAAC GACGGCGCGC GCGGTGGTCT GTATTATCGA

M   A   A
                                                                        EcoRI
                                                                        ------

1921  GACAGACTAA CAGACTGTTC CTTTCCATGG GTCTTTTCTG CAGTCACCGT CGTCGACCTA AGAATTCACC ATGGCTGCAT
      CTGTCTGATT GTCTGACAAG GAAAGGTACC CAGAAAAGAC GTCAGTGGCA GCAGCTGGAT TCTTAAGTGG TACCGACGTA

+2 Y   A   A   Q   G   Y   K   V   L   V   L   N   P   S   V   A   A   T   L   G   F   G   A   Y   M   S   K
2001  ATGCAGCTCA GGGCTATAAG GTGCTAGTAC TCAACCCCTC TGTTGCTGCA ACACTGGGCT TTGGTGCTTA CATGTCCAAG
      TACGTCGAGT CCCGATATTC CACGATCATG AGTTGGGGAG ACAACGACGT TGTGACCCGA AACCACGAAT GTACAGGTTC
```

FIG. 3-3 pCMV-NS35

```
     A  H  G  I  D  P  N     I  R  T     G  V  R  T  I  T  T     G  S  P     I  T  Y  S     T  Y  G
 +2  GCTCATGGGA TCGATCCTAA CATCAGGACC GGGGTGAGAA CAATTACCAC TGGCAGCCCC ATCACGTACT CCACCTACGG
2081 CGAGTACCCT AGCTAGGATT GTAGTCCTGG CCCCACTCTT GTTAATGGTG ACCGTCGGGG TAGTGCATGA GGTGGATGCC

K  F  L     A  D  G  G     C  S  G     G  A  Y     D  I  I  I     C  D  E     C  H  S     T  D  A
 +2  CAAGTTCCTT GCCGACGGCG GTGTCTCGGG GGGCGCTTAT GACATAATAA TTTGTGACGA GTGCCACTCC ACGGATGCCA
2161 GTTCAAGGAA CGGCTGCCGC CACAGAGCCC CCCGCGAATA CTGTATTATT AAACACTGCT CACGGTGAGG TGCCTACGGT

T  S  I  L     G  I  G     T  V  L  D     Q  A  E     T  A  G     A  R  L  V     V  L  A     T  T
 +2  CATCCATCTT GGGCATTGGC ACTGTCCTTG ACCAAGCAGA GACTGCGGGG GCCAGACTGG TTGTGCTCGC CACCGCCACC
2241 GTAGTAGAA CCCGTAACCG TGACAGGAAC TGGTTCGTCT CTGACGCCCC CGGTCTGACC AACACGAGCG GTGGCGGTGG

P  P  G  S     V  T  V     P  H  P     N  I  E  E     V  A  L     S  T  T     G  E  I  P     F  Y  G
 +2  CCTCCGGGCT CCGTCACTGT GCCCCATCCC AACATCGAGG AGGTTGCTCT GTCCACCACC GGAGAGATCC CTTTTTACGG
2321 GGAGGCCCGA GGCAGTGACA CGGGGTAGGG TTGTAGCTCC TCCAACGAGA CAGGTGGTGG CCTCTCTAGG GAAAAATGCC

K  A  I     P  L  E  V     I  K  G     G  R  H     L  I  F  C     H  S  K     K  K  C     D  E  L
 +2  CAAGGCTATC CCCCTCGAAG TAATCAAGGG GGGGAGACAT CTCATCTTCT GTCATTCAAA AAGAAGTGC GACGAACTCG
2401 GTTCCGATAG GGGGAGCTTC ATTAGTTCCC CCCCTCTGTA GAGTAGAAGA CAGTAAGTTT CTTCTTCACG CTGCTTGAGC

A  A  K  L     V  A  L     G  I  N  A     V  A  Y     Y  R  G     L  D  V  S     V  I  P     T  S  G
 +2  CAAGCTAAAGCT GGTCGCATTG GGCATCAATG CCGTGGCCTA CTACCGCGGT CTTGACGTGT CCGTCATCCC GACCAGCGGC
2481 GGGCTTTCGA CCAGCGTAAC CCGTAGTTAC GGCACCGGAT GATGGCGCCA GAACTGCACA GGCAGTAGGG CTGGTCGCCG

D  V  V  V     A  T     D  A  L     M  T  G  Y     T  G  D     F  D  S     V  I  D  C     N  T  C
 +2  GATGTTGTCG TCGTGGCAAC CGATGCCCTC ATGACCGGCT ATACCGGCGA CTTCGACTCG GTGATAGACT GCAATACGTG
2561 CTACAACAGC AGCACCGTTG GCTACGGGAG TACTGGCCGA TATGGCCGCT GAAGCTGAGC CACTATCTGA CGTTATGCAC
```

FIG. 3-4 pCMV-NS35

```
      V  T  Q     T  V  D  F     S  L  D     P  T  F     T  I  E  T     I  T  L     P  Q  D     A  V  S
  +2  TGTCACCCAG ACAGTCGATT TCAGCCTTGA CCCTACCTTC ACCATTGAGA CAATCACGCT CCCCAAGAT GCTGTCTCCC
2641  ACAGTGGGTC TGTCAGCTAA AGTCGGAACT GGGATGGAAG TGGTAACTCT GTTAGTGCGA GGGGTTCTA CGACAGAGGG

R  T  Q  R     R  G  R     T  G  R  G     I  Y  R     K  P  G     I  Y  R     F  V  A  P     G  E  R     P  S  G
  +2  GCACTCAACG TCGGGGCAGG ACTGGGCAGG GGAAGCCAGG CATCTACAGA TTTGTGGCAC CGGGGGAGCG CCCCTCCGGC
2721  CGTGAGTTGC AGCCCCGTCC TGACCCGTCC CCTTCGGTCC GTAGATGTCT AAACACCGTG GCCCCCTCGC GGGGAGGCCG

M  F  D  S     V  L     C  E  C     Y  D  A  G     C  A  W     Y  E  L     T  P  A  E     T  T  V
  +2  ATGTTCGACT CGTCCGTCCT CTGTGAGTGC TATGACGCAG GCTGTGCTTG GTATGAGCTC ACGCCCGCCG AGACTACAGT
2801  TACAAGCTGA GCAGGCAGGA GACACTCACG GACACTCACG ATACTGCGTC CGACACGAAC CATACTCGAG TCTGATGTCA

R  L  R     A  Y  M  N     T  P  G     L  P  V     C  Q  D     H  L  E  F     W  E  G     V  F  T
                                                                                                 StuI
  +2  TAGGCTACGA GCCTACATGA ACACCCCGGG GCTTCCCGTG TGCCAGGACC ATCTTGAATT TTGGGAGGGC GTCTTTACAG
2881  ATCCGATGCT CGGATGTACT TGTGGGGCCC CGAAGGGCAC ACGGTCCTGG TAGAACTTAA AACCCTCCCG CAGAAATGTC

G  L  T  H     I  D  A     H  F  L  S     Q  T  K     Q  S  G     E  N  L  P     Y  L  V     A  Y  Q
      StuI
  +2  GCCTCACTCA TATAGATGCC CACTTTCTAT CCCAGACAAA GCAGAGTGGG GAGAACCTTC CTTACCTGT  AGCGTACCAA
2961  CGGAGTGAGT ATATCTACGG GTGAAAGATA GGGTCTGTTT CGTCTCACCC CTCTTGGAAG GAATGGACCA TCGCATGGTT

A  T  V  C     A  R  A     Q  A  P     P  P  S  W     D  Q  M     W  K  C     L  I  R  L     K  P  T
  +2  GCCACCGTGT GGCTAGGGC  TCAAGCCCCT CCCCCATCGT GGGACCAGAT GTGGAAGTGT TTGATTCGCC TCAAGCCCAC
3041  CGGTGGCACA CCGATCCCG  AGTTCGGGGA GGGGGTAGCA CCCTGGTCTA CACCTTCACA AACTAAGCGG AGTTCGGGTG
```

FIG. 3-5 pCMV-NS35

```
      L   H   G   P   T   P   L   L   Y   R   L   G   A   V   Q   N   E   I   T   L   T   H   P   V   T   K
 +2   CCTCCATGGG CCAACACCCC TGCTATACAG ACTGGGCGCT GTTCAGAATG AAATCACCCT GACGCACCCA GTCACCAAAT
3121  GGAGGTACCC GGTTGTGGGG ACGATATGTC TGACCCGCGA CAAGTCTTAC TTTAGTGGGA CTGCCGTGGGT CAGTGGTTTA

Y   I   M   T   C   M   S   A   D   L   E   V   V   T   S   T   W   V   L   V   G   G   V   L   A   A   L
 +2   ACATCATGAC ATGCTCTCAAC GCCGACCTGG AGGTCGTCAC GAGCACCTGG GTGCTCGTTG GCGGGGTCCT GGCTGCTTTG
3201  TGTAGTACTG TACGTACAGTG CGGCTGGACC TCCAGCAGTG CTCGTGGACC CACGAGCAAC CGCCCCAGGA CCGACGAAAC

A   A   Y   C   L   S   T   G   C   V   V   I   V   G   R   V   V   L   S   G   K   P   A   I   I   P   D
 +2   GCCGCGTATT GCCTCTCAAC GGGCTGCGTG GTCATAGTGG GCAGGGTCGT CTTGTCCGGG AAGCCGGCAA TCATACCTGA
3281  CGGCGCATAA CGGACAGTTG CCCGACGCAC CAGTATCACC CGTCCCAGCA GAACAGGCCC TTCGGCCGTT AGTATGGACT

R   E   V   L   Y   R   E   F   D   E   M   E   E   C   S   Q   H   L   P   Y   I   E   Q   G   M   M
 +2   CAGGGAAGTC CTCTACCGAG AGTTCGATGA GATGGAAGAG TGCTCTCAGC ACTTACCGTA CATCGAGCAA GGGATGATGC
3361  GTCCCTTCAG GAGATGGCTC TCAAGCTACT TCAAGCTACT CTACCTTCTC ACGAGAGTCG TGAATGGCAT GTAGCTCGTT CCCTACTACG

L   A   E   Q   F   K   Q   K   A   L   G   L   L   Q   T   A   S   R   Q   A   E   V   I   A   P   A   V
 +2   TCGCCGAGCA GTTCAAGCAG AAGGCCCTCG GCCTCCTGCA GACCGCGTCC CGTCAGGCAG AGTTATCGC CCCTGCTGTC
3441  AGCGGCTCGT CAAGTTCGTC TTCCGGGAGC CGGAGGACGT CTGGCGCAGG GCAGTCCGTC TCCAATAGCG GGACGACAG

Q   T   N   W   Q   K   L   E   T   F   W   A   K   H   M   W   N   F   I   S   G   I   Q   Y   L   A   G
 +2   CAGACCAACT GGCAAAAACT CGAGACCTTC TGGGCAAGC ATATGTGGAA CTTCATCAGT GGGATACAAT ACTTGGCGGG
3521  GTCTGGTTGA CCGTTTTTGA GCTCTGGAAG ACCCGCTTCG TATACACCTT GAAGTAGTCA CCCTATGTTA TGAACCGCCC

L   S   T   L   P   G   N   P   A   I   A   S   L   M   A   F   T   A   A   V   T   S   P   L   T   T
 +2   CTTGTCAACG CTGCCTGGTA ACCCCGGCCAT TGCTTCATTG ATGGCTTTTA CAGCTGCTGT CACCAGCCCA CTAACCACTA
3601  GAACAGTTGC GACGGACCAT TGGGGCCGTA ACGAAGTAAC TACCGAAAAT GTCGACGACA GTGGTCGGGT GATTGGTGAT
```

FIG. 3-6 pCMV-NS35

```
      S   Q   T   L   L   F   N   I   L   G   G   W   V   A   A   Q   L   A   A   P   G   A   A   T   A   F   V
+2   GCCAAACCCT CCTCTTCAAC ATATTGGGGG GGTGGGTGGC TGCCCAGCTC GCCGCCCCCG GTGCCGCTAC TGCCCTTGTG
3681 CGGTTTGGGA GGAGAAGTTG TATAACCCCC CCACCCACCG ACGGGTCGAG CGGCGGGGGC CACGGCGATG ACGGAAACAC

G   A   G   L   A   G   A   A   I   G   S   V   G   L   G   K   V   L   I   D   I   L   A   G   Y   G   A
+2   GGGGCTGGCT TAGCTGGCGC CGCCATCGGC AGTGTTGGAC TGGGGAAGGT CCTCATAGAC ATCCTTGCAG GGTATGGCGC
3761 CCCCGACCGA ATCGACCGCG GCGGTAGCCG TCACAACCTG ACCCCTTCCA GGAGTATCTG TAGGAACGTC CCATACCGCG

G   V   A   G   A   L   V   A   F   K   I   M   S   G   E   V   P   S   T   E   D   L   V   N   L   L
+2   GGGGTGGCG GGAGCTCTTG TGGCATTCAA GATCATGAGC GGTGAGGTCC CCTCCACGGA GGACCTGGTC AATCTACTGC
3841 CCCCACCGC CCTCGAGAAC ACCGTAAGTT CTAGTACTCG CCACTCCAGG GGAGGTGCCT CCTGGACCAG TTAGATGACG

P   A   I   L   S   P   G   A   L   V   V   G   V   V   C   A   A   I   L   R   R   H   V   G   P   G   E
+2   CCGGCCATCCT CTCGCCCGGA GCCCTCGTAG TCGGCGTGGT CTGTGCAGCA ATACTGCGCC GGCACGTTGG CCCGGGCGAG
3921 GGCCGGTAGGA GAGCGGGCCT CGGGAGCATC AGCCGCACCA GACACGTCGT TATGACGCGG CCGTGCAACC GGGCCCGCTC

G   A   V   Q   W   M   N   R   L   I   A   F   A   S   R   G   N   H   V   S   P   T   H   Y   V   P   E
+2   GGGGCAGTGC AGTGGATGAA CCGGCTGATA GCCTTCGCCT CCCGGGGGAA CCATGTTTCC CCACGCCACT ACGTGCCGGA
4001 CCCCGTCACG TCACCTACTT GGCCGACTAT CGGAAGCGGA GGGCCCCCTT GGTACAAAGG GGTGCGGTGA TGCACGGCCT

G   A   V   Q   S   D   A   A   A   R   V   T   A   I   L   S   S   L   T   V   T   Q   L   L   R   R   L   H   Q   W
+2   GAGGCAGTGCA GCTGCCGCG TCACTGTGCCAT ACTCAGCAGC CTCACTGTAA CCCAGCTCCT GAGGCGACTG CACCAGTGGA
4081 CTCGCTACGT CGACGGGCGC AGTGACGGTA TGAGTCGTCG GAGTGACATT GGGTCGAGGA CTCCGCTGAC GTGGTCACCT

I   S   S   E   C   T   T   P   C   S   G   S   W   L   R   D   I   W   D   W   I   C   E   V   L   S   D
+2   TAAGCTCGGA GTGTACCACT CCATGCTCCG GTTCCTGGCT AAGGGACATC TGGGACTGGA TATGCGAGGT GTTGAGCGAC
4161 ATTCGAGCCT CACATGGTGA GGTACGAGGC CAAGGACCGA TTCCCTGTAG ACCCTGACCT ATACGCTCCA CAACTCGCTG
```

FIG. 3-7 pCMV-NS35

```
      F  K  T  W  L  K  A  K  L  M  P  Q  L  P  G  I  P  F  V  S  C  Q  R  G  Y  K  G
+2 TTTAAGACCT GGCTAAAAGC TAAGCTCATG CCACAGCTGC CTGGGATCCC CTTTGTGTCC TGCCAGGCGC GGTATAAGGG
4241 AAATTCTGGA CCGATTTTCG ATTCGAGTAC GGTGTCGACG GACCCTAGGG GAAACACAGG ACGGTCGCGC CCATATTCCC
                                              BamHI
                                              -------

V  W  R  G  D  G  I  M  H  T  R  C  H  C  G  A  E  I  T  G  H  V  K  N  G  T
+2 GGTCTGGCGA GGGACGGCA TCATGCACAC TCGCTGCCAC TGTGGAGCTG AGATCACTGG ACATGTCAAA AACGGGACGA
4321 CCAGACCGCT CCCCTGCCGT AGTACGTGTG AGCGACGGTG ACACCTCGAC TCTAGTGACC TGTACAGTTT TTGCCCTGCT

M  R  I  V  G  P  R  T  C  R  N  M  W  S  G  T  F  P  I  N  A  Y  T  T  G  P  C
+2 TGAGGATCGT CGGTCCTAGG ACCTGCAGGA ACATGTGGAG TGGGACCTTC CCCATTAATG CCTACACCAC GGGCCCCTGT
4401 ACTCCTAGCA GCCAGGATCC TGGACGTCCT TGTACACCTC ACCCTGGAAG GGGTAATTAC GGATGTGGTG CCCGGGGACA

T  P  L  P  A  P  N  Y  T  F  A  L  W  R  V  S  A  E  E  Y  V  E  I  R  Q  V  G
+2 ACCCCCCTTC CTGCCCCGAA CTACACGTTC GGCTATGGA GGGTGTCTGC AGAGGAATAC GTGGAGATAA GGCAGGTGGG
4481 TGGGGGGAAG GACGGGGCTT GATGTGCAAG CCGATATACC TCCCACAGACG TCTCCTTATG CACCTCTATT CCGTCCACCC

D  F  H  Y  V  T  G  M  T  T  D  N  L  K  C  P  C  Q  V  P  S  P  E  F  F  T
+2 GGACTTCCAC TACGTGACGG GTATGACTAC TGACAATCTT AAATGCCCGT GCCAGGTCCC ATCGCCCGAA TTTTTCACAG
4561 CCTGAAGGTG ATGCACTGCC CATACTGATG ACTGTTAGAA TTTACGGGCA CGGTCCAGGG TAGCGGGCTT AAAAAGTGTC

E  L  D  G  V  R  L  H  R  F  A  P  P  C  K  P  L  L  R  E  E  V  S  F  R  V  G
+2 GAATTGGACGG GGTGCGCCTA CATAGGTTTG CGCCCCCCTG CAAGCCCTTG CTGCGGGAGG AGGTATCATT CAGAGTAGGA
4641 TTAACCTGCC CCACGCGGAT GTATCCAAAC GCGGGGGGAC GTTCGGGAAC GACGCCCTCC TCCATAGTAA GTCTCATCCT

L  H  E  Y  P  V  G  S  Q  L  P  C  E  P  E  P  D  V  A  V  L  T  S  M  L  T  D
+2 CTCCACGAAT ACCCGGTAGG GTCGCAATTA CCTTGCGAGC CCGAACCGGA CGTGGCCGTG TTGACGTCCA TGCTCACTGA
4721 GAGGTGCTTA TGGGCCATCC CAGCGTTAAT GGAACGCTCG GGCTTGGCCT GCACCGGCAC AACTGCAGGT ACGAGTGACT
```

FIG. 3-8 pCMV-NS35

```
        P   S   H     I   T   A   E     A   A   G     R   R   L     A   R   G   S     P   P   S     V   A   S     S   S   A
+2   TCCCTCCCAT ATAACAGCAG AGGGGGCCGG GCGAAGGTTG GCGAGGGGAT CACCCCCCTC TGTGCCAGC TCCTCGGCTA
4801 AGGGAGGGTA TATTGTCGTC TCCCCGCGGCC CGCTTCCAAC CGCTCCCCTA GTGGGGGGAG ACACCGGTCG AGGAGCCGAT

S   Q   L   S     A   P   S     L   K   A   T     C   T   A     N   H   D     S   P   D   A     E   L   I     E   A   N
+2   GCCAGCTATC CGCTCCATCT CTCAAGGCAA CTTGCACCGC TAACCATGAC TCCCCTGATG CTGAGCTCAT AGAGGCCAAC
4881 CGGTCGATAG GCGAGGTAGA GAGTTCCGTT GAACGTGGCG ATTGGTACTG AGGGGACTAC GACTCGAGTA TCTCCGGTTG

L   L   W   R     Q   E   M     G   G   N     I   T   R   V     E   S   E     N   K   V     V   I   L   D     S   F   D
+2   CTCCTATGGA GGCAGGAGAT GGGGGGCAAC ATCACCAGGG TTGAGTCAGA AAACAAAGTG GTGATTCTGG ACTCCTTCGA
4961 GAGGATACCT CCGTCCTCTA CCCCCCGTTG TAGTGGTCCC AACTCAGTCT TTTGTTTCAC CACTAAGACC TGAGGAAGCT

P   L   V     A   E   E   D     E   R   E     I   S   V     P   A   E   I     L   R   K     S   R   R     F   A   Q
+2   TCCGCTTGTG GCGGAGGAGG ACGAGCGGGA GATCTCCGTA CCCGCAGAGA TCCTGCGGAA GTCTCGGAGA TTCGCCCAGG
5041 AGGCGAACAC CGCCTCCTCC TGCTCGCCCT CTAGAGGCAT GGGCGTCTCT AGGACGCCTT CAGAGCCTCT AAGCGGGTCC

A   L   P   V     W   A   R     P   D   Y   N     P   P   L     V   E   T     W   K   K   P     D   Y   E     P   P   V
+2   CCCTGCCCGT TTGGGCGCGG CCGGACTATA ACCCCCCGCT AGTGGAGACG TGGAAAAAGC CCGACTACGA ACCACCTGTG
5121 GGGACGGGCA AACCCGCGCC GGCCTGATAT TGGGGGGCGA TCACCTCTGC ACCTTTTTCG GGCTGATGCT TGGTGGACAC

V   H   G   C     P   L   P     P   P   K     S   P   P   V     P   P   P     R   K   K     R   T   V   V     L   T   E
+2   GTCCATGGCT GCCCGCTTCC ACCTCCAAAG TCCCCCTCCTG TGCCTCCGCC TCGGAAGAAG CGGACGGTGG TCCTCACTGA
5201 CAGGTACCGA CGGGCGAAGG TGGAGGTTTC AGGGGAGGAC ACGGAGGCGG AGCCTTCTTC GCCTGCCACC AGGAGTGACT

S   T   L     S   T   A   L     A   E   L     A   T   R     S   F   G   S     S   S   T     S   G   I     T   G   D
+2   ATCAACCCTA TCTACTGCCT CGCCACCAGA AGCTTTGGCA GCTCCTCAAC TTCCGGCATT ACGGGCGACA
5281 TAGTTGGGAT AGATGACGGA GCGGTGGTCT TCGAAACCGT CGAGGAGTTG AAGGCCGTAA TGCCCGCTGT
```

FIG. 3-9 pCMV-NS35

```
     N  T  T  T   S  S  E   P  A  P  S   G  C  P  P  D  S   D  A  E  S   Y  S  S   M  P  P
+2   ATACGACAAC ATCCTCTGAG CCCGCCCCTT CTGGCTGCCC CCCCGACTCC GACGCTGAGT CCTATTCCTC CATGCCCCCC
5361 TATGCTGTTG TAGGAGACTC GGGCGGGGAA GACCGACGGG GGGGCTGAGG CTGCGACTCA GGATAAGGAG GTACGGGGGG
                                                                                          |

L  E  G  E   P  P  G  D   P  D  L   S  D  G  S   W  S  T   V  S  S   E  A  N  A   E  D  V
+2   CTGGAGGGGG AGCCTGGGGA TCCGGATCTT AGCGGACGGGT CATGGTCAAC GGTCAGTAGT GAGGCCAACG CGGAGGATGT
5441 GACCTCCCCC TCGGACCCCT AGGCCTAGAA TCGCTGCCCA GTACCAGTTG CCAGTCATCA CTCCGGTTGC GCCTCCTACA
                         BamHI

V  C  C   S  M  S  Y   S  W  T   G  A  L   V  T  P  C   A  A  E   E  Q  K   L  P  I
+2   CGTGTGCTGC TCAATGTCTT ACTCTTGGAC AGGCGCACTC GTCACCCCGT GCGCCGGCGA AGAACAGAAA CTGCCCATCA
5521 GCACACGACG AGTTACAGAA TGAGAACCTG TCCGCGTGAG CAGTGGGGCA CGCGGCCGCT TCTTGTCTTT GACGGGTAGT

N  A  L  S   N  S  L   L  R  H  H   N  L  V   Y  S  T   T  S  R  S   A  C  Q   R  Q  K
+2   ATGGCACTAAG CAACTCGTTG CTACGTCACC ACAATTTGGT GTATTCCACC ACCTCACGCA GTGCTTGCCA AAGGCAGAAG
5601 TACGTGATTC GTTGAGCAAC GATGCAGTGG TGTTAAACCA CATAAGGTGG TGGAGTGCGT CACGAACGGT TTCCGTCTTC

K  V  T  F   D  R  L   Q  V  L   D  S  H  Y   Q  D  V   L  K  E   V  K  A  A  S  K
+2   AAAGTCACAT TGACAGACT GCAAGTTCTG GACAGCCATT ACCAGGACGT ACTCAAGGAG GTTAAAGCAG CGGCGTCAAA
5681 TTTCAGTGTA ACTGTCTGA CGTTCAAGAC CTGTCGGTAA TGGTCCTGCA TGAGTTCCTC CAATTTCGTC GCCGCAGTTT

V  K  A   N  L  L  S   V  E  E   A  C  S   L  T  P  P   H  S  A   K  S  K   F  G  Y
+2   AGTGAAGGCT AACTGCTAT CCGTAGAGGA AGCTTGCAGC CTGACGCCCC CACACTCAGC AAATCCAAG TTTGGTTATG
5761 TCACTTCCGA TTGAACGATA GGCATCTCCT TCGAACGTCG GACTGCGGGG GTGTGAGTCG GTTTAGGTTC AAACCAATAC
```

FIG. 3-10 pCMV-NS35

```
         G  A  K  D     V  R  C     H  A  R  K     A  V  T     H  I  N     S  V  W  K     D  L  L     E  D  N
  +2  GGCAAAGA CGTCCGTTGC CATGCCAGAA AGGCCGTAAC CCACAATCAAC TCCGTGTGGA AAGACCTTCT GGAAGACAAT
5841  CCCGTTTTCT GCAGGCAACG GTACGGTCTT TCCGGCATTG GGTGTAGTTG AGGCACACCT TTCTGGAAGA CCTTCTGTTA

V  T  P  I     D  T  T     I  M  A     K  N  E  V     F  C  V     Q  P  E     K  G  G  R     K  P  A
  +2  GTAACACCAA TAGACACTAC CATCATGGCT AAGAACGAGG TTTTCTGCGT TCAGCCTGAG AAGGGGGGTC GTAAGCCAGC
5921  CATTGTGGTT ATCTGTGATG GTAGTACCGA TTCTTGCTCC AAAAGACGCA AGTCGGACTC TTCCCCCCAG CATTCGGTCG

R  L  I     V  F  P  D     L  G  V     R  V  C     E  K  M  A     L  Y  D     V  V  T     K  L  P
  +2  TCGTCTCATC GTGTTCCCCG ATCTGGGCGT GCGCGTGTGC GAAAAGATGG CTTTGTACGA CGTGGTTACA AAGCTCCCCT
6001  AGCAGAGTAG CACAAGGGGC TAGACCCGCA CGCGCACACG CTTTTCTACC GAAACATGCT GCACCAATGT TTCGAGGGGA

L  A  V  M     G  S  S     Y  G  F  F  Q     Y  S  P     G  Q  R     V  E  F  L     V  Q  A  W  K  S
                                                                                  EcoRI
  +2  TGGCCGTGAT GGGAAGCTCC TACGGATTCC AATACTCACC AGGACAGCGG GTTGAATTCC TCGTCAAGC GTGGAAGTCC
6081  ACCGGCACTA CCCTTCGAGG ATGCCTAAGG TTATGAGTGG TCCTGTCGCC CAACTTAAGG AGCACGTTCG CACCTTCAGG

K  K  T  P     M  G  F     S  Y  D     T  R  C  F     D  S  T     V  T  E     S  D  I  R     T  E  E
  +2  AAGAAAACCC CAATGGGGTT CTCGTATGAT ACCCGCTGCT TTGACTCCAC AGTCACTGAG AGCGACATCC GTACGGAGGA
6161  TTCTTTTGGG GTTACCCCAA GAGCATACTA TGGGCGACGA AACTGAGGTG TCAGTGACTC TCGCTGTAGG CATGCCTCCT

A  I  Y     Q  C  C  D     L  D  P     Q  A  R     V  A  I  K     S  L  T     E  R  L     Y  V  G
  +2  GGCAATCTAC CAATGTTGTG ACCTCGACCC CCAAGCCCGC GTGGCCATCA AGTCCCTCAC CGAGAGGCTT TATGTTGGGG
6241  CCGTTAGATG GTTACAACAC TGGAGCTGGG GGTTCGGGCG CACCGGTAGT TCAGGGAGTG GCTCTCCGAA ATACAACCCC

G  P  L  T     N  S  R     G  E  N  C     G  Y  R     C  R     A  S  G  V     L  T  T     S  C  G
  +2  GCCCTCTTAC CAATTCAAGG GGGAGAACT GCGGCTATCG CAGTTGCCGC GCGAGCCGGG TACTGACAAC TAGTCTGTGT
6321  CGGGAGAATG GTTAAGTTCC CCCTCTTGA CGCCGATAGC GTCACGGCCG CGCTCGGCGC ATGACTGTTG ATCGACACCA
```

FIG. 3-11 pCMV-NS35

```
        N  T  L  T  C  Y  I     K  A  R     A  A  C  R     A  A  G     L  Q  D     C  T  M  L     V  C  G
   +2 AACACCCTCA CTTGCTACAT CAAGGCCCGG GCAGCCTGTC GAGCCGCAGG GCTCCAGGAC TGCACCATGC TCGTGTGTGG
 6401 TTGTGGGAGT GAACGATGTA GTTCCGGGCC CGTCGGACAG CTCGGCGTCC CGAGGTCCTG ACGTGGTACG AGCACACACC

D  D  L     V  V  I  C     E  S  A     G  V  Q     E  D  A  A     S  L  R     A  F  T     E  A  M
   +2 CGACGACTTA GTCGTTATCT GTGAAAGCGC GGGGGTCCAG GAGGACGCGG CAGCCTGAG AGCCTTCACG GAGGCTATGA
 6481 GCTGCTGAAT CAGCAATAGA CACTTTCGCG CCCCCAGGTC CTCCTGCGCC GTCGGACTC TCGGAAGTGC CTCCGATACT

T  R  Y  S     A  P  P     G  D  P  P     Q  P  E     Y  D  L     E  L  I  T     S  C  S     S  N  V
   +2 CCAGGTACTC CGCCCCCCCT GGGGACCCCCCC CACAACCAGA ATACGACTTG GAGCTCATAA CATCATGCTC CTCCAACGTG
 6561 GGTCCATGAG GCGGGGGGGA CCCCTGGGGG GTGTTGGTCT TATGCTGAAC CTCGAGTATT GTAGTACGAG GAGGTTGCAC

S  V  A  H     D  G  A     G  K  R     V  Y  Y  L     T  R  D     P  T  T     P  L  A  R     A  A  W
   +2 TCAGTGCGCC ACGACGGCGC TGGAAAGAGG GTCTACTACC TCACCCGTGA CCCTACAACC CCCCTCGGGA GAGCTGCCTG
 6641 AGTCAGCGGG TGCTGCCGCG ACCTTTCTCC CAGATGATGG AGTGGGCACT GGGATGTTGG GGGAGCGCCT CTCGACGGAC

E  T  A     R  H  T  P     V  N  S     W  L  G     N  I  I  M     F  A  P     T  L  W     A  R  M
   +2 GGAGACAGCA AGACACACTC CAGTCAATTC CTGGCTAGGC AACATAATCA TGTTTGCCCC CACACTGTGG GCGAGGATGA
 6721 CCTCTGTCGT TCTGTGTGAG GTCAGTTAAG GACCGATCCG TTGTATTAGT ACAAACGGGG GTGTGACACC CGCTCCTACT

I  L  M  T     H  F  F     S  V  L  I     A  R  D     Q  L  E     Q  A  L  D     C  E  I     Y  G  A
   +2 TACTGATGAC CCATTTCTTT AGCGTCCTTA TAGCCAGGGA CCAGCTTGAA CAGGCCCTCG ATTGCGAGAT CTACGGGGCC
 6801 ATGACTACTG GGTAAAGAAA TCGCAGGAAT ATCGGTCCCT GGTCGAACTT GTCCGGGAGC TAACGCTCTA GATGCCCCGG

C  Y  S     I  E  P  L     D  L  P     P  I  I  Q     R  L  H     G  L  S     A  F  S  L     H  S  Y
   +2 TGCTACTCCA TAGAACCACT GGATCTACCT CCAATCATTC AAAGACTCCA TGGCCTCAGC GCATTTTCAC TCCACAGTTA
 6881 ACGATGAGGT ATCTTGGTGA CCTAGATGGA GGTTAGTAAG TTTCTGAGGT ACCGGAGTCG CGTAAAAGTG AGGTGTCAAT
```

FIG. 3-12 pCMV-NS35

```
       S   P   G   E   I   N   R   V   A   A   C   L   R   K   L   G   V   P   P   L   R   A   W   R   H   R
 +2 CTCTCCAGGT GAAATCAATA GGGTGGCCGC ATGCCTCAGA AAACTTGGGG TACCGCCCTT GCGAGCTTGG AGACACCGGG
6961 GAGAGGTCCA CTTTAGTTAT CCCACCGGCG TACGGAGTCT TTTGAACCCC ATGGCGGGAA CGCTCGAACC TCTGTGCCC

A   R   S   V   R   A   R   L   L   A   R   G   G   R   A   A   I   C   G   K   Y   L   F   N   W   A   V
 +2 CCCGGAGCGT CCGCGGCTAGG CTTCTGGCCA GAGGAGGCAG GGCTGCCATA TGTGGCAAGT ACCTCTTCAA CTGGGCAGTA
7041 GGGCCTCGCA GGCGCCGATCC GAAGACCGGT CTCCTCCGTC CCGACGGTAT ACACCGTTCA TGGAGAAGTT GACCCGTCAT

R   T   K   L   K   L   T   P   I   A   A   A   G   Q   L   D   L   S   G   W   F   T   A   G   Y   S   G
 +2 AGAACAAAGC TCAAACTCAC TCCAATAGCG GCCGCTGGCC AGCTGGACTT GTCCGGCTGG TTCACGGCTG GCTACAGCGG
7121 TCTTGTTTCG AGTTTGAGTG AGGTTATCGC CGGCGACCGG TCGACCTGAA CAGGCCGACC AAGTGCCGAC CGATGTCGCC

G   D   I   Y   H   S   V   S   H   A   R   P   R   W   I   W   F   C   L   L   L   L   A   G   V
 +2 GGGAGACATT TATCACAGCG TGTCTCATGC CCGGCCCCGC TGGATCTGGT TTTGCCTACT CCTGCTTGCT GCAGGGGTAG
7201 CCCTCTGTAA ATAGTGTCGC ACAGAGTACG GGCCGGGGCG ACCTAGACCA AAACGGATGA GGACGAACGA CGTCCCCATC

G   I   Y   L   L   P   N   R
 +2 GCATCTACCT CCTCCCCAAC CGATGAAGGT TGGGGTAAAC ACTCCGGCCT AAAAAAAAAA AAAAATCTAG AAAGGCGCGC
7281 CGTAGATGGA GGAGGGGTTG GCTACTTCCA ACCCCATTTG TGAGGCCGGA TTTTTTTTTT TTTTTAGATC TTTCCGCGCG

BAMHI         MluI
                  -----         -----
7361 CAAGATATCA AGGATCCACT ACGGCGTTAGA GCTCGCCTGA CAGCCCTCGAC TGTGCCCTTCT AGTTGCCAGC CATCTCTGTGT
     GTTCTATAGT TCCTAGGTGA TGCGCCAATCT CGAGCGGACTA GTCGGAGCTG ACACGGAAGA TCAACGGTCG GTAGACAACA

7441 TTGCCCCTCC CCCGTGCCTT CCTTGACCCT GGAAGGTGCC ACTCCCACTG TCCTTTCCTA ATAAAATGAG GAAATTGCAT
     AACGGGGAGG GGGCACGGAA GGAACTGGGA CCTTCCACGG TGAGGGTGAC AGGAAAGGAT TATTTTACTC CTTTAACGTA
```

FIG. 3-13 pCMV-NS35

| | | | | | | | |
|---|---|---|---|---|---|---|---|
|7521|CGCATTGTCT GCGTAACAGA|GAGTAGGTGT CTCATCCACA|CATTCTATTC GTAAGATAAG|TGGGGGGTGG ACCCCCCACC|GGTGGGCAG CCACCCCGTC|GACAGCAAGG CTGTCGTTCC|GGGAGGATTG CCCTCCTAAC|GGAAGACAAT CCTTCTGTTA|
|7601|AGCAGGCATG TCGTCCGTAC|CTGGGGAGCT GACCCCTCGA|CTTCCGCTTC GAAGGCGAAG|CTCGCTCACT GAGCGAGTGA|GACTCGCTGC CTGAGCGACG|GCTCGGTCGT CGAGCCAGCA|TCGGCTGCGG AGCCGACGCC|CGAGCGGTAT GCTCGCCATA|
|7681|CAGCTCACTC GTCGAGTGAG|AAAGGCGGTA TTTCGCCCAT|ATACGGTTAT TATGCCAATA|CCACAGAATC GGTGTCTTAG|AGGGGATAAC TCCCCTATTG|GCAGGAAAGA CGTCCTTTCT|ACATGTGAGC TGTACACTCG|AAAAGGCCAG TTTTCCGGTC|
|7761|CAAAAGGCCA GTTTCCGGT|GGAACCGTAA CCTTGGCATT|AAAGGCCGCG TTTCCGGCGC|GGCGAAACCC CCGGCTTTGG|GACAGGACTA CTGTCCTGAT|TAAAGATACC ATTTCTATGG|GCTCCGCCCC CGAGGCGGGG|ATCACAAAAA TAGTGTTTTT|
|7841|TCGACGCTCA AGCTGCGAGT|AGTCAGAGGT TCAGTCTCCA|GGCGAAACCC CCGGCTTTGG|GACAGGACTA CTGTCCTGAT|TAAAGATACC ATTTCTATGG|AGGCGTTTCC TCCGCAAAGG|CCCTGAAGC GGGACCTTCG|TCCCTCGTGC AGGGAGCACG|
|7921|GCTCTCCTGT CGAGAGGACA|TCCGACCCTG AGGCTGGGAC|CCGCTTACCG GGCGAATGGC|GATACCTGTC CTATGACAG|CGCCTTTCTC GCGAAAGAG|CCTTCGGGAA GGAAGCCCTT|GCTGGCCTGCT CGCACGCGA|TTTCTCAATGC AAGAGTTACG|
|8001|TCACGCTGTA AGTGCGACAT|GGTATCTCAG CCATAGAGTC|TTCGGTGTAG AAGCCACATG|GTCGTTCGCT CAGCAAGGCA|CCAAGCTGGG GGTTCGACCC|CTGTGTGCAC GACACACGTG|GAACCCCCG CTTGGGGGC|TTCAGCCCGA AAGTCGGGCT|
|8081|CCGCTGCGCC GGGCGACGCGG|TTATCCGGTA AATAGGCCAT|ACTATCGTCT TGATAGCAGA|TGAGTCCAAC ACTCAGGTTG|CCGGTAAGAC GGCCATTCTG|ACGACTTATC TGCTGAATAG|GCCACTGGCA CGGTGACCGT|GCAGCCACTG CGTCGGTGAC|
|8161|GTAACAGGAT CATTGTCCTA|TAGCAGAGCG ATCGTCTCGC|AGGTATGTAG TCCATACATC|GCGGTGCTAC CGCCACGAT|AGAGTTCTTG TCTCAAGAAC|AAGTGGTGCC TTCACCACCG|CTAACTACGG CTAGAGA|CTAGACTAGA GATTGATCT|

FIG. 3-14 pCMV-NS35

```
8241  AGGACAGTAT TTGGTATCTG CGCTCTGCTG AAGCCAGTTA CCTTCGGAAA AAGAGTTGGT AGTCTTTGAT CCGGCAAACA
      TCCTGTCATA AACCATAGAC GCGAGACGAC TTCGGTCAAT GGAAGCCTTT TTCTCAACCA TCGAGAACTA GGCCGTTTGT

8321  AACCACCGCT GGTAGCGGTG GTTTTTTTGT TTGCAAGCAG CAGATTACGC GCAGAAAAAA AGGATCTCAA GAAGATCCTT
      TTGGTGGCGA CCATCGCCAC CAAAAAAACA AACGTTCGTC GTCTAATGCG CGTCTTTTTT TCCTAGAGTT CTTCTAGGAA

8401  TGATCTTTTC TACGGGGTCT GACGCTCAGT GGAACGAAAA CTCACGTTAA GGGATTTTGG TCATGAGATT ATCAAAAAGG
      ACTAGAAAAG ATGCCCCAGA CTGCGAGTCA CCTTGCTTTT GAGTGCAATT CCCTAAAACC AGTACTCTAA TAGTTTTTCC

8481  ATCTTCACCT AGATCCTTTT AAATTAAAAA TGAAGTTTTA AATCAATCTA AAGTATATAT GAGTAAACTT GGTCTGACAG
      TAGAAGTGGA TCTAGGAAAA TTTAATTTTT ACTTCAAAAT TTAGTTAGAT TTCATATATA CTCATTTGAA CCAGACTGTC

8561  TTAACCAATGC TTAATCAGTG AGGCACCTAT CTCAGCGATC TGTCTATTTC GTTCATCCAT AGTTGCCTGA CTCCCCGTCG
      AATTGGTTACG AATTAGTCAC TCCGTGGATA GAGTCGCTAG ACAGATAAAG CAAGTAGGTA TCAACGGACT GAGGGGCAGC

8641  TGTAGATAAC TACGATACGG GAGGGCTTAC CATCTGGCCC CAGTGCTGCA ATGATACCGC GAGACCCACG CTCACCGGCT
      ACATCTATTG ATGCTATGCC CTCCCGAATG GTAGACCGGG GTCACGACGT TACTATGGCG CTCTGGGTGC GAGTGGCCGA

8721  CCAGATTTAT CAGCAATAAA CCAGCCAGCC GGAAGGGCCG AGCGCAGAAG TGGTCCTGCA ACTTTATCCG CCTCCATCCA
      GGTCTAAATA GTCGTTATTT GGTCGGTCGG CCTTCCCGGC TCGCGTCTTC ACCAGGACGT TGAAATAGGC GGAGTAGGT

8801  GTCTATTAAT TGTTGCCGGG AAGCTAGAGT AAGTAGTTCG CCAGTTAATA GTTTGCGCAA CGTTGTTGCC ATTGCTACAG
      CAGATAATTA ACAACGGCCC TTCGATCTCA TTCATCAAGC GGTCAATTAT CAAACGCGTT GCAACAACGG TAACGATGTC

8881  GCATCGTGGT GTCACGCTCG TCGTTTGGTA TGGCTTCATT CAGCTCCGGT TCCCAACGAT CAAGGCGAGT TACATGATCC
      CGTAGCACCA CAGTGCGAGC AGCAAACCAT ACCGAAGTAA GTCGAGGCCA AGGGTTGCTA GTTCCGCTCA ATGTACTAGG
```

FIG. 3-15 pCMV-NS35

8961  CCCATGTTGT GCAAAAAAGC GGTTAGCTCC TTCGGTCCTC CGATCGTTGT CAGAAGTAAG TTGGCCGCAG TGTTATCACT
      GGGTACAACA CGTTTTTTCG CCAATCGAGG AAGCCAGGAG GCTAGCAACA GTCTTCATTC AACCGGCGTC ACAATAGTGA

9041  CATGGTTATG GCAGCACTGC ATAATTCTCT TACTGTCATG CCATCCGTAA GATGCTTTTC TGTGACTGGT GAGTACTCAA
      GTACCAATAC CGTCGTGACG TATTAAGAGA ATGACAGTAC GGTAGGCATT CTACGAAAAG ACACTGACCA CTCATGAGTT

9121  CCAAGTCATT CTGAGAATAG TGTATGCGGC GACCGAGTTG CTCTTGCCCG GCGTCAATAC GGGATAATAC CGCGCCACAT
      GGTTCAGTAA GACTCTTATC ACATACGCCG CTGGCTCAAC GAGAACGGGC CGCAGTTATG CCCTATTATG GCGCGGTGTA

9201  AGCAGAACTT TAAAAGTGCT CATCATTGGA AAACGTTCTT CGGGGCGAAA ACTCTCAAGG ATCTTACCGC TGTTGAGATC
      TCGTCTTGAA ATTTTCACGA GTAGTAACCT TTTGCAAGAA GCCCCGCTTT TGAGAGTTCC TAGAATGGCG ACAACTCTAG

9281  CAGTTCGATG TAACCCACTC GTGCACCCAA CTGATCTTCA GCATCTTTTA CTTTCACCAG CGTTTCTGGG TGAGCAAAAA
      GTCAAGCTAC ATTGGGTGAG CACGTGGGTT GACTAGAAGT CGTAGAAAAT GAAAGTGGTC GCAAAGACCC ACTCGTTTTT

9361  CAGGAAGGCA AAATGCCGCA AAAAAGGGAA TAAGGGCGAC ACGGAAATGT TGAATACTCA ACATATTTGA TACTCTTCCT TTTTCAATAT
      GTCCTTCCGT TTTACGGCGT TTTTTCCCTT ATTCCCGCTG TGCCTTTACA ACTTATGAGT TGTATAAACT ATGAGAAGGA AAAAGTTATA

9441  TATTGAAGCA TTTATCAGGG TTATTGTCTC ATGAGCGGAT ACATATTTGA ATGTATTTAG AAAAATAAAC AAATAGGGGT
      ATAACTTCGT AAATAGTCCC AATAACAGAG TACTCGCCTA TGTATAAACT TACATAAATC TTTTTATTTG TTTATCCCCA

9521  TCCCGCCACA TTTCCCCGAA AAGTGCCACC TGACGTCTAA GAAACCATTA TTATCATGAC ATTAACCTAT AAAAATAGGC
      AGGGCGGTGT AAAGGGGCTT TTCACGGTGG ACTGCAGATT CTTTGGTAAT AATAGTACTG TAATTGGATA TTTTTATCCG

9601  GTATCACGAG GCCCTTTCGT C
      CATAGTGCTC CGGGAAAGCA G

FIG. 3-16 pCMV-delNS35

```
  1  TCGGCGCGTTT CGGTGATGAC GGTGAAAACC TCTGACACAT GCAGCTCCCG GAGACGGTCA CAGCTTGTCT GTAAGCGGAT
     AGCCGCGCAAA GCCACTACTG CCACTTTTGG AGACTGTGTA CGTCGAGGGC CTCTGCCAGT GTCGAACAGA CATTCGCCTA

81  GCCGGGAGCA GACAAGCCCG TCAGCGGGCG TTGGCGGGTG TCGGGGGCTG CTTAACTATG CGGCATCAGA
     CGGCCCTCGT CTGTTCGGGC AGTCGCCCGC AACCGCCCAC AGCCCCGACC GAATTGATAC GCCGTAGTCT

StuI
                                                                 - - - - - - -
161  GCAGATTGTA CTGAGAGTGC ACCATATGAA GCTTTTTGCA AAAGCCTAGG CCTCCAAAAA AGCCTCCTCA CTACTTCTGG
     CGTCTAACAT GACTCTCACG TGGTATACTT CGAAAAACGT TTTCGGATCC GGAGGTTTTT TCGGAGGAGT GATGAAGACC

241  AATAGCTCAG AGGCCGAGGC GGCCTCGGCC TCTGCATAAA TAAAAAAAAT TAGTCAGCCA TATATCATAA TATGTACATT
     TTATCGAGTC TCCGGCTCCG CCGGAGCCGG AGACGTATTT ATTTTTTTTA ATCAGTCGGT ATATAGTATT ATACATGTAA

321  ACTGGGCGGG GAGGAATTA TTGGCTATTG GCCATTGCAT AGTTGTATC AGTTGTATC ACGTGTATC TAGTTATTAA TTACGGGTC ATTAGTTCAT
     TGACCCGCCC CTCCCTTAAT AACCGATAAC CGGTAACGTA TCAACATAG TCAACATAG TGCAACATAG ATCATTAATT AATGCCCCAG TAATCAAGTA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC ATTGACGTCA ATGGGTGGAG TATTTACGGT
     CTGCAGTTAT TACTGCATAC AAGGGTATCA TTGCGGTTAT CCCTGAAAGG TAACTGCAGT TACCCACCTC ATAAATGCCA
```

FIG. 5-1 pCMV-deINS35

```
641   AAACTGCCCA CTTGGCAGTA CATCAAGTGT ATCATATGCC AAGTCCGCCC CCTATTGACG TCAATGACGG TAAATGGCCC
      TTTGACGGGT GAACCGTCAT GTAGTTCACA TAGTATACGG TTCAGGCGGG GGATAACTGC AGTTACTGCC ATTTACCGGG

721   GCCTGGCATT ATGCCCAGTA CATGACCTTA CGGGACTTTC CTACTTGGCA GTACATCTAC GTATTAGTCA TCGCTATTAC
      CGGACCGTAA TACGGGTCAT GTACTGGAAT GCCCTGAAAG GATGAACCGT CATGTAGATG CATAATCAGT AGCGATAATG

801   CATGGTGATG CGGTTTTGGC AGTACACCAA TGGGCGTGGA TAGCGGTTTG ACTCACGGGG ATTTCCAAGT CTCCACCCCA
      GTACCACTAC GCCAAAACCG TCATGTGGTT ACCCGCACCT ATCGCCAAAC TGAGTGCCCC TAAAGGTTCA GAGGTGGGGT

881   TTGACGTCAA TGGGAGTTTG TTTTGGCACC AAAATCAACG GGACTTTCCA AAATGTCGTA ATAACCCCGC CCCGTTGACG
      AACTGCAGTT ACCCTCAAAC AAAACCGTGG TTTTAGTTGC CCTGAAAGGT TTTACAGCAT TATTGGGGCG GGGCAACTGC

961   CAAATGGGCG GTAGGCGTGT ACGGTGGGAG GTCTATATAA GCAGAGCTCG TTTAGTGAAC CGTCAGATCG CCTGAGACG
      GTTTACCCGC CATCCGCACA TGCCACCCTC CAGATATATT CGTCTCGAGC AAATCACTTG GCAGTCTAGC GGACTCTGC

1041  CCATCCACGC TGTTTTGACC TCCATAGAAG ACACCGGGAC CGATCCAGCC TCCCGGGCCG GGAACGGTGC ATTGGAACGC
      GGTAGGTGCG ACAAAACTGG AGGTATCTTC TGTGGCCCTG GCTAGGTCGG AGGGCCGGGC CCTTGCCACG TAACCTTGCG

1121  GGATTCCCCG TGCCAAGAGT GACGTAAGTA CCGCCTATAG ACTCTATAGG CACACCCCTT TGGCTCTTAT GCATGCTATA
      CCTAAGGGGC ACGGTTCTCA CTGCATTCAT GGCGGATATC TGAGATATCC GTGTGGGGAA ACCGAGAATA CGTACGATAT

1201  CTGTTTTTGG CTTGGGCCCT ATACCCCCCC GCTCCCTATG CTATAGGTGA TGGTATAGCT TAGCCTATAG GTGTGGGTTA
      GACAAAAACC GAACCCGGGA TATGTGGGGG CGAGGGATAC GATATCCACT ACCATATCGA ATCGGATATC CACACCCAAT

1281  TTGACCATTA TTGACCACTC CCCTATTGGT GACGATACTT TCCATTACTA ATCCATAACA TGGCTCTTTG CCAGAACTAT
      AACTGGTAAT AACTGGTGAG GGGATAACCA CTGCTATGAA AGGTAATGAT TAGGTATTGT ACCGAGAAAC GGTGTTGATA
```

FIG. 5-2 pCMV-delNS35

```
1361  CTCTATTGGC TATATGCCAA TACTCTGTCC TTCAGAGACT GACACGGACT CTGTATTTTT ACAGGATGGG GTCCATTTAT
      GAGATAACCG ATATACGGTT ATGAGACAGG AAGTCTCTGA CTGTGCCTGA GACATAAAAA TGTCCTACCC CAGGTAAATA

1441  TATTTACAAA TTCACATATA CAACAACGCC GTCCCCCGTG CCCGCAGTTT TTATTAAACA TAGGCGTGGA TCTCCGACAT
      ATAAATGTTT AAGTGTATAT GTTGTTGCGG CAGGGGGCAC GGGCGTCAAA AATAATTTGT ATCGCACCCT AGAGGCTGTA

1521  CTCGGGTACG TGTTCCGGAC ATGGGCTCTT CTCCGGTAGC GGGGGAGCTT CCACATCCGA GCCCTGGTCC CATCCGTCCA
      GAGCCCATGC ACAAGGCCTG TACCCGAGAA GAGGCCATCG CCCCCTCGAA GGTGTAGGCT CGGGACCAGG GTAGGCAGGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCCAGCCG TCGAGGAACG AGGATTGTCA CCTCCGGTCT GAATCCGTGT CGTGTTACGG GTGGTGGTGG

1681  AGTGTGCCGC ACAAGGCCGT GGGCGGTAGG TATGTGTCTG AAAATGAGCT CGGAGATTGG GCTCCGCACCT GGACGCAGAT
      TCACACGGCG TGTTCCGGCA CCCGCCATCC ATACACAGAC TTTTACTCGA GCCTCTAACC CGAGCGGTGA CCTGCGTCTA

1761  GGAAGACTTA AGGCAGCGGC AGAAGAAGAT GCAGGCAGCT GAGTTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CTCAGTCTCC ATTGAGGGCA

1841  TGCGGTGCTG TTAACGGTGG AGGGCAGTGT AGTCTGAGCA GTACTCGTTG CTGCCGCGCG CGGCCACCAGA CATAATAGCT
      ACGCCACGAC AATTGCCACC TCCCGTCACA TCAGACTCGT CATGAGCAAC GACGGCGCGC GCCGGTGGTCT GTATTATCGA

M   A   A
                                                                           EcoRI
                                                                           ------
+2
1921  GACAGACTAA CAGACTGTTC CTTTCCATGG GTCTTTTCTG CAGTCACCGT CGTCGACCTA AGAATTCACC ATGGCTGCAT
      CTGTCTGATT GTCTGACAAG GAAAGGTACC CAGAAAAGAC GTCAGTGGCA GCAGCTGGAT TCTTAAGTGG TACCGACGTA
```

FIG. 5-3 pCMV-delNS35

```
  +2 Y  A  A  Q   G  Y  K   V  L  V  L   N  P  S   V  A  A   T  L  G  F   G  A  Y   M  S  K
2001 ATGCAGCTCA GGGCTATAAG GTGCTAGTAC TCAACCCCTC TGTTGCTGCA ACACTGGGCT TTGGTGCTTA CATGTCCAAG
     TACGTCGAGT CCCGATATTC CACGATCATG AGTTGGGGAG ACAACGACGT TGTGACCCGA AACCACGAAT GTACAGGTTC

+2  A  H  G  I   D  P  N   I  R  T   G  V  R  T   I  T  T   G  S  P   I  T  Y  S   T  Y  G
2081 GCTCATGGGA TCGATCCTAA CATCAGGACC GGGGTGAGAA CAATTACCAC TGGCAGCCCC ATCACGTACT CCACCTACGG
     CGAGTACCCT AGCTAGGATT GTAGTCCTGG CCCCACTCTT GTTAATGGTG ACCGTCGGGG TAGTGCATGA GGTGGATGCC

+2  K  F  L   A  D  G  G   C  S  G   G  A  Y   D  I  I  I   C  D  E   C  H  S   T  D  A
2161 CAAGTTCCTT GCCGACGGCG GGTGCTCGGG GGGCGCTTAT GACATAATAA TTTGTGACGA GTGCCACTCC ACGGATGCCA
     GTTCAAGGAA CGGCTGCCGC CCACGAGCCC CCCGCGAATA CTGTATTATT AAACACTGCT CACGGTGAGG TGCCTACGGT

+2 T  S  I  L   G  I  G   T  V  L  D   Q  A  E   T  A  G   A  R  L  V   V  L  A   T  A  T
2241 CATCCATCTT GGGCATTGGC ACTGTCCTTG ACCAAGCAGA GACTGCGGGG GCGAGACTGG TTGTGCTCGC CACCGCCACC
     GTAGGTAGAA CCCGTAACCG TGACAGGAAC TGGTTCGTCT CTGACGCCCC CGCTCTGACC AACACGAGCG GTGGCGGTGG

+2  P  P  G  S   V  T  V   P  H  P   N  I  E  E   V  A  L   S  T  T   G  E  I  P   F  Y  G
2321 CCTCCGGGCT CCGTCACTGT GCCCCATCCC AACATCGAGG AGGTTGCTCT GTCCACCACC GGAGAGATCC CTTTTTACGG
     GGAGGCCCGA GGCAGTGACA CGGGGTAGGG TTGTAGCTCC TCCAACGAGA CAGGTGGTGG CCTCTCTAGG GAAAAATGCC

+2  K  A  I   P  L  E  V   I  K  G   G  R  H   L  I  F  C   H  S  K   K  K  C   D  E  L
2401 CAAGGCTATC CCCCTCGAAG TAATCAAGGG GGGGAGACAT CTCATCTTCT GTCATTCAAA GAAGAAGTGC GACGAACTCG
     GTTCCGATAG GGGGAGCTTC ATTAGTTCCC CCCCTCTGTA GAGTAGAAGA CAGTAAGTTT CTTCTTCACG CTGCTTGAGC

+2 A  A  K  L   V  A  L   G  I  N  A   V  A  Y   Y  R  G   L  D  V  S   V  I  P   T  S  G
2481 CCGCAAAGCT GGTCGCATTG GGCATCAATG CCGTGGCCTA CTACCGCGGT CTTGACGTGT CCGTCATCCC GACCAGCGGC
     GGCGTTTCGA CCAGCGTAAC CCGTAGTTAC GGCACCGGAT GATGGCGCCA GAACTGCACA GGCAGTAGGG CTGGTCGCCG
```

FIG. 5-4 pCMV-delNS35

```
      D V V V V A T   D A L   M T G Y T G D   F D S   V I D C   N T C
+2    GATGTTGTCG TCTGGCAAC CGATGCCCTC ATGACCGGCT ATACCGGGGA CTTCGACTCG GTGATAGACT GCAATACGTG
2561  CTACAACAGC AGACCGTTG GCTACGGGAG TACTGGCCGA TATGGCCGCT GAAGCTGAGC CACTATCTGA CGTTATGCAC

V T Q   T V D F   S L D   P T F   T I E T   T L   P Q D   A V S
+2    TGTCACCCAG ACAGTCGATT TCAGCCTTGA CCCTACCTTC ACCATTGAGA CAATCACGCT CCCCAAGAT GCTGTCTCCC
2641  ACAGTGGGTC TGTCAGCTAA AGTCGGAACT GGGATGGAAG TGGTAACTCT GTTAGTGCGA GGGGTTCTA CGACAGAGGG

R T Q R   R G R   T G R G   K P G   I Y R   F V A P   G E R   P S G
+2    GCACTCAACG TCGGGGCAGG ACTGGGACGG GGAAGCCAGG CATCTACAGA TTTGTGGCAC CGGGGGAGCG CCCCTCCGGC
2721  CGTGAGTTGC AGCCCCGTCC TGACCCTGCC CCTTCGGTCC GTAGATGTCT AAACACCGTG GCCCCCTCGC GGGGAGGCCG

M F D S   S V L   C E C   Y D A G   C A W   Y E L   T P A E   T T V
+2    ATGTTCGACT CGTCCGTCCT CTGTGAGTGC TATGACGCAG GCTGCGCTTG GTATGAGCTC ACGCCCGCCG AGACTACAGT
2801  TACAAGCTGA GCAGGCAGGA GACACTCACG ATACTGCGTC CGACGCGAAC CATACTCGAG TGCGGGCGGC TCTGATGTCA

R L R   A Y M N   T P G   L P V   C Q D H   L E F   W E G   V F T
+2    TAGGCTACGA GGCTACATGA ACACCCCGGG GCTTCCCGTG TGCCAGGACC ATCTTGAATT TTGGGAGGGC GTCTTTACAG
2881  ATCCGATGCT CCGATGTACT TGTGGGGCCC CGAAGGGCAC ACGGTCCTGG TAGAACTTAA AACCCTCCCG CAGAAATGTC
                                                                                    StuI

G L T H   I D A   H F L S   Q T K   Q S G   E N L P   Y L V   A Y Q
+2    GCCTCACTCA TATAGATGCC CACTTTCTAT CCCAGACAAA GCAGAGTGGG GAGAACCTTC CTTACCTGGT AGCGTACCAA
2961  CGGAGTGAGT ATATCTACGG GTGAAAGATA GGGTCTGTTT CGTCTCACCC CTCTTGGAAG GAATGGACCA TCGCATGGTT
      StuI
```

FIG. 5-5 pCMV-delNS35

```
      A  T  V  C   A  R  A    Q  A  P    P  P  S  W    D  Q  M    W  K  C    L  I  R  L    K  P  T
+2    GCCACCGTGT GCGCTAGGGC TCAAGCCCCT CCCCCATCGT GGGACCAGAT GTGGAAGTGT TTGATTCGCC TCAAGCCCAC
3041  CGGTGGCACA CGCGATCCCG AGTTCGGGGA GGGGGTAGCA CCCTGGTCTA CACCTTCACA AACTAAGCGG AGTTCGGGTG

L  H  G   P  T  P  L    L  Y  R    L  G  A    V  Q  N  E    I  T  L    T  H  P    V  T  K
+2    CCTCCATGGG CCAACACCCC TGCTATACAG ACTGGGCGCT GTTCAGAATG AAATCACCCT GACGCACCCA GTCACCAAAT
3121  GGAGGTACCC GGTTGTGGGG ACGATATGTC TGACCCGCGA CAAGTCTTAC TTTAGTGGGA CTGCGTGGGT CAGTGGTTTA

Y  I  M  T   C  M  S    A  D  L  E    V  V  T    S  T  W    V  L  V  G    G  V  L    A  A  L
+2    ACATCATGAC ATGCATGTCG GCCGACCTGG AGGTCGTCAC GAGCACCTGG GTGCTCGTTG GCGGCGTCCT GGCTGCTTTG
3201  TGTAGTACTG TACGTACAGC CGGCTGGACC TCCAGCAGTG CTCGTGGACC CACGAGCAAC CGCCGCAGGA CCGACGAAAC

A  A  Y  C   L  S  T    G  C  V    V  I  V  G    R  V  V    L  S  G    K  P  A  I    I  P  D
+2    GCCGCGTATT GCCTGTCAAC AGGCTGCGTG GTCATAGTGG GCAGGGTCGT CTTGTCCGGG AAGCCGGCAA TCATACCTGA
3281  CGGCGCATAA CGGACAGTTG TCCGACGCAC CAGTATCACC CGTCCCAGCA GAACAGGCCC TTCGGCCGTT AGTATGGACT

R  E  V   L  Y  R  E    F  D  E    M  E  E    C  S  Q  H    L  P  Y    I  E  Q    G  M  M
+2    CAGGGAAGTC CTCTACCGAG AGTTCGATGA GATGGAAGAG TGCTCTCAGC ACTTACCGTA CATCGAGCAA GGGATGATGC
3361  GTCCCTTCAG GAGATGGCTC TCAAGCTACT CTACCTTCTC ACGAGAGTCG TGAATGGCAT GTAGCTCGTT CCCTACTACG

L  A  E  Q   F  K  Q    K  A  L  G    L  L  Q    T  A  S    R  Q  A  E    V  I  A    P  A  V
+2    TGGCCGAGCA GTTCAAGCAG AAGGCCCTCG GCCTCCTGCA GACCGCGTCC CGTCAGGCAG AGGTTATCGC CCCTGCTGTC
3441  ACCGGCTCGT CAAGTTCGTC TTCCGGGAGC CGGAGGACGT CTGGCGCAGG GCAGTCCGTC TCCAATAGCG GGGACGACAG

Q  T  N  W   Q  K  L    E  T  F    W  A  K  H    M  W  N    F  I  S    G  I  Q  Y    L  A  G
+2    CAGACCAACT GGCAAAAACT CGAGACCTTC TGGGCGAAGC ATATGTGGAA CTTCATCAGT GGGATACAAT ACTTGGCGGG
3521  GTCTGGTTGA CCGTTTTTGA GCTCTGGAAG ACCCGCTTCG TATACACCTT GAAGTAGTCA CCCTATGTTA TGAACCGCCC
```

FIG. 5-6 pCMV-deINS35

```
          L   S   T       L   P   G   N       P   A   I       A   S   L       M   A   F   T       A   A   V       T   S   P       L   T   T
+2  CTTGTCAACG CTGCCTGGTA ACCCCGGCCAT TGCTTCATTG ATGGCTTTTA CAGCTGCTGT CACCAGCCCA CTAACCACTA
3601 GAACAGTTGC GACGGACCAT TGGGGCGGTA ACGAAGTAAC TACCGAAAAT GTCGACGACA GTGGTCGGGT GATTGGTGAT

S   Q   T   L       L   F   N       I   L   G   G       G   W   V   A       A   Q   L       A   A   P   G       A   A   T       A   F   V
+2  GCCAAACCCT CCTCTTCAAC ATATTGGGGG GGTGGGTGGC TGCCCAGCTC GCCGCCCCCG GTGCCCTTGTC
3681 CGGTTTGGGA GGAGAAGTTG TATAACCCCC CCACCCACCG ACGGGTCGAG CGGCGGGGGC CACGGCGATG ACGGAAACAC

G   A   G   L       A   G   A       A   I   G       S   V   G   L       G   K   V       L   I   D       I   L   A   G       Y   G   A
+2  GGGCTGGCT TAGCTGGCGC CGCCATCGGC AGTGTTGGAC TGGGGAAGGT CCTCATAGAC ATCCTTGCAG GGTATGGCGC
3761 CCGGACCGA ATCGACCGCG GCGGTAGCCG TCACAACCTG ACCCCTTCCA GGAGTATCTG TAGGAACGTC CCATACCGCG

G   V   A       G   A   L   V       A   F   K       I   M   S       G   E   V   P       S   T   E       D   L   V       N   L   L
+2  GGGCGTGGCG GGAGCTCTTG TGGCATTCAA GATCATGAGC GGTGAGGTCC CCTCCACGGA GGACCTGGTC AATCTACTGC
3841 CCCGCACCGC CCTCGAGAAC ACCGTAAGTT CTAGTACTCG CCACTCCAGG GGAGGTGCCT CCTGGACCAG TTAGATGACG

P   A   I   L       S   P   G       A   L   V   V       G   V   V       C   A   A       I   L   R   R       H   V   G       P   G   E
+2  CCGGCCATCCT CTCGCCCGGA GCCCTCGTAG TCGGCGTTGGT CTGTCAGCA ATACTGCGCC GGCACGTTGG CCCGGGCGAG
3921 GGCGGTAGGA GAGCGGGCCT CGGGAGCATC AGCCGCACCA GACAGTCGT TATGACGCGG CCGTGCAACC GGGCCCGCTC

G   A   V   Q       W   M   N       R   L   I       A   F   A   S       R   G   N       H   V   S       P   T   H   Y       V   P   E
+2  GGGGCAGTGC AGTGGATGAA CCGGCTGATA GCCTTCGCCT CCCGGGGGAA CCATGTTTCC CCACGCACT ACGTGCCGGA
4001 CCCCGTCACG TCACCTACTT GGCCGACTAT CGGAAGCGGA GGGCCCCCTT GGTACAAAGG GGTGCGTGA TGCACGGCCT

S   D   A       A   A   R   V       T   A   I       L   S   S       L   T   V   T       Q   L   L       R   R   L       H   Q   W
+2  GAGGCCATGCA GCTGCCCGCG TCACTGCCAT CTCAGCAGC CTCACTGTAA CCCAGCTCCT GAGGCGACTG CACCAGTGGA
4081 CTCCGTACGT CGACGGGCGC AGTGACGGTA GAGTCGTCG TGAGTGACATT GGGTCGAGGA CTCCGCTGAC GTGGTCACCT
```

FIG. 5-7 pCMV-deINS35

```
       I   S   S   E   C   T   T   P   C   S   G   S   W   L   R   D   I   W   D   W   I   C   E   V   L   S   D
+2  TAAGCTCGGA GTGTACCACT CCATGCTCCG GTTCCTGGCT AAGGGACATC TGGGACTGGA TATGCGAGGT GTTGAGCGAC
4161 ATTCGAGCCT CACATGGTGA GGTACGAGGC CAAGGACCGA TTCCCGTGTAG ACCCTGACCT ATACGCTCCA CAACTCGCTG

F   K   T   W   L   K   A   K   L   M   P   Q   L   P   G   I   P   F   V   S   C   Q   R   G   Y   K   G
+2  TTTAAGACCT GGCTAAAAGC TAAGCTCATG CCACAGCTGC CTGGGATCCC CTTTGTGTCC TGCCAGCGCG GGTATAAGGG
4241 AAATTCTGGA CCGATTTTCG ATTCGAGTAC GGTGTCGACG GACCCTAGGG GAAACACAGG ACGGTCGCGC CCATATTCCC
                                                        BamHI
                                                        ------

V   W   R   G   D   G   I   M   H   T   R   C   H   C   G   A   E   I   T   G   H   V   K   N   G   T
+2  GGTCTGGCGA GGGGACGGCA TCATGCACAC TCGCTGCCAC TGTGGAGCTG AGATCACTGG ACATGTCAAA AACGGACGA
4321 CCAGACCGCT CCCCTGCCGT AGTACGTGTG AGCGACGGTG ACACCTCGAC TCTAGTGACC TGTACAGTTT TTGCCCTGCT

M   R   I   V   G   P   R   T   C   R   N   M   W   S   G   T   F   P   I   N   A   Y   T   T   G   P   C
+2  TCAGGATCGT CGGTCCTAGG ACCTGCAGGA ACATGTGGAG TGGGACCTTC CCCATTAATG CCTACACCAC GGGCCCCTGT
4401 ACTCCTAGCA GCCAGGATCC TGGACGTCCT TGTACACCTC ACCCTGGAAG GGGTAATTAC GGATGTGGTG CCCGGGGACA

T   P   L   P   A   P   N   Y   T   F   A   L   W   R   V   S   A   E   E   Y   V   E   I   R   Q   V   G
+2  ACCCCCCTTC CTGCGCCCGAA CTACACGTTC GGGCTATGCC GGGTGTCTGC AGAGGAATAC GTGGAGATAA GGCAGGTGGG
4481 TGGGGGGAAG GACGCGGGCTT GATGTGCAAG CCCGATACGGT CCCACAGACG TCTCCTTATG CACCTCTATT CCGTCCACCC

D   F   H   Y   V   T   G   M   T   T   D   N   L   K   C   P   C   Q   V   P   S   P   E   F   F   T
+2  GGACTTCCAC TACGTGACGG GTATGACTAC TGACAATCTT AAATGCCCGT GCCAGGTCCC ATCGCCCGAA TTTTTCACAG
4561 CCTGAAGGTG ATGCACTGCC CATACTGATG ACTGTTAGAA TTTACGGGCA CGGTCCAGGG TAGCGGGCTT AAAAAGTGTC

E   L   D   G   V   R   L   H   R   F   A   P   P   C   K   P   L   L   R   E   E   V   S   F   R   V   G
+2  AATTGGACGG GGTGCGCCTA CATAGGTTTG CGCCCCCCTG CAAGCCCCTG CTGCGGGAGG AGTATCATT CAGAGTAGGA
4641 TTAACCTGCC CCACGCGGAT GTATCCAAAC GCGGGGGGAC GTTCGGGAAC GACGCCCTCC TCCATAGTAA GTCTCATCCT
```

FIG. 5-8 pCMV-delNS35

```
       L  H  E  Y  P  V  G  S  Q  L  P  C  E  P  E  P  D  V  A  V  L  T  S  M  L  T  D
+2  CTCCACGAAT ACCCGGTAGG GTCGCAATTA CCTTGCGAGC CCGAACCGGA CGTGGCCGTG TTGACGTCCA TGCTCACTGA
4721 GAGGTGCTTA TGGGCCATCC CAGCGTTAAT GGAACGCTCG GGCTTGGCCT GCACCGGCAC AACTGCAGGT ACGAGTGACT

P  S  H  I  T  A  E  A  A  G  R  R  L  A  R  G  S  P  P  S  V  A  S  S  S  A
+2  TCCCTCCCAT ATAACAGCAG AGGCGGCCGG GCGAAGGTTG CGCTTCCCAG CACCCCCCTC TGTGGCCAGC TCCTCGGCTA
4801 AGGGAGGGTA TATTGTCGTC TCCGCCGGCC CGCTTCCAAC GCGAAGGGTC GTGGGGGGAG ACACCGGTCG AGGAGCCGAT

S  Q  L  S  A  P  S  L  K  A  T  C  T  A  N  H  D  S  P  D  A  E  L  I  E  A  N
+2  GCCAGCTATC CGGTCCATCT CTCAAGGCAA CTTGCACCGC TAACCATGAC TCCCCTGATG CTGAGCTCAT AGAGGCCAAC
4881 CGGTCGATAG GCCAGGTAGA GAGTTCCGTT GAACGTGGCG ATTGGTACTG AGGGGACTAC GACTCGAGTA TCTCCGGTTG

L  L  W  R  Q  E  M  G  G  N  I  T  R  V  E  S  E  N  K  V  V  I  L  D  S  F  D
+2  CTCCTATGGA GGCAGGAGAG ACGAGCGGGA ATCACCAGGG TTGAGTCAGA AAACAAAGTG GTGATTCTGG ACTCCTTCGA
4961 GAGGATACCT CCGTCCTCTC TGCTCGCCCT TAGTGGTCCC AACTCAGTCT TTTGTTTCAC CACTAAGACC TGAGGAAGCT

P  L  V  A  E  E  D  E  R  E  I  S  V  P  A  E  I  L  R  K  S  R  R  F  A  Q
+2  TCCGCTTGTG GCGGAGGAGG ACGAGCGGGA GATCTCCGTA CCCGCAGAAA TCCTGCGGAA GTCTCGGAGA TTCGCCCAGG
5041 AGGCGAACAC CGCCTCCTCC TGCTCGCCCT CTAGAGGCAT GGGCGTCTTT AGGACGCCTT CAGAGCCTCT AAGCGGGTCC

A  L  P  V  W  A  R  P  D  Y  N  P  P  L  V  E  T  W  K  K  P  D  Y  E  P  P  V
+2  CCCTGCCCGT TTGGGCGCGG CCGGACTATA ACCCCCCGCT AGTGGAGACG TGGAAAAAGC CGGACTACGA ACCACCTGTG
5121 GGGACGGGCA AACCCGCGCC GGCCTGATAT TGGGGGGCGA TCACCTCTGC ACCTTTTTCG GCCTGATGCT TGGTGGACAC

V  H  G  C  L  P  P  P  K  S  P  P  V  P  P  P  R  K  K  R  T  V  V  L  T  E
+2  GTCCATGGCT GCCCGGCTTC CACCTCCGAA GTCCCCTCCT GCCCTCCGCC TCGGAAGAAG CGGACGGTGG TCCTCACTGA
5201 CAGGTACCGA CGGGCCGAAG GTGGAGGCTT CAGGGGAGGA CGGGAGGCGG AGCCTTCTTC GCCTGCCACC AGGAGTGACT
```

FIG. 5-9 pCMV-delNS35

```
       S   T   L     S   T   A   L     A   E   L     A   T   R     S   F   G   S     S   S   T     S   G   I     T   G   D
+2     ATCAACCCTA  TCTACTGCCT  TGGCCCGAGCT  CGCCACCAGA  AGCTTTGGCA  GCTCCTCAAC  TTCCGGCATT  ACGGGGACA
5281   TAGTTGGGAT  AGATGACGGA  ACCGGGCTCGA  GCGGTGGTCT  TCGAAACCGT  CGAGGAGTTG  AAGGCCGTAA  TGCCCGCTGT

N   T   T     S   S   E     P   A   P   S     G   C   P     P   D   S     D   A   E   S     Y   S   S     M   P   P
+2     ATACGACAAC  ATCCTCTGAG  CCCGCCCCTT  CTGGCTGCCC  CCCGACTCC  GACGCTGAGT  CCTATTCCTC  CATGCCCCCC
5361   TATGCTGTTG  TAGGAGACTC  GGGCGGGGAA  GACCGACGGG  GGGGCTGAGG  CTGCGACTCA  GGATAAGGAG  GTACGGGGGG

L   E   G   E     P   G   D     P   D   L     S   D   G   S     W   S   T     V   S   S     E   A   N   A     E   D   V
+2     CTGGAGGGGG  AGCCTCCCGA  TCCGGATCTT  AGCGACGGGT  CATGGTCAAC  GGTCAGTAGT  GAGGCCAACG  CGGAGGATGT
5441   GACCTCCCCC  TCGGAGGGCT  AGGCCTAGAA  TCGCTGCCCA  GTACCAGTTG  CCAGTCATCA  CTCCGGTTGC  GCCTCCTACA
                       BamHI
                      -----

V   C   C     S   M   S   Y     S   W   T     G   A   L     V   T   P   C     A   A   E     E   Q   K     L   P   I
+2     CGTGTGCTGC  TCAATGTCTT  ACTCTTGGAC  AGGGCCACTC  GTCACCCCGT  GCGCCGGGA  AGAACAGAAA  CTGCCCATCA
5521   GCACACGACG  AGTTACAGAA  TGAGAACCTG  TCCGCGTGAG  CAGTGGGGCA  CGCGGCCCT  TCTTGTCTTT  GACGGGTAGT

N   A   L   S     N   S   L     L   R   H   H     N   L   V     Y   S   T     T   S   R   S     A   C   Q     R   Q   K
+2     ATGCACTAAG  CAACTCGTTG  CTACGTCACC  GATGCAGTGG  ACAATTTGGT  GTATTCCACC  ACCTCACGCA  GTGCTTGCCA  AAGGCAGAAG
5601   TACGTGATTC  GTTGAGCAAC  GATGCAGTGG  CTACGTCACC  TGTTAAACCA  CATAAGGTGG  TGGAGTGCGT  CACGAACGGT  TTCCGTCTTC

K   V   T   F     D   R   L     Q   V   L     D   S   H   Y     Q   D   V     L   K   E     V   K   A   A     A   S   K
+2     AAAGTCACAT  TTGACAGACT  GCAAGTTCTG  GACAGCCATT  ACCAGGACGT  TGGTCCTGCA  ACTCAAGGAG  GTTAAAGCAG  CGGCGTCAAA
5681   TTTCAGTGTA  AACTGTCTGA  CGTTCAAGAC  CTGTCGGTAA  TGGTCCTGCA  ACCAGGACGT  TGAGTTCCTC  CAATTTCGTC  GCCGCAGTTT

V   K   A     N   L   L   S     V   E   E     A   C   S     L   T   P   P     H   S   A     K   S   K     F   G   Y
+2     AGTGAAGGCT  AACTTGCTAT  CCGTAGAGGA  AGCTTGCAGC  CTGACGCCCC  CACACTCAGC  CAAATCCAGC  TTTGGTTATG
5761   TCACTTCCGA  TTGAACGATA  GGCATCTCCT  TCGAACGTCG  GACTGCGGGG  GTGTGAGTCG  GTTTAGGTTC  AAACCAATAC
```

FIG. 5-10 pCMV-delNS35

```
        G  A  K  D     V  R  C     H  A  R  K     A  V  T     H  I  N     S  V  W  K     D  L  L     E  D  N
  +2  GGGCAAAGA CGTCCGTTGC CATGCCAGAA AGGCCGTAAC CCACATCAAC TCCGTGTGGA AAGACCTTCT GGAAGACAAT
5841  CCCGTTTCT GCAGGCAACG GTACGGTCTT TCCGGCATTG pCMV-delNS35

```
      N  T  L  T  C  Y  I     K  A  R     A  A  C  R  A  A  G     L  Q  D     C  T  M  L     V  C  G
+2 AACACCCTCA CTTGCTACAT CAAGGCCCGG GCAGCCTGTC GAGCCGCAGG GCTCCAGGAC TGCACCATGC TCGTGTGTGG
6401 TTGTGGGAGT GAACGATGTA GTTCCGGGCC CGTCGGACAG CTCGGCGTCC CGAGGTCCTG ACGTGGTACG AGCACACACC

D  D  L     V  V  I  C     E  S  A     G  V  Q     E  D  A  A  S  L  R     A  F  T     E  A  M
+2 CGACGACTTA GTCGTTATCT GTGAAAGCGC GGGGGTCCAG GAGGACGCGG CGAGCCTCAG AGCCTTCACG GAGGCTATGA
6481 GCTGCTGAAT CAGCAATAGA CACTTTCGCG CCCCCAGGTC CTCCTGCGCC GCTCGGACTC TCGGAAGTGC CTCCGATACT

T  R  Y  S     A  P  P     G  D  P  P     Q  P  E     Y  D  L     E  L  I  I  T     S  C  S     S  N  V
+2 CCAGTACTCC CGCCCCCCCT GGGGACCCCC CACAACCAGA ATACGACTTG GAGCTCATAA TCATCATGCT CTCCAACGTG
6561 GGTCATGAGG GCGGGGGGGA CCCCTGGGGG GTGTTGGTCT TATGCTGAAC CTCGAGTATT AGTAGTACGA GAGGTTGCAC

S  V  A  H     D  G  A     G  K  R     V  Y  Y  L     T  R  D     P  T  T     P  L  A  R     A  A  W
+2 TCAGTCGCGC ACGACGGCGC TGGAAAGAGG GTCTACTACC TCACCCGTGA CCCTACAACC CCTCGCGCCA GAGCTGCGTG
6641 AGTCAGCGCG TGCTGCCGCG ACCTTTCTCC CAGATGATGG AGTGGGCACT GGGATGTTGG GGAGCGCGGT CTCGACGCAC

E  T  A     R  H  T  P     V  N  S     W  L  G     N  I  I  M     F  A  P     T  L  W     A  R  M
+2 GGAGACAGCA AGACACACTC CAGTCAATTC CTGGCTAGGC AACATAATCA TGTTTGCCCC CACACTGTGG GCGAGGATGA
6721 CCTCTGTCGT TCTGTGTGAG GTCAGTTAAG GACCGATCCG TTGTATTAGT ACAAACGGGG GTGTGACACC CGCTCCTACT

I  L  M  T     H  F  F     S  V  L  I     A  R  D     Q  L  E     Q  A  L  D     C  E  I     Y  G  A
+2 TACTGATGAC CCATTTCTTT AGGGTCCTTA TAGCCAGGGA CCAGCTTGAA CAGGCCCTCG ATTGCGAGAT CTACGGGGCC
6801 ATGACTACTG GGTAAAGAAA TCGCAGGAAT ATCGGTCCCT GGTCGAACTT GTCCGGGAGC TAACGCTCTA GATGCCCCGG

C  Y  S     I  E  P  L     D  L  P     P  I  I  Q     R  L  H     G  L  S     A  F  S  L  H  S  Y
+2 TGTTACTCCA TAGAACCACT GGATCTACCT CCAATCATTC AAAGACTCCA TGGCCTCAGC GCATTTTCAC TCCACAGTTA
6881 ACGATGAGGT ATCTTGGTGA CCTAGATGGA GGTTAGTAAG TTTCTGAGGT ACCGGAGTCG CGTAAAAGTG AGGTGTCAAT
```

FIG. 5-12 pCMV-delNS35

```
      S  P  G   E  I  N  R   V  A  A   C  L  R   K  L  G   V  P  P  L   R  A  W   R  H  R
+2    CTCTCCAGGT GAAATCAATA GGGTGGCCGC ATGCCTCAGA AAACTTGGGG TACGCCCTT GGGAGCTTGG AGAGACCGGG
6961  GAGAGGTCCA CTTTAGTTAT CCCACCGGCG TACGGAGTCT TTTGAACCCC ATGGCGGGAA CGCTCGAACC TCTGTGCCC

A  R  S  V   R  A  R   L  L  A  R   G  G  R   A  A  I   C  G  K  Y   L  F  N   W  A  V
+2    CCCGGAGCGT CCGCGGCTAGG CTTCTGGCCA GAGGAGGCAG GGCTGCCATA TGTGGCAAGT ACCTCTTCAA CTGGGCAGTA
7041  GGGCCTCGCA GGCGCCGATCC GAAGACCGGT CTCCTCCGTC CCGACGGTAT ACACCGTTCA TGGAGAAGTT GACCCGTCAT

R  T  K  L  T   P  I  A   A  A  G  Q   L  D  L   S  G  W   F  T  A  G   Y  S  G
+2    AGAACAAAGC TCAAACTCAC TCCAATAGCC GCCGCTGGCC AGCTGGACTT GTCCGGCTGG TTCACGGCTG GCTACAGCGG
7121  TCTTGTTTCG AGTTTGAGTG AGGTTATCGG CGGCGACCGG TCGACCTGAA CAGGCCGACC AAGTGCCGAC CGATGTCGCC

G  D  I   Y  H  S  V   S  H  A   R  P  R   W  I  W  F   C  L  L   L  L  A   A  G  V
+2    GGGAGACATT TATCACAGCG TGTCTCATGC CCGGCCCCGC TGGATCTGGT TTTGCCTACT CCTGCTTGCT GCAGGGGTAG
7201  CCCTCTGTAA ATAGTGTCGC ACAGAGTACG GGCCGGGGCG ACCTAGACCA AAACGGATGA GGACGAACGA CGTCCCCATC

G  I  Y  L   L  P  N   R
+2    GCATCTACCT CCTCCCCAAC CGATGAAGGT TGGGTAAAC ACTCCGGCCT AAAAAAAAAA AAAAATCTAG AAAGGCGCGC
7281  CGTAGATGGA GGAGGGGTTG GCTACTTCCA ACCCCATTTG TGAGGCCGGA TTTTTTTTTT TTTTTAGATC TTTCCGCGCG

BamHI       MluI
                        -----       ----
7361  CAAGATATCA AGGATCCACT ACGCGTTAGA GCTCGCTGAT CAGCCTCGAC TGTGCCTTCT AGTTGCCAGC CATCTGTTGT
      GTTCTATAGT TCCTAGGTGA TGCGCAATCT CGAGCGACTA GTCGGAGCTG ACACGGAAGA TCAACGGTCG GTAGACAACA

7441  TTGCCCCTCC CCGTGCCTT CCTTGACCCT GGAAGTGCC ACTCCCACTG TCCTTTCCTA ATAAAATGAG GAAATTGCAT
      AACGGGGAGG GGCACGGAA GGAACTGGGA CCTTCACGG TGAGGGTGAC AGGAAAGGAT TATTTTACTC CTTTAACGTA
```

FIG. 5-13 pCMV-deINS35

```
7521  CGCATTGTCT GAGTAGGTGT CATTCTATTC TGGGGGGTGG GACAGCAAGG GGGAGGATTG GGAAGACAAT
      GCGTAACAGA CTCATCCACA GTAAGATAAG ACCCCCCACC CGACCGTTCC CCCTCCTAAC CCTTCTGTTA

7601  AGCAGGCATG CTGGGGAGCT CTTCCGCTTC GACTCGCTGC GCTCGGTCGT TCGGCTGCGG CGAGCGGTAT
      TCGTCCGTAC GACCCCTCGA GAAGGCGAAG CTGAGCGACG CGAGCCAGCA AGCCGACGCC GCTCGCCATA

7681  CAGCTCACTC AAAGGCGGTA ATACGGTTAT CCACAGAATC AGGGGATAAC GCAGGAAAGA ACATGTGAGC AAAAGGCCAG
      GTCGAGTGAG TTTCCGCCAT TATGCCAATA GGTGTCTTAG TCCCCTATTG CGTCCTTTCT TGTACACTCG TTTTCCGGTC

7761  CAAAAGGCCA GGAACCGTAA AAAGGCCGCG TTGCTGGCGT TTTTCCATAG CTCCGCCCCC CCTGACGAGC ATCACAAAAA
      GTTTTCCGGT CCTTGGCATT TTTCCGGCGC AACGACCGCA AAAAGGTATC GAGGCGGGGG GGACTGCTCG TAGTGTTTTT

7841  TCGACGCTCA AGTCAGAGGT GGCGAAACCC GACAGGACTA TAAAGATACC AGGCGTTTCC CCCTGGAAGC TCCCTCCTGC
      AGCTGCGAGT TCAGTCTCCA CCGCTTTGGG CTGTCCTGAT ATTTCTATGG TCCGCAAAGG GGGACCTTCG AGGGAGCACG

7921  GCTCTCCTGT TCCGACCCTG CCGCTTACCG GATACCTGTC GCCTTTCTC CCTTCGGGAA GCGTGGCGCT TTCTCAATGC
      CGAGAGGACA AGGCTGGGAC GGCGAATGGC CTATGGACAG CGGAAAGAG GGAAGCCCTT CGCACCGCGA AAGAGTTACG

8001  TCACGCTGTA GGTATCTCAG TTCGGTGTAG GTCGTTCGCT CCAAGCTGGG CTGTGTGCAC GAACCCCCCG TTCAGCCCGA
      AGTGCGACAT CCATAGAGTC AAGCCACATC CAGCAAGCGA GGTTCGACCC GACACACGTG CTTGGGGGGC AAGTCGGGCT

8081  CCGCTGCGCC TTATCCGGTA ACTATCGTCT TGAGTCCAAC CCGGTAAGAC ACGACTTATC GCCACTGGCA GCAGCCACTG
      GGCGACGCGG AATAGGCCAT TGATAGCAGA ACTCAGGTTG GGCCATTCTG TGCTGAATAG CGGTGACCGT CGTCGGTGAC

8161  GTAACAGGAT TAGCAGAGCG AGGTATGTAG GCGGTGCTAC AGAGTTCTTG AAGTGGTGGC CTAACTACGG CTACACTAGA
      CATTGTCCTA ATCGTCTCGC TCCATACATC CGCCACGATG TCTCAAGAAC TTCACCACCG GATTGATGCC GATGTGATCT
```

FIG. 5-14 pCMV-delNS35

```
8241  AGGACAGTAT TTGGTATCTG CGCTCTGCTG AAGCCAGTTA CCTTCGGAAA AAGAGTTGGT AGCTCTTGAT CCGGCAAACA
      TCCTGTCATA AACCATAGAC GCGAGACGAC TTCGGTCAAT GGAAGCCTTT TTCTCAACCA TCGAGAACTA GGCCGTTTGT

8321  AACCACCGCT GGTAGCGGTG GTTTTTTTGT TTGCAAGCAG CAGATTACGC GCAGAAAAAA AGGATCTCAA GAAGATCCTT
      TTGGTGGCGA CCATCGCCAC CAAAAAAACA AACGTTCGTC GTCTAATGCG CGTCTTTTTT TCCTAGAGTT CTTCTAGGAA

8401  TGATCTTTTC TACGGGGTCT GACGCTCAGT GGAACGAAAA CTCACGTTAA GGGATTTTGG TCATGAGATT ATCAAAAAGG
      ACTAGAAAAG ATGCCCCAGA CTGCGAGTCA CCTTGCTTTT GAGTGCAATT CCCTAAAACC AGTACTCTAA TAGTTTTTCC

8481  ATCTTCACCT AGATCCTTTT AAATTAAAAA TGAAGTTTTA AATCAATCTA AAGTATATAT GAGTAAACTT GGTCTGACAG
      TAGAAGTGGA TCTAGGAAAA TTTAATTTTT ACTTCAAAAT TTAGTTAGAT TTCATATATA CTCATTTGAA CCAGACTGTC

8561  TTACCAATGC TTAATCAGTG AGGCACCTAT CTCAGCGATC TGTCTATTTC GTTCATCCAT AGTTGCCTGA CTCCCCGTCG
      AATGGTTACG AATTAGTCAC TCCGTGGATA GAGTCGCTAG ACAGATAAAG CAAGTAGGTA TCAACGGACT GAGGGGCAGC

8641  TGTAGATAAC TACGATACGG GAGGGCTTAC CATCTGGCCC CAGTGCTGCA ATGATACCGC GAGACCCACG CTCACCGGCT
      ACATCTATTG ATGCTATGCC CTCCCGAATG GTAGACCGGG GTCACGACGT TACTATGGCG CTCTGGGTGC GAGTGGCCGA

8721  CCAGATTTAT CAGCAATAAA CCAGCCAGCC GGAAGGGCCG AGCGCAGAAG TGGTCCTGCA ACTTTATCCG CCTCCATCCA
      GGTCTAAATA GTCGTTATTT GGTCGGTCGG CCTTCCCGGC TCGCGTCTTC ACCAGGACGT TGAAATAGGC GGAGGTAGGT

8801  GTCTATTAAT TGTTGCCGGG AAGCTAGAGT AAGTAGTTCG CCAGTTAATA GTTTGCGCAA CGTTGTTGCC ATTGCTACAG
      CAGATAATTA ACAACGGCCC TTCGATCTCA TTCATCAAGC GGTCAATTAT CAAACGCGTT GCAACAACGG TAACGATGTC

8881  GCATCGTGGT GTCACGCTCG TCGTTTGGTA TGGCTTCATT CAGCTCCGGT TCCCAACGAT CAAGGCGAGT TACATGATCC
      CGTAGCACCA CAGTGCGAGC AGCAAACCAT ACCGAAGTAA GTCGAGGCCA AGGGTTGCTA GTTCCGCTCA ATGTACTAGG
```

FIG. 5-15 pCMV-delNS35

| | | | | | | |
|---|---|---|---|---|---|---|
| 8961 | CCCATGTTGT GGGTACAACA | GCAAAAAAGC CGTTTTTTCG | GGTTAGCTCC CCAATCGAGG | TTCGGTCCTC AAGCCAGGAG | CGATCGTTGT GCTAGCAACA | CAGAAGTAAG GTCTTCATTC | TTGGCCCGCAG AACCGGGTC | TGTTATCACT ACAATAGTGA |
| 9041 | CATGGTTATG GTACCAATAC | GCAGCACTGC CGTCGTGACG | ATAATTCTCT TATTAAGAGA | TACTGTCATG ATGACAGTAC | CCATCCGTAA GGTAGGCATT | GATGCTTTTC CTACGAAAAG | TGTGACTGGT ACACTGACCA | GAGTACTCAA CTCATGAGTT |
| 9121 | CCAAGTCATT GGTTCAGTAA | CTGAGAATAG GACTCTTATC | TGTATGCGGC ACATACGCCG | GACCGAGTTG CTGGCTCAAC | CTCTTGCCCG GAGAACGGGC | AAACGTTCTT TTTGCAAGAA | CATCATTGGA GTAGTAACCT | CGGGGCGAAA GCCCCGCTTT | ACTCTCAAGG TGAGAGTTCC | CGTTGAGATC ACAACTCTAG |
| 9201 | AGCAGAACTT TCGTCTTGAA | TAAAAGTGCT ATTTTCACGA | CATCATTGGA GTAGTAACCT | GTGCACCCAA CACGTGGGTT | AAAAAGGGAA TTTTTCCCTT | TTATTGTCTC AATAACAGAG | AAGTGCCACC TTCACGGTGG | ACATATTTGA TGTATAAACT | AAAAATAAAC TTTTTATTTG | AAATAGGGGT TTTTATCCCA |
| 9281 | CAGTTCGATG GTCAAGCTAC | TAACCCACTC ATTGGGTGAG | CTGATCTTTA GACTAGAAAT | GCATTCATCA CGTAGAAGAT | CTTTCACCAG GAAAGTGGTC | CGTTTCTGGG GCAAAGACCC | TGAGCAAAAA ACTCGTTTTT |
| 9361 | CAGGAAGGCA GTCCTTCCGT | AAATGCCGCA TTTACGGCGT | AAAAAGGGAA TTTTTCCCTT | TTATTGTCTC AATAACAGAG | ATGAGCGGAT TACTCGCCTA | ACGGAAATGT TGCCTTTACA | ACATATTTGA TGTATAAACT | ATGTATTTAG TACATAAATC | AAAAATAAAC TTTTTATTTG | AAATAGGGGT TTTTATCCCA |
| 9441 | TATTGAAGCA ATAACTTCGT | TTTATCAGGG AAATAGTCCC | TTCCCCGAA AAGGGGCTT | AAGTGCCACC TTCACGGTGG | GAAACCATTA CTTTGGTAAT | CTTTGCAGATT GAATAAATC | ATTAACCTAT TAATTGGATA | AAAAATAGGC TTTTTATCCG |
| 9521 | TCCGCGCACA AGGCGCGTGT | TTTCCCCGAA AAGGGGCTT | AAGTGCCACC TTCACGGTGG | TGACGTCTAA ACTGCAGATT | GAAACCATTA CTTTGGTAAT | CTTTGCAGATT GAATAAATC | ATTAACCTAT TAATTGGATA | AAAAATAGGC TTTTTATCCG |
| 9601 | GTATCACGAG CATAGTGCTC | GCCCTTTCGT CGGGAAAGCA | C G | | | | | |

FIG. 5-16 pCMV-II

```
  1  TCGCGCGTTT CGGTGATGAC GGTGAAAACC TCTGACACAT GCAGCTCCCG GAGACGGTCA CAGCTTGTCT GTAAGCGGAT
     AGCGCGCAAA GCCACTACTG CCACTTTTGG AGACTGTGTA CGTCGAGGGC CTCTGCCAGT GTCGAACAGA CATTCGCCTA

81  GCCGGGAGCA GACAAGCCCG TCAGGGGCGC GTCAGGGGGTG TCGGGGCTGG CTTAACTATG CGGCATCAGA
     CGGCCCTCGT CTGTTCGGGC AGTCCCCGCGC AGTCGCCAC AGCCCCGACC GAATTGATAC GCCGTAGTCT

161  GCAGATTGTA CTGAGAGTGC ACCATATGCG GCTTTTTGCA AAAGCCTAGG CCTCCAAAAA AGCCTCCTCA CTACTTCTGG
     CGTCTAACAT GACTCTCACG TGGTATACTT CGAAAAACGT TTTCGGATCC GGAGGAGT TCGGAGAGT GATGAAGACC

241  AATAGCTCAG AGGCCGAGGC GGCCTCGGCC TCTGCATAAA TAAAAAAAAT ATTTTTTTA TAGTCAGCCA TGGGGCGGGA
     TTATCGAGTC TCCGGCTCCG CCGGAGCCGG AGACGTATTT ATTTTTTTTA TAAAAAAT ATCAGTCGGT ACCCGCCCT

321  ACTGGGGCGG GAGGGAATTA TTGGCTATTG GCCATTGCAT ACGTTGTATC TATATCATAA TATGTACATT TATATTGGCT
     TGACCCCGCC CTCCCTTAAT AACCGATAAC CGGTAACGTA TGCAACATAG ATATAGTATT ATACATGTAA ATATAACCGA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC AAGTCCGCCC ATTGACGTCA ATGGGTGGAG TATTTACGGT
     CTGCAGTTAT TACTGCATAC AAGGGTATCA TTGCGGTTAT CCCTGAAAGG TTCAGGCGGG TAACTGCAGT TACCCACCTC ATAAATGCCA

641  AAACTGCCCA CTTGGCAGTA CATCAAGTGT ATCATATGCC AAGTCCGCCC CCTATTGACG TCAATGACGG TAAATGGCCC
     TTTGACGGGT GAACCGTCAT GTAGTTCACA TAGTATACGG TTCAGGCGGG GGATAACTGC AGTTACTGCC ATTTACCGGG
```

FIG. 7-1 pCMV-II

```
 721  GCCTGGCATT ATGCCCAGTA CATGACCTTA CGGACTTTC CTACTTGGCA GTACATCTAC GTATTAGTCA TCGCTATTAC
      CGGACCGTAA TACGGGTCAT GTACTGGAAT GCCCTGAAAG GATGAACCGT CATGTAGATG CATAATCAGT AGCGATAATG

801  CATGGTGATG CGGTTTTGGC AGTACACCAA TGGGCGTGGA TAGGGCTTTG ACTCACGGGG ATTTCCAAGT CTCCACCCCA
      GTACCACTAC GCCAAAAACCG TCATGTGGTT ACCCGCACCT ATCGCCAAAC TGAGTGCCCC TAAAGGTTCA GAGGTGGGGT

881  TTGACGTCAA TGGGAGTTTG TTTTGGCACC AAAATCAACG GGACTTTCCA AAATGTCGTA ATAACCCCGC CCCGTTGACG
      AACTGCAGTT ACCCTCAAAC AAAACCGTGG TTTTAGTTGC CCTGAAAGGT TTTACAGCAT TATTGGGGCG GGGCAACTGC

961  CAAATGGGCG GTAGGCGTGT ACGGTGGGAG GTCTATATAA GCAGAGCTCG TTTAGTGAAC CGTCAGATCG CCTGGAGACG
      GTTTACCCGC CATCCGCACA TGCCACCCTC CAGATATATT CGTCTCGAGC AAATCACTTG GCAGTCTAGC GGACCTCTGC

1041  CCATCCACGC TGTTTTGACC TCCATAGAAG ACACCGGGAC CGATCCAGCC TCCGGCGGCC GGAACGGTGC ATTGGAACGC
      GGTAGGTGCG ACAAAACTGG AGGTATCTTC TGTGGCCCTG GCTAGGTCGG AGGCCGCCGG CCTTGCCACG TAACCTTGCG

1121  GGATTCCCCG TGCCAAGAGT GACGTAAGTA CCGCCTATAG ACTCTATAGG CACACCCCTT TGGCTCTTAT CCATGCTATA
      CCTAAGGGGC ACGGTTCTCA CTGCATTCAT GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTCA TGGTATAGCT TAGCCTATAG GTGTGGTTA
      GACAAAAACC GAACCCCGGA TATGTGGGGG CGAGGAATAC GATATCCAGT ACCATATCGA ATCGGATATC CACACCCAAT

1281  TTGACCATTA TTGACCACTC CCCTATTGGT GACGATACTT TCCATTACTA ATCCATAACA TGGCTCTTTG CCAACAACTAT
      AACTGGTAAT AACTGGTGAG GGGATAACCA CTGCTATGAA AGGTAATGAT TAGGTATTGT ACCGAGAAAC GGTGTTGATA

1361  CTCTATTGGC TATATGCCAA TACTCTGTCC GACACGGACT TTCAGAGACT ACAGGATGG GTCCATTTAT
      GAGATAACCG ATATACGGTT ATGAGACAGG CTGTGCCTGA AAGTCTCTGA TGTCCTACCC CAGGTAAATA
```

FIG. 7-2 pCMV-II

```
1441  TATTTACAAA TTCACATATA CAACAACGCC GTCCCCCGTG CCCGCAGTTG TTATTAAACA TAGCGTGGGA TCTCCGACAT
      ATAAATGTTT AAGTGTATAT GTTGTTGCGG CAGGGGGCAC GGGCGTCAAC AATAATTTGT ATCGCACCCT AGAGGCTGTA

1521  CTCGGGTACG TGTTCCGGAC ATGGGCTCTT CTCCGTAGC  GGCGGAGCTT CCACATCCGA GCCCTGGTCC CATCCGTCCA
      GAGCCCATGC ACAAGGCCTG TACCCGAGAA GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGTGT CGTGTTACGG GTGGTGGTGG

1681  AGTGTGCCGC ACAAGGCCGT GGCGGTAGGG TATGTGTCTG AAAATGAGCT CGGAGATTGG GCTCCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAAGGG TAACTCCCGT
      CCTTCTGAAT TCCGTCGCCG TCTTCTTCTA CGTCCGTCGA CTCAACAACA TAAGACTATT CTCAGTTCCC ATTGAGGGCA

1841  TGCGGGTGCT TTAACGGTGG AGGGCAGTGT AGTCTGAGCA GTACTCGTTG CTGCCGCGCG CGCCACCAGA CATAATAGCT
      ACGCCCACGAC AATTGCCACC TCCCGTCACA TCAGACTCGT CATGAGCAAC GACGGCGCGC GCGGTGGTCT GTATTATCGA

EcoRI
                                                                              -----
1921  GACAGACTAA CAGACTGTTC CTTTCCATGG GTCTTTTCTG CAGTCACCGT CGTCGACCTA AGAATTCAGA CTCGAGCAAG
      CTGTCTGATT GTCTGACAAG GAAAGGTACC CAGAAAAGAC GTCAGTGGCA GCAGCTGGAT TCTTAAGTCT GAGCTCGTTC

XbaI        BamHI       MluI
      -----       -----       -----
2001  TCTAGAAAGG CGGCCCAAGA TATCAAGGAT CCACTACGCG TTAGAGCTCG CTGATCAGCC TCGACTGTGC CTTCTAGTTG
      AGATCTTTCC GCCGGGTTCT ATAGTTCCTA GGTGATGCGC AATCTCGAGC GACTAGTCGG AGCTGACACG GAAGATCAAC
```

FIG. 7-3 pCMV-II

```
2081  CCAGCCATCT GTTGTTTGCC CCTCCCCCGT GCCTTCCTTG ACCCTGGAAG GTGCCACTCC CACTGTCCTT TCCTAATAAA
      GGTCGGTAGA CAACAAACGG GGAGGGGGCA GGAAGGAAC TGGGACCTTC CACGGTGAGG GTGACAGGAA AGGATTATTT

2161  ATGAGGAAAT TGCATCGCAT TGTCTGAGTA TATTCTGGGG GCTTCCTTCG ACCCTGGAAG GGCAGGACAG CAAGGGGGAG
      TACTCCTTTA ACGTAGCGTA ACAGACTCAT ATAAGACCCC CGAAGGAGCG CCGTTCCTGT CGTCCCCCTC

2241  GATTGGGAAG ACAATAGCAG GCATGCTGGG GAGCTCTTCC GCTTCCTCGC GTTATCCACA GAATCAGGGG ATAACGCAGG AAAGAACATG
      CTAACCCTTC TGTTATCGTC CGTACGACCC CTCGAGAAGG CGAAGGAGCG CAATAGGTGT CTTAGTCCCC TATTGCGTCC TTTCTTGTAC

2321  TGCGGCGAGC GGTATCAGCT CACTCAAAGG CGGTAATACG GTTATCCACA CCGCGTTGCT CATAGGCTCC GCCCCCCTGA
      ACGCCGCTCG CCATAGTCGA GTGAGTTTCC GCCATTATGC CAATAGGTGT GGCGCAACGA GTATCCGAGG CGGGGGGACT

2401  TGAGCAAAAG GCCAGCAAAA GGCCAGGAAC CGTAAAAAGG CCGCGTTGCT CCGCAAAAAG GCCGTTTTTC CATAGGCTCC
      ACTCGTTTTC CGGTCGTTTT CCGGTCCTTG GCATTTTTCC GGCGCAACGA CCGCAAAAAG

2481  CGAGCATCAC AAAAATCGAC GCTCAAGTCA GAGGTGGCGA AACCCGACAG GACTATAAAG ATACCAGGCG TTTCCCCCTG
      GCTCGTAGTG TTTTAGCTG CGAGTTCAGT CTCCACCGCT TTGGGCTGTC CTGATATTTC TATGGTCCGC AAGGGGGAC

2561  GAAGCTCCCT CGTGCGCTCT CCTGTTCCGA CCCTGCCGCT TACCGGATAC CTCAGTTCGG TGTAGGTCGT TCGCTCCAAG
      CTTCGAGGGA GCACGCGAGA GGACAAGGCT GGGACGGCGA ATGGCCTATG GAGTCAAGCC ACATCCAGCA AGCGAGGTTC GACAGGGAAG CCCTTCGCAC

2641  GCGCTTTCTC AATGCTCACG CTGTAGGTAT CTCAGTTCGG TGTAGGTCGT TCGCTCCAAG CTGGGCTGTG TGCACGAACC
      CGCGAAAGAG TTACGAGTGC GACATCCATA GAGTCAAGCC ACATCCAGCA AGCGAGGTTC GACCCGACAC ACGTGCTTGG

2721  CCCCGTTCAG CCCGACCGCT GCGCCTTATC CGGTAACTAT CGTCTTGAGT CCAACCCGGT AAGACACGAC TTATCGCCAC
      GGGGCAAGTC GGGCTGGCGA CGCGGAATAG GCCATTGATA GCAGAACTCA GGTTGGGCCA TTCTGTGCTG AATAGCGGTG
```

FIG. 7-4 pCMV-II

| | | | | | |
|---|---|---|---|---|---|
| 2801 | TGGCAGCAGC ACCGTCGTCG | CACTGGTAAC GTGACCATTG | AGGATTAGCA TCCTAATCGT | GAGGAGGTA CTCGGCTCCAT | TGTAGGCGGT ACATCCGCCA | GCTACAGAGT CGATGTCTCA | TCTTGAAGTG AGAACTTCAC | GTGGCCTAAC CACCGGATTG |
| 2881 | TACGGCTACA ATGCCGATGT | CTAGAAGGAC GATCTTCCTG | AGTATTTGGT TCATAAACCA | ATCTGCGCTC TAGACGCGAG | TGCTGAAGCC ACGACTTCGG | AGTTACCTTC TCAATGGAAG | GGAAAAAGAG CCTTTTTCTC | TTGGTAGCTC AACCATCGAG |
| 2961 | TTGATCCGGC AACTAGGCCG | AAACAAACCA TTTGTTTGGT | CCGCTGGTAG GGCGACCATC | CGGTGGTTTT GCCACCAAAA | TTTGTTTGCA AACAAACGT | AGCAGCAGAT TCGTCGTCTA | TACGGCGAGA ATGCGGCGTCT | AAAAAGGAT TTTTTTCCTA |
| 3041 | CTCAAGAAGA GAGTTCTTCT | TCCTTTGATC AGGAAACTAG | GGTCTGACGC CCAGACTGCG | TCAGTGGAAC AGTCACCTTG | GAAAACTCAC CTTTTGAGTG | GTTAAGGAT CAATTCCCTA | TTTGGTCATG AAACCAGTAC | |
| 3121 | AGATTATCAA TCTAATAGTT | AAAGGATCTT TTTCCTAGAA | CACCTAGATC GTGGATCTAG | CTTTTTAAAT GAAAATTTAA | AAAAATGAAG TTTTTACTTC | TTTTAAATCA AAAATTTAGT | ATCTAAAGTA TAGATTTCAT | TATATGAGTA ATATACTCAT |
| 3201 | AACTTGGTCT TTGAACCAGA | GACAGTTACC CTGTCAATGG | AATGCTTAAT TTACGAATTA | CAGTGAGGCA GTCACTCCGT | CCTATCTCAG GGATAGAGTC | CGATCTGTCT GCTAGACAGA | ATTTCGTTCA TAAAGCAAGT | TCCATAGTTG AGTATCAAC |
| 3281 | CCTGACTCCC GGACTGAGGG | CGTCGTGTAG GCAGCACATC | ATAACTACGA TATTGATGCT | TACGGAGGG ATGCCCTCCC | CTTACCATCT GAATGGTAGA | GGCCCCAGTG CCGGGGTCAC | CTGCAATGAT GACGTTACTA | ACCGCGAGAC TGGCGCTCTG |
| 3361 | CCACGCTCAC GGTGCGAGTG | CGGCTCCAGA GCCGAGGTCT | ATAAACCAGC TATTTGGTCG | CAGCCGGAAG GTCGGCCTTC | GGCCGAGCGC CCGGCTCGCG | AGAAGTGGTC TCTTCACCAG | CTGCAACTTT GACGTTGAAA | |
| 3441 | ATCCGCCTCC TAGGCGGAGG | ATCCAGTCTA TAGGTCAGAT | TTAATTGTTG AATTAACAAC | CCGGGAAGCT GGCCCTTCGA | AGAGTAAGTA TCTCATTCAT | GTTCGCCAGT CAAGCGGTCA | TAATAGTTG ATTATCAAAC | CGCAACGTTG GCGTTGCAAC |

FIG. 7-5 pCMV-II

```
3521  TTGCCATTGC TACAGGCATC GTGGTGTCAC GCTCGTCGTT TGGTATGGCT TCATTCAGCT CCGGTTCCCA ACGATCAAGG
      AACGGTAACG ATGTCCGTAG CACCACAGTG CGAGCAGCAA ACCATACCGA AGTAAGTCGA GGCCAAGGGT TGCTAGTTCC

3601  CGAGTTACAT GATCCCCCAT GTTGTGCAAA AAAGCGGTTA GCTCCTTCGG TCCTCCGATC GTTGTCAGAA GTAAGTTGGC
      GCTCAATGTA CTAGGGGGTA CAACACGTTT TTTCGCCAAT CGAGGAAGCC AGGAGGCTAG CAACAGTCTT CATTCAACCG

3681  CGCAGTGTTA TCACTCATGG TTATGGCAGC ACTGCATAAT TCTCTTACTG TCATGCCATC CGTAAGATGC TTTTCTGTGA
      GCGTCACAAT AGTGAGTACC AATACCGTCG TGACGTATTA AGAGAATGAC AGTACGGTAG GCATTCTACG AAAAGACACT

3761  CTGGTGAGTA CTCAACCAAG TCATTCTGAG AATAGTGTAT GCGGCGACCG AGTTGCTCTT GCCCGGGGTC AATACGGGAT
      GACCACTCAT GAGTTGGTTC AGTAAGACTC TTATCACATA CGCCGCTGGC TCAACGAGAA CGGGCCCCAG TTATGCCCTA

3841  AATACCGCGC CACATAGCAG AACTTTAAAA GTGCTCATCA TTGGAAAACG TTCTTCGGGG CGAAAACTCT CAAGGATCTT
      TTATGGCGCG GTGTATCGTC TTGAAATTTT CACGAGTAGT AACCTTTTGC AAGAAGCCCC GCTTTTGAGA GTTCCTAGAA

3921  ACCGCTGTTG AGATCCAGTT CGATGTAACC CACTCGTGCA CCCAACTGAT CTTCAGCATC TTTTACTTTC ACCAGCGTTT
      TGGCGACAAC TCTAGGTCAA GCTACATTGG GTGAGCACGT GGGTTGACTA GAAGTCGTAG AAAATGAAAG TGGTCGCAAA

4001  CTGGGTGAGC AAAAACAGGA AGGCAAAATG CCGCAAAAAA GGGAATAAGG GCGACACGGA AATGTTGAAT ACTCATACTC
      GACCCACTCG TTTTTGTCCT TCCGTTTTAC GGCGTTTTTT CCCTTATTCC CGCTGTGCCT TTACAACTTA TGAGTATGAG

4081  TTCCTTTTTC AATATTATTG AAGCATTTAT CAGGGTTATT GTCTCATGAG CGGATACATA TTTGAATGTA TTTAGAAAAA
      AAGGAAAAAG TTATAATAAC TTCGTAAATA GTCCCAATAA CAGAGTACTC GCCTATGTAT AAACTTACAT AAATCTTTTT

4161  TAAACAAATA GGGGTTCCGC GCACATTTCC CCGAAAAGTG CCACCTGACG TCTAAGAAAC CATTATTATC ATGACATTAA
      ATTTGTTTAT CCCCAAGGCG CGTGTAAAGG GGCTTTTCAC GGTGGACTGC AGATTCTTTG GTAATAATAG TACTGTAATT

4241  CCTATAAAAA TAGGCGTATC ACGAGGCCCT TTCGTC
      GGATATTTTT ATCCGCATAG TGCTCCGGGA AAGCAG
```

FIG. 7-6 pCMV-NS34A

```
  1  TCGCGCGTTT CGGTGATGAC GGTGAAAACC TCTGACACAT GCAGCTCCCG
     AGCGCGCAAA GCCACTACTG CCACTTTTGG AGACTGTGTA CGTCGAGGGC

51  GAGACGGTCA CAGCTTGTCT GTAAGCGGAT GCCGGGAGCA GACAAGCCCG
     CTCTGCCAGT GTCGAACAGA CATTCGCCTA CGGCCCTCGT CTGTTCGGGC

101  TCAGGGCGCG TCAGCGGGTG TTGGCGGGTG TCGGGGCTGG CTTAACTATG
     AGTCCCGCGC AGTCGCCCAC AACCGCCCAC AGCCCCGACC GAATTGATAC

151  CGGCATCAGA GCAGATTGTA CTGAGAGTGC ACCATATGAA GCTTTTTGCA
     GCCGTAGTCT CGTCTAACAT GACTCTCACG TGGTATACTT CGAAAAACGT

StuI
        -------
201  AAAGCCTAGG CCTCCAAAAA AGCCTCCTCA CTACTTCTGG AATAGCTCAG
     TTTCGGATCC GGAGGTTTTT TCGGAGGAGT GATGAAGACC TTATCGAGTC

251  AGGCCGAGGC GGCCTCGGCC TCTGCATAAA TAAAAAAAAT TAGTCAGCCA
     TCCGGCTCCG CCGGAGCCGG AGACGTATTT ATTTTTTTTA ATCAGTCGGT

301  TGGGGCGGAG AATGGGCGGA ACTGGGCGGG GAGGGAATTA TTGGCTATTG
     ACCCCGCCTC TTACCCGCCT TGACCCGCCC CTCCCTTAAT AACCGATAAC

351  GCCATTGCAT ACGTTGTATC TATATCATAA TATGTACATT TATATTGGCT
     CGGTAACGTA TGCAACATAG ATATAGTATT ATACATGTAA ATATAACCGA

401  CATGTCCAAT ATGACCGCCA TGTTGACATT GATTATTGAC TAGTTATTAA
     GTACAGGTTA TACTGGCGGT ACAACTGTAA CTAATAACTG ATCAATAATT

451  TAGTAATCAA TTACGGGGTC ATTAGTTCAT AGCCCATATA TGGAGTTCCG
     ATCATTAGTT AATGCCCCAG TAATCAAGTA TCGGGTATAT ACCTCAAGGC

501  CGTTACATAA CTTACGGTAA ATGGCCCGCC TGGCTGACCG CCCAACGACC
     GCAATGTATT GAATGCCATT TACCGGGCGG ACCGACTGGC GGGTTGCTGG

551  CCCGCCCATT GACGTCAATA ATGACGTATG TTCCCATAGT AACGCCAATA
     GGGCGGGTAA CTGCAGTTAT TACTGCATAC AAGGGTATCA TTGCGGTTAT

601  GGGACTTTCC ATTGACGTCA ATGGGTGGAG TATTTACGGT AAACTGCCCA
     CCCTGAAAGG TAACTGCAGT TACCCACCTC ATAAATGCCA TTTGACGGGT

651  CTTGGCAGTA CATCAAGTGT ATCATATGCC AAGTCCGCCC CCTATTGACG
     GAACCGTCAT GTAGTTCACA TAGTATACGG TTCAGGCGGG GGATAACTGC

701  TCAATGACGG TAAATGGCCC GCCTGGCATT ATGCCCAGTA CATGACCTTA
     AGTTACTGCC ATTTACCGGG CGGACCGTAA TACGGGTCAT GTACTGGAAT

751  CGGGACTTTC CTACTTGGCA GTACATCTAC GTATTAGTCA TCGCTATTAC
     GCCCTGAAAG GATGAACCGT CATGTAGATG CATAATCAGT AGCGATAATG

801  CATGGTGATG CGGTTTTGGC AGTACACCAA TGGGCGTGGA TAGCGGTTTG
     GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
     TGAGTGCCCC TAAAGGTTCA GAGGTGGGGT AACTGCAGTT ACCCTCAAAC
```

FIG. 9-1 pCMV-NS34A

```
 901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG

1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGGAACGC GGATTCCCCG TGCCAAGAGT GACGTAAGTA
      CCTTGCCACG TAACCTTGCG CCTAAGGGGC ACGGTTCTCA CTGCATTCAT

1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT

1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT

1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT

1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA

1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA

1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC
```

FIG. 9-2 pCMV-NS34A

```
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC
```

```
      +2                                                    M  A  P
                                          EcoRI
1951  GTCTTTTCTG CAGTCACCGT CGTCGACCTA AGAATTCACC ATGGCGCCCA
      CAGAAAAGAC GTCAGTGGCA GCAGCTGGAT TCTTAAGTGG TACCGCGGGT
```

```
      +2  I  T  A  Y   A  Q  Q    T  R  G  L   L  G  C   I  I  T
2001  TCACGGCGTA CGCCCAGCAG ACAAGGGGCC TCCTAGGGTG CATAATCACC
      AGTGCCGCAT GCGGGTCGTC TGTTCCCCGG AGGATCCCAC GTATTAGTGG
```

```
      +2  S  L  T  G   R  D  K   N  Q  V   E  G  E  V   Q  I  V
2051  AGCCTAACTG GCCGGGACAA AAACCAAGTG GAGGGTGAGG TCCAGATTGT
      TCGGATTGAC CGGCCCTGTT TTTGGTTCAC CTCCCACTCC AGGTCTAACA
```

```
      +2  S  T  A   A  Q  T  F   L  A  T   C  I  N   G  V  C
2101  GTCAACTGCT GCCCAAACCT TCCTGGCAAC GTGCATCAAT GGGGTGTGCT
      CAGTTGACGA CGGGTTTGGA AGGACCGTTG CACGTAGTTA CCCCACACGA
```

```
      +2  W  T  V  Y   H  G  A   G  T  R  T   I  A  S   P  K  G
2151  GGACTGTCTA CCACGGGGCC GGAACGAGGA CCATCGCGTC ACCCAAGGGT
      CCTGACAGAT GGTGCCCCGG CCTTGCTCCT GGTAGCGCAG TGGGTTCCCA
```

```
      +2  P  V  I  Q   M  Y  T   N  V  D   Q  D  L  V   G  W  P
2201  CCTGTCATCC AGATGTATAC CAATGTAGAC CAAGACCTTG TGGGCTGGCC
      GGACAGTAGG TCTACATATG GTTACATCTG GTTCTGGAAC ACCCGACCGG
```

```
      +2  A  S  Q   G  T  R  S   L  T  P   C  T  C   G  S  S
2251  CGCTTCGCAA GGTACCCGCT CATTGACACC CTGCACTTGC GGCTCCTCGG
      GCGAAGCGTT CCATGGGCGA GTAACTGTGG GACGTGAACG CCGAGGAGCC
```

```
      +2  D  L  Y  L   V  T  R   H  A  D  V   I  P  V   R  R  R
2301  ACCTTTACCT GGTCACGAGG CACGCCGATG TCATTCCCGT GCGCCGGCGG
      TGGAAATGGA CCAGTGCTCC GTGCGGCTAC AGTAAGGGCA CGCGGCCGCC
```

```
      +2  G  D  S  R   G  S  L   L  S  P   R  P  I  S   Y  L  K
2351  GGTGATAGCA GGGGCAGCCT GCTGTCGCCC CGGCCCATTT CCTACTTGAA
      CCACTATCGT CCCCGTCGGA CGACAGCGGG GCCGGGTAAA GGATGAACTT
```

```
      +2  G  S  S   G  G  P  L   L  C  P   A  G  H   A  V  G
2401  AGGCTCCTCG GGGGGTCCGC TGTTGTGCCC CGCGGGGCAC GCCGTGGGCA
      TCCGAGGAGC CCCCCAGGCG ACAACACGGG GCGCCCCGTG CGGCACCCGT
```

```
      +2  I  F  R  A   A  V  C   T  R  G  V   A  K  A   V  D  F
2451  TATTTAGGGC CGCGGTGTGC ACCCGTGGAG TGGCTAAGGC GGTGGACTTT
      ATAAATCCCG GCGCCACACG TGGGCACCTC ACCGATTCCG CCACCTGAAA
```

```
      +2  I  P  V  E   N  L  E   T  T  M   R  S  P  V   F  T  D
2501  ATCCCTGTGG AGAACCTAGA GACAACCATG AGGTCCCCGG TGTTCACGGA
      TAGGGACACC TCTTGGATCT CTGTTGGTAC TCCAGGGGCC ACAAGTGCCT
```

FIG. 9-3 pCMV-NS34A

```
     +2  N   S   S     P   P   V   V     P   Q   S     F   Q   V     A   H   L
2551    TAACTCCTCT    CCACCAGTAG    TGCCCCAGAG    CTTCCAGGTG    GCTCACCTCC
        ATTGAGGAGA    GGTGGTCATC    ACGGGGTCTC    GAAGGTCCAC    CGAGTGGAGG

+2  H   A   P   T     G   S   G     K   S   T   K     V   P   A     A   Y   A
2601    ATGCTCCCAC    AGGCAGCGGC    AAAAGCACCA    AGGTCCCGGC    TGCATATGCA
        TACGAGGGTG    TCCGTCGCCG    TTTTCGTGGT    TCCAGGGCCG    ACGTATACGT

+2  A   Q   G     Y   K   V   L     V   L   N     P   S   V     A   A   T   L
2651    GCTCAGGGCT    ATAAGGTGCT    AGTACTCAAC    CCCTCTGTTG    CTGCAACACT
        CGAGTCCCGA    TATTCCACGA    TCATGAGTTG    GGGAGACAAC    GACGTTGTGA

+2  G   F   G     A   Y   M   S     K   A   H     G   I   D     P   N   I
2701    GGGCTTTGGT    GCTTACATGT    CCAAGGCTCA    TGGGATCGAT    CCTAACATCA
        CCCGAAACCA    CGAATGTACA    GGTTCCGAGT    ACCCTAGCTA    GGATTGTAGT

+2  R   T   G   V     R   T   I     T   T   G   S     P   I   T     Y   S   T
2751    GGACCGGGGT    GAGAACAATT    ACCACTGGCA    GCCCCATCAC    GTACTCCACC
        CCTGGCCCCA    CTCTTGTTAA    TGGTGACCGT    CGGGGTAGTG    CATGAGGTGG

+2  Y   G   K   F     L   A   D     G   G   C     S   G   G     A   Y   D   I
2801    TACGGCAAGT    TCCTTGCCGA    CGGCGGGTGC    TCGGGGGGCG    CTTATGACAT
        ATGCCGTTCA    AGGAACGGCT    GCCGCCCACG    AGCCCCCGC     GAATACTGTA

+2  I   I   C     D   E   C   H     S   T   D     A   T   S     I   L   G
2851    AATAATTTGT    GACGAGTGCC    ACTCCACGGA    TGCCACATCC    ATCTTGGGCA
        TTATTAAACA    CTGCTCACGG    TGAGGTGCCT    ACGGTGTAGG    TAGAACCCGT

+2  I   G   T   V     L   D   Q     A   E   T     A   G   A   R     L   V   V
2901    TTGGCACTGT    CCTTGACCAA    GCAGAGACTG    CGGGGGCGAG    ACTGGTTGTG
        AACCGTGACA    GGAACTGGTT    CGTCTCTGAC    GCCCCCGCTC    TGACCAACAC

+2  L   A   T   A     T   P   P     G   S   V     T   V   P   H     P   N   I
2951    CTCGCCACCG    CCACCCCTCC    GGGCTCCGTC    ACTGTGCCCC    ATCCCAACAT
        GAGCGGTGGC    GGTGGGGAGG    CCCGAGGCAG    TGACACGGGG    TAGGGTTGTA

+2  E   E   V     A   L   S   T     T   G   E     I   P   F     Y   G   K
3001    CGAGGAGGTT    GCTCTGTCCA    CCACCGGAGA    GATCCCTTTT    TACGGCAAGG
        GCTCCTCCAA    CGAGACAGGT    GGTGGCCTCT    CTAGGGAAAA    ATGCCGTTCC

+2  A   I   P   L     E   V   I     K   G   G   R     H   L   I     F   C   H
3051    CTATCCCCCT    CGAAGTAATC    AAGGGGGGGA    GACATCTCAT    CTTCTGTCAT
        GATAGGGGGA    GCTTCATTAG    TTCCCCCCCT    CTGTAGAGTA    GAAGACAGTA

+2  S   K   K   K     C   D   E     L   A   A     K   L   V     A   L   G   I
3101    TCAAAGAAGA    AGTGCGACGA    ACTCGCCGCA    AAGCTGGTCG    CATTGGGCAT
        AGTTTCTTCT    TCACGCTGCT    TGAGCGGCGT    TTCGACCAGC    GTAACCCGTA

+2  N   A   V     A   Y   Y   R     G   L   D     V   S   V     I   P   T
3151    CAATGCCGTG    GCCTACTACC    GCGGTCTTGA    CGTGTCCGTC    ATCCCGACCA
        GTTACGGCAC    CGGATGATGG    CGCCAGAACT    GCACAGGCAG    TAGGGCTGGT

+2  S   G   D   V     V   V   V     A   T   D   A     L   M   T     G   Y   T
3201    GCGGCGATGT    TGTCGTCGTG    GCAACCGATG    CCCTCATGAC    CGGCTATACC
        CGCCGCTACA    ACAGCAGCAC    CGTTGGCTAC    GGGAGTACTG    GCCGATATGG
```

FIG. 9-4 pCMV-NS34A

```
     +2  G   D   F     D   S   V   I     D   C   N     T   C   V   T     Q   T   V
3251     GGCGACTTCG  ACTCGGTGAT  AGACTGCAAT  ACGTGTGTCA  CCCAGACAGT
         CCGCTGAAGC  TGAGCCACTA  TCTGACGTTA  TGCACACAGT  GGGTCTGTCA

+2  D   F   S     L   D   P   T     F   T   I     E   T   I     T   L   P
3301     CGATTTCAGC  CTTGACCCTA  CCTTCACCAT  TGAGACAATC  ACGCTCCCCC
         GCTAAAGTCG  GAACTGGGAT  GGAAGTGGTA  ACTCTGTTAG  TGCGAGGGGG

+2  Q   D   A   V     S   R   T     Q   R   R   G     R   T   G     R   G   K
3351     AAGATGCTGT  CTCCCGCACT  CAACGTCGGG  GCAGGACTGG  CAGGGGGAAG
         TTCTACGACA  GAGGGCGTGA  GTTGCAGCCC  CGTCCTGACC  GTCCCCCTTC

+2  P   G   I   Y     R   F   V     A   P   G     E   R   P     S   G   M   F
3401     CCAGGCATCT  ACAGATTTGT  GGCACCGGGG  GAGCGCCCCT  CCGGCATGTT
         GGTCCGTAGA  TGTCTAAACA  CCGTGGCCCC  CTCGCGGGGA  GGCCGTACAA

+2  D   S   S     V   L   C   E     C   Y   D     A   G   C     A   W   Y
3451     CGACTCGTCC  GTCCTCTGTG  AGTGCTATGA  CGCAGGCTGT  GCTTGGTATG
         GCTGAGCAGG  CAGGAGACAC  TCACGATACT  GCGTCCGACA  CGAACCATAC

+2  E   L   T   P     A   E   T     T   V   R   L     R   A   Y     M   N   T
3501     AGCTCACGCC  CGCCGAGACT  ACAGTTAGGC  TACGAGCGTA  CATGAACACC
         TCGAGTGCGG  GCGGCTCTGA  TGTCAATCCG  ATGCTCGCAT  GTACTTGTGG

+2  P   G   L   P     V   C   Q     D   H   L     E   F   W     E   G   V   F
3551     CCGGGGCTTC  CCGTGTGCCA  GGACCATCTT  GAATTTTGGG  AGGGCGTCTT
         GGCCCCGAAG  GGCACACGGT  CCTGGTAGAA  CTTAAAACCC  TCCCGCAGAA

+2      T   G   L     T   H   I   D     A   H   F     L   S   Q     T   K   Q
             StuI
             ------
3601     TACAGGCCTC  ACTCATATAG  ATGCCCACTT  TCTATCCCAG  ACAAAGCAGA
         ATGTCCGGAG  TGAGTATATC  TACGGGTGAA  AGATAGGGTC  TGTTTCGTCT

+2  S   G   E   N     L   P   Y     L   V   A   Y     Q   A   T     V   C   A
3651     GTGGGGAGAA  CCTTCCTTAC  CTGGTAGCGT  ACCAAGCCAC  CGTGTGCGCT
         CACCCCTCTT  GGAAGGAATG  GACCATCGCA  TGGTTCGGTG  GCACACGCGA

+2  R   A   Q   A     P   P   P     S   W   D     Q   M   W     K   C   L   I
3701     AGGGCTCAAG  CCCCTCCCCC  ATCGTGGGAC  CAGATGTGGA  AGTGTTTGAT
         TCCCGAGTTC  GGGGAGGGGG  TAGCACCCTG  GTCTACACCT  TCACAAACTA

+2  R   L   K     P   T   L   H     G   P   T     P   L   L     Y   R   L
3751     TCGCCTCAAG  CCCACCCTCC  ATGGGCCAAC  ACCCTGCTA   TACAGACTGG
         AGCGGAGTTC  GGGTGGGAGG  TACCCGGTTG  TGGGACGAT   ATGTCTGACC

+2  G   A   V   Q     N   E   I     T   L   T   H     P   V   T     K   Y   I
3801     GCGCTGTTCA  GAATGAAATC  ACCCTGACGC  ACCCAGTCAC  CAAATACATC
         CGCGACAAGT  CTTACTTTAG  TGGGACTGCG  TGGGTCAGTG  GTTTATGTAG

+2  M   T   C   M     S   A   D     L   E   V     T   S   T     W   V   L
3851     ATGACATGCA  TGTCGGCCGA  CCTGGAGGTC  GTCACGAGCA  CCTGGGTGCT
         TACTGTACGT  ACAGCCGGCT  GGACCTCCAG  CAGTGCTCGT  GGACCCACGA

+2  V   G   G     V   L   A   A     L   A   A     Y   C   L     S   T   G
3901     CGTTGGCGGC  GTCCTGGCTG  CTTTGGCCGC  GTATTGCCTG  TCAACAGGCT
         GCAACCGCCG  CAGGACCGAC  GAAACCGGCG  CATAACGGAC  AGTTGTCCGA
```

FIG. 9-5 pCMV-NS34A

```
      +2  C   V   V   I     V   G   R     V   V   L   S     G   K   P     A   I   I
3951      GCGTGGTCAT AGTGGGCAGG GTCGTCTTGT CCGGGAAGCC GGCAATCATA
          CGCACCAGTA TCACCCGTCC CAGCAGAACA GGCCCTTCGG CCGTTAGTAT

+2  P   D   R   E     V   L   Y     R   E   F     D   E   H   E     E   C
4001      CCTGACAGGG AAGTCCTCTA CCGAGAGTTC GATGAGATGG AAGAGTGCTA
          GGACTGTCCC TTCAGGAGAT GGCTCTCAAG CTACTCTACC TTCTCACGAT

BamHI     MluI
              -----     -----
4051      GGATCCACTA CGCGTTAGAG CTCGCTGATC AGCCTCGACT GTGCCTTCTA
          CCTAGGTGAT GCGCAATCTC GAGCGACTAG TCGGAGCTGA CACGGAAGAT

4101      GTTGCCAGCC ATCTGTTGTT TGCCCCTCCC CCGTGCCTTC CTTGACCCTG
          CAACGGTCGG TAGACAACAA ACGGGGAGGG GGCACGGAAG GAACTGGGAC

4151      GAAGGTGCCA CTCCCACTGT CCTTTCCTAA TAAAATGAGG AAATTGCATC
          CTTCCACGGT GAGGGTGACA GGAAAGGATT ATTTTACTCC TTTAACGTAG

4201      GCATTGTCTG AGTAGGTGTC ATTCTATTCT GGGGGGTGGG GTGGGGCAGG
          CGTAACAGAC TCATCCACAG TAAGATAAGA CCCCCCACCC CACCCCGTCC

4251      ACAGCAAGGG GGAGGATTGG GAAGACAATA GCAGGCATGC TGGGGAGCTC
          TGTCGTTCCC CCTCCTAACC CTTCTGTTAT CGTCCGTACG ACCCCTCGAG

4301      TTCCGCTTCC TCGCTCACTG ACTCGCTGCG CTCGGTCGTT CGGCTGCGGC
          AAGGCGAAGG AGCGAGTGAC TGAGCGACGC GAGCCAGCAA GCCGACGCCG

4351      GAGCGGTATC AGCTCACTCA AAGGCGGTAA TACGGTTATC CACAGAATCA
          CTCGCCATAG TCGAGTGAGT TTCCGCCATT ATGCCAATAG GTGTCTTAGT

4401      GGGGATAACG CAGGAAAGAA CATGTGAGCA AAAGGCCAGC AAAAGGCCAG
          CCCCTATTGC GTCCTTTCTT GTACACTCGT TTTCCGGTCG TTTTCCGGTC

4451      GAACCGTAAA AAGGCCGCGT TGCTGGCGTT TTTCCATAGG CTCCGCCCCC
          CTTGGCATTT TTCCGGCGCA ACGACCGCAA AAAGGTATCC GAGGCGGGGG

4501      CTGACGAGCA TCACAAAAAT CGACGCTCAA GTCAGAGGTG GCGAAACCCG
          GACTGCTCGT AGTGTTTTTA GCTGCGAGTT CAGTCTCCAC CGCTTTGGGC

4551      ACAGGACTAT AAAGATACCA GGCGTTTCCC CCTGGAAGCT CCCTCGTGCG
          TGTCCTGATA TTTCTATGGT CCGCAAAGGG GGACCTTCGA GGGAGCACGC

4601      CTCTCCTGTT CCGACCCTGC CGCTTACCGG ATACCTGTCC GCCTTTCTCC
          GAGAGGACAA GGCTGGGACG GCGAATGGCC TATGGACAGG CGGAAAGAGG

4651      CTTCGGGAAG CGTGGCGCTT TCTCAATGCT CACGCTGTAG GTATCTCAGT
          GAAGCCCTTC GCACCGCGAA AGAGTTACGA GTGCGACATC CATAGAGTCA

4701      TCGGTGTAGG TCGTTCGCTC CAAGCTGGGC TGTGTGCACG AACCCCCCGT
          AGCCACATCC AGCAAGCGAG GTTCGACCCG ACACACGTGC TTGGGGGGCA

4751      TCAGCCCGAC CGCTGCGCCT TATCCGGTAA CTATCGTCTT GAGTCCAACC
          AGTCGGGCTG GCGACGCGGA ATAGGCCATT GATAGCAGAA CTCAGGTTGG

4801      CGGTAAGACA CGACTTATCG CCACTGGCAG CAGCCACTGG TAACAGGATT
          GCCATTCTGT GCTGAATAGC GGTGACCGTC GTCGGTGACC ATTGTCCTAA
```

FIG. 9-6 pCMV-NS34A

```
4851  AGCAGAGCGA GGTATGTAGG CGGTGCTACA GAGTTCTTGA AGTGGTGGCC
      TCGTCTCGCT CCATACATCC GCCACGATGT CTCAAGAACT TCACCACCGG

4901  TAACTACGGC TACACTAGAA GGACAGTATT TGGTATCTGC GCTCTGCTGA
      ATTGATGCCG ATGTGATCTT CCTGTCATAA ACCATAGACG CGAGACGACT

4951  AGCCAGTTAC CTTCGGAAAA AGAGTTGGTA GCTCTTGATC CGGCAAACAA
      TCGGTCAATG GAAGCCTTTT TCTCAACCAT CGAGAACTAG GCCGTTTGTT

5001  ACCACCGCTG GTAGCGGTGG TTTTTTTGTT TGCAAGCAGC AGATTACGCG
      TGGTGGCGAC CATCGCCACC AAAAAAACAA ACGTTCGTCG TCTAATGCGC

5051  CAGAAAAAAA GGATCTCAAG AAGATCCTTT GATCTTTTCT ACGGGGTCTG
      GTCTTTTTTT CCTAGAGTTC TTCTAGGAAA CTAGAAAAGA TGCCCCAGAC

5101  ACGCTCAGTG GAACGAAAAC TCACGTTAAG GGATTTTGGT CATGAGATTA
      TGCGAGTCAC CTTGCTTTTG AGTGCAATTC CCTAAAACCA GTACTCTAAT

5151  TCAAAAAGGA TCTTCACCTA GATCCTTTTA AATTAAAAAT GAAGTTTTAA
      AGTTTTTCCT AGAAGTGGAT CTAGGAAAAT TTAATTTTTA CTTCAAAATT

5201  ATCAATCTAA AGTATATATG AGTAAACTTG GTCTGACAGT TACCAATGCT
      TAGTTAGATT TCATATATAC TCATTTGAAC CAGACTGTCA ATGGTTACGA

5251  TAATCAGTGA GGCACCTATC TCAGCGATCT GTCTATTTCG TTCATCCATA
      ATTAGTCACT CCGTGGATAG AGTCGCTAGA CAGATAAAGC AAGTAGGTAT

5301  GTTGCCTGAC TCCCCGTCGT GTAGATAACT ACGATACGGG AGGGCTTACC
      CAACGGACTG AGGGGCAGCA CATCTATTGA TGCTATGCCC TCCCGAATGG

5351  ATCTGGCCCC AGTGCTGCAA TGATACCGCG AGACCCACGC TCACCGGCTC
      TAGACCGGGG TCACGACGTT ACTATGGCGC TCTGGGTGCG AGTGGCCGAG

5401  CAGATTTATC AGCAATAAAC CAGCCAGCCG GAAGGGCCGA GCGCAGAAGT
      GTCTAAATAG TCGTTATTTG GTCGGTCGGC CTTCCCGGCT CGCGTCTTCA

5451  GGTCCTGCAA CTTTATCCGC CTCCATCCAG TCTATTAATT GTTGCCGGGA
      CCAGGACGTT GAAATAGGCG GAGGTAGGTC AGATAATTAA CAACGGCCCT

5501  AGCTAGAGTA AGTAGTTCGC CAGTTAATAG TTTGCGCAAC GTTGTTGCCA
      TCGATCTCAT TCATCAAGCG GTCAATTATC AAACGCGTTG CAACAACGGT

5551  TTGCTACAGG CATCGTGGTG TCACGCTCGT CGTTTGGTAT GGCTTCATTC
      AACGATGTCC GTAGCACCAC AGTGCGAGCA GCAAACCATA CCGAAGTAAG

5601  AGCTCCGGTT CCCAACGATC AAGGCGAGTT ACATGATCCC CCATGTTGTG
      TCGAGGCCAA GGGTTGCTAG TTCCGCTCAA TGTACTAGGG GGTACAACAC

5651  CAAAAAAGCG GTTAGCTCCT TCGGTCCTCC GATCGTTGTC AGAAGTAAGT
      GTTTTTTCGC CAATCGAGGA AGCCAGGAGG CTAGCAACAG TCTTCATTCA

5701  TGGCCGCAGT GTTATCACTC ATGGTTATGG CAGCACTGCA TAATTCTCTT
      ACCGGCGTCA CAATAGTGAG TACCAATACC GTCGTGACGT ATTAAGAGAA

5751  ACTGTCATGC CATCCGTAAG ATGCTTTTCT GTGACTGGTG AGTACTCAAC
      TGACAGTACG GTAGGCATTC TACGAAAAGA CACTGACCAC TCATGAGTTG
```

FIG. 9-7 pCMV-NS34A

```
5801   CAAGTCATTC TGAGAATAGT GTATGCGGCG ACCGAGTTGC TCTTGCCCGG
       GTTCAGTAAG ACTCTTATCA CATACGCCGC TGGCTCAACG AGAACGGGCC

5851   CGTCAATACG GGATAATACC GCGCCACATA GCAGAACTTT AAAAGTGCTC
       GCAGTTATGC CCTATTATGG CGCGGTGTAT CGTCTTGAAA TTTTCACGAG

5901   ATCATTGGAA AACGTTCTTC GGGGCGAAAA CTCTCAAGGA TCTTACCGCT
       TAGTAACCTT TTGCAAGAAG CCCCGCTTTT GAGAGTTCCT AGAATGGCGA

5951   GTTGAGATCC AGTTCGATGT AACCCACTCG TGCACCCAAC TGATCTTCAG
       CAACTCTAGG TCAAGCTACA TTGGGTGAGC ACGTGGGTTG ACTAGAAGTC

6001   CATCTTTTAC TTTCACCAGC GTTTCTGGGT GAGCAAAAAC AGGAAGGCAA
       GTAGAAAATG AAAGTGGTCG CAAAGACCCA CTCGTTTTTG TCCTTCCGTT

6051   AATGCCGCAA AAAAGGGAAT AAGGGCGACA CGGAAATGTT GAATACTCAT
       TTACGGCGTT TTTTCCCTTA TTCCCGCTGT GCCTTTACAA CTTATGAGTA

6101   ACTCTTCCTT TTTCAATATT ATTGAAGCAT TTATCAGGGT TATTGTCTCA
       TGAGAAGGAA AAAGTTATAA TAACTTCGTA AATAGTCCCA ATAACAGAGT

6151   TGAGCGGATA CATATTTGAA TGTATTTAGA AAAATAAACA AATAGGGGTT
       ACTCGCCTAT GTATAAACTT ACATAAATCT TTTTATTTGT TTATCCCCAA

6201   CCGCGCACAT TTCCCCGAAA AGTGCCACCT GACGTCTAAG AAACCATTAT
       GGCGCGTGTA AAGGGGCTTT TCACGGTGGA CTGCAGATTC TTTGGTAATA

6251   TATCATGACA TTAACCTATA AAAATAGGCG TATCACGAGG CCCTTTCGTC
       ATAGTACTGT AATTGGATAT TTTTATCCGC ATAGTGCTCC GGGAAAGCAG
```

FIG. 9-8

```
                                    MetAlaAlaTyrAlaAlaGlnGlyTyrLysValLeuVal
  2  AGCTTACAAAACAAATTCACCATGGCTGCATATGCAGCTCAGGGCTATAAGGTGCTAGTA
     TCGAATGTTTTGTTTAAGTGGTACCGACGTATACGTCGAGTCCCGATATTCCACGATCAT
     ^          ^        ^                ^
     1 HIND3,  21 NCOI, 30 NDEI,         58 SCAI,

LeuAsnProSerValAlaAlaThrLeuGlyPheGlyAlaTyrMetSerLysAlaHisGly
 62  CTCAACCCCTCTGTTGCTGCAACACTGGGCTTTGGTGCTTACATGTCCAAGGCTCATGGG
     GAGTTGGGGAGACAACGACGTTGTGACCCGAAACCACGAATGTACAGGTTCCGAGTACCC

IleAspProAsnIleArgThrGlyValArgThrIleThrThrGlySerProIleThrTyr
122  ATCGATCCTAACATCAGGACCGGGGTGAGAACAATTACCACTGGCAGCCCCATCACGTAC
     TAGCTAGGATTGTAGTCCTGGCCCCACTCTTGTTAATGGTGACCGTCGGGGTAGTGCATG
     ^
     122 CLAI,

SerThrTyrGlyLysPheLeuAlaAspGlyGlyCysSerGlyGlyAlaTyrAspIleIle
182  TCCACCTACGGCAAGTTCCTTGCCGACGGCGGGTGCTCGGGGGGCGCTTATGACATAATA
     AGGTGGATGCCGTTCAAGGAACGGCTGCCGCCCACGAGCCCCCCGCGAATACTGTATTAT

IleCysAspGluCysHisSerThrAspAlaThrSerIleLeuGlyIleGlyThrValLeu
242  ATTTGTGACGAGTGCCACTCCACGGATGCCACATCCATCTTGGGCATTGGCACTGTCCTT
     TAAACACTGCTCACGGTGAGGTGCCTACGGTGTAGGTAGAACCCGTAACCGTGACAGGAA

AspGlnAlaGluThrAlaGlyAlaArgLeuValValLeuAlaThrAlaThrProProGly
302  GACCAAGCAGAGACTGCGGGGGCGAGACTGGTTGTGCTCGCCACCGCCACCCCTCCGGGC
     CTGGTTCGTCTCTGACGCCCCCGCTCTGACCAACACGAGCGGTGGCGGTGGGGAGGCCCG
                  ^
     309 ALWN1,

SerValThrValProHisProAsnIleGluGluValAlaLeuSerThrThrGlyGluIle
362  TCCGTCACTGTGCCCCATCCCAACATCGAGGAGGTTGCTCTGTCCACCACCGGAGAGATC
     AGGCAGTGACACGGGGTAGGGTTGTAGCTCCTCCAACGAGACAGGTGGTGGCCTCTCTAG

ProPheTyrGlyLysAlaIleProLeuGluValIleLysGlyGlyArgHisLeuIlePhe
422  CCTTTTTACGGCAAGGCTATCCCCCTCGAAGTAATCAAGGGGGGGAGACATCTCATCTTC
     GGAAAAATGCCGTTCCGATAGGGGGAGCTTCATTAGTTCCCCCCCTCTGTAGAGTAGAAG

CysHisSerLysLysLysCysAspGluLeuAlaAlaLysLeuValAlaLeuGlyIleAsn
482  TGTCATTCAAAGAAGAAGTGCGACGAACTCGCCGCAAAGCTGGTCGCATTGGGCATCAAT
     ACAGTAAGTTTCTTCTTCACGCTGCTTGAGCGGCGTTTCGACCAGCGTAACCCGTAGTTA

AlaValAlaTyrTyrArgGlyLeuAspValSerValIleProThrSerGlyAspValVal
542  GCCGTGGCCTACTACCGCGGTCTTGACGTGTCCGTCATCCCGACCAGCGGCGATGTTGTC
     CGGCACCGGATGATGGCGCCAGAACTGCACAGGCAGTAGGGCTGGTCGCCGCTACAACAG
                     ^          ^
     556 SAC2,      566 DRD1,

ValValAlaThrAspAlaLeuMetThrGlyTyrThrGlyAspPheAspSerValIleAsp
602  GTCGTGGCAACCGATGCCCTCATGACCGGCTATACCGGCGACTTCGACTCGGTGATAGAC
     CAGCACCGTTGGCTACGGGAGTACTGGCCGATATGGCCGCTGAAGCTGAGCCACTATCTG
                                                   ^
     621 BSPH1,

CysAsnThrCysValThrGlnThrValAspPheSerLeuAspProThrPheThrIleGlu
```

FIG. 11-1

```
662  TGCAATACGTGTGTCACCCAGACAGTCGATTTCAGCCTTGACCCTACCTTCACCATTGAG
     ACGTTATGCACACAGTGGGTCTGTCAGCTAAAGTCGGAACTGGGATGGAAGTGGTAACTC

ThrIleThrLeuProGlnAspAlaValSerArgThrGlnArgArgGlyArgThrGlyArg
722  ACAATCACGCTCCCCCAAGATGCTGTCTCCCGCACTCAACGTCGGGGCAGGACTGGCAGG
     TGTTAGTGCGAGGGGGTTCTACGACAGAGGGCGTGAGTTGCAGCCCCGTCCTGACCGTCC

GlyLysProGlyIleTyrArgPheValAlaProGlyGluArgProSerGlyMetPheAsp
782  GGGAAGCCAGGCATCTACAGATTTGTGGCACCGGGGGAGCGCCCCTCCGGCATGTTCGAC
     CCCTTCGGTCCGTAGATGTCTAAACACCGTGGCCCCCTCGCGGGGAGGCCGTACAAGCTG
                                                    ^            ^
     822 BGLI, 839 DRD1,

SerSerValLeuCysGluCysTyrAspAlaGlyCysAlaTrpTyrGluLeuThrProAla
842  TCGTCCGTCCTCTGTGAGTGCTATGACGCAGGCTGTGCTTGGTATGAGCTCACGCCCGCC
     AGCAGGCAGGAGACACTCACGATACTGCGTCCGACACGAACCATACTCGAGTGCGGGCGG
                                                           ^
     887 SACI,

GluThrThrValArgLeuArgAlaTyrMetAsnThrProGlyLeuProValCysGlnAsp
902  GAGACTACAGTTAGGCTACGAGCGTACATGAACACCCCGGGGCTTCCCGTGTGCCAGGAC
     CTCTGATGTCAATCCGATGCTCGCATGTACTTGTGGGGCCCCGAAGGGCACACGGTCCTG
                                           ^
     937 SMAI XMAI,

HisLeuGluPheTrpGluGlyValPheThrGlyLeuThrHisIleAspAlaHisPheLeu
962  CATCTTGAATTTTGGGAGGGCGTCTTTACAGGCCTCACTCATATAGATGCCCACTTTCTA
     GTAGAACTTAAAACCCTCCCGCAGAAATGTCCGGAGTGAGTATATCTACGGGTGAAAGAT
                                                ^
     991 STUI,

SerGlnThrLysGlnSerGlyGluAsnLeuProTyrLeuValAlaTyrGlnAlaThrVal
1022 TCCCAGACAAAGCAGAGTGGGGAGAACCTTCCTTACCTGGTAGCGTACCAAGCCACCGTG
     AGGGTCTGTTTCGTCTCACCCCTCTTGGAAGGAATGGACCATCGCATGGTTCGGTGGCAC
                                                        ^
     1075 DRA3,

CysAlaArgAlaGlnAlaProProProSerTrpAspGlnMetTrpLysCysLeuIleArg
1082 TGCGCTAGGGCTCAAGCCCCTCCCCCATCGTGGGACCAGATGTGGAAGTGTTTGATTCGC
     ACGCGATCCCGAGTTCGGGGAGGGGGTAGCACCCTGGTCTACACCTTCACAAACTAAGCG

LeuLysProThrLeuHisGlyProThrProLeuLeuTyrArgLeuGlyAlaValGlnAsn
1142 CTCAAGCCCACCCTCCATGGGCCAACACCCCTGCTATACAGACTGGGCGCTGTTCAGAAT
     GAGTTCGGGTGGGAGGTACCCGGTTGTGGGGACGATATGTCTGACCCGCGACAAGTCTTA
         ^
     1156 NCOI,

GluIleThrLeuThrHisProValThrLysTyrIleMetThrCysMetSerAlaAspLeu
1202 GAAATCACCCTGACGCACCCAGTCACCAAATACATCATGACATGCATGTCGGCCGACCTG
     CTTTAGTGGGACTGCGTGGGTCAGTGGTTTATGTAGTACTGTACGTACAGCCGGCTGGAC
                                    ^    ^   ^         ^     ^
     1236 BSPH1, 1240 DRD1, 1243 AVA3, 1251 EAG1 XMA3, 1256 DRD1,

GluValValThrSerThrTrpValLeuValGlyGlyValLeuAlaAlaLeuAlaAlaTyr
1262 GAGGTCGTCACGAGCACCTGGGTGCTCGTTGGCGGCGTCCTGGCTGCTTTGGCCGCGTAT
     CTCCAGCAGTGCTCGTGGACCCACGAGCAACCGCCGCAGGACCGACGAAACCGGCGCATA
```

FIG. 11-2

```
                CysLeuSerThrGlyCysValValIleValGlyArgValValLeuSerGlyLysProAla
1322            TGCCTGTCAACAGGCTGCGTGGTCATAGTGGGCAGGGTCGTCTTGTCCGGGAAGCCGGCA
                ACGGACAGTTGTCCGACGCACCAGTATCACCCGTCCCAGCAGAACAGGCCCTTCGGCCGT
                                                                           ^
        1375 NAEI,

IleIleProAspArgGluValLeuTyrArgGluPheAspGluMetGluGluCysSerGln
1382            ATCATACCTGACAGGGAAGTCCTCTACCGAGAGTTCGATGAGATGGAAGAGTGCTCTCAG
                TAGTATGGACTGTCCCTTCAGGAGATGGCTCTCAAGCTACTCTACCTTCTCACGAGAGTC
                                    ^
        1391 DRD1,

HisLeuProTyrIleGluGlnGlyMetMetLeuAlaGluGlnPheLysGlnLysAlaLeu
1442            CACTTACCGTACATCGAGCAAGGGATGATGCTCGCCGAGCAGTTCAAGCAGAAGGCCCTC
                GTGAATGGCATGTAGCTCGTTCCCTACTACGAGCGGCTCGTCAAGTTCGTCTTCCGGGAG

GlyLeuLeuGlnThrAlaSerArgGlnAlaGluValIleAlaProAlaValGlnThrAsn
1502            GGCCTCCTGCAGACCGCGTCCCGTCAGGCAGAGGTTATCGCCCCTGCTGTCCAGACCAAC
                CCGGAGGACGTCTGGCGCAGGGCAGTCCGTCTCCAATAGCGGGGACGACAGGTCTGGTTG
                   ^      ^
        1508 PSTI,   1513 TTH3I,

TrpGlnLysLeuGluThrPheTrpAlaLysHisMetTrpAsnPheIleSerGlyIleGln
1562            TGGCAAAAACTCGAGACCTTCTGGGCGAAGCATATGTGGAACTTCATCAGTGGGATACAA
                ACCGTTTTTGAGCTCTGGAAGACCCGCTTCGTATACACCTTGAAGTAGTCACCCTATGTT
                           ^                  ^
        1571 XHOI, 1592 NDEI,

TyrLeuAlaGlyLeuSerThrLeuProGlyAsnProAlaIleAlaSerLeuMetAlaPhe
1622            TACTTGGCGGGCTTGTCAACGCTGCCTGGTAACCCCGCCATTGCTTCATTGATGGCTTTT
                ATGAACCGCCCGAACAGTTGCGACGGACCATTGGGGCGGTAACGAAGTAACTACCGAAAA
                                                   ^
        1649 BSTE2,

ThrAlaAlaValThrSerProLeuThrThrSerGlnThrLeuLeuPheAsnIleLeuGly
1682            ACAGCTGCTGTCACCAGCCCACTAACCACTAGCCAAACCCTCCTCTTCAACATATTGGGG
                TGTCGACGACAGTGGTCGGGTGATTGGTGATCGGTTTGGGAGGAGAAGTTGTATAACCCC
                   ^
        1683 ALWN1 PVU2,

GlyTrpValAlaAlaGlnLeuAlaAlaProGlyAlaAlaThrAlaPheValGlyAlaGly
1742            GGGTGGGTGGCTGCCCAGCTCGCCGCCCCCGGTGCCGCTACTGCCTTTGTGGGCGCTGGC
                CCCACCCACCGACGGGTCGAGCGGCGGGGCCACGGCGATGACGGAAACACCCGCGACCG
                                                                           ^
        1800 ESP1,

LeuAlaGlyAlaAlaIleGlySerValGlyLeuGlyLysValLeuIleAspIleLeuAla
1802            TTAGCTGGCGCCGCCATCGGCAGTGTTGGACTGGGGAAGGTCCTCATAGACATCCTTGCA
                AATCGACCGCGGCGGTAGCCGTCACAACCTGACCCCTTCCAGGAGTATCTGTAGGAACGT
                         ^
        1808 KAS1 NARI,

GlyTyrGlyAlaGlyValAlaGlyAlaLeuValAlaPheLysIleMetSerGlyGluVal
1862            GGGTATGGCGCGGGCGTGGCGGGAGCTCTTGTGGCATTCAAGATCATGAGCGGTGAGGTC
                CCCATACCGCGCCCGCACCGCCCTCGAGAACACCGTAAGTTCTAGTACTCGCCACTCCAG
                              ^                        ^
```

FIG. 11-3

1884 SACI, 1905 BSPH1,

```
       ProSerThrGluAspLeuValAsnLeuLeuProAlaIleLeuSerProGlyAlaLeuVal
1922   CCCTCCACGGAGGACCTGGTCAATCTACTGCCCGCCATCCTCTCGCCCGGAGCCCTCGTA
       GGGAGGTGCCTCCTGGACCAGTTAGATGACGGGCGGTAGGAGAGCGGGCCTCGGGAGCAT
                                   ^
```

1934 TTH3I,

```
       ValGlyValValCysAlaAlaIleLeuArgArgHisValGlyProGlyGluGlyAlaVal
1982   GTCGGCGTGGTCTGTGCAGCAATACTGCGCCGGCACGTTGGCCCGGGCGAGGGGGCAGTG
       CAGCCGCACCAGACACGTCGTTATGACGCGGCCGTGCAACCGGGCCCGCTCCCCCGTCAC
                                     ^                 ^
```

2010 NAEI, 2023 SMAI XMAI,

```
       GlnTrpMetAsnArgLeuIleAlaPheAlaSerArgGlyAsnHisValSerProThrHis
2042   CAGTGGATGAACCGGCTGATAGCCTTCGCCTCCCGGGGGAACCATGTTTCCCCCACGCAC
       GTCACCTACTTGGCCGACTATCGGAAGCGGAGGGCCCCCTTGGTACAAAGGGGGTGCGTG
                                  ^                              ^
```

2073 SMAI XMAI, 2099 DRA3,

```
       TyrValProGluSerAspAlaAlaAlaArgValThrAlaIleLeuSerSerLeuThrVal
2102   TACGTGCCGGAGAGCGATGCAGCTGCCCGCGTCACTGCCATACTCAGCAGCCTCACTGTA
       ATGCACGGCCTCTCGCTACGTCGACGGGCGCAGTGACGGTATGAGTCGTCGGAGTGACAT
                                 ^
```

2121 PVU2,

```
       ThrGlnLeuLeuArgArgLeuHisGlnTrpIleSerSerGluCysThrThrProCysSer
2162   ACCCAGCTCCTGAGGCGACTGCACCAGTGGATAAGCTCGGAGTGTACCACTCCATGCTCC
       TGGGTCGAGGACTCCGCTGACGTGGTCACCTATTCGAGCCTCACATGGTGAGGTACGAGG
                  ^    ^
```

2165 ALWN1, 2170 MST2,

```
       GlySerTrpLeuArgAspIleTrpAspTrpIleCysGluValLeuSerAspPheLysThr
2222   GGTTCCTGGCTAAGGGACATCTGGGACTGGATATGCGAGGTGTTGAGCGACTTTAAGACC
       CCAAGGACCGATTCCCTGTAGACCCTGACCTATACGCTCCACAACTCGCTGAAATTCTGG
                ^
```

2226 ECON1,

```
       TrpLeuLysAlaLysLeuMetProGlnLeuProGlyIleProPheValSerCysGlnArg
2282   TGGCTAAAAGCTAAGCTCATGCCACAGCTGCCTGGGATCCCCTTTGTGTCCTGCCAGCGC
       ACCGATTTTCGATTCGAGTACGGTGTCGACGGACCCTAGGGGAAACACAGGACGGTCGCG
                ^                ^                ^
```

2291 ESP1, 2306 PVU2, 2316 BAMHI,

```
       GlyTyrLysGlyValTrpArgGlyAspGlyIleMetHisThrArgCysHisCysGlyAla
2342   GGGTATAAGGGGGTCTGGCGAGGGGACGGCATCATGCACACTCGCTGCCACTGTGGAGCT
       CCCATATTCCCCCAGACCGCTCCCCTGCCGTAGTACGTGTGAGCGACGGTGACACCTCGA
```

```
       GluIleThrGlyHisValLysAsnGlyThrMetArgIleValGlyProArgThrCysArg
2402   GAGATCACTGGACATGTCAAAAACGGGACGATGAGGATCGTCGGTCCTAGGACCTGCAGG
       CTCTAGTGACCTGTACAGTTTTTGCCCTGCTACTCCTAGCAGCCAGGATCCTGGACGTCC
                        ^                         ^              ^^
```

2431 BSAB1, 2447 AVR2, 2454 SSE83871, 2455 PSTI,

```
       AsnMetTrpSerGlyThrPheProIleAsnAlaTyrThrThrGlyProCysThrProLeu
2462   AACATGTGGAGTGGGACCTTCCCCATTAATGCCTACACCACGGGCCCTGTACCCCCCTT
       TTGTACACCTCACCCTGGAAGGGGTAATTACGGATGTGGTGCCCGGGGACATGGGGGGAA
```

FIG. 11-4

2486 ASE1, 2503 APAI,

```
     ProAlaProAsnTyrThrPheAlaLeuTrpArgValSerAlaGluGluTyrValGluIle
2522 CCTGCGCCGAACTACACGTTCGCGCTATGGAGGGTGTCTGCAGAGGAATACGTGGAGATA
     GGACGCGGCTTGATGTGCAAGCGCGATACCTCCCACAGACGTCTCCTTATGCACCTCTAT
                                                    ^
```

2559 PSTI,

```
     ArgGlnValGlyAspPheHisTyrValThrGlyMetThrThrAspAsnLeuLysCysPro
2582 AGGCAGGTGGGGGACTTCCACTACGTGACGGGTATGACTACTGACAATCTTAAATGCCCG
     TCCGTCCACCCCCTGAAGGTGATGCACTGCCCATACTGATGACTGTTAGAATTTACGGGC
                ^
```

2600 DRA3,

```
     CysGlnValProSerProGluPhePheThrGluLeuAspGlyValArgLeuHisArgPhe
2642 TGCCAGGTCCCATCGCCCGAATTTTTCACAGAATTGGACGGGGTGCGCCTACATAGGTTT
     ACGGTCCAGGGTAGCGGGCTTAAAAAGTGTCTTAACCTGCCCCACGCGGATGTATCCAAA
```

```
     AlaProProCysLysProLeuLeuArgGluGluValSerPheArgValGlyLeuHisGlu
2702 GCGCCCCCCTGCAAGCCCTTGCTGCGGGAGGAGGTATCATTCAGAGTAGGACTCCACGAA
     CGCGGGGGGACGTTCGGGAACGACGCCCTCCTCCATAGTAAGTCTCATCCTGAGGTGCTT
```

```
     TyrProValGlySerGlnLeuProCysGluProGluProAspValAlaValLeuThrSer
2762 TACCCGGTAGGGTCGCAATTACCTTGCGAGCCCGAACCGGACGTGGCCGTGTTGACGTCC
     ATGGGCCATCCCAGCGTTAATGGAACGCTCGGGCTTGGCCTGCACCGGCACAACTGCAGG
      ^                                                      ^
```

2763 HGIE2, 2815 AAT2,

```
      MetLeuThrAspProSerHisIleThrAlaGluAlaAlaGlyArgArgLeuAlaArgGly
2822 ATGCTCACTGATCCCTCCCATATAACAGCAGAGGCGGCCGGGCGAAGGTTGGCGAGGGGA
     TACGAGTGACTAGGGAGGGTATATTGTCGTCTCCGCCGGCCCGCTTCCAACCGCTCCCCT
                                                    ^
```

2856 EAG1 XMA3,

```
     SerProProSerValAlaSerSerSerAlaSerGlnLeuSerAlaProSerLeuLysAla
2882 TCACCCCCCTCTGTGGCCAGCTCCTCGGCTAGCCAGCTATCCGCTCCATCTCTCAAGGCA
     AGTGGGGGGAGACACCGGTCGAGGAGCCGATCGGTCGATAGGCGAGGTAGAGAGTTCCGT
           ^        ^
```

2895 BALI, 2909 NHEI,

```
     ThrCysThrAlaAsnHisAspSerProAspAlaGluLeuIleGluAlaAsnLeuLeuTrp
2942 ACTTGCACCGCTAACCATGACTCCCCTGATGCTGAGCTCATAGAGGCCAACCTCCTATGG
     TGAACGTGGCGATTGGTACTGAGGGGACTACGACTCGAGTATCTCCGGTTGGAGGATACC
                                      ^      ^
```

2972 ESP1, 2975 SACI,

```
     ArgGlnGluMetGlyGlyAsnIleThrArgValGluSerGluAsnLysValValIleLeu
3002 AGGCAGGAGATGGGCGGCAACATCACCAGGGTTGAGTCAGAAAACAAAGTGGTGATTCTG
     TCCGTCCTCTACCCGCCGTTGTAGTGGTCCCAACTCAGTCTTTTGTTTCACCACTAAGAC
```

```
     AspSerPheAspProLeuValAlaGluGluAspGluArgGluIleSerValProAlaGlu
3062 GACTCCTTCGATCCGCTTGTGGCGGAGGAGGACGAGCGGGAGATCTCCGTACCCGCAGAA
     CTGAGGAAGCTAGGCGAACACCGCCTCCTCCTGCTCGCCCTCTAGAGGCATGGGCGTCTT
                                                       ^
```

3102 BGL2,

FIG. 11-5

```
         IleLeuArgLysSerArgArgPheAlaGlnAlaLeuProValTrpAlaArgProAspTyr
3122     ATCCTGCGGAAGTCTCGGAGATTCGCCCAGGCCCTGCCCGTTTGGGCGCGGCCGGACTAT
         TAGGACGCCTTCAGAGCCTCTAAGCGGGTCCGGGACGGGCAAACCCGCGCCGGCCTGATA
                                                        ^           ^
3149 ALWN1, 3170 EAG1 XMA3,

AsnProProLeuValGluThrTrpLysLysProAspTyrGluProProValValHisGly
3182     AACCCCCCGCTAGTGGAGACGTGGAAAAAGCCCGACTACGAACCACCTGTGGTCCATGGC
         TTGGGGGCGATCACCTCTGCACCTTTTTCGGGCTGATGCTTGGTGGACACCAGGTACCG
                                                    ^           ^
3223 HGIE2, 3235 NCOI,

CysProLeuProProProLysSerProProValProProProArgLysLysArgThrVal
3242     TGCCCGCTTCCACCTCCAAAGTCCCCTCCTGTGCCTCCGCCTCGGAAGAAGCGGACGGTG
         ACGGGCGAAGGTGGAGGTTTCAGGGGAGGACACGGAGGCGGAGCCTTCTTCGCCTGCCAC

ValLeuThrGluSerThrLeuSerThrAlaLeuAlaGluLeuAlaThrArgSerPheGly
3302     GTCCTCACTGAATCAACCCTATCTACTGCCTTGGCCGAGCTCGCCACCAGAAGCTTTGGC
         CAGGAGTGACTTAGTTGGGATAGATGACGGAACCGGCTCGAGCGGTGGTCTTCGAAACCG
                                                 ^           ^
3338 SACI, 3352 HIND3,

SerSerSerThrSerGlyIleThrGlyAspAsnThrThrThrSerSerGluProAlaPro
3362     AGCTCCTCAACTTCCGGCATTACGGGCGACAATACGACAACATCCTCTGAGCCCGCCCCT
         TCGAGGAGTTGAAGGCCGTAATGCCCGCTGTTATGCTGTTGTAGGAGACTCGGGCGGGGA

SerGlyCysProProAspSerAspAlaGluSerTyrSerSerMetProProLeuGluGly
3422     TCTGGCTGCCCCCCCGACTCCGACGCTGAGTCCTATTCCTCCATGCCCCCCCTGGAGGGG
         AGACCGACGGGGGGGCTGAGGCTGCGACTCAGGATAAGGAGGTACGGGGGGGACCTCCCC
                         ^
3443 EAM11051,

GluProGlyAspProAspLeuSerAspGlySerTrpSerThrValSerSerGluAlaAsn
3482     GAGCCTGGGGATCCGGATCTTAGCGACGGGTCATGGTCAACGGTCAGTAGTGAGGCCAAC
         CTCGGACCCCTAGGCCTAGAATCGCTGCCCAGTACCAGTTGCCAGTCATCACTCCGGTTG
                  ^^ ^
3490 BAMHI, 3491 BSAB1, 3493 BSPE1,

AlaGluAspValValCysCysSerMetSerTyrSerTrpThrGlyAlaLeuValThrPro
3542     GCGGAGGATGTCGTGTGCTGCTCAATGTCTTACTCTTGGACAGGCGCACTCGTCACCCCG
         CGCCTCCTACAGCACACGACGAGTTACAGAATGAGAACCTGTCCGCGTGAGCAGTGGGGC
                                                                  ^
3595 DRA3,

CysAlaAlaGluGluGlnLysLeuProIleAsnAlaLeuSerAsnSerLeuLeuArgHis
3602     TGCGCCGCGGAAGAACAGAAACTGCCCATCAATGCACTAAGCAACTCGTTGCTACGTCAC
         ACGCGGCGCCTTCTTGTCTTTGACGGGTAGTTACGTGATTCGTTGAGCAACGATGCAGTG
              ^        ^                                           ^
3606 SAC2, 3617 ALWN1, 3661 PFLM1,

HisAsnLeuValTyrSerThrThrSerArgSerAlaCysGlnArgGlnLysLysValThr
3662     CACAATTTGGTGTATTCCACCACCTCACGCAGTGCTTGCCAAAGGCAGAAGAAAGTCACA
         GTGTTAAACCACATAAGGTGGTGGAGTGCGTCACGAACGGTTTCCGTCTTCTTTCAGTGT
                                              ^
3687 DRA3,

PheAspArgLeuGlnValLeuAspSerHisTyrGlnAspValLeuLysGluValLysAla
```

FIG. 11-6

```
3722 TTTGACAGACTGCAAGTTCTGGACAGCCATTACCAGGACGTACTCAAGGAGGTTAAAGCA
     AAACTGTCTGACGTTCAAGACCTGTCGGTAATGGTCCTGCATGAGTTCCTCCAATTTCGT

AlaAlaSerLysValLysAlaAsnLeuLeuSerValGluGluAlaCysSerLeuThrPro
3782 GCGGCGTCAAAAGTGAAGGCTAACTTGCTATCCGTAGAGGAAGCTTGCAGCCTGACGCCC
     CGCCGCAGTTTTCACTTCCGATTGAACGATAGGCATCTCCTTCGAACGTCGGACTGCGGG
                                            ^
3822 HIND3,

ProHisSerAlaLysSerLysPheGlyTyrGlyAlaLysAspValArgCysHisAlaArg
3842 CCACACTCAGCCAAATCCAAGTTTGGTTATGGGGCAAAAGACGTCCGTTGCCATGCCAGA
     GGTGTGAGTCGGTTTAGGTTCAAACCAATACCCCGTTTTCTGCAGGCAACGGTACGGTCT
                                            ^              ^
3881 AAT2, 3896 BGLI,

LysAlaValThrHisIleAsnSerValTrpLysAspLeuLeuGluAspAsnValThrPro
3902 AAGGCCGTAACCCACATCAACTCCGTGTGGAAAGACCTTCTGGAAGACAATGTAACACCA
     TTCCGGCATTGGGTGTAGTTGAGGCACACCTTTCTGGAAGACCTTCTGTTACATTGTGGT

IleAspThrThrIleMetAlaLysAsnGluValPheCysValGlnProGluLysGlyGly
3962 ATAGACACTACCATCATGGCTAAGAACGAGGTTTTCTGCGTTCAGCCTGAGAAGGGGGGT
     TATCTGTGATGGTAGTACCGATTCTTGCTCCAAAAGACGCAAGTCGGACTCTTCCCCCCA

ArgLysProAlaArgLeuIleValPheProAspLeuGlyValArgValCysGluLysMet
4022 CGTAAGCCAGCTCGTCTCATCGTGTTCCCCGATCTGGGCGTGCGCGTGTGCGAAAAGATG
     GCATTCGGTCGAGCAGAGTAGCACAAGGGGCTAGACCCGCACGCGCACACGCTTTTCTAC

AlaLeuTyrAspValValThrLysLeuProLeuAlaValMetGlySerSerTyrGlyPhe
4082 GCTTTGTACGACGTGGTTACAAAGCTCCCCTTGGCCGTGATGGGAAGCTCCTACGGATTC
     CGAAACATGCTGCACCAATGTTTCGAGGGGAACCGGCACTACCCTTCGAGGATGCCTAAG

GlnTyrSerProGlyGlnArgValGluPheLeuValGlnAlaTrpLysSerLysLysThr
4142 CAATACTCACCAGGACAGCGGGTTGAATTCCTCGTGCAAGCGTGGAAGTCCAAGAAAACC
     GTTATGAGTGGTCCTGTCGCCCAACTTAAGGAGCACGTTCGCACCTTCAGGTTCTTTTGG
                                ^
4166 ECORI,

ProMetGlyPheSerTyrAspThrArgCysPheAspSerThrValThrGluSerAspIle
4202 CCAATGGGGTTCTCGTATGATACCCGCTGCTTTGACTCCACAGTCACTGAGAGCGACATC
     GGTTACCCCAAGAGCATACTATGGGCGACGAAACTGAGGTGTCAGTGACTCTCGCTGTAG
                                            ^       ^
4235 DRD1, 4242 ALWN1,

ArgThrGluGluAlaIleTyrGlnCysCysAspLeuAspProGlnAlaArgValAlaIle
4262 CGTACGGAGGAGGCAATCTACCAATGTTGTGACCTCGACCCCCAAGCCCGCGTGGCCATC
     GCATGCCTCCTCCGTTAGATGGTTACAACACTGGAGCTGGGGGTTCGGGCGCACCGGTAG
                                                  ^    ^
4307 BGLI, 4314 BALI,

LysSerLeuThrGluArgLeuTyrValGlyGlyProLeuThrAsnSerArgGlyGluAsn
4322 AAGTCCCTCACCGAGAGGCTTTATGTTGGGGGCCCTCTTACCAATTCAAGGGGGGAGAAC
     TTCAGGGAGTGGCTCTCCGAAATACAACCCCCGGGAGAATGGTTAAGTTCCCCCCTCTTG
                                      ^
4351 APAI,

CysGlyTyrArgArgCysArgAlaSerGlyValLeuThrThrSerCysGlyAsnThrLeu
4382 TGCGGCTATCGCAGGTGCCGCGCGAGCGGCGTACTGACAACTAGCTGTGGTAACACCCTC
```

FIG. 11-7

```
                ACGCCGATAGCGTCCACGGCGCGCTCGCCGCATGACTGTTGATCGACACCATTGTGGGAG

ThrCysTyrIleLysAlaArgAlaAlaCysArgAlaAlaGlyLeuGlnAspCysThrMet
       4442     ACTTGCTACATCAAGGCCCGGGCAGCCTGTCGAGCCGCAGGGCTCCAGGACTGCACCATG
                TGAACGATGTAGTTCCGGGCCCGTCGGACAGCTCGGCGTCCCGAGGTCCTGACGTGGTAC
                                        ^
       4458 SMAI XMAI,

LeuValCysGlyAspAspLeuValValIleCysGluSerAlaGlyValGlnGluAspAla
       4502     CTCGTGTGTGGCGACGACTTAGTCGTTATCTGTGAAAGCGCGGGGGTCCAGGAGGACGCG
                GAGCACACACCGCTGCTGAATCAGCAATAGACACTTTCGCGCCCCCAGGTCCTCCTGCGC
                                   ^  ^
       4514 DRD1,  4517 TTH3I,

AlaSerLeuArgAlaPheThrGluAlaMetThrArgTyrSerAlaProProGlyAspPro
       4562     GCGAGCCTGAGAGCCTTCACGGAGGCTATGACCAGGTACTCCGCCCCCCTGGGGACCCC
                CGCTCGGACTCTCGGAAGTGCCTCCGATACTGGTCCATGAGGCGGGGGGGACCCCTGGGG

ProGlnProGluTyrAspLeuGluLeuIleThrSerCysSerSerAsnValSerValAla
       4622     CCACAACCAGAATACGACTTGGAGCTCATAACATCATGCTCCTCCAACGTGTCAGTCGCC
                GGTGTTGGTCTTATGCTGAACCTCGAGTATTGTAGTACGAGGAGGTTGCACAGTCAGCGG
                                        ^
       4643 SACI,

HisAspGlyAlaGlyLysArgValTyrTyrLeuThrArgAspProThrThrProLeuAla
       4682     CACGACGGCGCTGGAAAGAGGGTCTACTACCTCACCCGTGACCCTACAACCCCCCTCGCG
                GTGCTGCCGCGACCTTTCTCCCAGATGATGGAGTGGGCACTGGGATGTTGGGGGGAGCGC
                                                                      ^
       4737 NRUI,

ArgAlaAlaTrpGluThrAlaArgHisThrProValAsnSerTrpLeuGlyAsnIleIle
       4742     AGAGCTGCGTGGGAGACAGCAAGACACACTCCAGTCAATTCCTGGCTAGGCAACATAATC
                TCTCGACGCACCCTCTGTCGTTCTGTGTGAGGTCAGTTAAGGACCGATCCGTTGTATTAG

MetPheAlaProThrLeuTrpAlaArgMetIleLeuMetThrHisPhePheSerValLeu
       4802     ATGTTTGCCCCCACACTGTGGGCGAGGATGATACTGATGACCCATTTCTTTAGCGTCCTT
                TACAAACGGGGGTGTGACACCCGCTCCTACTATGACTACTGGGTAAAGAAATCGCAGGAA
                                        ^^
       4812 PFLM1,  4813 DRA3,

IleAlaArgAspGlnLeuGluGlnAlaLeuAspCysGluIleTyrGlyAlaCysTyrSer
       4862     ATAGCCAGGGACCAGCTTGAACAGGCCCTCGATTGCGAGATCTACGGGGCCTGCTACTCC
                TATCGGTCCCTGGTCGAACTTGTCCGGGAGCTAACGCTCTAGATGCCCCGGACGATGAGG
                                                          ^
       4899 BGL2,

IleGluProLeuAspLeuProProIleIleGlnArgLeuHisGlyLeuSerAlaPheSer
       4922     ATAGAACCACTGGATCTACCTCCAATCATTCAAAGACTCCATGGCCTCAGCGCATTTTCA
                TATCTTGGTGACCTAGATGGAGGTTAGTAAGTTTCTGAGGTACCGGAGTCGCGTAAAAGT
                                                            ^
       4960 NCOI,

LeuHisSerTyrSerProGlyGluIleAsnArgValAlaAlaCysLeuArgLysLeuGly
       4982     CTCCACAGTTACTCTCCAGGTGAAATCAATAGGGTGGCCGCATGCCTCAGAAAACTTGGG
                GAGGTGTCAATGAGAGGTCCACTTTAGTTATCCCACCGGCGTACGGAGTCTTTTGAACCC
                                                    ^                   ^
       5021 SPHI,  5041 KPNI,
```

FIG. 11-8

```
     ValProProLeuArgAlaTrpArgHisArgAlaArgSerValArgAlaArgLeuLeuAla
5042 GTACCGCCCTTGCGAGCTTGGAGACACCGGGCCCGGAGCGTCCGCGCTAGGCTTCTGGCC
     CATGGCGGGAACGCTCGAACCTCTGTGGCCCGGGCCTCGCAGGCGCGATCCGAAGACCGG
                              ^                           ^
5070 APAI,  5097 BALI,

ArgGlyGlyArgAlaAlaIleCysGlyLysTyrLeuPheAsnTrpAlaValArgThrLys
5102 AGAGGAGGCAGGGCTGCCATATGTGGCAAGTACCTCTTCAACTGGGCAGTAAGAACAAAG
     TCTCCTCCGTCCCGACGGTATACACCGTTCATGGAGAAGTTGACCCGTCATTCTTGTTTC
                        ^
5119 NDEI,

LeuLysLeuThrProIleAlaAlaAlaGlyGlnLeuAspLeuSerGlyTrpPheThrAla
5162 CTCAAACTCACTCCAATAGCGGCCGCTGGCCAGCTGGACTTGTCCGGCTGGTTCACGGCT
     GAGTTTGAGTGAGGTTATCGCCGGCGACCGGTCGACCTGAACAGGCCGACCAAGTGCCGA
                        ^^      ^       ^
5180 NOTI, 5181 EAG1 XMA3, 5188 BALI, 5192 PVU2,

GlyTyrSerGlyGlyAspIleTyrHisSerValSerHisAlaArgProArgTrpIleTrp
5222 GGCTACAGCGGGGGAGACATTTATCACAGCGTGTCTCATGCCCGGCCCCGCTGGATCTGG
     CCGATGTCGCCCCCTCTGTAAATAGTGTCGCACAGAGTACGGGCCGGGGCGACCTAGACC
                                  ^
5246 DRA3,

PheCysLeuLeuLeuLeuAlaAlaGlyValGlyIleTyrLeuLeuProAsnArgOP
5282 TTTTGCCTACTCCTGCTTGCTGCAGGGGTAGGCATCTACCTCCTCCCCAACCGATGAAGG
     AAAACGGATGAGGACGAACGACGTCCCCATCCGTAGATGGAGGAGGGGTTGGCTACTTCC
                    ^                              ^
5301 PSTI,  5331 HGIE2,

5342 TTGGGGTAAACACTCCGGCCTAAAAAAAAAAAAAAAATCTAGAACCCGAGTCGAC
     AACCCCATTTGTGAGGCCGGATTTTTTTTTTTTTAGATCTTGGGCTCAGCTG
                                    ^           ^
5378 XBAI,  5390 SALI,
```

FIG. 11-9

```
                                      MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
                             ^                ^                   ^
  1  HIND3,  24  NDEI,  52  SCAI,

ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                              ^
 116 CLAI,

ProAsnIleArgThrGlyValArgThrIleThrThrGlySerProIleThrTyrSerThr
 122 CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

TyrGlyLysPheLeuAlaAspGlyGlyCysSerGlyGlyAlaTyrAspIleIleIleCys
 182 TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCCGCGAATACTGTATTATTAAACA

AspGluCysHisSerThrAspAlaThrSerIleLeuGlyIleGlyThrValLeuAspGln
 242 GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

AlaGluThrAlaGlyAlaArgLeuValValLeuAlaThrAlaThrProProGlySerVal
 302 GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
           ^
 303 ALWN1,

ThrValProHisProAsnIleGluGluValAlaLeuSerThrThrGlyGluIleProPhe
 362 ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

TyrGlyLysAlaIleProLeuGluValIleLysGlyGlyArgHisLeuIlePheCysHis
 422 TACGGCAAGGCTATCCCCCTCGAAGTAATCAAGGGGGGGAGACATCTCATCTTCTGTCAT
     ATGCCGTTCCGATAGGGGGAGCTTCATTAGTTCCCCCCTCTGTAGAGTAGAAGACAGTA

SerLysLysLysCysAspGluLeuAlaAlaLysLeuValAlaLeuGlyIleAsnAlaVal
 482 TCAAAGAAGAAGTGCGACGAACTCGCCGCAAAGCTGGTCGCATTGGGCATCAATGCCGTG
     AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
 542 GCCTACTACCGCGGTCTTGACGTGTCCGTCATCCCGACCAGCGGCGATGTTGTCGTCGTG
     CGGATGATGGCGCCAGAACTGCACAGGCAGTAGGGCTGGTCGCCGCTACAACAGCAGCAC
                   ^         ^
 550 SAC2,  560 DRD1,

AlaThrAspAlaLeuMetThrGlyTyrThrGlyAspPheAspSerValIleAspCysAsn
 602 GCAACCGATGCCCTCATGACCGGCTATACCGGCGACTTCGACTCGGTGATAGACTGCAAT
     CGTTGGCTACGGGAGTACTGGCCGATATGGCCGCTGAAGCTGAGCCACTATCTGACGTTA
                                       ^
 615 BSPH1,

ThrCysValThrGlnThrValAspPheSerLeuAspProThrPheThrIleGluThrIle
```

FIG. 14-1

662 ACGTGTGTCACCCAGACAGTCGATTTCAGCCTTGACCCTACCTTCACCATTGAGACAATC
TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
722 ACGCTCCCCCAAGATGCTGTCTCCCGCACTCAACGTCGGGGCAGGACTGGCAGGGGGAAG
TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
782 CCAGGCATCTACAGATTTGTGGCACCGGGGGAGCGCCCCTCCGGCATGTTCGACTCGTCC
GGTCCGTAGATGTCTAAACACCGTGGCCCCCTCGCGGGGAGGCCGTACAAGCTGAGCAGG
                ^        ^

816 BGLI, 833 DRD1,

ValLeuCysGluCysTyrAspAlaGlyCysAlaTrpTyrGluLeuThrProAlaGluThr
842 GTCCTCTGTGAGTGCTATGACGCAGGCTGTGCTTGGTATGAGCTCACGCCCGCCGAGACT
CAGGAGACACTCACGATACTGCGTCCGACACGAACCATACTCGAGTGCGGGCGGCTCTGA
                            ^

881 SACI,

ThrValArgLeuArgAlaTyrMetAsnThrProGlyLeuProValCysGlnAspHisLeu
902 ACAGTTAGGCTACGAGCGTACATGAACACCCCGGGGCTTCCCGTGTGCCAGGACCATCTT
TGTCAATCCGATGCTCGCATGTACTTGTGGGGCCCCGAAGGGCACACGGTCCTGGTAGAA
                        ^

931 SMAI XMAI,

GluPheTrpGluGlyValPheThrGlyLeuThrHisIleAspAlaHisPheLeuSerGln
962 GAATTTTGGGAGGGCGTCTTTACAGGCCTCACTCATATAGATGCCCACTTTCTATCCCAG
CTTAAAACCCTCCCGCAGAAATGTCCGGAGTGAGTATATCTACGGGTGAAAGATAGGGTC
                      ^

985 STUI,

ThrLysGlnSerGlyGluAsnLeuProTyrLeuValAlaTyrGlnAlaThrValCysAla
1022 ACAAAGCAGAGTGGGGAGAACCTTCCTTACCTGGTAGCGTACCAAGCCACCGTGTGCGCT
TGTTTCGTCTCACCCCTCTTGGAAGGAATGGACCATCGCATGGTTCGGTGGCACACGCGA
                                                ^

1069 DRA3,

ArgAlaGlnAlaProProProSerTrpAspGlnMetTrpLysCysLeuIleArgLeuLys
1082 AGGGCTCAAGCCCCTCCCCCATCGTGGGACCAGATGTGGAAGTGTTTGATTCGCCTCAAG
TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
1142 CCCACCCTCCATGGGCCAACACCCCTGCTATACAGACTGGGCGCTGTTCAGAATGAAATC
GGGTGGGAGGTACCCGGTTGTGGGGACGATATGTCTGACCCGCGACAAGTCTTACTTTAG
                 ^

1150 NCOI,

ThrLeuThrHisProValThrLysTyrIleMetThrCysMetSerAlaAspLeuGluVal
1202 ACCCTGACGCACCCAGTCACCAAATACATCATGACATGCATGTCGGCCGACCTGGAGGTC
TGGGACTGCGTGGGTCAGTGGTTTATGTAGTACTGTACGTACAGCCGGCTGGACCTCCAG
                 ^   ^  ^     ^    ^

1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
1262 GTCACGAGCACCTGGGTGCTCGTTGGCGGCGTCCTGGCTGCTTTGGCCGCGTATTGCCTG
CAGTGCTCGTGGACCCACGAGCAACCGCCGCAGGACCGACGAAACCGGCGCATAACGGAC

FIG. 14-2

```
            SerThrGlyCysValValIleValGlyArgValValLeuSerGlyLysProAlaIleIle
     1322   TCAACAGGCTGCGTGGTCATAGTGGGCAGGGTCGTCTTGTCCGGGAAGCCGGCAATCATA
            AGTTGTCCGACGCACCAGTATCACCCGTCCCAGCAGAACAGGCCCTTCGGCCGTTAGTAT
                                                                     ^
     1369   NAEI,

ProAspArgGluValLeuTyrArgGluPheAspGluMetGluGluCysSerGlnHisLeu
     1382   CCTGACAGGGAAGTCCTCTACCGAGAGTTCGATGAGATGGAAGAGTGCTCTCAGCACTTA
            GGACTGTCCCTTCAGGAGATGGCTCTCAAGCTACTCTACCTTCTCACGAGAGTCGTGAAT
              ^
     1385   DRDI,

ProTyrIleGluGlnGlyMetMetLeuAlaGluGlnPheLysGlnLysAlaLeuGlyLeu
     1442   CCGTACATCGAGCAAGGGATGATGCTCGCCGAGCAGTTCAAGCAGAAGGCCCTCGGCCTC
            GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
     1502   CTGCAGACCGCGTCCCGTCAGGCAGAGGTTATCGCCCCTGCTGTCCAGACCAACTGGCAA
            GACGTCTGGCGCAGGGCAGTCCGTCTCCAATAGCGGGGACGACAGGTCTGGTTGACCGTT
            ^       ^
     1502   PSTI,  1507 TTH3I,

LysLeuGluThrPheTrpAlaLysHisMetTrpAsnPheIleSerGlyIleGlnTyrLeu
     1562   AAACTCGAGACCTTCTGGGCGAAGCATATGTGGAACTTCATCAGTGGGATACAATACTTG
            TTTGAGCTCTGGAAGACCCGCTTCGTATACACCTTGAAGTAGTCACCCTATGTTATGAAC
                 ^                   ^
     1565   XHOI,  1586 NDEI,

AlaGlyLeuSerThrLeuProGlyAsnProAlaIleAlaSerLeuMetAlaPheThrAla
     1622   GCGGGCTTGTCAACGCTGCCTGGTAACCCCGCCATTGCTTCATTGATGGCTTTTACAGCT
            CGCCCGAACAGTTGCGACGGACCATTGGGGCGGTAACGAAGTAACTACCGAAAATGTCGA
                                 ^                         ^
     1643   BSTE2, 1677 ALWN1 PVU2,

AlaValThrSerProLeuThrThrSerGlnThrLeuLeuPheAsnIleLeuGlyGlyTrp
     1682   GCTGTCACCAGCCCACTAACCACTAGCCAAACCCTCCTCTTCAACATATTGGGGGGGTGG
            CGACAGTGGTCGGGTGATTGGTGATCGGTTTGGGAGGAGAAGTTGTATAACCCCCCCACC

ValAlaAlaGlnLeuAlaAlaProGlyAlaAlaThrAlaPheValGlyAlaGlyLeuAla
     1742   GTGGCTGCCCAGCTCGCCGCCCCCGGTGCCGCTACTGCCTTTGTGGGCGCTGGCTTAGCT
            CACCGACGGGTCGAGCGGCGGGGGCCACGGCGATGACGGAAACACCCGCGACCGAATCGA
                                                                    ^
     1794   ESP1,

GlyAlaAlaIleGlySerValGlyLeuGlyLysValLeuIleAspIleLeuAlaGlyTyr
     1802   GGCGCCGCCATCGGCAGTGTTGGACTGGGGAAGGTCCTCATAGACATCCTTGCAGGGTAT
            CCGCGGCGGTAGCCGTCACAACCTGACCCCTTCCAGGAGTATCTGTAGGAACGTCCCATA
            ^                                                    ^
     1802   KAS1 NARI,

GlyAlaGlyValAlaGlyAlaLeuValAlaPheLysIleMetSerGlyGluValProSer
     1862   GGCGCGGGCGTGGCGGGAGCTCTTGTGGCATTCAAGATCATGAGCGGTGAGGTCCCCTCC
            CCGCGCCCGCACCGCCCTCGAGAACACCGTAAGTTCTAGTACTCGCCACTCCAGGGGAGG
                                  ^                   ^
     1878   SACI,  1899 BSPH1,
```

FIG. 14-3

```
         ThrGluAspLeuValAsnLeuLeuProAlaIleLeuSerProGlyAlaLeuValValGly
1922 ACGGAGGACCTGGTCAATCTACTGCCCGCCATCCTCTCGCCCGGAGCCCTCGTAGTCGGC
     TGCCTCCTGGACCAGTTAGATGACGGGCGGTAGGAGAGCGGGCCTCGGGAGCATCAGCCG
                    ^
1928 TTH3I,

ValValCysAlaAlaIleLeuArgArgHisValGlyProGlyGluGlyAlaValGlnTrp
1982 GTGGTCTGTGCAGCAATACTGCGCCGGCACGTTGGCCCGGGCGAGGGGGCAGTGCAGTGG
     CACCAGACACGTCGTTATGACGCGGCCGTGCAACCGGGCCCGCTCCCCCGTCACGTCACC
                              ^                  ^
2004 NAEI, 2017 SMAI XMAI,

MetAsnArgLeuIleAlaPheAlaSerArgGlyAsnHisValSerProThrHisTyrVal
2042 ATGAACCGGCTGATAGCCTTCGCCTCCCGGGGGAACCATGTTTCCCCCACGCACTACGTG
     TACTTGGCCGACTATCGGAAGCGGAGGGCCCCCTTGGTACAAAGGGGGTGCGTGATGCAC
                                   ^                          ^
2067 SMAI XMAI, 2093 DRA3,

ProGluSerAspAlaAlaAlaArgValThrAlaIleLeuSerSerLeuThrValThrGln
2102 CCGGAGAGCGATGCAGCTGCCCGCGTCACTGCCATACTCAGCAGCCTCACTGTAACCCAG
     GGCCTCTCGCTACGTCGACGGGCGCAGTGACGGTATGAGTCGTCGGAGTGACATTGGGTC
                   ^                                          ^
2115 PVU2, 2159 ALWN1,

LeuLeuArgArgLeuHisGlnTrpIleSerSerGluCysThrThrProCysSerGlySer
2162 CTCCTGAGGCGACTGCACCAGTGGATAAGCTCGGAGTGTACCACTCCATGCTCCGGTTCC
     GAGGACTCCGCTGACGTGGTCACCTATTCGAGCCTCACATGGTGAGGTACGAGGCCAAGG
            ^                                       ^
2164 MST2, 2220 ECON1,

TrpLeuArgAspIleTrpAspTrpIleCysGluValLeuSerAspPheLysThrTrpLeu
2222 TGGCTAAGGGACATCTGGGACTGGATATGCGAGGTGTTGAGCGACTTTAAGACCTGGCTA
     ACCGATTCCCTGTAGACCCTGACCTATACGCTCCACAACTCGCTGAAATTCTGGACCGAT

LysAlaLysLeuMetProGlnLeuProGlyIleProPheValSerCysGlnArgGlyTyr
2282 AAAGCTAAGCTCATGCCACAGCTGCCTGGGATCCCCTTTGTGTCCTGCCAGCGCGGGTAT
     TTTCGATTCGAGTACGGTGTCGACGGACCCTAGGGGAAACACAGGACGGTCGCGCCCATA
         ^              ^         ^
2285 ESPI, 2300 PVU2, 2310 BAMHI,

LysGlyValTrpArgGlyAspGlyIleMetHisThrArgCysHisCysGlyAlaGluIle
2342 AAGGGGGTCTGGCGAGGGGACGGCATCATGCACACTCGCTGCCACTGTGGAGCTGAGATC
     TTCCCCCAGACCGCTCCCCTGCCGTAGTACGTGTGAGCGACGGTGACACCTCGACTCTAG

ThrGlyHisValLysAsnGlyThrMetArgIleValGlyProArgThrCysArgAsnMet
2402 ACTGGACATGTCAAAAACGGGACGATGAGGATCGTCGGTCCTAGGACCTGCAGGAACATG
     TGACCTGTACAGTTTTTGCCCTGCTACTCCTAGCAGCCAGGATCCTGGACGTCCTTGTAC
                 ^              ^    ^^
2425 BSAB1, 2441 AVR2, 2448 SSE83871, 2449 PSTI,

TrpSerGlyThrPheProIleAsnAlaTyrThrThrGlyProCysThrProLeuProAla
2462 TGGAGTGGGACCTTCCCCATTAATGCCTACACCACGGGCCCCTGTACCCCCCTTCCTGCG
     ACCTCACCCTGGAAGGGGTAATTACGGATGTGGTGCCCGGGGACATGGGGGGAAGGACGC
                         ^             ^
2480 ASE1, 2497 APAI,

ProAsnTyrThrPheAlaLeuTrpArgValSerAlaGluGluTyrValGluIleArgGln
```

FIG. 14-4

2522 CCGAACTACACGTTCGCGCTATGGAGGGTGTCTGCAGAGGAATACGTGGAGATAAGGCAG
GGCTTGATGTGCAAGCGCGATACCTCCCACAGACGTCTCCTTATGCACCTCTATTCCGTC
                                ^
2553 PSTI,

ValGlyAspPheHisTyrValThrGlyMetThrThrAspAsnLeuLysCysProCysGln
2582 GTGGGGGACTTCCACTACGTGACGGGTATGACTACTGACAATCTTAAATGCCCGTGCCAG
CACCCCCTGAAGGTGATGCACTGCCCATACTGATGACTGTTAGAATTTACGGGCACGGTC
                                         ^
2594 DRA3,

ValProSerProGluPhePheThrGluLeuAspGlyValArgLeuHisArgPheAlaPro
2642 GTCCCATCGCCCGAATTTTTCACAGAATTGGACGGGGTGCGCCTACATAGGTTTGCGCCC
CAGGGTAGCGGGCTTAAAAAGTGTCTTAACCTGCCCCACGCGGATGTATCCAAACGCGGG

ProCysLysProLeuLeuArgGluGluValSerPheArgValGlyLeuHisGluTyrPro
2702 CCCTGCAAGCCCTTGCTGCGGGAGGAGGTATCATTCAGAGTAGGACTCCACGAATACCCG
GGGACGTTCGGGAACGACGCCCTCCTCCATAGTAAGTCTCATCCTGAGGTGCTTATGGGC
                                                           ^
2757 HGIE2,

ValGlySerGlnLeuProCysGluProGluProAspValAlaValLeuThrSerMetLeu
2762 GTAGGGTCGCAATTACCTTGCGAGCCCGAACCGGACGTGGCCGTGTTGACGTCCATGCTC
CATCCCAGCGTTAATGGAACGCTCGGGCTTGGCCTGCACCGGCACAACTGCAGGTACGAG
                                                       ^
2809 AAT2,

ThrAspProSerHisIleThrAlaGluAlaAlaGlyArgArgLeuAlaArgGlySerPro
2822 ACTGATCCCTCCCATATAACAGCAGAGGCGGCCGGGCGAAGGTTGGCGAGGGGATCACCC
TGACTAGGGAGGGTATATTGTCGTCTCCGCCGGCCCGCTTCCAACCGCTCCCCTAGTGGG
                                   ^
2850 EAG1 XMA3,

ProSerValAlaSerSerSerAlaSerGlnLeuSerAlaProSerLeuLysAlaThrCys
2882 CCCTCTGTGGCCAGCTCCTCGGCTAGCCAGCTATCCGCTCCATCTCTCAAGGCAACTTGC
GGGAGACACCGGTCGAGGAGCCGATCGGTCGATAGGCGAGGTAGAGAGTTCCGTTGAACG
                       ^         ^
2889 BALI, 2903 NHEI,

ThrAlaAsnHisAspSerProAspAlaGluLeuIleGluAlaAsnLeuLeuTrpArgGln
2942 ACCGCTAACCATGACTCCCCTGATGCTGAGCTCATAGAGGCCAACCTCCTATGGAGGCAG
TGGCGATTGGTACTGAGGGGACTACGACTCGAGTATCTCCGGTTGGAGGATACCTCCGTC
                                  ^ ^
2966 ESP1, 2969 SACI,

GluMetGlyGlyAsnIleThrArgValGluSerGluAsnLysValValIleLeuAspSer
3002 GAGATGGGCGGCAACATCACCAGGGTTGAGTCAGAAAACAAAGTGGTGATTCTGGACTCC
CTCTACCCGCCGTTGTAGTGGTCCCAACTCAGTCTTTTGTTTCACCACTAAGACCTGAGG

PheAspProLeuValAlaGluGluAspGluArgGluIleSerValProAlaGluIleLeu
3062 TTCGATCCGCTTGTGGCGGAGGAGGACGAGCGGGAGATCTCCGTACCCGCAGAAATCCTG
AAGCTAGGCGAACACCGCCTCCTCCTGCTCGCCCTCTAGAGGCATGGGCGTCTTTAGGAC
                                              ^
3096 BGL2,

ArgLysSerArgArgPheAlaGlnAlaLeuProValTrpAlaArgProAspTyrAsnPro
3122 CGGAAGTCTCGGAGATTCGCCCAGGCCCTGCCCGTTTGGGCGCGGCCGGACTATAACCCC

FIG. 14-5

```
              GCCTTCAGAGCCTCTAAGCGGGTCCGGGACGGGCAAACCCGCGCCGGCCTGATATTGGGG
                              ^                                   ^
         3143 ALWN1, 3164 EAG1 XMA3,

ProLeuValGluThrTrpLysLysProAspTyrGluProProValValHisGlyCysPro
         3182 CCGCTAGTGGAGACGTGGAAAAAGCCCGACTACGAACCACCTGTGGTCCATGGCTGCCCG
              GGCGATCACCTCTGCACCTTTTTCGGGCTGATGCTTGGTGGACACCAGGTACCGACGGGC
                                                    ^           ^
         3217 HGIE2, 3229 NCOI,

LeuProProProLysSerProProValProProProArgLysLysArgThrValValLeu
         3242 CTTCCACCTCCAAAGTCCCCTCCTGTGCCTCCGCCTCGGAAGAAGCGGACGGTGGTCCTC
              GAAGGTGGAGGTTTCAGGGGAGGACACGGAGGCGGAGCCTTCTTCGCCTGCCACCAGGAG

ThrGluSerThrLeuSerThrAlaLeuAlaGluLeuAlaThrArgSerPheGlySerSer
         3302 ACTGAATCAACCCTATCTACTGCCTTGGCCGAGCTCGCCACCAGAAGCTTTGGCAGCTCC
              TGACTTAGTTGGGATAGATGACGGAACCGGCTCGAGCGGTGGTCTTCGAAACCGTCGAGG
                                              ^           ^
         3332 SACI, 3346 HIND3,

SerThrSerGlyIleThrGlyAspAsnThrThrThrSerSerGluProAlaProSerGly
         3362 TCAACTTCCGGCATTACGGGCGACAATACGACAACATCCTCTGAGCCCGCCCCTTCTGGC
              AGTTGAAGGCCGTAATGCCCGCTGTTATGCTGTTGTAGGAGACTCGGGCGGGGAAGACCG

CysProProAspSerAspAlaGluSerTyrSerSerMetProProLeuGluGlyGluPro
         3422 TGCCCCCCCGACTCCGACGCTGAGTCCTATTCCTCCATGCCCCCCCTGGAGGGGGAGCCT
              ACGGGGGGGCTGAGGCTGCGACTCAGGATAAGGAGGTACGGGGGGGACCTCCCCCTCGGA
                          ^
         3437 EAM11051,

GlyAspProAspLeuSerAspGlySerTrpSerThrValSerSerGluAlaAsnAlaGlu
         3482 GGGGATCCGGATCTTAGCGACGGGTCATGGTCAACGGTCAGTAGTGAGGCCAACGCGGAG
              CCCCTAGGCCTAGAATCGCTGCCCAGTACCAGTTGCCAGTCATCACTCCGGTTGCGCCTC
                 ^^ ^
         3484 BAMHI, 3485 BSAB1, 3487 BSPE1,

AspValValCysCysSerMetSerTyrSerTrpThrGlyAlaLeuValThrProCysAla
         3542 GATGTCGTGTGCTGCTCAATGTCTTACTCTTGGACAGGCGCACTCGTCACCCCGTGCGCC
              CTACAGCACACGACGAGTTACAGAATGAGAACCTGTCCGCGTGAGCAGTGGGGCACGCGG
                                                        ^           ^
         3589 DRA3, 3600 SAC2,

AlaGluGluGlnLysLeuProIleAsnAlaLeuSerAsnSerLeuLeuArgHisHisAsn
         3602 GCGGAAGAACAGAAACTGCCCATCAATGCACTAAGCAACTCGTTGCTACGTCACCACAAT
              CGCCTTCTTGTCTTTGACGGGTAGTTACGTGATTCGTTGAGCAACGATGCAGTGGTGTTA
                 ^                                                  ^
         3611 ALWN1, 3655 PFLM1,

LeuValTyrSerThrThrSerArgSerAlaCysGlnArgGlnLysLysValThrPheAsp
         3662 TTGGTGTATTCCACCACCTCACGCAGTGCTTGCCAAAGGCAGAAGAAAGTCACATTTGAC
              AACCACATAAGGTGGTGGAGTGCGTCACGAACGGTTTCCGTCTTCTTTCAGTGTAAACTG
                                    ^
         3681 DRA3,

ArgLeuGlnValLeuAspSerHisTyrGlnAspValLeuLysGluValLysAlaAlaAla
         3722 AGACTGCAAGTTCTGGACAGCCATTACCAGGACGTACTCAAGGAGGTTAAAGCAGCGGCG
              TCTGACGTTCAAGACCTGTCGGTAATGGTCCTGCATGAGTTCCTCCAATTTCGTCGCCGC
```

FIG. 14-6

```
                 SerLysValLysAlaAsnLeuLeuSerValGluGluAlaCysSerLeuThrProProHis
      3782       TCAAAAGTGAAGGCTAACTTGCTATCCGTAGAGGAAGCTTGCAGCCTGACGCCCCCACAC
                 AGTTTTCACTTCCGATTGAACGATAGGCATCTCCTTCGAACGTCGGACTGCGGGGTGTG
                                                      ^
      3816 HIND3,

SerAlaLysSerLysPheGlyTyrGlyAlaLysAspValArgCysHisAlaArgLysAla
      3842       TCAGCCAAATCCAAGTTTGGTTATGGGGCAAAAGACGTCCGTTGCCATGCCAGAAAGGCC
                 AGTCGGTTTAGGTTCAAACCAATACCCCGTTTTCTGCAGGCAACGGTACGGTCTTTCCGG
                                            ^                  ^
      3875 AAT2, 3890 BGLI,

ValThrHisIleAsnSerValTrpLysAspLeuLeuGluAspAsnValThrProIleAsp
      3902       GTAACCCACATCAACTCCGTGTGGAAAGACCTTCTGGAAGACAATGTAACACCAATAGAC
                 CATTGGGTGTAGTTGAGGCACACCTTTCTGGAAGACCTTCTGTTACATTGTGGTTATCTG

ThrThrIleMetAlaLysAsnGluValPheCysValGlnProGluLysGlyGlyArgLys
      3962       ACTACCATCATGGCTAAGAACGAGGTTTTCTGCGTTCAGCCTGAGAAGGGGGGTCGTAAG
                 TGATGGTAGTACCGATTCTTGCTCCAAAAGACGCAAGTCGGACTCTTCCCCCCAGCATTC

ProAlaArgLeuIleValPheProAspLeuGlyValArgValCysGluLysMetAlaLeu
      4022       CCAGCTCGTCTCATCGTGTTCCCCGATCTGGGCGTGCGCGTGTGCGAAAAGATGGCTTTG
                 GGTCGAGCAGAGTAGCACAAGGGGCTAGACCCGCACGCGCACACGCTTTTCTACCGAAAC

TyrAspValValThrLysLeuProLeuAlaValMetGlySerSerTyrGlyPheGlnTyr
      4082       TACGACGTGGTTACAAAGCTCCCCTTGGCCGTGATGGGAAGCTCCTACGGATTCCAATAC
                 ATGCTGCACCAATGTTTCGAGGGGAACCGGCACTACCCTTCGAGGATGCCTAAGGTTATG

SerProGlyGlnArgValGluPheLeuValGlnAlaTrpLysSerLysLysThrProMet
      4142       TCACCAGGACAGCGGGTTGAATTCCTCGTGCAAGCGTGGAAGTCCAAGAAAACCCCAATG
                 AGTGGTCCTGTCGCCCAACTTAAGGAGCACGTTCGCACCTTCAGGTTCTTTTGGGGTTAC
                                       ^
      4160 ECORI,

GlyPheSerTyrAspThrArgCysPheAspSerThrValThrGluSerAspIleArgThr
      4202       GGGTTCTCGTATGATACCCGCTGCTTTGACTCCACAGTCACTGAGAGCGACATCCGTACG
                 CCCAAGAGCATACTATGGGCGACGAAACTGAGGTGTCAGTGACTCTCGCTGTAGGCATGC
                                          ^      ^
      4229 DRD1, 4236 ALWN1,

GluGluAlaIleTyrGlnCysCysAspLeuAspProGlnAlaArgValAlaIleLysSer
      4262       GAGGAGGCAATCTACCAATGTTGTGACCTCGACCCCCAAGCCCGCGTGGCCATCAAGTCC
                 CTCCTCCGTTAGATGGTTACAACACTGGAGCTGGGGGTTCGGGCGCACCGGTAGTTCAGG
                                                     ^       ^
      4301 BGLI, 4308 BALI,

LeuThrGluArgLeuTyrValGlyGlyProLeuThrAsnSerArgGlyGluAsnCysGly
      4322       CTCACCGAGAGGCTTTATGTTGGGGGCCCTCTTACCAATTCAAGGGGGGAGAACTGCGGC
                 GAGTGGCTCTCCGAAATACAACCCCGGGAGAATGGTTAAGTTCCCCCCTCTTGACGCCG
                                                  ^
      4345 APAI,

TyrArgArgCysArgAlaSerGlyValLeuThrThrSerCysGlyAsnThrLeuThrCys
      4382       TATCGCAGGTGCCGCGCGAGCGGCGTACTGACAACTAGCTGTGGTAACACCCTCACTTGC
                 ATAGCGTCCACGGCGCGCTCGCCGCATGACTGTTGATCGACACCATTGTGGGAGTGAACG
```

FIG. 14-7

```
                    TyrIleLysAlaArgAlaAlaCysArgAlaAlaGlyLeuGlnAspCysThrMetLeuVal
      4442  TACATCAAGGCCCGGGCAGCCTGTCGAGCCGCAGGGCTCCAGGACTGCACCATGCTCGTG
            ATGTAGTTCCGGGCCCGTCGGACAGCTCGGCGTCCCGAGGTCCTGACGTGGTACGAGCAC
                                  ^
            4452 SMAI XMAI,

CysGlyAspAspLeuValValIleCysGluSerAlaGlyValGlnGluAspAlaAlaSer
      4502  TGTGGCGACGACTTAGTCGTTATCTGTGAAAGCGCGGGGGTCCAGGAGGACGCGGCGAGC
            ACACCGCTGCTGAATCAGCAATAGACACTTTCGCGCCCCCAGGTCCTCCTGCGCCGCTCG
                        ^    ^
            4508 DRD1, 4511 TTH3I,

LeuArgAlaPheThrGluAlaMetThrArgTyrSerAlaProProGlyAspProProGln
      4562  CTGAGAGCCTTCACGGAGGCTATGACCAGGTACTCCGCCCCCCCTGGGGACCCCCCACAA
            GACTCTCGGAAGTGCCTCCGATACTGGTCCATGAGGCGGGGGGGACCCCTGGGGGGTGTT

ProGluTyrAspLeuGluLeuIleThrSerCysSerSerAsnValSerValAlaHisAsp
      4622  CCAGAATACGACTTGGAGCTCATAACATCATGCTCCTCCAACGTGTCAGTCGCCCACGAC
            GGTCTTATGCTGAACCTCGAGTATTGTAGTACGAGGAGGTTGCACAGTCAGCGGGTGCTG
                              ^
            4637 SACI,

GlyAlaGlyLysArgValTyrTyrLeuThrArgAspProThrThrProLeuAlaArgAla
      4682  GGCGCTGGAAAGAGGGTCTACTACCTCACCCGTGACCCTACAACCCCCCTCGCGAGAGCT
            CCGCGACCTTTCTCCCAGATGATGGAGTGGGCACTGGGATGTTGGGGGGAGCGCTCTCGA

4731 NRUI,

AlaTrpGluThrAlaArgHisThrProValAsnSerTrpLeuGlyAsnIleIleMetPhe
      4742  GCGTGGGAGACAGCAAGACACACTCCAGTCAATTCCTGGCTAGGCAACATAATCATGTTT
            CGCACCCTCTGTCGTTCTGTGTGAGGTCAGTTAAGGACCGATCCGTTGTATTAGTACAAA

AlaProThrLeuTrpAlaArgMetIleLeuMetThrHisPhePheSerValLeuIleAla
      4802  GCCCCCACACTGTGGGCGAGGATGATACTGATGACCCATTTCTTTAGCGTCCTTATAGCC
            CGGGGGTGTGACACCCGCTCCTACTATGACTACTGGGTAAAGAAATCGCAGGAATATCGG
                 ^^
            4806 PFLM1, 4807 DRA3,

ArgAspGlnLeuGluGlnAlaLeuAspCysGluIleTyrGlyAlaCysTyrSerIleGlu
      4862  AGGGACCAGCTTGAACAGGCCCTCGATTGCGAGATCTACGGGGCCTGCTACTCCATAGAA
            TCCCTGGTCGAACTTGTCCGGGAGCTAACGCTCTAGATGCCCCGGACGATGAGGTATCTT
                                        ^
            4893 BGL2,

ProLeuAspLeuProProIleIleGlnArgLeuHisGlyLeuSerAlaPheSerLeuHis
      4922  CCACTGGATCTACCTCCAATCATTCAAAGACTCCATGGCCTCAGCGCATTTCACTCCAC
            GGTGACCTAGATGGAGGTTAGTAAGTTTCTGAGGTACCGGAGTCGCGTAAAAGTGAGGTG
                                           ^
            4954 NCOI,

SerTyrSerProGlyGluIleAsnArgValAlaAlaCysLeuArgLysLeuGlyValPro
      4982  AGTTACTCTCCAGGTGAAATCAATAGGGTGGCCGCATGCCTCAGAAAACTTGGGGTACCG
            TCAATGAGAGGTCCACTTTAGTTATCCCACCGGCGTACGGAGTCTTTTGAACCCCATGGC
                                              ^                  ^
            5015 SPHI, 5035 KPNI,

ProLeuArgAlaTrpArgHisArgAlaArgSerValArgAlaArgLeuLeuAlaArgGly
```

FIG. 14-8

```
                                             GlyArgAlaAlaIleCysGlyLysTyrLeuPheAsnTrpAlaValArgThrLysLeuLys
5042  CCCTTGCGAGCTTGGAGACACCGGGCCCGGAGCGTCCGCGCTAGGCTTCTGGCCAGAGGA
      GGGAACGCTCGAACCTCTGTGGCCCGGGCCTCGCAGGCGCGATCCGAAGACCGGTCTCCT
                         ^                                ^
      5064 APAI, 5091 BALI,

GlyArgAlaAlaIleCysGlyLysTyrLeuPheAsnTrpAlaValArgThrLysLeuLys
5102  GGCAGGGCTGCCATATGTGGCAAGTACCTCTTCAACTGGGCAGTAAGAACAAAGCTCAAA
      CCGTCCCGACGGTATACACCGTTCATGGAGAAGTTGACCCGTCATTCTTGTTTCGAGTTT
                 ^
      5113 NDEI,

LeuThrProIleAlaAlaAlaGlyGlnLeuAspLeuSerGlyTrpPheThrAlaGlyTyr
5162  CTCACTCCAATAGCGGCCGCTGGCCAGCTGGACTTGTCCGGCTGGTTCACGGCTGGCTAC
      GAGTGAGGTTATCGCCGGCGACCGGTCGACCTGAACAGGCCGACCAAGTGCCGACCGATG
                     ^^         ^       ^
      5174 NOTI, 5175 EAG1 XMA3, 5182 BALI, 5186 PVU2,

SerGlyGlyAspIleTyrHisSerValSerHisAlaArgProArgTrpIleTrpPheCys
5222  AGCGGGGGAGACATTTATCACAGCGTGTCTCATGCCCGGCCCCGCTGGATCTGGTTTTGC
      TCGCCCCCTCTGTAAATAGTGTCGCACAGAGTACGGGCCGGGGCGACCTAGACCAAAACG
                                           ^
      5240 DRA3,

LeuLeuLeuLeuAlaAlaGlyValGlyIleTyrLeuLeuProAsnArgOP
5282  CTACTCCTGCTTGCTGCAGGGGTAGGCATCTACCTCCTCCCCAACCGATGAATAGTCGAC
      GATGAGGACGAACGACGTCCCCATCCGTAGATGGAGGAGGGGTTGGCTACTTATCAGCTG
                ^^                                            ^^
      5295 PSTI, 5336 SALI,
```

FIG. 14-9

```
                        MetAlaAlaTyrAlaAlaGlnGlyTyrLysValLeuValLeuAsn
  2 AGCTTACAAAACAAAATGGCTGCATATGCAGCTCAGGGCTATAAGGTGCTAGTACTCAAC
    TCGAATGTTTTGTTTTACCGACGTATACGTCGAGTCCCGATATTCCACGATCATGAGTTG
    ^                       ^                       ^
  1 HIND3, 24 NDEI, 52 SCAI,

ProSerValAlaAlaThrLeuGlyPheGlyAlaTyrMetSerLysAlaHisGlyIleAsp
 62 CCCTCTGTTGCTGCAACACTGGGCTTTGGTGCTTACATGTCCAAGGCTCATGGGATCGAT
    GGGAGACAACGACGTTGTGACCCGAAACCACGAATGTACAGGTTCCGAGTACCCTAGCTA
                                                              ^
 116 CLAI,

ProAsnIleArgThrGlyValArgThrIleThrThrGlySerProIleThrTyrSerThr
 122 CCTAACATCAGGACCGGGGTGAGAACAATTACCACTGGCAGCCCCATCACGTACTCCACC
    GGATTGTAGTCCTGGCCCCACTCTTGTTAATGGTGACCGTCGGGGTAGTGCATGAGGTGG

TyrGlyLysPheLeuAlaAspGlyGlyCysSerGlyGlyAlaTyrAspIleIleIleCys
 182 TACGGCAAGTTCCTTGCCGACGGCGGGTGCTCGGGGGGCGCTTATGACATAATAATTTGT
    ATGCCGTTCAAGGAACGGCTGCCGCCCACGAGCCCCCCGCGAATACTGTATTATTAAACA

AspGluCysHisSerThrAspAlaThrSerIleLeuGlyIleGlyThrValLeuAspGln
 242 GACGAGTGCCACTCCACGGATGCCACATCCATCTTGGGCATTGGCACTGTCCTTGACCAA
    CTGCTCACGGTGAGGTGCCTACGGTGTAGGTAGAACCCGTAACCGTGACAGGAACTGGTT

AlaGluThrAlaGlyAlaArgLeuValValLeuAlaThrAlaThrProProGlySerVal
 302 GCAGAGACTGCGGGGGCGAGACTGGTTGTGCTCGCCACCGCCACCCCTCCGGGCTCCGTC
    CGTCTCTGACGCCCCGCTCTGACCAACACGAGCGGTGGCGGTGGGGAGGCCCGAGGCAG
    ^
 303 ALWN1,

ThrValProHisProAsnIleGluGluValAlaLeuSerThrThrGlyGluIleProPhe
 362 ACTGTGCCCCATCCCAACATCGAGGAGGTTGCTCTGTCCACCACCGGAGAGATCCCTTTT
    TGACACGGGGTAGGGTTGTAGCTCCTCCAACGAGACAGGTGGTGGCCTCTCTAGGGAAAA

TyrGlyLysAlaIleProLeuGluValIleLysGlyGlyArgHisLeuIlePheCysHis
 422 TACGGCAAGGCTATCCCCCTCGAAGTAATCAAGGGGGGGAGACATCTCATCTTCTGTCAT
    ATGCCGTTCCGATAGGGGGAGCTTCATTAGTTCCCCCCCTCTGTAGAGTAGAAGACAGTA
```

FIG. 17-1

```
         SerLysLysLysCysAspGluLeuAlaAlaLysLeuValAlaLeuGlyIleAsnAlaVal
482      TCAAAGAAGAAGTGCGACGAACTCGCCGCAAAGCTGGTCGCATTGGGCATCAATGCCGTG
         AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
542      GCCTACTACCGCGGTCTTGACGTGTCCGTCATCCCGACCAGCGGCGATGTTGTCGTCGTG
         CGGATGATGGCGCCAGAACTGCACAGGCAGTAGGGCTGGTCGCCGCTACAACAGCAGCAC
                    ^                              ^
         550 SAC2,   560 DRD1,

AlaThrAspAlaLeuMetThrGlyTyrThrGlyAspPheAspSerValIleAspCysAsn
602      GCAACCGATGCCCTCATGACCGGCTATACCGGCGACTTCGACTCGGTGATAGACTGCAAT
         CGTTGGCTACGGGAGTACTGGCCGATATGGCCGCTGAAGCTGAGCCACTATCTGACGTTA
                              ^
         615 BSPH1,

ThrCysValThrGlnThrValAspPheSerLeuAspProThrPheThrIleGluThrIle
662      ACGTGTGTCACCCAGACAGTCGATTTCAGCCTTGACCCTACCTTCACCATTGAGACAATC
         TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
722      ACGCTCCCCCAAGATGCTGTCTCCCGCACTCAACGTCGGGGCAGGACTGGCAGGGGGAAG
         TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
782      CCAGGCATCTACAGATTTGTGGCACCGGGGGAGCGCCCCTCCGGCATGTTCGACTCGTCC
         GGTCCGTAGATGTCTAAACACCGTGGCCCCCTCGCGGGGAGGCCGTACAAGCTGAGCAGG
                                        ^                ^
         816 BGLI, 833 DRD1,

ValLeuCysGluCysTyrAspAlaGlyCysAlaTrpTyrGluLeuThrProAlaGluThr
842      GTCCTCTGTGAGTGCTATGACGCAGGCTGTGCTTGGTATGAGCTCACGCCCGCCGAGACT
         CAGGAGACACTCACGATACTGCGTCCGACACGAACCATACTCGAGTGCGGGCGGCTCTGA
                                                    ^
         881 SACI,

ThrValArgLeuArgAlaTyrMetAsnThrProGlyLeuProValCysGlnAspHisLeu
902      ACAGTTAGGCTACGAGCGTACATGAACACCCCGGGGCTTCCCGTGTGCCAGGACCATCTT
         TGTCAATCCGATGCTCGCATGTACTTGTGGGGCCCCGAAGGGCACACGGTCCTGGTAGAA
                                       ^
         931 SMAI XMAI,

GluPheTrpGluGlyValPheThrGlyLeuThrHisIleAspAlaHisPheLeuSerGln
962      GAATTTTGGGAGGGCGTCTTTACAGGCCTCACTCATATAGATGCCCACTTTCTATCCCAG
         CTTAAAACCCTCCCGCAGAAATGTCCGGAGTGAGTATATCTACGGGTGAAAGATAGGGTC
                                           ^
         985 STUI,

ThrLysGlnSerGlyGluAsnLeuProTyrLeuValAlaTyrGlnAlaThrValCysAla
1022     ACAAAGCAGAGTGGGGAGAACCTTCCTTACCTGGTAGCGTACCAAGCCACCGTGTGCGCT
         TGTTTCGTCTCACCCCTCTTGGAAGGAATGGACCATCGCATGGTTCGGTGGCACACGCGA
                                                              ^
         1069 DRA3,

ArgAlaGlnAlaProProProSerTrpAspGlnMetTrpLysCysLeuIleArgLeuLys
1082     AGGGCTCAAGCCCCTCCCCCATCGTGGGACCAGATGTGGAAGTGTTTGATTCGCCTCAAG
```

FIG. 17-2

```
                TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
         1142   CCCACCCTCCATGGGCCAACACCCCTGCTATACAGACTGGGCGCTGTTCAGAATGAAATC
                GGGTGGGAGGTACCCGGTTGTGGGGACGATATGTCTGACCCGCGACAAGTCTTACTTTAG
                    ^
                1150 NCOI,

.  ThrLeuThrHisProValThrLysTyrIleMetThrCysMetSerAlaAspLeuGluVal
         1202   ACCCTGACGCACCCAGTCACCAAATACATCATGACATGCATGTCGGCCGACCTGGAGGTC
                TGGGACTGCGTGGGTCAGTGGTTTATGTAGTACTGTACGTACAGCCGGCTGGACCTCCAG
                        ^       ^    ^          ^          ^
                1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
         1262   GTCACGAGCACCTGGGTGCTCGTTGGCGGCGTCCTGGCTGCTTTGGCCGCGTATTGCCTG
                CAGTGCTCGTGGACCCACGAGCAACCGCCGCAGGACCGACGAAACCGGCGCATAACGGAC

SerThrGlyCysValValIleValGlyArgValValLeuSerGlyLysProAlaIleIle
         1322   TCAACAGGCTGCGTGGTCATAGTGGGCAGGGTCGTCTTGTCCGGGAAGCCGGCAATCATA
                AGTTGTCCGACGCACCAGTATCACCCGTCCCAGCAGAACAGGCCCTTCGGCCGTTAGTAT
                                                                      ^
                1369 NAEI,

ProAspArgGluValLeuTyrArgGluPheAspGluMetGluGluCysSerGlnHisLeu
         1382   CCTGACAGGGAAGTCCTCTACCGAGAGTTCGATGAGATGGAAGAGTGCTCTCAGCACTTA
                GGACTGTCCCTTCAGGAGATGGCTCTCAAGCTACTCTACCTTCTCACGAGAGTCGTGAAT
                   ^
                1385 DRD1,

ProTyrIleGluGlnGlyMetMetLeuAlaGluGlnPheLysGlnLysAlaLeuGlyLeu
         1442   CCGTACATCGAGCAAGGGATGATGCTCGCCGAGCAGTTCAAGCAGAAGGCCCTCGGCCTC
                GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
         1502   CTGCAGACCGCGTCCCGTCAGGCAGAGGTTATCGCCCCTGCTGTCCAGACCAACTGGCAA
                GACGTCTGGCGCAGGGCAGTCCGTCTCCAATAGCGGGGACGACAGGTCTGGTTGACCGTT
                ^      ^
                1502 PSTI, 1507 TTH3I,

LysLeuGluThrPheTrpAlaLysHisMetTrpAsnPheIleSerGlyIleGlnTyrLeu
         1562   AAACTCGAGACCTTCTGGGCGAAGCATATGTGGAACTTCATCAGTGGGATACAATACTTG
                TTTGAGCTCTGGAAGACCCGCTTCGTATACACCTTGAAGTAGTCACCCTATGTTATGAAC
                      ^                  ^
                1565 XHOI, 1586 NDEI,

AlaGlyLeuSerThrLeuProGlyAsnProAlaIleAlaSerLeuMetAlaPheThrAla
         1622   GCGGGCTTGTCAACGCTGCCTGGTAACCCCGCCATTGCTTCATTGATGGCTTTTACAGCT
                CGCCCGAACAGTTGCGACGGACCATTGGGGCGGTAACGAAGTAACTACCGAAAATGTCGA
                                 ^                                    ^
                1643 BSTE2, 1677 ALWN1 PVU2,

AlaValThrSerProLeuThrThrSerGlnThrLeuLeuPheAsnIleLeuGlyGlyTrp
         1682   GCTGTCACCAGCCCACTAACCACTAGCCAAACCCTCCTCTTCAACATATTGGGGGGGTGG
                CGACAGTGGTCGGGTGATTGGTGATCGGTTTGGGAGGAGAAGTTGTATAACCCCCCCACC
```

FIG. 17-3

```
            ValAlaAlaGlnLeuAlaAlaProGlyAlaAlaThrAlaPheValGlyAlaGlyLeuAla
   1742     GTGGCTGCCCAGCTCGCCGCCCCCGGTGCCGCTACTGCCTTTGTGGGCGCTGGCTTAGCT
            CACCGACGGGTCGAGCGGCGGGGGCCACGGCGATGACGGAAACACCCGCGACCGAATCGA
                                                                       ^
   1794 ESP1,

GlyAlaAlaIleGlySerValGlyLeuGlyLysValLeuIleAspIleLeuAlaGlyTyr
   1802     GGCGCCGCCATCGGCAGTGTTGGACTGGGGAAGGTCCTCATAGACATCCTTGCAGGGTAT
            CCGCGGCGGTAGCCGTCACAACCTGACCCCTTCCAGGAGTATCTGTAGGAACGTCCCATA
            ^
   1802 KAS1 NAR1,

GlyAlaGlyValAlaGlyAlaLeuValAlaPheLysIleMetSerGlyGluValProSer
   1862     GGCGCGGGCGTGGCGGGAGCTCTTGTGGCATTCAAGATCATGAGCGGTGAGGTCCCCTCC
            CCGCGCCCGCACCGCCCTCGAGAACACCGTAAGTTCTAGTACTCGCCACTCCAGGGGAGG
                              ^                  ^
   1878 SACI, 1899 BSPH1,

ThrGluAspLeuValAsnLeuLeuProAlaIleLeuSerProGlyAlaLeuValValGly
   1922     ACGGAGGACCTGGTCAATCTACTGCCCGCCATCCTCTCGCCCGGAGCCCTCGTAGTCGGC
            TGCCTCCTGGACCAGTTAGATGACGGGCGGTAGGAGAGCGGGCCTCGGGAGCATCAGCCG
                      ^
   1928 TTH3I,

ValValCysAlaAlaIleLeuArgArgHisValGlyProGlyGluGlyAlaValGlnTrp
   1982     GTGGTCTGTGCAGCAATACTGCGCCGGCACGTTGGCCCGGGCGAGGGGGCAGTGCAGTGG
            CACCAGACACGTCGTTATGACGCGGCCGTGCAACCGGGCCCGCTCCCCCGTCACGTCACC
                                      ^             ^
   2004 NAEI, 2017 SMAI XMAI,

MetAsnArgLeuIleAlaPheAlaSerArgGlyAsnHisValSerProThrHisTyrVal
   2042     ATGAACCGGCTGATAGCCTTCGCCTCCCGGGGGAACCATGTTTCCCCCACGCACTACGTG
            TACTTGGCCGACTATCGGAAGCGGAGGGCCCCCTTGGTACAAAGGGGGTGCGTGATGCAC
                                    ^                   ^
   2067 SMAI XMAI, 2093 DRA3,

ProGluSerAspAlaAlaAlaArgValThrAlaIleLeuSerSerLeuThrValThrGln
   2102     CCGGAGAGCGATGCAGCTGCCCGCGTCACTGCCATACTCAGCAGCCTCACTGTAACCCAG
            GGCCTCTCGCTACGTCGACGGGCGCAGTGACGGTATGAGTCGTCGGAGTGACATTGGGTC
                           ^                                     ^
   2115 PVU2, 2159 ALWN1,

LeuLeuArgArgLeuHisGlnTrpIleSerSerGluCysThrThrProCysSerGlySer
   2162     CTCCTGAGGCGACTGCACCAGTGGATAAGCTCGGAGTGTACCACTCCATGCTCCGGTTCC
            GAGGACTCCGCTGACGTGGTCACCTATTCGAGCCTCACATGGTGAGGTACGAGGCCAAGG
            ^                                                           ^
   2164 MST2, 2220 ECON1,

TrpLeuArgAspIleTrpAspTrpIleCysGluValLeuSerAspPheLysThrTrpLeu
   2222     TGGCTAAGGGACATCTGGGACTGGATATGCGAGGTGTTGAGCGACTTTAAGACCTGGCTA
            ACCGATTCCCTGTAGACCCTGACCTATACGCTCCACAACTCGCTGAAATTCTGGACCGAT

LysAlaLysLeuMetProGlnLeuProGlyIleProPheValSerCysGlnArgGlyTyr
   2282     AAAGCTAAGCTCATGCCACAGCTGCCTGGGATCCCCTTTGTGTCCTGCCAGCGCGGGTAT
            TTTCGATTCGAGTACGGTGTCGACGGACCCTAGGGGAAACACAGGACGGTCGCGCCCATA
                    ^                     ^         ^
   2285 ESP1, 2300 PVU2, 2310 BAMHI,
```

FIG. 17-4

```
     LysGlyValTrpArgGlyAspGlyIleMetHisThrArgCysHisCysGlyAlaGluIle
2342 AAGGGGGTCTGGCGAGGGGACGGCATCATGCACACTCGCTGCCACTGTGGAGCTGAGATC
     TTCCCCCAGACCGCTCCCCTGCCGTAGTACGTGTGAGCGACGGTGACACCTCGACTCTAG

ThrGlyHisValLysAsnGlyThrMetArgIleValGlyProArgThrCysArgAsnMet
2402 ACTGGACATGTCAAAAACGGGACGATGAGGATCGTCGGTCCTAGGACCTGCAGGAACATG
     TGACCTGTACAGTTTTTGCCCTGCTACTCCTAGCAGCCAGGATCCTGGACGTCCTTGTAC
                       ^                  ^         ^^
     2425 BSAB1, 2441 AVR2, 2448 SSE83871, 2449 PSTI,

TrpSerGlyThrPheProIleAsnAlaTyrThrThrGlyProCysThrProLeuProAla
2462 TGGAGTGGGACCTTCCCCATTAATGCCTACACCACGGGCCCCTGTACCCCCCTTCCTGCG
     ACCTCACCCTGGAAGGGGTAATTACGGATGTGGTGCCCGGGGACATGGGGGGAAGGACGC
                   ^                    ^
     2480 ASE1, 2497 APAI,

ProAsnTyrThrPheAlaLeuTrpArgValSerAlaGluGluTyrValGluIleArgGln
2522 CCGAACTACACGTTCGCGCTATGGAGGGTGTCTGCAGAGGAATACGTGGAGATAAGGCAG
     GGCTTGATGTGCAAGCGCGATACCTCCCACAGACGTCTCCTTATGCACCTCTATTCCGTC
                                     ^
     2553 PSTI,

ValGlyAspPheHisTyrValThrGlyMetThrThrAspAsnLeuLysCysProCysGln
2582 GTGGGGGACTTCCACTACGTGACGGGTATGACTACTGACAATCTTAAATGCCCGTGCCAG
     CACCCCCTGAAGGTGATGCACTGCCCATACTGATGACTGTTAGAATTTACGGGCACGGTC
                 ^
     2594 DRA3,

ValProSerProGluPhePheThrGluLeuAspGlyValArgLeuHisArgPheAlaPro
2642 GTCCCATCGCCCGAATTTTTCACAGAATTGGACGGGGTGCGCCTACATAGGTTTGCGCCC
     CAGGGTAGCGGGCTTAAAAAGTGTCTTAACCTGCCCCACGCGGATGTATCCAAACGCGGG

ProCysLysProLeuLeuArgGluGluValSerPheArgValGlyLeuHisGluTyrPro
2702 CCCTGCAAGCCCTTGCTGCGGGAGGAGGTATCATTCAGAGTAGGACTCCACGAATACCCG
     GGGACGTTCGGGAACGACGCCCTCCTCCATAGTAAGTCTCATCCTGAGGTGCTTATGGGC
                                                              ^
     2757 HGIE2,

ValGlySerGlnLeuProCysGluProGluProAspValAlaValLeuThrSerMetLeu
2762 GTAGGGTCGCAATTACCTTGCGAGCCCGAACCGGACGTGGCCGTGTTGACGTCCATGCTC
     CATCCCAGCGTTAATGGAACGCTCGGGCTTGGCCTGCACCGGCACAACTGCAGGTACGAG
                                                         ^
     2809 AAT2,

ThrAspProSerHisIleThrAlaGluAlaAlaGlyArgArgLeuAlaArgGlySerPro
2822 ACTGATCCCTCCCATATAACAGCAGAGGCGGCCGGGCGAAGGTTGGCGAGGGGATCACCC
     TGACTAGGGAGGGTATATTGTCGTCTCCGCCGGCCCGCTTCCAACCGCTCCCCTAGTGGG
                                                ^
     2850 EAG1 XMA3,

ProSerValAlaSerSerSerAlaSerGlnLeuSerAlaProSerLeuLysAlaThrCys
2882 CCCTCTGTGGCCAGCTCCTCGGCTAGCCAGCTATCCGCTCCATCTCTCAAGGCAACTTGC
     GGGAGACACCGGTCGAGGAGCCGATCGGTCGATAGGCGAGGTAGAGAGTTCCGTTGAACG
                 ^         ^
     2889 BALI, 2903 NHEI,
```

FIG. 17-5

```
                ThrAlaAsnHisAspSerProAspAlaGluLeuIleGluAlaAsnLeuLeuTrpArgGln
     2942  ACCGCTAACCATGACTCCCCTGATGCTGAGCTCATAGAGGCCAACCTCCTATGGAGGCAG
           TGGCGATTGGTACTGAGGGGACTACGACTCGAGTATCTCCGGTTGGAGGATACCTCCGTC
                                        ^  ^
     2966 ESP1, 2969 SACI,

GluMetGlyGlyAsnIleThrArgValGluSerGluAsnLysValValIleLeuAspSer
     3002  GAGATGGGCGGCAACATCACCAGGGTTGAGTCAGAAAACAAAGTGGTGATTCTGGACTCC
           CTCTACCCGCCGTTGTAGTGGTCCCAACTCAGTCTTTTGTTTCACCACTAAGACCTGAGG

PheAspProLeuValAlaGluGluAspGluArgGluIleSerValProAlaGluIleLeu
     3062  TTCGATCCGCTTGTGGCGGAGGAGGACGAGCGGGAGATCTCCGTACCCGCAGAAATCCTG
           AAGCTAGGCGAACACCGCCTCCTCCTGCTCGCCCTCTAGAGGCATGGGCGTCTTTAGGAC
                                                        ^
     3096 BGL2,

ArgLysSerArgArgPheAlaGlnAlaLeuProValTrpAlaArgProAspTyrAsnPro
     3122  CGGAAGTCTCGGAGATTCGCCCAGGCCCTGCCCGTTTGGGCGCGGCCGGACTATAACCCC
           GCCTTCAGAGCCTCTAAGCGGGTCCGGGACGGGCAAACCCGCGCCGGCCTGATATTGGGG
                                ^                     ^
     3143 ALWN1, 3164 EAG1 XMA3,

ProLeuValGluThrTrpLysLysProAspTyrGluProProValValHisGlyCysPro
     3182  CCGCTAGTGGAGACGTGGAAAAAGCCCGACTACGAACCACCTGTGGTCCATGGCTGCCCG
           GGCGATCACCTCTGCACCTTTTTCGGGCTGATGCTTGGTGGACACCAGGTACCGACGGGC
                                       ^                ^
     3217 HGIE2, 3229 NCOI,

LeuProProProLysSerProProValProProProArgLysLysArgThrValValLeu
     3242  CTTCCACCTCCAAAGTCCCCTCCTGTGCCTCCGCCTCGGAAGAAGCGGACGGTGGTCCTC
           GAAGGTGGAGGTTTCAGGGGAGGACACGGAGGCGGAGCCTTCTTCGCCTGCCACCAGGAG

ThrGluSerThrLeuSerThrAlaLeuAlaGluLeuAlaThrArgSerPheGlySerSer
     3302  ACTGAATCAACCCTATCTACTGCCTTGGCCGAGCTCGCCACCAGAAGCTTTGGCAGCTCC
           TGACTTAGTTGGGATAGATGACGGAACCGGCTCGAGCGGTGGTCTTCGAAACCGTCGAGG
                                     ^              ^
     3332 SACI, 3346 HIND3,

SerThrSerGlyIleThrGlyAspAsnThrThrThrSerSerGluProAlaProSerGly
            TCAACTTCCGGCATTACGGGCGACAATACGACAACATCCTCTGAGCCCGCCCCTTCTGGC
            AGTTGAAGGCCGTAATGCCCGCTGTTATGCTGTTGTAGGAGACTCGGGCGGGGAAGACCG

CysProProAspSerAspAlaGluSerTyrSerSerMetProProLeuGluGlyGluPro
            TGCCCCCCCGACTCCGACGCTGAGTCCTATTCCTCCATGCCCCCCCTGGAGGGGGAGCCT
            ACGGGGGGGCTGAGGCTGCGACTCAGGATAAGGAGGTACGGGGGGGACCTCCCCCTCGGA
                   ^
     3437 EAM11051,

GlyAspProAspLeuSerAspGlySerTrpSerThrValSerSerGluAlaAsnAlaGlu
            GGGGATCCGGATCTTAGCGACGGGTCATGGTCAACGGTCAGTAGTGAGGCCAACGCGGAG
            CCCCTAGGCCTAGAATCGCTGCCCAGTACCAGTTGCCAGTCATCACTCCGGTTGCGCCTC
              ^^ ^
     3484 BAMHI, 3485 BSAB1, 3487 BSPE1,

AspValValCysCysSerMetSerTyrSerTrpThrGlyAlaLeuValThrProCysAla
     3542  GATGTCGTGTGCTGCTCAATGTCTTACTCTTGGACAGGCGCACTCGTCACCCCGTGCGCC
           CTACAGCACACGACGAGTTACAGAATGAGAACCTGTCCGCGTGAGCAGTGGGGCACGCGG
```

FIG. 17-6

```
              AlaGluGlnLysLeuProIleAsnAlaLeuSerAsnSerLeuLeuArgHisHisAsn
3602   GCGGAAGAACAGAAACTGCCCATCAATGCACTAAGCAACTCGTTGCTACGTCACCACAAT
       CGCCTTCTTGTCTTTGACGGGTAGTTACGTGATTCGTTGAGCAACGATGCAGTGGTGTTA
                        ^                                  ^
3611 ALWN1,  3655 PFLM1,

LeuValTyrSerThrThrSerArgSerAlaCysGlnArgGlnLysLysValThrPheAsp
3662   TTGGTGTATTCCACCACCTCACGCAGTGCTTGCCAAAGGCAGAAGAAAGTCACATTTGAC
       AACCACATAAGGTGGTGGAGTGCGTCACGAACGGTTTCCGTCTTCTTTCAGTGTAAACTG
                            ^
3681 DRA3,

ArgLeuGlnValLeuAspSerHisTyrGlnAspValLeuLysGluValLysAlaAlaAla
3722   AGACTGCAAGTTCTGGACAGCCATTACCAGGACGTACTCAAGGAGGTTAAAGCAGCGGCG
       TCTGACGTTCAAGACCTGTCGGTAATGGTCCTGCATGAGTTCCTCCAATTTCGTCGCCGC

SerLysValLysAlaAsnLeuLeuSerValGluGluAlaCysSerLeuThrProProHis
3782   TCAAAAGTGAAGGCTAACTTGCTATCCGTAGAGGAAGCTTGCAGCCTGACGCCCCCACAC
       AGTTTTCACTTCCGATTGAACGATAGGCATCTCCTTCGAACGTCGGACTGCGGGGGTGTG
                                                ^
3816 HIND3,

SerAlaLysSerLysPheGlyTyrGlyAlaLysAspValArgCysHisAlaArgLysAla
3842   TCAGCCAAATCCAAGTTTGGTTATGGGGCAAAAGACGTCCGTTGCCATGCCAGAAAGGCC
       AGTCGGTTTAGGTTCAAACCAATACCCCGTTTTCTGCAGGCAACGGTACGGTCTTTCCGG
                                        ^              ^
3875 AAT2,  3890 BGLI,

ValThrHisIleAsnSerValTrpLysAspLeuLeuGluAspAsnValThrProIleAsp
3902   GTAACCCACATCAACTCCGTGTGGAAAGACCTTCTGGAAGACAATGTAACACCAATAGAC
       CATTGGGTGTAGTTGAGGCACACCTTTCTGGAAGACCTTCTGTTACATTGTGGTTATCTG

ThrThrIleMetAlaLysAsnGluValPheCysValGlnProGluLysGlyGlyArgLys
3962   ACTACCATCATGGCTAAGAACGAGGTTTTCTGCGTTCAGCCTGAGAAGGGGGGTCGTAAG
       TGATGGTAGTACCGATTCTTGCTCCAAAAGACGCAAGTCGGACTCTTCCCCCCAGCATTC

ProAlaArgLeuIleValPheProAspLeuGlyValArgValCysGluLysMetAlaLeu
4022   CCAGCTCGTCTCATCGTGTTCCCCGATCTGGGCGTGCGCGTGTGCGAAAAGATGGCTTTG
       GGTCGAGCAGAGTAGCACAAGGGGCTAGACCCGCACGCGCACACGCTTTTCTACCGAAAC

TyrAspValValThrLysLeuProLeuAlaValMetGlySerSerTyrGlyPheGlnTyr
4082   TACGACGTGGTTACAAAGCTCCCCTTGGCCGTGATGGGAAGCTCCTACGGATTCCAATAC
       ATGCTGCACCAATGTTTCGAGGGGAACCGGCACTACCCTTCGAGGATGCCTAAGGTTATG

SerProGlyGlnArgValGluPheLeuValGlnAlaTrpLysSerLysLysThrProMet
4142   TCACCAGGACAGCGGGTTGAATTCCTCGTGCAAGCGTGGAAGTCCAAGAAAACCCCAATG
       AGTGGTCCTGTCGCCCAACTTAAGGAGCACGTTCGCACCTTCAGGTTCTTTTGGGGTTAC
                        ^
4160 ECORI,

GlyPheSerTyrAspThrArgCysPheAspSerThrValThrGluSerAspIleArgThr
4202   GGGTTCTCGTATGATACCCGCTGCTTTGACTCCACAGTCACTGAGAGCGACATCCGTACG
       CCCAAGAGCATACTATGGGCGACGAAACTGAGGTGTCAGTGACTCTCGCTGTAGGCATGC
                                              ^      ^
```

FIG. 17-7

4229 DRD1, 4236 ALWN1,

```
           GluGluAlaIleTyrGlnCysCysAspLeuAspProGlnAlaArgValAlaIleLysSer
     4262  GAGGAGGCAATCTACCAATGTTGTGACCTCGACCCCCAAGCCCGCGTGGCCATCAAGTCC
           CTCCTCCGTTAGATGGTTACAACACTGGAGCTGGGGGTTCGGGCGCACCGGTAGTTCAGG
                                                    ^           ^
```

4301 BGLI, 4308 BALI,

```
           LeuThrGluArgLeuTyrValGlyGlyProLeuThrAsnSerArgGlyGluAsnCysGly
     4322  CTCACCGAGAGGCTTTATGTTGGGGGCCCTCTTACCAATTCAAGGGGGGAGAACTGCGGC
           GAGTGGCTCTCCGAAATACAACCCCCGGGAGAATGGTTAAGTTCCCCCCTCTTGACGCCG
                                          ^
```

4345 APAI,

```
           TyrArgArgCysArgAlaSerGlyValLeuThrThrSerCysGlyAsnThrLeuThrCys
     4382  TATCGCAGGTGCCGCGCGAGCGGCGTACTGACAACTAGCTGTGGTAACACCCTCACTTGC
           ATAGCGTCCACGGCGCGCTCGCCGCATGACTGTTGATCGACACCATTGTGGGAGTGAACG
```

```
           TyrIleLysAlaArgAlaAlaCysArgAlaAlaGlyLeuGlnAspCysThrMetLeuVal
     4442  TACATCAAGGCCCGGGCAGCCTGTCGAGCCGCAGGGCTCCAGGACTGCACCATGCTCGTG
           ATGTAGTTCCGGGCCCGTCGGACAGCTCGGCGTCCCGAGGTCCTGACGTGGTACGAGCAC
                                  ^
```

4452 SMAI XMAI,

```
           CysGlyAspAspLeuValValIleCysGluSerAlaGlyValGlnGluAspAlaAlaSer
     4502  TGTGGCGACGACTTAGTCGTTATCTGTGAAAGCGCGGGGGTCCAGGAGGACGCGGCGAGC
           ACACCGCTGCTGAATCAGCAATAGACACTTTCGCGCCCCAGGTCCTCCTGCGCCGCTCG
                ^   ^
```

4508 DRD1, 4511 TTH3I,

```
           LeuArgAlaPheThrGluAlaMetThrArgTyrSerAlaProProGlyAspProProGln
     4562  CTGAGAGCCTTCACGGAGGCTATGACCAGGTACTCCGCCCCCCCTGGGGACCCCCCACAA
           GACTCTCGGAAGTGCCTCCGATACTGGTCCATGAGGCGGGGGGGACCCCTGGGGGGTGTT
```

```
           ProGluTyrAspLeuGluLeuIleThrSerCysSerSerAsnValSerValAlaHisAsp
     4622  CCAGAATACGACTTGGAGCTCATAACATCATGCTCCTCCAACGTGTCAGTCGCCCACGAC
           GGTCTTATGCTGAACCTCGAGTATTGTAGTACGAGGAGGTTGCACAGTCAGCGGGTGCTG
                                   ^
```

4637 SACI,

```
           GlyAlaGlyLysArgValTyrTyrLeuThrArgAspProThrThrProLeuAlaArgAla
     4682  GGCGCTGGAAAGAGGGTCTACTACCTCACCCGTGACCCTACAACCCCCTCGCGAGAGCT
           CCGCGACCTTTCTCCCAGATGATGGAGTGGGCACTGGGATGTTGGGGGAGCGCTCTCGA
                                                                   ^
```

4731 NRUI,

```
           AlaTrpGluThrAlaArgHisThrProValAsnSerTrpLeuGlyAsnIleIleMetPhe
     4742  GCGTGGGAGACAGCAAGACACACTCCAGTCAATTCCTGGCTAGGCAACATAATCATGTTT
           CGCACCCTCTGTCGTTCTGTGTGAGGTCAGTTAAGGACCGATCCGTTGTATTAGTACAAA
```

```
           AlaProThrLeuTrpAlaArgMetIleLeuMetThrHisPhePheSerValLeuIleAla
     4802  GCCCCCACACTGTGGGCGAGGATGATACTGATGACCCATTTCTTTAGCGTCCTTATAGCC
           CGGGGGTGTGACACCCGCTCCTACTATGACTACTGGGTAAAGAAATCGCAGGAATATCGG
                ^^
```

4806 PFLM1, 4807 DRA3,

```
           ArgAspGlnLeuGluGlnAlaLeuAspCysGluIleTyrGlyAlaCysTyrSerIleGlu
```

FIG. 17-8

```
4862 AGGGACCAGCTTGAACAGGCCCTCGATTGCGAGATCTACGGGGCCTGCTACTCCATAGAA
     TCCCTGGTCGAACTTGTCCGGGAGCTAACGCTCTAGATGCCCCGGACGATGAGGTATCTT
                                                 ^
4893 BGL2,

ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
     GGTGACCTAGATGGAGGTTAGTAAGTTTCTGAGGTACCGGAGTCGCGTAAAAGTGAGGTG
                                         ^
4954 NCOI,

SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
     TCAATGAGAGGTCCACTTTAGTTATCCCACCGGCGTACGGAGTCTTTTGAACCCCATGGC
                                        ^                ^
5015 SPHI, 5035 KPNI,

ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
     GGGAACGCTCGAACCTCTGTGGCCCGGGCCTCGCAGGCGCGATCCGAAGACCGGTCTCCT
                            ^                     ^
5064 APAI, 5091 BALI,

GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
     CCGTCCCGACGGTATACACCGTTCATGGAGAAGTTGACCCGTCATTCTTGTTTCGAGTTT
                     ^
5113 NDEI,

LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
     GAGTGAGGTTATCGCCGGCGACCGGTCGACCTGAACAGGCCGACCAAGTGCCGACCGATG
                    ^^   ^                           ^        ^
5174 NOTI, 5175 EAG1 XMA3, 5182 BALI, 5186 PVU2,

SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
     TCGCCCCCTCTGTAAATAGTGTCGCACAGAGTACGGGCCGGGGCGACCTAGACCAAAACG
                     ^
5240 DRA3,

LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
     GATGAGGACGAACGACGTCCCCATCCGTAGATGGAGGAGGGGTTGGCTTACTCGTGCTTA
                          ^
5295 PSTI,

ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
     GGATTTGGAGTTTCTTTCTGGTTTGCATTGTGGTTGGCCGCCGGCGTCCTGCAGTTCAAG
                                           ^^       ^         ^
5380 NOTI, 5381 EAG1 XMA3, 5390 AAT2, 5401 SMAI XMAI,

ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
     GGCCCACCGCCAGTCTAGCAACCACCTCAAATGAACAACGGCGCGTCCCCGGGATCTAAC
                                                        ^
```

FIG. 17-9

```
      5449 APAI,

GlyValArgAlaThrArgLysThrSerGluArgSerGlnProArgGlyArgArgGlnPro
5462  GGTGTGCGCGCGACGAGAAAGACTTCCGAGCGGTCGCAACCTCGAGGTAGACGTCAGCCT
      CCACACGCGCGCTGCTCTTTCTGAAGGCTCGCCAGCGTTGGAGCTCCATCTGCAGTCGGA
               ^             ^              ^              ^
      5467 BSSH2, 5478 XMNI, 5502 XHOI, 5511 AAT2,

IleProLysAlaArgArgProGluGlyArgThrTrpAlaGlnProGlyTyrProTrpPro
5522  ATCCCCAAGGCTCGTCGGCCCGAGGGCAGGACCTGGGCTCAGCCCGGGTACCCTTGGCCC
      TAGGGGTTCCGAGCAGCCGGGCTCCCGTCCTGGACCCGAGTCGGGCCCATGGGAACCGGG
                             ^              ^       ^      ^
      5548 ALWN1, 5558 ESP1, 5564 SMAI XMAI, 5568 KPNI,

LeuTyrGlyAsnGluGlyCysGlyTrpAlaGlyTrpLeuLeuSerProArgGlySerArg
5582  CTCTATGGCAATGAGGGCTGCGGGTGGGCGGGATGGCTCCTGTCTCCCCGTGGCTCTCGG
      GAGATACCGTTACTCCCGACGCCCACCCGCCCTACCGAGGACAGAGGGGCACCGAGAGCC

ProSerTrpGlyProThrAspProArgArgArgSerArgAsnLeuGlyLysOC AM
5642  CCTAGCTGGGGCCCCACAGACCCCCGGCGTAGGTCGCGCAATTTGGGTAAGTAATAGTCG
      GGATCGACCCCGGGGTGTCTGGGGGCCGCATCCAGCGCGTTAAACCCATTCATTATCAGC
      ^                                                         ^
      5650 APAI, 5698 SALI,

5702  AC
      TG
                              FIG. 17-10
```

```
                           MetAlaAlaTyrAlaAlaGlnGlyTyrLysValLeuValLeuAsn
  2 AGCTTACAAAACAAAATGGCTGCATATGCAGCTCAGGGCTATAAGGTGCTAGTACTCAAC
    TCGAATGTTTTGTTTTACCGACGTATACGTCGAGTCCCGATATTCCACGATCATGAGTTG
    ^                      ^                           ^
  1 HIND3,  24 NDEI,  52 SCAI,

ProSerValAlaAlaThrLeuGlyPheGlyAlaTyrMetSerLysAlaHisGlyIleAsp
 62 CCCTCTGTTGCTGCAACACTGGGCTTTGGTGCTTACATGTCCAAGGCTCATGGGATCGAT
    GGGAGACAACGACGTTGTGACCCGAAACCACGAATGTACAGGTTCCGAGTACCCTAGCTA
                                                              ^
 116 CLAI,

ProAsnIleArgThrGlyValArgThrIleThrThrGlySerProIleThrTyrSerThr
122 CCTAACATCAGGACCGGGGTGAGAACAATTACCACTGGCAGCCCCATCACGTACTCCACC
    GGATTGTAGTCCTGGCCCCACTCTTGTTAATGGTGACCGTCGGGGTAGTGCATGAGGTGG

TyrGlyLysPheLeuAlaAspGlyGlyCysSerGlyGlyAlaTyrAspIleIleIleCys
182 TACGGCAAGTTCCTTGCCGACGGCGGGTGCTCGGGGGGCGCTTATGACATAATAATTTGT
    ATGCCGTTCAAGGAACGGCTGCCGCCCACGAGCCCCCCGCGAATACTGTATTATTAAACA

AspGluCysHisSerThrAspAlaThrSerIleLeuGlyIleGlyThrValLeuAspGln
242 GACGAGTGCCACTCCACGGATGCCACATCCATCTTGGGCATTGGCACTGTCCTTGACCAA
    CTGCTCACGGTGAGGTGCCTACGGTGTAGGTAGAACCCGTAACCGTGACAGGAACTGGTT

AlaGluThrAlaGlyAlaArgLeuValValLeuAlaThrAlaThrProProGlySerVal
302 GCAGAGACTGCGGGGGCGAGACTGGTTGTGCTCGCCACCGCCACCCCTCCGGGCTCCGTC
    CGTCTCTGACGCCCCCGCTCTGACCAACACGAGCGGTGGCGGTGGGGAGGCCCGAGGCAG
    ^
 303 ALWN1,

ThrValProHisProAsnIleGluGluValAlaLeuSerThrThrGlyGluIleProPhe
362 ACTGTGCCCCATCCCAACATCGAGGAGGTTGCTCTGTCCACCACCGGAGAGATCCCTTTT
    TGACACGGGGTAGGGTTGTAGCTCCTCCAACGAGACAGGTGGTGGCCTCTCTAGGGAAAA

TyrGlyLysAlaIleProLeuGluValIleLysGlyGlyArgHisLeuIlePheCysHis
422 TACGGCAAGGCTATCCCCCTCGAAGTAATCAAGGGGGGGAGACATCTCATCTTCTGTCAT
    ATGCCGTTCCGATAGGGGGAGCTTCATTAGTTCCCCCCCTCTGTAGAGTAGAAGACAGTA

SerLysLysLysCysAspGluLeuAlaAlaLysLeuValAlaLeuGlyIleAsnAlaVal
482 TCAAAGAAGAAGTGCGACGAACTCGCCGCAAAGCTGGTCGCATTGGGCATCAATGCCGTG
    AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
542 GCCTACTACCGCGGTCTTGACGTGTCCGTCATCCCGACCAGCGGCGATGTTGTCGTCGTG
    CGGATGATGGCGCCAGAACTGCACAGGCAGTAGGGCTGGTCGCCGCTACAACAGCAGCAC
                                           ^        ^
 550 SAC2,  560 DRD1,

AlaThrAspAlaLeuMetThrGlyTyrThrGlyAspPheAspSerValIleAspCysAsn
602 GCAACCGATGCCCTCATGACCGGCTATACCGGCGACTTCGACTCGGTGATAGACTGCAAT
    CGTTGGCTACGGGAGTACTGGCCGATATGGCCGCTGAAGCTGAGCCACTATCTGACGTTA
                                                     ^
 615 BSPH1,
```

FIG. 18-1

```
                    ThrCysValThrGlnThrValAspPheSerLeuAspProThrPheThrIleGluThrIle
        662  ACGTGTGTCACCCAGACAGTCGATTTCAGCCTTGACCCTACCTTCACCATTGAGACAATC
             TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
        722  ACGCTCCCCCAAGATGCTGTCTCCCGCACTCAACGTCGGGGCAGGACTGGCAGGGGGAAG
             TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
        782  CCAGGCATCTACAGATTTGTGGCACCGGGGGAGCGCCCCTCCGGCATGTTCGACTCGTCC
             GGTCCGTAGATGTCTAAACACCGTGGCCCCCTCGCGGGGAGGCCGTACAAGCTGAGCAGG
                                                        ^              ^
             816 BGLI, 833 DRD1,

ValLeuCysGluCysTyrAspAlaGlyCysAlaTrpTyrGluLeuThrProAlaGluThr
        842  GTCCTCTGTGAGTGCTATGACGCAGGCTGTGCTTGGTATGAGCTCACGCCCGCCGAGACT
             CAGGAGACACTCACGATACTGCGTCCGACACGAACCATACTCGAGTGCGGGCGGCTCTGA
                                                              ^
             881 SACI,

ThrValArgLeuArgAlaTyrMetAsnThrProGlyLeuProValCysGlnAspHisLeu
        902  ACAGTTAGGCTACGAGCGTACATGAACACCCCGGGGCTTCCCGTGTGCCAGGACCATCTT
             TGTCAATCCGATGCTCGCATGTACTTGTGGGGCCCCGAAGGGCACACGGTCCTGGTAGAA
                                            ^
             931 SMAI XMAI,

GluPheTrpGluGlyValPheThrGlyLeuThrHisIleAspAlaHisPheLeuSerGln
        962  GAATTTTGGGAGGGCGTCTTTACAGGCCTCACTCATATAGATGCCCACTTTCTATCCCAG
             CTTAAAACCCTCCCGCAGAAATGTCCGGAGTGAGTATATCTACGGGTGAAAGATAGGGTC
                                                   ^
             985 STUI,

ThrLysGlnSerGlyGluAsnLeuProTyrLeuValAlaTyrGlnAlaThrValCysAla
       1022  ACAAAGCAGAGTGGGGAGAACCTTCCTTACCTGGTAGCGTACCAAGCCACCGTGTGCGCT
             TGTTTCGTCTCACCCCTCTTGGAAGGAATGGACCATCGCATGGTTCGGTGGCACACGCGA
                                                              ^
             1069 DRA3,

ArgAlaGlnAlaProProProSerTrpAspGlnMetTrpLysCysLeuIleArgLeuLys
       1082  AGGGCTCAAGCCCCTCCCCCATCGTGGGACCAGATGTGGAAGTGTTTGATTCGCCTCAAG
             TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
       1142  CCCACCCTCCATGGGCCAACACCCCTGCTATACAGACTGGGCGCTGTTCAGAATGAAATC
             GGGTGGGAGGTACCCGGTTGTGGGGACGATATGTCTGACCCGCGACAAGTCTTACTTTAG
                                ^
             1150 NCOI,

ThrLeuThrHisProValThrLysTyrIleMetThrCysMetSerAlaAspLeuGluVal
       1202  ACCCTGACGCACCCAGTCACCAAATACATCATGACATGCATGTCGGCCGACCTGGAGGTC
             TGGGACTGCGTGGGTCAGTGGTTTATGTAGTACTGTACGTACAGCCGGCTGGACCTCCAG
                          ^       ^    ^          ^    ^
             1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
       1262  GTCACGAGCACCTGGGTGCTCGTTGGCGGCGTCCTGGCTGCTTTGGCCGCGTATTGCCTG
```

FIG. 18-2

```
                  CAGTGCTCGTGGACCCACGAGCAACCGCCGCAGGACCGACGAAACCGGCGCATAACGGAC

SerThrGlyCysValValIleValGlyArgValValLeuSerGlyLysProAlaIleIle
1322   TCAACAGGCTGCGTGGTCATAGTGGGCAGGGTCGTCTTGTCCGGGAAGCCGGCAATCATA
       AGTTGTCCGACGCACCAGTATCACCCGTCCAGCAGAACAGGCCCTTCGGCCGTTAGTAT
                                                           ^
1369 NAEI,

ProAspArgGluValLeuTyrArgGluPheAspGluMetGluGluCysSerGlnHisLeu
1382   CCTGACAGGGAAGTCCTCTACCGAGAGTTCGATGAGATGGAAGAGTGCTCTCAGCACTTA
       GGACTGTCCCTTCAGGAGATGGCTCTCAAGCTACTCTACCTTCTCACGAGAGTCGTGAAT
                          ^
1385 DRD1,

ProTyrIleGluGlnGlyMetMetLeuAlaGluGlnPheLysGlnLysAlaLeuGlyLeu
1442   CCGTACATCGAGCAAGGGATGATGCTCGCCGAGCAGTTCAAGCAGAAGGCCCTCGGCCTC
       GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
1502   CTGCAGACCGCGTCCCGTCAGGCAGAGGTTATCGCCCCTGCTGTCCAGACCAACTGGCAA
       GACGTCTGGCGCAGGGCAGTCCGTCTCCAATAGCGGGGACGACAGGTCTGGTTGACCGTT
       ^          ^
1502 PSTI,  1507 TTH3I,

LysLeuGluThrPheTrpAlaLysHisMetTrpAsnPheIleSerGlyIleGlnTyrLeu
1562   AAACTCGAGACCTTCTGGGCGAAGCATATGTGGAACTTCATCAGTGGGATACAATACTTG
       TTTGAGCTCTGGAAGACCCGCTTCGTATACACCTTGAAGTAGTCACCCTATGTTATGAAC
            ^                 ^
1565 XHOI,  1586 NDEI,

AlaGlyLeuSerThrLeuProGlyAsnProAlaIleAlaSerLeuMetAlaPheThrAla
1622   GCGGGCTTGTCAACGCTGCCTGGTAACCCCGCCATTGCTTCATTGATGGCTTTTACAGCT
       CGCCCGAACAGTTGCGACGGACCATTGGGGCGGTAACGAAGTAACTACCGAAAATGTCGA
                           ^                    ^
1643 BSTE2, 1677 ALWN1 PVU2,

AlaValThrSerProLeuThrThrSerGlnThrLeuLeuPheAsnIleLeuGlyGlyTrp
1682   GCTGTCACCAGCCCACTAACCACTAGCCAAACCCTCCTCTTCAACATATTGGGGGGGTGG
       CGACAGTGGTCGGGTGATTGGTGATCGGTTTGGGAGGAGAAGTTGTATAACCCCCCCACC

ValAlaAlaGlnLeuAlaAlaProGlyAlaAlaThrAlaPheValGlyAlaGlyLeuAla
1742   GTGGCTGCCCAGCTCGCCGCCCCGGTGCCGCTACTGCCTTTGTGGGCGCTGGCTTAGCT
       CACCGACGGGTCGAGCGGCGGGGGCCACGGCGATGACGGAAACACCCGCGACCGAATCGA
                                                             ^
1794 ESP1,

GlyAlaAlaIleGlySerValGlyLeuGlyLysValLeuIleAspIleLeuAlaGlyTyr
1802   GGCGCCGCCATCGGCAGTGTTGGACTGGGGAAGGTCCTCATAGACATCCTTGCAGGGTAT
       CCGCGGCGGTAGCCGTCACAACCTGACCCCTTCCAGGAGTATCTGTAGGAACGTCCCATA
            ^
1802 KAS1 NARI,

GlyAlaGlyValAlaGlyAlaLeuValAlaPheLysIleMetSerGlyGluValProSer
1862   GGCGCGGGCGTGGCGGGAGCTCTTGTGGCATTCAAGATCATGAGCGGTGAGGTCCCCTCC
       CCGCGCCCGCACCGCCCTCGAGAACACCGTAAGTTCTAGTACTCGCCACTCCAGGGGAGG
                   ^                               ^
1878 SACI, 1899 BSPH1,
```

FIG. 18-3

```
                ThrGluAspLeuValAsnLeuLeuProAlaIleLeuSerProGlyAlaLeuValValGly
     1922       ACGGAGGACCTGGTCAATCTACTGCCCGCCATCCTCTCGCCCGGAGCCCTCGTAGTCGGC
                TGCCTCCTGGACCAGTTAGATGACGGGCGGTAGGAGAGCGGGCCTCGGGAGCATCAGCCG
                                              ^
     1928 TTH3I,

ValValCysAlaAlaIleLeuArgArgHisValGlyProGlyGluGlyAlaValGlnTrp
     1982       GTGGTCTGTGCAGCAATACTGCGCCGGCACGTTGGCCCGGGCGAGGGGGCAGTGCAGTGG
                CACCAGACACGTCGTTATGACGCGGCCGTGCAACCGGGCCCGCTCCCCCGTCACGTCACC
                                        ^                         ^
     2004 NAEI, 2017 SMAI XMAI,

MetAsnArgLeuIleAlaPheAlaSerArgGlyAsnHisValSerProThrHisTyrVal
     2042       ATGAACCGGCTGATAGCCTTCGCCTCCCGGGGGAACCATGTTTCCCCCACGCACTACGTG
                TACTTGGCCGACTATCGGAAGCGGAGGGCCCCCTTGGTACAAAGGGGGTGCGTGATGCAC
                                             ^                       ^
     2067 SMAI XMAI, 2093 DRA3,

ProGluSerAspAlaAlaAlaArgValThrAlaIleLeuSerSerLeuThrValThrGln
     2102       CCGGAGAGCGATGCAGCTGCCCGCGTCACTGCCATACTCAGCAGCCTCACTGTAACCCAG
                GGCCTCTCGCTACGTCGACGGGCGCAGTGACGGTATGAGTCGTCGGAGTGACATTGGGTC
                              ^                                         ^
     2115 PVU2, 2159 ALWN1,

LeuLeuArgArgLeuHisGlnTrpIleSerSerGluCysThrThrProCysSerGlySer
     2162       CTCCTGAGGCGACTGCACCAGTGGATAAGCTCGGAGTGTACCACTCCATGCTCCGGTTCC
                GAGGACTCCGCTGACGTGGTCACCTATTCGAGCCTCACATGGTGAGGTACGAGGCCAAGG
                  ^                                                      ^
     2164 MST2, 2220 ECON1,

TrpLeuArgAspIleTrpAspTrpIleCysGluValLeuSerAspPheLysThrTrpLeu
     2222       TGGCTAAGGGACATCTGGGACTGGATATGCGAGGTGTTGAGCGACTTTAAGACCTGGCTA
                ACCGATTCCCTGTAGACCCTGACCTATACGCTCCACAACTCGCTGAAATTCTGGACCGAT

LysAlaLysLeuMetProGlnLeuProGlyIleProPheValSerCysGlnArgGlyTyr
     2282       AAAGCTAAGCTCATGCCACAGCTGCCTGGGATCCCCTTTGTGTCCTGCCAGCGCGGGTAT
                TTTCGATTCGAGTACGGTGTCGACGGACCCTAGGGGAAACACAGGACGGTCGCGCCCATA
                            ^             ^         ^
     2285 ESP1, 2300 PVU2, 2310 BAMHI,

LysGlyValTrpArgGlyAspGlyIleMetHisThrArgCysHisCysGlyAlaGluIle
     2342       AAGGGGGTCTGGCGAGGGGACGGCATCATGCACACTCGCTGCCACTGTGGAGCTGAGATC
                TTCCCCCAGACCGCTCCCCTGCCGTAGTACGTGTGAGCGACGGTGACACCTCGACTCTAG

ThrGlyHisValLysAsnGlyThrMetArgIleValGlyProArgThrCysArgAsnMet
     2402       ACTGGACATGTCAAAAACGGGACGATGAGGATCGTCGGTCCTAGGACCTGCAGGAACATG
                TGACCTGTACAGTTTTTGCCCTGCTACTCCTAGCAGCCAGGATCCTGGACGTCCTTGTAC
                         ^                    ^          ^^
     2425 BSAB1, 2441 AVR2, 2448 SSE83871, 2449 PSTI,

TrpSerGlyThrPheProIleAsnAlaTyrThrThrGlyProCysThrProLeuProAla
     2462       TGGAGTGGGACCTTCCCCATTAATGCCTACACCACGGGCCCCTGTACCCCCCTTCCTGCG
                ACCTCACCCTGGAAGGGGTAATTACGGATGTGGTGCCCGGGGACATGGGGGGAAGGACGC
                                  ^                                 ^
     2480 ASE1, 2497 APAI,
```

FIG. 18-4

```
       ProAsnTyrThrPheAlaLeuTrpArgValSerAlaGluGluTyrValGluIleArgGln
2522   CCGAACTACACGTTCGCGCTATGGAGGGTGTCTGCAGAGGAATACGTGGAGATAAGGCAG
       GGCTTGATGTGCAAGCGCGATACCTCCCACAGACGTCTCCTTATGCACCTCTATTCCGTC
                                    ^
2553 PSTI,

ValGlyAspPheHisTyrValThrGlyMetThrThrAspAsnLeuLysCysProCysGln
2582   GTGGGGGACTTCCACTACGTGACGGGTATGACTACTGACAATCTTAAATGCCCGTGCCAG
       CACCCCCTGAAGGTGATGCACTGCCCATACTGATGACTGTTAGAATTTACGGGCACGGTC
                   ^
2594 DRA3,

ValProSerProGluPhePheThrGluLeuAspGlyValArgLeuHisArgPheAlaPro
2642   GTCCCATCGCCCGAATTTTTCACAGAATTGGACGGGGTGCGCCTACATAGGTTTGCGCCC
       CAGGGTAGCGGGCTTAAAAAGTGTCTTAACCTGCCCCACGCGGATGTATCCAAACGCGGG

ProCysLysProLeuLeuArgGluGluValSerPheArgValGlyLeuHisGluTyrPro
2702   CCCTGCAAGCCCTTGCTGCGGGAGGAGGTATCATTCAGAGTAGGACTCCACGAATACCCG
       GGGACGTTCGGGAACGACGCCCTCCTCCATAGTAAGTCTCATCCTGAGGTGCTTATGGGC
                                                              ^
2757 HGIE2,

ValGlySerGlnLeuProCysGluProGluProAspValAlaValLeuThrSerMetLeu
2762   GTAGGGTCGCAATTACCTTGCGAGCCCGAACCGGACGTGGCCGTGTTGACGTCCATGCTC
       CATCCCAGCGTTAATGGAACGCTCGGGCTTGGCCTGCACCGGCACAACTGCAGGTACGAG
                                                         ^
2809 AAT2,

ThrAspProSerHisIleThrAlaGluAlaAlaGlyArgArgLeuAlaArgGlySerPro
2822   ACTGATCCCTCCCATATAACAGCAGAGGCGGCCGGGCGAAGGTTGGCGAGGGGATCACCC
       TGACTAGGGAGGGTATATTGTCGTCTCCGCCGGCCCGCTTCCAACCGCTCCCCTAGTGGG

2850 EAG1 XMA3,

ProSerValAlaSerSerSerAlaSerGlnLeuSerAlaProSerLeuLysAlaThrCys
2882   CCCTCTGTGGCCAGCTCCTCGGCTAGCCAGCTATCCGCTCCATCTCTCAAGGCAACTTGC
       GGGAGACACCGGTCGAGGAGCCGATCGGTCGATAGGCGAGGTAGAGAGTTCCGTTGAACG
                ^              ^
2889 BALI, 2903 NHEI,

ThrAlaAsnHisAspSerProAspAlaGluLeuIleGluAlaAsnLeuLeuTrpArgGln
2942   ACCGCTAACCATGACTCCCCTGATGCTGAGCTCATAGAGGCCAACCTCCTATGGAGGCAG
       TGGCGATTGGTACTGAGGGGACTACGACTCGAGTATCTCCGGTTGGAGGATACCTCCGTC
                                      ^   ^
2966 ESP1, 2969 SACI,

GluMetGlyGlyAsnIleThrArgValGluSerGluAsnLysValValIleLeuAspSer
3002   GAGATGGGCGGCAACATCACCAGGGTTGAGTCAGAAAACAAAGTGGTGATTCTGGACTCC
       CTCTACCCGCCGTTGTAGTGGTCCCAACTCAGTCTTTTGTTTCACCACTAAGACCTGAGG

PheAspProLeuValAlaGluGluAspGluArgGluIleSerValProAlaGluIleLeu
3062   TTCGATCCGCTTGTGGCGGAGGAGGACGAGCGGGAGATCTCCGTACCCGCAGAAATCCTG
       AAGCTAGGCGAACACCGCCTCCTCCTGCTCGCCCTCTAGAGGCATGGGCGTCTTTAGGAC
                                              ^
3096 BGL2,

ArgLysSerArgArgPheAlaGlnAlaLeuProValTrpAlaArgProAspTyrAsnPro
```

FIG. 18-5

```
3122 CGGAAGTCTCGGAGATTCGCCCAGGCCCTGCCCGTTTGGGCGCGGCCGGACTATAACCCC
     GCCTTCAGAGCCTCTAAGCGGGTCCGGGACGGGCAAACCCGCGCCGGCCTGATATTGGGG
                                 ^                 ^
     3143 ALWN1, 3164 EAG1 XMA3,

ProLeuValGluThrTrpLysLysProAspTyrGluProProValValHisGlyCysPro
3182 CCGCTAGTGGAGACGTGGAAAAAGCCCGACTACGAACCACCTGTGGTCCATGGCTGCCCG
     GGCGATCACCTCTGCACCTTTTTCGGGCTGATGCTTGGTGGACACCAGGTACCGACGGGC
                                       ^                ^
     3217 HGIE2, 3229 NCO1,

LeuProProProLysSerProProValProProProArgLysLysArgThrValValLeu
3242 CTTCCACCTCCAAAGTCCCCTCCTGTGCCTCCGCCTCGGAAGAAGCGGACGGTGGTCCTC
     GAAGGTGGAGGTTTCAGGGGAGGACACGGAGGCGGAGCCTTCTTCGCCTGCCACCAGGAG

ThrGluSerThrLeuSerThrAlaLeuAlaGluLeuAlaThrArgSerPheGlySerSer
3302 ACTGAATCAACCCTATCTACTGCCTTGGCCGAGCTCGCCACCAGAAGCTTTGGCAGCTCC
     TGACTTAGTTGGGATAGATGACGGAACCGGCTCGAGCGGTGGTCTTCGAAACCGTCGAGG
                                       ^           ^
     3332 SAC1, 3346 HIND3,

SerThrSerGlyIleThrGlyAspAsnThrThrThrSerSerGluProAlaProSerGly
3362 TCAACTTCCGGCATTACGGGCGACAATACGACAACATCCTCTGAGCCCGCCCCTTCTGGC
     AGTTGAAGGCCGTAATGCCCGCTGTTATGCTGTTGTAGGAGACTCGGGCGGGGAAGACCG

CysProProAspSerAspAlaGluSerTyrSerSerMetProProLeuGluGlyGluPro
3422 TGCCCCCCCGACTCCGACGCTGAGTCCTATTCCTCCATGCCCCCCTGGAGGGGGAGCCT
     ACGGGGGGGCTGAGGCTGCGACTCAGGATAAGGAGGTACGGGGGGACCTCCCCCTCGGA
                ^
     3437 EAM11051,

GlyAspProAspLeuSerAspGlySerTrpSerThrValSerSerGluAlaAsnAlaGlu
3482 GGGGATCCGGATCTTAGCGACGGGTCATGGTCAACGGTCAGTAGTGAGGCCAACGCGGAG
     CCCCTAGGCCTAGAATCGCTGCCCAGTACCAGTTGCCAGTCATCACTCCGGTTGCGCCTC
       ^^ ^
     3484 BAMHI, 3485 BSAB1, 3487 BSPE1,

AspValValCysCysSerMetSerTyrSerTrpThrGlyAlaLeuValThrProCysAla
3542 GATGTCGTGTGCTGCTCAATGTCTTACTCTTGGACAGGCGCACTCGTCACCCCGTGCGCC
     CTACAGCACACGACGAGTTACAGAATGAGAACCTGTCCGCGTGAGCAGTGGGGCACGCGG
                                                  ^           ^
     3589 DRA3, 3600 SAC2,

AlaGluGluGlnLysLeuProIleAsnAlaLeuSerAsnSerLeuLeuArgHisHisAsn
3602 GCGGAAGAACAGAAACTGCCCATCAATGCACTAAGCAACTCGTTGCTACGTCACCACAAT
     CGCCTTCTTGTCTTTGACGGGTAGTTACGTGATTCGTTGAGCAACGATGCAGTGGTGTTA
         ^                                                    ^
     3611 ALWN1, 3655 PFLM1,

LeuValTyrSerThrThrSerArgSerAlaCysGlnArgGlnLysLysValThrPheAsp
3662 TTGGTGTATTCCACCACCTCACGCAGTGCTTGCCAAAGGCAGAAGAAAGTCACATTTGAC
     AACCACATAAGGTGGTGGAGTGCGTCACGAACGGTTTCCGTCTTCTTTCAGTGTAAACTG
                                    ^
     3681 DRA3,

ArgLeuGlnValLeuAspSerHisTyrGlnAspValLeuLysGluValLysAlaAlaAla
3722 AGACTGCAAGTTCTGGACAGCCATTACCAGGACGTACTCAAGGAGGTTAAAGCAGCGGCG
```

FIG. 18-6

```
         TCTGACGTTCAAGACCTGTCGGTAATGGTCCTGCATGAGTTCCTCCAATTTCGTCGCCGC

SerLysValLysAlaAsnLeuLeuSerValGluGluAlaCysSerLeuThrProProHis
  3782   TCAAAAGTGAAGGCTAACTTGCTATCCGTAGAGGAAGCTTGCAGCCTGACGCCCCCACAC
         AGTTTTCACTTCCGATTGAACGATAGGCATCTCCTTCGAACGTCGGACTGCGGGGGTGTG
                                                ^
  3816 HIND3,

SerAlaLysSerLysPheGlyTyrGlyAlaLysAspValArgCysHisAlaArgLysAla
  3842   TCAGCCAAATCCAAGTTTGGTTATGGGGCAAAAGACGTCCGTTGCCATGCCAGAAAGGCC
         AGTCGGTTTAGGTTCAAACCAATACCCCGTTTTCTGCAGGCAACGGTACGGTCTTTCCGG
                                            ^          ^
  3875 AAT2,  3890 BGLI,

ValThrHisIleAsnSerValTrpLysAspLeuLeuGluAspAsnValThrProIleAsp
  3902   GTAACCCACATCAACTCCGTGTGGAAAGACCTTCTGGAAGACAATGTAACACCAATAGAC
         CATTGGGTGTAGTTGAGGCACACCTTTCTGGAAGACCTTCTGTTACATTGTGGTTATCTG

ThrThrIleMetAlaLysAsnGluValPheCysValGlnProGluLysGlyGlyArgLys
  3962   ACTACCATCATGGCTAAGAACGAGGTTTTCTGCGTTCAGCCTGAGAAGGGGGGTCGTAAG
         TGATGGTAGTACCGATTCTTGCTCCAAAAGACGCAAGTCGGACTCTTCCCCCCAGCATTC

ProAlaArgLeuIleValPheProAspLeuGlyValArgValCysGluLysMetAlaLeu
  4022   CCAGCTCGTCTCATCGTGTTCCCCGATCTGGGCGTGCGCGTGTGCGAAAAGATGGCTTTG
         GGTCGAGCAGAGTAGCACAAGGGGCTAGACCCGCACGCGCACACGCTTTTCTACCGAAAC

TyrAspValValThrLysLeuProLeuAlaValMetGlySerSerTyrGlyPheGlnTyr
  4082   TACGACGTGGTTACAAAGCTCCCCTTGGCCGTGATGGGAAGCTCCTACGGATTCCAATAC
         ATGCTGCACCAATGTTTCGAGGGGAACCGGCACTACCCTTCGAGGATGCCTAAGGTTATG

SerProGlyGlnArgValGluPheLeuValGlnAlaTrpLysSerLysLysThrProMet
  4142   TCACCAGGACAGCGGGTTGAATTCCTCGTGCAAGCGTGGAAGTCCAAGAAAACCCCAATG
         AGTGGTCCTGTCGCCCAACTTAAGGAGCACGTTCGCACCTTCAGGTTCTTTTGGGGTTAC
                                ^
  4160 ECORI,

GlyPheSerTyrAspThrArgCysPheAspSerThrValThrGluSerAspIleArgThr
  4202   GGGTTCTCGTATGATACCCGCTGCTTTGACTCCACAGTCACTGAGAGCGACATCCGTACG
         CCCAAGAGCATACTATGGGCGACGAAACTGAGGTGTCAGTGACTCTCGCTGTAGGCATGC
                                               ^       ^
  4229 DRD1,  4236 ALWN1,

GluGluAlaIleTyrGlnCysCysAspLeuAspProGlnAlaArgValAlaIleLysSer
  4262   GAGGAGGCAATCTACCAATGTTGTGACCTCGACCCCCAAGCCCGCGTGGCCATCAAGTCC
         CTCCTCCGTTAGATGGTTACAACACTGGAGCTGGGGGTTCGGGCGCACCGGTAGTTCAGG
                                                  ^        ^
  4301 BGLI,  4308 BALI,

LeuThrGluArgLeuTyrValGlyGlyProLeuThrAsnSerArgGlyGluAsnCysGly
  4322   CTCACCGAGAGGCTTTATGTTGGGGGCCCTCTTACCAATTCAAGGGGGGAGAACTGCGGC
         GAGTGGCTCTCCGAAATACAACCCCCGGGAGAATGGTTAAGTTCCCCCCTCTTGACGCCG
                                        ^
  4345 APAI,

TyrArgArgCysArgAlaSerGlyValLeuThrThrSerCysGlyAsnThrLeuThrCys
  4382   TATCGCAGGTGCCGCGCGAGCGGCGTACTGACAACTAGCTGTGGTAACACCCTCACTTGC
         ATAGCGTCCACGGCGCGCTCGCCGCATGACTGTTGATCGACACCATTGTGGGAGTGAACG
```

FIG. 18-7

```
        TyrIleLysAlaArgAlaAlaCysArgAlaAlaGlyLeuGlnAspCysThrMetLeuVal
4442    TACATCAAGGCCCGGGCAGCCTGTCGAGCCGCAGGGCTCCAGGACTGCACCATGCTCGTG
        ATGTAGTTCCGGGCCCGTCGGACAGCTCGGCGTCCCGAGGTCCTGACGTGGTACGAGCAC
                 ^
4452 SMAI XMAI,

CysGlyAspAspLeuValValIleCysGluSerAlaGlyValGlnGluAspAlaAlaSer
4502    TGTGGCGACGACTTAGTCGTTATCTGTGAAAGCGCGGGGGTCCAGGAGGACGCGGCGAGC
        ACACCGCTGCTGAATCAGCAATAGACACTTTCGCGCCCCCAGGTCCTCCTGCGCCGCTCG
                     ^  ^
4508 DRD1, 4511 TTH3I,

LeuArgAlaPheThrGluAlaMetThrArgTyrSerAlaProProGlyAspProProGln
4562    CTGAGAGCCTTCACGGAGGCTATGACCAGGTACTCCGCCCCCCTGGGGACCCCCCACAA
        GACTCTCGGAAGTGCCTCCGATACTGGTCCATGAGGCGGGGGGGACCCCTGGGGGGTGTT

ProGluTyrAspLeuGluLeuIleThrSerCysSerSerAsnValSerValAlaHisAsp
4622    CCAGAATACGACTTGGAGCTCATAACATCATGCTCCTCCAACGTGTCAGTCGCCCACGAC
        GGTCTTATGCTGAACCTCGAGTATTGTAGTACGAGGAGGTTGCACAGTCAGCGGGTGCTG
                        ^
4637 SACI,

GlyAlaGlyLysArgValTyrTyrLeuThrArgAspProThrThrProLeuAlaArgAla
4682    GGCGCTGGAAAGAGGGTCTACTACCCTCACCCGTGACCCTACAACCCCCCTCGCGAGAGCT
        CCGCGACCTTTCTCCCAGATGATGGAGTGGGCACTGGGATGTTGGGGGAGCGCTCTCGA
                                                            ^
4731 NRUI,

AlaTrpGluThrAlaArgHisThrProValAsnSerTrpLeuGlyAsnIleIleMetPhe
4742    GCGTGGGAGACAGCAAGACACACTCCAGTCAATTCCTGGCTAGGCAACATAATCATGTTT
        CGCACCCTCTGTCGTTCTGTGTGAGGTCAGTTAAGGACCGATCCGTTGTATTAGTACAAA

AlaProThrLeuTrpAlaArgMetIleLeuMetThrHisPhePheSerValLeuIleAla
4802    GCCCCCACACTGTGGGCGAGGATGATACTGATGACCCATTTCTTTAGCGTCCTTATAGCC
        CGGGGGTGTGACACCCGCTCCTACTATGACTACTGGGTAAAGAAATCGCAGGAATATCGG
           ^^
4806 PFLM1, 4807 DRA3,

ArgAspGlnLeuGluGlnAlaLeuAspCysGluIleTyrGlyAlaCysTyrSerIleGlu
4862    AGGGACCAGCTTGAACAGGCCCTCGATTGCGAGATCTACGGGGCCTGCTACTCCATAGAA
        TCCCTGGTCGAACTTGTCCGGGAGCTAACGCTCTAGATGCCCCGGACGATGAGGTATCTT
                                        ^
4893 BGL2,

ProLeuAspLeuProProIleIleGlnArgLeuHisGlyLeuSerAlaPheSerLeuHis
4922    CCACTGGATCTACCTCCAATCATTCAAAGACTCCATGGCCTCAGCGCATTTCACTCCAC
        GGTGACCTAGATGGAGGTTAGTAAGTTTCTGAGGTACCGGAGTCGCGTAAAGTGAGGTG
                                                    ^
4954 NCOI,

SerTyrSerProGlyGluIleAsnArgValAlaAlaCysLeuArgLysLeuGlyValPro
4982    AGTTACTCTCCAGGTGAAATCAATAGGGTGGCCGCATGCCTCAGAAAACTTGGGGTACCG
        TCAATGAGAGGTCCACTTTAGTTATCCCACCGGCGTACGGAGTCTTTTGAACCCCATGGC
                                            ^                ^
5015 SPHI, 5035 KPNI,
```

FIG. 18-8

```
                ProLeuArgAlaTrpArgHisArgAlaArgSerValArgAlaArgLeuLeuAlaArgGly
       5042     CCCTTGCGAGCTTGGAGACACCGGGCCCGGAGCGTCCGCGCTAGGCTTCTGGCCAGAGGA
                GGGAACGCTCGAACCTCTGTGGCCCGGGCCTCGCAGGCGCGATCCGAAGACCGGTCTCCT
                                        ^                         ^
       5064 APAI,  5091 BALI,

GlyArgAlaAlaIleCysGlyLysTyrLeuPheAsnTrpAlaValArgThrLysLeuLys
       5102     GGCAGGGCTGCCATATGTGGCAAGTACCTCTTCAACTGGGCAGTAAGAACAAAGCTCAAA
                CCGTCCCGACGGTATACACCGTTCATGGAGAAGTTGACCCGTCATTCTTGTTTCGAGTTT
                                ^
       5113 NDEI,

LeuThrProIleAlaAlaAlaGlyGlnLeuAspLeuSerGlyTrpPheThrAlaGlyTyr
       5162     CTCACTCCAATAGCGGCCGCTGGCCAGCTGGACTTGTCCGGCTGGTTCACGGCTGGCTAC
                GAGTGAGGTTATCGCCGGCGACCGGTCGACCTGAACAGGCCGACCAAGTGCCGACCGATG
                             ^^   ^    ^          ^          ^
       5174 NOTI,  5175 EAG1 XMA3,  5182 BALI,  5186 PVU2,

SerGlyGlyAspIleTyrHisSerValSerHisAlaArgProArgTrpIleTrpPheCys
       5222     AGCGGGGGGAGACATTTATCACAGCGTGTCTCATGCCCGGCCCCGCTGGATCTGGTTTTGC
                TCGCCCCCTCTGTAAATAGTGTCGCACAGAGTACGGGCCGGGGCGACCTAGACCAAAACG
                                                ^
       5240 DRA3,

LeuLeuLeuLeuAlaAlaGlyValGlyIleTyrLeuLeuProAsnArgMetSerThrAsn
       5282     CTACTCCTGCTTGCTGCAGGGGTAGGCATCTACCTCCTCCCCAACCGAATGAGCACGAAT
                GATGAGGACGAACGACGTCCCCATCCGTAGATGGAGGAGGGGTTGGCTTACTCGTGCTTA
                              ^
       5295 PSTI,

ProLysProGlnArgLysThrLysArgAsnThrAsnArgArgProGlnAspValLysPhe
       5342     CCTAAACCTCAAAGAAAGACCAAACGTAACACCAACCGGCGGCCGCAGGACGTCAAGTTC
                GGATTTGGAGTTTCTTTCTGGTTTGCATTGTGGTTGGCCGCCGGCGTCCTGCAGTTCAAG
                                                       ^^   ^         ^
       5380 NOTI,  5381 EAG1 XMA3,  5390 AAT2,  5401 SMAI XMAI,

ProGlyGlyGlyGlnIleValGlyGlyValTyrLeuLeuProArgArgGlyProArgLeu
       5402     CCGGGTGGCGGTCAGATCGTTGGTGGAGTTTACTTGTTGCCGCGCAGGGGCCCTAGATTG
                GGCCCACCGCCAGTCTAGCAACCACCTCAAATGAACAACGGCGCGTCCCCGGGATCTAAC
                                                            ^
       5449 APAI,

GlyValArgAlaThrArgLysThrSerGluArgSerGlnProArgGlyArgArgGlnPro
       5462     GGTGTGCGCGCGACGAGAAAGACTTCCGAGCGGTCGCAACCTCGAGGTAGACGTCAGCCT
                CCACACGCGCGCTGCTCTTTCTGAAGGCTCGCCAGCGTTGGAGCTCCATCTGCAGTCGGA
                       ^      ^             ^         ^
       5467 BSSH2,  5478 XMNI,  5502 XHOI,  5511 AAT2,

IleProLysAlaArgArgProGluGlyArgThrTrpAlaGlnProGlyTyrProTrpPro
       5522     ATCCCCAAGGCTCGTCGGCCCGAGGGCAGGACCTGGGCTCAGCCCGGGTACCCTTGGCCC
                TAGGGGTTCCGAGCAGCCGGGCTCCCGTCCTGGACCCGAGTCGGGCCCATGGGAACCGGG
                                                 ^        ^     ^    ^
       5548 ALWN1,  5558 ESP1,  5564 SMAI XMAI,  5568 KPNI,

LeuTyrGlyAsnGluGlyCysGlyTrpAlaGlyTrpLeuLeuSerProArgGlySerArg
       5582     CTCTATGGCAATGAGGGCTGCGGGTGGGCGGGATGGCTCCTGTCTCCCCGTGGCTCTCGG
                GAGATACCGTTACTCCCGACGCCCACCCGCCCTACCGAGGACAGAGGGGCACCGAGAGCC
```

FIG. 18-9

```
        ProSerTrpGlyProThrAspProArgArgArgSerArgAsnLeuGlyLysValIleAsp
5642    CCTAGCTGGGGCCCCACAGACCCCCGGCGTAGGTCGCGCAATTTGGGTAAGGTCATCGAT
        GGATCGACCCCGGGGTGTCTGGGGGCCGCATCCAGCGCGTTAAACCCATTCCAGTAGCTA
                ^                                           ^
5650 APAI, 5696 CLAI,

ThrLeuThrCysGlyPheAlaAspLeuMetGlyTyrIleProLeuValGlyAlaProLeu
5702    ACCCTTACGTGCGGCTTCGCCGACCTCATGGGGTACATACCGCTCGTCGGCGCCCCTCTT
        TGGGAATGCACGCCGAAGCGGCTGGAGTACCCCATGTATGGCGAGCAGCCGCGGGGAGAA
                          ^                   ^       ^
5724 HGIE2, 5750 KAS1 NARI, 5756 ECON1,

GlyGlyAlaAlaArgAlaLeuAlaHisGlyValArgValLeuGluAspGlyValAsnTyr
5762    GGAGGCGCTGCCAGGGCCCTGGCGCATGGCGTCCGGGTTCTGGAAGACGGCGTGAACTAT
        CCTCCGCGACGGTCCCGGGACCGCGTACCGCAGGCCCAAGACCTTCTGCCGCACTTGATA
                    ^ ^
5772 BSTXI, 5775 APAI,

AlaThrGlyAsnLeuProGlyCysSerOC AM
5822    GCAACAGGGAACCTTCCTGGTTGCTCTTAATAGTCGAC
        CGTTGTCCCTTGGAAGGACCAACGAGAATTATCAGCTG
                                       ^
5854 SALI,
```

FIG. 18-10

```
                              MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
     ^                       ^                           ^
     1 HIND3,  24 NDEI,   52 SCAI,

ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                              ^
     116 CLAI,

ProAsnIleArgThrGlyValArgThrIleThrThrGlySerProIleThrTyrSerThr
122  CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

TyrGlyLysPheLeuAlaAspGlyGlyCysSerGlyGlyAlaTyrAspIleIleIleCys
182  TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCGCGAATACTGTATTATTAAACA

AspGluCysHisSerThrAspAlaThrSerIleLeuGlyIleGlyThrValLeuAspGln
242  GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

AlaGluThrAlaGlyAlaArgLeuValValLeuAlaThrAlaThrProProGlySerVal
302  GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
     ^
     303 ALWN1,

ThrValProHisProAsnIleGluGluValAlaLeuSerThrThrGlyGluIleProPhe
362  ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

TyrGlyLysAlaIleProLeuGluValIleLysGlyGlyArgHisLeuIlePheCysHis
422  TACGGCAAGGCTATCCCCCTCGAAGTAATCAAGGGGGGAGACATCTCATCTTCTGTCAT
     ATGCCGTTCCGATAGGGGGAGCTTCATTAGTTCCCCCCTCTGTAGAGTAGAAGACAGTA
```

FIG. 21-1

```
          SerLysLysLysCysAspGluLeuAlaAlaLysLeuValAlaLeuGlyIleAsnAlaVal
  482     TCAAAGAAGAAGTGCGACGAACTCGCCGCAAAGCTGGTCGCATTGGGCATCAATGCCGTG
          AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
  542     GCCTACTACCGCGGTCTTGACGTGTCCGTCATCCCGACCAGCGGCGATGTTGTCGTCGTG
          CGGATGATGGCGCCAGAACTGCACAGGCAGTAGGGCTGGTCGCCGCTACAACAGCAGCAC
                            ^                     ^
  550 SAC2,  560 DRD1,

AlaThrAspAlaLeuMetThrGlyTyrThrGlyAspPheAspSerValIleAspCysAsn
  602     GCAACCGATGCCCTCATGACCGGCTATACCGGCGACTTCGACTCGGTGATAGACTGCAAT
          CGTTGGCTACGGGAGTACTGGCCGATATGGCCGCTGAAGCTGAGCCACTATCTGACGTTA
                                                ^
  615 BSPH1,

ThrCysValThrGlnThrValAspPheSerLeuAspProThrPheThrIleGluThrIle
  662     ACGTGTGTCACCCAGACAGTCGATTTCAGCCTTGACCCTACCTTCACCATTGAGACAATC
          TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
  722     ACGCTCCCCCAAGATGCTGTCTCCCGCACTCAACGTCGGGGCAGGACTGGCAGGGGGAAG
          TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
  782     CCAGGCATCTACAGATTTGTGGCACCGGGGGAGCGCCCCTCCGGCATGTTCGACTCGTCC
          GGTCCGTAGATGTCTAAACACCGTGGCCCCCTCGCGGGGAGGCCGTACAAGCTGAGCAGG
                                      ^                ^
  816 BGLI,  833 DRD1,

ValLeuCysGluCysTyrAspAlaGlyCysAlaTrpTyrGluLeuThrProAlaGluThr
  842     GTCCTCTGTGAGTGCTATGACGCAGGCTGTGCTTGGTATGAGCTCACGCCCGCCGAGACT
          CAGGAGACACTCACGATACTGCGTCCGACACGAACCATACTCGAGTGCGGGCGGCTCTGA
                                                        ^
  881 SACI,

ThrValArgLeuArgAlaTyrMetAsnThrProGlyLeuProValCysGlnAspHisLeu
  902     ACAGTTAGGCTACGAGCGTACATGAACACCCCGGGGCTTCCCGTGTGCCAGGACCATCTT
          TGTCAATCCGATGCTCGCATGTACTTGTGGGGCCCCGAAGGGCACACGGTCCTGGTAGAA
                                      ^
  931 SMAI XMAI,

GluPheTrpGluGlyValPheThrGlyLeuThrHisIleAspAlaHisPheLeuSerGln
  962     GAATTTTGGGAGGGCGTCTTTACAGGCCTCACTCATATAGATGCCCACTTTCTATCCCAG
          CTTAAAACCCTCCCGCAGAAATGTCCGGAGTGAGTATATCTACGGGTGAAAGATAGGGTC
                                            ^
  985 STUI,

ThrLysGlnSerGlyGluAsnLeuProTyrLeuValAlaTyrGlnAlaThrValCysAla
  1022    ACAAAGCAGAGTGGGGAGAACCTTCCTTACCTGGTAGCGTACCAAGCCACCGTGTGCGCT
          TGTTTCGTCTCACCCCTCTTGGAAGGAATGGACCATCGCATGGTTCGGTGGCACACGCGA
                                                                ^
  1069 DRA3,

ArgAlaGlnAlaProProProSerTrpAspGlnMetTrpLysCysLeuIleArgLeuLys
  1082    AGGGCTCAAGCCCCTCCCCCATCGTGGGACCAGATGTGGAAGTGTTTGATTCGCCTCAAG
```

FIG. 21-2

```
       TCCCGAGTTCGGGGAGGGGGTAGCACCCTGGTCTACACCTTCACAAACTAAGCGGAGTTC

ProThrLeuHisGlyProThrProLeuLeuTyrArgLeuGlyAlaValGlnAsnGluIle
1142   CCCACCCTCCATGGGCCAACACCCCTGCTATACAGACTGGGCGCTGTTCAGAATGAAATC
       GGGTGGGAGGTACCCGGTTGTGGGGACGATATGTCTGACCCGCGACAAGTCTTACTTTAG
                     ^
       1150 NCOI,

ThrLeuThrHisProValThrLysTyrIleMetThrCysMetSerAlaAspLeuGluVal
1202   ACCCTGACGCACCCAGTCACCAAATACATCATGACATGCATGTCGGCCGACCTGGAGGTC
       TGGGACTGCGTGGGTCAGTGGTTTATGTAGTACTGTACGTACAGCCGGCTGGACCTCCAG
                  ^    ^  ^        ^     ^
       1230 BSPH1, 1234 DRD1, 1237 AVA3, 1245 EAG1 XMA3, 1250 DRD1,

ValThrSerThrTrpValLeuValGlyGlyValLeuAlaAlaLeuAlaAlaTyrCysLeu
1262   GTCACGAGCACCTGGGTGCTCGTTGGCGGCGTCCTGGCTGCTTTGGCCGCGTATTGCCTG
       CAGTGCTCGTGGACCCACGAGCAACCGCCGCAGGACCGACGAAACCGGCGCATAACGGAC

SerThrGlyCysValValIleValGlyArgValValLeuSerGlyLysProAlaIleIle
1322   TCAACAGGCTGCGTGGTCATAGTGGGCAGGGTCGTCTTGTCCGGGAAGCCGGCAATCATA
       AGTTGTCCGACGCACCAGTATCACCCGTCCCAGCAGAACAGGCCCTTCGGCCGTTAGTAT
                                                          ^
       1369 NAEI,

ProAspArgGluValLeuTyrArgGluPheAspGluMetGluGluCysSerGlnHisLeu
1382   CCTGACAGGGAAGTCCTCTACCGAGAGTTCGATGAGATGGAAGAGTGCTCTCAGCACTTA
       GGACTGTCCCTTCAGGAGATGGCTCTCAAGCTACTCTACCTTCTCACGAGAGTCGTGAAT
          ^
       1385 DRD1,

ProTyrIleGluGlnGlyMetMetLeuAlaGluGlnPheLysGlnLysAlaLeuGlyLeu
1442   CCGTACATCGAGCAAGGGATGATGCTCGCCGAGCAGTTCAAGCAGAAGGCCCTCGGCCTC
       GGCATGTAGCTCGTTCCCTACTACGAGCGGCTCGTCAAGTTCGTCTTCCGGGAGCCGGAG

LeuGlnThrAlaSerArgGlnAlaGluValIleAlaProAlaValGlnThrAsnTrpGln
1502   CTGCAGACCGCGTCCCGTCAGGCAGAGGTTATCGCCCCTGCTGTCCAGACCAACTGGCAA
       GACGTCTGGCGCAGGGCAGTCCGTCTCCAATAGCGGGGACGACAGGTCTGGTTGACCGTT
            ^    ^
       1502 PSTI, 1507 TTH3I,

LysLeuGluThrPheTrpAlaLysHisMetTrpAsnPheIleSerGlyIleGlnTyrLeu
1562   AAACTCGAGACCTTCTGGGCGAAGCATATGTGGAACTTCATCAGTGGGATACAATACTTG
       TTTGAGCTCTGGAAGACCCGCTTCGTATACACCTTGAAGTAGTCACCCTATGTTATGAAC
            ^              ^
       1565 XHOI, 1586 NDEI,

AlaGlyLeuSerThrLeuProGlyAsnProAlaIleAlaSerLeuMetAlaPheThrAla
1622   GCGGGCTTGTCAACGCTGCCTGGTAACCCCGCCATTGCTTCATTGATGGCTTTTACAGCT
       CGCCCGAACAGTTGCGACGGACCATTGGGGCGGTAACGAAGTAACTACCGAAAATGTCGA
                        ^                                    ^
       1643 BSTE2,   1677 ALWN1 PVU2,

AlaValThrSerProLeuThrThrSerGlnThrLeuLeuPheAsnIleLeuGlyGlyTrp
1682   GCTGTCACCAGCCCACTAACCACTAGCCAAACCCTCCTCTTCAACATATTGGGGGGGTGG
       CGACAGTGGTCGGGTGATTGGTGATCGGTTTGGGAGGAGAAGTTGTATAACCCCCCCACC
```

FIG. 21-3

```
                ValAlaAlaGlnLeuAlaAlaProGlyAlaAlaThrAlaPheValGlyAlaGlyLeuAla
     1742       GTGGCTGCCCAGCTCGCCGCCCCCGGTGCCGCTACTGCCTTTGTGGGCGCTGGCTTAGCT
                CACCGACGGGTCGAGCGGCGGGGGCCACGGCGATGACGGAAACACCCGCGACCGAATCGA
                                                                         ^
     1794 ESP1,

GlyAlaAlaIleGlySerValGlyLeuGlyLysValLeuIleAspIleLeuAlaGlyTyr
     1802       GGCGCCGCCATCGGCAGTGTTGGACTGGGGAAGGTCCTCATAGACATCCTTGCAGGGTAT
                CCGCGGCGGTAGCCGTCACAACCTGACCCCTTCCAGGAGTATCTGTAGGAACGTCCCATA
                 ^
     1802 KAS1 NAR1,

GlyAlaGlyValAlaGlyAlaLeuValAlaPheLysIleMetSerGlyGluValProSer
     1862       GGCGCGGGCGTGGCGGGAGCTCTTGTGGCATTCAAGATCATGAGCGGTGAGGTCCCCTCC
                CCGCGCCCGCACCGCCCTCGAGAACACCGTAAGTTCTAGTACTCGCCACTCCAGGGGAGG
                         ^                           ^
     1878 SAC1, 1899 BSPH1,

ThrGluAspLeuValAsnLeuLeuProAlaIleLeuSerProGlyAlaLeuValValGly
     1922       ACGGAGGACCTGGTCAATCTACTGCCCGCCATCCTCTCGCCCGGAGCCCTCGTAGTCGGC
                TGCCTCCTGGACCAGTTAGATGACGGGCGGTAGGAGAGCGGGCCTCGGGAGCATCAGCCG
                       ^
     1928 TTH3I,

ValValCysAlaAlaIleLeuArgArgHisValGlyProGlyGluGlyAlaValGlnTrp
     1982       GTGGTCTGTGCAGCAATACTGCGCCGGCACGTTGGCCCGGGCGAGGGGGCAGTGCAGTGG
                CACCAGACACGTCGTTATGACGCGGCCGTGCAACCGGGCCCGCTCCCCGTCACGTCACC
                                 ^            ^
     2004 NAE1, 2017 SMA1 XMA1,

MetAsnArgLeuIleAlaPheAlaSerArgGlyAsnHisValSerProThrHisTyrVal
     2042       ATGAACCGGCTGATAGCCTTCGCCTCCCGGGGGAACCATGTTTCCCCCACGCACTACGTG
                TACTTGGCCGACTATCGGAAGCGGAGGGCCCCCTTGGTACAAAGGGGGTGCGTGATGCAC
                                     ^                          ^
     2067 SMA1 XMA1, 2093 DRA3,

ProGluSerAspAlaAlaAlaArgValThrAlaIleLeuSerSerLeuThrValThrGln
     2102       CCGGAGAGCGATGCAGCTGCCCGCGTCACTGCCATACTCAGCAGCCTCACTGTAACCCAG
                GGCCTCTCGCTACGTCGACGGGCGCAGTGACGGTATGAGTCGTCGGAGTGACATTGGGTC
                              ^                                            ^
     2115 PVU2, 2159 ALWN1,

LeuLeuArgArgLeuHisGlnTrpIleSerSerGluCysThrThrProCysSerGlySer
     2162       CTCCTGAGGCGACTGCACCAGTGGATAAGCTCGGAGTGTACCACTCCATGCTCCGGTTCC
                GAGGACTCCGCTGACGTGGTCACCTATTCGAGCCTCACATGGTGAGGTACGAGGCCAAGG
                 ^                                                          ^
     2164 MST2, 2220 ECON1,

TrpLeuArgAspIleTrpAspTrpIleCysGluValLeuSerAspPheLysThrTrpLeu
     2222       TGGCTAAGGGACATCTGGGACTGGATATGCGAGGTGTTGAGCGACTTTAAGACCTGGCTA
                ACCGATTCCCTGTAGACCCTGACCTATACGCTCCACAACTCGCTGAAATTCTGGACCGAT

LysAlaLysLeuMetProGlnLeuProGlyIleProPheValSerCysGlhArgGlyTyr
     2282       AAAGCTAAGCTCATGCCACAGCTGCCTGGGATCCCCTTTGTGTCCTGCCAGCGCGGGTAT
                TTTCGATTCGAGTACGGTGTCGACGGACCCTAGGGGAAACACAGGACGGTCGCGCCCATA
                      ^          ^           ^
     2285 ESP1, 2300 PVU2, 2310 BAMHI,
```

FIG. 21-4

```
        LysGlyValTrpArgGlyAspGlyIleMetHisThrArgCysHisCysGlyAlaGluIle
2342    AAGGGGGTCTGGCGAGGGGACGGCATCATGCACACTCGCTGCCACTGTGGAGCTGAGATC
        TTCCCCCAGACCGCTCCCCTGCCGTAGTACGTGTGAGCGACGGTGACACCTCGACTCTAG

ThrGlyHisValLysAsnGlyThrMetArgIleValGlyProArgThrCysArgAsnMet
2402    ACTGGACATGTCAAAAACGGGACGATGAGGATCGTCGGTCCTAGGACCTGCAGGAACATG
        TGACCTGTACAGTTTTTGCCCTGCTACTCCTAGCAGCCAGGATCCTGGACGTCCTTGTAC
                                   ^              ^     ^^
        2425 BSAB1,  2441 AVR2,  2448 SSE83871,  2449 PSTI,

TrpSerGlyThrPheProIleAsnAlaTyrThrThrGlyProCysThrProLeuProAla
2462    TGGAGTGGGACCTTCCCCATTAATGCCTACACCACGGGCCCCTGTACCCCCCTTCCTGCG
        ACCTCACCCTGGAAGGGGTAATTACGGATGTGGTGCCCGGGGACATGGGGGGAAGGACGC
                         ^                ^
        2480 ASE1,  2497 APAI,

ProAsnTyrThrPheAlaLeuTrpArgValSerAlaGluGluTyrValGluIleArgGln
2522    CCGAACTACACGTTCGCGCTATGGAGGGTGTCTGCAGAGGAATACGTGGAGATAAGGCAG
        GGCTTGATGTGCAAGCGCGATACCTCCCACAGACGTCTCCTTATGCACCTCTATTCCGTC
                                         ^
        2553 PSTI,

ValGlyAspPheHisTyrValThrGlyMetThrThrAspAsnLeuLysCysProCysGln
2582    GTGGGGGACTTCCACTACGTGACGGGTATGACTACTGACAATCTTAAATGCCCGTGCCAG
        CACCCCCTGAAGGTGATGCACTGCCCATACTGATGACTGTTAGAATTTACGGGCACGGTC
                     ^
        2594 DRA3,

ValProSerProGluPhePheThrGluLeuAspGlyValArgLeuHisArgPheAlaPro
2642    GTCCCATCGCCCGAATTTTTCACAGAATTGGACGGGGTGCGCCTACATAGGTTTGCGCCC
        CAGGGTAGCGGGCTTAAAAAGTGTCTTAACCTGCCCCACGCGGATGTATCCAAACGCGGG

ProCysLysProLeuLeuArgGluGluValSerPheArgValGlyLeuHisGluTyrPro
2702    CCCTGCAAGCCCTTGCTGCGGGAGGAGGTATCATTCAGAGTAGGACTCCACGAATACCCG
        GGGACGTTCGGGAACGACGCCCTCCTCCATAGTAAGTCTCATCCTGAGGTGCTTATGGGC
                                                                 ^
        2757 HGIE2,

ValGlySerGlnLeuProCysGluProGluProAspValAlaValLeuThrSerMetLeu
2762    GTAGGGTCGCAATTACCTTGCGAGCCCGAACCGGACGTGGCCGTGTTGACGTCCATGCTC
        CATCCCAGCGTTAATGGAACGCTCGGGCTTGGCCTGCACCGGCACAACTGCAGGTACGAG
                                   ^
        2809 AAT2,

ThrAspProSerHisIleThrAlaGluAlaAlaGlyArgArgLeuAlaArgGlySerPro
2822    ACTGATCCCTCCCATATAACAGCAGAGGCGGCCGGGCGAAGGTTGGCGAGGGGATCACCC
        TGACTAGGGAGGGTATATTGTCGTCTCCGCCGGCCCGCTTCCAACCGCTCCCCTAGTGGG
                                     ^
        2850 EAG1 XMA3,

ProSerValAlaSerSerSerAlaSerGlnLeuSerAlaProSerLeuLysAlaThrCys
2882    CCCTCTGTGGCCAGCTCCTCGGCTAGCCAGCTATCCGCTCCATCTCTCAAGGCAACTTGC
        GGGAGACACCGGTCGAGGAGCCGATCGGTCGATAGGCGAGGTAGAGAGTTCCGTTGAACG
                    ^             ^
        2889 BALI,  2903 NHEI,
```

FIG. 21-5

```
            ThrAlaAsnHisAspSerProAspAlaGluLeuIleGluAlaAsnLeuLeuTrpArgGln
2942        ACCGCTAACCATGACTCCCCTGATGCTGAGCTCATAGAGGCCAACCTCCTATGGAGGCAG
            TGGCGATTGGTACTGAGGGGACTACGACTCGAGTATCTCCGGTTGGAGGATACCTCCGTC
                                       ^  ^
            2966 ESP1, 2969 SACI,

GluMetGlyGlyAsnIleThrArgValGluSerGluAsnLysValValIleLeuAspSer
3002        GAGATGGGCGGCAACATCACCAGGGTTGAGTCAGAAAACAAAGTGGTGATTCTGGACTCC
            CTCTACCCGCCGTTGTAGTGGTCCCAACTCAGTCTTTTGTTTCACCACTAAGACCTGAGG

PheAspProLeuValAlaGluGluAspGluArgGluIleSerValProAlaGluIleLeu
3062        TTCGATCCGCTTGTGGCGGAGGAGGACGAGCGGGAGATCTCCGTACCCGCAGAAATCCTG
            AAGCTAGGCGAACACCGCCTCCTCCTGCTCGCCCTCTAGAGGCATGGGCGTCTTTAGGAC
                                                  ^
            3096 BGL2,

ArgLysSerArgArgPheAlaGlnAlaLeuProValTrpAlaArgProAspTyrAsnPro
3122        CGGAAGTCTCGGAGATTCGCCCAGGCCCTGCCCGTTTGGGCGCGGCCGGACTATAACCCC
            GCCTTCAGAGCCTCTAAGCGGGTCCGGGACGGGCAAACCCGCGCCGGCCTGATATTGGGG
                                  ^                         ^
            3143 ALWN1, 3164 EAG1 XMA3,

ProLeuValGluThrTrpLysLysProAspTyrGluProProValValHisGlyCysPro
3182        CCGCTAGTGGAGACGTGGAAAAAGCCCGACTACGAACCACCTGTGGTCCATGGCTGCCCG
            GGCGATCACCTCTGCACCTTTTTCGGGCTGATGCTTGGTGGACACCAGGTACCGACGGGC
                                   ^                   ^
            3217 HGIE2, 3229 NCOI,

LeuProProProLysSerProProValProProProArgLysLysArgThrValValLeu
3242        CTTCCACCTCCAAAGTCCCCTCCTGTGCCTCCGCCTCGGAAGAAGCGGACGGTGGTCCTC
            GAAGGTGGAGGTTTCAGGGGAGGACACGGAGGCGGAGCCTTCTTCGCCTGCCACCAGGAG

ThrGluSerThrLeuSerThrAlaLeuAlaGluLeuAlaThrArgSerPheGlySerSer
3302        ACTGAATCAACCCTATCTACTGCCTTGGCCGAGCTCGCCACCAGAAGCTTTGGCAGCTCC
            TGACTTAGTTGGGATAGATGACGGAACCGGCTCGAGCGGTGGTCTTCGAAACCGTCGAGG
                                          ^             ^
            3332 SACI, 3346 HIND3,

SerThrSerGlyIleThrGlyAspAsnThrThrThrSerSerGluProAlaProSerGly
3362        TCAACTTCCGGCATTACGGGCGACAATACGACAACATCCTCTGAGCCCGCCCCTTCTGGC
            AGTTGAAGGCCGTAATGCCCGCTGTTATGCTGTTGTAGGAGACTCGGGCGGGGAAGACCG

CysProProAspSerAspAlaGluSerTyrSerSerMetProProLeuGluGlyGluPro
3422        TGCCCCCCCGACTCCGACGCTGAGTCCTATTCCTCCATGCCCCCCCTGGAGGGGGAGCCT
            ACGGGGGGGCTGAGGCTGCGACTCAGGATAAGGAGGTACGGGGGGGACCTCCCCCTCGGA
                        ^
            3437 EAM11051,

GlyAspProAspLeuSerAspGlySerTrpSerThrValSerSerGluAlaAsnAlaGlu
3482        GGGGATCCGGATCTTAGCGACGGGTCATGGTCAACGGTCAGTAGTGAGGCCAACGCGGAG
            CCCCTAGGCCTAGAATCGCTGCCCAGTACCAGTTGCCAGTCATCACTCCGGTTGCGCCTC
               ^^ ^
            3484 BAMHI, 3485 BSAB1, 3487 BSPE1,

AspValValCysCysSerMetSerTyrSerTrpThrGlyAlaLeuValThrProCysAla
3542        GATGTCGTGTGCTGCTCAATGTCTTACTCTTGGACAGGCGCACTCGTCACCCCGTGCGCC
            CTACAGCACACGACGAGTTACAGAATGAGAACCTGTCCGCGTGAGCAGTGGGGCACGCGG
```

FIG. 21-6

3589 DRA3, 3600 SAC2,

```
              AlaGluGluGlnLysLeuProIleAsnAlaLeuSerAsnSerLeuLeuArgHisHisAsn
      3602    GCGGAAGAACAGAAACTGCCCATCAATGCACTAAGCAACTCGTTGCTACGTCACCACAAT
              CGCCTTCTTGTCTTTGACGGGTAGTTACGTGATTCGTTGAGCAACGATGCAGTGGTGTTA
                                    ^                               ^
```

3611 ALWN1, 3655 PFLM1,

```
              LeuValTyrSerThrThrSerArgSerAlaCysGlnArgGlnLysLysValThrPheAsp
      3662    TTGGTGTATTCCACCACCTCACGCAGTGCTTGCCAAAGGCAGAAGAAAGTCACATTTGAC
              AACCACATAAGGTGGTGGAGTGCGTCACGAACGGTTTCCGTCTTCTTTCAGTGTAAACTG
                                                  ^
```

3681 DRA3,

```
              ArgLeuGlnValLeuAspSerHisTyrGlnAspValLeuLysGluValLysAlaAlaAla
      3722    AGACTGCAAGTTCTGGACAGCCATTACCAGGACGTACTCAAGGAGGTTAAAGCAGCGGCG
              TCTGACGTTCAAGACCTGTCGGTAATGGTCCTGCATGAGTTCCTCCAATTTCGTCGCCGC
```

```
              SerLysValLysAlaAsnLeuLeuSerValGluGluAlaCysSerLeuThrProProHis
      3782    TCAAAAGTGAAGGCTAACTTGCTATCCGTAGAGGAAGCTTGCAGCCTGACGCCCCCACAC
              AGTTTTCACTTCCGATTGAACGATAGGCATCTCCTTCGAACGTCGGACTGCGGGGGTGTG
                                                         ^
```

3816 HIND3,

```
              SerAlaLysSerLysPheGlyTyrGlyAlaLysAspValArgCysHisAlaArgLysAla
      3842    TCAGCCAAATCCAAGTTTGGTTATGGGGCAAAAGACGTCCGTTGCCATGCCAGAAAGGCC
              AGTCGGTTTAGGTTCAAACCAATACCCCGTTTTCTGCAGGCAACGGTACGGTCTTTCCGG
                                  ^                  ^
```

3875 AAT2, 3890 BGLI,

```
              ValThrHisIleAsnSerValTrpLysAspLeuLeuGluAspAsnValThrProIleAsp
      3902    GTAACCCACATCAACTCCGTGTGGAAAGACCTTCTGGAAGACAATGTAACACCAATAGAC
              CATTGGGTGTAGTTGAGGCACACCTTTCTGGAAGACCTTCTGTTACATTGTGGTTATCTG
```

```
              ThrThrIleMetAlaLysAsnGluValPheCysValGlnProGluLysGlyGlyArgLys
      3962    ACTACCATCATGGCTAAGAACGAGGTTTTCTGCGTTCAGCCTGAGAAGGGGGGTCGTAAG
              TGATGGTAGTACCGATTCTTGCTCCAAAAGACGCAAGTCGGACTCTTCCCCCCAGCATTC
```

```
              ProAlaArgLeuIleValPheProAspLeuGlyValArgValCysGluLysMetAlaLeu
      4022    CCAGCTCGTCTCATCGTGTTCCCCGATCTGGGCGTGCGCGTGTGCGAAAAGATGGCTTTG
              GGTCGAGCAGAGTAGCACAAGGGGCTAGACCCGCACGCGCACACGCTTTTCTACCGAAAC
```

```
              TyrAspValValThrLysLeuProLeuAlaValMetGlySerSerTyrGlyPheGlnTyr
      4082    TACGACGTGGTTACAAAGCTCCCCTTGGCCGTGATGGGAAGCTCCTACGGATTCCAATAC
              ATGCTGCACCAATGTTTCGAGGGGAACCGGCACTACCCTTCGAGGATGCCTAAGGTTATG
```

```
              SerProGlyGlnArgValGluPheLeuValGlnAlaTrpLysSerLysLysThrProMet
      4142    TCACCAGGACAGCGGGTTGAATTCCTCGTGCAAGCGTGGAAGTCCAAGAAAACCCCAATG
              AGTGGTCCTGTCGCCCAACTTAAGGAGCACGTTCGCACCTTCAGGTTCTTTTGGGGTTAC
                                  ^
```

4160 ECORI,

```
              GlyPheSerTyrAspThrArgCysPheAspSerThrValThrGluSerAspIleArgThr
      4202    GGGTTCTCGTATGATACCCGCTGCTTTGACTCCACAGTCACTGAGAGCGACATCCGTACG
              CCCAAGAGCATACTATGGGCGACGAAACTGAGGTGTCAGTGACTCTCGCTGTAGGCATGC
                                                ^       ^
```

FIG. 21-7

4229 DRD1, 4236 ALWN1,

```
        GluGluAlaIleTyrGlnCysCysAspLeuAspProGlnAlaArgValAlaIleLysSer
4262    GAGGAGGCAATCTACCAATGTTGTGACCTCGACCCCCAAGCCCGCGTGGCCATCAAGTCC
        CTCCTCCGTTAGATGGTTACAACACTGGAGCTGGGGGTTCGGGCGCACCGGTAGTTCAGG
                                              ^           ^
```

4301 BGLI, 4308 BALI,

```
        LeuThrGluArgLeuTyrValGlyGlyProLeuThrAsnSerArgGlyGluAsnCysGly
4322    CTCACCGAGAGGCTTTATGTTGGGGGCCCTCTTACCAATTCAAGGGGGGAGAACTGCGGC
        GAGTGGCTCTCCGAAATACAACCCCCGGGAGAATGGTTAAGTTCCCCCCTCTTGACGCCG
                                ^
```

4345 APAI,

```
        TyrArgArgCysArgAlaSerGlyValLeuThrThrSerCysGlyAsnThrLeuThrCys
4382    TATCGCAGGTGCCGCGCGAGCGGCGTACTGACAACTAGCTGTGGTAACACCCTCACTTGC
        ATAGCGTCCACGGCGCGCTCGCCGCATGACTGTTGATCGACACCATTGTGGGAGTGAACG

TyrIleLysAlaArgAlaAlaCysArgAlaAlaGlyLeuGlnAspCysThrMetLeuVal
4442    TACATCAAGGCCCGGGCAGCCTGTCGAGCCGCAGGGCTCCAGGACTGCACCATGCTCGTG
        ATGTAGTTCCGGGCCCGTCGGACAGCTCGGCGTCCCGAGGTCCTGACGTGGTACGAGCAC
                                          ^
```

4452 SMAI XMAI,

```
        CysGlyAspAspLeuValValIleCysGluSerAlaGlyValGlnGluAspAlaAlaSer
4502    TGTGGCGACGACTTAGTCGTTATCTGTGAAAGCGCGGGGGTCCAGGAGGACGCGGCGAGC
        ACACCGCTGCTGAATCAGCAATAGACACTTTCGCGCCCCAGGTCCTCCTGCGCCGCTCG
           ^  ^
```

4508 DRD1, 4511 TTH3I,

```
        LeuArgAlaPheThrGluAlaMetThrArgTyrSerAlaProProGlyAspProProGln
4562    CTGAGAGCCTTCACGGAGGCTATGACCAGGTACTCCGCCCCCCCTGGGGACCCCCCACAA
        GACTCTCGGAAGTGCCTCCGATACTGGTCCATGAGGCGGGGGGGACCCCTGGGGGGTGTT

ProGluTyrAspLeuGluLeuIleThrSerCysSerSerAsnValSerValAlaHisAsp
4622    CCAGAATACGACTTGGAGCTCATAACATCATGCTCCTCCAACGTGTCAGTCGCCCACGAC
        GGTCTTATGCTGAACCTCGAGTATTGTAGTACGAGGAGGTTGCACAGTCAGCGGGTGCTG
                                ^
```

4637 SACI,

```
        GlyAlaGlyLysArgValTyrTyrLeuThrArgAspProThrThrProLeuAlaArgAla
4682    GGCGCTGGAAAGAGGGTCTACTACCTCACCCGTGACCCTACAACCCCCCTCGCGAGAGCT
        CCGCGACCTTTCTCCCAGATGATGGAGTGGGCACTGGGATGTTGGGGGAGCGCTCTCGA
                                                                ^
```

4731 NRUI,

```
        AlaTrpGluThrAlaArgHisThrProValAsnSerTrpLeuGlyAsnIleIleMetPhe
4742    GCGTGGGAGACAGCAAGACACACTCCAGTCAATTCCTGGCTAGGCAACATAATCATGTTT
        CGCACCCTCTGTCGTTCTGTGTGAGGTCAGTTAAGGACCGATCCGTTGTATTAGTACAAA

AlaProThrLeuTrpAlaArgMetIleLeuMetThrHisPhePheSerValLeuIleAla
4802    GCCCCCACACTGTGGGCGAGGATGATACTGATGACCCATTTCTTTAGCGTCCTTATAGCC
        CGGGGGTGTGACACCCGCTCCTACTATGACTACTGGGTAAAGAAATCGCAGGAATATCGG
                                                          ^^
```

4806 PFLM1, 4807 DRA3,

```
        ArgAspGlnLeuGluGlnAlaLeuAspCysGluIleTyrGlyAlaCysTyrSerIleGlu
```

FIG. 21-8

```
4862  AGGGACCAGCTTGAACAGGCCCTCGATTGCGAGATCTACGGGGCCTGCTACTCCATAGAA
      TCCCTGGTCGAACTTGTCCGGGAGCTAACGCTCTAGATGCCCCGGACGATGAGGTATCTT
                                                  ^
4893 BGL2,

ProLeuAspLeuProProIleIleGlnArgLeuHisGlyLeuSerAlaPheSerLeuHis
4922  CCACTGGATCTACCTCCAATCATTCAAAGACTCCATGGCCTCAGCGCATTTTCACTCCAC
      GGTGACCTAGATGGAGGTTAGTAAGTTTCTGAGGTACCGGAGTCGCGTAAAAGTGAGGTG
                                        ^
4954 NCOI,

SerTyrSerProGlyGluIleAsnArgValAlaAlaCysLeuArgLysLeuGlyValPro
4982  AGTTACTCTCCAGGTGAAATCAATAGGGTGGCCGCATGCCTCAGAAAACTTGGGGTACCG
      TCAATGAGAGGTCCACTTTAGTTATCCCACCGGCGTACGGAGTCTTTTGAACCCCATGGC
                                        ^                  ^
5015 SPHI, 5035 KPNI,

ProLeuArgAlaTrpArgHisArgAlaArgSerValArgAlaArgLeuLeuAlaArgGly
5042  CCCTTGCGAGCTTGGAGACACCGGGCCCGGAGCGTCCGCGCTAGGCTTCTGGCCAGAGGA
      GGGAACGCTCGAACCTCTGTGGCCCGGGCCTCGCAGGCGCGATCCGAAGACCGGTCTCCT
                              ^                    ^
5064 APAI, 5091 BALI,

GlyArgAlaAlaIleCysGlyLysTyrLeuPheAsnTrpAlaValArgThrLysLeuLys
5102  GGCAGGGCTGCCATATGTGGCAAGTACCTCTTCAACTGGGCAGTAAGAACAAAGCTCAAA
      CCGTCCCGACGGTATACACCGTTCATGGAGAAGTTGACCCGTCATTCTTGTTTCGAGTTT
                      ^
5113 NDEI,

LeuThrProIleAlaAlaAlaGlyGlnLeuAspLeuSerGlyTrpPheThrAlaGlyTyr
5162  CTCACTCCAATAGCGGCCGCTGGCCAGCTGGACTTGTCCGGCTGGTTCACGGCTGGCTAC
      GAGTGAGGTTATCGCCGGCGACCGGTCGACCTGAACAGGCCGACCAAGTGCCGACCGATG
                    ^^    ^   ^
5174 NOTI, 5175 EAG1 XMA3, 5182 BALI, 5186 PVU2,

SerGlyGlyAspIleTyrHisSerValSerHisAlaArgProArgTrpIleTrpPheCys
5222  AGCGGGGGAGACATTTATCACAGCGTGTCTCATGCCCGGCCCCGCTGGATCTGGTTTTGC
      TCGCCCCCTCTGTAAATAGTGTCGCACAGAGTACGGGCCGGGGCGACCTAGACCAAAACG
                                              ^
5240 DRA3,

LeuLeuLeuLeuAlaAlaGlyValGlyIleTyrLeuLeuProAsnArgMetSerThrAsn
5282  CTACTCCTGCTTGCTGCAGGGGTAGGCATCTACCTCCTCCCCAACCGAATGAGCACGAAT
      GATGAGGACGAACGACGTCCCCATCCGTAGATGGAGGAGGGGTTGGCTTACTCGTGCTTA
                                  ^
5295 PSTI,

ProLysProGlnArgLysThrLysArgAsnThrAsnArgArgProGlnAspValLysPhe
5342  CCTAAACCTCAAAGAAAGACCAAACGTAACACCAACCGGCGGCCGCAGGACGTCAAGTTC
      GGATTTGGAGTTTCTTTCTGGTTTGCATTGTGGTTGGCCGCCGGCGTCCTGCAGTTCAAG
                                                ^^      ^        ^
5380 NOTI, 5381 EAG1 XMA3, 5390 AAT2, 5401 SMAI XMAI,

ProGlyGlyGlyGlnIleValGlyGlyValTyrLeuLeuProArgArgGlyProArgLeu
5402  CCGGGTGGCGGTCAGATCGTTGGTGGAGTTTACTTGTTGCCGCGCAGGGGCCCTAGATTG
      GGCCCACCGCCAGTCTAGCAACCACCTCAAATGAACAACGGCGCGTCCCCGGGATCTAAC
                                                              ^
```

FIG. 21-9

5449 APAI,

```
       GlyValArgAlaThrArgLysThrSerGluArgSerGlnProArgGlyArgArgGlnPro
5462   GGTGTGCGCGCGACGAGAAAGACTTCCGAGCGGTCGCAACCTCGAGGTAGACGTCAGCCT
       CCACACGCGCGCTGCTCTTTCTGAAGGCTCGCCAGCGTTGGAGCTCCATCTGCAGTCGGA
```

5467 BSSH2, 5478 XMNI, 5502 XHOI, 5511 AAT2,

```
       IleProLysAlaArgArgProGluGlyArgThrTrpAlaGlnProGlyTyrProTrpPro
5522   ATCCCCAAGGCTCGTCGGCCCGAGGGCAGGACCTGGGCTCAGCCCGGGTACCCTTGGCCC
       TAGGGGTTCCGAGCAGCCGGGCTCCCGTCCTGGACCCGAGTCGGGCCCATGGGAACCGGG
```

5548 ALWN1, 5558 ESP1, 5564 SMAI XMAI, 5568 KPNI,

```
       LeuTyrGlyAsnGluGlyCysGlyTrpAlaGlyTrpLeuLeuSerProArgGlySerArg
5582   CTCTATGGCAATGAGGGCTGCGGGTGGGCGGGATGGCTCCTGTCTCCCCGTGGCTCTCGG
       GAGATACCGTTACTCCCGACGCCCACCCGCCCTACCGAGGACAGAGGGGCACCGAGAGCC
```

```
       ProSerTrpGlyProThrAspProArgArgArgSerArgAsnLeuGlyLysValIleAsp
5642   CCTAGCTGGGGCCCCACAGACCCCCGGCGTAGGTCGCGCAATTTGGGTAAGGTCATCGAT
       GGATCGACCCCGGGGTGTCTGGGGGCCGCATCCAGCGCGTTAAACCCATTCCAGTAGCTA
```

5650 APAI, 5696 CLAI,

```
       ThrLeuThrCysGlyPheAlaAspLeuMetGlyTyrIleProLeuValOC AM
5702   ACCCTTACGTGCGGCTTCGCCGACCTCATGGGGTACATACCGCTCGTCTAATAGTCGAC
       TGGGAATGCACGCCGAAGCGGCTGGAGTACCCCATGTATGGCGAGCAGATTATCAGCTG
```

5724 HGIE2, 5755 SALI,

FIG. 21-10

```
                         MetAlaAlaTyrAlaAlaGlnGlyTyrLysValLeuValLeuAsn
  2  AGCTTACAAAACAAAATGGCTGCATATGCAGCTCAGGGCTATAAGGTGCTAGTACTCAAC
     TCGAATGTTTTGTTTTACCGACGTATACGTCGAGTCCCGATATTCCACGATCATGAGTTG
     ^                  ^                       ^
  1 HIND3,   24 NDEI,   52 SCAI,

ProSerValAlaAlaThrLeuGlyPheGlyAlaTyrMetSerLysAlaHisGlyIleAsp
 62  CCCTCTGTTGCTGCAACACTGGGCTTTGGTGCTTACATGTCCAAGGCTCATGGGATCGAT
     GGGAGACAACGACGTTGTGACCCGAAACCACGAATGTACAGGTTCCGAGTACCCTAGCTA
                                                               ^
   116 CLAI,

ProAsnIleArgThrGlyValArgThrIleThrThrGlySerProIleThrTyrSerThr
122  CCTAACATCAGGACCGGGGTGAGAACAATTACCACTGGCAGCCCCATCACGTACTCCACC
     GGATTGTAGTCCTGGCCCCACTCTTGTTAATGGTGACCGTCGGGGTAGTGCATGAGGTGG

TyrGlyLysPheLeuAlaAspGlyGlyCysSerGlyGlyAlaTyrAspIleIleIleCys
182  TACGGCAAGTTCCTTGCCGACGGCGGGTGCTCGGGGGGCGCTTATGACATAATAATTTGT
     ATGCCGTTCAAGGAACGGCTGCCGCCCACGAGCCCCCCGCGAATACTGTATTATTAAACA

AspGluCysHisSerThrAspAlaThrSerIleLeuGlyIleGlyThrValLeuAspGln
242  GACGAGTGCCACTCCACGGATGCCACATCCATCTTGGGCATTGGCACTGTCCTTGACCAA
     CTGCTCACGGTGAGGTGCCTACGGTGTAGGTAGAACCCGTAACCGTGACAGGAACTGGTT

AlaGluThrAlaGlyAlaArgLeuValValLeuAlaThrAlaThrProProGlySerVal
302  GCAGAGACTGCGGGGGCGAGACTGGTTGTGCTCGCCACCGCCACCCCTCCGGGCTCCGTC
     CGTCTCTGACGCCCCCGCTCTGACCAACACGAGCGGTGGCGGTGGGGAGGCCCGAGGCAG
     ^
   303 ALWN1,

ThrValProHisProAsnIleGluGluValAlaLeuSerThrThrGlyGluIleProPhe
362  ACTGTGCCCCATCCCAACATCGAGGAGGTTGCTCTGTCCACCACCGGAGAGATCCCTTTT
     TGACACGGGGTAGGGTTGTAGCTCCTCCAACGAGACAGGTGGTGGCCTCTCTAGGGAAAA

TyrGlyLysAlaIleProLeuGluValIleLysGlyGlyArgHisLeuIlePheCysHis
422  TACGGCAAGGCTATCCCCCTCGAAGTAATCAAGGGGGGGAGACATCTCATCTTCTGTCAT
     ATGCCGTTCCGATAGGGGGAGCTTCATTAGTTCCCCCCCTCTGTAGAGTAGAAGACAGTA
```

FIG. 22-1

```
       SerLysLysLysCysAspGluLeuAlaAlaLysLeuValAlaLeuGlyIleAsnAlaVal
482    TCAAAGAAGAAGTGCGACGAACTCGCCGCAAAGCTGGTCGCATTGGGCATCAATGCCGTG
       AGTTTCTTCTTCACGCTGCTTGAGCGGCGTTTCGACCAGCGTAACCCGTAGTTACGGCAC

AlaTyrTyrArgGlyLeuAspValSerValIleProThrSerGlyAspValValValVal
542    GCCTACTACCGCGGTCTTGACGTGTCCGTCATCCCGACCAGCGGCGATGTTGTCGTCGTG
       CGGATGATGGCGCCAGAACTGCACAGGCAGTAGGGCTGGTCGCCGCTACAACAGCAGCAC
                    ^                    ^
       550 SAC2, 560 DRD1,

AlaThrAspAlaLeuMetThrGlyTyrThrGlyAspPheAspSerValIleAspCysAsn
602    GCAACCGATGCCCTCATGACCGGCTATACCGGCGACTTCGACTCGGTGATAGACTGCAAT
       CGTTGGCTACGGGAGTACTGGCCGATATGGCCGCTGAAGCTGAGCCACTATCTGACGTTA
                            ^
       615 BSPH1,

ThrCysValThrGlnThrValAspPheSerLeuAspProThrPheThrIleGluThrIle
662    ACGTGTGTCACCCAGACAGTCGATTTCAGCCTTGACCCTACCTTCACCATTGAGACAATC
       TGCACACAGTGGGTCTGTCAGCTAAAGTCGGAACTGGGATGGAAGTGGTAACTCTGTTAG

ThrLeuProGlnAspAlaValSerArgThrGlnArgArgGlyArgThrGlyArgGlyLys
722    ACGCTCCCCCAAGATGCTGTCTCCGCACTCAACGTCGGGGCAGGACTGGCAGGGGGAAG
       TGCGAGGGGGTTCTACGACAGAGGGCGTGAGTTGCAGCCCCGTCCTGACCGTCCCCCTTC

ProGlyIleTyrArgPheValAlaProGlyGluArgProSerGlyMetPheAspSerSer
782    CCAGGCATCTACAGATTTGTGGCACCGGGGGAGCGCCCCTCCGGCATGTTCGACTCGTCC
       GGTCCGTAGATGTCTAAACACCGTGGCCCCCTCGCGGGGAGGCCGTACAAGCTGAGCAGG
                          ^                        ^
       816 BGLI, 833 DRD1,

ValLeuCysGluCysTyrAspAlaGlyCysAlaTrpTyrGluLeuThrProAlaGluThr
842    GTCCTCTGTGAGTGCTATGACGCAGGCTGTGCTTGGTATGAGCTCACGCCCGCCGAGACT
       CAGGAGACACTCACGATACTGCGTCCGACACGAACCATACTCGAGTGCGGGCGGCTCTGA
                                                              ^
       881 SACI,

ThrValArgLeuArgAlaTyrMetAsnThrProGlyLeuProValCysGlnAspHisLeu
902    ACAGTTAGGCTACGAGCGTACATGAACACCCCGGGGCTTCCCGTGTGCCAGGACCATCTT
       TGTCAATCCGATGCTCGCATGTACTTGTGGGGCCCCGAAGGGCACACGGTCCTGGTAGAA
                                ^
       931 SMAI XMAI,

GluPheTrpGluGlyValPheThrGlyLeuThrHisIleAspAlaHisPheLeuSerGln
962    GAATTTTGGGAGGGCGTCTTTACAGGCCTCACTCATATAGATGCCCACTTTCTATCCCAG
       CTTAAAACCCTCCCGCAGAAATGTCCGGAGTGAGTATATCTACGGGTGAAAGATAGGGTC
                                           ^
       985 STUI,

ThrLysGlnSerGlyGluAsnLeuProTyrLeuValAlaTyrGlnAlaThrValCysAla
1022   ACAAAGCAGAGTGGGGAGAACCTTCCTTACCTGGTAGCGTACCAAGCCACCGTGTGCGCT
       TGTTTCGTCTCACCCCTCTTGGAAGGAATGGACCATCGCATGGTTCGGTGGCACACGCGA
                                                          ^
       1069 DRA3,

ArgAlaGlnAlaProProProSerTrpAspGlnMetTrpLysCysLeuIleArgLeuLys
1082   AGGGCTCAAGCCCCTCCCCCATCGTGGGACCAGATGTGGAAGTGTTTGATTCGCCTCAAG
```

FIG. 22-2

TCCCGAGTTCGGGGAGGGGGTAGCACCCTGGTCTACACCTTCACAAACTAAGCGGAGTTC

```
     ProThrLeuHisGlyProThrProLeuLeuTyrArgLeuGlyAlaValGlnAsnGluIle
1142 CCCACCCTCCATGGGCCAACACCCCTGCTATACAGACTGGGCGCTGTTCAGAATGAAATC
     GGGTGGGAGGTACCCGGTTGTGGGGACGATATGTCTGACCCGCGACAAGTCTTACTTTAG
                  ^
1150 NCOI,
```

```
     ThrLeuThrHisProValThrLysTyrIleMetThrCysMetSerAlaAspLeuGluVal
1202 ACCCTGACGCACCCAGTCACCAAATACATCATGACATGCATGTCGGCCGACCTGGAGGTC
     TGGGACTGCGTGGGTCAGTGGTTTATGTAGTACTGTACGTACAGCCGGCTGGACCTCCAG
              ^    ^    ^       ^    ^
1230 BSPH1, 1234 DRD1, 1237 AVA3, 1245 EAG1 XMA3, 1250 DRD1,
```

```
     ValThrSerThrTrpValLeuValGlyGlyValLeuAlaAlaLeuAlaAlaTyrCysLeu
1262 GTCACGAGCACCTGGGTGCTCGTTGGCGGCGTCCTGGCTGCTTTGGCCGCGTATTGCCTG
     CAGTGCTCGTGGACCCACGAGCAACCGCCGCAGGACCGACGAAACCGGCGCATAACGGAC
```

```
     SerThrGlyCysValValIleValGlyArgValValLeuSerGlyLysProAlaIleIle
1322 TCAACAGGCTGCGTGGTCATAGTGGGCAGGGTCGTCTTGTCCGGGAAGCCGGCAATCATA
     AGTTGTCCGACGCACCAGTATCACCCGTCCCAGCAGAACAGGCCCTTCGGCCGTTAGTAT
                                                      ^
1369 NAEI,
```

```
     ProAspArgGluValLeuTyrArgGluPheAspGluMetGluGluCysSerGlnHisLeu
1382 CCTGACAGGGAAGTCCTCTACCGAGAGTTCGATGAGATGGAAGAGTGCTCTCAGCACTTA
     GGACTGTCCCTTCAGGAGATGGCTCTCAAGCTACTCTACCTTCTCACGAGAGTCGTGAAT
         ^
1385 DRD1,
```

```
     ProTyrIleGluGlnGlyMetMetLeuAlaGluGlnPheLysGlnLysAlaLeuGlyLeu
1442 CCGTACATCGAGCAAGGGATGATGCTCGCCGAGCAGTTCAAGCAGAAGGCCCTCGGCCTC
     GGCATGTAGCTCGTTCCCTACTACGAGCGGCTCGTCAAGTTCGTCTTCCGGGAGCCGGAG
```

```
     LeuGlnThrAlaSerArgGlnAlaGluValIleAlaProAlaValGlnThrAsnTrpGln
1502 CTGCAGACCGCGTCCCGTCAGGCAGAGGTTATCGCCCCTGCTGTCCAGACCAACTGGCAA
     GACGTCTGGCGCAGGGCAGTCCGTCTCCAATAGCGGGGACGACAGGTCTGGTTGACCGTT
     ^    ^
1502 PSTI, 1507 TTH3I,
```

```
     LysLeuGluThrPheTrpAlaLysHisMetTrpAsnPheIleSerGlyIleGlnTyrLeu
1562 AAACTCGAGACCTTCTGGGCGAAGCATATGTGGAACTTCATCAGTGGGATACAATACTTG
     TTTGAGCTCTGGAAGACCCGCTTCGTATACACCTTGAAGTAGTCACCCTATGTTATGAAC
         ^                ^
1565 XHOI, 1586 NDEI,
```

```
     AlaGlyLeuSerThrLeuProGlyAsnProAlaIleAlaSerLeuMetAlaPheThrAla
1622 GCGGGCTTGTCAACGCTGCCTGGTAACCCCGCCATTGCTTCATTGATGGCTTTTACAGCT
     CGCCCGAACAGTTGCGACGGACCATTGGGGCGGTAACGAAGTAACTACCGAAAATGTCGA
                 ^                                          ^
1643 BSTE2, 1677 ALWN1 PVU2,
```

```
     AlaValThrSerProLeuThrThrSerGlnThrLeuLeuPheAsnIleLeuGlyGlyTrp
1682 GCTGTCACCAGCCCACTAACCACTAGCCAAACCCTCCTCTTCAACATATTGGGGGGGTGG
     CGACAGTGGTCGGGTGATTGGTGATCGGTTTGGGAGGAGAAGTTGTATAACCCCCCCACC
```

FIG. 22-3

```
                ValAlaAlaGlnLeuAlaAlaProGlyAlaAlaThrAlaPheValGlyAlaGlyLeuAla
       1742     GTGGCTGCCCAGCTCGCCGCCCCCGGTGCCGCTACTGCCTTTGTGGGCGCTGGCTTAGCT
                CACCGACGGGTCGAGCGGCGGGGGCCACGGCGATGACGGAAACACCCGCGACCGAATCGA
                                                                           ^
       1794 ESP1,

GlyAlaAlaIleGlySerValGlyLeuGlyLysValLeuIleAspIleLeuAlaGlyTyr
       1802     GGCGCCGCCATCGGCAGTGTTGGACTGGGGAAGGTCCTCATAGACATCCTTGCAGGGTAT
                CCGCGGCGGTAGCCGTCACAACCTGACCCCTTCCAGGAGTATCTGTAGGAACGTCCCATA
                ^
       1802 KAS1 NARI,

GlyAlaGlyValAlaGlyAlaLeuValAlaPheLysIleMetSerGlyGluValProSer
       1862     GGCGCGGGCGTGGCGGGAGCTCTTGTGGCATTCAAGATCATGAGCGGTGAGGTCCCCTCC
                CCGCGCCCGCACCGCCCTCGAGAACACCGTAAGTTCTAGTACTCGCCACTCCAGGGGAGG
                                         ^              ^
       1878 SACI, 1899 BSPH1,

ThrGluAspLeuValAsnLeuLeuProAlaIleLeuSerProGlyAlaLeuValValGly
       1922     ACGGAGGACCTGGTCAATCTACTGCCCGCCATCCTCTCGCCCGGAGCCCTCGTAGTCGGC
                TGCCTCCTGGACCAGTTAGATGACGGGCGGTAGGAGAGCGGGCCTCGGGAGCATCAGCCG
                                ^
       1928 TTH3I,

ValValCysAlaAlaIleLeuArgArgHisValGlyProGlyGluGlyAlaValGlnTrp
       1982     GTGGTCTGTGCAGCAATACTGCGCCGGCACGTTGGCCCGGGCGAGGGGGCAGTGCAGTGG
                CACCAGACACGTCGTTATGACGCGGCCGTGCAACCGGGCCCGCTCCCCCGTCACGTCACC
                                        ^           ^
       2004 NAEI, 2017 SMAI XMAI,

MetAsnArgLeuIleAlaPheAlaSerArgGlyAsnHisValSerProThrHisTyrVal
       2042     ATGAACCGGCTGATAGCCTTCGCCTCCCGGGGGAACCATGTTTCCCCCACGCACTACGTG
                TACTTGGCCGACTATCGGAAGCGGAGGGCCCCCTTGGTACAAAGGGGGTGCGTGATGCAC
                                   ^                      ^
       2067 SMAI XMAI, 2093 DRA3,

ProGluSerAspAlaAlaAlaArgValThrAlaIleLeuSerSerLeuThrValThrGln
       2102     CCGGAGAGCGATGCAGCTGCCCGCGTCACTGCCATACTCAGCAGCCTCACTGTAACCCAG
                GGCCTCTCGCTACGTCGACGGGCGCAGTGACGGTATGAGTCGTCGGAGTGACATTGGGTC
                             ^                                           ^
       2115 PVU2, 2159 ALWN1,

LeuLeuArgArgLeuHisGlnTrpIleSerSerGluCysThrThrProCysSerGlySer
       2162     CTCCTGAGGCGACTGCACCAGTGGATAAGCTCGGAGTGTACCACTCCATGCTCCGGTTCC
                GAGGACTCCGCTGACGTGGTCACCTATTCGAGCCTCACATGGTGAGGTACGAGGCCAAGG
                  ^                                                        ^
       2164 MST2, 2220 ECON1,

TrpLeuArgAspIleTrpAspTrpIleCysGluValLeuSerAspPheLysThrTrpLeu
       2222     TGGCTAAGGGACATCTGGGACTGGATATGCGAGGTGTTGAGCGACTTTAAGACCTGGCTA
                ACCGATTCCCTGTAGACCCTGACCTATACGCTCCACAACTCGCTGAAATTCTGGACCGAT

LysAlaLysLeuMetProGlnLeuProGlyIleProPheValSerCysGlnArgGlyTyr
       2282     AAAGCTAAGCTCATGCCACAGCTGCCTGGGATCCCCTTTGTGTCCTGCCAGCGCGGGTAT
                TTTCGATTCGAGTACGGTGTCGACGGACCCTAGGGGAAACACAGGACGGTCGCGCCCATA
                       ^                     ^     ^
       2285 ESP1, 2300 PVU2, 2310 BAMHI,
```

FIG. 22-4

```
       LysGlyValTrpArgGlyAspGlyIleMetHisThrArgCysHisCysGlyAlaGluIle
2342   AAGGGGGTCTGGCGAGGGGACGGCATCATGCACACTCGCTGCCACTGTGGAGCTGAGATC
       TTCCCCCAGACCGCTCCCCTGCCGTAGTACGTGTGAGCGACGGTGACACCTCGACTCTAG

ThrGlyHisValLysAsnGlyThrMetArgIleValGlyProArgThrCysArgAsnMet
2402   ACTGGACATGTCAAAAACGGGACGATGAGGATCGTCGGTCCTAGGACCTGCAGGAACATG
       TGACCTGTACAGTTTTTGCCCTGCTACTCCTAGCAGCCAGGATCCTGGACGTCCTTGTAC
                    ^                    ^             ^^
       2425 BSAB1,  2441 AVR2,  2448 SSE83871,  2449 PSTI,

TrpSerGlyThrPheProIleAsnAlaTyrThrThrGlyProCysThrProLeuProAla
2462   TGGAGTGGGACCTTCCCCATTAATGCCTACACCACGGGCCCCTGTACCCCCCTTCCTGCG
       ACCTCACCCTGGAAGGGGTAATTACGGATGTGGTGCCCGGGGACATGGGGGGAAGGACGC
                         ^                ^
       2480 ASE1,  2497 APAI,

ProAsnTyrThrPheAlaLeuTrpArgValSerAlaGluGluTyrValGluIleArgGln
2522   CCGAACTACACGTTCGCGCTATGGAGGGTGTCTGCAGAGGAATACGTGGAGATAAGGCAG
       GGCTTGATGTGCAAGCGCGATACCTCCCACAGACGTCTCCTTATGCACCTCTATTCCGTC
                                         ^
       2553 PSTI,

ValGlyAspPheHisTyrValThrGlyMetThrThrAspAsnLeuLysCysProCysGln
2582   GTGGGGGACTTCCACTACGTGACGGGTATGACTACTGACAATCTTAAATGCCCGTGCCAG
       CACCCCCTGAAGGTGATGCACTGCCCATACTGATGACTGTTAGAATTTACGGGCACGGTC
                      ^
       2594 DRA3,

ValProSerProGluPhePheThrGluLeuAspGlyValArgLeuHisArgPheAlaPro
2642   GTCCCATCGCCCGAATTTTTCACAGAATTGGACGGGGTGCGCCTACATAGGTTTGCGCCC
       CAGGGTAGCGGGCTTAAAAAGTGTCTTAACCTGCCCCACGCGGATGTATCCAAACGCGGG

ProCysLysProLeuLeuArgGluGluValSerPheArgValGlyLeuHisGluTyrPro
2702   CCCTGCAAGCCCTTGCTGCGGGAGGAGGTATCATTCAGAGTAGGACTCCACGAATACCCG
       GGGACGTTCGGGAACGACGCCCTCCTCCATAGTAAGTCTCATCCTGAGGTGCTTATGGGC
                                                                ^
       2757 HGIE2,

ValGlySerGlnLeuProCysGluProGluProAspValAlaValLeuThrSerMetLeu
2762   GTAGGGTCGCAATTACCTTGCGAGCCCGAACCGGACGTGGCCGTGTTGACGTCCATGCTC
       CATCCCAGCGTTAATGGAACGCTCGGGCTTGGCCTGCACCGGCACAACTGCAGGTACGAG
                                                           ^
       2809 AAT2,

ThrAspProSerHisIleThrAlaGluAlaAlaGlyArgArgLeuAlaArgGlySerPro
2822   ACTGATCCCTCCCATATAACAGCAGAGGCGGCCGGGCGAAGGTTGGCGAGGGGATCACCC
       TGACTAGGGAGGGTATATTGTCGTCTCCGCCGGCCCGCTTCCAACCGCTCCCCTAGTGGG
                                               ^
       2850 EAG1 XMA3,

ProSerValAlaSerSerSerAlaSerGlnLeuSerAlaProSerLeuLysAlaThrCys
2882   CCCTCTGTGGCCAGCTCCTCGGCTAGCCAGCTATCCGCTCCATCTCTCAAGGCAACTTGC
       GGGAGACACCGGTCGAGGAGCCGATCGGTCGATAGGCGAGGTAGAGAGTTCCGTTGAACG
                 ^        ^
       2889 BALI,  2903 NHEI,
```

FIG. 22-5

```
                ThrAlaAsnHisAspSerProAspAlaGluLeuIleGluAlaAsnLeuLeuTrpArgGln
2942    ACCGCTAACCATGACTCCCCTGATGCTGAGCTCATAGAGGCCAACCTCCTATGGAGGCAG
        TGGCGATTGGTACTGAGGGGACTACGACTCGAGTATCTCCGGTTGGAGGATACCTCCGTC
                                    ^   ^
2966 ESP1, 2969 SACI,

GluMetGlyGlyAsnIleThrArgValGluSerGluAsnLysValValIleLeuAspSer
3002    GAGATGGGCGGCAACATCACCAGGGTTGAGTCAGAAAACAAAGTGGTGATTCTGGACTCC
        CTCTACCCGCCGTTGTAGTGGTCCCAACTCAGTCTTTTGTTTCACCACTAAGACCTGAGG

PheAspProLeuValAlaGluGluAspGluArgGluIleSerValProAlaGluIleLeu
3062    TTCGATCCGCTTGTGGCGGAGGAGGACGAGCGGGAGATCTCCGTACCCGCAGAAATCCTG
        AAGCTAGGCGAACACCGCCTCCTCCTGCTCGCCCTCTAGAGGCATGGGCGTCTTTAGGAC
                                                        ^
3096 BGL2,

ArgLysSerArgArgPheAlaGlnAlaLeuProValTrpAlaArgProAspTyrAsnPro
3122    CGGAAGTCTCGGAGATTCGCCCAGGCCCTGCCCGTTTGGGCGCGGCCGGACTATAACCCC
        GCCTTCAGAGCCTCTAAGCGGGTCCGGGACGGGCAAACCCGCGCCGGCCTGATATTGGGG
                                    ^           ^
3143 ALWN1, 3164 EAG1 XMA3,

ProLeuValGluThrTrpLysLysProAspTyrGluProProValValHisGlyCysPro
3182    CCGCTAGTGGAGACGTGGAAAAAGCCCGACTACGAACCACCTGTGGTCCATGGCTGCCCG
        GGCGATCACCTCTGCACCTTTTTCGGGCTGATGCTTGGTGGACACCAGGTACCGACGGGC
                                ^                   ^
3217 HGIE2, 3229 NCOI,

LeuProProProLysSerProProValProProProArgLysLysArgThrValValLeu
3242    CTTCCACCTCCAAAGTCCCCTCCTGTGCCTCCGCCTCGGAAGAAGCGGACGGTGGTCCTC
        GAAGGTGGAGGTTTCAGGGGAGGACACGGAGGCGGAGCCTTCTTCGCCTGCCACCAGGAG

ThrGluSerThrLeuSerThrAlaLeuAlaGluLeuAlaThrArgSerPheGlySerSer
? 02    ACTGAATCAACCCTATCTACTGCCTTGGCCGAGCTCGCCACCAGAAGCTTTGGCAGCTCC
        TGACTTAGTTGGGATAGATGACGGAACCGGCTCGAGCGGTGGTCTTCGAAACCGTCGAGG
                                            ^               ^
3332 SACI, 3346 HIND3,

SerThrSerGlyIleThrGlyAspAsnThrThrThrSerSerGluProAlaProSerGly
3362    TCAACTTCCGGCATTACGGGCGACAATACGACAACATCCTCTGAGCCCGCCCCTTCTGGC
        AGTTGAAGGCCGTAATGCCCGCTGTTATGCTGTTGTAGGAGACTCGGGCGGGGAAGACCG

CysProProAspSerAspAlaGluSerTyrSerSerMetProProLeuGluGlyGluPro
3422    TGCCCCCCCGACTCCGACGCTGAGTCCTATTCCTCCATGCCCCCCCTGGAGGGGGAGCCT
        ACGGGGGGGCTGAGGCTGCGACTCAGGATAAGGAGGTACGGGGGGGACCTCCCCCTCGGA
                            ^
3437 EAM11051,

GlyAspProAspLeuSerAspGlySerTrpSerThrValSerSerGluAlaAsnAlaGlu
3482    GGGGATCCGGATCTTAGCGACGGGTCATGGTCAACGGTCAGTAGTGAGGCCAACGCGGAG
        CCCCTAGGCCTAGAATCGCTGCCCAGTACCAGTTGCCAGTCATCACTCCGGTTGCGCCTC
        ^^  ^
3484 BAMHI, 3485 BSAB1, 3487 BSPE1,

AspValValCysCysSerMetSerTyrSerTrpThrGlyAlaLeuValThrProCysAla
3542    GATGTCGTGTGCTGCTCAATGTCTTACTCTTGGACAGGCGCACTCGTCACCCCGTGCGCC
        CTACAGCACACGACGAGTTACAGAATGAGAACCTGTCCGCGTGAGCAGTGGGGCACGCGG
```

FIG. 22-6

3589 DRA3, 3600 SAC2,

```
       AlaGluGluGlnLysLeuProIleAsnAlaLeuSerAsnSerLeuLeuArgHisHisAsn
3602   GCGGAAGAACAGAAACTGCCCATCAATGCACTAAGCAACTCGTTGCTACGTCACCACAAT
       CGCCTTCTTGTCTTTGACGGGTAGTTACGTGATTCGTTGAGCAACGATGCAGTGGTGTTA
```

3611 ALWN1, 3655 PFLM1,

```
       LeuValTyrSerThrThrSerArgSerAlaCysGlnArgGlnLysLysValThrPheAsp
3662   TTGGTGTATTCCACCACCTCACGCAGTGCTTGCCAAAGGCAGAAGAAAGTCACATTTGAC
       AACCACATAAGGTGGTGGAGTGCGTCACGAACGGTTTCCGTCTTCTTTCAGTGTAAACTG
```

3681 DRA3,

```
       ArgLeuGlnValLeuAspSerHisTyrGlnAspValLeuLysGluValLysAlaAlaAla
3722   AGACTGCAAGTTCTGGACAGCCATTACCAGGACGTACTCAAGGAGGTTAAAGCAGCGGCG
       TCTGACGTTCAAGACCTGTCGGTAATGGTCCTGCATGAGTTCCTCCAATTTCGTCGCCGC
```

```
       SerLysValLysAlaAsnLeuLeuSerValGluGluAlaCysSerLeuThrProProHis
3782   TCAAAAGTGAAGGCTAACTTGCTATCCGTAGAGGAAGCTTGCAGCCTGACGCCCCCACAC
       AGTTTTCACTTCCGATTGAACGATAGGCATCTCCTTCGAACGTCGGACTGCGGGGGTGTG
```

3816 HIND3,

```
       SerAlaLysSerLysPheGlyTyrGlyAlaLysAspValArgCysHisAlaArgLysAla
3842   TCAGCCAAATCCAAGTTTGGTTATGGGGCAAAAGACGTCCGTTGCCATGCCAGAAAGGCC
       AGTCGGTTTAGGTTCAAACCAATACCCCGTTTTCTGCAGGCAACGGTACGGTCTTTCCGG
```

3875 AAT2, 3890 BGLI,

```
       ValThrHisIleAsnSerValTrpLysAspLeuLeuGluAspAsnValThrProIleAsp
3902   GTAACCCACATCAACTCCGTGTGGAAAGACCTTCTGGAAGACAATGTAACACCAATAGAC
       CATTGGGTGTAGTTGAGGCACACCTTTCTGGAAGACCTTCTGTTACATTGTGGTTATCTG
```

```
       ThrThrIleMetAlaLysAsnGluValPheCysValGlnProGluLysGlyGlyArgLys
3962   ACTACCATCATGGCTAAGAACGAGGTTTTCTGCGTTCAGCCTGAGAAGGGGGGTCGTAAG
       TGATGGTAGTACCGATTCTTGCTCCAAAAGACGCAAGTCGGACTCTTCCCCCCAGCATTC
```

```
       ProAlaArgLeuIleValPheProAspLeuGlyValArgValCysGluLysMetAlaLeu
4022   CCAGCTCGTCTCATCGTGTTCCCCGATCTGGGCGTGCGCGTGTGCGAAAAGATGGCTTTG
       GGTCGAGCAGAGTAGCACAAGGGGCTAGACCCGCACGCGCACACGCTTTTCTACCGAAAC
```

```
       TyrAspValValThrLysLeuProLeuAlaValMetGlySerSerTyrGlyPheGlnTyr
4082   TACGACGTGGTTACAAAGCTCCCCTTGGCCGTGATGGGAAGCTCCTACGGATTCCAATAC
       ATGCTGCACCAATGTTTCGAGGGGAACCGGCACTACCCTTCGAGGATGCCTAAGGTTATG
```

```
       SerProGlyGlnArgValGluPheLeuValGlnAlaTrpLysSerLysLysThrProMet
4142   TCACCAGGACAGCGGGTTGAATTCCTCGTGCAAGCGTGGAAGTCCAAGAAAACCCCAATG
       AGTGGTCCTGTCGCCCAACTTAAGGAGCACGTTCGCACCTTCAGGTTCTTTTGGGGTTAC
```

4160 ECORI,

```
       GlyPheSerTyrAspThrArgCysPheAspSerThrValThrGluSerAspIleArgThr
4202   GGGTTCTCGTATGATACCCGCTGCTTTGACTCCACAGTCACTGAGAGCGACATCCGTACG
       CCCAAGAGCATACTATGGGCGACGAAACTGAGGTGTCAGTGACTCTCGCTGTAGGCATGC
```

FIG. 22-7

4229 DRD1, 4236 ALWN1,

```
        GluGluAlaIleTyrGlnCysCysAspLeuAspProGlnAlaArgValAlaIleLysSer
4262    GAGGAGGCAATCTACCAATGTTGTGACCTCGACCCCCAAGCCCGCGTGGCCATCAAGTCC
        CTCCTCCGTTAGATGGTTACAACACTGGAGCTGGGGGTTCGGGCGCACCGGTAGTTCAGG
                                                 ^       ^
```

4301 BGLI, 4308 BALI,

```
        LeuThrGluArgLeuTyrValGlyGlyProLeuThrAsnSerArgGlyGluAsnCysGly
4322    CTCACCGAGAGGCTTTATGTTGGGGCCCTCTTACCAATTCAAGGGGGGAGAACTGCGGC
        GAGTGGCTCTCCGAAATACAACCCCGGGAGAATGGTTAAGTTCCCCCCTCTTGACGCCG
                    ^
```

4345 APAI,

```
        TyrArgArgCysArgAlaSerGlyValLeuThrThrSerCysGlyAsnThrLeuThrCys
4382    TATCGCAGGTGCCGCGCGAGCGGCGTACTGACAACTAGCTGTGGTAACACCCTCACTTGC
        ATAGCGTCCACGGCGCGCTCGCCGCATGACTGTTGATCGACACCATTGTGGGAGTGAACG
```

```
        TyrIleLysAlaArgAlaAlaCysArgAlaAlaGlyLeuGlnAspCysThrMetLeuVal
4442    TACATCAAGGCCCGGGCAGCCTGTCGAGCCGCAGGGCTCCAGGACTGCACCATGCTCGTG
        ATGTAGTTCCGGGCCCGTCGGACAGCTCGGCGTCCCGAGGTCCTGACGTGGTACGAGCAC
                ^
```

4452 SMAI XMAI,

```
        CysGlyAspAspLeuValValIleCysGluSerAlaGlyValGlnGluAspAlaAlaSer
4502    TGTGGCGACGACTTAGTCGTTATCTGTGAAAGCGCGGGGGTCCAGGAGGACGCGGCGAGC
        ACACCGCTGCTGAATCAGCAATAGACACTTTCGCGCCCCCAGGTCCTCCTGCGCCGCTCG
              ^ ^
```

4508 DRD1, 4511 TTH3I,

```
        LeuArgAlaPheThrGluAlaMetThrArgTyrSerAlaProProGlyAspProProGln
4562    CTGAGAGCCTTCACGGAGGCTATGACCAGGTACTCCGCCCCCCCTGGGGACCCCCCACAA
        GACTCTCGGAAGTGCCTCCGATACTGGTCCATGAGGCGGGGGGGACCCCTGGGGGGTGTT
```

```
        ProGluTyrAspLeuGluLeuIleThrSerCysSerSerAsnValSerValAlaHisAsp
4622    CCAGAATACGACTTGGAGCTCATAACATCATGCTCCTCCAACGTGTCAGTCGCCCACGAC
        GGTCTTATGCTGAACCTCGAGTATTGTAGTACGAGGAGGTTGCACAGTCAGCGGGTGCTG
                                ^
```

4637 SACI,

```
        GlyAlaGlyLysArgValTyrTyrLeuThrArgAspProThrThrProLeuAlaArgAla
4682    GGCGCTGGAAAGAGGGTCTACTACCTCACCCGTGACCCTACAACCCCCCTCGCGAGAGCT
        CCGCGACCTTTCTCCCAGATGATGGAGTGGGCACTGGGATGTTGGGGGGAGCGCTCTCGA
                                                              ^
```

4731 NRUI,

```
        AlaTrpGluThrAlaArgHisThrProValAsnSerTrpLeuGlyAsnIleIleMetPhe
4742    GCGTGGGAGACAGCAAGACACACTCCAGTCAATTCCTGGCTAGGCAACATAATCATGTTT
        CGCACCCTCTGTCGTTCTGTGTGAGGTCAGTTAAGGACCGATCCGTTGTATTAGTACAAA
```

```
        AlaProThrLeuTrpAlaArgMetIleLeuMetThrHisPhePheSerValLeuIleAla
4802    GCCCCCACACTGTGGGCGAGGATGATACTGATGACCCATTTCTTTAGCGTCCTTATAGCC
        CGGGGGTGTGACACCCGCTCCTACTATGACTACTGGGTAAAGAAATCGCAGGAATATCGG
              ^^
```

4806 PFLM1, 4807 DRA3,

ArgAspGlnLeuGluGlnAlaLeuAspCysGluIleTyrGlyAlaCysTyrSerIleGlu

FIG. 22-8

4862 AGGGACCAGCTTGAACAGGCCCTCGATTGCGAGATCTACGGGGCCTGCTACTCCATAGAA
     TCCCTGGTCGAACTTGTCCGGGAGCTAACGCTCTAGATGCCCCGGACGATGAGGTATCTT
                                          ^
4893 BGL2,

ProLeuAspLeuProProIleIleGlnArgLeuHisGlyLeuSerAlaPheSerLeuHis
4922 CCACTGGATCTACCTCCAATCATTCAAAGACTCCATGGCCTCAGCGCATTTTCACTCCAC
     GGTGACCTAGATGGAGGTTAGTAAGTTTCTGAGGTACCGGAGTCGCGTAAAAGTGAGGTG
                                          ^
4954 NCOI,

SerTyrSerProGlyGluIleAsnArgValAlaAlaCysLeuArgLysLeuGlyValPro
4982 AGTTACTCTCCAGGTGAAATCAATAGGGTGGCCGCATGCCTCAGAAAACTTGGGGTACCG
     TCAATGAGAGGTCCACTTTAGTTATCCCACCGGCGTACGGAGTCTTTTGAACCCCATGGC
                                      ^                 ^
5015 SPHI, 5035 KPNI,

ProLeuArgAlaTrpArgHisArgAlaArgSerValArgAlaArgLeuLeuAlaArgGly
5042 CCCTTGCGAGCTTGGAGACACCGGGCCCGGAGCGTCCGCGCTAGGCTTCTGGCCAGAGGA
     GGGAACGCTCGAACCTCTGTGGCCCGGGCCTCGCAGGCGCGATCCGAAGACCGGTCTCCT
                             ^                   ^
5064 APAI, 5091 BALI,

GlyArgAlaAlaIleCysGlyLysTyrLeuPheAsnTrpAlaValArgThrLysLeuLys
5102 GGCAGGGCTGCCATATGTGGCAAGTACCTCTTCAACTGGGCAGTAAGAACAAAGCTCAAA
     CCGTCCCGACGGTATACACCGTTCATGGAGAAGTTGACCCGTCATTCTTGTTTCGAGTTT
                    ^
5113 NDEI,

LeuThrProIleAlaAlaAlaGlyGlnLeuAspLeuSerGlyTrpPheThrAlaGlyTyr
5162 CTCACTCCAATAGCGGCCGCTGGCCAGCTGGACTTGTCCGGCTGGTTCACGGCTGGCTAC
     GAGTGAGGTTATCGCCGGCGACCGGTCGACCTGAACAGGCCGACCAAGTGCCGACCGATG
                    ^^     ^          ^          ^
5174 NOTI, 5175 EAG1 XMA3, 5182 BALI, 5186 PVU2,

SerGlyGlyAspIleTyrHisSerValSerHisAlaArgProArgTrpIleTrpPheCys
5222 AGCGGGGGAGACATTTATCACAGCGTGTCTCATGCCCGGCCCCGCTGGATCTGGTTTTGC
     TCGCCCCCTCTGTAAATAGTGTCGCACAGAGTACGGGCCGGGGCGACCTAGACCAAAACG
                                            ^
5240 DRA3,

LeuLeuLeuLeuAlaAlaGlyValGlyIleTyrLeuLeuProAsnArgMetSerThrAsn
5282 CTACTCCTGCTTGCTGCAGGGGTAGGCATCTACCTCCTCCCCAACCGAATGAGCACGAAT
     GATGAGGACGAACGACGTCCCCATCCGTAGATGGAGGAGGGGTTGGCTTACTCGTGCTTA
              ^
5295 PSTI,

ProLysProGlnArgLysThrLysArgAsnThrAsnArgArgProGlnAspValLysPhe
5342 CCTAAACCTCAAAGAAAGACCAAACGTAACACCAACCGGCGGCCGCAGGACGTCAAGTTC
     GGATTTGGAGTTTCTTTCTGGTTTGCATTGTGGTTGGCCGCCGGCGTCCTGCAGTTCAAG
                                            ^^       ^         ^
5380 NOTI, 5381 EAG1 XMA3, 5390 AAT2, 5401 SMAI XMAI,

ProGlyGlyGlyGlnIleValGlyGlyValTyrLeuLeuProArgArgGlyProArgLeu
5402 CCGGGTGGCGGTCAGATCGTTGGTGGAGTTTACTTGTTGCCGCGCAGGGGCCCTAGATTG
     GGCCCACCGCCAGTCTAGCAACCACCTCAAATGAACAACGGCGCGTCCCCGGGATCTAAC
                                                        ^

FIG. 22-9

```
        5449 APAI,

GlyValArgAlaThrArgLysThrSerGluArgSerGlnProArgGlyArgArgGlnPro
5462   GGTGTGCGCGCGACGAGAAAGACTTCCGAGCGGTCGCAACCTCGAGGTAGACGTCAGCCT
       CCACACGCGCGCTGCTCTTTCTGAAGGCTCGCCAGCGTTGGAGCTCCATCTGCAGTCGGA

5467 BSSH2, 5478 XMNI, 5502 XHOI, 5511 AAT2,

IleProLysAlaArgArgProGluGlyArgThrTrpAlaGlnProGlyTyrProTrpPro
5522   ATCCCCAAGGCTCGTCGGCCCGAGGGCAGGACCTGGGCTCAGCCCGGGTACCCTTGGCCC
       TAGGGGTTCCGAGCAGCCGGGCTCCCGTCCTGGACCCGAGTCGGGCCCATGGGAACCGGG

5548 ALWN1, 5558 ESP1, 5564 SMAI XMAI, 5568 KPNI,

LeuTyrGlyAsnGluGlyCysGlyTrpAlaGlyTrpLeuLeuSerProArgGlySerArg
5582   CTCTATGGCAATGAGGGCTGCGGGTGGGCGGGATGGCTCCTGTCTCCCCGTGGCTCTCGG
       GAGATACCGTTACTCCCGACGCCCACCCGCCCTACCGAGGACAGAGGGGCACCGAGAGCC

ProSerTrpGlyProThrAspProArgArgArgSerArgAsnLeuGlyLysValIleAsp
5642   CCTAGCTGGGGCCCCACAGACCCCCGGCGTAGGTCGCGCAATTTGGGTAAGGTCATCGAT
       GGATCGACCCCGGGGTGTCTGGGGGCCGCATCCAGCGCGTTAAACCCATTCCAGTAGCTA

5650 APAI, 5696 CLAI,

ThrLeuThrCysGlyPheAlaAspLeuMetGlyTyrIleProLeuValGlyAlaProLeu
5702   ACCCTTACGTGCGGCTTCGCCGACCTCATGGGGTACATACCGCTCGTCGGCGCCCCTCTT
       TGGGAATGCACGCCGAAGCGGCTGGAGTACCCCATGTATGGCGAGCAGCCGCGGGGAGAA

5724 HGIE2, 5750 KAS1 NARI, 5756 ECON1,

GlyGlyAlaAlaArgAlaOC AM
5762   GGAGGCGCTGCCAGGGCCTAATAGTCGAC
       CCTCCGCGACGGTCCCGGATTATCAGCTG

5785 SALI,
                    FIG. 22-10
```

HCV NON-STRUCTURAL POLYPEPTIDE

CROSS-REFERENCE TO RELATED APPLICATIONS

This application is a continuation of U.S. Ser. No. 11/195,009, filed Aug. 2, 2005, now U.S. Pat. No. 7,449,566, which is a continuation of U.S. application Ser. No. 09/721,479, filed Nov. 22, 2000, now U.S. Pat. No. 6,986,892, from which applications priority is claimed pursuant to 35 USC §120. U.S. application Ser. No. 09/721,479 claims the benefit under 35 USC §119(e)(1) of provisional application Ser. No. 60/167,502, filed Nov. 24, 1999. The foregoing applications are incorporated herein by reference in their entireties.

FIELD OF THE INVENTION

The present invention relates to polypeptides comprising a mutant non-structural Hepatitis C virus ("HCV") polypeptide useful for immunogenic compounds for use against HCV, methods of preparing and using the same, and immunogenic compositions comprising the same. The present invention also relates to compositions comprising (a) a mutant non-structural HCV polypeptide and (b) a viral polypeptide that is not a non-structural HCV polypeptide and methods of using these compositions.

BACKGROUND OF THE INVENTION

HCV is now recognized as the major agent of chronic hepatitis and liver disease worldwide. It is estimated that HCV infects about 400 million people worldwide, corresponding to more than 3% of the world population.

Hepatitis C virus ("HCV") is a small enveloped RNA flavivirus, which contains a positive-stranded RNA genome of about 10 kilobases. The genome has a single uninterrupted ORF that encodes a protein of 3010-3011 amino acids. The structural proteins of HCV include a core protein (C), which is highly immunogenic, as well as two envelope proteins (E1 and E2), which likely form a heterodimer in vivo, and non-structural proteins NS2-NS5. It is known that the NS3 region of the virus is important for post-translational processing of the polyprotein into individual proteins, and the NS5 region encodes an RNA-dependant RNA polymerase.

Virus-specific T lymphocytes, along with neutralizing antibodies, are the mainstay of the antiviral immune defense in established viral infections. Whereas $CD8^+$ cytotoxic T cells eliminate virus-infected-cells, $CD4^+$ T helper cells are essential for the efficient regulation of the antiviral immune response. $CD4^+$ T helper cells recognize specific antigens as peptides bound to autologous HLA class II molecules (viral antigens or particles are taken up by professional antigen-presenting cells, processed to peptides, bound to HLA class II molecules in the lysosomal compartment, and transported back to the cell surface). Several observations support an important role of $CD4^+$ T cells in the elimination of HCV infection. Tsai et al., 1997 Hepatology 25:449-458; Diepolder et al 1995 Lancet 346: 1-6-1009; Missale et al 1996 JCI 98: 706-714; Botarelli et al 1993; Gastro 104: 580-587; Diepolder et al 1997 J. Virol 71: 6011. Immunogenic peptides usually have a minimal length of 8-11 amino acids. However, since the peptide binding groove of HLA class II molecules seems to be open at both ends, longer peptides are tolerated. Thus peptides eluted from HLA class II molecules are typically in the range of 15-25 amino acids. HLA class II molecules are extremely polymorphic and each allele seems to have its individual requirements for peptide binding. Thus the HLA class II repertoire of a given individual determines which viral peptides can be presented to T cells. Recognition of the specific HLA-peptide complex by the T, cell receptor accompanied by appropriate costimulatory signals lead to T cell activation, secretion of cytokines, and T cell proliferation.

Numerous studies demonstrate that HLA Class II restricted $CD4^+$ responses are determined by stimulating peripheral blood mononuclear cells with recombinant viral antigens or peptides. Botarelli et al., (1993) Gastroenterology 104:580-587; Farrari et al., (1994) Hepatology 19:286-295; Minutello et al., (1993) C. J. Exp. Med. 178:17-25; Hoffmann et al., (1995) Hepatology 21:632-638; Iwata et al., (1995) Hepatology 22:1057-1064; and Tsai et al., (1995) Hepatology 21:908-912.

Polyclonal multispecific $CD8^+$ T cell responses have been detected in patients with chronic hepatitis C. Additionally, $CD8^+$ CTL's were shown to be important in resolving acute HCV infection in chimpanzees (Cooper et al., Immunity 1999). About 50% of patients with chronic hepatitis C demonstrate a detectable virus-specific $CD4^+$ T cell response, which is most frequently directed against HCV core and/or NS4 and tends to be more common in patients who achieve sustained viral clearance during interferon-α therapy.

Depending on the pattern of lymphokines, $CD4^+$ T helper cells have been classified as TH1, TH0, or TH2. Cytokines of the TH1 type are typically-IFN-γ, lymphotoxin, and interleukin-2 (IL-2), which are believed to support activation of virus-specific $CD8^+$ T cells and natural killer cells. The TH2 cytokines IL-4, IL-5, IL-10, and IL-13 are important for B cell activation and differentiation, thus inducing a humoral immune response.

During acute hepatitis C infection a strong and sustained TH1/TH0 response to NS3 and possibly to other nonstructural proteins is associated with a self-limited course of the disease. Diapolder et al., (1995) Lancet 346:1006-1007, showed all $CD4^+$ T cell clones to have a TH1 or TH0 cytokine profile, suggesting that the clones support cytotoxic immune mechanisms in vivo. The majority of $CD4^+$ T cell clones responded to a relatively short segment of NS3, namely amino acids 1207-1278, suggesting that this region of NS3 is immunodominant for $CD4^+$ T cells. More than 70% of those who contract HCV develop chronic infection and hepatitis, and a significant portion of them progress to cirrhosis and eventually hepatocellular carcinoma. The only approved therapy at present is a 6- to 12-month course of interferon α, which leads to sustained improvement in only 20% of patients. So far, no commercial vaccine is available.

Thus, there remains a need for compositions and methods capable of promoting anti-HCV responses.

SUMMARY OF THE INVENTION

In one aspect, the present invention relates to isolated polypeptides comprising mutant hepatitis C ("HCV") polypeptides comprising at least portions of NS3, NS4, and NS5. In a preferred aspect, NS3 is encoded by a nucleic acid sequence having an N-terminal deletion to remove the catalytic domain. The NS mutant polypeptides can include NS3, NS4s, NS4b, NS5a, NS5b or portions thereof. For example, in various embodiments, the mutant NS polypeptide comprises NS3, NS4 (NS4a and NS4b) and NS5 (NS5a and NS5b). In other embodiments, the NS polypeptide consists of NS3 and NS4 (for example, NS4a and/or NS4b) or NS3 and NS5 (for example, NS5a and/or NS5b). Other combinations of full-length or fragments of non-structural components are also contemplated.

In another preferred aspect, the polypeptides further comprise a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. Thus, the invention includes an isolated mutant non-structural ("NS") HCV polypeptide comprising a polypeptide having a mutation in the catalytic domain of NS3 that functionally disrupts the catalytic domain. The mutation can be, for example, a deletion or a substitution mutation. In certain embodiments, the mutant NS polypeptide comprises NS3, NS4 and NS5. In other embodiments, the mutant NS polypeptides described herein further comprise a second viral polypeptide that is not NS3, NS4, or NS5 of HCV, for example an HCV Core polypeptide ("C"), or fragment thereof, or an HCV envelope protein ("E"), for example E1 and/or E2. In certain embodiments, C is truncated (e.g., at amino acid 121).

In another aspect, the present invention relates to compositions comprising any of the mutant hepatitis C ("HCV") polypeptides described herein, for example polypeptides comprising at least portions of NS3, NS4, and NS5. In a preferred aspect, NS3 is encoded by a nucleic acid sequence having an N-terminal deletion to disrupt the function of the catalytic domain, for example by removing this domain. In another preferred aspect, the polypeptides further comprise a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV Such polypeptides need not be encoded by a natural HCV genome, and include, for example, truncated or otherwise mutant HCV polypeptides or polypeptides derived from other genomes, such as, for example, polypeptides of HBV. In another aspect, the invention includes a composition comprising (a) any of the polypeptides described herein; and (b) a pharmaceutically acceptable excipient (e.g., carrier and/or adjuvant).

In another aspect, the invention includes an isolated and purified polynucleotide which encodes any of the mutant HCV polypeptides described herein. In certain embodiments, the invention includes a composition comprising (a) the isolated purified polynucleotide encoding any of the mutant HCV polypeptides; and (b) a pharmaceutically acceptable excipient. The polynucleotide, can be for example, DNA in a plasmid, or is in a plasmid. Additionally, the polynucleotides described herein may be included in an expression vector as shown in the attached Figures and Sequence Listings.

In another aspect, the present invention relates to host cells transformed with expression vectors comprising a nucleic acid sequence encoding a mutant HCV polypeptide comprising at least portions of NS3, NS4, and NS5. In a preferred aspect, the expression vectors of the host cells further comprises at least one nucleic acid sequence encoding a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. In another preferred aspect the nucleic acid sequences of the expression vectors are coexpressed. In yet another preferred aspect, the host cells are yeast cells or mammalian cells.

In another aspect, the present invention relates to expression vectors comprising a nucleic acid sequence encoding a mutant HCV polypeptide comprising NS3, NS4, and NS5. In a preferred aspect, the expression vectors of the host cells further comprises at least one nucleic acid sequence encoding a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Importantly, such polypeptides need not be encoded by a natural HCV genome, such as, for example, truncated or otherwise mutant HCV polypeptides or polypeptides derived from other genomes, such as, for example, polypeptides of HBV. In another aspect, the present invention relates to methods of preparing a mutant HCV polypeptides. In a preferred aspect, the method comprises the steps of transforming a host cell with an expression vector, said vector comprising a nucleic acid sequence encoding a mutant HCV polypeptide comprising at least portions of NS3, NS4, and NS5, and isolating said polypeptide. In another preferred aspect the HCV polypeptide further comprises a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, and include, for example, truncated or otherwise mutant HCV polypeptides or polypeptides derived from other genomes, such as, for example, polypeptides of HBV. In another preferred aspect the host cells are yeast cells or mammalian cells.

In another aspect, the present invention relates to antibodies which specifically bind to mutant HCV polypeptide comprising NS3, NS4, and NS5, and to methods of making and using the same. In a preferred aspect, the HCV polypeptide further comprises a viral polypeptide that is not a non-structural HCV polypeptide. Such polypeptides are preferably C, or antigenic fragments thereof, more preferably, truncated C of HCV. Other polypeptides are preferably E, or antigenic fragments thereof, more preferably, E1 or E2 of HCV. Such polypeptides need not be encoded by a natural HCV genome, such as, for example, truncated or otherwise mutant HCV polypeptides or polypeptides derived from other genomes, and include, for example, polypeptides of HBV. In another preferred aspect, the antibody is either monoclonal or polyclonal.

In yet another aspect, a method of preparing a mutant NS HCV polypeptide, wherein the method comprises the steps of (a) transforming a host cell with any of the expression vectors described herein, under conditions wherein the polypeptide is expressed; and (b) isolating the polypeptide. The host cell can be, for example, a yeast cell, a mammalian cell a plant cell or an insect cell. The polypeptide can be expressed and isolated intracellularly or can be secreted and isolated from the surrounding environment.

In a still further aspect, a method of eliciting an immune response in a subject is provided. The immune response can be elicited by administering any of the polynucleotides and/or polypeptides described herein in one or multiple doses.

These and other embodiments of the subject invention will readily occur to those of skill in the art in light of the disclosure herein.

BRIEF DESCRIPTION OF THE FIGURES

FIG. 3 shows the nucleic acid sequence of pCMV-NS35 (SEQ ID NO:1), including the nucleic acid sequence of the NS35 ORF, and also the translation of NS35 (SEQ ID NO:2).

FIG. 5 shows the nucleic acid sequence of pCMV-delNS35 (SEQ ID NO:3), including the nucleic acid sequence of the delNS35 ORF, and also the translation of the delNS35 polypeptide (SEQ ID NO:4).

FIG. 7 shows the nucleic acid sequence of pCMV-II (SEQ ID NO:5).

FIG. 9 shows the nucleic acid sequence of pCMV-NS34A (SEQ ID NO:6), including the nucleic acid sequence of the NS34A ORF, and also the translation of NS34A (SEQ ID NO:7).

FIG. 11 shows the nucleic and amino acid sequences of pd.ΔNS3NS5 (SEQ ID NO:8 and 9).

FIG. 14 shows the nucleic and amino acid sequences of pd.ΔNS3NS5.pj (SEQ ID NO: 10 and 11).

FIG. 17 shows the nucleic and amino acid sequences of pd.ΔNS3NS5.pj.core121 (SEQ ID NO:12 and 13).

FIG. 18 shows the nucleic and amino acid sequences of pd.ΔNS3NS5.pj.core173 (SEQ ID NO:14 and 15).

FIG. 21 shows the nucleic and amino acid sequences of pd.ΔNS3NS5.pj.core140 (SEQ ID NO:16 and 17).

FIG. 22 shows the nucleic and amino acid sequences of pd.ΔNS3NS5.pj.core150 (SEQ ID NO:18 and 19).

DETAILED DESCRIPTION OF THE INVENTION

Figure 1:
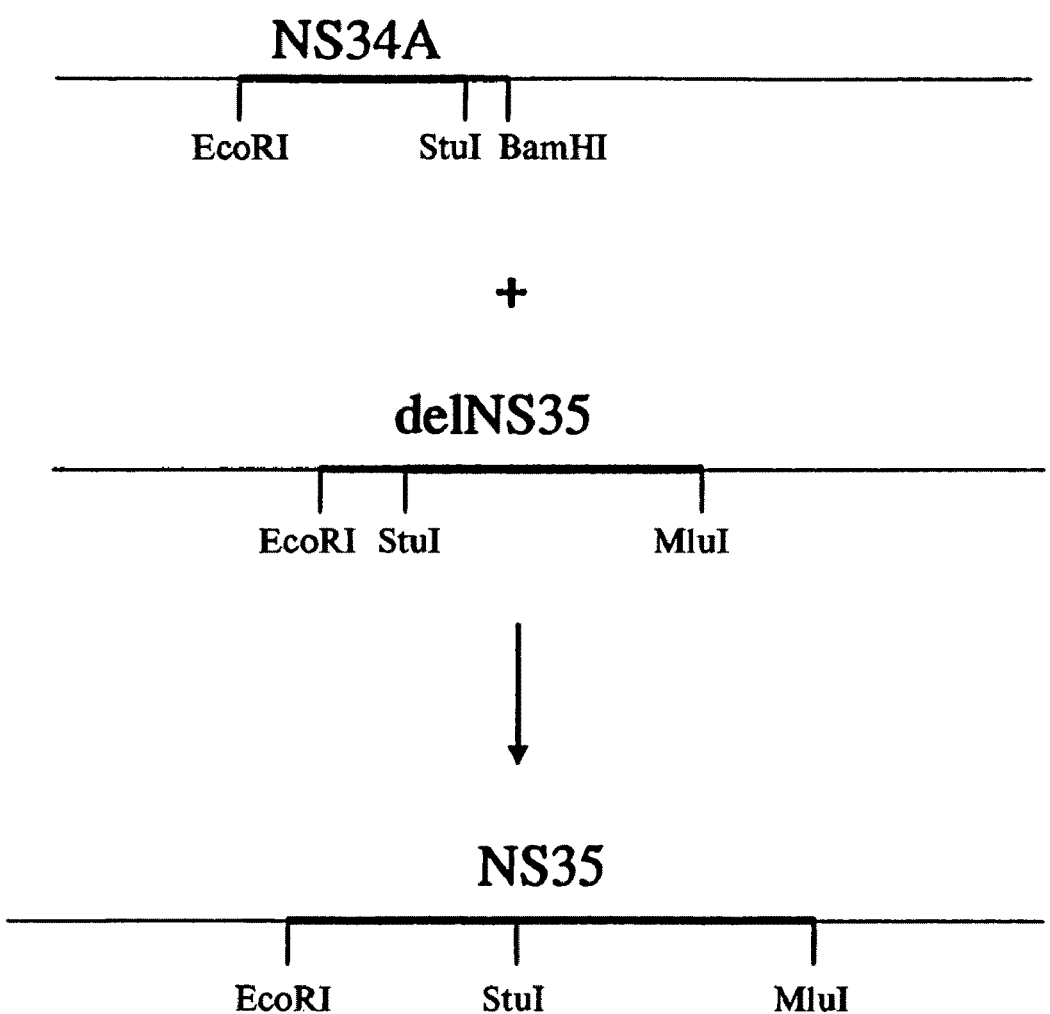
FIG. 1 shows the cloning scheme for generating pCMV-NS35.
Figure 2:
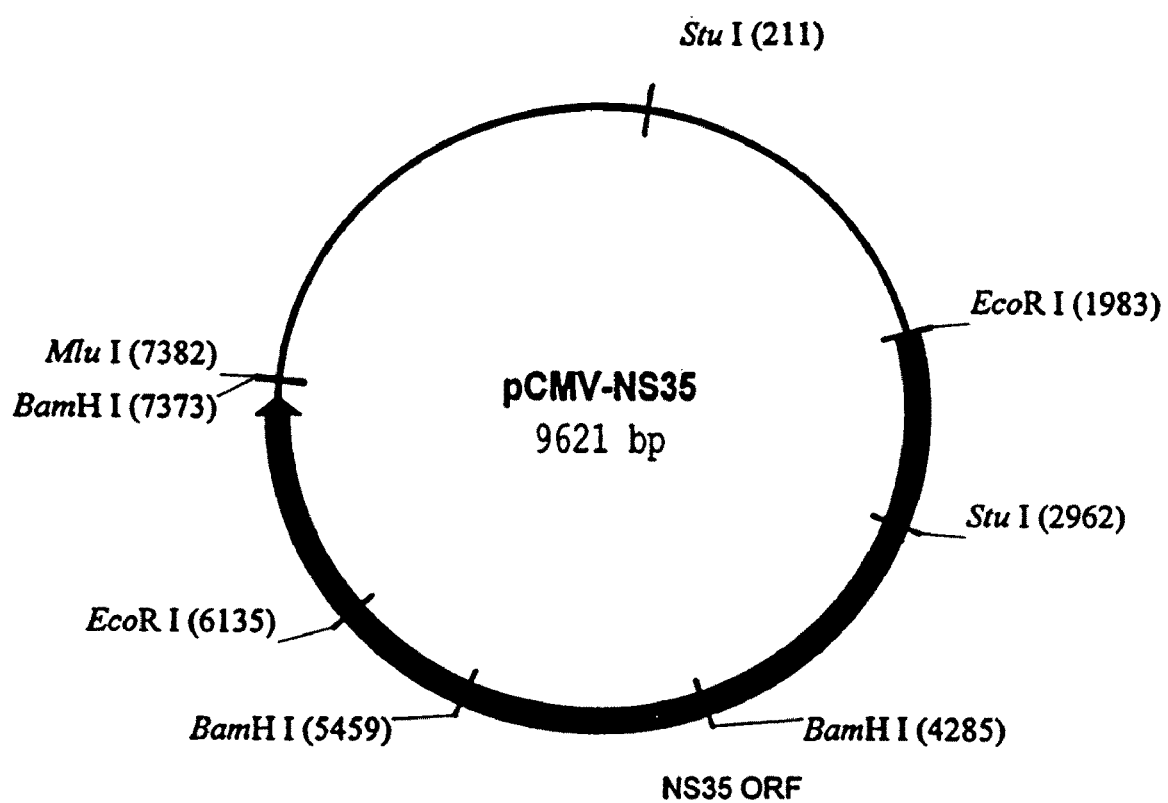
FIG. 2 shows the 9621 bp vector pCMV-NS35.
Figure 4:
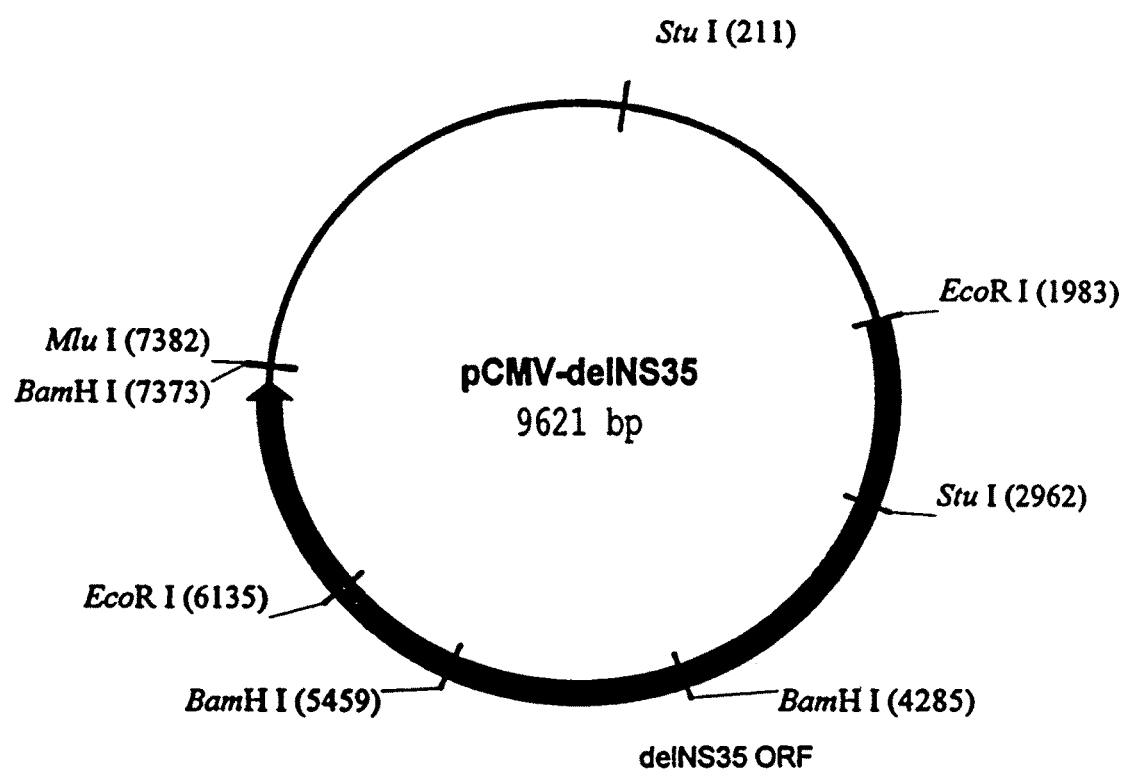
FIG. 4 shows the 9621 bp pCMV-delNS35.
Figure 6:
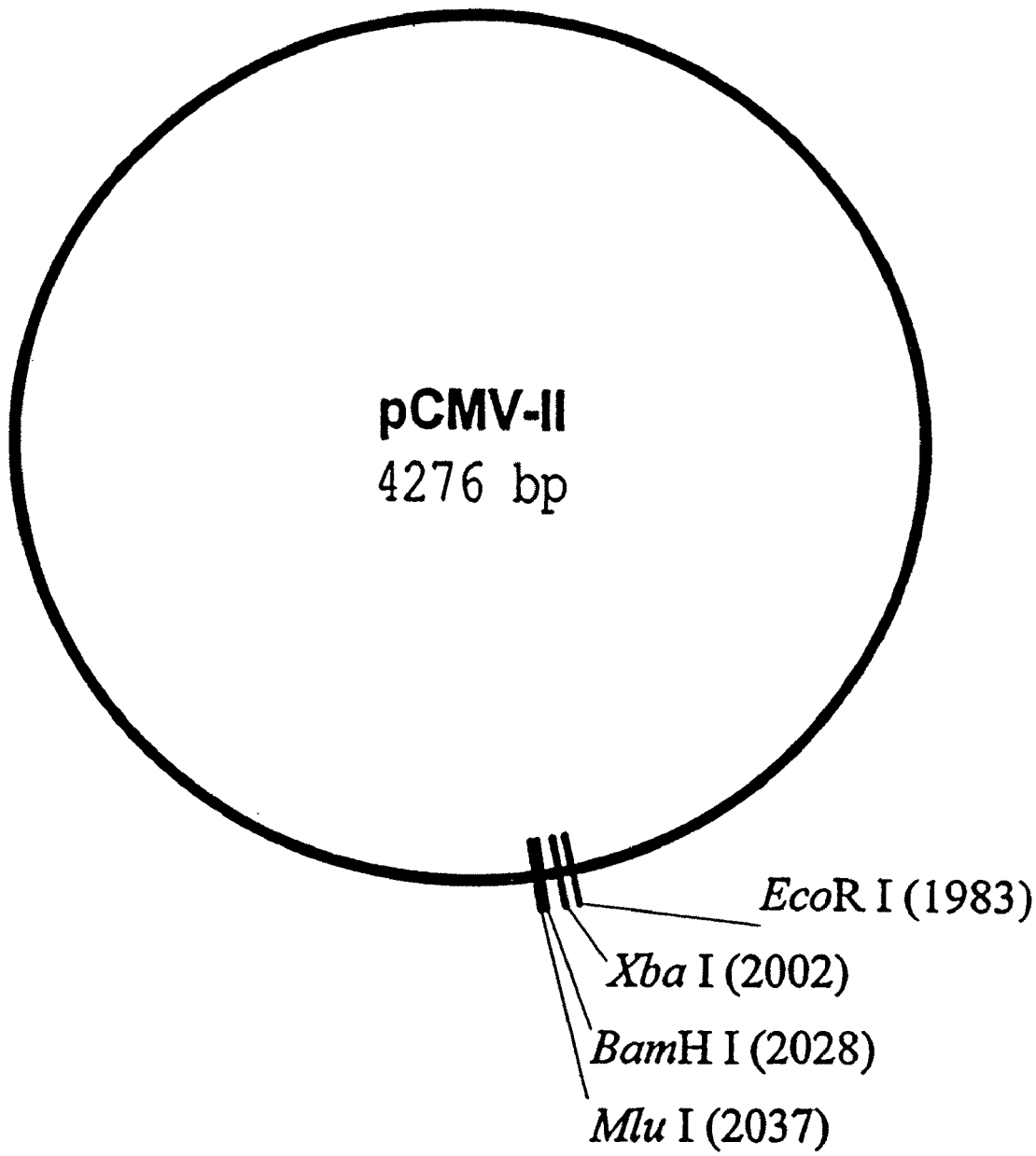
FIG. 6 shows the 4276 bp pCMV-II.
Figure 8:
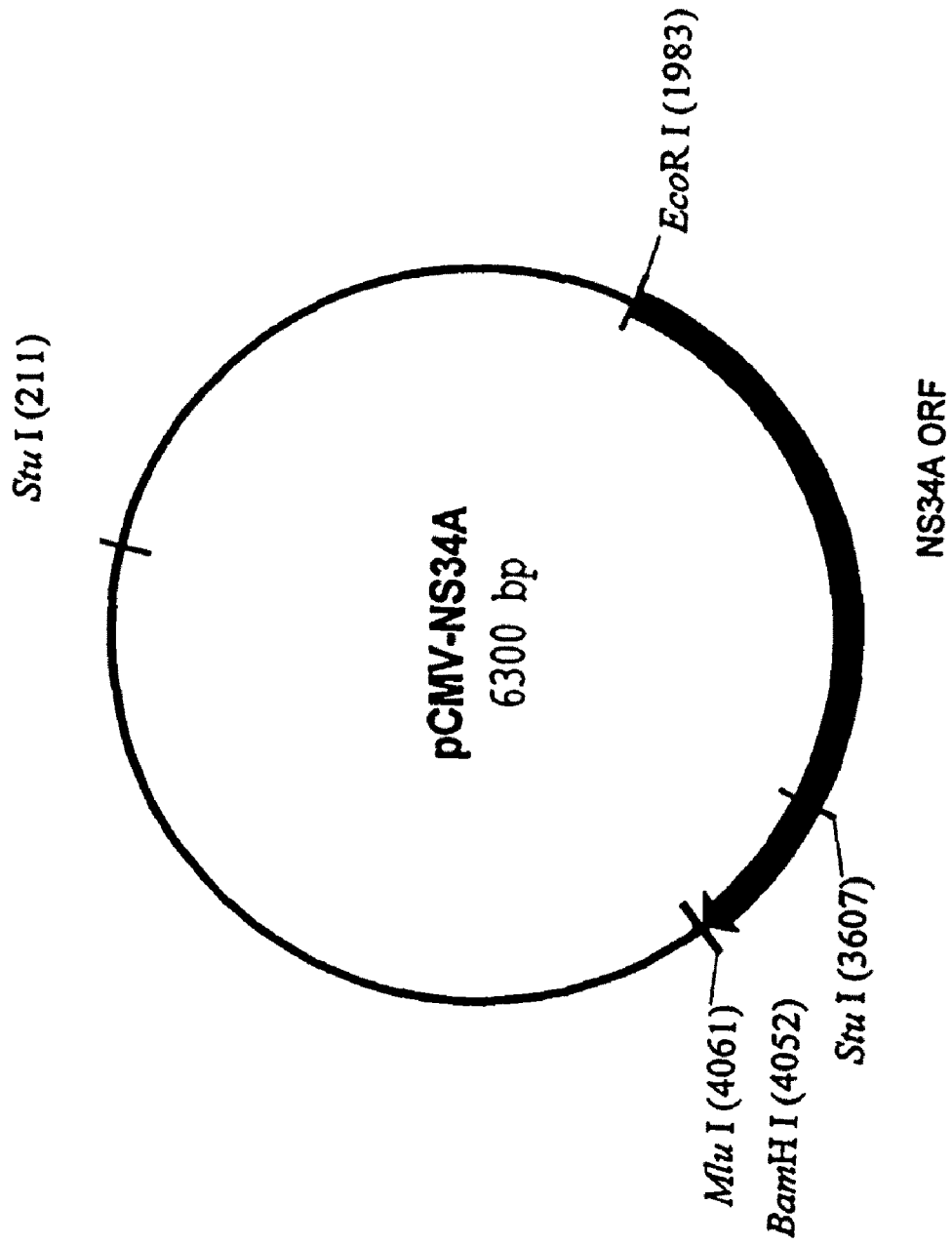
FIG. 8 shows the 6300 bp pCMV-NS34A.

The practice of the present invention will employ, unless otherwise indicated, conventional techniques of molecular biology, microbiology, recombinant DNA techniques, and immunology, which are within the skill of the art. Such techniques are explained fully in the literature. See e.g., Sambrook, et al., MOLECULAR CLONING; A LABORATORY MANUAL (1989); DNA CLONING, VOLUMES I AND II (D. N. Glover ed. 1985); OLIGONUCLEOTIDE SYNTHESIS (M. J. Gait ed., 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS OF ENZYMOLOGY (Academic Press, Inc.); GENE TRANSFER VECTORS FOR MAMMALIAN CELLS (J. H. Miller and M. P. Calos eds. 1987, Cold Springs Harbor Laboratory), Methods in Enzymology Vol. 154 and Vol. 155 (Wu and Grossman, and Wu, eds., respectively); Mayer and Walker eds. (1987), IMMUNOHISTOCHEMICAL METHODS IN CELL AND MOLECULAR BIOLOGY (Academic Press, London); Scopes, (1987), PROTEIN PURIFICATION: PRINCIPALS AND PRACTICE, Second Edition (Springer-Verlag, New York); and HANDBOOK OF EXPERIMENTAL IMMUNOLOGY, VOLUMES I-IV (D. M. Weir and C. C. Blackwell eds. 1986).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

I. DEFINITIONS

In describing the present invention, the following terms will be employed, and are intended to be defined as indicated below.

The term "hepatitis C virus" (HCV) refers to an agent causative of Non-A, Non-B Hepatitis (NANBH). The nucleic acid sequence and putative amino acid sequence of HCV is described in U.S. Pat. Nos. 5,856,437 and 5,350,671. The disease caused by HCV is called hepatitis C, formerly called NANBH. The term HCV, as used herein, denotes a viral species of which pathenogenic strains cause NANBH, as well as attenuated strains or defective interfering particles derived therefrom.

HCV is a member of the viral family flaviviridae. The morphology and composition of Flavivirus particles are known, and are discussed in Reed et al., *Curr. Stud. Hematol. Blood Transfus.* (1998), 62:1-37; HEPATITIS C VIRUSES IN FIELDS VIROLOGY (B. N. Fields, D. M. Knipe, P. M. Howley, eds.) (3d ed. 1996). It has recently been found that portions of the HCV genome are also homologous to pestiviruses. Generally, with respect to morphology, Flaviviruses contain a central nucleocapsid surrounded by a lipid bilayer. Virions are spherical and have a diameter of about 40-50 nm. Their cores are about 25-30 nm in diameter. Along the outer surface of the virion envelope are projections that are about 5-10 nm long with terminal knobs about 2 nm in diameter.

The HCV genome is comprised of RNA. It is known that RNA containing viruses have relatively high rates of spontaneous mutation. Therefore, there can be multiple strains, which can be virulent or a virulent, within the HCV class or species. The ORF of HCV, including the translation spans of the core, non-structural, and envelope proteins, is shown in U.S. Pat. Nos. 5,856,437 and 5,350,671.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains, such as from strains 1, 2, 3 or 4 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned and homology determined by any of the programs or algorithms described herein. Thus, for example, the term "NS4" polypeptide refers to native NS4 from any of the various HCV strains, as well as NS4 analogs, muteins and immunogenic fragments, as defined further below.

Further, the terms "ΔNS35," "delNS35," "ΔNS3NS5," and "ΔNS3-5" as used herein refer to a mutant polypeptide, comprising at least portions of NS3, NS4, or NS5, comprising a deletion in, or mutation of, the NS3 protease active site region to render the protease non-functional. In one embodiment, ΔNS3-5 comprises amino acids 1242-3011, as shown in FIG. 5, or polypeptides substantially homologous thereto. It will be readily apparent to one of ordinary skill in the art how to determine that NS3 protease has been rendered non-functional. If the protease is functional, one will obtain protein of the expected molecular weight upon expression. As set forth in Example 2 and FIG. 15, using SDS-page, 4-20%, a protein having a molecular weight of approximately 194 kD was obtained when strain AD3 was transformed with pd.ΔNS3NS5.PJ clone #5. One skilled in the art could readily determine whether a protein of the desired molecular weight was expressed for any given deletion or mutation.

The terms "analog" and "mutein" refer to biologically active derivatives of the reference molecule, or fragments of such derivatives, that retain desired activity, such as the ability to stimulate a cell-mediated immune response, as defined below. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunogenic activity, as measured by the assays described herein. For a description of various HCV epitopes, see, e.g., Chien et al., Proc. Natl. Acad. Sci. USA (1992) 89:10011-10015; Chien et al., J. Gastroent. Hepatol. (1993) 8:S33-39; Chien et al., International Publication No. WO 93/00365; Chien, D. Y., International Publication No. WO 94/01778; commonly owned, allowed U.S. patent application Ser. Nos. 08/403,590 and 08/444,818.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana-Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety.

An "immunological response" to an HCV antigen (including both polypeptide and polynucleotides encoding polypeptides that are expressed in vivo) or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (SMC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of biological macromolecules of the same type are present.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98%, or more, sequence identity over a defined length of the molecules. As used herein, substantially homologous also refers to sequences showing complete identity to the specified DNA or polypeptide sequence. The term "substantially homologous" as used herein in reference to ΔNS35 generally refers to an HCV nucleic or amino acid sequence that is at least 60% identical to the entire sequence of the polypeptide encoded by ΔNS35 (see FIG. 5), where the sequence identity is preferably at least 75%, more preferably at least 80%, still more preferably at least about 85%, especially more than about 90%, most preferably 95% or greater, particularly 98% or greater. These homologous polypeptides include fragments, including mutants and allelic variants of the fragments. Identity between the two sequences is preferably determined by the Smith-Waterman homology search algorithm as implemented in the MPSRCH program (Oxford Molecular), using an affine gap search with parameters gap open penalty=12 and gap extension penalty=1. Thus, for example, the present invention includes an isolate which is 80% identical to a polypeptide encoded by ΔNS35. In some aspects of the invention, the polypeptide of the present invention is substantially homologous to the ΔNS35.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters; For example, BLASTN and BLASTP can be used using the following default parameters: genetic code=standard; filter=none; strand=both; cutoff 60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%\ (G+C)]-0.6(\%\ \text{formamide})-600/n-1.5(\%\ \text{mismatch}).$$

where Ci is the salt concentration (monovalent ions) and n is the length of the hybrid in base pairs (slightly modified from Meinkoth & Wahl (1984) *Anal. Biochem.* 138: 267-284). In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

An "open reading frame" or ORF is a region of a polynucleotide sequence which encodes a polypeptide; this region can represent a portion of a coding sequence or a total coding sequence.

As used herein, the term "antibody" refers to a polypeptide or group of polypeptides which comprise at least one antigen binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops which contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide bearing an HCV epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

Monoclonal antibodies directed against HCV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc. As used herein, a "single domain antibody" (dAb) is an antibody which is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies can also be comprised of VH and VL domains, as well as other known antigen binding domains. Examples of these types of antibodies and methods for their preparation and known in the art (see, e.g., U.S. Pat. No. 4,816,467, which is incorporated herein by reference), and include the following. For example, "vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic know antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295: 712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

"Immunogenic polypeptide" refers to a polypeptide that elicits a cellular and/or humoral immune response in a mammal, whether alone or linked to a carrier, in the presence or absence of an adjuvant.

"Antigenic determinant" refers to the site on an antigen or hapten to which a specific antibody molecule or specific cell surface receptor binds.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

General Overview

An aim of an HCV vaccine is to generate broad immunity to a wide breadth of antigens because HCV is so divergent and because humoral as well as cellular immune responses are desirable to combat this human pathogen. While antibodies generated against the envelope glycoprotein(s) might aid in virus neutralization, there is additional benefit to be derived from a vaccine that includes other regions. The likelihood of T-helper responses generated against a polypeptide would be helpful in a vaccine setting as would generation of cytotoxic T cells. The non-structural region represents such a candidate antigen, but processing by the protease generates several polypeptides, making purification complicated. It would be advantageous, therefore, to derive a non-structural cassette that is unprocessed by the NS3 protease.

The present invention solves this and other problems using compositions and methods involving an N-terminal deletion in NS3, which removes the catalytic domain. As such, some or all of the remainder of the non-structural region (through NS5B) is expressed as an intact polypeptide. Expression of this species has been documented in mammalian cells as well as in yeast. Further, in certain aspects, polynucleotides encoding HCV core polypeptides (or fragments thereof) are added (e.g. operably linked) to the carboxy-terminus of the non-structural cassette. As the core coding region is relatively highly conserved among HCV isolates, the presence of this region may enhance the immune response. Because core has at its C-terminus a very hydrophobic domain (amino acids 174-191), shorter versions of core were also engineered onto the polypeptide. As described in detail herein, the truncation of core to amino acid 121 yielded higher expression than the amino acid 173 truncation when engineered onto the C-terminus of the mutant NS polypeptide. The combination of most of the non-structural region fused to a C-terminally truncated core into a polypeptide is novel and has advantages for vaccine immunization. Moreover, because the aim is not necessarily to generate antibody responses to this polypeptide, there is no need to maintain a native conformation, enabling a more facile purification protocol.

Mutant HCV Non-Structural Polypeptides

Genomes of HCV strains contain a single open reading frame of approximately 9,000 to 12,000 nucleotides, which is transcribed into a polyprotein. An HCV polyprotein is cleaved to produce at least ten distinct products, in the order of $NH_2$-Core-E1-E2-p7-NS2-NS3-NS4a-NS4b-NS5a-NS5b-COOH. Mutant HCV polypeptides of the invention contain an N-terminal deletion in NS3, which removes or disables the catalytic domain. Preferably, the polypeptides also include the remainder of the non-structural region, although in certain embodiments, the polypeptides may include less than all of the remaining NS polypeptides, for example mutant NS polypeptides including any combinations of NS2-NS3-NS4a-NS4b-NS5a-NS5b (e.g., NS3NS3-NS5a-NS5b; NS3-NS4a-NS4b; NS3-NS4a-NS4b-NS5a; NS3-NS4b-NS5a-NS5b; NS3-NS4a-NS5a; NS3-NS4b-NS5a; NS3-NS4b-NS5b; etc.).

The HCV NS3 protein functions as a protease and a helicase and occurs at approximately amino acid 1027 to amino acid 1657 of the polyprotein (numbered relative to HCV-1). See Choo et al. (1991) Proc. Natl. Acad. Sci. USA 88:2451-2455. HCV NS4 occurs at approximately amino acid 1658 to amino acid 1972, NS5a occurs at approximately amino acid 1973 to amino acid 2420, and HCV NS5b occurs at approximately amino acid 2421 to amino acid 3011 of the polyprotein (numbered relative to HCV-1) (Choo et al., 1991).

The mutant polypeptides described herein can either be full-length polypeptides or portions of NS3, NS4 (NS4a and NS4b), NS5a, and NS5b polypeptides. Epitopes of NS3, NS4 (NS4a and NS4b), NS5a, NS5b, NS3NS4NS5a, and NS3NS4NS5aNS5b can be identified by several methods. For example, NS3, NS4, NS5a, NS5b polypeptides or fusion proteins comprising any combination of the above, can be isolated, for example, by immunoaffinity purification using a monoclonal antibody for the polypeptide or protein. The isolated protein sequence can then be screened by preparing a series of short peptides by proteolytic cleavage of the purified protein, which together span the entire protein sequence. By starting with, for example, 100-mer polypeptides, each polypeptide can be tested for the presence of epitopes recognized by a T cell receptor on an HCV-activated T cell, progressively smaller and overlapping fragments can then be tested from an identified 100-mer to map the epitope of interest.

Epitopes recognized by a T cell receptor on an HCV-activated T cell can be identified by, for example, $^{51}Cr$ release assay (see Example 2) or by lymphoproliferation assay (see Example 4). In a $^{51}Cr$ release assay, target cells can be constructed that display the epitope of interest by cloning a polynucleotide encoding the epitope into an expression vector and transforming the expression vector into the target cells. Non-structural polypeptides can occur in any order in the fusion protein. If desired, at least 2, 3, 4, 5, 6, 7, 8, 9, or 10 or more of one or more of the polypeptides may occur in the fusion protein. Multiple viral strains of HCV occur, and NS3, NS4, NS5a, and NS5b polypeptides of any of these strains can be used in a fusion protein.

Nucleic acid and amino acid sequences of a number of HCV strains and isolates, including nucleic acid and amino acid sequences of NS3, NS4, NS5a, NS5b genes and polypeptides have been determined. For example, isolate HCV J1.1 is described in Kubo et al. (1989) Japan. Nucl. Acids Res. 17:10367-10372, Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113 respectively.

Publications that describe HCV-1 isolates include Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem.

Biophys. Res. Commun. 170:1021-1025. HCV isolates A, C, D & E are described in Tsukiyama-Kohara et al. (1991) Virus Genes 5:243-254.

Each of the mutant HCV polypeptides containing at least portions of NS3, NS4 and NS5 can be obtained from the same HCV strain or isolate or from different HCV strains or isolates. Thus, each non-structural region of the polypeptide can be from the same HCV strain or isolate or from each different HCV strains or isolates. In addition to the mutant HCV non-structural polypeptides described herein, the proteins can contain other polypeptides derived from the HCV polyprotein. For example, it may be desirable to include polypeptides derived from the core region of the HCV polyprotein. This region occurs at amino acid positions 1-191 of the HCV polyprotein, numbered relative to HCV-1. Either the full-length protein or epitopes of the full-length protein may be used in the subject fusions, such as those epitopes found between amino acids 10-53, amino acids 10-45, amino acids 67-88, amino acids 120-130, or any of the core epitopes identified in, e.g., Houghton et al., U.S. Pat. No. 5,350,671; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and commonly owned, U.S. Pat. No. 6,150,087, the disclosures of which are incorporated herein by reference in their entireties. When present, additional non-structural HCV polypeptides such as core can be obtained from the same HCV strain or isolate or from different HCV strains or isolates.

Preferably, the above-described mutant proteins, as well as the individual components of these proteins, are produced recombinantly. A polynucleotide encoding these proteins can be introduced into an expression vector which can be expressed in a suitable expression system. A variety of bacterial, yeast, mammalian, insect and plant expression systems are available in the art and any such expression system can be used. Optionally, a polynucleotide encoding these proteins can be translated in a cell-free translation system. Such methods are well known in the art. The proteins also can be constructed by solid phase protein synthesis.

If desired, the mutant polypeptides, or the individual components of these, polypeptides, also can contain other amino acid sequences, such as amino acid linkers or signal sequences, as well as ligands useful in protein purification, such as glutathione-S-transferase and staphylococcal protein A.

Polynucleotides

The polynucleotides of the present invention are not necessarily physically derived from the nucleotide sequences shown, but can be generated in any manner, including, for example, chemical synthesis or DNA replication or reverse transcription or transcription. In addition, combinations of regions corresponding to that of the designated sequences can be modified in ways known to the art to be consistent with an intended use.

The DNA encoding the desired polypeptide, whether in fused or mature form, and whether or not containing a signal sequence to permit secretion, can be ligated into expression vectors suitable for any convenient host. Both eukaryotic and prokaryotic host systems are presently used in forming recombinant polypeptides, and a summary of some of the more common control systems and host cell is given below. The polypeptide produced in such host cells is then isolated from lysed cells or from the culture medium and purified to the extent needed for its intended use.

Purification can be by techniques known in the art, for example, differential extraction, salt fractionation, chromatography on ion exchange resins, affinity chromatography, centrifugation, alkali resolubilization of insoluble protein, and the like. See, for example, Methods in Enzymology for a variety of methods for purifying proteins.

Polynucleotides contain less than an entire HCV genome and can be RNA or single- or double-stranded DNA. Preferably, the polynucleotides are isolated free of other components, such as proteins and lipids. Polynucleotides of the invention can also comprise other nucleotide sequences, such as sequences coding for linkers, signal sequences, or ligands useful in protein purification such as glutathione-S-transferase and staphylococcal protein A.

Polynucleotides encoding mutant HCV non-structural polypeptides can be isolated from a genomic library derived from nucleic acid sequences present in, for example, the plasma, serum, or liver homogenate of an HCV infected individual or can be synthesized in the laboratory, for example, using an automatic synthesizer. An amplification method such as PCR can be used to amplify polynucleotides from either HCV genomic DNA or cDNA.

Further, while the polypeptides that are not NS3, NS4, or NS5 of HCV of the present invention can comprise a substantially complete viral domain, in many applications all that is required is that the polypeptide comprise an antigenic or immunogenic region of the virus. An antigenic region of a polypeptide is generally relatively small-typically 8 to 10 amino acids or less in length. Fragments of as few as 5 amino acids can characterize an antigenic region. These segments can correspond to regions of, for example, C, E1, or E2 epitopes. Accordingly, using the cDNAs of C, E1, or E2 as a basis, DNAs encoding short segments of C, E1, or E2 polypeptides can be expressed recombinantly either as fusion proteins, or as isolated polypeptides. In addition, short amino acid sequences can be conveniently obtained by chemical synthesis.

Polynucleotides encoding the polypeptides described herein can comprise coding sequences for these polypeptides which occur naturally or can be artificial sequences which do not occur in nature. These polynucleotides can be ligated to form a coding sequence for the fusion proteins using standard molecular biology techniques. If desired, polynucleotides can be cloned into an expression vector and transformed into, for example, bacterial, yeast, insect, plant or mammalian cells so that the fusion proteins of the invention can be expressed in and isolated from a cell culture.

The expression of polypeptides containing these domains in a variety of recombinant host cells, including, for example, bacteria, yeast, insect, plant and vertebrate cells, give rise to important immunological reagents which can be used for diagnosis, detection, and vaccines.

The general techniques used in extracting the genome from a virus, preparing and probing a cDNA library, sequencing clones, constructing expression vectors, transforming cells, performing immunological assays such as radioimmunoassays and ELISA assays, for growing cells in culture, and the like are known in the art and laboratory manuals are available describing these techniques. However, as a general guide, the following sets forth some sources currently available for such procedures, and for materials useful in carrying them out.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang et al. (1977), Nature 198: 1056), the tryptophan (trp) promoter system (Goeddel et al. (1980) Nucleic Acid Res. 8:4057), the lambda-derived P[L] promoter and N gene ribosome binding site (Shimatake et al. (1981) Nature 292:128) and the hybrid tac promoter (De Boer et al. (1983) Proc. Natl. Acad. Sci. U.S.A. 292:128) derived from sequences of the trp and lac UV5 promoters. The foregoing systems are particularly compatible with E. coli; if desired, other prokaryotic hosts such as strains of *Bacillus* or *Pseudomonas* may be used, with corresponding control sequences.

Eukaryotic hosts include mammalian and yeast cells in culture systems. Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978), Nature 273:113), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitopes into the host genome.

The vaccinia virus system can also be used to express foreign DNA in mammalian cells. To express heterologous genes, the foreign DNA is usually inserted into the thymidine kinase gene of the vaccinia virus and then infected cells can be selected. This procedure is known in the art and further information can be found in these references (Mackett et al. J. Virol. 49: 857-864 (1984) and Chapter 7 in DNA Cloning, Vol. 2, IRL Press).

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences (Myanohara et al. (1983) *Proc. Natl. Acad. Sci. USA* 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, (Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercereau-Puigalon et al. (1980) *Gene* 11:163; Panthier et al. (1980) *Curr. Genet.* 2:109).

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EP-A-0 196 056. Another example is a ubiquitin fusion protein. Such a fusion protein is made with the ubiquitin region that preferably retains a site for a processing enzyme (e.g., ubiquitin-specific processing protease) to cleave the ubiquitin from the foreign protein. Through this method, therefore, native foreign protein can be isolated (e.g., WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g., see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 (Botstein et al. (1979) *Gene* 8:17-24), pC1/1 (Brake et al. (1984) *Proc. Natl. Acad. Sci. USA* 81:4642-4646), and YRp17 (Stinchcomb et al. (1982) *J. Mol. Biol.* 158:157). In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flankig the expression construct. Integrations appear to result from recombinations between homologous DNA in the vector and the yeast chromosome (Orr-Weaver et al. (1983) *Methods in Enzymol.* 101:228-245). An integrating vector may be directed to a specific locus in yeast by selecting the appropriate homologous sequence for inclusion in the vector. See Orr-Weaver et al., supra. One or more expression construct may integrate, possibly affecting levels of recombinant protein produced (Rine et al. (1983) *Proc. Natl. Acad. Sci. USA* 80:6750). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions (Butt et al. (1987) *Microbiol, Rev.* 51:351).

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al. (1986) *Mol. Cell. Biol.,* 6:142), *Candida maltosa* (Kunze, et al. (1985) *J. Basic Microbiol.* 25:141). *Hansenula polymorpha* (Gleeson, et al. (1986) *J. Gen. Microbiol.* 132:3459; Roggenkamp et al. (1986) *Mol. Gen. Genet.* 202:302), *Kluyveromyces fragilis* (Das, et al. (1984) *J. Bacteriol.* 158:1165), *Kluyveromyces lactis* (De Louvencourt et al. (1983) *J. Bacteriol.* 154:737; Van den Berg et al. (1990) *Bio/Technology* 8:135), *Pichia guillerimondii* (Kunze et al. (1985) *J. Basic Microbiol.* 25:141), *Pichia pastoris* (Cregg, et al. (1985) *Mol. Cell. Biol.* 5:3376; U.S. Pat. Nos. 4,837,148 and 4,929,555), *Saccharomyces cerevisiae* (Hinnen et al. (1978) *Proc. Natl. Acad. Sci. USA* 75:1929; Ito et al. (1983) *J. Bacteriol.* 153:163), *Schizosaccharomyces pombe* (Beach and Nurse (1981) *Nature* 300:706), and *Yarrowia lipolytica* (Davidow, et al. (1985) *Curr. Genet.* 10:380471 Gaillardin, et al. (1985) *Curr. Genet.* 10:49).

Methods of introducing exogenous DNA into yeast hosts are well-known in the art, and usually include either the transformation of spheroplasts or of intact yeast cells treated with alkali cations. Transformation procedures usually vary with the yeast species to be transformed. (See e.g., Kurtz et al. (1986) *Mol. Cell. Biol.* 6:142; Kunze et al. (1985) *J. Basic Microbiol.* 25:141; *Candida*; Gleeson et al. (1986) *J. Gen. Microbiol.* 132:3459; Roggenkamp et al. (1986) *Mol. Gen. Genet.* 202:302; *Hansenula*; Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*; Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*; Hinnen et al. (1978) *Proc. Natl. Acad. Sci. USA* 75; 1929; Ito et al. (1983) *J. Bacteriol.* 153:163 *Saccharomyces*; Beach and Nurse (1981) *Nature* 300:706; *Schizosaccharomyces*; Davidow et al. (1985) *Curr. Genet.* 10:39; Gaillardin et al. (1985) *Curr. Genet.* 10:49; *Yarrowia*).

Bacterial expression techniques are known in the art. A bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al. (1984) *Annu. Rev. Genet.* 18:173). Regulated expression may therefore be either positive or negative, thereby either enhancing or reducing transcription.

Expression and transformation vectors, either extra-chromosomal replicons or integrating vectors, have been developed for transformation into many bacteria. For example, expression vectors have been developed for, inter alia, the following bacteria: *Bacillus subtilis* (Palva et al. (1982) *Proc. Natl. Acad. Sci. USA* 79:5582; EP-A-0 036 259 and EP-A-0 063 953; WO 84/04541), *Escherichia coli* (Shimatake et al. (1981) *Nature* 292: 128; Amann et al. (1985) *Gene* 40:183; Studier et al. (1986) *J. Mol. Biol.* 189:113; EP-A-0 036 776, EP-A-0 136 829 and EP-A-0 136 907), *Streptococcus cremoris* (Powell et al. (1988) *Appl. Environ. Microbiol.* 54:655); *Streptococcus lividans* (Powell et al. (1988) *Appl. Environ. Microbiol.* 54:655), *Streptomyces lividans* (U.S. Pat. No. 4,745,056).

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. (See e.g., Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*, Miller et al. (1988) *Proc. Natl. Acad. Sci.* 85:856; Wang et al. (1990) *J. Bacteriol.* 172:949; *Campylobacter*, Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering Proceedings of the International Symposium on Genetic Engineering* (eds. H. W. Boyer and S, Nicosia); Mandel et al. (1970) *J. Mol. Biol.* 53:159; Taketo (1988) *Biochim. Biophys. Acta* 949:318; *Escherichia*; Chassy et al. (1987) *FEMS Microbiol. Lett.* 44:173 *Lactobacillus*; Fiedler et al. (1988) *Anal. Biochem* 170:38, *Pseudomonas*; Augustin et al. (1990) *FEMS Microbiol. Lett.* 66:203, *Staphylococcus*, Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*).

In addition, viral antigens can be expressed in insect cells by the Baculovirus system. A general guide to Baculovirus expression by Summer and Smith is A Manual of Methods for Baculovirus Vectors and Insect Cell Culture Procedures (Texas Agricultural Experiment Station Bulletin No. 1555). To incorporate the heterologous gene into the Baculovirus genome the gene is first cloned into a transfer vector containing some Baculovirus sequences. This transfer vector, when it is cotransfected with wild-type virus into insect cells, will recombine with the wild-type virus. Usually, the transfer vector will be engineered so that the heterologous gene will disrupt the wild-type Baculovirus polyhedron gene. This disruption enables easy selection of the recombinant virus since the cells infected with the recombinant virus will appear phenotypically different from the cells infected with the wild-type virus. The purified recombinant virus can be used to infect cells to express the heterologous gene. The foreign protein can be secreted into the medium if a signal peptide is linked in frame to the heterologous gene; otherwise, the protein will be bound in the cell lysates. For further information, see Smith et al *Mol. & Cell. Biol.* 3:2156-2165 (1983) or Luckow and Summers in *Virology* 17: 31-39 (1989).

Baculovirus expression can also be affected in plant cells. There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., *Nucleic Acids Research* 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, *Gibberellins*: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038 (1990); Maas et al., *EMBO J.* 9:3447-3452 (1990); Benkel and Hickey, *Proc. Natl. Acad. Sci.* 84:1337-1339 (1987).

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Transformation can be by any method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen (1972), *Proc. Natl. Acad. Sci. U.S.A.* 69:2110; Maniatis et al. (1982), MOLECULAR CLONING; A LABORATORY MANUAL (Cold Spring Harbor Press, Cold Spring Harbor, N.Y.). Yeast transformation by direct uptake may be carried out using the method of Hinnen et al. (1978) *Proc. Natl. Acad. Sci. U.S.A.* 75: 1929. Mammalian transformations by direct uptake may be conducted using the calcium phosphate precipitation method of Graham and Van der Eb (1978), Virology 52:546 or the various known modifications thereof.

Vector construction employs techniques which are known in the art. Site-specific DNA cleavage is performed by treating with suitable restriction enzymes under conditions which generally are specified by the manufacturer of these commercially available enzymes. The cleaved fragments may be separated using polyacrylamide or agarose gel electrophoresis techniques, according to the general procedures found in Methods in Enzymology (1980) 65:499-560. Sticky ended cleavage fragments may be blunt ended using E. coli DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation. Ligation mixtures are transformed into suitable cloning hosts, such as E. coli, and successful transformants selected by, for example, antibiotic resistance, and screened for the correct construction.

Synthetic oligonucleotides may be prepared using an automated oligonucleotide synthesizer as described by Warner (1984), DNA 3:401. If desired, the synthetic strands may be labeled with $^{32}P$ by treatment with polynucleotide kinase in the presence of $^{32}P$-ATP, using standard conditions for the reaction. DNA sequences, including those isolated from cDNA libraries, may be modified by known techniques, including, for example site directed mutagenesis, as described by Zoller (1982), Nucleic Acids Res. 10:6487.

The expression constructs of the present invention, including the desired fusion, or individual expression constructs comprising the individual components of these fusions, may be used for nucleic acid immunization, to activate HCV-specific T cells, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991) 1097:1-17; Straubinger et al., in Methods of Enzymology (1983), Vol. 101, pp. 512-527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:419-44198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA can also be delivered in cochleate lipid compositions similar to those described by Papahadjopoulos et al., Biochem. Biophys. Acta. (1975) 394:483-491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476).

Molecular conjugate vectors, such as the adenovirus chimeric vectors described in Michael et al., J. Biol. Chem.

(1993) 268:6866-6869 and Wagner et al., *Proc. Natl. Acad. Sci. USA* (1992) 89:6099-6103, can also be used for gene delivery.

Members of the *Alphavirus* genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508-519; and International Publication Nos. WO 95/07995 and WO 96/17072.

Other vectors can be used, including but not limited to simian virus 40, cytomegalovirus. Bacterial vectors, such as *Salmonella* ssp. *Yersinia enterocolitica, Shigella* spp., *Vibrio cholerae, Mycobacterium* strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. One particularly effective method of delivering DNA using electroporation is described in International Publication No. WO/0045823.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Compositions

The invention also provides compositions comprising the HCV polypeptides or polynucleotides described herein. Such compositions are useful as diagnostics, for example, using the mutant polypeptides (or polynucleotides encoding these polypeptides) in diagnostic reagents. Diagnostics using polypeptides and polynucleotides are known to those of skill in the art.

In addition, immunogenic compounds can be prepared from one or more immunogenic polypeptides derived from the polypeptides described herein, for example the ΔNS35 polypeptide. The preparation of immunogenic compounds which contain immunogenic polypeptide(s) as active ingredients is known to one skilled in the art. Typically, such immunogenic compounds are prepared as injectables, either as liquid solutions or suspensions; solid forms suitable for solution in, or suspension in, liquid prior to injection can also be prepared. The preparation can also be emulsified, or the protein encapsulated in liposomes.

Immunogenic and diagnostic compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention, such liposomes are described above.

If desired, co-stimulatory molecules which improve immunogen presentation to lymphocytes, such as B7-1 or B7-2, or cytokines such as GM-CSF, IL-2, and IL-12, can be included in a composition of the invention. Optionally, adjuvants can also be included in a composition. Adjuvants which can be used include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE), formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an *E. coli* heat-labile toxin (LT), particularly LT-K63, LT-R72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described in copending U.S. patent application Ser. No. 09/285,855 (filed Apr. 2, 1999) and international Patent Application Serial No. PCT/US99/17308 (filed Jul. 29, 1999). Alum and MF59 are preferred. The effectiveness of an adjuvant can be determined by measuring the amount of antibodies directed against an immunogenic polypeptide containing an HCV antigenic sequence resulting from administration of this polypeptide in immunogenic compounds which are also comprised of the various adjuvants.

As mentioned above, muramyl peptides include, but are not limited to, N-acetyl-muramyl-L-threonyl-D-isoglutamine (thr-MDP), -acetyl-normuramyl-L-alanyl-D-isoglutamine (CGP 11637, referred to nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), etc.

Thus, such recombinant or synthetic HCV polypeptides can be used in vaccines and as diagnostics. Further, antibodies raised against these polypeptides can also be used as diagnostics, or for passive immunotherapy. In addition, antibodies to these polypeptides are useful for isolating and identifying HCV particles.

Native HCV antigens can also be isolated from HCV virions. The virions can be grown in HCV infected cells in tissue culture, or in an infected host.

Administration and Delivery

The polynucleotide and polypeptide compositions described herein (e.g., immunogenic compounds) may be administered to a subject using any suitable delivery means. Methods of delivering nucleic acids into host cells are discussed above. Further, HCV polynucleotides and/or polypeptides can be administered parenterally, by injection, usually, subcutaneously, intramuscularly, transdermally or transcutaneously. Certain adjuvants, e.g. LTK63, LTR72 or PLG formulations, can be administered intranasally or orally. Additional formulations which are suitable for other modes of administration include suppositories. For suppositories, traditional binders and carriers can include, for example, polyalkylene glycols or triglycerides; such suppositories can be formed from mixtures containing the active ingredient in the range of 0.5% to 10%, preferably 1%-2%. Other oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The polypeptides of the present invention can be formulated into the immunogenic compound as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The immunogenic compounds are administered in a manner compatible with the dosage formulation, and in such amount as will be prophylactically and/or therapeutically effective. The quantity to be administered, which is generally in the range of 5 micrograms to 250 micrograms of polypeptide per dose, depends on the subject to be treated, capacity of the subject's immune system to synthesize antibodies, and the degree of protection desired. Precise amounts of active ingredient required to be administered may depend on the judgment of the practitioner and can be peculiar to each subject.

The immunogenic compound can be given in a single dose schedule, or preferably in a multiple dose schedule. A multiple dose schedule is one in which a primary course of vaccination can be with 1-10 separate doses, followed by other doses given at subsequent time intervals required to maintain and or reinforce the immune response, for example, at 1-4 months for a second dose, and if needed, a subsequent dose(s) after several months. Further, the course of administration may include polynucleotides and polypeptides, together or sequentially (for example, priming with a polynucleotide composition and boosting with a polypeptide composition). The dosage regimen will also, at least in part, be determined by the need of the individual and be dependent upon the judgment of the practitioner.

In certain embodiments, administration of the polynucleotides and polypeptides described herein is used to activate T cells. In addition to the practical advantages of simplicity of construction and modification, administration of polynucleotides encoding mutant NS polypeptides results in the synthesis of a mutant NS polypeptide in the host. Thus, these immunogens are presented to the host immune system with native post-translational modifications, structure, and conformation. The polynucleotides are preferably injected intramuscularly to a large mammal, such as a human, at a dose of 0.5, 0.75, 1.0, 1.5, 2.0, 2.5, 5 or 10 mg/kg.

The proteins and/or polynucleotides can be administered either to a mammal which is not infected with an HCV or can be administered to an HCV-infected mammal. The particular dosages of the polynucleotides or fusion proteins in a composition or will depend on many factors including, but not limited to the species, age, and general condition of the mammal to which the composition is administered, and the mode of administration of the composition. An effective amount of the composition of the invention can be readily determined using only routine experimentation. In vitro and in vivo models can be employed to identify appropriate doses. Generally, 0.5, 0.75, 1.0, 1.5, 2.0, 2.5, 5 or 10 mg will be administered to a large mammal, such as a baboon, chimpanzee, or human. If desired, co-stimulatory molecules or adjuvants can also be provided before, after, or together with the compositions.

Antibodies and Diagnostics

Antibodies, both monoclonal and polyclonal, which are directed against HCV epitopes are particularly useful in diagnosis, and those which are neutralizing are useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134:1225. These anti-idiotype antibodies may also be useful for treatment and/or diagnosis of NANBH, as well as for an elucidation of the immunogenic regions of HCV antigens.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polygonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization calorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated calorimetrically, and related to antigen concentration.

The HCV fusion proteins, such as NS3 mutant and core fusion proteins, can also be used to produce HCV-specific polyclonal and monoclonal antibodies. HCV-specific polyclonal and monoclonal antibodies specifically bind to HCV antigens.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against HCV-specific epitopes present in the fusion proteins can also be readily produced. Normal B cells from a mammal, such as a mouse, immunized with, e.g., a mutant NS3 polypeptide or NS-core fusion protein can be fused with, for example, HAT-sensitive mouse myeloma cells to produce hybridomas. Hybridomas producing HCV-specific antibodies can be identified using RIA or ELISA and isolated by cloning in semi-solid agar or by limiting dilution. Clones producing HCV-specific antibodies are isolated by another round of screening.

Antibodies, either monoclonal and polyclonal, which are directed against HCV epitopes, are particularly useful for detecting the presence of HCV or HCV antigens in a sample, such as a serum sample from an HCV-infected human. An immunoassay for an HCV antigen may utilize one antibody or several antibodies. An immunoassay for an HCV antigen may use, for example, a monoclonal antibody directed towards an HCV epitope, a combination of monoclonal antibodies directed towards epitopes of one HCV polypeptide, monoclonal antibodies directed towards epitopes of different HCV polypeptides, polyclonal antibodies directed towards the same HCV antigen, polyclonal antibodies directed towards different HCV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate HCV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HCV particles or antigens from a biological sample, such as blood or plasma. The bound HCV particles or antigens are recovered from the column matrix by, for example, a change in pH.

Methods of Eliciting Immune Responses

HCV-specific T cells that are activated by the above-described polypeptides, expressed in vivo or in vitro preferably recognize an epitope of an HCV polypeptide such as a mutant NS3 polypeptide, including an epitope of a mutant HCV polypeptide. HCV-specific T cells can be $CD8^+$ or $CD4^+$.

HCV-specific $CD8^+$ T cells preferably are cytotoxic T lymphocytes (CTL) which can kill HCV-infected cells that display NS3, NS4, NS5a, NS5b epitopes complexed with an MHC class I molecule. HCV-specific $CD8^+$ T cells may also express interferon-γ (IFN-γ). HCV-specific $CD8^+$ T cells can be detected by, for example, $^{51}Cr$ release assays. $^{51}Cr$ release assays measure the ability of HCV-specific $CD8^+$ T cells to lyse target cells displaying an nonstructural (e.g., mutant NS) epitope. HCV-specific $CD8^+$ T cells which express IFN-γ can also be detected by immunological methods, preferably by intracellular staining for IFN-γ after in vitro stimulation with a mutant NS polypeptide.

HCV-specific $CD4^+$ cells activated by the above-described polypeptides, expressed in vivo or in vitro, and combinations of the individual components of these proteins, preferably recognize an epitope of a mutant non-structural polypeptide, including an epitope of a mutant protein, that is bound to an MHC class II molecule on an HCV-infected cell and proliferate in response to stimulating mutant peptides.

HCV-specific $CD4^+$ T cells can be detected by a lymphoproliferation assay. Lymphoproliferation assays measure the ability of HCV-specific $CD4^+$ T cells to proliferate in response to an epitope.

Mutant NS (or fusions thereof with core, envelope or other viral polypeptides) can be used to activate HCV-specific T cells either in vitro or in vivo. Activation of HCV-specific T cells can be used, inter alia, to provide model systems to optimize CTL responses to HCV and to provide prophylactic or therapeutic treatment against HCV infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with an HCV. Preferred mammals include mice, chimpanzees, baboons, and humans. The HCV serves to expand the number of activated HCV-specific T cells in the mammal. The HCV-specific T cells derived from the mammal can then be restimulated in vitro by adding HCV epitopic peptides to the T cells. The HCV-specific T cells can then be tested for, inter alia, proliferation (e.g., lymphoproliferation assays known in the art), the production of IFN-γ, and the ability to lyse target cells displaying HCV NS epitopes in vitro.

The following examples are meant to illustrate the invention and are not meant to limit it in any way. Those of ordinary skill in the art will recognize modifications within the spirit and scope of the invention as set forth herein.

EXAMPLES

Example 1

Figure 10:
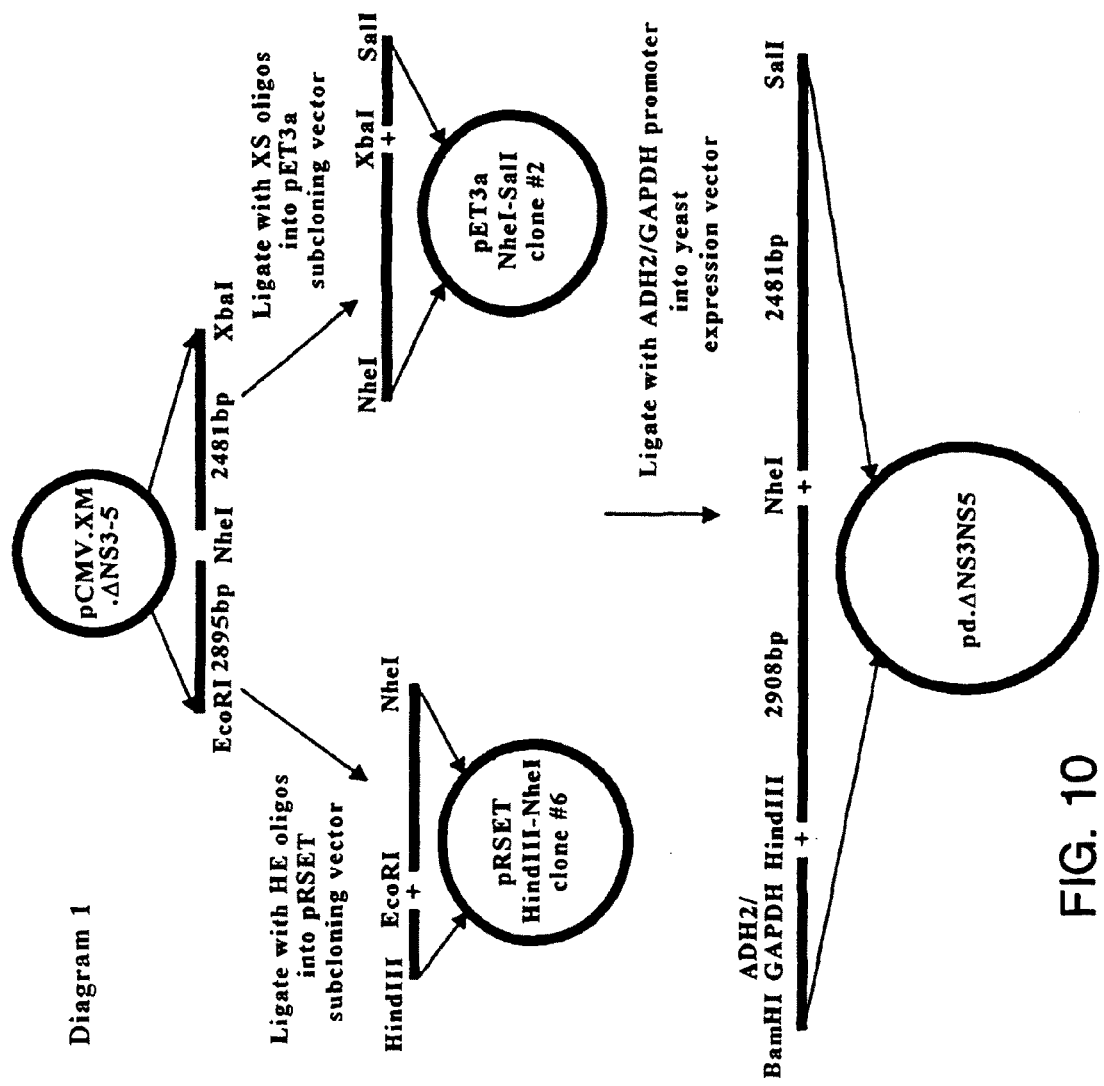
FIG. 10 shows the cloning scheme for generating pd.ΔNS3NS5.
Figure 13:
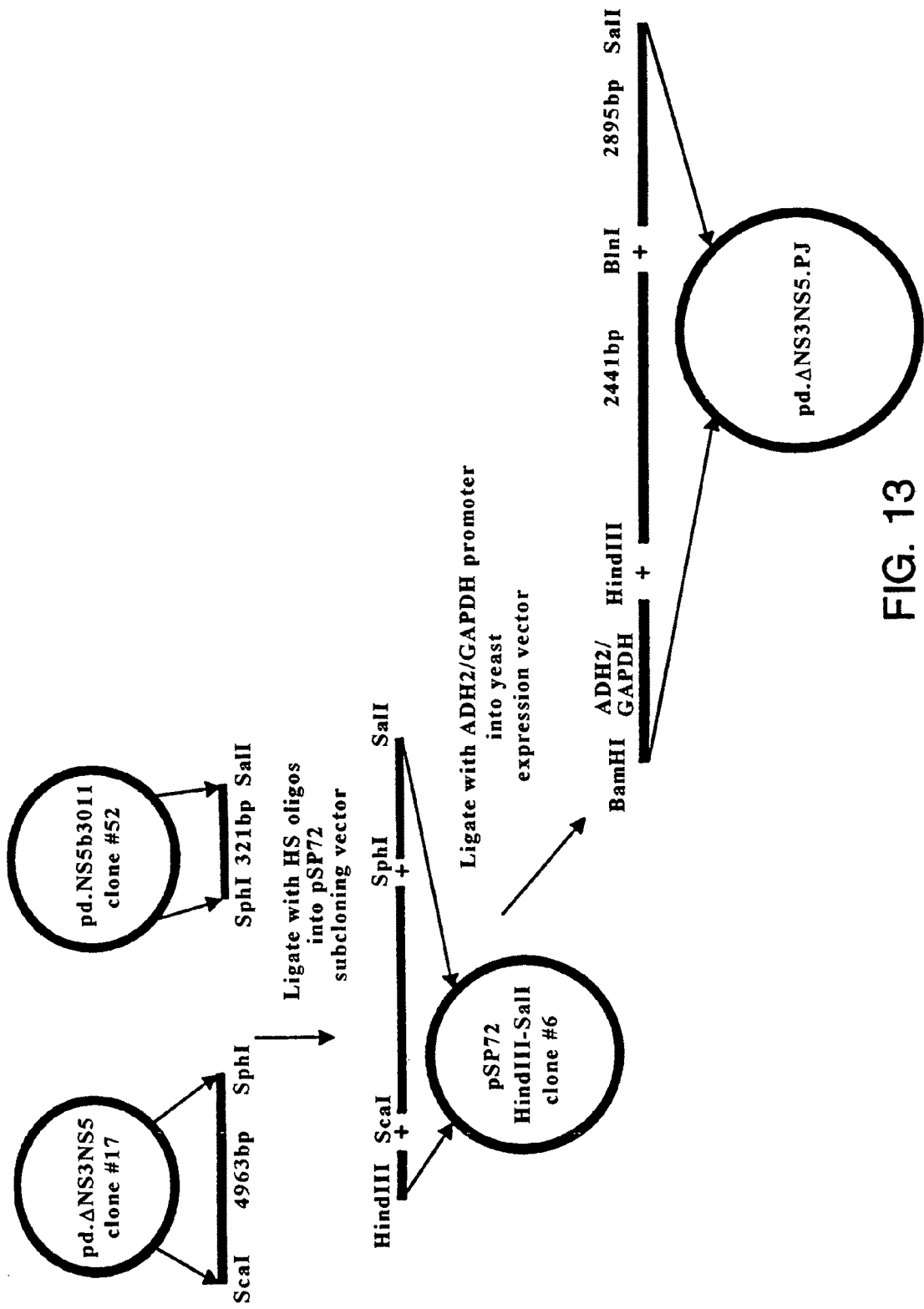
FIG. 13 shows the cloning scheme for generating pd.ΔNS3NS5.pj.

Constructs pCMV-II: pCMV-II (FIG. 7, SEQ ID NO:5) was created to contain the human CMV promoter, enhancer, intron A, polylinker and the bovine growth hormone terminator in a deleted-pUC backbone (Life Technologies).

pT7-HCV: pT7-HCV was created in a polylinker-modified pUC vector to contain full-length HCV cDNA preceded by a synthetic T7 promoter. pT7-HCV also contains the complete 5' UTR and the poly A version of the 3' UTR.

pCMV.ΔNS35: To generate pCMV.ΔNS35 (FIG. 5, SEQ ID NO:3), a two step procedure was undertaken. First, a PCR product was generated from pT7-HCV that corresponded to the following: a 5' EcoRI site, followed by the Kozak sequence of ACCATGG; the initiator ATG followed by amino acid #1242 and continuing to the StuI site. Second, the StuI to XbaI fragment from a full-length genomic clone was isolated. The genomic clone consisted of the T7 promoter fused to the full-length HCV cDNA with the poly A version of the 3' end, in a pUC vector. Finally, the EcoRI-StuI and StuI-XbaI fragments were ligated into the pCMV-II expression vector, transformed into HB101 competent cells and plated onto ampicillin (100 μg/ml). Miniprep analyses led to the identification of the desired clone which was amplified on a larger scale using a Quigen Gigaprep kit following the manufacturer's specifications. The resulting clone was named pCMV.ΔNS35 (FIG. 5, SEQ ID NO:3).

pd.ΔNS3NS5: As shown schematically in FIG. 10, the yeast expression plasmid pd.ΔNS3NS5 (SEQ ID NO:8) was constructed using restriction fragments obtained from the mammalian expression plasmid pCMV.KM.ΔNS35. pCMV.KM.ΔNS35 is identical to pCMV.ΔNS35 (FIG. 5, SEQ ID NO:3) except that it contains a kanamycin resistance gene in the viral backbone. pCMV.KM.ΔNS35 was digested with EcoRI and NheI to obtain 2895 bp EcoRI-NheI fragment. EcoRI-NheI fragment was ligated into pRSET HindIII-NheI subcloning vector with oligos (HE) from HindIII to EcoRI. After sequence verification, pRSETHindIII-NheI #6 was digested with HindIII and NheI to obtain a 2908 bp HindIII-NheI fragment.

pCMV.KM.ΔNS35 was linearized with XbaI and ligated with synthetic oligos (XS) from XbaI-SalI. The ligation was digested with NheI and SalI to obtain 2481 bp NheI-SalI fragment. The fragment was ligated into pET3a NheI-SalI subcloning vector. After sequence verification, pET3a NheI-SalI #2 was digested with NheI and SalI to obtain a 2481 bp NheI-SalI fragment. BamHI-HindIII ADH2/GAPDH promoter fragment was then ligated with HindIII-NheI and NheI-SalI fragments into pBS24.1 BamHI-SalI yeast expression vector.

pd.ΔNS3NS5.PJ: pd.ΔNS3NS5.PJ (FIGS. 13 and 14; SEQ ID NO:10) was generated to create a "perfect junction" at the 5' and 3' end of the HCV coding region. At the 5' end of pd.ΔNS3NS5, there were 6 extra bases between the yeast ADH2/GAPDH promoter and the ATG of the polypeptide. At the 3' end, there were 52 bases of untranslated sequence between the stop codon of the polypeptide and the α-factor terminator in the yeast expression vector. pd.ΔNS3NS5.PJ was created by digesting pd.ΔNS3NS5 #17 with ScaI and SphI to obtain 4963 bp ScaI-SphI fragment. pd.NS5b3011 was digested with SphI and SalI to obtain a 321 bp SphI-SalI fragment which gave the "perfect junction" at the 3' end of the polypeptide. The ScaI-SphI and SphI-SalI fragments were ligated into pSP72 HindIII-SalI subcloning vector with synthetic oligos from HindIII-ScaI(HS) for the "perfect junction" at the 5' end.

Figures 1, 16:
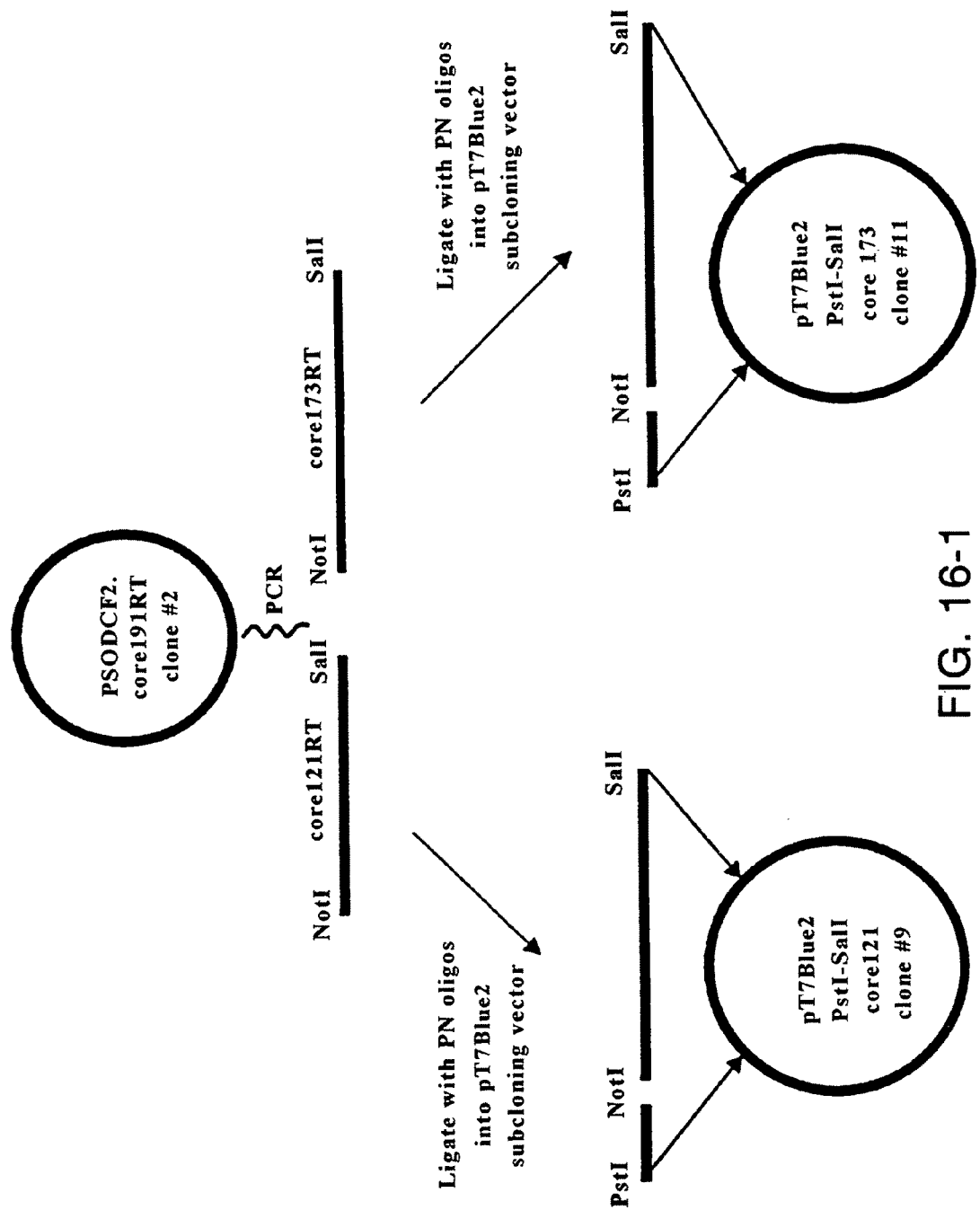
FIG. 16 shows the cloning scheme for generating pdΔNS3NS5.pj.core121RT and pdΔNS3NS5.pj.core173RT.
Figures 2, 16:
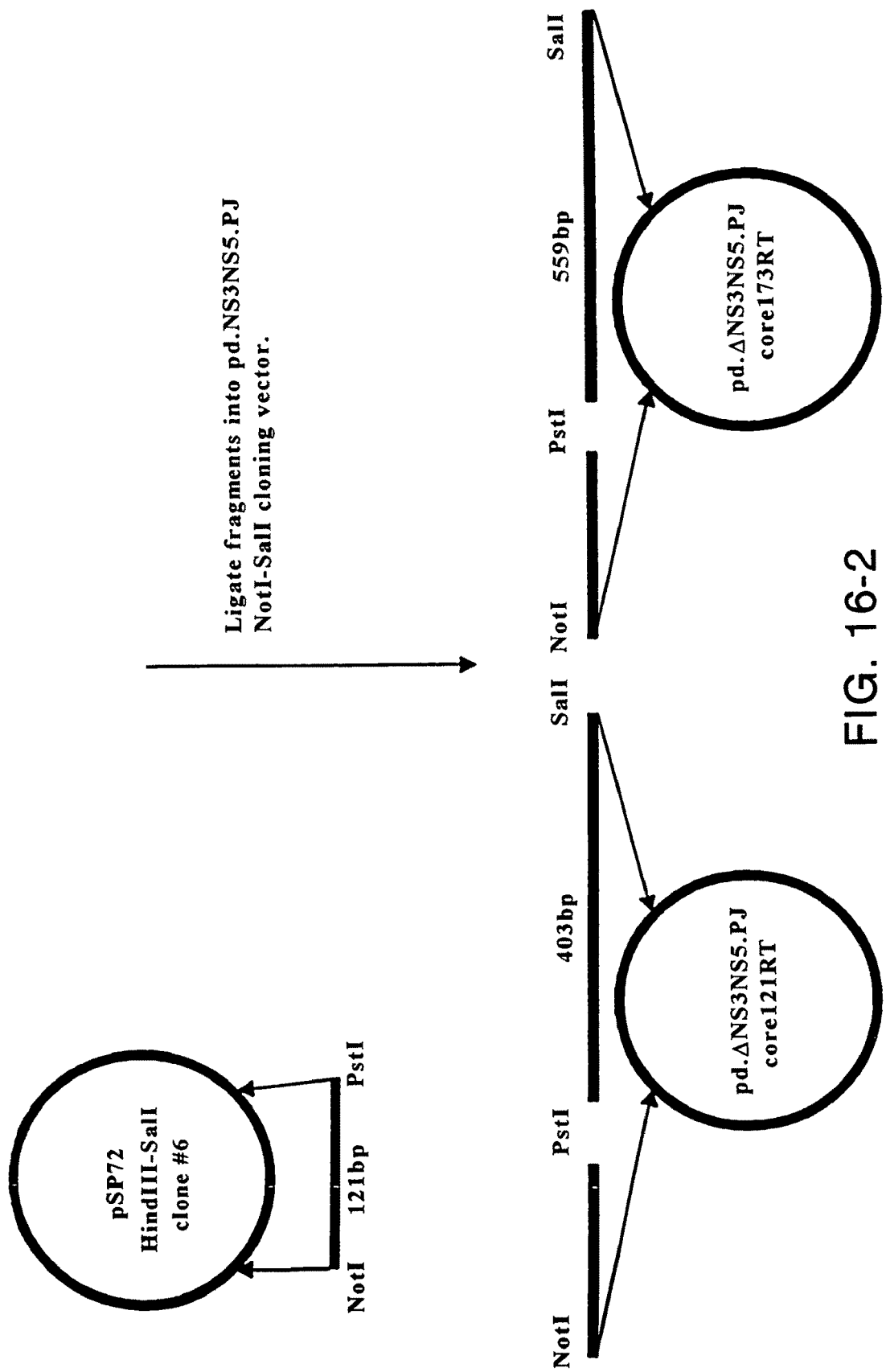

The region of synthetic sequence in pSP72 HindIII-SalI clone# 6 was verified. pSP72 HindIII-SalI clone#6 was digested with HindIII and BlnI or with BlnI and SalI to obtain 2441 bp HindIII-BlnI and 2895 bp BlnI-SalI fragments, respectively. The BamHI-HindIII ADH2/GAPDH promoter fragment was ligated to HindIII-BlnI and BlnI-SalI fragments into pBS24.1 BamHI-SalI yeast expression vector.

pd.ΔNS3NS5.PJ.core121RT and pd.ΔNS3NS5.PJ.core173RT were generated and encode HCV core aa 1-121 at the C-terminus of the ΔNS3NS5 polypeptide (designated pd.ΔNS3NS5.PJ.core121RT, SEQ ID NO:12) and core aa 1-173 at the C-terminus of the ΔNS3NS5 polypeptide (designated pd.ΔNS3NS5.PJ.core173RT, SEQ ID NO: 14). The core sequence had aa 9 mutated from Lys to Arg and aa 11 mutated from Asn to Thr, designated as core 121RT or 173RT.

pd.ΔNS3NS5.PJ.core121RT and pd.ΔNS3NS5.PJ.core173RT: To generate pd.ΔNS3NS5.PJ.core121RT (FIG. 17, SEQ ID NO:12) and pd.ΔNS3NS5.PJ.core173RT (FIG. 18, SEQ ID NO:14). As shown in FIG. 16, a NotI-SalI HCVcore121RT and HCVcore173RT were amplified by PCR, from an E. coli expression plasmid, pSODCF2.HCVcore191RT #2. Either the core 121RT Not-SalI PCR product or the core 173RT Not-SalI PCR product were ligated into a pT7Blue2 PstI-SalI subcloning vector with synthetic oligos (PN) from PstI to NotI. After sequence confirmation, pT7Blue2core121RT clone#9 and pT7Blue2core173RT clone#11 was digested with PstI and SalI to obtain 403 bp and 559 bp PstI-SalI fragments, respectively, for further cloning.

A 121 bp NotI-PstI fragment from pSP72 HindIII-SalI clone #6 was isolated as described above during the cloning of pd.ΔNS3NS5.PJ. NotI-PstI and PstI-SalI fragments were assembled into a vector made by digesting pd.NS3NS5.PJ clone#5 (described above) with NotI and SalI.

Figures 1, 20:
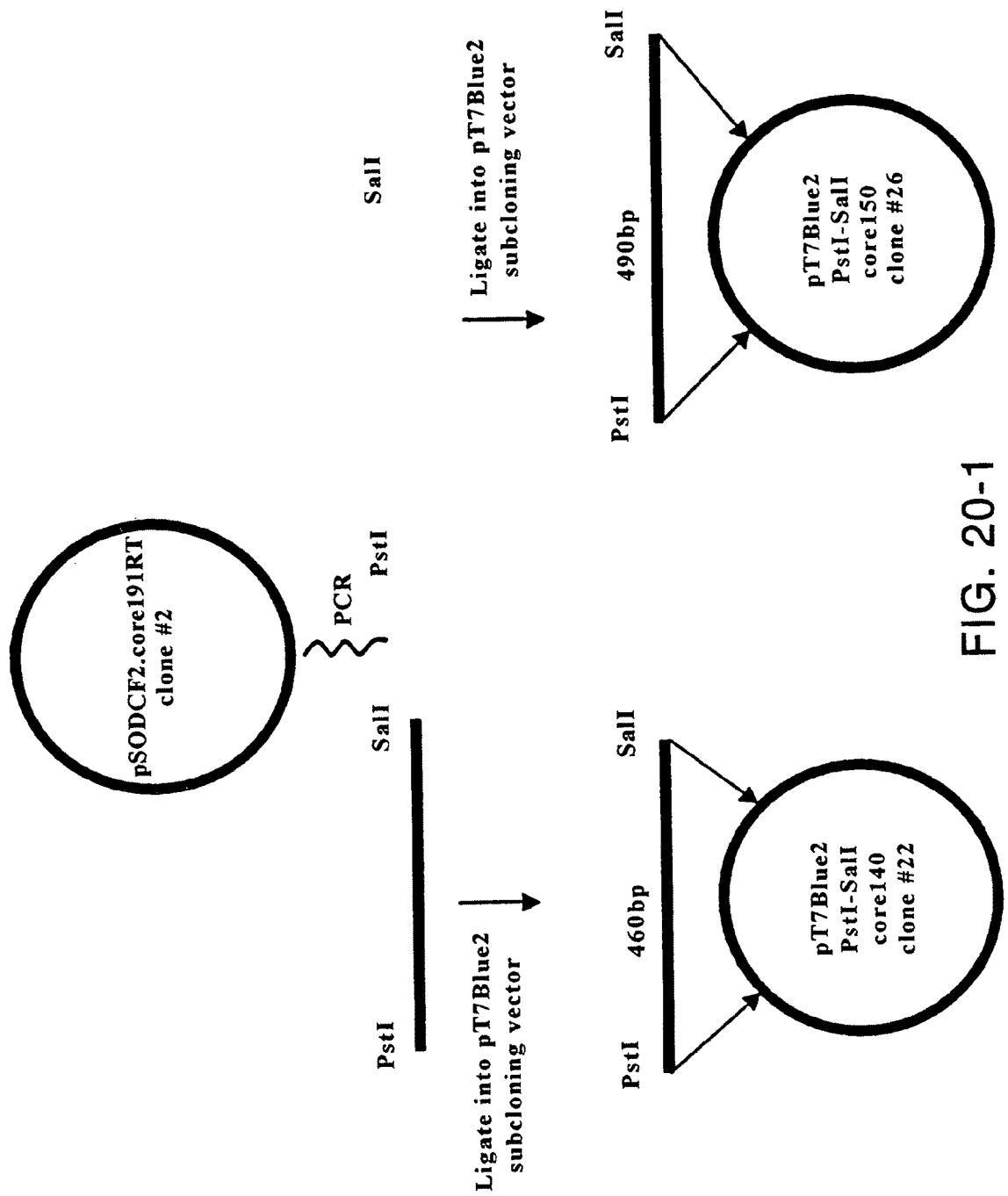
FIG. 20 shows the cloning scheme for generating pdΔNS3NS5.pj.core140RT and pdΔNS3NS5.pj.core150RT.
Figures 2, 20:
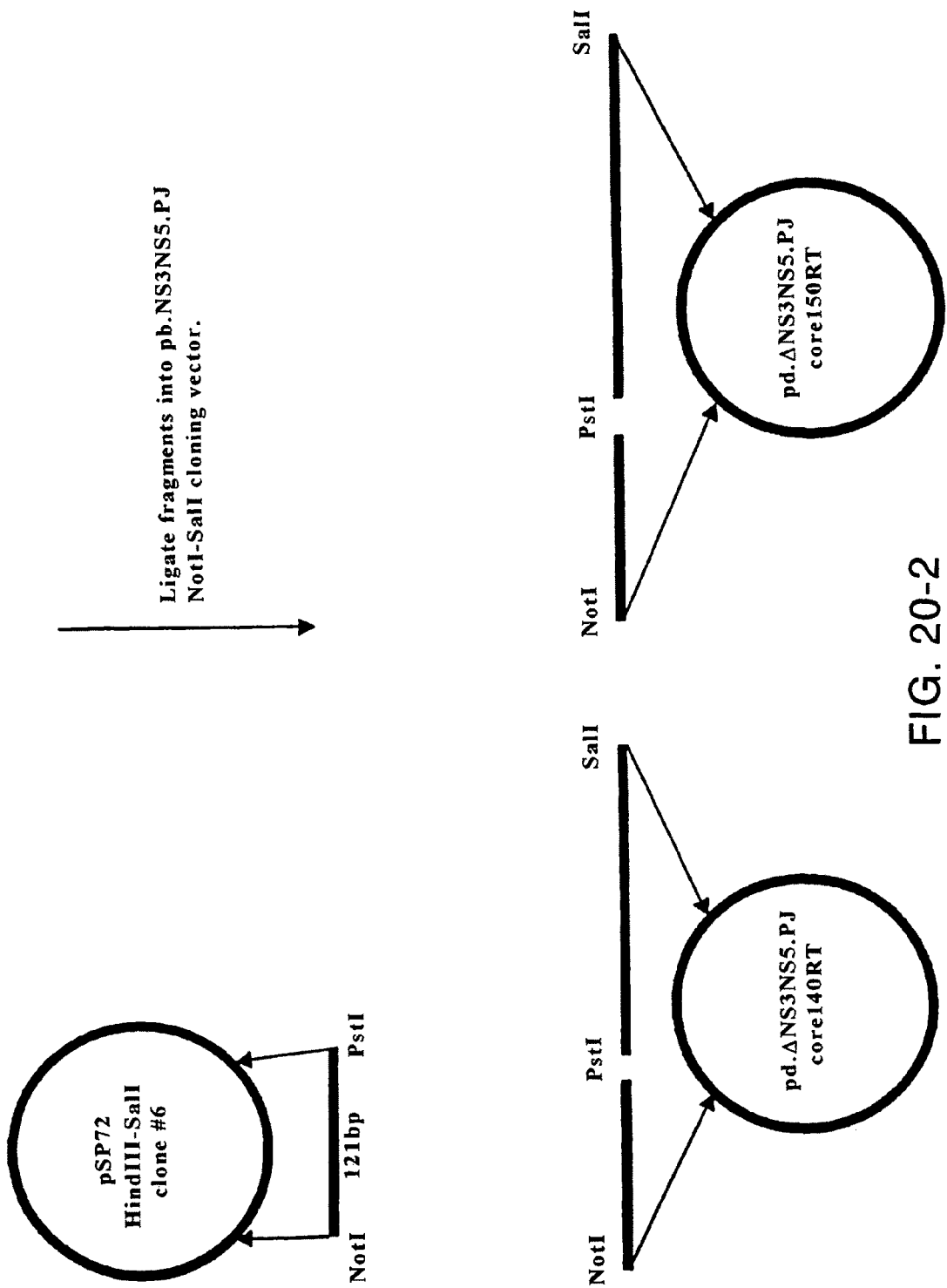

ΔNS3NS5 and Core 140 and Core 150: An HCV core epitope was found which elicits CTLs in baboons (HCV core aa 121-135). Since pd.ΔNS3NS5.PJ.core121RT ends right before this potentially important epitope and was expressed better than the longer pd.ΔNS3NS5.PJ.core173RT construct (Example 2), two intermediate constructs were made which include this epitope, possibly giving intermediate expression levels. The two new constructs fused HCV core aa 1-140 or HCV core aa1-150 to the C terminus of ΔNS3NS5.PJ.

pd.ΔNS3NS5.PJ.core140RT (FIG. 21. SEQ ID NO:16) and pd.ΔNS3NS5.PJ.core150RT (FIG. 22, SEQ ID NO:18): As shown in FIG. 20, a PstI-SalI HCVcore140RT and a PstI-SalI HCVcore150RT fragment were amplified by PCR from pd.ΔNS3NS5.PJ.core173RT clone #16. Ligate either HCV core PstI-SalI PCR products into pT7Blue2 PstI-SalI subcloning vector. After sequence confirmation, pT7Blue2core140RT clone#22 and pT7Blue2core150RT clone#26 were digested with PstI-SalI to obtain 460 bp and 490 bp PstI-SalI fragments, respectively, for further cloning.

A 121 bp NotI-PstI fragment was isolated from pSP72 HindIII-SalI clone #6 (as described above during the cloning of pd.ΔNS3NS5.PJ. NotI-PstI and PstI-SalI fragments were assembled into a vector made by digesting pd.ΔNS3NS5.PJ clone#5 (described above) with NotI and SalI.

Example 2

Protein Expression

Figure 12:
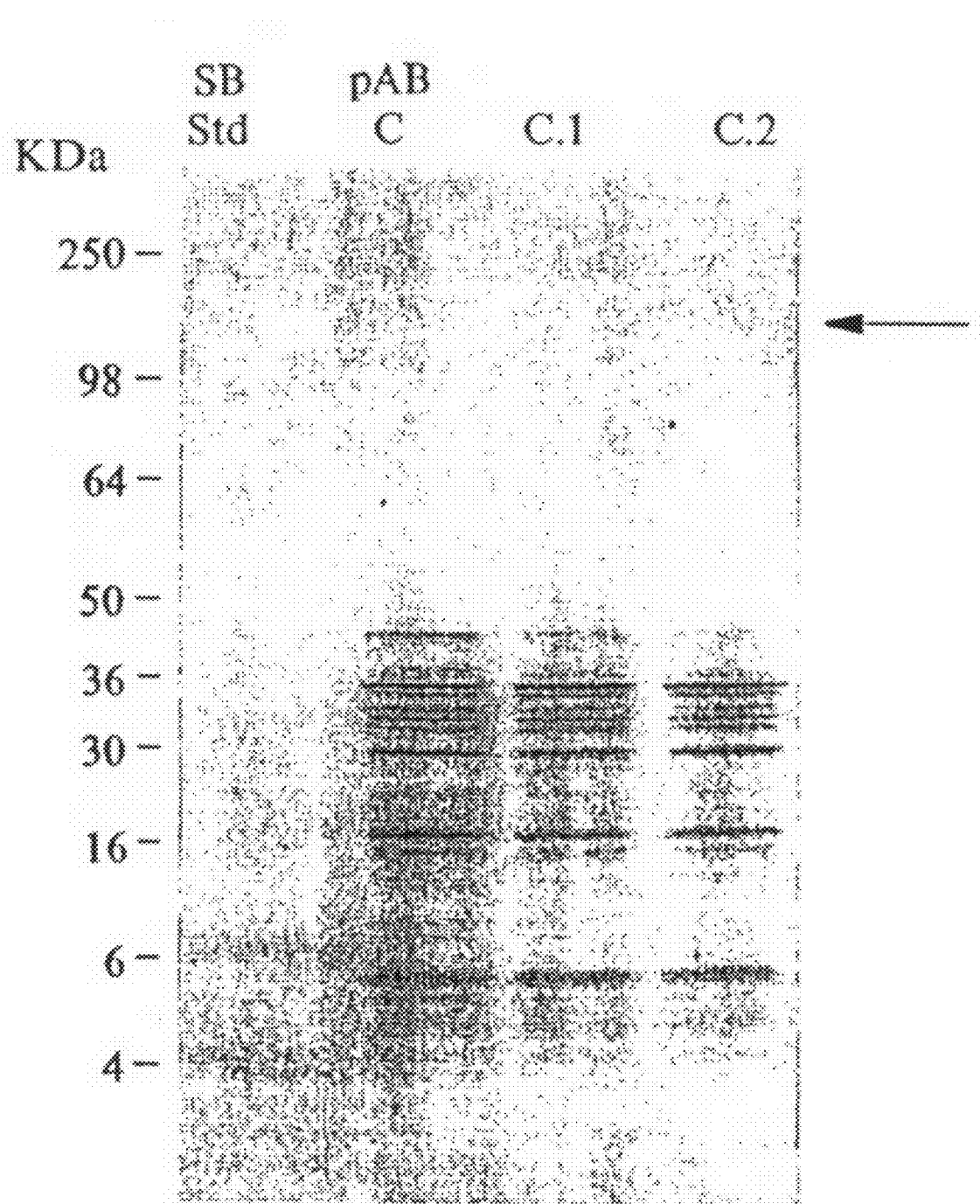
FIG. 12 shows the Western blot of proteins expressed by *S. cerevisiae* strain AD3 transformed with pd.ΔNS3NS5.
Figure 15:
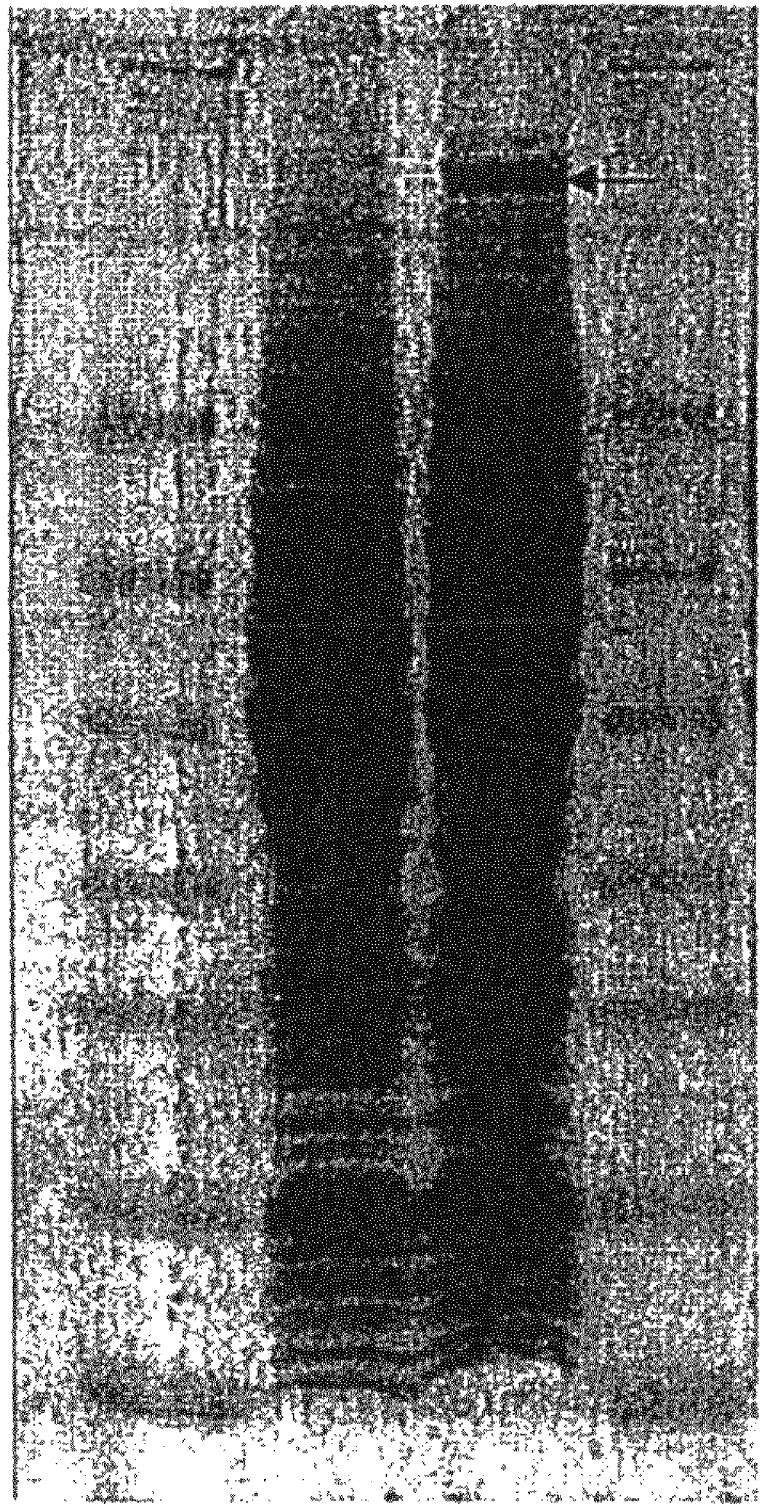
FIG. 15 shows the Western blot of proteins expressed by *S. cerevisiae* strain AD3 transformed with pd.ΔNS3NS5.pj, specifically demonstrating the expression of ΔNS3NS5 polypeptide.
Figure 19:
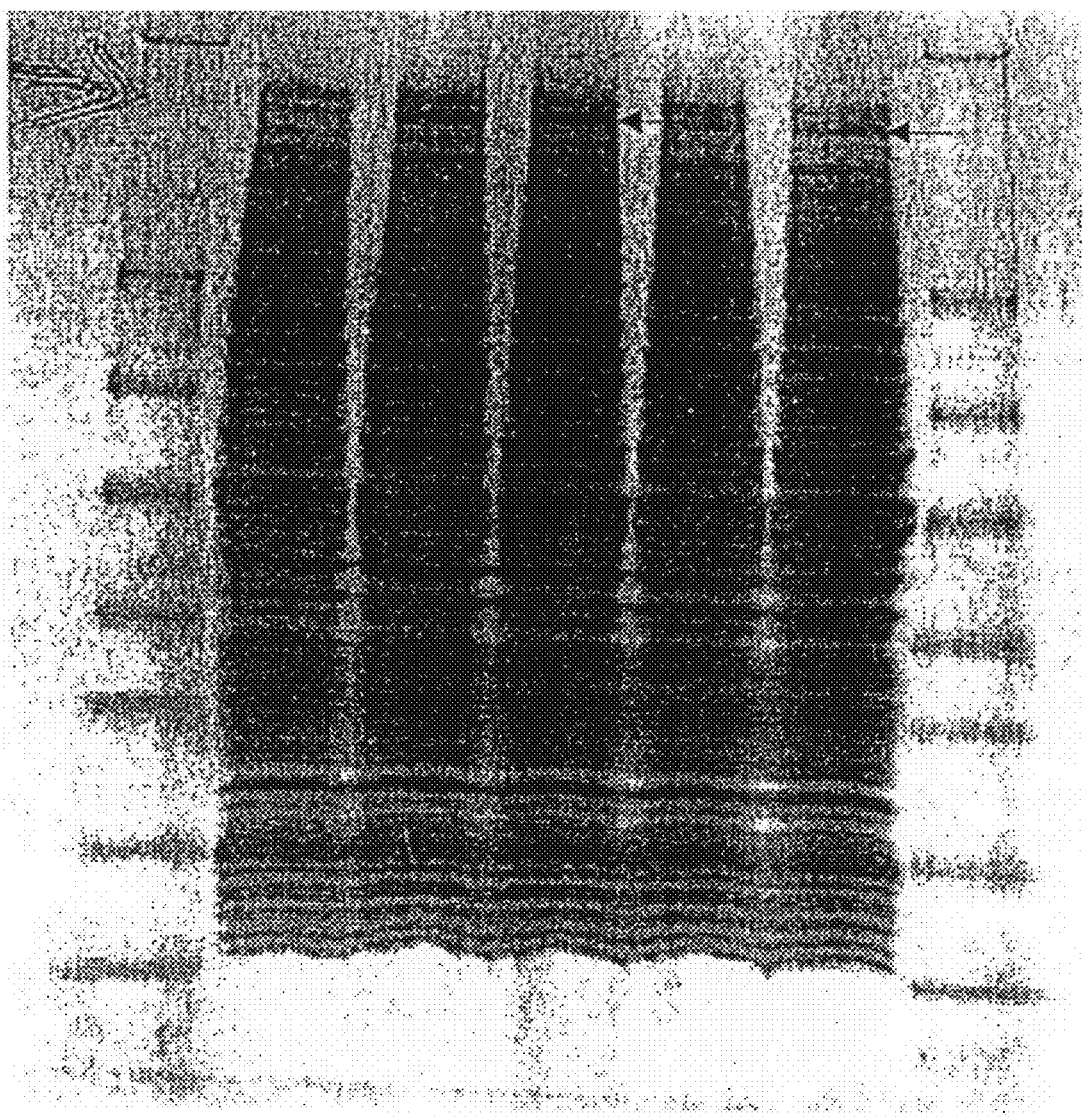
FIG. 19 shows the Western blot of proteins expressed by *S. cerevisiae* strain AD3 transformed with pd.ΔNS3NS5.pj, specifically demonstrating the expression of ΔNS3NS5.core121 and ΔNS3NS5.core173 polypeptides. Lanes 1 and 7 show See Blue Standards. Lane 2 shows control yeast plasmid. Lanes 3 and 4 show ΔNS3NS5.core121RT polypeptide, colonies 1 and 2. Lanes 5 and 6 show ΔNS3NS5.core173RT polypeptide, colonies 3 and 4.

Various of the constructs described herein, encoding HCV-1 ΔNS3 to NS5 antigen (aa 1242-3611), were expressed in yeast. *S. cerevisiae* strain AD3 was transformed with pd.ΔNS3NS5 and checked for expression. A stained protein band at the expected molecular weight of 194 kD was not observed (FIG. 12). Strain AD3 was also transformed with pd.ΔNS3NS5.PJ clone #5 and checked for expression. A protein band of the expected molecular weight of 194 kD was detected (FIG. 15). Strain AD3 was transformed with pd.ΔNS3NS5.PJ.core121RT clone #6 and pd.ΔNS3NS5.PJ.core173RT clone#15 and checked for expression. Protein bands of the expected molecular weight of 206 kD and 210 kD, respectively, were observed. Expression levels of the pd.ΔNS3NS5.PJ.core173RT construct were much less than that of the pd.ΔNS3NS5.PJ.core121RT construct. (See FIG. 19). Thus, there is a correlation of protein expression levels and the length of HCV core.

Figure 23:
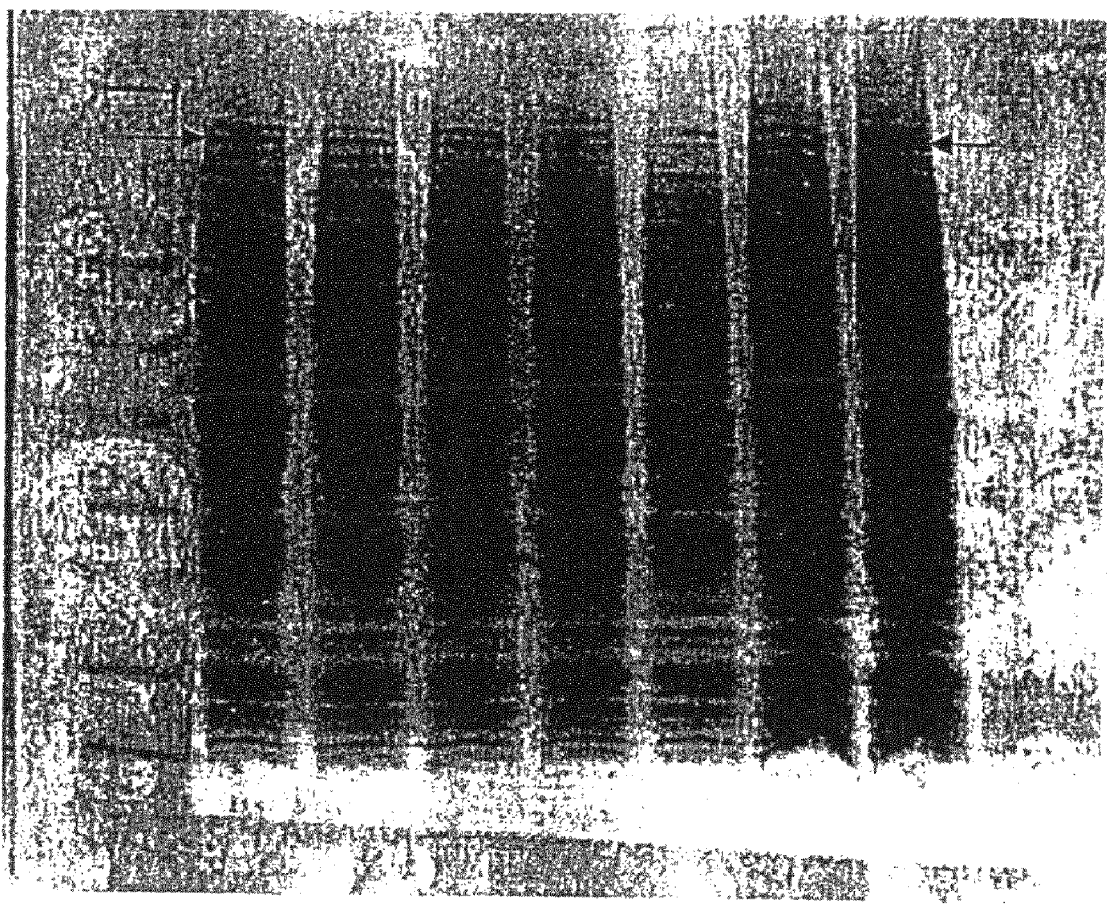
FIG. 23 shows the Western blot of proteins expressed by *S. cerevisiae* strain AD3 transformed with pd.ΔNS3NS5.pj, specifically demonstrating the expression of ΔNS3NS5core140 and ΔNS3NS5core150 polypeptides. Lane 1 shows See Blue Standards. Lanes 2 and 3 show ΔNS3NS5core140RT polypeptide, colonies 5 and 6. Lanes 4 and 5 show ΔNS3NS5core150RT polypeptide, colonies 7 and 8. Lane 6 shows control yeast plasmid. Lane 7 shows ΔNS3NS5core121RT polypeptide, colony 1. Lane 8 shows ΔNS3NS5core173RT polypeptide, colony 5.

Strain AD3 were transformed with pd.ΔNS3NS5.PJ.core140RT clone# 29 and pd.ΔNS3NS5.PJ.core150RT clone#35 and checked for expression. Bands of the expected molecular weights of 208 kD and 209 kD were seen by stain at levels close to those of pd.ΔNS3NS5core173RT (FIG. 23).

Example 3

Eliciting Immune Responses

A. Immunization

To evaluate the immunogenicity of the mutant NS polypeptides, studies using guinea pigs, rabbits, mice, rhesus macaques and/or baboons are performed. The studies are structured as follows: DNA immunization alone (single or multiple); DNA immunization followed by protein immunization (boost); DNA immunization followed by protein immunization; immunization by PLG particles. Immunization is intramuscular or mucosally.

B. Humoral Immune Response

The humoral immune response is checked in serum specimens from immunized animals with anti-NS antibody ELISAs (enzyme-linked immunosorbent assays) at various times post-immunization. Briefly, serum from immunized animals is screened for antibodies directed against the NS or mutant NS proteins. Wells of ELISA microtiter plates are coated overnight with the selected HCV protein and washed four times; subsequently, blocking is done with PBS-0.2% Tween (Sigma). After removal of the blocking solution, diluted mouse serum is added. Sera are tested at various dilutions. Microtiter plates are washed and incubated with a secondary, peroxidase-coupled anti-mouse IgG antibody (Pierce, Rockford, Ill.). ELISA plates are washed and 3,3',5,5'-tetramethyl benzidine (TMB; Pierce) is added per well. The optical density of each well is measured. Titers are typically reported as the reciprocal of the dilution of serum that gave a half-maximum optical density (O.D.). Similarly, generation of neutralization of binding (NOB) antibodies can be measured by methods known in the art.

C. Cellular Immune Response

The frequency of specific cytotoxic T-lymphocytes (CTL) is evaluated by a standard chromium release assay of peptide pulsed Balb/c mouse CD4 cells. Briefly, spleen cells (Effector cells, E) are obtained from the BALB/c mice immunized, cultured, restimulated, and assayed for CTL activity against HCV peptide-pulsed target cells. Cytotoxic activity is measured in a standard $^{51}Cr$ release assay.

Example 4

Immunization with PLG-delivered DNA

The polylactide-co-glycolide (PLG) polymers are obtained from Boehringer Ingelheim, U.S.A. The PLG polymer is RG505, which has a copolymer ratio of 50/50 and a molecular weight of 65 kDa (manufacturers data). Cationic microparticles with adsorbed DNA are prepared using a modified solvent evaporation process, essentially as described in Singh et al., *Proc. Natl. Acad. Sci. USA* (2000) 97:811-816. Briefly, the microparticles are prepared by emulsifying a 5% w/v polymer solution in methylene chloride with PBS at high speed using an IKA homogenizer. The primary emulsion is then added to distilled water containing cetyl trimethyl ammonium bromide (CTAB) (0.5% w/v). This results in the formation of a w/o/w emulsion which was stirred at room temperature, allowing the methylene chloride to evaporate. The resulting microparticles are washed in distilled water by centrifugation and freeze dried. Following preparation, washing and collection, DNA is adsorbed onto the microparticles by incubating cationic microparticles in a solution of DNA. The microparticles are then separated by centrifugation, the pellet washed with TE buffer and the microparticles are freeze dried, resuspended and administered to animals. Antibody titers are measured by ELISA assays.

All patents, patent applications, and other publications mentioned herein, are hereby incorporated herein by reference in their entireties.

SEQUENCE LISTING

```
<160> NUMBER OF SEQ ID NOS: 19

<210> SEQ ID NO 1
<211> LENGTH: 9620
<212> TYPE: DNA
<213> ORGANISM: Artificial Sequence
<220> FEATURE:
<221> NAME/KEY: CDS
```

<222> LOCATION: (1990)..(7302)
<223> OTHER INFORMATION: Description of Artificial Sequence: Hepatitis C pns345

<400> SEQUENCE: 1

| | |
|---|---|
| cgcgcgtttc ggtgatgacg gtgaaaacct ctgacacatg cagctcccgg agacggtcac | 60 |
| agcttgtctg taagcggatg ccgggagcag acaagcccgt cagggcgcgt cagcgggtgt | 120 |
| tggcgggtgt cggggctggc ttaactatgc ggcatcagag cagattgtac tgagagtgca | 180 |
| ccatatgaag cttttgcaa aagcctaggc ctccaaaaaa gcctcctcac tacttctgga | 240 |
| atagctcaga ggccgaggcg gcctcggcct ctgcataaat aaaaaaaatt agtcagccat | 300 |
| ggggcggaga atgggcggaa ctgggcgggg agggaattat tggctattgg ccattgcata | 360 |
| cgttgtatct atatcataat atgtacattt atattggctc atgtccaata tgaccgccat | 420 |
| gttgacattg attattgact agttattaat agtaatcaat tacggggtca ttagttcata | 480 |
| gcccatatat ggagttccgc gttacataac ttacggtaaa tggcccgcct ggctgaccgc | 540 |
| ccaacgaccc ccgcccattg acgtcaataa tgacgtatgt tcccatagta acgccaatag | 600 |
| ggactttcca ttgacgtcaa tgggtggagt atttacggta aactgcccac ttggcagtac | 660 |
| atcaagtgta tcatatgcca agtccgcccc ctattgacgt caatgacggt aaatggcccg | 720 |
| cctggcatta tgcccagtac atgaccttac gggactttcc tacttggcag tacatctacg | 780 |
| tattagtcat cgctattacc atggtgatgc ggttttggca gtacaccaat gggcgtggat | 840 |
| agcggtttga ctcacgggga tttccaagtc tccaccccat tgacgtcaat gggagtttgt | 900 |
| tttggcacca aaatcaacgg gactttccaa aatgtcgtaa taaccccgcc ccgttgacgc | 960 |
| aaatgggcgg taggcgtgta cggtgggagg tctatataag cagagctcgt ttagtgaacc | 1020 |
| gtcagatcgc ctggagacgc catccacgct gttttgacct ccatagaaga caccgggacc | 1080 |
| gatccagcct ccgcggccgg gaacggtgca ttggaacgcg gattcccgt gccaagagtg | 1140 |
| acgtaagtac cgcctataga ctctataggc accccctttt ggctcttatg catgctatac | 1200 |
| tgtttttggc ttggggccta tacaccccg ctccttatgc tataggtgat ggtatagctt | 1260 |
| agcctatagg tgtgggttat tgaccattat tgaccactcc cctattggtg acgatacttt | 1320 |
| ccattactaa tccataacat ggctctttgc cacaactatc tctattggct atatgccaat | 1380 |
| actctgtcct tcagagactg acacggactc tgtattttta caggatgggg tccatttatt | 1440 |
| atttacaaat tcatatatac aacaacgccg tccccgtgc ccgcagtttt tattaaacat | 1500 |
| agcgtgggat ctccgacatc tcgggtacgt gttccggaca tgggctcttc tccggtagcg | 1560 |
| gcggagcttc cacatccgag ccctggtccc atccgtccag cggctcatgg tcgctcggca | 1620 |
| gctccttgct cctaacagtg gaggccagac ttaggcacag cacaatgccc accaccacca | 1680 |
| gtgtgccgca caaggccgtg gcggtagggt atgtgtctga aaatgagctc ggagattggg | 1740 |
| ctcgcacctg gacgcagatg gaagacttaa ggcagcggca gaagaagatg caggcagctg | 1800 |
| agttgttgta ttctgataag agtcagaggt aactcccgtt gcggtgctgt taacggtgga | 1860 |
| gggcagtgta gtctgagcag tactcgttgc tgccgcgcgc gccaccagac ataatagctg | 1920 |
| acagactaac agactgttcc tttccatggg tctttctgc agtcaccgtc gtcgacctaa | 1980 |

| | | |
|---|---|---|
| gaattcacc atg gct gca tat gca gct cag ggc tat aag gtg cta gta ctc | | 2031 |
| Met Ala Ala Tyr Ala Ala Gln Gly Tyr Lys Val Leu Val Leu | | |
| 1 5 10 | | |

| | | |
|---|---|---|
| aac ccc tct gtt gct gca aca ctg ggc ttt ggt gct tac atg tcc aag | | 2079 |
| Asn Pro Ser Val Ala Ala Thr Leu Gly Phe Gly Ala Tyr Met Ser Lys | | |
| 15 20 25 30 | | |

```
gct cat ggg atc gat cct aac atc agg acc ggg gtg aga aca att acc      2127
Ala His Gly Ile Asp Pro Asn Ile Arg Thr Gly Val Arg Thr Ile Thr
                 35                  40                  45 act ggc agc ccc atc acg tac tcc acc tac ggc aag ttc ctt gcc gac      2175
Thr Gly Ser Pro Ile Thr Tyr Ser Thr Tyr Gly Lys Phe Leu Ala Asp
             50                  55                  60 ggc ggg tgc tcg ggg ggc gct tat gac ata ata att tgt gac gag tgc      2223
Gly Gly Cys Ser Gly Gly Ala Tyr Asp Ile Ile Ile Cys Asp Glu Cys
         65                  70                  75 cac tcc acg gat gcc aca tcc atc ttg ggc att ggc act gtc ctt gac      2271
His Ser Thr Asp Ala Thr Ser Ile Leu Gly Ile Gly Thr Val Leu Asp
     80                  85                  90 caa gca gag act gcg ggg gcg aga ctg gtt gtg ctc gcc acc gcc acc      2319
Gln Ala Glu Thr Ala Gly Ala Arg Leu Val Val Leu Ala Thr Ala Thr
 95                 100                 105                 110 cct ccg ggc tcc gtc act gtg ccc cat ccc aac atc gag gag gtt gct      2367
Pro Pro Gly Ser Val Thr Val Pro His Pro Asn Ile Glu Glu Val Ala
                115                 120                 125 ctg tcc acc acc gga gag atc cct ttt tac ggc aag gct atc ccc ctc      2415
Leu Ser Thr Thr Gly Glu Ile Pro Phe Tyr Gly Lys Ala Ile Pro Leu
            130                 135                 140 gaa gta atc aag ggg ggg aga cat ctc atc ttc tgt cat tca aag aag      2463
Glu Val Ile Lys Gly Gly Arg His Leu Ile Phe Cys His Ser Lys Lys
        145                 150                 155 aag tgc gac gaa ctc gcc gca aag ctg gtc gca ttg ggc atc aat gcc      2511
Lys Cys Asp Glu Leu Ala Ala Lys Leu Val Ala Leu Gly Ile Asn Ala
    160                 165                 170 gtg gcc tac tac cgc ggt ctt gac gtg tcc gtc atc ccg acc agc ggc      2559
Val Ala Tyr Tyr Arg Gly Leu Asp Val Ser Val Ile Pro Thr Ser Gly
175                 180                 185                 190 gat gtt gtc gtc gtg gca acc gat gcc ctc atg acc ggc tat acc ggc      2607
Asp Val Val Val Val Ala Thr Asp Ala Leu Met Thr Gly Tyr Thr Gly
                195                 200                 205 gac ttc gac tcg gtg ata gac tgc aat acg tgt gtc acc cag aca gtc      2655
Asp Phe Asp Ser Val Ile Asp Cys Asn Thr Cys Val Thr Gln Thr Val
            210                 215                 220 gat ttc agc ctt gac cct acc ttc acc att gag aca atc acg ctc ccc      2703
Asp Phe Ser Leu Asp Pro Thr Phe Thr Ile Glu Thr Ile Thr Leu Pro
        225                 230                 235 caa gat gct gtc tcc cgc act caa cgt cgg ggc agg act ggc agg ggg      2751
Gln Asp Ala Val Ser Arg Thr Gln Arg Arg Gly Arg Thr Gly Arg Gly
    240                 245                 250 aag cca ggc atc tac aga ttt gtg gca ccg ggg gag cgc ccc tcc ggc      2799
Lys Pro Gly Ile Tyr Arg Phe Val Ala Pro Gly Glu Arg Pro Ser Gly
255                 260                 265                 270 atg ttc gac tcg tcc gtc ctc tgt gag tgc tat gac gca ggc tgt gct      2847
Met Phe Asp Ser Ser Val Leu Cys Glu Cys Tyr Asp Ala Gly Cys Ala
                275                 280                 285 tgg tat gag ctc acg ccc gcc gag act aca gtt agg cta cga gcg tac      2895
Trp Tyr Glu Leu Thr Pro Ala Glu Thr Thr Val Arg Leu Arg Ala Tyr
            290                 295                 300 atg aac acc ccg ggg ctt ccc gtg tgc cag gac cat ctt gaa ttt tgg      2943
Met Asn Thr Pro Gly Leu Pro Val Cys Gln Asp His Leu Glu Phe Trp
        305                 310                 315 gag ggc gtc ttt aca ggc ctc act cat ata gat gcc cac ttt cta tcc      2991
Glu Gly Val Phe Thr Gly Leu Thr His Ile Asp Ala His Phe Leu Ser
    320                 325                 330 cag aca aag cag agt ggg gag aac ctt cct tac ctg gta gcg tac caa      3039
Gln Thr Lys Gln Ser Gly Glu Asn Leu Pro Tyr Leu Val Ala Tyr Gln
```

```
                        -continued
335                 340                 345                 350 gcc acc gtg tgc gct agg gct caa gcc cct ccc cca tcg tgg gac cag    3087
Ala Thr Val Cys Ala Arg Ala Gln Ala Pro Pro Pro Ser Trp Asp Gln
            355                 360                 365 atg tgg aag tgt ttg att cgc ctc aag ccc acc ctc cat ggg cca aca    3135
Met Trp Lys Cys Leu Ile Arg Leu Lys Pro Thr Leu His Gly Pro Thr
        370                 375                 380 ccc ctg cta tac aga ctg ggc gct gtt cag aat gaa atc acc ctg acg    3183
Pro Leu Leu Tyr Arg Leu Gly Ala Val Gln Asn Glu Ile Thr Leu Thr
    385                 390                 395 cac cca gtc acc aaa tac atc atg aca tgc atg tcg gcc gac ctg gag    3231
His Pro Val Thr Lys Tyr Ile Met Thr Cys Met Ser Ala Asp Leu Glu
400                 405                 410 gtc gtc acg agc acc tgg gtg ctc gtt ggc ggc gtc ctg gct gct ttg    3279
Val Val Thr Ser Thr Trp Val Leu Val Gly Gly Val Leu Ala Ala Leu
415                 420                 425                 430 gcc gcg tat tgc ctg tca aca ggc tgc gtg gtc ata gtg ggc agg gtc    3327
Ala Ala Tyr Cys Leu Ser Thr Gly Cys Val Val Ile Val Gly Arg Val
            435                 440                 445 gtc ttg tcc ggg aag ccg gca atc ata cct gac agg gaa gtc ctc tac    3375
Val Leu Ser Gly Lys Pro Ala Ile Ile Pro Asp Arg Glu Val Leu Tyr
        450                 455                 460 cga gag ttc gat gag atg gaa gag tgc tct cag cac tta ccg tac atc    3423
Arg Glu Phe Asp Glu Met Glu Glu Cys Ser Gln His Leu Pro Tyr Ile
    465                 470                 475 gag caa ggg atg atg ctc gcc gag cag ttc aag cag aag gcc ctc ggc    3471
Glu Gln Gly Met Met Leu Ala Glu Gln Phe Lys Gln Lys Ala Leu Gly
480                 485                 490 ctc ctg cag acc gcg tcc cgt cag gca gag gtt atc gcc cct gct gtc    3519
Leu Leu Gln Thr Ala Ser Arg Gln Ala Glu Val Ile Ala Pro Ala Val
495                 500                 505                 510 cag acc aac tgg caa aaa ctc gag acc ttc tgg gcg aag cat atg tgg    3567
Gln Thr Asn Trp Gln Lys Leu Glu Thr Phe Trp Ala Lys His Met Trp
            515                 520                 525 aac ttc atc agt ggg ata caa tac ttg gcg ggc ttg tca acg ctg cct    3615
Asn Phe Ile Ser Gly Ile Gln Tyr Leu Ala Gly Leu Ser Thr Leu Pro
        530                 535                 540 ggt aac ccc gcc att gct tca ttg atg gct ttt aca gct gct gtc acc    3663
Gly Asn Pro Ala Ile Ala Ser Leu Met Ala Phe Thr Ala Ala Val Thr
    545                 550                 555 agc cca cta acc act agc caa acc ctc ctc ttc aac ata ttg ggg ggg    3711
Ser Pro Leu Thr Thr Ser Gln Thr Leu Leu Phe Asn Ile Leu Gly Gly
560                 565                 570 tgg gtg gct gcc cag ctc gcc gcc ccc ggt gcc gct act gcc ttt gtg    3759
Trp Val Ala Ala Gln Leu Ala Ala Pro Gly Ala Ala Thr Ala Phe Val
575                 580                 585                 590 ggc gct ggc tta gct ggc gcc gcc atc ggc agt gtt gga ctg ggg aag    3807
Gly Ala Gly Leu Ala Gly Ala Ala Ile Gly Ser Val Gly Leu Gly Lys
            595                 600                 605 gtc ctc ata gac atc ctt gca ggg tat ggc gcg ggc gtg gcg gga gct    3855
Val Leu Ile Asp Ile Leu Ala Gly Tyr Gly Ala Gly Val Ala Gly Ala
        610                 615                 620 ctt gtg gca ttc aag atc atg agc ggt gag gtc ccc tcc acg gag gac    3903
Leu Val Ala Phe Lys Ile Met Ser Gly Glu Val Pro Ser Thr Glu Asp
    625                 630                 635 ctg gtc aat cta ctg ccc gcc atc ctc tcg ccc gga gcc ctc gta gtc    3951
Leu Val Asn Leu Leu Pro Ala Ile Leu Ser Pro Gly Ala Leu Val Val
640                 645                 650 ggc gtg gtc tgt gca gca ata ctg cgc cgg cac gtt ggc ccg ggc gag    3999
```

```
Gly Val Val Cys Ala Ala Ile Leu Arg Arg His Val Gly Pro Gly Glu
655                 660                 665                 670 ggg gca gtg cag tgg atg aac cgg ctg ata gcc ttc gcc tcc cgg ggg     4047
Gly Ala Val Gln Trp Met Asn Arg Leu Ile Ala Phe Ala Ser Arg Gly
            675                 680                 685 aac cat gtt tcc ccc acg cac tac gtg ccg gag agc gat gca gct gcc     4095
Asn His Val Ser Pro Thr His Tyr Val Pro Glu Ser Asp Ala Ala Ala
                690                 695                 700 cgc gtc act gcc ata ctc agc agc ctc act gta acc cag ctc ctg agg     4143
Arg Val Thr Ala Ile Leu Ser Ser Leu Thr Val Thr Gln Leu Leu Arg
    705                 710                 715 cga ctg cac cag tgg ata agc tcg gag tgt acc act cca tgc tcc ggt     4191
Arg Leu His Gln Trp Ile Ser Ser Glu Cys Thr Thr Pro Cys Ser Gly
720                 725                 730 tcc tgg cta agg gac atc tgg gac tgg ata tgc gag gtg ttg agc gac     4239
Ser Trp Leu Arg Asp Ile Trp Asp Trp Ile Cys Glu Val Leu Ser Asp
735                 740                 745                 750 ttt aag acc tgg cta aaa gct aag ctc atg cca cag ctg cct ggg atc     4287
Phe Lys Thr Trp Leu Lys Ala Lys Leu Met Pro Gln Leu Pro Gly Ile
                755                 760                 765 ccc ttt gtg tcc tgc cag cgc ggg tat aag ggg gtc tgg cga ggg gac     4335
Pro Phe Val Ser Cys Gln Arg Gly Tyr Lys Gly Val Trp Arg Gly Asp
            770                 775                 780 ggc atc atg cac act cgc tgc cac tgt gga gct gag atc act gga cat     4383
Gly Ile Met His Thr Arg Cys His Cys Gly Ala Glu Ile Thr Gly His
                785                 790                 795 gtc aaa aac ggg acg atg agg atc gtc ggt cct agg acc tgc agg aac     4431
Val Lys Asn Gly Thr Met Arg Ile Val Gly Pro Arg Thr Cys Arg Asn
    800                 805                 810 atg tgg agt ggg acc ttc ccc att aat gcc tac acc acg ggc ccc tgt     4479
Met Trp Ser Gly Thr Phe Pro Ile Asn Ala Tyr Thr Thr Gly Pro Cys
815                 820                 825                 830 acc ccc ctt cct gcg ccg aac tac acg ttc gcg cta tgg agg gtg tct     4527
Thr Pro Leu Pro Ala Pro Asn Tyr Thr Phe Ala Leu Trp Arg Val Ser
                835                 840                 845 gca gag gaa tac gtg gag ata agg cag gtg ggg gac ttc cac tac gtg     4575
Ala Glu Glu Tyr Val Glu Ile Arg Gln Val Gly Asp Phe His Tyr Val
            850                 855                 860 acg ggt atg act act gac aat ctt aaa tgc ccg tgc cag gtc cca tcg     4623
Thr Gly Met Thr Thr Asp Asn Leu Lys Cys Pro Cys Gln Val Pro Ser
                865                 870                 875 ccc gaa ttt ttc aca gaa ttg gac ggg gtg cgc cta cat agg ttt gcg     4671
Pro Glu Phe Phe Thr Glu Leu Asp Gly Val Arg Leu His Arg Phe Ala
    880                 885                 890 ccc ccc tgc aag ccc ttg ctg cgg gag gag gta tca ttc aga gta gga     4719
Pro Pro Cys Lys Pro Leu Leu Arg Glu Glu Val Ser Phe Arg Val Gly
895                 900                 905                 910 ctc cac gaa tac ccg gta ggg tcg caa tta cct tgc gag ccc gaa ccg     4767
Leu His Glu Tyr Pro Val Gly Ser Gln Leu Pro Cys Glu Pro Glu Pro
                915                 920                 925 gac gtg gcc gtg ttg acg tcc atg ctc act gat ccc tcc cat ata aca     4815
Asp Val Ala Val Leu Thr Ser Met Leu Thr Asp Pro Ser His Ile Thr
            930                 935                 940 gca gag gcg gcc ggg cga agg ttg gcg agg gga tca ccc ccc tct gtg     4863
Ala Glu Ala Ala Gly Arg Arg Leu Ala Arg Gly Ser Pro Pro Ser Val
                945                 950                 955 gcc agc tcc tcg gct agc cag cta tcc gct cca tct ctc aag gca act     4911
Ala Ser Ser Ser Ala Ser Gln Leu Ser Ala Pro Ser Leu Lys Ala Thr
960                 965                 970
```

```
tgc acc gct aac cat gac tcc cct gat gct gag ctc ata gag gcc aac      4959
Cys Thr Ala Asn His Asp Ser Pro Asp Ala Glu Leu Ile Glu Ala Asn
975                 980                 985                 990 ctc cta tgg agg cag gag atg ggc ggc aac atc acc agg gtt gag tca      5007
Leu Leu Trp Arg Gln Glu Met Gly Gly Asn Ile Thr Arg Val Glu Ser
                995                 1000                1005 gaa aac aaa gtg gtg att ctg gac tcc ttc gat ccg ctt gtg gcg gag      5055
Glu Asn Lys Val Val Ile Leu Asp Ser Phe Asp Pro Leu Val Ala Glu
            1010                1015                1020 gag gac gag cgg gag atc tcc gta ccc gca gaa atc ctg cgg aag tct      5103
Glu Asp Glu Arg Glu Ile Ser Val Pro Ala Glu Ile Leu Arg Lys Ser
        1025                1030                1035 cgg aga ttc gcc cag gcc ctg ccc gtt tgg gcg cgg ccg gac tat aac      5151
Arg Arg Phe Ala Gln Ala Leu Pro Val Trp Ala Arg Pro Asp Tyr Asn
    1040                1045                1050 ccc ccg cta gtg gag acg tgg aaa aag ccc gac tac gaa cca cct gtg      5199
Pro Pro Leu Val Glu Thr Trp Lys Lys Pro Asp Tyr Glu Pro Pro Val
1055                1060                1065                1070 gtc cat ggc tgc ccg ctt cca cct cca aag tcc cct cct gtg cct ccg      5247
Val His Gly Cys Pro Leu Pro Pro Pro Lys Ser Pro Pro Val Pro Pro
                1075                1080                1085 cct cgg aag aag cgg acg gtg gtc ctc act gaa tca acc cta tct act      5295
Pro Arg Lys Lys Arg Thr Val Val Leu Thr Glu Ser Thr Leu Ser Thr
            1090                1095                1100 gcc ttg gcc gag ctc gcc acc aga agc ttt ggc agc tcc tca act tcc      5343
Ala Leu Ala Glu Leu Ala Thr Arg Ser Phe Gly Ser Ser Ser Thr Ser
        1105                1110                1115 ggc att acg ggc gac aat acg aca aca tcc tct gag ccc gcc cct tct      5391
Gly Ile Thr Gly Asp Asn Thr Thr Thr Ser Ser Glu Pro Ala Pro Ser
    1120                1125                1130 ggc tgc ccc ccc gac tcc gac gct gag tcc tat tcc tcc atg ccc ccc      5439
Gly Cys Pro Pro Asp Ser Asp Ala Glu Ser Tyr Ser Ser Met Pro Pro
1135                1140                1145                1150 ctg gag ggg gag cct ggg gat ccg gat ctt agc gac ggg tca tgg tca      5487
Leu Glu Gly Glu Pro Gly Asp Pro Asp Leu Ser Asp Gly Ser Trp Ser
                1155                1160                1165 acg gtc agt agt gag gcc aac gcg gag gat gtc gtg tgc tgc tca atg      5535
Thr Val Ser Ser Glu Ala Asn Ala Glu Asp Val Val Cys Cys Ser Met
            1170                1175                1180 tct tac tct tgg aca ggc gca ctc gtc acc ccg tgc gcc gcg gaa gaa      5583
Ser Tyr Ser Trp Thr Gly Ala Leu Val Thr Pro Cys Ala Ala Glu Glu
        1185                1190                1195 cag aaa ctg ccc atc aat gca cta agc aac tcg ttg cta cgt cac cac      5631
Gln Lys Leu Pro Ile Asn Ala Leu Ser Asn Ser Leu Leu Arg His His
    1200                1205                1210 aat ttg gtg tat tcc acc acc tca cgc agt gct tgc caa agg cag aag      5679
Asn Leu Val Tyr Ser Thr Thr Ser Arg Ser Ala Cys Gln Arg Gln Lys
1215                1220                1225                1230 aaa gtc aca ttt gac aga ctg caa gtt ctg gac agc cat tac cag gac      5727
Lys Val Thr Phe Asp Arg Leu Gln Val Leu Asp Ser His Tyr Gln Asp
                1235                1240                1245 gta ctc aag gag gtt aaa gca gcg gcg tca aaa gtg aag gct aac ttg      5775
Val Leu Lys Glu Val Lys Ala Ala Ala Ser Lys Val Lys Ala Asn Leu
            1250                1255                1260 cta tcc gta gag gaa gct tgc agc ctg acg ccc cca cac tca gcc aaa      5823
Leu Ser Val Glu Glu Ala Cys Ser Leu Thr Pro Pro His Ser Ala Lys
        1265                1270                1275 tcc aag ttt ggt tat ggg gca aaa gac gtc cgt tgc cat gcc aga aag      5871
Ser Lys Phe Gly Tyr Gly Ala Lys Asp Val Arg Cys His Ala Arg Lys
    1280                1285                1290
```

-continued

| | |
|---|---|
| gcc gta acc cac atc aac tcc gtg tgg aaa gac ctt ctg gaa gac aat<br>Ala Val Thr His Ile Asn Ser Val Trp Lys Asp Leu Leu Glu Asp Asn<br>1295                      1300                 1305               1310 | 5919 |
| gta aca cca ata gac act acc atc atg gct aag aac gag gtt ttc tgc<br>Val Thr Pro Ile Asp Thr Thr Ile Met Ala Lys Asn Glu Val Phe Cys<br>              1315                 1320               1325 | 5967 |
| gtt cag cct gag aag ggg ggt cgt aag cca gct cgt ctc atc gtg ttc<br>Val Gln Pro Glu Lys Gly Gly Arg Lys Pro Ala Arg Leu Ile Val Phe<br>                1330               1335               1340 | 6015 |
| ccc gat ctg ggc gtg cgc gtg tgc gaa aag atg gct ttg tac gac gtg<br>Pro Asp Leu Gly Val Arg Val Cys Glu Lys Met Ala Leu Tyr Asp Val<br>1345                      1350                 1355 | 6063 |
| gtt aca aag ctc ccc ttg gcc gtg atg gga agc tcc tac gga ttc caa<br>Val Thr Lys Leu Pro Leu Ala Val Met Gly Ser Ser Tyr Gly Phe Gln<br>            1360                 1365               1370 | 6111 |
| tac tca cca gga cag cgg gtt gaa ttc ctc gtg caa gcg tgg aag tcc<br>Tyr Ser Pro Gly Gln Arg Val Glu Phe Leu Val Gln Ala Trp Lys Ser<br>1375                      1380                 1385               1390 | 6159 |
| aag aaa acc cca atg ggg ttc tcg tat gat acc cgc tgc ttt gac tcc<br>Lys Lys Thr Pro Met Gly Phe Ser Tyr Asp Thr Arg Cys Phe Asp Ser<br>              1395                 1400               1405 | 6207 |
| aca gtc act gag agc gac atc cgt acg gag gag gca atc tac caa tgt<br>Thr Val Thr Glu Ser Asp Ile Arg Thr Glu Glu Ala Ile Tyr Gln Cys<br>            1410                 1415               1420 | 6255 |
| tgt gac ctc gac ccc caa gcc cgc gtg gcc atc aag tcc ctc acc gag<br>Cys Asp Leu Asp Pro Gln Ala Arg Val Ala Ile Lys Ser Leu Thr Glu<br>1425                      1430                 1435 | 6303 |
| agg ctt tat gtt ggg ggc cct ctt acc aat tca agg ggg gag aac tgc<br>Arg Leu Tyr Val Gly Gly Pro Leu Thr Asn Ser Arg Gly Glu Asn Cys<br>            1440                 1445               1450 | 6351 |
| ggc tat cgc agg tgc cgc gcg agc ggc gta ctg aca act agc tgt ggt<br>Gly Tyr Arg Arg Cys Arg Ala Ser Gly Val Leu Thr Thr Ser Cys Gly<br>1455                      1460                 1465               1470 | 6399 |
| aac acc ctc act tgc tac atc aag gcc cgg gca gcc tgt cga gcc gca<br>Asn Thr Leu Thr Cys Tyr Ile Lys Ala Arg Ala Ala Cys Arg Ala Ala<br>              1475                 1480               1485 | 6447 |
| ggg ctc cag gac tgc acc atg ctc gtg tgt ggc gac gac tta gtc gtt<br>Gly Leu Gln Asp Cys Thr Met Leu Val Cys Gly Asp Asp Leu Val Val<br>            1490                 1495               1500 | 6495 |
| atc tgt gaa agc gcg ggg gtc cag gag gac gcg gcg agc ctg aga gcc<br>Ile Cys Glu Ser Ala Gly Val Gln Glu Asp Ala Ala Ser Leu Arg Ala<br>1505                      1510                 1515 | 6543 |
| ttc acg gag gct atg acc agg tac tcc gcc ccc cct ggg gac ccc cca<br>Phe Thr Glu Ala Met Thr Arg Tyr Ser Ala Pro Pro Gly Asp Pro Pro<br>            1520                 1525               1530 | 6591 |
| caa cca gaa tac gac ttg gag ctc ata aca tca tgc tcc tcc aac gtg<br>Gln Pro Glu Tyr Asp Leu Glu Leu Ile Thr Ser Cys Ser Ser Asn Val<br>1535                      1540                 1545               1550 | 6639 |
| tca gtc gcc cac gac ggc gct gga aag agg gtc tac tac ctc acc cgt<br>Ser Val Ala His Asp Gly Ala Gly Lys Arg Val Tyr Tyr Leu Thr Arg<br>              1555                 1560               1565 | 6687 |
| gac cct aca acc ccc ctc gcg aga gct gcg tgg gag aca gca aga cac<br>Asp Pro Thr Thr Pro Leu Ala Arg Ala Ala Trp Glu Thr Ala Arg His<br>            1570                 1575               1580 | 6735 |
| act cca gtc aat tcc tgg cta ggc aac ata atc atg ttt gcc ccc aca<br>Thr Pro Val Asn Ser Trp Leu Gly Asn Ile Ile Met Phe Ala Pro Thr<br>1585                      1590                 1595 | 6783 |
| ctg tgg gcg agg atg ata ctg atg acc cat ttc ttt agc gtc ctt ata<br>Leu Trp Ala Arg Met Ile Leu Met Thr His Phe Phe Ser Val Leu Ile | 6831 |

-continued

```
                1600              1605              1610
gcc agg gac cag ctt gaa cag gcc ctc gat tgc gag atc tac ggg gcc    6879
Ala Arg Asp Gln Leu Glu Gln Ala Leu Asp Cys Glu Ile Tyr Gly Ala
1615              1620              1625              1630 tgc tac tcc ata gaa cca ctg gat cta cct cca atc att caa aga ctc    6927
Cys Tyr Ser Ile Glu Pro Leu Asp Leu Pro Pro Ile Ile Gln Arg Leu
        1635              1640              1645 cat ggc ctc agc gca ttt tca ctc cac agt tac tct cca ggt gaa atc    6975
His Gly Leu Ser Ala Phe Ser Leu His Ser Tyr Ser Pro Gly Glu Ile
    1650              1655              1660 aat agg gtg gcc gca tgc ctc aga aaa ctt ggg gta ccg ccc ttg cga    7023
Asn Arg Val Ala Ala Cys Leu Arg Lys Leu Gly Val Pro Pro Leu Arg
1665              1670              1675 gct tgg aga cac cgg gcc cgg agc gtc cgc gct agg ctt ctg gcc aga    7071
Ala Trp Arg His Arg Ala Arg Ser Val Arg Ala Arg Leu Leu Ala Arg
    1680              1685              1690 gga ggc agg gct gcc ata tgt ggc aag tac ctc ttc aac tgg gca gta    7119
Gly Gly Arg Ala Ala Ile Cys Gly Lys Tyr Leu Phe Asn Trp Ala Val
1695              1700              1705              1710 aga aca aag ctc aaa ctc act cca ata gcg gcc gct ggc cag ctg gac    7167
Arg Thr Lys Leu Lys Leu Thr Pro Ile Ala Ala Ala Gly Gln Leu Asp
        1715              1720              1725 ttg tcc ggc tgg ttc acg gct ggc tac agc ggg gga gac att tat cac    7215
Leu Ser Gly Trp Phe Thr Ala Gly Tyr Ser Gly Gly Asp Ile Tyr His
    1730              1735              1740 agc gtg tct cat gcc cgg ccc cgc tgg atc tgg ttt tgc cta ctc ctg    7263
Ser Val Ser His Ala Arg Pro Arg Trp Ile Trp Phe Cys Leu Leu Leu
    1745              1750              1755 ctt gct gca ggg gta ggc atc tac ctc ctc ccc aac cga tgaaggttgg    7312
Leu Ala Ala Gly Val Gly Ile Tyr Leu Leu Pro Asn Arg
    1760              1765              1770 ggtaaacact ccggcctaaa aaaaaaaaaa aatctagaaa ggcgcgccaa gatatcaagg    7372
atccactacg cgttagagct cgctgatcag cctcgactgt gccttctagt tgccagccat    7432
ctgttgtttg cccctccccc gtgccttcct tgaccctgga aggtgccact cccactgtcc    7492
tttcctaata aaatgaggaa attgcatcgc attgtctgag taggtgtcat tctattctgg    7552
ggggtggggt ggggcaggac agcaaggggg aggattggga agacaatagc aggcatgctg    7612
gggagctctt ccgcttcctc gctcactgac tcgctgcgct cggtcgttcg ctgcggcga    7672
gcggtatcag ctcactcaaa ggcggtaata cggttatcca cagaatcagg ggataacgca    7732
ggaaagaaca tgtgagcaaa aggccagcaa aaggccagga accgtaaaaa ggccgcgttg    7792
ctggcgtttt tccataggct ccgcccccct gacgagcatc acaaaaatcg acgctcaagt    7852
cagaggtggc gaaacccgac aggactataa agataccagg cgtttccccc tggaagctcc    7912
ctcgtgcgct ctcctgttcc gaccctgccg cttaccggat acctgtccgc ctttctccct    7972
tcgggaagcg tggcgctttc tcaatgctca cgctgtaggt atctcagttc ggtgtaggtc    8032
gttcgctcca agctgggctg tgtgcacgaa ccccccgttc agcccgaccg ctgcgcctta    8092
tccggtaact atcgtcttga gtccaacccg gtaagacacg acttatcgcc actggcagca    8152
gccactggta acaggattag cagagcgagg tatgtaggcg gtgctacaga gttcttgaag    8212
tggtggccta actacggcta cactagaagg acagtatttg gtatctgcgc tctgctgaag    8272
ccagttacct tcggaaaaag agttggtagc tcttgatccg gcaaacaaac caccgctggt    8332
agcggtggtt tttttgtttg caagcagcag attacgcgca gaaaaaaagg atctcaagaa    8392
gatcctttga tcttttctac ggggtctgac gctcagtgga acgaaaactc acgttaaggg    8452
```

-continued

```
atttggtca tgagattatc aaaaaggatc ttcacctaga tccttttaaa ttaaaaatga   8512
agttttaaat caatctaaag tatatatgag taaacttggt ctgacagtta ccaatgctta   8572
atcagtgagg cacctatctc agcgatctgt ctatttcgtt catccatagt tgcctgactc   8632
cccgtcgtgt agataactac gatacgggag ggcttaccat ctggccccag tgctgcaatg   8692
ataccgcgag acccacgctc accggctcca gatttatcag caataaacca gccagccgga   8752
agggccgagc gcagaagtgg tcctgcaact ttatccgcct ccatccagtc tattaattgt   8812
tgccgggaag ctagagtaag tagttcgcca gttaatagtt tgcgcaacgt tgttgccatt   8872
gctacaggca tcgtggtgtc acgctcgtcg tttggtatgg cttcattcag ctccggttcc   8932
caacgatcaa ggcgagttac atgatccccc atgttgtgca aaaaagcggt tagctccttc   8992
ggtcctccga tcgttgtcag aagtaagttg gccgcagtgt tatcactcat ggttatggca   9052
gcactgcata attctcttac tgtcatgcca tccgtaagat gcttttctgt gactggtgag   9112
tactcaacca agtcattctg agaatagtgt atgcggcgac cgagttgctc ttgcccggcg   9172
tcaatacggg ataataccgc gccacatagc agaactttaa aagtgctcat cattggaaaa   9232
cgttcttcgg ggcgaaaact ctcaaggatc ttaccgctgt tgagatccag ttcgatgtaa   9292
cccactcgtg cacccaactg atcttcagca tcttttactt tcaccagcgt ttctgggtga   9352
gcaaaaacag gaaggcaaaa tgccgcaaaa aagggaataa gggcgacacg gaaatgttga   9412
atactcatac tcttcctttt tcaatattat tgaagcattt atcagggtta ttgtctcatg   9472
agcggataca tatttgaatg tatttagaaa aataaacaaa taggggttcc gcgcacattt   9532
ccccgaaaag tgccacctga cgtctaagaa accattatta tcatgacatt aacctataaa   9592
aataggcgta tcacgaggcc ctttcgtc                                      9620
```

<210> SEQ ID NO 2
<211> LENGTH: 1771
<212> TYPE: PRT
<213> ORGANISM: Hepatitis C virus
<220> FEATURE:
<223> OTHER INFORMATION: Description of Artificial Sequence: Hepatitis C pns345

<400> SEQUENCE: 2

```
Met Ala Ala Tyr Ala Ala Gln Gly Tyr Lys Val Leu Val Leu Asn Pro
 1               5                  10                  15

Ser Val Ala Ala Thr Leu Gly Phe Gly Ala Tyr Met Ser Lys Ala His
            20                  25                  30

Gly Ile Asp Pro Asn Ile Arg Thr Gly Val Arg Thr Ile Thr Thr Gly
        35                  40                  45

Ser Pro Ile Thr Tyr Ser Thr Tyr Gly Lys Phe Leu Ala Asp Gly Gly
    50                  55                  60

Cys Ser Gly Gly Ala Tyr Asp Ile Ile Ile Cys Asp Glu Cys His Ser
65                  70                  75                  80

Thr Asp Ala Thr Ser Ile Leu Gly Ile Gly Thr Val Leu Asp Gln Ala
                85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140
```

-continued

```
Ile Lys Gly Gly Arg His Leu Ile Phe Cys His Ser Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
```

-continued

```
                565                 570                 575
Ala Ala Gln Leu Ala Ala Pro Gly Ala Ala Thr Ala Phe Val Gly Ala
                580                 585                 590

Gly Leu Ala Gly Ala Ala Ile Gly Ser Val Gly Leu Gly Lys Val Leu
            595                 600                 605

Ile Asp Ile Leu Ala Gly Tyr Gly Ala Gly Val Ala Gly Ala Leu Val
            610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
            675                 680                 685

Val Ser Pro Thr His Tyr Val Pro Glu Ser Asp Ala Ala Arg Val
            690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
            755                 760                 765

Val Ser Cys Gln Arg Gly Tyr Lys Gly Val Trp Arg Gly Asp Gly Ile
            770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
            835                 840                 845

Glu Tyr Val Glu Ile Arg Gln Val Gly Asp Phe His Tyr Val Thr Gly
            850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
            915                 920                 925

Ala Val Leu Thr Ser Met Leu Thr Asp Pro Ser His Ile Thr Ala Glu
930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990
```

```
Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
    1010                1015                1020

Glu Arg Glu Ile Ser Val Pro Ala Glu Ile Leu Arg Lys Ser Arg Arg
1025                1030                1035                1040

Phe Ala Gln Ala Leu Pro Val Trp Ala Arg Pro Asp Tyr Asn Pro Pro
            1045                1050                1055

Leu Val Glu Thr Trp Lys Lys Pro Asp Tyr Glu Pro Pro Val Val His
        1060                1065                1070

Gly Cys Pro Leu Pro Pro Lys Ser Pro Val Pro Pro Pro Arg
        1075                1080                1085

Lys Lys Arg Thr Val Val Leu Thr Glu Ser Thr Leu Ser Thr Ala Leu
    1090                1095                1100

Ala Glu Leu Ala Thr Arg Ser Phe Gly Ser Ser Ser Thr Ser Gly Ile
1105                1110                1115                1120

Thr Gly Asp Asn Thr Thr Thr Ser Ser Glu Pro Ala Pro Ser Gly Cys
            1125                1130                1135

Pro Pro Asp Ser Asp Ala Glu Ser Tyr Ser Ser Met Pro Pro Leu Glu
        1140                1145                1150

Gly Glu Pro Gly Asp Pro Asp Leu Ser Asp Gly Ser Trp Ser Thr Val
        1155                1160                1165

Ser Ser Glu Ala Asn Ala Glu Asp Val Val Cys Cys Ser Met Ser Tyr
    1170                1175                1180

Ser Trp Thr Gly Ala Leu Val Thr Pro Cys Ala Ala Glu Glu Gln Lys
1185                1190                1195                1200

Leu Pro Ile Asn Ala Leu Ser Asn Ser Leu Leu Arg His His Asn Leu
            1205                1210                1215

Val Tyr Ser Thr Thr Ser Arg Ser Ala Cys Gln Arg Gln Lys Lys Val
        1220                1225                1230

Thr Phe Asp Arg Leu Gln Val Leu Asp Ser His Tyr Gln Asp Val Leu
        1235                1240                1245

Lys Glu Val Lys Ala Ala Ala Ser Lys Val Lys Ala Asn Leu Leu Ser
1250                1255                1260

Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
            1285                1290                1295

Thr His Ile Asn Ser Val Trp Lys Asp Leu Leu Glu Asp Asn Val Thr
        1300                1305                1310

Pro Ile Asp Thr Thr Ile Met Ala Lys Asn Glu Val Phe Cys Val Gln
    1315                1320                1325

Pro Glu Lys Gly Gly Arg Lys Pro Ala Arg Leu Ile Val Phe Pro Asp
1330                1335                1340

Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
            1365                1370                1375

Pro Gly Gln Arg Val Glu Phe Leu Val Gln Ala Trp Lys Ser Lys Lys
        1380                1385                1390

Thr Pro Met Gly Phe Ser Tyr Asp Thr Arg Cys Phe Asp Ser Thr Val
        1395                1400                1405
```

```
Thr Glu Ser Asp Ile Arg Thr Glu Glu Ala Ile Tyr Gln Cys Cys Asp
    1410                1415                1420

Leu Asp Pro Gln Ala Arg Val Ala Ile Lys Ser Leu Thr Glu Arg Leu
1425                1430                1435                1440

Tyr Val Gly Gly Pro Leu Thr Asn Ser Arg Gly Glu Asn Cys Gly Tyr
                1445                1450                1455

Arg Arg Cys Arg Ala Ser Gly Val Leu Thr Thr Ser Cys Gly Asn Thr
            1460                1465                1470

Leu Thr Cys Tyr Ile Lys Ala Arg Ala Ala Cys Arg Ala Ala Gly Leu
        1475                1480                1485

Gln Asp Cys Thr Met Leu Val Cys Gly Asp Asp Leu Val Val Ile Cys
    1490                1495                1500

Glu Ser Ala Gly Val Gln Glu Asp Ala Ala Ser Leu Arg Ala Phe Thr
1505                1510                1515                1520

Glu Ala Met Thr Arg Tyr Ser Ala Pro Pro Gly Asp Pro Pro Gln Pro
                1525                1530                1535

Glu Tyr Asp Leu Glu Leu Ile Thr Ser Cys Ser Ser Asn Val Ser Val
            1540                1545                1550

Ala His Asp Gly Ala Gly Lys Arg Val Tyr Tyr Leu Thr Arg Asp Pro
        1555                1560                1565

Thr Thr Pro Leu Ala Arg Ala Ala Trp Glu Thr Ala Arg His Thr Pro
    1570                1575                1580

Val Asn Ser Trp Leu Gly Asn Ile Ile Met Phe Ala Pro Thr Leu Trp
1585                1590                1595                1600

Ala Arg Met Ile Leu Met Thr His Phe Phe Ser Val Leu Ile Ala Arg
                1605                1610                1615

Asp Gln Leu Glu Gln Ala Leu Asp Cys Glu Ile Tyr Gly Ala Cys Tyr
            1620                1625                1630

Ser Ile Glu Pro Leu Asp Leu Pro Pro Ile Ile Gln Arg Leu His Gly
        1635                1640                1645

Leu Ser Ala Phe Ser Leu His Ser Tyr Ser Pro Gly Glu Ile Asn Arg
    1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
                1685                1690                1695

Arg Ala Ala Ile Cys Gly Lys Tyr Leu Phe Asn Trp Ala Val Arg Thr
            1700                1705                1710

Lys Leu Lys Leu Thr Pro Ile Ala Ala Ala Gly Gln Leu Asp Leu Ser
        1715                1720                1725

Gly Trp Phe Thr Ala Gly Tyr Ser Gly Gly Asp Ile Tyr His Ser Val
    1730                1735                1740

Ser His Ala Arg Pro Arg Trp Ile Trp Phe Cys Leu Leu Leu Leu Ala
1745                1750                1755                1760

Ala Gly Val Gly Ile Tyr Leu Leu Pro Asn Arg
                1765                1770

<210> SEQ ID NO 3
<211> LENGTH: 9620
<212> TYPE: DNA
<213> ORGANISM: Artificial Sequence
<220> FEATURE:
<221> NAME/KEY: CDS
<222> LOCATION: (1990)..(7302)
<223> OTHER INFORMATION: Description of Artificial Sequence:
      pDeltaNS3NS5
```

<400> SEQUENCE: 3

```
cgcgcgtttc ggtgatgacg gtgaaaacct ctgacacatg cagctcccgg agacggtcac      60
agcttgtctg taagcggatg ccgggagcag acaagcccgt cagggcgcgt cagcgggtgt     120
tggcgggtgt cggggctggc ttaactatgc ggcatcagag cagattgtac tgagagtgca     180
ccatatgaag cttttttgcaa aagcctaggc ctccaaaaaa gcctcctcac tacttctgga     240
atagctcaga ggccgaggcg gcctcggcct ctgcataaat aaaaaaaatt agtcagccat     300
ggggcggaga atgggcggaa ctgggcgggg agggaattat tggctattgg ccattgcata     360
cgttgtatct atatcataat atgtacattt atattggctc atgtccaata tgaccgccat     420
gttgacattg attattgact agttattaat agtaatcaat tacggggtca ttagttcata     480
gcccatatat ggagttccgc gttacataac ttacggtaaa tggcccgcct ggctgaccgc     540
ccaacgaccc ccgcccattg acgtcaataa tgacgtatgt tcccatagta acgccaatag     600
ggactttcca ttgacgtcaa tgggtggagt atttacggta aactgcccac ttggcagtac     660
atcaagtgta tcatatgcca agtccgcccc ctattgacgt caatgacggt aaatggcccg     720
cctggcatta tgcccagtac atgaccttac gggactttcc tacttggcag tacatctacg     780
tattagtcat cgctattacc atggtgatgc ggttttggca gtacaccaat gggcgtggat     840
agcggtttga ctcacgggga tttccaagtc tccaccccat tgacgtcaat gggagtttgt     900
tttggcacca aaatcaacgg gactttccaa aatgtcgtaa taaccccgcc ccgttgacgc     960
aaatgggcgg taggcgtgta cggtgggagg tctatataag cagagctcgt ttagtgaacc    1020
gtcagatcgc ctggagacgc catccacgct gttttgacct ccatagaaga caccgggacc    1080
gatccagcct ccgcggccgg gaacggtgca ttggaacgcg gattcccgt gccaagagtg     1140
acgtaagtac cgcctataga ctctataggc acaccccttt ggctcttatg catgctatac    1200
tgtttttggc ttggggccta tacaccccg ctccttatgc tataggtgat ggtatagctt    1260
agcctatagg tgtgggttat tgaccattat tgaccactcc ctattggtg acgatacttt     1320
ccattactaa tccataacat ggctctttgc cacaactatc tctattggct atatgccaat    1380
actctgtcct tcagagactg acacggactc tgtattttta caggatgggg tccatttatt    1440
atttacaaat tcatatatac aacaacgccg tccccccgtgc ccgcagtttt tattaaacat    1500
agcgtgggat ctccgacatc tcgggtacgt gttccggaca tgggctcttc tccggtagcg    1560
gcggagcttc cacatccgag ccctggtccc atccgtccag cggctcatgg tcgctcggca    1620
gctccttgct cctaacagtg gaggccagac ttaggcacag cacaatgccc accaccacca    1680
gtgtgccgca caaggccgtg gcggtagggt atgtgtctga aaatgagctc ggagattggg    1740
ctcgcacctg gacgcagatg gaagacttaa ggcagcggca gaagaagatg caggcagctg    1800
agttgttgta ttctgataag agtcagaggt aactcccgtt gcggtgctgt taacggtgga    1860
gggcagtgta gtctgagcag tactcgttgc tgccgcgcgc gccaccagac ataatagctg    1920
acagactaac agactgttcc tttccatggg tcttttctgc agtcaccgtc gtcgacctaa    1980
``` gaattcacc atg gct gca tat gca gct cag ggc tat aag gtg cta gta ctc   2031
         Met Ala Ala Tyr Ala Ala Gln Gly Tyr Lys Val Leu Val Leu
           1               5                  10 aac ccc tct gtt gct gca aca ctg ggc ttt ggt gct tac atg tcc aag      2079
Asn Pro Ser Val Ala Ala Thr Leu Gly Phe Gly Ala Tyr Met Ser Lys
 15                  20                  25                  30 gct cat ggg atc gat cct aac atc agg acc ggg gtg aga aca att acc      2127
Ala His Gly Ile Asp Pro Asn Ile Arg Thr Gly Val Arg Thr Ile Thr

```
                 35                  40                  45
act ggc agc ccc atc acg tac tcc acc tac ggc aag ttc ctt gcc gac         2175
Thr Gly Ser Pro Ile Thr Tyr Ser Thr Tyr Gly Lys Phe Leu Ala Asp
             50                  55                  60 ggc ggg tgc tcg ggg ggc gct tat gac ata ata att tgt gac gag tgc         2223
Gly Gly Cys Ser Gly Gly Ala Tyr Asp Ile Ile Ile Cys Asp Glu Cys
         65                  70                  75 cac tcc acg gat gcc aca tcc atc ttg ggc att ggc act gtc ctt gac         2271
His Ser Thr Asp Ala Thr Ser Ile Leu Gly Ile Gly Thr Val Leu Asp
     80                  85                  90 caa gca gag act gcg ggg gcg aga ctg gtt gtg ctc gcc acc gcc acc         2319
Gln Ala Glu Thr Ala Gly Ala Arg Leu Val Val Leu Ala Thr Ala Thr
 95                 100                 105                 110 cct ccg ggc tcc gtc act gtg ccc cat ccc aac atc gag gag gtt gct         2367
Pro Pro Gly Ser Val Thr Val Pro His Pro Asn Ile Glu Glu Val Ala
                115                 120                 125 ctg tcc acc acc gga gag atc cct ttt tac ggc aag gct atc ccc ctc         2415
Leu Ser Thr Thr Gly Glu Ile Pro Phe Tyr Gly Lys Ala Ile Pro Leu
            130                 135                 140 gaa gta atc aag ggg ggg aga cat ctc atc ttc tgt cat tca aag aag         2463
Glu Val Ile Lys Gly Gly Arg His Leu Ile Phe Cys His Ser Lys Lys
        145                 150                 155 aag tgc gac gaa ctc gcc gca aag ctg gtc gca ttg ggc atc aat gcc         2511
Lys Cys Asp Glu Leu Ala Ala Lys Leu Val Ala Leu Gly Ile Asn Ala
    160                 165                 170 gtg gcc tac tac cgc ggt ctt gac gtg tcc gtc atc ccg acc agc ggc         2559
Val Ala Tyr Tyr Arg Gly Leu Asp Val Ser Val Ile Pro Thr Ser Gly
175                 180                 185                 190 gat gtt gtc gtc gtg gca acc gat gcc ctc atg acc ggc tat acc ggc         2607
Asp Val Val Val Val Ala Thr Asp Ala Leu Met Thr Gly Tyr Thr Gly
                195                 200                 205 gac ttc gac tcg gtg ata gac tgc aat acg tgt gtc acc cag aca gtc         2655
Asp Phe Asp Ser Val Ile Asp Cys Asn Thr Cys Val Thr Gln Thr Val
            210                 215                 220 gat ttc agc ctt gac cct acc ttc acc att gag aca atc acg ctc ccc         2703
Asp Phe Ser Leu Asp Pro Thr Phe Thr Ile Glu Thr Ile Thr Leu Pro
        225                 230                 235 caa gat gct gtc tcc cgc act caa cgt cgg ggc agg act ggc agg ggg         2751
Gln Asp Ala Val Ser Arg Thr Gln Arg Arg Gly Arg Thr Gly Arg Gly
    240                 245                 250 aag cca ggc atc tac aga ttt gtg gca ccg ggg gag cgc ccc tcc ggc         2799
Lys Pro Gly Ile Tyr Arg Phe Val Ala Pro Gly Glu Arg Pro Ser Gly
255                 260                 265                 270 atg ttc gac tcg tcc gtc ctc tgt gag tgc tat gac gca ggc tgt gct         2847
Met Phe Asp Ser Ser Val Leu Cys Glu Cys Tyr Asp Ala Gly Cys Ala
                275                 280                 285 tgg tat gag ctc acg ccc gcc gag act aca gtt agg cta cga gcg tac         2895
Trp Tyr Glu Leu Thr Pro Ala Glu Thr Thr Val Arg Leu Arg Ala Tyr
            290                 295                 300 atg aac acc ccg ggg ctt ccc gtg tgc cag gac cat ctt gaa ttt tgg         2943
Met Asn Thr Pro Gly Leu Pro Val Cys Gln Asp His Leu Glu Phe Trp
        305                 310                 315 gag ggc gtc ttt aca ggc ctc act cat ata gat gcc cac ttt cta tcc         2991
Glu Gly Val Phe Thr Gly Leu Thr His Ile Asp Ala His Phe Leu Ser
    320                 325                 330 cag aca aag cag agt ggg gag aac ctt cct tac ctg gta gcg tac caa         3039
Gln Thr Lys Gln Ser Gly Glu Asn Leu Pro Tyr Leu Val Ala Tyr Gln
335                 340                 345                 350 gcc acc gtg tgc gct agg gct caa gcc cct ccc cca tcg tgg gac cag         3087
```

```
                Ala Thr Val Cys Ala Arg Ala Gln Ala Pro Pro Ser Trp Asp Gln
                                355                 360                 365 atg tgg aag tgt ttg att cgc ctc aag ccc acc ctc cat ggg cca aca          3135
Met Trp Lys Cys Leu Ile Arg Leu Lys Pro Thr Leu His Gly Pro Thr
            370                 375                 380 ccc ctg cta tac aga ctg ggc gct gtt cag aat gaa atc acc ctg acg          3183
Pro Leu Leu Tyr Arg Leu Gly Ala Val Gln Asn Glu Ile Thr Leu Thr
        385                 390                 395 cac cca gtc acc aaa tac atc atg aca tgc atg tcg gcc gac ctg gag          3231
His Pro Val Thr Lys Tyr Ile Met Thr Cys Met Ser Ala Asp Leu Glu
    400                 405                 410 gtc gtc acg agc acc tgg gtg ctc gtt ggc ggc gtc ctg gct gct ttg          3279
Val Val Thr Ser Thr Trp Val Leu Val Gly Gly Val Leu Ala Ala Leu
415                 420                 425                 430 gcc gcg tat tgc ctg tca aca ggc tgc gtg gtc ata gtg ggc agg gtc          3327
Ala Ala Tyr Cys Leu Ser Thr Gly Cys Val Val Ile Val Gly Arg Val
                435                 440                 445 gtc ttg tcc ggg aag ccg gca ata ata cct gac agg gaa gtc ctc tac          3375
Val Leu Ser Gly Lys Pro Ala Ile Ile Pro Asp Arg Glu Val Leu Tyr
            450                 455                 460 cga gag ttc gat gag atg gaa gag tgc tct cag cac tta ccg tac atc          3423
Arg Glu Phe Asp Glu Met Glu Glu Cys Ser Gln His Leu Pro Tyr Ile
        465                 470                 475 gag caa ggg atg atg ctc gcc gag cag ttc aag cag aag gcc ctc ggc          3471
Glu Gln Gly Met Met Leu Ala Glu Gln Phe Lys Gln Lys Ala Leu Gly
    480                 485                 490 ctc ctg cag acc gcg tcc cgt cag gca gag gtt atc gcc cct gct gtc          3519
Leu Leu Gln Thr Ala Ser Arg Gln Ala Glu Val Ile Ala Pro Ala Val
495                 500                 505                 510 cag acc aac tgg caa aaa ctc gag acc ttc tgg gcg aag cat atg tgg          3567
Gln Thr Asn Trp Gln Lys Leu Glu Thr Phe Trp Ala Lys His Met Trp
                515                 520                 525 aac ttc atc agt ggg ata caa tac ttg gcg ggc ttg tca acg ctg cct          3615
Asn Phe Ile Ser Gly Ile Gln Tyr Leu Ala Gly Leu Ser Thr Leu Pro
            530                 535                 540 ggt aac ccc gcc att gct tca ttg atg gct ttt aca gct gct gtc acc          3663
Gly Asn Pro Ala Ile Ala Ser Leu Met Ala Phe Thr Ala Ala Val Thr
        545                 550                 555 agc cca cta acc act agc caa acc ctc ctc ttc aac ata ttg ggg ggg          3711
Ser Pro Leu Thr Thr Ser Gln Thr Leu Leu Phe Asn Ile Leu Gly Gly
    560                 565                 570 tgg gtg gct gcc cag ctc gcc gcc ccc ggt gcc gct act gcc ttt gtg          3759
Trp Val Ala Ala Gln Leu Ala Ala Pro Gly Ala Ala Thr Ala Phe Val
575                 580                 585                 590 ggc gct ggc tta gct ggc gcc gcc atc ggc agt gtt gga ctg ggg aag          3807
Gly Ala Gly Leu Ala Gly Ala Ala Ile Gly Ser Val Gly Leu Gly Lys
                595                 600                 605 gtc ctc ata gac atc ctt gca ggg tat ggc gcg ggc gtg gcg gga gct          3855
Val Leu Ile Asp Ile Leu Ala Gly Tyr Gly Ala Gly Val Ala Gly Ala
            610                 615                 620 ctt gtg gca ttc aag atc atg agc ggt gag gtc ccc tcc acg gag gac          3903
Leu Val Ala Phe Lys Ile Met Ser Gly Glu Val Pro Ser Thr Glu Asp
        625                 630                 635 ctg gtc aat cta ctg ccc gcc atc ctc tcg ccc gga gcc ctc gta gtc          3951
Leu Val Asn Leu Leu Pro Ala Ile Leu Ser Pro Gly Ala Leu Val Val
    640                 645                 650 ggc gtg gtc tgt gca gca ata ctg cgc cgg cac gtt ggc ccg ggc gag          3999
Gly Val Val Cys Ala Ala Ile Leu Arg Arg His Val Gly Pro Gly Glu
655                 660                 665                 670
```

```
ggg gca gtg cag tgg atg aac cgg ctg ata gcc ttc gcc tcc cgg ggg      4047
Gly Ala Val Gln Trp Met Asn Arg Leu Ile Ala Phe Ala Ser Arg Gly
                675                 680                 685 aac cat gtt tcc ccc acg cac tac gtg ccg gag agc gat gca gct gcc      4095
Asn His Val Ser Pro Thr His Tyr Val Pro Glu Ser Asp Ala Ala Ala
            690                 695                 700 cgc gtc act gcc ata ctc agc agc ctc act gta acc cag ctc ctg agg      4143
Arg Val Thr Ala Ile Leu Ser Ser Leu Thr Val Thr Gln Leu Leu Arg
        705                 710                 715 cga ctg cac cag tgg ata agc tcg gag tgt acc act cca tgc tcc ggt      4191
Arg Leu His Gln Trp Ile Ser Ser Glu Cys Thr Thr Pro Cys Ser Gly
    720                 725                 730 tcc tgg cta agg gac atc tgg gac tgg ata tgc gag gtg ttg agc gac      4239
Ser Trp Leu Arg Asp Ile Trp Asp Trp Ile Cys Glu Val Leu Ser Asp
735                 740                 745                 750 ttt aag acc tgg cta aaa gct aag ctc atg cca cag ctg cct ggg atc      4287
Phe Lys Thr Trp Leu Lys Ala Lys Leu Met Pro Gln Leu Pro Gly Ile
                755                 760                 765 ccc ttt gtg tcc tgc cag cgc ggg tat aag ggg gtc tgg cga ggg gac      4335
Pro Phe Val Ser Cys Gln Arg Gly Tyr Lys Gly Val Trp Arg Gly Asp
            770                 775                 780 ggc atc atg cac act cgc tgc cac tgt gga gct gag atc act gga cat      4383
Gly Ile Met His Thr Arg Cys His Cys Gly Ala Glu Ile Thr Gly His
        785                 790                 795 gtc aaa aac ggg acg atg agg atc gtc ggt cct agg acc tgc agg aac      4431
Val Lys Asn Gly Thr Met Arg Ile Val Gly Pro Arg Thr Cys Arg Asn
    800                 805                 810 atg tgg agt ggg acc ttc ccc att aat gcc tac acc acg ggc ccc tgt      4479
Met Trp Ser Gly Thr Phe Pro Ile Asn Ala Tyr Thr Thr Gly Pro Cys
815                 820                 825                 830 acc ccc ctt cct gcg ccg aac tac acg ttc gcg cta tgg agg gtg tct      4527
Thr Pro Leu Pro Ala Pro Asn Tyr Thr Phe Ala Leu Trp Arg Val Ser
                835                 840                 845 gca gag gaa tac gtg gag ata agg cag gtg ggg gac ttc cac tac gtg      4575
Ala Glu Glu Tyr Val Glu Ile Arg Gln Val Gly Asp Phe His Tyr Val
            850                 855                 860 acg ggt atg act act gac aat ctt aaa tgc ccg tgc cag gtc cca tcg      4623
Thr Gly Met Thr Thr Asp Asn Leu Lys Cys Pro Cys Gln Val Pro Ser
        865                 870                 875 ccc gaa ttt ttc aca gaa ttg gac ggg gtg cgc cta cat agg ttt gcg      4671
Pro Glu Phe Phe Thr Glu Leu Asp Gly Val Arg Leu His Arg Phe Ala
    880                 885                 890 ccc ccc tgc aag ccc ttg ctg cgg gag gag gta tca ttc aga gta gga      4719
Pro Pro Cys Lys Pro Leu Leu Arg Glu Glu Val Ser Phe Arg Val Gly
895                 900                 905                 910 ctc cac gaa tac ccg gta ggg tcg caa tta cct tgc gag ccc gaa ccg      4767
Leu His Glu Tyr Pro Val Gly Ser Gln Leu Pro Cys Glu Pro Glu Pro
                915                 920                 925 gac gtg gcc gtg ttg acg tcc atg ctc act gat ccc tcc cat ata aca      4815
Asp Val Ala Val Leu Thr Ser Met Leu Thr Asp Pro Ser His Ile Thr
            930                 935                 940 gca gag gcg gcc ggg cga agg ttg gcg agg gga tca ccc ccc tct gtg      4863
Ala Glu Ala Ala Gly Arg Arg Leu Ala Arg Gly Ser Pro Pro Ser Val
        945                 950                 955 gcc agc tcc tcg gct agc cag cta tcc gct cca tct ctc aag gca act      4911
Ala Ser Ser Ser Ala Ser Gln Leu Ser Ala Pro Ser Leu Lys Ala Thr
    960                 965                 970 tgc acc gct aac cat gac tcc cct gat gct gag ctc ata gag gcc aac      4959
Cys Thr Ala Asn His Asp Ser Pro Asp Ala Glu Leu Ile Glu Ala Asn
975                 980                 985                 990
```

```
ctc cta tgg agg cag gag atg ggc ggc aac atc acc agg gtt gag tca      5007
Leu Leu Trp Arg Gln Glu Met Gly Gly Asn Ile Thr Arg Val Glu Ser
            995                 1000                1005 gaa aac aaa gtg gtg att ctg gac tcc ttc gat ccg ctt gtg gcg gag      5055
Glu Asn Lys Val Val Ile Leu Asp Ser Phe Asp Pro Leu Val Ala Glu
        1010                1015                1020 gag gac gag cgg gag atc tcc gta ccc gca gaa atc ctg cgg aag tct      5103
Glu Asp Glu Arg Glu Ile Ser Val Pro Ala Glu Ile Leu Arg Lys Ser
    1025                1030                1035 cgg aga ttc gcc cag gcc ctg ccc gtt tgg gcg cgg ccg gac tat aac      5151
Arg Arg Phe Ala Gln Ala Leu Pro Val Trp Ala Arg Pro Asp Tyr Asn
1040                1045                1050 ccc ccg cta gtg gag acg tgg aaa aag ccc gac tac gaa cca cct gtg      5199
Pro Pro Leu Val Glu Thr Trp Lys Lys Pro Asp Tyr Glu Pro Pro Val
1055                1060                1065                1070 gtc cat ggc tgc ccg ctt cca cct cca aag tcc cct cct gtg cct ccg      5247
Val His Gly Cys Pro Leu Pro Pro Pro Lys Ser Pro Pro Val Pro Pro
            1075                1080                1085 cct cgg aag aag cgg acg gtg gtc ctc act gaa tca acc cta tct act      5295
Pro Arg Lys Lys Arg Thr Val Val Leu Thr Glu Ser Thr Leu Ser Thr
        1090                1095                1100 gcc ttg gcc gag ctc gcc acc aga agc ttt ggc agc tcc tca act tcc      5343
Ala Leu Ala Glu Leu Ala Thr Arg Ser Phe Gly Ser Ser Ser Thr Ser
    1105                1110                1115 ggc att acg ggc gac aat acg aca aca tcc tct gag ccc gcc cct tct      5391
Gly Ile Thr Gly Asp Asn Thr Thr Thr Ser Ser Glu Pro Ala Pro Ser
1120                1125                1130 ggc tgc ccc ccc gac tcc gac gct gag tcc tat tcc tcc atg ccc ccc      5439
Gly Cys Pro Pro Asp Ser Asp Ala Glu Ser Tyr Ser Ser Met Pro Pro
1135                1140                1145                1150 ctg gag ggg gag cct ggg gat ccg gat ctt agc gac ggg tca tgg tca      5487
Leu Glu Gly Glu Pro Gly Asp Pro Asp Leu Ser Asp Gly Ser Trp Ser
            1155                1160                1165 acg gtc agt agt gag gcc aac gcg gag gat gtc gtg tgc tgc tca atg      5535
Thr Val Ser Ser Glu Ala Asn Ala Glu Asp Val Val Cys Cys Ser Met
        1170                1175                1180 tct tac tct tgg aca ggc gca ctc gtc acc ccg tgc gcc gcg gaa gaa      5583
Ser Tyr Ser Trp Thr Gly Ala Leu Val Thr Pro Cys Ala Ala Glu Glu
    1185                1190                1195 cag aaa ctg ccc atc aat gca cta agc aac tcg ttg cta cgt cac cac      5631
Gln Lys Leu Pro Ile Asn Ala Leu Ser Asn Ser Leu Leu Arg His His
1200                1205                1210 aat ttg gtg tat tcc acc acc tca cgc agt gct tgc caa agg cag aag      5679
Asn Leu Val Tyr Ser Thr Thr Ser Arg Ser Ala Cys Gln Arg Gln Lys
1215                1220                1225                1230 aaa gtc aca ttt gac aga ctg caa gtt ctg gac agc cat tac cag gac      5727
Lys Val Thr Phe Asp Arg Leu Gln Val Leu Asp Ser His Tyr Gln Asp
            1235                1240                1245 gta ctc aag gag gtt aaa gca gcg gcg tca aaa gtg aag gct aac ttg      5775
Val Leu Lys Glu Val Lys Ala Ala Ala Ser Lys Val Lys Ala Asn Leu
        1250                1255                1260 cta tcc gta gag gaa gct tgc agc ctg acg ccc cca cac tca gcc aaa      5823
Leu Ser Val Glu Glu Ala Cys Ser Leu Thr Pro Pro His Ser Ala Lys
    1265                1270                1275 tcc aag ttt ggt tat ggg gca aaa gac gtc cgt tgc cat gcc aga aag      5871
Ser Lys Phe Gly Tyr Gly Ala Lys Asp Val Arg Cys His Ala Arg Lys
1280                1285                1290 gcc gta acc cac atc aac tcc gtg tgg aaa gac ctt ctg gaa gac aat      5919
Ala Val Thr His Ile Asn Ser Val Trp Lys Asp Leu Leu Glu Asp Asn
```

-continued

| | |
|---|---|
| gta aca cca ata gac act acc atc atg gct aag aac gag gtt ttc tgc<br>Val Thr Pro Ile Asp Thr Thr Ile Met Ala Lys Asn Glu Val Phe Cys<br>              1315                   1320                    1325 | 5967 |
| gtt cag cct gag aag ggg ggt cgt aag cca gct cgt ctc atc gtg ttc<br>Val Gln Pro Glu Lys Gly Gly Arg Lys Pro Ala Arg Leu Ile Val Phe<br>            1330               1335               1340 | 6015 |
| ccc gat ctg ggc gtg cgc gtg tgc gaa aag atg gct ttg tac gac gtg<br>Pro Asp Leu Gly Val Arg Val Cys Glu Lys Met Ala Leu Tyr Asp Val<br>  1345                   1350                  1355 | 6063 |
| gtt aca aag ctc ccc ttg gcc gtg atg gga agc tcc tac gga ttc caa<br>Val Thr Lys Leu Pro Leu Ala Val Met Gly Ser Ser Tyr Gly Phe Gln<br>        1360               1365               1370 | 6111 |
| tac tca cca gga cag cgg gtt gaa ttc ctc gtg caa gcg tgg aag tcc<br>Tyr Ser Pro Gly Gln Arg Val Glu Phe Leu Val Gln Ala Trp Lys Ser<br>1375                1380               1385              1390 | 6159 |
| aag aaa acc cca atg ggg ttc tcg tat gat acc cgc tgc ttt gac tcc<br>Lys Lys Thr Pro Met Gly Phe Ser Tyr Asp Thr Arg Cys Phe Asp Ser<br>            1395               1400               1405 | 6207 |
| aca gtc act gag agc gac atc cgt acg gag gag gca atc tac caa tgt<br>Thr Val Thr Glu Ser Asp Ile Arg Thr Glu Glu Ala Ile Tyr Gln Cys<br>  1410                   1415                  1420 | 6255 |
| tgt gac ctc gac ccc caa gcc cgc gtg gcc atc aag tcc ctc acc gag<br>Cys Asp Leu Asp Pro Gln Ala Arg Val Ala Ile Lys Ser Leu Thr Glu<br>        1425               1430               1435 | 6303 |
| agg ctt tat gtt ggg ggc cct ctt acc aat tca agg ggg gag aac tgc<br>Arg Leu Tyr Val Gly Gly Pro Leu Thr Asn Ser Arg Gly Glu Asn Cys<br>1440                1445               1450 | 6351 |
| ggc tat cgc agg tgc cgc gcg agc ggc gta ctg aca act agc tgt ggt<br>Gly Tyr Arg Arg Cys Arg Ala Ser Gly Val Leu Thr Thr Ser Cys Gly<br>1455                1460               1465              1470 | 6399 |
| aac acc ctc act tgc tac atc aag gcc cgg gca gcc tgt cga gcc gca<br>Asn Thr Leu Thr Cys Tyr Ile Lys Ala Arg Ala Ala Cys Arg Ala Ala<br>            1475               1480               1485 | 6447 |
| ggg ctc cag gac tgc acc atg ctc gtg tgt ggc gac gac tta gtc gtt<br>Gly Leu Gln Asp Cys Thr Met Leu Val Cys Gly Asp Asp Leu Val Val<br>  1490                   1495                  1500 | 6495 |
| atc tgt gaa agc gcg ggg gtc cag gag gac gcg gcg agc ctg aga gcc<br>Ile Cys Glu Ser Ala Gly Val Gln Glu Asp Ala Ala Ser Leu Arg Ala<br>        1505               1510               1515 | 6543 |
| ttc acg gag gct atg acc agg tac tcc gcc ccc cct ggg gac ccc cca<br>Phe Thr Glu Ala Met Thr Arg Tyr Ser Ala Pro Pro Gly Asp Pro Pro<br>    1520                 1525               1530 | 6591 |
| caa cca gaa tac gac ttg gag ctc ata aca tca tgc tcc tcc aac gtg<br>Gln Pro Glu Tyr Asp Leu Glu Leu Ile Thr Ser Cys Ser Ser Asn Val<br>1535                1540               1545              1550 | 6639 |
| tca gtc gcc cac gac ggc gct gga aag agg gtc tac tac ctc acc cgt<br>Ser Val Ala His Asp Gly Ala Gly Lys Arg Val Tyr Tyr Leu Thr Arg<br>            1555               1560               1565 | 6687 |
| gac cct aca acc ccc ctc gcg aga gct gcg tgg gag aca gca aga cac<br>Asp Pro Thr Thr Pro Leu Ala Arg Ala Ala Trp Glu Thr Ala Arg His<br>  1570                   1575                  1580 | 6735 |
| act cca gtc aat tcc tgg cta ggc aac ata atc atg ttt gcc ccc aca<br>Thr Pro Val Asn Ser Trp Leu Gly Asn Ile Ile Met Phe Ala Pro Thr<br>        1585               1590               1595 | 6783 |
| ctg tgg gcg agg atg ata ctg atg acc cat ttc ttt agc gtc ctt ata<br>Leu Trp Ala Arg Met Ile Leu Met Thr His Phe Phe Ser Val Leu Ile<br>            1600               1605               1610 | 6831 |
| gcc agg gac cag ctt gaa cag gcc ctc gat tgc gag atc tac ggg gcc | 6879 |

```
                                                              -continued

Ala Arg Asp Gln Leu Glu Gln Ala Leu Asp Cys Glu Ile Tyr Gly Ala
1615                1620                1625                1630 tgc tac tcc ata gaa cca ctg gat cta cct cca atc att caa aga ctc       6927
Cys Tyr Ser Ile Glu Pro Leu Asp Leu Pro Pro Ile Ile Gln Arg Leu
        1635                1640                1645 cat ggc ctc agc gca ttt tca ctc cac agt tac tct cca ggt gaa atc       6975
His Gly Leu Ser Ala Phe Ser Leu His Ser Tyr Ser Pro Gly Glu Ile
1650                1655                1660 aat agg gtg gcc gca tgc ctc aga aaa ctt ggg gta ccg ccc ttg cga       7023
Asn Arg Val Ala Ala Cys Leu Arg Lys Leu Gly Val Pro Pro Leu Arg
        1665                1670                1675 gct tgg aga cac cgg gcc cgg agc gtc cgc gct agg ctt ctg gcc aga       7071
Ala Trp Arg His Arg Ala Arg Ser Val Arg Ala Arg Leu Leu Ala Arg
    1680                1685                1690 gga ggc agg gct gcc ata tgt ggc aag tac ctc ttc aac tgg gca gta       7119
Gly Gly Arg Ala Ala Ile Cys Gly Lys Tyr Leu Phe Asn Trp Ala Val
1695                1700                1705                1710 aga aca aag ctc aaa ctc act cca ata gcg gcc gct ggc cag ctg gac       7167
Arg Thr Lys Leu Lys Leu Thr Pro Ile Ala Ala Ala Gly Gln Leu Asp
        1715                1720                1725 ttg tcc ggc tgg ttc acg gct ggc tac agc ggg gga gac att tat cac       7215
Leu Ser Gly Trp Phe Thr Ala Gly Tyr Ser Gly Gly Asp Ile Tyr His
            1730                1735                1740 agc gtg tct cat gcc cgg ccc cgc tgg atc tgg ttt tgc cta ctc ctg       7263
Ser Val Ser His Ala Arg Pro Arg Trp Ile Trp Phe Cys Leu Leu Leu
        1745                1750                1755 ctt gct gca ggg gta ggc atc tac ctc ctc ccc aac cga tgaaggttgg       7312
Leu Ala Ala Gly Val Gly Ile Tyr Leu Leu Pro Asn Arg
1760                1765                1770 ggtaaacact ccggcctaaa aaaaaaaaaa aatctagaaa ggcgcgccaa gatatcaagg     7372
atccactacg cgttagagct cgctgatcag cctcgactgt gccttctagt tgccagccat    7432
ctgttgtttg cccctccccc gtgccttcct gacccctgga aggtgccact cccactgtcc    7492
tttcctaata aaatgaggaa attgcatcgc attgtctgag taggtgtcat tctattctgg    7552
ggggtggggt ggggcaggac agcaagggg aggattggga agacaatagc aggcatgctg    7612
gggagctctt ccgcttcctc gctcactgac tcgctgcgct cggtcgttcg ctgcggcga     7672
gcggtatcag ctcactcaaa ggcggtaata cggttatcca cagaatcagg ggataacgca    7732
ggaaagaaca tgtgagcaaa aggccagcaa aaggccagga accgtaaaaa ggccgcgttg    7792
ctggcgtttt tccataggct ccgccccccct gacgagcatc acaaaaatcg acgctcaagt   7852
cagaggtggc gaaacccgac aggactataa agataccagg cgtttccccc tggaagctcc    7912
ctcgtgcgct ctcctgttcc gaccctgccg cttaccggat acctgtccgc ctttctccct    7972
tcgggaagcg tggcgctttc tcaatgctca cgctgtaggt atctcagttc ggtgtaggtc    8032
gttcgctcca agctgggctg tgtgcacgaa ccccccgttc agcccgaccg ctgcgcctta    8092
tccggtaact atcgtcttga gtccaacccg gtaagacacg acttatcgcc actggcagca    8152
gccactggta acaggattag cagagcgagg tatgtaggcg gtgctacaga gttcttgaag    8212
tggtggccta actacggcta cactagaagg acagtatttg gtatctgcgc tctgctgaag    8272
ccagttacct tcggaaaaag agttggtagc tcttgatccg gcaaacaaac caccgctggt    8332
agcggtggtt ttttttgtttg caagcagcag attacgcgca gaaaaaaagg atctcaagaa    8392
gatcctttga tcttttctac ggggtctgac gctcagtgga acgaaaactc acgttaaggg    8452
attttggtca tgagattatc aaaaaggatc ttcacctaga tccttttaaa ttaaaaatga    8512
```

-continued

```
agttttaaat caatctaaag tatatatgag taaacttggt ctgacagtta ccaatgctta   8572
atcagtgagg cacctatctc agcgatctgt ctatttcgtt catccatagt tgcctgactc   8632
cccgtcgtgt agataactac gatacgggag ggcttaccat ctggccccag tgctgcaatg   8692
ataccgcgag acccacgctc accggctcca gatttatcag caataaacca gccagccgga   8752
agggccgagc gcagaagtgg tcctgcaact ttatccgcct ccatccagtc tattaattgt   8812
tgccgggaag ctagagtaag tagttcgcca gttaatagtt tgcgcaacgt tgttgccatt   8872
gctacaggca tcgtggtgtc acgctcgtcg tttggtatgg cttcattcag ctccggttcc   8932
caacgatcaa ggcgagttac atgatccccc atgttgtgca aaaaagcggt tagctccttc   8992
ggtcctccga tcgttgtcag aagtaagttg gccgcagtgt tatcactcat ggttatggca   9052
gcactgcata attctcttac tgtcatgcca tccgtaagat gcttttctgt gactggtgag   9112
tactcaacca agtcattctg agaatagtgt atgcggcgac cgagttgctc ttgcccggcg   9172
tcaatacggg ataataccgc gccacatagc agaactttaa aagtgctcat cattggaaaa   9232
cgttcttcgg ggcgaaaact ctcaaggatc ttaccgctgt tgagatccag ttcgatgtaa   9292
cccactcgtg cacccaactg atcttcagca tcttttactt tcaccagcgt ttctgggtga   9352
gcaaaaacag gaaggcaaaa tgccgcaaaa aagggaataa gggcgacacg gaaatgttga   9412
atactcatac tcttcctttt tcaatattat tgaagcattt atcagggtta ttgtctcatg   9472
agcggataca tatttgaatg tatttagaaa aataaacaaa taggggttcc gcgcacattt   9532
ccccgaaaag tgccacctga cgtctaagaa accattatta tcatgacatt aacctataaa   9592
aataggcgta tcacgaggcc ctttcgtc                                      9620
```

<210> SEQ ID NO 4
<211> LENGTH: 1771
<212> TYPE: PRT
<213> ORGANISM: Artificial Sequence
<220> FEATURE:
<223> OTHER INFORMATION: Description of Artificial Sequence:
      pDeltaNS3NS5

<400> SEQUENCE: 4

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

```
Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
    275                 280                 285

Glu Leu Thr Pro Ala Glu Thr Thr Val Arg Leu Arg Ala Tyr Met Asn
290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
            325                 330                 335

Lys Gln Ser Gly Glu Asn Leu Pro Tyr Leu Val Ala Tyr Gln Ala Thr
        340                 345                 350

Val Cys Ala Arg Ala Gln Ala Pro Pro Pro Ser Trp Asp Gln Met Trp
    355                 360                 365

Lys Cys Leu Ile Arg Leu Lys Pro Thr Leu His Gly Pro Thr Pro Leu
370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
            405                 410                 415

Thr Ser Thr Trp Val Leu Val Gly Gly Val Leu Ala Ala Leu Ala Ala
        420                 425                 430

Tyr Cys Leu Ser Thr Gly Cys Val Val Ile Val Gly Arg Val Val Leu
    435                 440                 445

Ser Gly Lys Pro Ala Ile Ile Pro Asp Arg Glu Val Leu Tyr Arg Glu
450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
            485                 490                 495

Gln Thr Ala Ser Arg Gln Ala Glu Val Ile Ala Pro Ala Val Gln Thr
        500                 505                 510

Asn Trp Gln Lys Leu Glu Thr Phe Trp Ala Lys His Met Trp Asn Phe
    515                 520                 525

Ile Ser Gly Ile Gln Tyr Leu Ala Gly Leu Ser Thr Leu Pro Gly Asn
530                 535                 540

Pro Ala Ile Ala Ser Leu Met Ala Phe Thr Ala Val Thr Ser Pro
545                 550                 555                 560

Leu Thr Thr Ser Gln Thr Leu Leu Phe Asn Ile Leu Gly Gly Trp Val
            565                 570                 575

Ala Ala Gln Leu Ala Ala Pro Gly Ala Ala Thr Ala Phe Val Gly Ala
```

-continued

```
                580                 585                 590
Gly Leu Ala Gly Ala Ala Ile Gly Ser Val Gly Leu Gly Lys Val Leu
            595                 600                 605

Ile Asp Ile Leu Ala Gly Tyr Gly Ala Gly Val Ala Gly Ala Leu Val
        610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
        690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
        770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
        850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
        930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005
```

-continued

Lys Val Val Ile Leu Asp Ser Phe Asp Pro Leu Val Ala Glu Glu Asp
    1010                1015                1020

Glu Arg Glu Ile Ser Val Pro Ala Glu Ile Leu Arg Lys Ser Arg Arg
1025                1030                1035                1040

Phe Ala Gln Ala Leu Pro Val Trp Ala Arg Pro Asp Tyr Asn Pro Pro
                1045                1050                1055

Leu Val Glu Thr Trp Lys Lys Pro Asp Tyr Glu Pro Pro Val Val His
            1060                1065                1070

Gly Cys Pro Leu Pro Pro Lys Ser Pro Val Pro Pro Arg
        1075                1080                1085

Lys Lys Arg Thr Val Val Leu Thr Glu Ser Thr Leu Ser Thr Ala Leu
    1090                1095                1100

Ala Glu Leu Ala Thr Arg Ser Phe Gly Ser Ser Ser Thr Ser Gly Ile
1105                1110                1115                1120

Thr Gly Asp Asn Thr Thr Thr Ser Ser Glu Pro Ala Pro Ser Gly Cys
                1125                1130                1135

Pro Pro Asp Ser Asp Ala Glu Ser Tyr Ser Ser Met Pro Pro Leu Glu
            1140                1145                1150

Gly Glu Pro Gly Asp Pro Asp Leu Ser Asp Gly Ser Trp Ser Thr Val
            1155                1160                1165

Ser Ser Glu Ala Asn Ala Glu Asp Val Val Cys Cys Ser Met Ser Tyr
    1170                1175                1180

Ser Trp Thr Gly Ala Leu Val Thr Pro Cys Ala Ala Glu Glu Gln Lys
1185                1190                1195                1200

Leu Pro Ile Asn Ala Leu Ser Asn Ser Leu Leu Arg His His Asn Leu
        1205                1210                1215

Val Tyr Ser Thr Thr Ser Arg Ser Ala Cys Gln Arg Gln Lys Lys Val
            1220                1225                1230

Thr Phe Asp Arg Leu Gln Val Leu Asp Ser His Tyr Gln Asp Val Leu
        1235                1240                1245

Lys Glu Val Lys Ala Ala Ala Ser Lys Val Lys Ala Asn Leu Leu Ser
    1250                1255                1260

Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
            1285                1290                1295

Thr His Ile Asn Ser Val Trp Lys Asp Leu Leu Glu Asp Asn Val Thr
        1300                1305                1310

Pro Ile Asp Thr Thr Ile Met Ala Lys Asn Glu Val Phe Cys Val Gln
        1315                1320                1325

Pro Glu Lys Gly Gly Arg Lys Pro Ala Arg Leu Ile Val Phe Pro Asp
    1330                1335                1340

Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
                1365                1370                1375

Pro Gly Gln Arg Val Glu Phe Leu Val Gln Ala Trp Lys Ser Lys Lys
            1380                1385                1390

Thr Pro Met Gly Phe Ser Tyr Asp Thr Arg Cys Phe Asp Ser Thr Val
            1395                1400                1405

Thr Glu Ser Asp Ile Arg Thr Glu Glu Ala Ile Tyr Gln Cys Cys Asp
    1410                1415                1420

Leu Asp Pro Gln Ala Arg Val Ala Ile Lys Ser Leu Thr Glu Arg Leu
1425                1430                1435                1440

Tyr Val Gly Gly Pro Leu Thr Asn Ser Arg Gly Glu Asn Cys Gly Tyr
            1445                1450                1455

Arg Arg Cys Arg Ala Ser Gly Val Leu Thr Thr Ser Cys Gly Asn Thr
            1460                1465                1470

Leu Thr Cys Tyr Ile Lys Ala Arg Ala Ala Cys Arg Ala Ala Gly Leu
        1475                1480                1485

Gln Asp Cys Thr Met Leu Val Cys Gly Asp Asp Leu Val Val Ile Cys
        1490                1495                1500

Glu Ser Ala Gly Val Gln Glu Asp Ala Ala Ser Leu Arg Ala Phe Thr
1505                1510                1515                1520

Glu Ala Met Thr Arg Tyr Ser Ala Pro Pro Gly Asp Pro Pro Gln Pro
            1525                1530                1535

Glu Tyr Asp Leu Glu Leu Ile Thr Ser Cys Ser Ser Asn Val Ser Val
            1540                1545                1550

Ala His Asp Gly Ala Gly Lys Arg Val Tyr Tyr Leu Thr Arg Asp Pro
        1555                1560                1565

Thr Thr Pro Leu Ala Arg Ala Ala Trp Glu Thr Ala Arg His Thr Pro
1570                1575                1580

Val Asn Ser Trp Leu Gly Asn Ile Ile Met Phe Ala Pro Thr Leu Trp
1585                1590                1595                1600

Ala Arg Met Ile Leu Met Thr His Phe Phe Ser Val Leu Ile Ala Arg
            1605                1610                1615

Asp Gln Leu Glu Gln Ala Leu Asp Cys Glu Ile Tyr Gly Ala Cys Tyr
            1620                1625                1630

Ser Ile Glu Pro Leu Asp Leu Pro Pro Ile Ile Gln Arg Leu His Gly
        1635                1640                1645

Leu Ser Ala Phe Ser Leu His Ser Tyr Ser Pro Gly Glu Ile Asn Arg
        1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
            1685                1690                1695

Arg Ala Ala Ile Cys Gly Lys Tyr Leu Phe Asn Trp Ala Val Arg Thr
            1700                1705                1710

Lys Leu Lys Leu Thr Pro Ile Ala Ala Ala Gly Gln Leu Asp Leu Ser
        1715                1720                1725

Gly Trp Phe Thr Ala Gly Tyr Ser Gly Gly Asp Ile Tyr His Ser Val
        1730                1735                1740

Ser His Ala Arg Pro Arg Trp Ile Trp Phe Cys Leu Leu Leu Leu Ala
1745                1750                1755                1760

Ala Gly Val Gly Ile Tyr Leu Leu Pro Asn Arg
            1765                1770

<210> SEQ ID NO 5
<211> LENGTH: 4282
<212> TYPE: DNA
<213> ORGANISM: Artificial Sequence
<220> FEATURE:
<223> OTHER INFORMATION: Description of Artificial Sequence: pCMVII

<400> SEQUENCE: 5
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120

```
ttggcgggtg tcggggctgg cttaactatg cggcatcaga gcagattgta ctgagagtgc    180
accatatgaa gcttttttgca aaagcctagg cctccaaaaa agcctcctca ctacttctgg   240
aatagctcag aggccgaggc ggcctcggcc tctgcataaa taaaaaaaat tagtcagcca   300
tggggcggag aatgggcgga actgggcggg gagggaatta ttggctattg gccattgcat   360
acgttgtatc tatatcataa tatgtacatt tatattggct catgtccaat atgaccgcca   420
tgttgacatt gattattgac tagttattaa tagtaatcaa ttacggggtc attagttcat   480
agcccatata tggagttccg cgttacataa cttacggtaa atggcccgcc tggctgaccg   540
cccaacgacc cccgcccatt gacgtcaata atgacgtatg ttcccatagt aacgccaata   600
gggactttcc attgacgtca atgggtggag tatttacggt aaactgccca cttggcagta   660
catcaagtgt atcatatgcc aagtccgccc cctattgacg tcaatgacgg taaatggccc   720
gcctggcatt atgcccagta catgacctta cgggactttc ctacttggca gtacatctac   780
gtattagtca tcgctattac catggtgatg cggttttggc agtacaccaa tgggcgtgga   840
tagcggtttg actcacgggg atttccaagt ctccacccca ttgacgtcaa tgggagtttg   900
ttttggcacc aaaatcaacg ggactttcca aatgtcgta ataaccccgc ccgttgacg    960
caaatgggcg gtaggcgtgt acggtgggag gtctatataa gcagagctcg tttagtgaac  1020
cgtcagatcg cctggagacg ccatccacgc tgttttgacc tccatagaag acaccggac   1080
cgatccagcc tccgcggccg ggaacggtgc attggaacgc ggattccccg tgccaagagt  1140
gacgtaagta ccgcctatag actctatagg cacaccccct tggctcttat gcatgctata  1200
ctgttttgg cttggggcct atacaccccc gcttccttat gctataggtg atggtatagc   1260
ttagcctata ggtgtgggtt attgaccatt attgaccact cccctattgg tgacgatact  1320
ttccattact aatccataac atggctcttt gccacaacta tctctattgg ctatatgcca  1380
atactctgtc cttcagagac tgacacggac tctgtatttt tacaggatgg ggtcccattt  1440
attatttaca aattcacata tacaacaacg ccgtccccg tgcccgcagt ttttattaaa    1500
catagcgtgg gatctccacg cgaatctcgg gtacgtgttc cggacatggg ctcttctccg  1560
gtagcggcgg agcttccaca tccgagccct ggtcccatgc ctccagcggc tcatggtcgc   1620
tcggcagctc cttgctccta acagtggagg ccagacttag gcacagcaca atgcccacca  1680
ccaccagtgt gccgcacaag gccgtggcgg tagggtatgt gtctgaaaat gagctcggag  1740
attgggctcg caccgctgac gcagatggaa gacttaaggc agcggcagaa gaagatgcag  1800
gcagctgagt tgttgtattc tgataagagt cagaggtaac tcccgttgcg gtgctgttaa  1860
cggtggaggg cagtgtagtc tgagcagtac tcgttgctgc cgcgcgcgcc accagacata  1920
atagctgaca gactaacaga ctgttccttt ccatgggtct tttctgcagt caccgtcgtc  1980
gacctaagaa ttcagactcg agcaagtcta gaaaggcgcg ccaagatatc aaggatccac  2040
tacgcgttag agctcgctga tcagcctcga ctgtgccttc tagttgccag ccatctgttg  2100
tttgccctc cccgtgcct tccttgaccc tggaaggtgc cactcccact gtcctttcct   2160
aataaaatga ggaaattgca tcgcattgtc tgagtaggtg tcattctatt ctgggggtg   2220
gggtggggca ggacagcaag ggggaggatt gggaagacaa tagcaggcat gctgggagc   2280
tcttccgctt cctcgctcac tgactcgctg cgctcggtcg ttcggctgcg gcgagcggta  2340
tcagctcact caaaggcggt aatacggtta tccacagaat cagggataa cgcaggaaag  2400
aacatgtgag caaaaggcca gcaaaaggcc aggaaccgta aaaaggccgc gttgctggcg  2460
```

-continued

```
tttttccata ggctccgccc ccctgacgag catcacaaaa atcgacgctc aagtcagagg    2520
tggcgaaacc cgacaggact ataaagatac caggcgtttc ccctggaag ctccctcgtg     2580 cgctctcctg ttccgaccct gccgcttacc ggatacctgt ccgcctttct cccttcggga    2640
agcgtggcgc tttctcaatg ctcacgctgt aggtatctca gttcggtgta ggtcgttcgc    2700
tccaagctgg gctgtgtgca cgaaccccc gttcagcccg accgctgcgc cttatccggt      2760
aactatcgtc ttgagtccaa cccggtaaga cacgacttat cgccactggc agcagccact    2820
ggtaacagga ttagcagagc gaggtatgta ggcggtgcta cagagttctt gaagtggtgg    2880
cctaactacg gctacactag aaggacagta tttggtatct gcgctctgct gaagccagtt    2940
accttcggaa aaagagttgg tagctcttga tccggcaaac aaaccaccgc tggtagcggt    3000 ggttttttg tttgcaagca gcagattacg cgcagaaaaa aaggatctca agaagatcct     3060
ttgatctttt ctacggggtc tgacgctcag tggaacgaaa actcacgtta agggattttg    3120
gtcatgagat tatcaaaaag gatcttcacc tagatccttt taaattaaaa atgaagtttt    3180
aaatcaatct aaagtatata tgagtaaact tggtctgaca gttaccaatg cttaatcagt    3240
gaggcaccta tctcagcgat ctgtctattt cgttcatcca tagttgcctg actccccgtc    3300
gtgtagataa ctacgatacg ggagggctta ccatctggcc ccagtgctgc aatgataccg    3360
cgagacccac gctcaccggc tccagattta tcagcaataa accagccagc cggaagggcc    3420
gagcgcagaa gtggtcctgc aactttatcc gcctccatcc agtctattaa ttgttgccgg    3480
gaagctagag taagtagttc gccagttaat agtttgcgca acgttgttgc cattgctaca    3540
ggcatcgtgg tgtcacgctc gtcgtttggt atggcttcat tcagctccgg ttcccaacga    3600
tcaaggcgag ttacatgatc ccccatgttg tgcaaaaaag cggttagctc cttcggtcct    3660
ccgatcgttg tcagaagtaa gttggccgca gtgttatcac tcatggttat ggcagcactg    3720
cataattctc ttactgtcat gccatccgta agatgctttt ctgtgactgg tgagtactca    3780
accaagtcat tctgagaata gtgtatgcgg cgaccgagtt gctcttgccc ggcgtcaata    3840
cgggataata ccgcgccaca tagcagaact ttaaaagtgc tcatcattgg aaaacgttct    3900
tcggggcgaa aactctcaag gatcttaccg ctgttgagat ccagttcgat gtaacccact    3960
cgtgcaccca actgatcttc agcatctttt actttcacca gcgtttctgg gtgagcaaaa    4020
acaggaaggc aaaatgccgc aaaaaaggga ataagggcga cacggaaatg ttgaatactc    4080
atactcttcc ttttcaata ttattgaagc atttatcagg gttattgtct catgagcgga     4140
tacatatttg aatgtattta gaaaaataaa caaatagggg ttccgcgcac atttccccga    4200
aaagtgccac ctgacgtcta agaaaccatt attatcatga cattaaccta taaaaatagg    4260
cgtatcacga ggccctttcg tc                                              4282
```

<210> SEQ ID NO 6
<211> LENGTH: 6299
<212> TYPE: DNA
<213> ORGANISM: Artificial Sequence
<220> FEATURE:
<223> OTHER INFORMATION: Description of Artificial Sequence: pNS34a
<220> FEATURE:
<221> NAME/KEY: CDS
<222> LOCATION: (1990)..(4047)

<400> SEQUENCE: 6

```
cgcgcgtttc ggtgatgacg gtgaaaacct ctgacacatg cagctcccgg agacggtcac      60
agcttgtctg taagcggatg ccgggagcag acaagcccgt cagggcgcgt cagcgggtgt     120
```

| | |
|---|---|
| tggcgggtgt cggggctggc ttaactatgc ggcatcagag cagattgtac tgagagtgca | 180 |
| ccatatgaag cttttttgcaa agcctaggc ctccaaaaaa gcctcctcac tacttctgga | 240 |
| atagctcaga ggccgaggcg gcctcggcct ctgcataaat aaaaaaaatt agtcagccat | 300 |
| ggggcggaga atgggcggaa ctgggcgggg agggaattat tggctattgg ccattgcata | 360 |
| cgttgtatct atatcataat atgtacattt atattggctc atgtccaata tgaccgccat | 420 |
| gttgacattg attattgact agttattaat agtaatcaat tacggggtca ttagttcata | 480 |
| gcccatatat ggagttccgc gttacataac ttacggtaaa tggcccgcct ggctgaccgc | 540 |
| ccaacgaccc ccgcccattg acgtcaataa tgacgtatgt tcccatagta acgccaatag | 600 |
| ggactttcca ttgacgtcaa tgggtggagt atttacggta aactgcccac ttggcagtac | 660 |
| atcaagtgta tcatatgcca agtccgcccc ctattgacgt caatgacggt aaatggcccg | 720 |
| cctggcatta tgcccagtac atgaccttac gggactttcc tacttggcag tacatctacg | 780 |
| tattagtcat cgctattacc atggtgatgc ggttttggca gtacaccaat gggcgtggat | 840 |
| agcggtttga ctcacgggga tttccaagtc tccaccccat tgacgtcaat gggagtttgt | 900 |
| tttggcacca aaatcaacgg gactttccaa aatgtcgtaa taacccccgcc cgttgacgc | 960 |
| aaatgggcgg taggcgtgta cggtgggagg tctatataag cagagctcgt ttagtgaacc | 1020 |
| gtcagatcgc ctggagacgc catccacgct gttttgacct ccatagaaga caccgggacc | 1080 |
| gatccagcct ccgcggccgg gaacggtgca ttggaacgcg gattcccgt gccaagagtg | 1140 |
| acgtaagtac cgcctataga ctctataggc accccctttt ggctcttatg catgctatac | 1200 |
| tgtttttggc ttgggggccta tacacccccg ctccttatgc tataggtgat ggtatagctt | 1260 |
| agcctatagg tgtgggttat tgaccattat tgaccactcc cctattggtg acgatacttt | 1320 |
| ccattactaa tccataacat ggctctttgc cacaactatc tctattggct atatgccaat | 1380 |
| actctgtcct tcagagactg acacggactc tgtatttta caggatgggg tccatttatt | 1440 |
| atttacaaat tcacatatac aacaacgccg tccccgtgc ccgcagtttt tattaaacat | 1500 |
| agcgtgggat ctccgacatc tcgggtacgt gttccggaca tggctcttc tccggtagcg | 1560 |
| gcggagcttc cacatccgag ccctggtccc atccgtccag cggctcatgg tcgctcggca | 1620 |
| gctccttgct cctaacagtg gaggccgac ttaggcacag cacaatgccc accaccacca | 1680 |
| gtgtgccgca caaggccgtg gcggtagggt atgtgtctga aaatgagctc ggagattggg | 1740 |
| ctcgcacctg gacgcagatg gaagacttaa ggcagcggca gaagaagatg caggcagctg | 1800 |
| agttgttgta ttctgataag agtcagaggt aactcccgtt gcggtgctgt taacggtgga | 1860 |
| gggcagtgta gtctgagcag tactcgttgc tgccgcgcgc gccaccagac ataatagctg | 1920 |
| acagactaac agactgttcc tttccatggg tcttttctgc agtcaccgtc gtcgacctaa | 1980 |

| | | | | | | | | | | | | | | | | |
|---|---|---|---|---|---|---|---|---|---|---|---|---|---|---|---|---|
| gaattcacc | atg | gcg | ccc | atc | acg | gcg | tac | gcc | cag | cag | aca | agg | ggc | ctc | | 2031 |
| | Met | Ala | Pro | Ile | Thr | Ala | Tyr | Ala | Gln | Gln | Thr | Arg | Gly | Leu | | |
| | 1 | | | | 5 | | | | | 10 | | | | | | |
| cta | ggg | tgc | ata | atc | acc | agc | cta | act | ggc | cgg | gac | aaa | aac | caa | gtg | 2079 |
| Leu | Gly | Cys | Ile | Ile | Thr | Ser | Leu | Thr | Gly | Arg | Asp | Lys | Asn | Gln | Val | |
| 15 | | | | | 20 | | | | | 25 | | | | | 30 | |
| gag | ggt | gag | gtc | cag | att | gtg | tca | act | gct | gcc | caa | acc | ttc | ctg | gca | 2127 |
| Glu | Gly | Glu | Val | Gln | Ile | Val | Ser | Thr | Ala | Ala | Gln | Thr | Phe | Leu | Ala | |
| | | | | 35 | | | | | 40 | | | | | 45 | | |
| acg | tgc | atc | aat | ggg | gtg | tgc | tgg | act | gtc | tac | cac | ggg | gcc | gga | acg | 2175 |
| Thr | Cys | Ile | Asn | Gly | Val | Cys | Trp | Thr | Val | Tyr | His | Gly | Ala | Gly | Thr | |
| | | | 50 | | | | | 55 | | | | | 60 | | | |
| agg | acc | atc | gcg | tca | ccc | aag | ggt | cct | gtc | atc | cag | atg | tat | acc | aat | 2223 |

```
                Arg Thr Ile Ala Ser Pro Lys Gly Pro Val Ile Gln Met Tyr Thr Asn
                            65                  70                  75 gta gac caa gac ctt gtg ggc tgg ccc gct tcg caa ggt acc cgc tca        2271
Val Asp Gln Asp Leu Val Gly Trp Pro Ala Ser Gln Gly Thr Arg Ser
         80                  85                  90 ttg aca ccc tgc act tgc ggc tcg gac ctt tac ctg gtc acg agg            2319
Leu Thr Pro Cys Thr Cys Gly Ser Ser Asp Leu Tyr Leu Val Thr Arg
 95                 100                 105                 110 cac gcc gat gtc att ccc gtg cgc cgg cgg ggt gat agc agg ggc agc        2367
His Ala Asp Val Ile Pro Val Arg Arg Arg Gly Asp Ser Arg Gly Ser
                    115                 120                 125 ctg ctg tcg ccc cgg ccc att tcc tac ttg aaa ggc tcc tcg ggg ggt        2415
Leu Leu Ser Pro Arg Pro Ile Ser Tyr Leu Lys Gly Ser Ser Gly Gly
                130                 135                 140 ccg ctg ttg tgc ccc gcg ggg cac gcc gtg ggc ata ttt agg gcc gcg        2463
Pro Leu Leu Cys Pro Ala Gly His Ala Val Gly Ile Phe Arg Ala Ala
            145                 150                 155 gtg tgc acc cgt gga gtg gct aag gcg gtg gac ttt atc cct gtg gag        2511
Val Cys Thr Arg Gly Val Ala Lys Ala Val Asp Phe Ile Pro Val Glu
        160                 165                 170 aac cta gag aca acc atg agg tcc ccg gtg ttc acg gat aac tcc tct        2559
Asn Leu Glu Thr Thr Met Arg Ser Pro Val Phe Thr Asp Asn Ser Ser
175                 180                 185                 190 cca cca gta gtg ccc cag agc ttc cag gtg gct cac ctc cat gct ccc        2607
Pro Pro Val Val Pro Gln Ser Phe Gln Val Ala His Leu His Ala Pro
                    195                 200                 205 aca ggc agc ggc aaa agc acc aag gtc ccg gct gca tat gca gct cag        2655
Thr Gly Ser Gly Lys Ser Thr Lys Val Pro Ala Ala Tyr Ala Ala Gln
                210                 215                 220 ggc tat aag gtg cta gta ctc aac ccc tct gtt gct gca aca ctg ggc        2703
Gly Tyr Lys Val Leu Val Leu Asn Pro Ser Val Ala Ala Thr Leu Gly
            225                 230                 235 ttt ggt gct tac atg tcc aag gct cat ggg atc gat cct aac atc agg        2751
Phe Gly Ala Tyr Met Ser Lys Ala His Gly Ile Asp Pro Asn Ile Arg
        240                 245                 250 acc ggg gtg aga aca att acc act ggc agc ccc atc acg tac tcc acc        2799
Thr Gly Val Arg Thr Ile Thr Thr Gly Ser Pro Ile Thr Tyr Ser Thr
255                 260                 265                 270 tac ggc aag ttc ctt gcc gac ggc ggg tgc tcg ggg ggc gct tat gac        2847
Tyr Gly Lys Phe Leu Ala Asp Gly Gly Cys Ser Gly Gly Ala Tyr Asp
                    275                 280                 285 ata ata att tgt gac gag tgc cac tcc acg gat gcc aca tcc atc ttg        2895
Ile Ile Ile Cys Asp Glu Cys His Ser Thr Asp Ala Thr Ser Ile Leu
                290                 295                 300 ggc att ggc act gtc ctt gac caa gca gag act gcg ggg gcg aga ctg        2943
Gly Ile Gly Thr Val Leu Asp Gln Ala Glu Thr Ala Gly Ala Arg Leu
            305                 310                 315 gtt gtg ctc gcc acc gcc acc cct ccg ggc tcc gtc act gtg ccc cat        2991
Val Val Leu Ala Thr Ala Thr Pro Pro Gly Ser Val Thr Val Pro His
        320                 325                 330 ccc aac atc gag gag gtt gct ctg tcc acc acc gga gag atc cct ttt        3039
Pro Asn Ile Glu Glu Val Ala Leu Ser Thr Thr Gly Glu Ile Pro Phe
335                 340                 345                 350 tac ggc aag gct atc ccc ctc gaa gta atc aag ggg ggg aga cat ctc        3087
Tyr Gly Lys Ala Ile Pro Leu Glu Val Ile Lys Gly Gly Arg His Leu
                    355                 360                 365 atc ttc tgt cat tca aag aag aag tgc gac gaa ctc gcc gca aag ctg        3135
Ile Phe Cys His Ser Lys Lys Lys Cys Asp Glu Leu Ala Ala Lys Leu
                370                 375                 380
```

```
gtc gca ttg ggc atc aat gcc gtg gcc tac tac cgc ggt ctt gac gtg      3183
Val Ala Leu Gly Ile Asn Ala Val Ala Tyr Tyr Arg Gly Leu Asp Val
            385                 390                 395 tcc gtc atc ccg acc agc ggc gat gtt gtc gtc gtg gca acc gat gcc      3231
Ser Val Ile Pro Thr Ser Gly Asp Val Val Val Val Ala Thr Asp Ala
400                 405                 410 ctc atg acc ggc tat acc ggc gac ttc gac tcg gtg ata gac tgc aat      3279
Leu Met Thr Gly Tyr Thr Gly Asp Phe Asp Ser Val Ile Asp Cys Asn
415                 420                 425                 430 acg tgt gtc acc cag aca gtc gat ttc agc ctt gac cct acc ttc acc      3327
Thr Cys Val Thr Gln Thr Val Asp Phe Ser Leu Asp Pro Thr Phe Thr
                435                 440                 445 att gag aca atc acg ctc ccc caa gat gct gtc tcc cgc act caa cgt      3375
Ile Glu Thr Ile Thr Leu Pro Gln Asp Ala Val Ser Arg Thr Gln Arg
            450                 455                 460 cgg ggc agg act ggc agg ggg aag cca ggc atc tac aga ttt gtg gca      3423
Arg Gly Arg Thr Gly Arg Gly Lys Pro Gly Ile Tyr Arg Phe Val Ala
            465                 470                 475 ccg ggg gag cgc ccc tcc ggc atg ttc gac tcg tcc gtc ctc tgt gag      3471
Pro Gly Glu Arg Pro Ser Gly Met Phe Asp Ser Ser Val Leu Cys Glu
480                 485                 490 tgc tat gac gca ggc tgt gct tgg tat gag ctc acg ccc gcc gag act      3519
Cys Tyr Asp Ala Gly Cys Ala Trp Tyr Glu Leu Thr Pro Ala Glu Thr
495                 500                 505                 510 aca gtt agg cta cga gcg tac atg aac acc ccg ggc ctt ccc gtg tgc      3567
Thr Val Arg Leu Arg Ala Tyr Met Asn Thr Pro Gly Leu Pro Val Cys
                515                 520                 525 cag gac cat ctt gaa ttt tgg gag ggc gtc ttt aca ggc ctc act cat      3615
Gln Asp His Leu Glu Phe Trp Glu Gly Val Phe Thr Gly Leu Thr His
            530                 535                 540 ata gat gcc cac ttt cta tcc cag aca aag cag agt ggg gag aac ctt      3663
Ile Asp Ala His Phe Leu Ser Gln Thr Lys Gln Ser Gly Glu Asn Leu
            545                 550                 555 cct tac ctg gta gcg tac caa gcc acc gtg tgc gct agg gct caa gcc      3711
Pro Tyr Leu Val Ala Tyr Gln Ala Thr Val Cys Ala Arg Ala Gln Ala
            560                 565                 570 cct ccc cca tcg tgg gac cag atg tgg aag tgt ttg att cgc ctc aag      3759
Pro Pro Pro Ser Trp Asp Gln Met Trp Lys Cys Leu Ile Arg Leu Lys
575                 580                 585                 590 ccc acc ctc cat ggg cca aca ccc ctg cta tac aga ctg ggc gct gtt      3807
Pro Thr Leu His Gly Pro Thr Pro Leu Leu Tyr Arg Leu Gly Ala Val
                595                 600                 605 cag aat gaa atc acc ctg acg cac cca gtc acc aaa tac atc atg aca      3855
Gln Asn Glu Ile Thr Leu Thr His Pro Val Thr Lys Tyr Ile Met Thr
            610                 615                 620 tgc atg tcg gcc gac ctg gag gtc gtc acg agc acc tgg gtg ctc gtt      3903
Cys Met Ser Ala Asp Leu Glu Val Val Thr Ser Thr Trp Val Leu Val
            625                 630                 635 ggc ggc gtc ctg gct gct ttg gcc gcg tat tgc ctg tca aca ggc tgc      3951
Gly Gly Val Leu Ala Ala Leu Ala Ala Tyr Cys Leu Ser Thr Gly Cys
            640                 645                 650 gtg gtc ata gtg ggc agg gtc gtc ttg tcc ggg aag ccg gca atc ata      3999
Val Val Ile Val Gly Arg Val Val Leu Ser Gly Lys Pro Ala Ile Ile
655                 660                 665                 670 cct gac agg gaa gtc ctc tac cga gag ttc gat gag atg gaa gag tgc      4047
Pro Asp Arg Glu Val Leu Tyr Arg Glu Phe Asp Glu Met Glu Glu Cys
                675                 680                 685 taggatccac tacgcgttag agctcgctga tcagcctcga ctgtgccttc tagttgccag      4107
ccatctgttg tttgccctc cccgtgcct tccttgaccc tggaaggtgc cactcccact         4167
```

```
gtcctttcct aataaaatga ggaaattgca tcgcattgtc tgagtaggtg tcattctatt    4227 ctgggggtg gggtggggca ggacagcaag ggggaggatt gggaagacaa tagcaggcat     4287
gctggggagc tcttccgctt cctcgctcac tgactcgctg cgctcggtcg ttcggctgcg    4347
gcgagcggta tcagctcact caaaggcggt aatacggtta tccacagaat caggggataa    4407
cgcaggaaag aacatgtgag caaaaggcca gcaaaaggcc aggaaccgta aaaaggccgc    4467
gttgctggcg ttttttccata ggctccgccc ccctgacgag catcacaaaa atcgacgctc    4527
aagtcagagg tggcgaaacc cgacaggact ataaagatac caggcgtttc ccctggaag     4587 ctccctcgtg cgctctcctg ttccgaccct gccgcttacc ggatacctgt ccgcctttct    4647
cccttcggga agcgtggcgc tttctcaatg ctcacgctgt aggtatctca gttcggtgta    4707
ggtcgttcgc tccaagctgg gctgtgtgca cgaaccccc gttcagcccg accgctgcgc    4767
cttatccggt aactatcgtc ttgagtccaa cccggtaaga cacgacttat cgccactggc    4827
agcagccact ggtaacagga ttagcagagc gaggtatgta ggcggtgcta cagagttctt    4887
gaagtggtgg cctaactacg gctacactag aaggacagta tttggtatct gcgctctgct    4947
gaagccagtt accttcggaa aaagagttgg tagctcttga tccggcaaac aaaccaccgc    5007
tggtagcggt ggtttttttg tttgcaagca gcagattacg cgcagaaaaa aaggatctca    5067
agaagatcct ttgatctttt ctacggggtc tgacgctcag tggaacgaaa actcacgtta    5127
agggattttg gtcatgagat tatcaaaaag gatcttcacc tagatccttt taaattaaaa    5187
atgaagtttt aaatcaatct aaagtatata tgagtaaact tggtctgaca gttaccaatg    5247
cttaatcagt gaggcaccta tctcagcgat ctgtctattt cgttcatcca tagttgcctg    5307
actccccgtc gtgtagataa ctacgatacg ggagggctta ccatctggcc ccagtgctgc    5367
aatgataccg cgagacccac gctcaccggc tccagattta tcagcaataa accagccagc    5427
cggaagggcc gagcgcagaa gtggtcctgc aactttatcc gcctccatcc agtctattaa    5487
ttgttgccgg gaagctagag taagtagttc gccagttaat agtttgcgca acgttgttgc    5547
cattgctaca gcatcgtgg tgtcacgctc gtcgtttggt atggcttcat tcagctccgg    5607
ttcccaacga tcaaggcgag ttacatgatc ccccatgttg tgcaaaaaag cggttagctc    5667
cttcggtcct ccgatcgttg tcagaagtaa gttggccgca gtgttatcac tcatggttat    5727
ggcagcactg cataattctc ttactgtcat gccatccgta agatgctttt ctgtgactgg    5787
tgagtactca accaagtcat tctgagaata gtgtatgcgg cgaccgagtt gctcttgccc    5847
ggcgtcaata cgggataata ccgcgccaca tagcagaact ttaaaagtgc tcatcattgg    5907
aaaacgttct tcggggcgaa aactctcaag gatcttaccg ctgttgagat ccagttcgat    5967
gtaacccact cgtgcaccca actgatcttc agcatctttt actttcacca gcgtttctgg    6027
gtgagcaaaa acaggaaggc aaaatgccgc aaaaaaggga ataagggcga cacggaaatg    6087
ttgaatactc atactcttcc ttttttcaata ttattgaagc atttatcagg gttattgtct    6147
catgagcgga tacatatttg aatgtattta gaaaaataaa caataggggg ttccgcgcac    6207
atttccccga aaagtgccac ctgacgtcta agaaaccatt attatcatga cattaaccta    6267
taaaaatagg cgtatcacga ggccctttcg tc                                 6299
```

<210> SEQ ID NO 7
<211> LENGTH: 686
<212> TYPE: PRT
<213> ORGANISM: Artificial Sequence
<220> FEATURE:

<223> OTHER INFORMATION: Description of Artificial Sequence: pNS34a

<400> SEQUENCE: 7

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
        50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Ser Gln Gly Thr Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Val Ile Lys Gly Gly Arg His Leu Ile Phe
        355                 360                 365

Cys His Ser Lys Lys Cys Asp Glu Leu Ala Ala Lys Leu Val Ala
    370                 375                 380

Leu Gly Ile Asn Ala Val Ala Tyr Tyr Arg Gly Leu Asp Val Ser Val
385                 390                 395                 400
```

Ile Pro Thr Ser Gly Asp Val Val Val Ala Thr Asp Ala Leu Met
            405                 410                 415

Thr Gly Tyr Thr Gly Asp Phe Asp Ser Val Ile Asp Cys Asn Thr Cys
        420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
        450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Ile Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Val Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 8
<211> LENGTH: 19912
<212> TYPE: DNA
<213> ORGANISM: Artificial Sequence
<220> FEATURE:
<223> OTHER INFORMATION: Description of Artificial Sequence:
      pd.deltaNS3NS5
<220> FEATURE:
<221> NAME/KEY: CDS
<222> LOCATION: (12745)..(18057)

<400> SEQUENCE: 8
atcgatccta cccccttgcgc taaagaagta tatgtgccta ctaacgcttg tctttgtctc    60
tgtcactaaa cactggatta ttactcccag atacttattt tggactaatt taaatgattt   120
cggatcaacg ttcttaatat cgctgaatct tccacaattg atgaaagtag ctaggaagag   180
gaattggtat aaagttttt g tttttgtaaa tctcgaagta tactcaaacg aatttagtat   240
tttctcagtg atctcccaga tgctttcacc ctcacttaga agtgctttaa gcatttttt   300 actgtggcta tttcccttat ctgcttcttc cgatgattcg aactgtaatt gcaaactact   360

```
tacaatatca gtgatatcag attgatgttt tgtccatag taaggaataa ttgtaaattc      420
ccaagcagga atcaatttct ttaatgaggc ttccagaatt gttgctttt gcgtcttgta      480 tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaatgcac cggccgcgca ttatttgtac tgcgaaaata attggtactg       900
cggtatcttc atttcatatt ttaaaaatgc acctttgctg cttttcctta attttagac     960 ggcccgcagg ttcgtttgc ggtactatct tgtgataaaa agttgttttg acatgtgatc      1020
tgcacagatt ttataatgta ataagcaaga atacattatc aaacgaacaa tactggtaaa    1080
agaaaaccaa aatggacgac attgaaacag ccaagaatct gacggtaaaa gcacgtacag    1140
cttatagcgt ctgggatgta tgtcggctgt ttattgaaat gattgctcct gatgtagata    1200
ttgatataga gagtaaacgt aagtctgatg agctactctt tccaggatat gtcataaggc    1260
ccatggaatc tctcacaacc ggtaggccgt atggtcttga ttctagcgca gaagattcca    1320
gcgtatcttc tgactccagt gctgaggtaa ttttgcctgc tgcgaagatg gttaaggaaa    1380
ggtttgattc gattggaaat ggtatgctct cttcacaaga agcaagtcag gctgccatag    1440
atttgatgct acagaataac aagctgttag acaatagaaa gcaactatac aaatctattg    1500
ctataataat aggaagattg cccgagaaag acaagaagag agctaccgaa atgctcatga    1560
gaaaaatgga ttgtacacag ttattagtcc caccagctcc aacggaagaa gatgttatga    1620
agctcgtaag cgtcgttacc caattgctta ctttagttcc accagatcgt caagctgctt    1680
taataggtga tttattcatc ccggaatctc taaaggatat attcaatagt ttcaatgaac    1740
tggcggcaga gaatcgttta cagcaaaaaa agagtgagtt ggaaggaagg actgaagtga    1800
accatgctaa tacaaatgaa gaagttccct ccaggcgaac aagaagtaga gacacaaatg    1860
caagaggagc atataaatta caaaacacca tcactgaggg ccctaaagcg gttcccacga    1920
aaaaaaggag agtagcaacg agggtaaggg gcagaaaatc acgtaatact tctagggtat    1980
gatccaatat caaggaaat gatagcattg aaggatgaga ctaatccaat tgaggagtgg      2040
cagcatatag aacagctaaa gggtagtgct gaaggaagca tacgataccc cgcatggaat    2100
gggataatat cacaggaggt actagactac ctttcatcct acataaatag acgcatataa    2160
gtacgcattt aagcataaac acgcactatg ccgttcttct catgtatata tatatacagg    2220
caacacgcag atataggtgc gacgtgaaca gtgagctgta tgtgcgcagc tcgcgttgca    2280
ttttcggaag cgctcgtttt cggaaacgct ttgaagttcc tattccgaag ttcctattct    2340
ctagaaagta taggaacttc agagcgcttt tgaaaaccaa aagcgctctg aagacgcact    2400
ttcaaaaaac caaaaacgca ccggactgta acagctact aaaatattgc gaataccgct     2460
tccacaaaca ttgctcaaaa gtatctcttt gctatatatc tctgtgctat atccctatat    2520
aacctaccca tccaccttc gctccttgaa cttgcatcta aactcgacct ctacatcaac     2580
aggcttccaa tgctcttcaa attttactgt caagtagacc catacggctg taatatgctg    2640
ctcttcataa tgtaagctta tctttatcga atcgtgtgaa aaactactac cgcgataaac    2700
```

```
ctttacggtt ccctgagatt gaattagttc ctttagtata tgatacaaga cacttttgaa    2760
ctttgtacga cgaattttga ggttcgccat cctctggcta tttccaatta tcctgtcggc    2820
gaaacatgct gcttaaaact ccaagcggta ggagaccgat aaaggttaat aggacagccg    2880
tattatctcc gcctcagttt gatcttccgc ttcagactgc cattttttcac ataatgaatc   2940 tatttcaccc cacaatcctt catccgcctc cgcatcttgt tccgttaaac tattgacttc    3000
atgttgtaca ttgtttagtt cacgagaagg gtcctcttca ggcggtagct cctgatctcc   3060
tatatgacct ttatcctgtt ctcttttccac aaacttagaa atgtattcat gaattatgga   3120
gcacctaata acattcttca aggcggagaa gtttgggcca gatgcccaat atgcttgaca    3180
tgaaaacgtg agaatgaatt tagtattatt gtgatattct gaggcaattt tattataatc    3240
tcgaagataa gagaagaatg cagtgacctt tgtattgaca aatggagatt ccatgtatct    3300
aaaaaatacg cctttaggcc ttctgatacc ctttcccctg cggtttagcg tgccttttac    3360
attaatatct aaaccctctc cgatggtggc ctttaactga ctaataaatg caaccgatat    3420
aaactgtgat aattctgggt gatttatgat tcgatcgaca attgtattgt acactagtgc    3480
aggatcaggc caatccagtt ctttttcaat taccggtgtg tcgtctgtat tcagtacatg    3540
tccaacaaat gcaaatgcta acgttttgta tttcttataa ttgtcaggaa ctggaaaagt    3600 ccccctttgtc gtctcgatta cacacctact ttcatcgtac accataggtt ggaagtgctg   3660
cataatacat tgcttaatac aagcaagcag tctctcgcca ttcatatttc agttattttc    3720
cattacagct gatgtcattg tatatcagcg ctgtaaaaat ctatctgtta cagaaggttt    3780
tcgcggtttt tataaacaaa actttcgtta cgaaatcgag caatcaccccc agctgcgtat   3840 ttggaaattc gggaaaaagt agagcaacgc gagttgcatt ttttacacca taatgcatga    3900
ttaacttcga gaagggatta aggctaattt cactagtatg tttcaaaaac ctcaatctgt    3960
ccattgaatg cctataaaaa cagctataga ttgcatagaa gagttagcta ctcaatgctt    4020
tttgtcaaag cttactgatg atgatgtgtc tactttcagg cgggtctgta gtaaggagaa    4080
tgacattata aagctggcac ttagaattcc acggactata gactatacta gtatactccg    4140
tctactgtac gatacacttc cgctcaggtc cttgtccttt aacgaggcct taccactctt    4200
ttgttactct attgatccag ctcagcaaag gcagtgtgat ctaagattct atcttcgcga    4260
tgtagtaaaa ctagctagac cgagaaagag actagaaatg caaaaggcac ttctacaatg    4320
gctgccatca ttattatccg atgtgacgct gcattttttt tttttttttt tttttttttt    4380
tttttttttt tttttttttt tttttggta caaatatcat aaaaaaagag aatcttttta    4440
agcaaggatt ttcttaactt cttcggcgac agcatcaccg acttcggtgg tactgttgga    4500
accacctaaa tcaccagttc tgatacctgc atccaaaacc ttttttaactg catcttcaat   4560 ggctttacct tcttcaggca agttcaatga caatttcaac atcattgcag cagacaagat    4620
agtggcgata gggttgacct tattctttgg caaatctgga gcggaaccat ggcatggttc    4680
gtacaaacca aatgcggtgt tcttgtctgg caaagaggcc aaggacgcag atggcaacaa    4740
acccaaggag cctgggataa cggaggcttc atcggagatg atatcaccaa acatgttgct    4800
ggtgattata ataccatttta ggtgggttgg gttcttaact aggatcatgg cggcagaatc   4860
aatcaattga tgttgaactt tcaatgtagg gaattcgttc ttgatggttt cctccacagt    4920
ttttctccat aatcttgaag aggccaaaac attagcttta tccaaggacc aaataggcaa    4980
tggtggctca tgttgtaggg ccatgaaagc ggccattctt gtgattcttt gcacttctgg    5040
aacggtgtat tgttcactat cccaagcgac accatcacca tcgtcttcct ttctcttacc    5100
```

```
aaagtaaata cctcccacta attctctaac aacaacgaag tcagtacctt tagcaaattg   5160
tggcttgatt ggagataagt ctaaaagaga gtcggatgca aagttacatg gtcttaagtt   5220
ggcgtacaat tgaagttctt tacggatttt tagtaaacct tgttcaggtc taacactacc   5280
ggtaccccat ttaggaccac ccacagcacc taacaaaacg gcatcagcct tcttggaggc   5340
ttccagcgcc tcatctggaa gtggaacacc tgtagcatcg atagcagcac caccaattaa   5400
atgattttcg aaatcgaact tgacattgga acgaacatca gaaatagctt taagaacctt   5460
aatggcttcg gctgtgattt cttgaccaac gtggtcacct ggcaaaacga cgatcttctt   5520
aggggcagac attacaatgg tatatccttg aaatatatat aaaaaaaaaa aaaaaaaaa   5580 aaaaaaaaaa atgcagcttc tcaatgatat tcgaatacgc tttgaggaga tacagcctaa   5640
tatccgacaa actgttttac agatttacga tcgtacttgt tacccatcat tgaattttga   5700
acatccgaac ctgggagttt tccctgaaac agatagtata tttgaacctg tataataata   5760
tatagtctag cgctttacgg aagacaatgt atgtatttcg gttcctggag aaactattgc   5820
atctattgca taggtaatct tgcacgtcgc atccccggtt cattttctgc gtttccatct   5880
tgcacttcaa tagcatatct ttgttaacga agcatctgtg cttcattttg tagaacaaaa   5940
atgcaacgcg agagcgctaa tttttcaaac aaagaatctg agctgcattt ttacagaaca   6000
gaaatgcaac gcgaaagcgc tattttacca acgaagaatc tgtgcttcat ttttgtaaaa   6060
caaaaatgca acgcgagagc gctaattttt caaacaaaga atctgagctg cattttttaca   6120 gaacagaaat gcaacgcgag agcgctattt taccaacaaa gaatctatac ttcttttttg   6180
ttctacaaaa atgcatcccg agagcgctat ttttctaaca aagcatctta gattacttt   6240 tttctccttt gtgcgctcta taatgcagtc tcttgataac tttttgcact gtaggtccgt   6300
taaggttaga agaaggctac tttggtgtct attttctctt ccataaaaaa agcctgactc   6360
cacttcccgc gtttactgat tactagcgaa gctgcgggtg catttttcca agataaaggc   6420
atccccgatt atattctata ccgatgtgga ttgcgcatac tttgtgaaca gaaagtgata   6480
gcgttgatga ttcttcattg gtcagaaaat tatgaacggt ttcttctatt ttgtctctat   6540
atactacgta taggaaatgt ttacattttc gtattgtttt cgattcactc tatgaatagt   6600
tcttactaca attttttgt ctaaagagta atactagaga taaacataaa aaatgtagag   6660
gtcgagttta gatgcaagtt caaggagcga aaggtggatg ggtaggttat atagggatat   6720
agcacagaga tatatagcaa agagatactt ttgagcaatg tttgtggaag cggtattcgc   6780
aatattttag tagctcgtta cagtccggtg cgttttggt ttttgaaag tgcgtcttca   6840 gagcgctttt ggttttcaaa agcgctctga agttcctata cttctagag aataggaact   6900 tcggaatagg aacttcaaag cgtttccgaa aacgagcgct tccgaaaatg caacgcgagc   6960
tgcgcacata cagctcactg ttcacgtcgc acctatatct gcgtgttgcc tgtatatata   7020
tatacatgag aagaacggca tagtgcgtgt ttatgcttaa atgcgtactt atatgcgtct   7080
atttatgtag gatgaaaggt agtctagtac ctcctgtgat attatcccat tccatgcggg   7140
gtatcgtatg cttccttcag cactacccctt tagctgttct atatgctgcc actcctcaat   7200
tggattagtc tcatccttca atgctatcat ttcctttgat attggatcat atgcatagta   7260
ccgagaaact agtgcgaagt agtgatcagg tattgctgtt atctgatgag tatacgttgt   7320
cctggccacg gcagaagcac gcttatcgct ccaatttccc acaacattag tcaactccgt   7380
taggcccttc attgaaagaa atgaggtcat caaatgtctt ccaatgtgag attttgggcc   7440
```

```
atttttata    gcaaagattg   aataaggcgc   attttctc     aaagctttat   tgtacgatct   7500
gactaagtta   tcttttaata   attggtattc   ctgtttattg   cttgaagaat   tgccggtcct   7560
atttactcgt   tttaggactg   gttcagaatt   cctcaaaaat   tcatccaaat   atacaagtgg   7620
atcgatgata   agctgtcaaa   catgagaatt   cttgaagacg   aaagggcctc   gtgatacgcc   7680
tatttttata   ggttaatgtc   atgataataa   tggtttctta   gacgtcaggt   ggcacttttc   7740
ggggaaatgt   gcgcggaacc   cctatttgtt   tattttcta    aatacattca   aatatgtatc   7800
cgctcatgag   acaataaccc   tgataaatgc   ttcaataata   ttgaaaaagg   aagagtatga   7860
gtattcaaca   tttccgtgtc   gcccttattc   ccttttttgc   ggcattttgc   cttcctgttt   7920
ttgctcaccc   agaaacgctg   gtgaaagtaa   aagatgctga   agatcagttg   ggtgcacgag   7980
tgggttacat   cgaactggat   ctcaacagcg   gtaagatcct   tgagagtttt   cgccccgaag   8040
aacgttttcc   aatgatgagc   acttttaaag   ttctgctatg   tggcgcggta   ttatcccgtg   8100
ttgacgccgg   gcaagagcaa   ctcggtcgcc   gcatacacta   ttctcagaat   gacttggttg   8160
agtactcacc   agtcacagaa   aagcatctta   cggatggcat   gacagtaaga   gaattatgca   8220
gtgctgccat   aaccatgagt   gataacactg   cggccaactt   acttctgaca   acgatcggag   8280
gaccgaagga   gctaaccgct   tttttgcaca   acatggggga   tcatgtaact   cgccttgatc   8340
gttgggaacc   ggagctgaat   gaagccatac   caaacgacga   gcgtgacacc   acgatgcctg   8400
cagcaatggc   aacaacgttg   cgcaaactat   taactggcga   actacttact   ctagcttccc   8460
ggcaacaatt   aatagactgg   atggaggcgg   ataaagttgc   aggaccactt   ctgcgctcgg   8520
cccttccggc   tggctggttt   attgctgata   aatctggagc   cggtgagcgt   gggtctcgcg   8580
gtatcattgc   agcactgggg   ccagatggta   agccctcccg   tatcgtagtt   atctacacga   8640
cggggagtca   ggcaactatg   gatgaacgaa   atagacagat   cgctgagata   ggtgcctcac   8700
tgattaagca   ttggtaactg   tcagaccaag   tttactcata   tatactttag   attgatttaa   8760
aacttcattt   ttaattttaaa  aggatctagg   tgaagatcct   ttttgataat   ctcatgacca   8820
aaatccctta   acgtgagttt   tcgttccact   gagcgtcaga   ccccgtagaa   aagatcaaag   8880
gatcttcttg   agatcctttt   tttctgcgcg   taatctgctg   cttgcaaaca   aaaaaaccac   8940
cgctaccagc   ggtggtttgt   ttgccggatc   aagagctacc   aactcttttt   ccgaaggtaa   9000
ctggcttcag   cagagcgcag   ataccaaata   ctgtccttct   agtgtagccg   tagttaggcc   9060
accacttcaa   gaactctgta   gcaccgccta   catacctcgc   tctgctaatc   ctgttaccag   9120
tggctgctgc   cagtggcgat   aagtcgtgtc   ttaccgggtt   ggactcaaga   cgatagttac   9180
cggataaggc   gcagcggtcg   ggctgaacgg   ggggttcgtg   cacacagccc   agcttggagc   9240
gaacgaccta   caccgaactg   agatacctac   agcgtgagct   atgagaaagc   gccacgcttc   9300
ccgaagggag   aaaggcggac   aggtatccgg   taagcggcag   ggtcggaaca   ggagagcgca   9360
cgagggagct   tccaggggga   aacgcctggt   atctttatag   tcctgtcggg   tttcgccacc   9420
tctgacttga   gcgtcgattt   ttgtgatgct   cgtcaggggg   gcggagccta   tggaaaaacg   9480
ccagcaacgc   ggccttttta   cggttcctgg   ccttttgctg   gccttttgct   cacatgttct   9540
ttcctgcgtt   atcccctgat   tctgtggata   accgtattac   cgcctttgag   tgagctgata   9600
ccgctcgccg   cagccgaacg   accgagcgca   gcgagtcagt   gagcgaggaa   gcggaagagc   9660
gcctgatgcg   gtattttctc   cttacgcatc   tgtgcggtat   ttcacaccgc   atatggtgca   9720
ctctcagtac   aatctgctct   gatgccgcat   agttaagcca   gtatacactc   cgctatcgct   9780
acgtgactgg   gtcatggctg   cgccccgaca   cccgccaaca   cccgctgacg   cgccctgacg   9840
```

-continued

```
ggcttgtctg ctcccggcat ccgcttacag acaagctgtg accgtctccg ggagctgcat    9900
gtgtcagagg ttttcaccgt catcaccgaa acgcgcgagg cagctgcggt aaagctcatc    9960
agcgtggtcg tgaagcgatt cacagatgtc tgcctgttca tccgcgtcca gctcgttgag   10020
tttctccaga agcgttaatg tctggcttct gataaagcgg gccatgttaa gggcggtttt   10080
ttcctgtttg gtcactgatg cctccgtgta aggggatttt ctgttcatgg gggtaatgat   10140
accgatgaaa cgagagagga tgctcacgat acgggttact gatgatgaac atgcccggtt   10200
actggaacgt tgtgagggta acaactggcg gtatgatgcg gcgggacc agagaaaaat   10260
cactcagggt caatgccagc gcttcgttaa tacagatgta ggtgttccac agggtagcca   10320
gcagcatcct gcgatgcaga tccggaacat aatggtgcag ggcgctgact tccgcgtttc   10380
cagactttac gaaacacgga aaccgaagac cattcatgtt gttgctcagg tcgcagacgt   10440
tttgcagcag cagtcgcttc acgttcgctc gcgtatcggt gattcattct gctaaccagt   10500
aaggcaaccc cgccagccta gccgggtcct caacgacagg agcacgatca tgcgcacccg   10560
tggccaggac ccaacgctgc ccgagatgcg ccgcgtgcgg ctgctggaga tggcggacgc   10620
gatggatatg ttctgccaag ggttggtttg cgcattcaca gttctccgca agaattgatt   10680
ggctccaatt cttggagtgg tgaatccgtt agcgaggtgc cgccggcttc cattcaggtc   10740
gaggtggccc ggctccatgc accgcgacgc aacgcgggga ggcagacaag gtatagggcg   10800
cgcctacaa tccatgccaa cccgttccat gtgctcgccg aggcggcata atcgccgtg   10860
acgatcagcg gtccaatgat cgaagttagg ctggtaagag ccgcgagcga tccttgaagc   10920
tgtccctgat ggtcgtcatc tacctgcctg acagcatgg cctgcaacgc gggcatcccg   10980
atgccgccgg aagcgagaag aatcataatg gggaaggcca tccagcctcg cgtcgcgaac   11040
gccagcaaga cgtagcccag cgcgtcggcc gccatgccgg cgataatggc ctgcttctcg   11100
ccgaaacgtt tggtggcggg accagtgacg aaggcttgag cgagggcgtg caagattccg   11160
aataccgcaa gcgacaggcc gatcatcgtc gcgctccagc gaaagcggtc ctcgccgaaa   11220
atgacccaga gcgctgccgg cacctgtcct acgagttgca tgataaagaa gacagtcata   11280
agtgcggcga cgatagtcat gccccgcgcc caccggaagg agctgactgg gttgaaggct   11340
ctcaagggca tcgtcgagg atccttcaat atgcgcacat acgctgttat gttcaaggtc   11400
ccttcgttta agaacgaaag cggtcttcct tttgagggat gtttcaagtt gttcaaatct   11460
atcaaatttg caaatcccca gtctgtatct agagcgttga atcggtgatg cgatttgtta   11520
attaaattga tggtgtcacc attaccaggt ctagatatac caatggcaaa ctgagcacaa   11580
caataccagt ccggatcaac tggcaccatc tctcccgtag tctcatctaa tttttcttcc   11640
ggatgaggtt ccagatatac cgcaacacct ttattatggt ttccctgagg gaataataga   11700
atgtcccatt cgaaatcacc aattctaaac ctgggcgaat tgtatttcgg gtttgttaac   11760
tcgttccagt caggaatgtt ccacgtgaag ctatcttcca gcaaagtctc cacttcttca   11820
tcaaattgtg gagaatactc ccaatgctct tatctatggg acttccggga aacacagtac   11880
cgatacttcc caattcgtct tcagagctca ttgtttgttt gaagagacta atcaaagaat   11940
cgttttctca aaaaaattaa tatcttaact gatagtttga tcaaagggc aaaacgtagg   12000
ggcaaacaaa cggaaaaatc gtttctcaaa ttttctgatg ccaagaactc taaccagtct   12060
tatctaaaaa ttgccttatg atccgtctct ccggttacag cctgtgtaac tgattaatcc   12120
tgcctttcta atcaccattc taatgtttta attaagggat tttgtcttca ttaacggctt   12180
```

```
                                 -continued
tcgctcataa aaatgttatg acgttttgcc cgcaggcggg aaaccatcca cttcacgaga    12240
ctgatctcct ctgccggaac accgggcatc tccaacttat aagttggaga ataagagaa    12300 tttcagattg agagaatgaa aaaaaaaaac ccttagttca taggtccatt ctcttagcgc    12360
aactacagag aacaggggca caaacaggca aaaacgggc acaacctcaa tggagtgatg    12420
caacctgcct ggagtaaatg atgacacaag gcaattgacc cacgcatgta tctatctcat    12480
tttcttacac cttctattac cttctgctct ctctgatttg gaaaaagctg aaaaaaaagg    12540
ttgaaaccag ttccctgaaa ttattcccct acttgactaa taagtatata aagacggtag    12600
gtattgattg taattctgta aatctatttc ttaaacttct taaattctac ttttatagtt    12660 agtcttttt ttagttttaa aacaccaaga acttagtttc gaataaacac acataaacaa    12720
acaagcttac aaaacaaatt cacc atg gct gca tat gca gct cag ggc tat       12771
                            Met Ala Ala Tyr Ala Ala Gln Gly Tyr
                             1               5 aag gtg cta gta ctc aac ccc tct gtt gct gca aca ctg ggc ttt ggt      12819
Lys Val Leu Val Leu Asn Pro Ser Val Ala Ala Thr Leu Gly Phe Gly
 10              15                  20                  25 gct tac atg tcc aag gct cat ggg atc gat cct aac atc agg acc ggg      12867
Ala Tyr Met Ser Lys Ala His Gly Ile Asp Pro Asn Ile Arg Thr Gly
                 30                  35                  40 gtg aga aca att acc act ggc agc ccc atc acg tac tcc acc tac ggc      12915
Val Arg Thr Ile Thr Thr Gly Ser Pro Ile Thr Tyr Ser Thr Tyr Gly
             45                  50                  55 aag ttc ctt gcc gac ggc ggg tgc tcg ggg ggc gct tat gac ata ata      12963
Lys Phe Leu Ala Asp Gly Gly Cys Ser Gly Gly Ala Tyr Asp Ile Ile
         60                  65                  70 att tgt gac gag tgc cac tcc acg gat gcc aca tcc atc ttg ggc att      13011
Ile Cys Asp Glu Cys His Ser Thr Asp Ala Thr Ser Ile Leu Gly Ile
 75                  80                  85 ggc act gtc ctt gac caa gca gag act gcg ggg gcg aga ctg gtt gtg      13059
Gly Thr Val Leu Asp Gln Ala Glu Thr Ala Gly Ala Arg Leu Val Val
         90                  95                 100                 105 ctc gcc acc gcc acc cct ccg ggc tcc gtc act gtg ccc cat ccc aac      13107
Leu Ala Thr Ala Thr Pro Pro Gly Ser Val Thr Val Pro His Pro Asn
                110                 115                 120 atc gag gag gtt gct ctg tcc acc acc gga gag atc cct ttt tac ggc      13155
Ile Glu Glu Val Ala Leu Ser Thr Thr Gly Glu Ile Pro Phe Tyr Gly
             125                 130                 135 aag gct atc ccc ctc gaa gta atc aag ggg ggg aga cat ctc atc ttc      13203
Lys Ala Ile Pro Leu Glu Val Ile Lys Gly Gly Arg His Leu Ile Phe
         140                 145                 150 tgt cat tca aag aag aag tgc gac gaa ctc gcc gca aag ctg gtc gca      13251
Cys His Ser Lys Lys Lys Cys Asp Glu Leu Ala Ala Lys Leu Val Ala
 155                 160                 165 ttg ggc atc aat gcc gtg gcc tac tac cgc ggt ctt gac gtg tcc gtc      13299
Leu Gly Ile Asn Ala Val Ala Tyr Tyr Arg Gly Leu Asp Val Ser Val
170                 175                 180                 185 atc ccg acc agc ggc gat gtt gtc gtc gtg gca acc gat gcc ctc atg      13347
Ile Pro Thr Ser Gly Asp Val Val Val Val Ala Thr Asp Ala Leu Met
                190                 195                 200 acc ggc tat acc ggc gac ttc gac tcg gtg ata gac tgc aat acg tgt      13395
Thr Gly Tyr Thr Gly Asp Phe Asp Ser Val Ile Asp Cys Asn Thr Cys
             205                 210                 215 gtc acc cag aca gtc gat ttc agc ctt gac cct acc ttc acc att gag      13443
Val Thr Gln Thr Val Asp Phe Ser Leu Asp Pro Thr Phe Thr Ile Glu
         220                 225                 230 aca atc acg ctc ccc caa gat gct gtc tcc cgc act caa cgt cgg ggc      13491
Thr Ile Thr Leu Pro Gln Asp Ala Val Ser Arg Thr Gln Arg Arg Gly
```

```
                Thr Ile Thr Leu Pro Gln Asp Ala Val Ser Arg Thr Gln Arg Arg Gly
                    235                 240                 245 agg act ggc agg ggg aag cca ggc atc tac aga ttt gtg gca ccg ggg              13539
Arg Thr Gly Arg Gly Lys Pro Gly Ile Tyr Arg Phe Val Ala Pro Gly
250                 255                 260                 265 gag cgc ccc tcc ggc atg ttc gac tcg tcc gtc ctc tgt gag tgc tat              13587
Glu Arg Pro Ser Gly Met Phe Asp Ser Ser Val Leu Cys Glu Cys Tyr
                    270                 275                 280 gac gca ggc tgt gct tgg tat gag ctc acg ccc gcc gag act aca gtt              13635
Asp Ala Gly Cys Ala Trp Tyr Glu Leu Thr Pro Ala Glu Thr Thr Val
                285                 290                 295 agg cta cga gcg tac atg aac acc ccg ggg ctt ccc gtg tgc cag gac              13683
Arg Leu Arg Ala Tyr Met Asn Thr Pro Gly Leu Pro Val Cys Gln Asp
            300                 305                 310 cat ctt gaa ttt tgg gag ggc gtc ttt aca ggc ctc act cat ata gat              13731
His Leu Glu Phe Trp Glu Gly Val Phe Thr Gly Leu Thr His Ile Asp
        315                 320                 325 gcc cac ttt cta tcc cag aca aag cag agt ggg gag aac ctt cct tac              13779
Ala His Phe Leu Ser Gln Thr Lys Gln Ser Gly Glu Asn Leu Pro Tyr
330                 335                 340                 345 ctg gta gcg tac caa gcc acc gtg tgc gct agg gct caa gcc cct ccc              13827
Leu Val Ala Tyr Gln Ala Thr Val Cys Ala Arg Ala Gln Ala Pro Pro
                    350                 355                 360 cca tcg tgg gac cag atg tgg aag tgt ttg att cgc ctc aag ccc acc              13875
Pro Ser Trp Asp Gln Met Trp Lys Cys Leu Ile Arg Leu Lys Pro Thr
                365                 370                 375 ctc cat ggg cca aca ccc ctg cta tac aga ctg ggc gct gtt cag aat              13923
Leu His Gly Pro Thr Pro Leu Leu Tyr Arg Leu Gly Ala Val Gln Asn
            380                 385                 390 gaa atc acc ctg acg cac cca gtc acc aaa tac atc atg aca tgc atg              13971
Glu Ile Thr Leu Thr His Pro Val Thr Lys Tyr Ile Met Thr Cys Met
        395                 400                 405 tcg gcc gac ctg gag gtc gtc acg agc acc tgg gtg ctc gtt ggc ggc              14019
Ser Ala Asp Leu Glu Val Val Thr Ser Thr Trp Val Leu Val Gly Gly
410                 415                 420                 425 gtc ctg gct gct ttg gcc gcg tat tgc ctg tca aca ggc tgc gtg gtc              14067
Val Leu Ala Ala Leu Ala Ala Tyr Cys Leu Ser Thr Gly Cys Val Val
                    430                 435                 440 ata gtg ggc agg gtc gtc ttg tcc ggg aag ccg gca atc ata cct gac              14115
Ile Val Gly Arg Val Val Leu Ser Gly Lys Pro Ala Ile Ile Pro Asp
                445                 450                 455 agg gaa gtc ctc tac cga gag ttc gat gag atg gaa gag tgc tct cag              14163
Arg Glu Val Leu Tyr Arg Glu Phe Asp Glu Met Glu Glu Cys Ser Gln
            460                 465                 470 cac tta ccg tac atc gag caa ggg atg atg ctc gcc gag cag ttc aag              14211
His Leu Pro Tyr Ile Glu Gln Gly Met Met Leu Ala Glu Gln Phe Lys
        475                 480                 485 cag aag gcc ctc ggc ctc ctg cag acc gcg tcc cgt cag gca gag gtt              14259
Gln Lys Ala Leu Gly Leu Leu Gln Thr Ala Ser Arg Gln Ala Glu Val
490                 495                 500                 505 atc gcc cct gct gtc cag acc aac tgg caa aaa ctc gag acc ttc tgg              14307
Ile Ala Pro Ala Val Gln Thr Asn Trp Gln Lys Leu Glu Thr Phe Trp
                    510                 515                 520 gcg aag cat atg tgg aac ttc atc agt ggg ata caa tac ttg gcg ggc              14355
Ala Lys His Met Trp Asn Phe Ile Ser Gly Ile Gln Tyr Leu Ala Gly
                525                 530                 535 ttg tca acg ctg cct ggt aac ccc gcc att gct tca ttg atg gct ttt              14403
Leu Ser Thr Leu Pro Gly Asn Pro Ala Ile Ala Ser Leu Met Ala Phe
            540                 545                 550
```

-continued

| | |
|---|---|
| aca gct gct gtc acc agc cca cta acc act agc caa acc ctc ctc ttc<br>Thr Ala Ala Val Thr Ser Pro Leu Thr Thr Ser Gln Thr Leu Leu Phe<br>555                          560                      565 | 14451 |
| aac ata ttg ggg ggg tgg gtg gct gcc cag ctc gcc gcc ccc ggt gcc<br>Asn Ile Leu Gly Gly Trp Val Ala Ala Gln Leu Ala Ala Pro Gly Ala<br>570                          575                      580                      585 | 14499 |
| gct act gcc ttt gtg ggc gct ggc tta gct ggc gcc gcc atc ggc agt<br>Ala Thr Ala Phe Val Gly Ala Gly Leu Ala Gly Ala Ala Ile Gly Ser<br>                    590                      595                      600 | 14547 |
| gtt gga ctg ggg aag gtc ctc ata gac atc ctt gca ggg tat ggc gcg<br>Val Gly Leu Gly Lys Val Leu Ile Asp Ile Leu Ala Gly Tyr Gly Ala<br>                    605                      610                      615 | 14595 |
| ggc gtg gcg gga gct ctt gtg gca ttc aag atc atg agc ggt gag gtc<br>Gly Val Ala Gly Ala Leu Val Ala Phe Lys Ile Met Ser Gly Glu Val<br>                    620                      625                      630 | 14643 |
| ccc tcc acg gag gac ctg gtc aat cta ctg ccc gcc atc ctc tcg ccc<br>Pro Ser Thr Glu Asp Leu Val Asn Leu Leu Pro Ala Ile Leu Ser Pro<br>635                          640                      645 | 14691 |
| gga gcc ctc gta gtc ggc gtg gtc tgt gca gca ata ctg cgc cgg cac<br>Gly Ala Leu Val Val Gly Val Val Cys Ala Ala Ile Leu Arg Arg His<br>650                          655                      660                      665 | 14739 |
| gtt ggc ccg ggc gag ggg gca gtg cag tgg atg aac cgg ctg ata gcc<br>Val Gly Pro Gly Glu Gly Ala Val Gln Trp Met Asn Arg Leu Ile Ala<br>                    670                      675                      680 | 14787 |
| ttc gcc tcc cgg ggg aac cat gtt tcc ccc acg cac tac gtg ccg gag<br>Phe Ala Ser Arg Gly Asn His Val Ser Pro Thr His Tyr Val Pro Glu<br>                    685                      690                      695 | 14835 |
| agc gat gca gct gcc cgc gtc act gcc ata ctc agc agc ctc act gta<br>Ser Asp Ala Ala Ala Arg Val Thr Ala Ile Leu Ser Ser Leu Thr Val<br>                    700                      705                      710 | 14883 |
| acc cag ctc ctg agg cga ctg cac cag tgg ata agc tcg gag tgt acc<br>Thr Gln Leu Leu Arg Arg Leu His Gln Trp Ile Ser Ser Glu Cys Thr<br>                    715                      720                      725 | 14931 |
| act cca tgc tcc ggt tcc tgg cta agg gac atc tgg gac tgg ata tgc<br>Thr Pro Cys Ser Gly Ser Trp Leu Arg Asp Ile Trp Asp Trp Ile Cys<br>730                          735                      740                      745 | 14979 |
| gag gtg ttg agc gac ttt aag acc tgg cta aaa gct aag ctc atg cca<br>Glu Val Leu Ser Asp Phe Lys Thr Trp Leu Lys Ala Lys Leu Met Pro<br>                    750                      755                      760 | 15027 |
| cag ctg cct ggg atc ccc ttt gtg tcc tgc cag cgc ggg tat aag ggg<br>Gln Leu Pro Gly Ile Pro Phe Val Ser Cys Gln Arg Gly Tyr Lys Gly<br>                  765                      770                      775 | 15075 |
| gtc tgg cga ggg gac ggc atc atg cac act cgc tgc cac tgt gga gct<br>Val Trp Arg Gly Asp Gly Ile Met His Thr Arg Cys His Cys Gly Ala<br>                  780                      785                      790 | 15123 |
| gag atc act gga cat gtc aaa aac ggg acg atg agg atc gtc ggt cct<br>Glu Ile Thr Gly His Val Lys Asn Gly Thr Met Arg Ile Val Gly Pro<br>795                          800                      805 | 15171 |
| agg acc tgc agg aac atg tgg agt ggg acc ttc ccc att aat gcc tac<br>Arg Thr Cys Arg Asn Met Trp Ser Gly Thr Phe Pro Ile Asn Ala Tyr<br>810                          815                      820                      825 | 15219 |
| acc acg ggc ccc tgt acc ccc ctt cct gcg ccg aac tac acg ttc gcg<br>Thr Thr Gly Pro Cys Thr Pro Leu Pro Ala Pro Asn Tyr Thr Phe Ala<br>                    830                      835                      840 | 15267 |
| cta tgg agg gtg tct gca gag gaa tac gtg gag ata agg cag gtg ggg<br>Leu Trp Arg Val Ser Ala Glu Glu Tyr Val Glu Ile Arg Gln Val Gly<br>                    845                      850                      855 | 15315 |
| gac ttc cac tac gtg acg ggt atg act act gac aat ctt aaa tgc ccg<br>Asp Phe His Tyr Val Thr Gly Met Thr Thr Asp Asn Leu Lys Cys Pro<br>                    860                      865                      870 | 15363 |

-continued

| | |
|---|---|
| tgc cag gtc cca tcg ccc gaa ttt ttc aca gaa ttg gac ggg gtg cgc<br>Cys Gln Val Pro Ser Pro Glu Phe Phe Thr Glu Leu Asp Gly Val Arg<br>875                     880                   885 | 15411 |
| cta cat agg ttt gcg ccc ccc tgc aag ccc ttg ctg cgg gag gag gta<br>Leu His Arg Phe Ala Pro Pro Cys Lys Pro Leu Leu Arg Glu Glu Val<br>890                     895                   900               905 | 15459 |
| tca ttc aga gta gga ctc cac gaa tac ccg gta ggg tcg caa tta cct<br>Ser Phe Arg Val Gly Leu His Glu Tyr Pro Val Gly Ser Gln Leu Pro<br>               910                   915                   920 | 15507 |
| tgc gag ccc gaa ccg gac gtg gcc gtg ttg acg tcc atg ctc act gat<br>Cys Glu Pro Glu Pro Asp Val Ala Val Leu Thr Ser Met Leu Thr Asp<br>925                     930                   935 | 15555 |
| ccc tcc cat ata aca gcg gag gcg gcc ggg cga agg ttg gcg agg gga<br>Pro Ser His Ile Thr Ala Glu Ala Ala Gly Arg Arg Leu Ala Arg Gly<br>               940                   945                   950 | 15603 |
| tca ccc ccc tct gtg gcc agc tcc tcg gct agc cag cta tcc gct cca<br>Ser Pro Pro Ser Val Ala Ser Ser Ser Ala Ser Gln Leu Ser Ala Pro<br>955                     960                   965 | 15651 |
| tct ctc aag gca act tgc acc gct aac cat gac tcc cct gat gct gag<br>Ser Leu Lys Ala Thr Cys Thr Ala Asn His Asp Ser Pro Asp Ala Glu<br>970                     975                   980               985 | 15699 |
| ctc ata gag gcc aac ctc cta tgg agg cag gag atg ggc ggc aac atc<br>Leu Ile Glu Ala Asn Leu Leu Trp Arg Gln Glu Met Gly Gly Asn Ile<br>               990                   995               1000 | 15747 |
| acc agg gtt gag tca gaa aac aaa gtg gtg att ctg gac tcc ttc gat<br>Thr Arg Val Glu Ser Glu Asn Lys Val Val Ile Leu Asp Ser Phe Asp<br>             1005                  1010                1015 | 15795 |
| ccg ctt gtg gcg gag gag gac gag cgg gag atc tcc gta ccc gca gaa<br>Pro Leu Val Ala Glu Glu Asp Glu Arg Glu Ile Ser Val Pro Ala Glu<br>             1020                  1025                1030 | 15843 |
| atc ctg cgg aag tct cgg aga ttc gcc cag gcc ctg ccc gtt tgg gcg<br>Ile Leu Arg Lys Ser Arg Arg Phe Ala Gln Ala Leu Pro Val Trp Ala<br>             1035                  1040                1045 | 15891 |
| cgg ccg gac tat aac ccc ccg cta gtg gag acg tgg aaa aag ccc gac<br>Arg Pro Asp Tyr Asn Pro Pro Leu Val Glu Thr Trp Lys Lys Pro Asp<br>1050                 1055                1060                1065 | 15939 |
| tac gaa cca cct gtg gtc cat ggc tgc ccg ctt cca cct cca aag tcc<br>Tyr Glu Pro Pro Val Val His Gly Cys Pro Leu Pro Pro Pro Lys Ser<br>             1070                  1075                1080 | 15987 |
| cct cct gtg cct ccg cct cgg aag aag cgg acg gtg gtc ctc act gaa<br>Pro Pro Val Pro Pro Pro Arg Lys Lys Arg Thr Val Val Leu Thr Glu<br>             1085                  1090                1095 | 16035 |
| tca acc cta tct act gcc ttg gcc gag ctc gcc acc aga agc ttt ggc<br>Ser Thr Leu Ser Thr Ala Leu Ala Glu Leu Ala Thr Arg Ser Phe Gly<br>1100                 1105                1110 | 16083 |
| agc tcc tca act tcc ggc att acg ggc gac aat acg aca aca tcc tct<br>Ser Ser Ser Thr Ser Gly Ile Thr Gly Asp Asn Thr Thr Thr Ser Ser<br>             1115                  1120                1125 | 16131 |
| gag ccc gcc cct tct ggc tgc ccc ccc gac tcc gac gct gag tcc tat<br>Glu Pro Ala Pro Ser Gly Cys Pro Pro Asp Ser Asp Ala Glu Ser Tyr<br>1130                 1135                1140                1145 | 16179 |
| tcc tcc atg ccc ccc ctg gag ggg gag cct ggg gat ccg gat ctt agc<br>Ser Ser Met Pro Pro Leu Glu Gly Glu Pro Gly Asp Pro Asp Leu Ser<br>               1150                  1155                1160 | 16227 |
| gac ggg tca tgg tca acg gtc agt agt gag gcc aac gcg gag gat gtc<br>Asp Gly Ser Trp Ser Thr Val Ser Ser Glu Ala Asn Ala Glu Asp Val<br>             1165                  1170                1175 | 16275 |
| gtg tgc tgc tca atg tct tac tct tgg aca ggc gca ctc gtc acc ccg<br>Val Cys Cys Ser Met Ser Tyr Ser Trp Thr Gly Ala Leu Val Thr Pro | 16323 |

-continued

```
                 1180                1185                1190
tgc gcc gcg gaa gaa cag aaa ctg ccc atc aat gca cta agc aac tcg      16371
Cys Ala Ala Glu Glu Gln Lys Leu Pro Ile Asn Ala Leu Ser Asn Ser
    1195                1200                1205 ttg cta cgt cac cac aat ttg gtg tat tcc acc acc tca cgc agt gct      16419
Leu Leu Arg His His Asn Leu Val Tyr Ser Thr Thr Ser Arg Ser Ala
1210                1215                1220                1225 tgc caa agg cag aag aaa gtc aca ttt gac aga ctg caa gtt ctg gac      16467
Cys Gln Arg Gln Lys Lys Val Thr Phe Asp Arg Leu Gln Val Leu Asp
            1230                1235                1240 agc cat tac cag gac gta ctc aag gag gtt aaa gca gcg gcg tca aaa      16515
Ser His Tyr Gln Asp Val Leu Lys Glu Val Lys Ala Ala Ala Ser Lys
        1245                1250                1255 gtg aag gct aac ttg cta tcc gta gag gaa gct tgc agc ctg acg ccc      16563
Val Lys Ala Asn Leu Leu Ser Val Glu Glu Ala Cys Ser Leu Thr Pro
    1260                1265                1270 cca cac tca gcc aaa tcc aag ttt ggt tat ggg gca aaa gac gtc cgt      16611
Pro His Ser Ala Lys Ser Lys Phe Gly Tyr Gly Ala Lys Asp Val Arg
1275                1280                1285 tgc cat gcc aga aag gcc gta acc cac atc aac tcc gtg tgg aaa gac      16659
Cys His Ala Arg Lys Ala Val Thr His Ile Asn Ser Val Trp Lys Asp
1290                1295                1300                1305 ctt ctg gaa gac aat gta aca cca ata gac act acc atc atg gct aag      16707
Leu Leu Glu Asp Asn Val Thr Pro Ile Asp Thr Thr Ile Met Ala Lys
            1310                1315                1320 aac gag gtt ttc tgc gtt cag cct gag aag ggg ggt cgt aag cca gct      16755
Asn Glu Val Phe Cys Val Gln Pro Glu Lys Gly Gly Arg Lys Pro Ala
        1325                1330                1335 cgt ctc atc gtg ttc ccc gat ctg ggc gtg cgc gtg tgc gaa aag atg      16803
Arg Leu Ile Val Phe Pro Asp Leu Gly Val Arg Val Cys Glu Lys Met
    1340                1345                1350 gct ttg tac gac gtg gtt aca aag ctc ccc ttg gcc gtg atg gga agc      16851
Ala Leu Tyr Asp Val Val Thr Lys Leu Pro Leu Ala Val Met Gly Ser
1355                1360                1365 tcc tac gga ttc caa tac tca cca gga cag cgg gtt gaa ttc ctc gtg      16899
Ser Tyr Gly Phe Gln Tyr Ser Pro Gly Gln Arg Val Glu Phe Leu Val
1370                1375                1380                1385 caa gcg tgg aag tcc aag aaa acc cca atg ggg ttc tcg tat gat acc      16947
Gln Ala Trp Lys Ser Lys Lys Thr Pro Met Gly Phe Ser Tyr Asp Thr
            1390                1395                1400 cgc tgc ttt gac tcc aca gtc act gag agc gac atc cgt acg gag gag      16995
Arg Cys Phe Asp Ser Thr Val Thr Glu Ser Asp Ile Arg Thr Glu Glu
        1405                1410                1415 gca atc tac caa tgt tgt gac ctc gac ccc caa gcc cgc gtg gcc atc      17043
Ala Ile Tyr Gln Cys Cys Asp Leu Asp Pro Gln Ala Arg Val Ala Ile
    1420                1425                1430 aag tcc ctc acc gag agg ctt tat gtt ggg ggc cct ctt acc aat tca      17091
Lys Ser Leu Thr Glu Arg Leu Tyr Val Gly Gly Pro Leu Thr Asn Ser
1435                1440                1445 agg ggg gag aac tgc ggc tat cgc agg tgc cgc gcg agc ggc gta ctg      17139
Arg Gly Glu Asn Cys Gly Tyr Arg Arg Cys Arg Ala Ser Gly Val Leu
1450                1455                1460                1465 aca act agc tgt ggt aac acc ctc act tgc tac atc aag gcc cgg gca      17187
Thr Thr Ser Cys Gly Asn Thr Leu Thr Cys Tyr Ile Lys Ala Arg Ala
            1470                1475                1480 gcc tgt cga gcc gca ggg ctc cag gac tgc acc atg ctc gtg tgt ggc      17235
Ala Cys Arg Ala Ala Gly Leu Gln Asp Cys Thr Met Leu Val Cys Gly
        1485                1490                1495 gac gac tta gtc gtt atc tgt gaa agc gcg ggg gtc cag gag gac gcg      17283
```

```
                Asp Asp Leu Val Val Ile Cys Glu Ser Ala Gly Val Gln Glu Asp Ala
                    1500                1505                1510 gcg agc ctg aga gcc ttc acg gag gct atg acc agg tac tcc gcc ccc         17331
Ala Ser Leu Arg Ala Phe Thr Glu Ala Met Thr Arg Tyr Ser Ala Pro
    1515                1520                1525 cct ggg gac ccc cca caa cca gaa tac gac ttg gag ctc ata aca tca         17379
Pro Gly Asp Pro Pro Gln Pro Glu Tyr Asp Leu Glu Leu Ile Thr Ser
1530                1535                1540                1545 tgc tcc tcc aac gtg tca gtc gcc cac gac ggc gct gga aag agg gtc         17427
Cys Ser Ser Asn Val Ser Val Ala His Asp Gly Ala Gly Lys Arg Val
                1550                1555                1560 tac tac ctc acc cgt gac cct aca acc ccc ctc gcg aga gct gcg tgg         17475
Tyr Tyr Leu Thr Arg Asp Pro Thr Thr Pro Leu Ala Arg Ala Ala Trp
    1565                1570                1575 gag aca gca aga cac act cca gtc aat tcc tgg cta ggc aac ata atc         17523
Glu Thr Ala Arg His Thr Pro Val Asn Ser Trp Leu Gly Asn Ile Ile
1580                1585                1590 atg ttt gcc ccc aca ctg tgg gcg agg atg ata ctg atg acc cat ttc         17571
Met Phe Ala Pro Thr Leu Trp Ala Arg Met Ile Leu Met Thr His Phe
                1595                1600                1605 ttt agc gtc ctt ata gcc agg gac cag ctt gaa cag gcc ctc gat tgc         17619
Phe Ser Val Leu Ile Ala Arg Asp Gln Leu Glu Gln Ala Leu Asp Cys
1610                1615                1620                1625 gag atc tac ggg gcc tgc tac tcc ata gaa cca ctg gat cta cct cca         17667
Glu Ile Tyr Gly Ala Cys Tyr Ser Ile Glu Pro Leu Asp Leu Pro Pro
                1630                1635                1640 atc att caa aga ctc cat ggc ctc agc gca ttt tca ctc cac agt tac         17715
Ile Ile Gln Arg Leu His Gly Leu Ser Ala Phe Ser Leu His Ser Tyr
    1645                1650                1655 tct cca ggt gaa atc aat agg gtg gcc gca tgc ctc aga aaa ctt ggg         17763
Ser Pro Gly Glu Ile Asn Arg Val Ala Ala Cys Leu Arg Lys Leu Gly
    1660                1665                1670 gta ccg ccc ttg cga gct tgg aga cac cgg gcc cgg agc gtc cgc gct         17811
Val Pro Pro Leu Arg Ala Trp Arg His Arg Ala Arg Ser Val Arg Ala
1675                1680                1685 agg ctt ctg gcc aga gga ggc agg gct gcc ata tgt ggc aag tac ctc         17859
Arg Leu Leu Ala Arg Gly Gly Arg Ala Ala Ile Cys Gly Lys Tyr Leu
1690                1695                1700                1705 ttc aac tgg gca gta aga aca aag ctc aaa ctc act cca ata gcg gcc         17907
Phe Asn Trp Ala Val Arg Thr Lys Leu Lys Leu Thr Pro Ile Ala Ala
                1710                1715                1720 gct ggc cag ctg gac ttg tcc ggc tgg ttc acg gct ggc tac agc ggg         17955
Ala Gly Gln Leu Asp Leu Ser Gly Trp Phe Thr Ala Gly Tyr Ser Gly
                1725                1730                1735 gga gac att tat cac agc gtg tct cat gcc cgg ccc cgc tgg atc tgg         18003
Gly Asp Ile Tyr His Ser Val Ser His Ala Arg Pro Arg Trp Ile Trp
    1740                1745                1750 ttt tgc cta ctc ctg ctt gct gca ggg gta ggc atc tac ctc ctc ccc         18051
Phe Cys Leu Leu Leu Leu Ala Ala Gly Val Gly Ile Tyr Leu Leu Pro
    1755                1760                1765 aac cga tgaaggttgg ggtaaacact ccggcctaaa aaaaaaaaaa aatctagaac         18107
Asn Arg
1770 ccgagtcgac tttgttccca ctgtacttt  agctcgtaca aaatacaata tactttcat         18167 ttctccgtaa acaacatgtt tcccatgta  atatccttt  ctatttttcg ttccgttacc         18227 aactttacac atactttata tagctattca cttctataca ctaaaaaact aagacaattt         18287 taatttttgct gcctgccata tttcaatttg ttataaattc ctataattta tcctattagt         18347
```

```
agctaaaaaa agatgaatgt gaatcgaatc ctaagagaat tggatctgat ccacaggacg   18407
ggtgtggtcg ccatgatcgc gtagtcgata gtggctccaa gtagcgaagc gagcaggact   18467
gggcggcggc caaagcggtc ggacagtgct ccgagaacgg gtgcgcatag aaattgcatc   18527
aacgcatata gcgctagcag cacgccatag tgactggcga tgctgtcgga atggacgata   18587
tcccgcaaga ggcccggcag taccggcata accaagccta tgcctacagc atccagggtg   18647
acggtgccga ggatgacgat gagcgcattg ttagatttca tacacggtgc ctgactgcgt   18707
tagcaattta actgtgataa actaccgcat aaagctttt tctttccaat ttttttttt    18767
tcgtcattat aaaaatcatt acgaccgaga ttcccgggta ataactgata taattaaatt   18827
gaagctctaa tttgtgagtt tagtatacat gcatttactt ataatacagt ttttagttt    18887
tgctggccgc atcttctcaa atatgcttcc cagcctgctt ttctgtaacg ttcaccctct   18947
accttagcat cccttccctt tgcaaatagt cctcttccaa caataataat gtcagatcct   19007
gtagagacca catcatccac ggttctatac tgttgaccca atgcgtctcc cttgtcatct   19067
aaacccacac cgggtgtcat aatcaaccaa tcgtaacctt catctcttcc acccatgtct   19127
ctttgagcaa taaagccgat aacaaaatct tgtcgctct tcgcaatgtc aacagtaccc    19187
ttagtatatt ctccagtaga tagggagccc ttgcatgaca attctgctaa catcaaaagg   19247
cctctaggtt cctttgttac ttcttctgcc gcctgcttca aaccgctaac aatacctggg   19307
cccaccacac cgtgtgcatt cgtaatgtct gcccattctg ctattctgta tacacccgca   19367
gagtactgca atttgactgt attaccaatg tcagcaaatt ttctgtcttc gaagagtaaa   19427
aaattgtact tggcggataa tgcctttagc ggcttaactg tgccctccat ggaaaaatca   19487
gtcaagatat ccacatgtgt ttttagtaaa caaattttgg gacctaatgc ttcaactaac   19547
tccagtaatt ccttggtggt acgaacatcc aatgaagcac acaagtttgt ttgcttttcg   19607
tgcatgatat taaatagctt ggcagcaaca ggactaggat gagtagcagc acgttcctta   19667
tatgtagctt tcgacatgat ttatcttcgt ttcctgcagg tttttgttct gtgcagttgg   19727
gttaagaata ctgggcaatt tcatgtttct tcaacactac atatgcgtat atataccaat   19787
ctaagtctgt gctccttcct tcgttcttcc ttctgttcgg agattaccga atcaaaaaaa   19847
tttcaaggaa accgaaatca aaaaaagaa taaaaaaaa atgatgaatt gaaaagctta    19907
tcgat                                                              19912
```

<210> SEQ ID NO 9
<211> LENGTH: 1771
<212> TYPE: PRT
<213> ORGANISM: Artificial Sequence
<220> FEATURE:
<223> OTHER INFORMATION: Description of Artificial Sequence:
      pd.deltaNS3NS5

<400> SEQUENCE: 9

Met Ala Ala Tyr Ala Ala Gln Gly Tyr Lys Val Leu Val Leu Asn Pro
1               5                   10                  15

Ser Val Ala Ala Thr Leu Gly Phe Gly Ala Tyr Met Ser Lys Ala His
                20                  25                  30

Gly Ile Asp Pro Asn Ile Arg Thr Gly Val Arg Thr Ile Thr Thr Gly
            35                  40                  45

Ser Pro Ile Thr Tyr Ser Thr Tyr Gly Lys Phe Leu Ala Asp Gly Gly
        50                  55                  60

Cys Ser Gly Gly Ala Tyr Asp Ile Ile Ile Cys Asp Glu Cys His Ser
65                  70                  75                  80

-continued

```
Thr Asp Ala Thr Ser Ile Leu Gly Ile Gly Thr Val Leu Asp Gln Ala
             85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
            115                 120                 125

Thr Thr Gly Glu Ile Pro Phe Tyr Gly Lys Ala Ile Pro Leu Glu Val
        130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
            195                 200                 205

Asp Ser Val Ile Asp Cys Asn Thr Cys Val Thr Gln Thr Val Asp Phe
        210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
        435                 440                 445

Ser Gly Lys Pro Ala Ile Ile Pro Asp Arg Glu Val Leu Tyr Arg Glu
450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495
```

```
Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
            515                 520                 525

Ile Ser Gly Ile Gln Tyr Leu Ala Gly Leu Ser Thr Leu Pro Gly Asn
            530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
                580                 585                 590

Gly Leu Ala Gly Ala Ala Ile Gly Ser Val Gly Leu Gly Lys Val Leu
            595                 600                 605

Ile Asp Ile Leu Ala Gly Tyr Gly Ala Gly Val Ala Gly Ala Leu Val
            610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
            675                 680                 685

Val Ser Pro Thr His Tyr Val Pro Glu Ser Asp Ala Ala Ala Arg Val
            690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
                740                 745                 750

Thr Trp Leu Lys Ala Lys Leu Met Pro Gln Leu Pro Gly Ile Pro Phe
            755                 760                 765

Val Ser Cys Gln Arg Gly Tyr Lys Gly Val Trp Arg Gly Asp Gly Ile
            770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
            835                 840                 845

Glu Tyr Val Glu Ile Arg Gln Val Gly Asp Phe His Tyr Val Thr Gly
            850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
                900                 905                 910

Glu Tyr Pro Val Gly Ser Gln Leu Pro Cys Glu Pro Glu Pro Asp Val
```

-continued

```
            915                 920                 925
Ala Val Leu Thr Ser Met Leu Thr Asp Pro Ser His Ile Thr Ala Glu
        930                 935                 940

Ala Ala Gly Arg Arg Leu Ala Arg Gly Ser Pro Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
    1010                1015                1020

Glu Arg Glu Ile Ser Val Pro Ala Glu Ile Leu Arg Lys Ser Arg Arg
1025                1030                1035                1040

Phe Ala Gln Ala Leu Pro Val Trp Ala Arg Pro Asp Tyr Asn Pro Pro
                1045                1050                1055

Leu Val Glu Thr Trp Lys Lys Pro Asp Tyr Glu Pro Pro Val Val His
            1060                1065                1070

Gly Cys Pro Leu Pro Pro Pro Lys Ser Pro Pro Val Pro Pro Pro Arg
        1075                1080                1085

Lys Lys Arg Thr Val Val Leu Thr Glu Ser Thr Leu Ser Thr Ala Leu
    1090                1095                1100

Ala Glu Leu Ala Thr Arg Ser Phe Gly Ser Ser Thr Ser Gly Ile
1105                1110                1115                1120

Thr Gly Asp Asn Thr Thr Thr Ser Ser Glu Pro Ala Pro Ser Gly Cys
                1125                1130                1135

Pro Pro Asp Ser Asp Ala Glu Ser Tyr Ser Ser Met Pro Pro Leu Glu
            1140                1145                1150

Gly Glu Pro Gly Asp Pro Asp Leu Ser Asp Gly Ser Trp Ser Thr Val
        1155                1160                1165

Ser Ser Glu Ala Asn Ala Glu Asp Val Val Cys Cys Ser Met Ser Tyr
    1170                1175                1180

Ser Trp Thr Gly Ala Leu Val Thr Pro Cys Ala Ala Glu Glu Gln Lys
1185                1190                1195                1200

Leu Pro Ile Asn Ala Leu Ser Asn Ser Leu Leu Arg His His Asn Leu
                1205                1210                1215

Val Tyr Ser Thr Thr Ser Arg Ser Ala Cys Gln Arg Gln Lys Lys Val
            1220                1225                1230

Thr Phe Asp Arg Leu Gln Val Leu Asp Ser His Tyr Gln Asp Val Leu
        1235                1240                1245

Lys Glu Val Lys Ala Ala Ser Lys Val Lys Ala Asn Leu Leu Ser
    1250                1255                1260

Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
                1285                1290                1295

Thr His Ile Asn Ser Val Trp Lys Asp Leu Leu Glu Asp Asn Val Thr
            1300                1305                1310

Pro Ile Asp Thr Thr Ile Met Ala Lys Asn Glu Val Phe Cys Val Gln
        1315                1320                1325

Pro Glu Lys Gly Gly Arg Lys Pro Ala Arg Leu Ile Val Phe Pro Asp
    1330                1335                1340
```

```
Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
            1365                1370                1375

Pro Gly Gln Arg Val Glu Phe Leu Val Gln Ala Trp Lys Ser Lys Lys
            1380                1385                1390

Thr Pro Met Gly Phe Ser Tyr Asp Thr Arg Cys Phe Asp Ser Thr Val
        1395                1400                1405

Thr Glu Ser Asp Ile Arg Thr Glu Glu Ala Ile Tyr Gln Cys Cys Asp
    1410                1415                1420

Leu Asp Pro Gln Ala Arg Val Ala Ile Lys Ser Leu Thr Glu Arg Leu
1425                1430                1435                1440

Tyr Val Gly Gly Pro Leu Thr Asn Ser Arg Gly Glu Asn Cys Gly Tyr
                1445                1450                1455

Arg Arg Cys Arg Ala Ser Gly Val Leu Thr Thr Ser Cys Gly Asn Thr
            1460                1465                1470

Leu Thr Cys Tyr Ile Lys Ala Arg Ala Ala Cys Arg Ala Ala Gly Leu
        1475                1480                1485

Gln Asp Cys Thr Met Leu Val Cys Gly Asp Asp Leu Val Val Ile Cys
    1490                1495                1500

Glu Ser Ala Gly Val Gln Glu Asp Ala Ala Ser Leu Arg Ala Phe Thr
1505                1510                1515                1520

Glu Ala Met Thr Arg Tyr Ser Ala Pro Pro Gly Asp Pro Pro Gln Pro
                1525                1530                1535

Glu Tyr Asp Leu Glu Leu Ile Thr Ser Cys Ser Ser Asn Val Ser Val
            1540                1545                1550

Ala His Asp Gly Ala Gly Lys Arg Val Tyr Tyr Leu Thr Arg Asp Pro
        1555                1560                1565

Thr Thr Pro Leu Ala Arg Ala Ala Trp Glu Thr Ala Arg His Thr Pro
    1570                1575                1580

Val Asn Ser Trp Leu Gly Asn Ile Ile Met Phe Ala Pro Thr Leu Trp
1585                1590                1595                1600

Ala Arg Met Ile Leu Met Thr His Phe Phe Ser Val Leu Ile Ala Arg
                1605                1610                1615

Asp Gln Leu Glu Gln Ala Leu Asp Cys Glu Ile Tyr Gly Ala Cys Tyr
            1620                1625                1630

Ser Ile Glu Pro Leu Asp Leu Pro Pro Ile Ile Gln Arg Leu His Gly
        1635                1640                1645

Leu Ser Ala Phe Ser Leu His Ser Tyr Ser Pro Gly Glu Ile Asn Arg
    1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
                1685                1690                1695

Arg Ala Ala Ile Cys Gly Lys Tyr Leu Phe Asn Trp Ala Val Arg Thr
            1700                1705                1710

Lys Leu Lys Leu Thr Pro Ile Ala Ala Ala Gly Gln Leu Asp Leu Ser
        1715                1720                1725

Gly Trp Phe Thr Ala Gly Tyr Ser Gly Gly Asp Ile Tyr His Ser Val
    1730                1735                1740

Ser His Ala Arg Pro Arg Trp Ile Trp Phe Cys Leu Leu Leu Leu Ala
1745                1750                1755                1760
```

Ala Gly Val Gly Ile Tyr Leu Leu Pro Asn Arg
          1765              1770

<210> SEQ ID NO 10
<211> LENGTH: 19798
<212> TYPE: DNA
<213> ORGANISM: Artificial Sequence
<220> FEATURE:
<223> OTHER INFORMATION: Description of Artificial Sequence:
      pd.deltaNS3NS5.pj
<220> FEATURE:
<221> NAME/KEY: CDS
<222> LOCATION: (12679)..(17991)

<400> SEQUENCE: 10

```
atcgatccta cccccttgcgc taaagaagta tatgtgccta ctaacgcttg tctttgtctc      60
tgtcactaaa cactggatta ttactcccag atacttattt tggactaatt taaatgattt     120
cggatcaacg ttcttaatat cgctgaatct tccacaattg atgaaagtag ctaggaagag     180
gaattggtat aaagttttg tttttgtaaa tctcgaagta tactcaaacg aatttagtat     240
tttctcagtg atctcccaga tgctttcacc ctcacttaga agtgctttaa gcatttttt     300
actgtggcta tttcccttat ctgcttcttc cgatgattcg aactgtaatt gcaaactact     360
tacaatatca gtgatatcag attgatgttt ttgtccatag taaggaataa ttgtaaattc     420
ccaagcagga atcaatttct ttaatgaggc ttccagaatt gttgcttttt gcgtcttgta     480
tttaaactgg agtgatttat tgacaatatc gaaactcagc gaattgctta tgatagtatt     540
atagctcatg aatgtggctc tcttgattgc tgttccgtta tgtgtaatca tccaacataa     600
ataggttagt tcagcagcac ataatgctat tttctcacct gaaggtcttt caaacctttc     660
cacaaactga cgaacaagca ccttaggtgg tgttttacat aatatatcaa attgtggcat     720
gcttagcgcc gatcttgtgt gcaattgata tctagtttca actactctat ttatcttgta     780
tcttgcagta ttcaaacacg ctaactcgaa aaactaactt taattgtcct gtttgtctcg     840
cgttctttcg aaaaatgcac cggccgcgca ttatttgtac tgcgaaaata attggtactg     900
cggtatcttc atttcatatt ttaaaaatgc acctttgctg cttttcctta attttttagac    960
ggcccgcagg ttcgttttgc ggtactatct tgtgataaaa agttgttttg acatgtgatc    1020
tgcacagatt ttataatgta ataagcaaga atacattatc aaacgaacaa tactggtaaa    1080
agaaaaccaa aatggacgac attgaaacag ccaagaatct gacggtaaaa gcacgtacag    1140
cttatagcgt ctgggatgta tgtcggctgt ttattgaaat gattgctcct gatgtagata    1200
ttgatataga gagtaaacgt aagtctgatg agctactctt tccaggatat gtcataaggc    1260
ccatggaatc tctcacaacc ggtaggccgt atggtcttga ttctagcgca gaagattcca    1320
gcgtatcttc tgactccagt gctgaggtaa ttttgcctgc tgcgaagatg gttaaggaaa    1380
ggtttgattc gattggaaat ggtatgctct cttcacaaga agcaagtcag gctgccatag    1440
atttgatgct acagaataac aagctgttag acaatagaaa gcaactatac aaatctattg    1500
ctataataat aggaagattg cccgagaaag acaagaagag agctaccgaa atgctcatga    1560
gaaaaatgga ttgtacacag ttattagtcc caccagctcc aacggaagaa gatgttatga    1620
agctcgtaag cgtcgttacc caattgctta ctttagttcc accagatcgt caagctgctt    1680
taataggtga tttattcatc ccggaatctc taaaggatat attcaatagt ttcaatgaac    1740
tggcggcaga gaatcgttta cagcaaaaaa agagtgagtt ggaaggaagg actgaagtga    1800
accatgctaa tacaaatgaa gaagttccct ccaggcgaac aagaagtaga gacacaaatg    1860
```

```
caagaggagc atataaatta caaaacacca tcactgaggg ccctaaagcg gttcccacga   1920
aaaaaaggag agtagcaacg agggtaaggg gcagaaaatc acgtaatact tctagggtat   1980
gatccaatat caaaggaaat gatagcattg aaggatgaga ctaatccaat tgaggagtgg   2040
cagcatatag aacagctaaa gggtagtgct gaaggaagca tacgatacccc cgcatggaat  2100 gggataatat cacaggaggt actagactac ctttcatcct acataaatag acgcatataa   2160
gtacgcattt aagcataaac acgcactatg ccgttcttct catgtatata tatatacagg   2220
caacacgcag ataggtgc gacgtgaaca gtgagctgta tgtgcgcagc tcgcgttgca     2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acgagctact aaaatattgc gaataccgct   2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cacttttgaa   2760
ctttgtacga cgaattttga ggttcgccat cctctggcta tttccaatta tcctgtcggc   2820
tattatctcc gcctcagttt gatcttccgc ttcagactgc catttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctcttttccac aaacttagaa atgtattcat gaattatgga  3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttccctg cggtttagcg tgccttttac    3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt cttttttcaat taccggtgtg tcgtctgtat tcagtacatg   3480
tccaacaaat gcaaatgcta acgttttgta tttcttataa ttgtcaggaa ctggaaaagt   3540
cccccttgtc gtctcgatta cacacctact ttcatcgtac accataggtt ggaagtgctg   3600
cataatacat tgcttaatac aagcaagcag tctctcgcca ttcatatttc agttattttc   3660
cattacagct gatgtcattg tatatcagcg ctgtaaaaat ctatctgtta cagaaggttt   3720
tcgcggtttt tataaacaaa actttcgtta cgaaatcgag caatcacccc agctgcgtat   3780
ttggaaattc gggaaaaagt agagcaacgc gagttgcatt tttacacca taatgcatga    3840 ttaacttcga gaagggatta aggctaattt cactagtatg tttcaaaaac ctcaatctgt   3900
ccattgaatg cctataaaaa cagctataga ttgcatagaa gagttagcta ctcaatgctt   3960
tttgtcaaag cttactgatg atgatgtgtc tactttcagg cgggtctgta gtaaggagaa   4020
tgacattata aagctggcac ttagaattcc acgactata gactatacta gtatactccg    4080
tctactgtac gatacacttc cgctcaggtc cttgtccttt aacgaggcct taccactctt   4140
ttgttactct attgatccag ctcagcaaag gcagtgtgat ctaagattct atcttcgcga   4200
tgtagtaaaa ctagctagac cgagaaagag actagaaatg caaaaggcac ttctacaatg   4260
```

```
gctgccatca ttattatccg atgtgacgct gcattttttt tttttttttt tttttttttt    4320
tttttttttt tttttttttt tttttggta caaatatcat aaaaaaagag aatctttta      4380 agcaaggatt tcttaactt cttcggcgac agcatcaccg acttcggtgg tactgttgga     4440
accacctaaa tcaccagttc tgatacctgc atccaaaacc tttttaactg catcttcaat    4500
ggctttacct tcttcaggca agttcaatga caatttcaac atcattgcag cagacaagat    4560
agtggcgata gggttgacct tattctttgg caaatctgga gcggaaccat ggcatggttc    4620
gtacaaacca aatgcggtgt tcttgtctgg caaagaggcc aaggacgcag atggcaacaa    4680
acccaaggag cctgggataa cggaggcttc atcggagatg atatcaccaa acatgttgct    4740
ggtgattata ataccattta ggtgggttgg gttcttaact aggatcatgg cggcagaatc    4800
aatcaattga tgttgaactt tcaatgtagg gaattcgttc ttgatggttt cctccacagt    4860
ttttctccat aatcttgaag aggccaaaac attagcttta tccaaggacc aaataggcaa    4920
tggtggctca tgttgtaggg ccatgaaagc ggccattctt gtgattcttt gcacttctgg    4980
aacggtgtat tgttcactat cccaagcgac accatcacca tcgtcttcct ttctcttacc    5040
aaagtaaata cctcccacta attctctaac aacaacgaag tcagtacctt tagcaaattg    5100
tggcttgatt ggagataagt ctaaaagaga gtcggatgca aagttacatg gtcttaagtt    5160
ggcgtacaat tgaagttctt tacgattttt tagtaaacct tgttcaggtc taacactacc    5220
ggtaccccat ttaggaccac ccacagcacc taacaaaacg gcatcagcct tcttggaggc    5280
ttccagcgcc tcatctggaa gtggaacacc tgtagcatcg atagcagcac caccaattaa    5340
atgattttcg aaatcgaact tgacattgga acgaacatca gaaatagctt taagaacctt    5400
aatggcttcg gctgtgattt cttgaccaac gtggtcacct ggcaaaacga cgatcttctt    5460
aggggcagac attacaatgg tatatccttg aaatatatat aaaaaaaaaa aaaaaaaaa    5520 aaaaaaaaaa atgcagcttc tcaatgatat tcgaatacgc tttgaggaga tacagcctaa    5580
tatccgacaa actgttttac agatttacga tcgtacttgt tacccatcat tgaattttga    5640
acatccgaac ctgggagttt tccctgaaac agatagtata tttgaacctg tataataata    5700
tatagtctag cgctttacgg aagacaatgt atgtatttcg gttcctggag aaactattgc    5760
atctattgca taggtaatct tgcacgtcgc atccccggtt catttctgc gtttccatct    5820 tgcacttcaa tagcatatct ttgttaacga agcatctgtg cttcattttg tagaacaaaa    5880
atgcaacgcg agagcgctaa tttttcaaac aaagaatctg agctgcattt ttacagaaca    5940
gaaatgcaac gcgaaagcgc tattttacca acgaagaatc tgtgcttcat ttttgtaaaa    6000
caaaatgcaa acgcgagagc gctaattttt caaacaaaga atctgagctg catttttaca    6060
gaacagaaat gcaacgcgag agcgctattt taccaacaaa gaatctatac ttcttttttg    6120
ttctacaaaa atgcatcccg agagcgctat ttttctaaca aagcatctta gattactttt    6180
tttctccttt gtgcgctcta taatgcagtc tcttgataac ttttttgcact gtaggtccgt    6240 taaggttaga agaaggctac tttggtgtct atttttctctt ccataaaaaa agcctgactc    6300
cacttcccgc gtttactgat tactagcgaa gctgcgggtg catttttttca agataaaggc    6360 atccccgatt atattctata ccgatgtgga ttgcgcatac tttgtgaaca gaaagtgata    6420
gcgttgatga ttcttcattg gtcagaaaat tatgaacggt ttcttctatt ttgtctctat    6480
atactacgta taggaaatgt ttacattttc gtattgtttt cgattcactc tatgaatagt    6540
tcttactaca atttttttgt ctaaagagta atactagaga taaacataaa aaatgtagag    6600
```

```
gtcgagttta gatgcaagtt caaggagcga aaggtggatg ggtaggttat atagggatat   6660
agcacagaga tatatagcaa agagatactt ttgagcaatg tttgtggaag cggtattcgc   6720 aatatttag tagctcgtta cagtccggtg cgttttggt tttttgaaag tgcgtcttca   6780
gagcgctttt ggttttcaaa agcgctctga agttcctata ctttctagag aataggaact   6840
tcggaatagg aacttcaaag cgtttccgaa aacgagcgct tccgaaaatg caacgcgagc   6900
tgcgcacata cagctcactg ttcacgtcgc acctatatct gcgtgttgcc tgtatatata   6960
tatacatgag aagaacggca tagtgcgtgt ttatgcttaa atgcgtactt atatgcgtct   7020
atttatgtag gatgaaaggt agtctagtac ctcctgtgat attatcccat tccatgcggg   7080
gtatcgtatg cttccttcag cactacccttt tagctgttct atatgctgcc actcctcaat   7140
tggattagtc tcatccttca atgctatcat ttcctttgat attggatcat atgcatagta   7200
ccgagaaact agtgcgaagt agtgatcagg tattgctgtt atctgatgag tatacgttgt   7260
cctggccacg gcagaagcac gcttatcgct ccaatttccc acaacattag tcaactccgt   7320
taggcccttc attgaaagaa atgaggtcat caaatgtctt ccaatgtgag attttgggcc   7380
attttttata gcaaagattg aataaggcgc attttcttc aaagctttat tgtacgatct   7440
gactaagtta tcttttaata attggtattc ctgtttattg cttgaagaat tgccggtcct   7500
atttactcgt tttaggactg gttcagaatt cctcaaaaat tcatccaaat atacaagtgg   7560
atcgatgata agctgtcaaa catgagaatt cttgaagacg aaagggcctc gtgatacgcc   7620
tatttttata ggttaatgtc atgataataa tggtttctta gacgtcaggt ggcacttttc   7680
ggggaaatgt gcgcggaacc cctatttgtt tattttcta aatacattca aatatgtatc   7740
cgctcatgag acaataaccc tgataaatgc ttcaataata ttgaaaaagg aagagtatga   7800
gtattcaaca tttccgtgtc gcccttattc cctttttgc ggcattttgc cttcctgttt   7860
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct ttttgcaca acatggggga tcatgtaact cgccttgatc   8280
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata atctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
```

```
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcagggggg gcggagccta tggaaaaacg   9420
ccagcaacgc ggcctttttta cggttcctgg ccttttgctg gccttttgct cacatgttct   9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg ccatgttaa gggcggtttt  10020 ttcctgtttg gtcactgatg cctccgtgta agggggattt ctgttcatgg gggtaatgat  10080
accgatgaaa cgagagagga tgctcacgat acgggttact gatgatgaac atgcccggtt  10140
actggaacgt tgtgagggta acaactggcg gtatggatg cggcgggacc agagaaaaat  10200
cactcagggt caatgccagc gcttcgttaa tacagatgta ggtgttccac agggtagcca  10260
gcagcatcct gcgatgcaga tccggaacat aatggtgcag ggcgctgact ccgcgtttc  10320 cagactttac gaaacacgga aaccgaagac cattcatgtt gttgctcagg tcgcagacgt  10380
tttgcagcag cagtcgcttc acgttcgctc gcgtatcggt gattcattct gctaaccagt  10440
aaggcaaccc cgccagccta gccgggtcct caacgacagg agcacgatca tgcgcacccg  10500
tggccaggac ccaacgctgc ccgagatgcg ccgcgtgcgg ctgctggaga tggcggacgc  10560
gatggatatg ttctgccaag ggttggttg cgcattcaca gttctccgca agaattgatt  10620
ggctccaatt cttggagtgg tgaatccgtt agcgaggtgc cgccggcttc cattcaggtc  10680
gaggtggccc ggctccatgc accgcgacgc aacgcgggga ggcagacaag gtatagggcg  10740
gcgcctacaa tccatgccaa cccgttccat gtgctcgccg aggcggcata aatcgccgtg  10800
acgatcagcg gtccaatgat cgaagttagg ctggtaagag ccgcgagcga tccttgaagc  10860
tgtccctgat ggtcgtcatc tacctgcctg gacagcatgg cctgcaacgc gggcatcccg  10920
atgccgccgg aagcgagaag aatcataatg gggaaggcca tccagcctcg cgtcgcgaac  10980
gccagcaaga cgtagcccag cgcgtcggcc gccatgccgg cgataatggc ctgcttctcg  11040
ccgaaacgtt tggtggcggg accagtgacg aaggcttgag cgagggcgtg caagattccg  11100
aataccgcaa cgacaggcc gatcatcgtc gcgctccagc gaaagcggtc ctcgccgaaa  11160
atgacccaga gcgctgccgg cacctgtcct acagattgca tgataaagaa gacagtcata  11220
agtgcggcga cgatagtcat gccccgcgcc caccggaagg agctgactgg gttgaaggct  11280
ctcaagggca tcggtcgagg atccttcaat atgcgcacat acgctgttat gttcaaggtc  11340
```

-continued

```
ccttcgttta agaacgaaag cggtcttcct tttgagggat gtttcaagtt gttcaaatct    11400
atcaaatttg caaatcccca gtctgtatct agagcgttga atcggtgatg cgatttgtta    11460
attaaattga tggtgtcacc attaccaggt ctagatatac caatggcaaa ctgagcacaa    11520
caataccagt ccggatcaac tggcaccatc tctcccgtag tctcatctaa ttttcttcc     11580 ggatgaggtt ccagatatac cgcaacacct ttattatggt ttccctgagg gaataataga    11640
atgtcccatt cgaaatcacc aattctaaac ctgggcgaat tgtatttcgg gtttgttaac    11700
tcgttccagt caggaatgtt ccacgtgaag ctatcttcca gcaaagtctc cacttcttca    11760
tcaaattgtg gagaatactc ccaatgctct tatctatggg acttccggga aacacagtac    11820
cgatacttcc caattcgtct tcagagctca ttgtttgttt gaagagacta atcaaagaat    11880
cgttttctca aaaaaattaa tatcttaact gatagtttga tcaaggggc aaaacgtagg     11940 ggcaaacaaa cggaaaaatc gtttctcaaa ttttctgatg ccaagaactc taaccagtct    12000
tatctaaaaa ttgccttatg atccgtctct ccggttacag cctgtgtaac tgattaatcc    12060
tgcctttcta atcaccattc taatgtttta attaagggat tttgtcttca ttaacggctt    12120
tcgctcataa aaatgttatg acgttttgcc cgcaggcggg aaaccatcca cttcacgaga    12180
ctgatctcct ctgccggaac accgggcatc tccaacttat aagttggaga aataagagaa    12240
tttcagattg agagaatgaa aaaaaaaaac ccttagttca taggtccatt ctcttagcgc    12300
aactacagag aacaggggca caaacaggca aaaacgggc acaacctcaa tggagtgatg     12360
caacctgcct ggagtaaatg atgacacaag gcaattgacc cacgcatgta tctatctcat    12420
tttcttacac cttctattac cttctgctct ctctgatttg gaaaaagctg aaaaaaaagg    12480
ttgaaaccag ttccctgaaa ttattcccct acttgactaa taagtatata aagacggtag    12540
gtattgattg taattctgta aatctatttc ttaaacttct taaattctac ttttatagtt    12600
agtctttttt ttagttttaa aacaccaaga acttagtttc gaataaacac acataaacaa    12660
acaagcttac aaaacaaa atg gct gca tat gca gct cag ggc tat aag gtg       12711
                    Met Ala Ala Tyr Ala Ala Gln Gly Tyr Lys Val
                     1               5                  10 cta gta ctc aac ccc tct gtt gct gca aca ctg ggc ttt ggt gct tac       12759
Leu Val Leu Asn Pro Ser Val Ala Ala Thr Leu Gly Phe Gly Ala Tyr
             15                  20                  25 atg tcc aag gct cat ggg atc gat cct aac atc agg acc ggg gtg aga       12807
Met Ser Lys Ala His Gly Ile Asp Pro Asn Ile Arg Thr Gly Val Arg
         30                  35                  40 aca att acc act ggc agc ccc atc acg tac tcc acc tac ggc aag ttc       12855
Thr Ile Thr Thr Gly Ser Pro Ile Thr Tyr Ser Thr Tyr Gly Lys Phe
     45                  50                  55 ctt gcc gac ggc ggg tgc tcg ggg ggc gct tat gac ata ata att tgt       12903
Leu Ala Asp Gly Gly Cys Ser Gly Gly Ala Tyr Asp Ile Ile Ile Cys
 60                  65                  70                  75 gac gag tgc cac tcc acg gat gcc aca tcc atc ttg ggc att ggc act       12951
Asp Glu Cys His Ser Thr Asp Ala Thr Ser Ile Leu Gly Ile Gly Thr
                 80                  85                  90 gtc ctt gac caa gca gag act gcg ggg gcg aga ctg gtt gtg ctc gcc       12999
Val Leu Asp Gln Ala Glu Thr Ala Gly Ala Arg Leu Val Val Leu Ala
             95                 100                 105 acc gcc acc cct ccg ggc tcc gtc act gtg ccc cat ccc aac atc gag       13047
Thr Ala Thr Pro Pro Gly Ser Val Thr Val Pro His Pro Asn Ile Glu
         110                 115                 120 gag gtt gct ctg tcc acc acc gga gag atc cct ttt tac ggc aag gct       13095
Glu Val Ala Leu Ser Thr Thr Gly Glu Ile Pro Phe Tyr Gly Lys Ala
    125                 130                 135
```

-continued

| | |
|---|---|
| atc ccc ctc gaa gta atc aag ggg ggg aga cat ctc atc ttc tgt cat<br>Ile Pro Leu Glu Val Ile Lys Gly Gly Arg His Leu Ile Phe Cys His<br>140                       145                         150                      155 | 13143 |
| tca aag aag aag tgc gac gaa ctc gcc gca aag ctg gtc gca ttg ggc<br>Ser Lys Lys Lys Cys Asp Glu Leu Ala Ala Lys Leu Val Ala Leu Gly<br>                    160                       165                    170 | 13191 |
| atc aat gcc gtg gcc tac tac cgc ggt ctt gac gtg tcc gtc atc ccg<br>Ile Asn Ala Val Ala Tyr Tyr Arg Gly Leu Asp Val Ser Val Ile Pro<br>             175                        180                      185 | 13239 |
| acc agc ggc gat gtt gtc gtc gtg gca acc gat gcc ctc atg acc ggc<br>Thr Ser Gly Asp Val Val Val Val Ala Thr Asp Ala Leu Met Thr Gly<br>                    190                       195                    200 | 13287 |
| tat acc ggc gac ttc gac tcg gtg ata gac tgc aat acg tgt gtc acc<br>Tyr Thr Gly Asp Phe Asp Ser Val Ile Asp Cys Asn Thr Cys Val Thr<br>     205                       210                      215 | 13335 |
| cag aca gtc gat ttc agc ctt gac cct acc ttc acc att gag aca atc<br>Gln Thr Val Asp Phe Ser Leu Asp Pro Thr Phe Thr Ile Glu Thr Ile<br>220                       225                         230                      235 | 13383 |
| acg ctc ccc caa gat gct gtc tcc cgc act caa cgt cgg ggc agg act<br>Thr Leu Pro Gln Asp Ala Val Ser Arg Thr Gln Arg Arg Gly Arg Thr<br>                    240                       245                    250 | 13431 |
| ggc agg ggg aag cca ggc atc tac aga ttt gtg gca ccg ggg gag cgc<br>Gly Arg Gly Lys Pro Gly Ile Tyr Arg Phe Val Ala Pro Gly Glu Arg<br>             255                        260                      265 | 13479 |
| ccc tcc ggc atg ttc gac tcg tcc gtc ctc tgt gag tgc tat gac gca<br>Pro Ser Gly Met Phe Asp Ser Ser Val Leu Cys Glu Cys Tyr Asp Ala<br>                    270                       275                    280 | 13527 |
| ggc tgt gct tgg tat gag ctc acg ccc gcc gag act aca gtt agg cta<br>Gly Cys Ala Trp Tyr Glu Leu Thr Pro Ala Glu Thr Thr Val Arg Leu<br>285                       290                         295 | 13575 |
| cga gcg tac atg aac acc ccg ggg ctt ccc gtg tgc cag gac cat ctt<br>Arg Ala Tyr Met Asn Thr Pro Gly Leu Pro Val Cys Gln Asp His Leu<br>300                       305                         310                      315 | 13623 |
| gaa ttt tgg gag ggc gtc ttt aca ggc ctc act cat ata gat gcc cac<br>Glu Phe Trp Glu Gly Val Phe Thr Gly Leu Thr His Ile Asp Ala His<br>                    320                       325                    330 | 13671 |
| ttt cta tcc cag aca aag cag agt ggg gag aac ctt cct tac ctg gta<br>Phe Leu Ser Gln Thr Lys Gln Ser Gly Glu Asn Leu Pro Tyr Leu Val<br>             335                        340                      345 | 13719 |
| gcg tac caa gcc acc gtg tgc gct agg gct caa gcc cct ccc cca tcg<br>Ala Tyr Gln Ala Thr Val Cys Ala Arg Ala Gln Ala Pro Pro Pro Ser<br>                    350                       355                    360 | 13767 |
| tgg gac cag atg tgg aag tgt ttg att cgc ctc aag ccc acc ctc cat<br>Trp Asp Gln Met Trp Lys Cys Leu Ile Arg Leu Lys Pro Thr Leu His<br>365                       370                         375 | 13815 |
| ggg cca aca ccc ctg cta tac aga ctg ggc gct gtt cag aat gaa atc<br>Gly Pro Thr Pro Leu Leu Tyr Arg Leu Gly Ala Val Gln Asn Glu Ile<br>380                       385                         390                      395 | 13863 |
| acc ctg acg cac cca gtc acc aaa tac atc atg aca tgc atg tcg gcc<br>Thr Leu Thr His Pro Val Thr Lys Tyr Ile Met Thr Cys Met Ser Ala<br>                    400                       405                    410 | 13911 |
| gac ctg gag gtc gtc acg agc acc tgg gtg ctc gtt ggc ggc gtc ctg<br>Asp Leu Glu Val Val Thr Ser Thr Trp Val Leu Val Gly Gly Val Leu<br>             415                        420                      425 | 13959 |
| gct gct ttg gcc gcg tat tgc ctg tca aca ggc tgc gtg gtc ata gtg<br>Ala Ala Leu Ala Ala Tyr Cys Leu Ser Thr Gly Cys Val Val Ile Val<br>                    430                       435                    440 | 14007 |
| ggc agg gtc gtc ttg tcc ggg aag ccg gca atc ata cct gac agg gaa<br>Gly Arg Val Val Leu Ser Gly Lys Pro Ala Ile Ile Pro Asp Arg Glu | 14055 |

```
                    -continued
     445              450              455 gtc ctc tac cga gag ttc gat gag atg gaa gag tgc tct cag cac tta   14103
Val Leu Tyr Arg Glu Phe Asp Glu Met Glu Glu Cys Ser Gln His Leu
460              465              470              475 ccg tac atc gag caa ggg atg atg ctc gcc gag cag ttc aag cag aag   14151
Pro Tyr Ile Glu Gln Gly Met Met Leu Ala Glu Gln Phe Lys Gln Lys
             480              485              490 gcc ctc ggc ctc ctg cag acc gcg tcc cgt cag gca gag gtt atc gcc   14199
Ala Leu Gly Leu Leu Gln Thr Ala Ser Arg Gln Ala Glu Val Ile Ala
             495              500              505 cct gct gtc cag acc aac tgg caa aaa ctc gag acc ttc tgg gcg aag   14247
Pro Ala Val Gln Thr Asn Trp Gln Lys Leu Glu Thr Phe Trp Ala Lys
             510              515              520 cat atg tgg aac ttc atc agt ggg ata caa tac ttg gcg ggc ttg tca   14295
His Met Trp Asn Phe Ile Ser Gly Ile Gln Tyr Leu Ala Gly Leu Ser
525              530              535 acg ctg cct ggt aac ccc gcc att gct tca ttg atg gct ttt aca gct   14343
Thr Leu Pro Gly Asn Pro Ala Ile Ala Ser Leu Met Ala Phe Thr Ala
540              545              550              555 gct gtc acc agc cca cta acc act agc caa acc ctc ctc ttc aac ata   14391
Ala Val Thr Ser Pro Leu Thr Thr Ser Gln Thr Leu Leu Phe Asn Ile
             560              565              570 ttg ggg ggg tgg gtg gct gcc cag ctc gcc gcc ccc ggt gcc gct act   14439
Leu Gly Gly Trp Val Ala Ala Gln Leu Ala Ala Pro Gly Ala Ala Thr
             575              580              585 gcc ttt gtg ggc gct ggc tta gct ggc gcc gcc atc ggc agt gtt gga   14487
Ala Phe Val Gly Ala Gly Leu Ala Gly Ala Ala Ile Gly Ser Val Gly
             590              595              600 ctg ggg aag gtc ctc ata gac atc ctt gca ggg tat ggc gcg ggc gtg   14535
Leu Gly Lys Val Leu Ile Asp Ile Leu Ala Gly Tyr Gly Ala Gly Val
605              610              615 gcg gga gct ctt gtg gca ttc aag atc atg agc ggt gag gtc ccc tcc   14583
Ala Gly Ala Leu Val Ala Phe Lys Ile Met Ser Gly Glu Val Pro Ser
620              625              630              635 acg gag gac ctg gtc aat cta ctg ccc gcc atc ctc tcg ccc gga gcc   14631
Thr Glu Asp Leu Val Asn Leu Leu Pro Ala Ile Leu Ser Pro Gly Ala
             640              645              650 ctc gta gtc ggc gtg gtc tgt gca gca ata ctg cgc cgg cac gtt ggc   14679
Leu Val Val Gly Val Val Cys Ala Ala Ile Leu Arg Arg His Val Gly
             655              660              665 ccg ggc gag ggg gca gtg cag tgg atg aac cgg ctg ata gcc ttc gcc   14727
Pro Gly Glu Gly Ala Val Gln Trp Met Asn Arg Leu Ile Ala Phe Ala
             670              675              680 tcc cgg ggg aac cat gtt tcc ccc acg cac tac gtg ccg gag agc gat   14775
Ser Arg Gly Asn His Val Ser Pro Thr His Tyr Val Pro Glu Ser Asp
685              690              695 gca gct gcc cgc gtc act gcc ata ctc agc agc ctc act gta acc cag   14823
Ala Ala Ala Arg Val Thr Ala Ile Leu Ser Ser Leu Thr Val Thr Gln
700              705              710              715 ctc ctg agg cga ctg cac cag tgg ata agc tcg gag tgt acc act cca   14871
Leu Leu Arg Arg Leu His Gln Trp Ile Ser Ser Glu Cys Thr Thr Pro
             720              725              730 tgc tcc ggt tcc tgg cta agg gac atc tgg gac tgg ata tgc gag gtg   14919
Cys Ser Gly Ser Trp Leu Arg Asp Ile Trp Asp Trp Ile Cys Glu Val
             735              740              745 ttg agc gac ttt aag acc tgg cta aaa gct aag ctc atg cca cag ctg   14967
Leu Ser Asp Phe Lys Thr Trp Leu Lys Ala Lys Leu Met Pro Gln Leu
             750              755              760 cct ggg atc ccc ttt gtg tcc tgc cag cgc ggg tat aag ggg gtc tgg   15015
```

-continued

| | | | | | | | | | | | | |
|---|---|---|---|---|---|---|---|---|---|---|---|---|
| Pro | Gly | Ile | Pro | Phe | Val | Ser | Cys | Gln | Arg | Gly | Tyr | Lys | Gly | Val | Trp |
| | 765 | | | | 770 | | | | 775 | | | |

```
cga ggg gac ggc atc atg cac act cgc tgc cac tgt gga gct gag atc     15063
Arg Gly Asp Gly Ile Met His Thr Arg Cys His Cys Gly Ala Glu Ile
780                 785                 790                 795 act gga cat gtc aaa aac ggg acg atg agg atc gtc ggt cct agg acc     15111
Thr Gly His Val Lys Asn Gly Thr Met Arg Ile Val Gly Pro Arg Thr
                800                 805                 810 tgc agg aac atg tgg agt ggg acc ttc ccc att aat gcc tac acc acg     15159
Cys Arg Asn Met Trp Ser Gly Thr Phe Pro Ile Asn Ala Tyr Thr Thr
            815                 820                 825 ggc ccc tgt acc ccc ctt cct gcg ccg aac tac acg ttc gcg cta tgg     15207
Gly Pro Cys Thr Pro Leu Pro Ala Pro Asn Tyr Thr Phe Ala Leu Trp
        830                 835                 840 agg gtg tct gca gag gaa tac gtg gag ata agg cag gtg ggg gac ttc     15255
Arg Val Ser Ala Glu Glu Tyr Val Glu Ile Arg Gln Val Gly Asp Phe
    845                 850                 855 cac tac gtg acg ggt atg act act gac aat ctt aaa tgc ccg tgc cag     15303
His Tyr Val Thr Gly Met Thr Thr Asp Asn Leu Lys Cys Pro Cys Gln
860                 865                 870                 875 gtc cca tcg ccc gaa ttt ttc aca gaa ttg gac ggg gtg cgc tta cat     15351
Val Pro Ser Pro Glu Phe Phe Thr Glu Leu Asp Gly Val Arg Leu His
                880                 885                 890 agg ttt gcg ccc ccc tgc aag ccc ttg ctg cgg gag gag gta tca ttc     15399
Arg Phe Ala Pro Pro Cys Lys Pro Leu Leu Arg Glu Glu Val Ser Phe
            895                 900                 905 aga gta gga ctc cac gaa tac ccg gta ggg tcg caa tta cct tgc gag     15447
Arg Val Gly Leu His Glu Tyr Pro Val Gly Ser Gln Leu Pro Cys Glu
        910                 915                 920 ccc gaa ccg gac gtg gcc gtg ttg acg tcc atg ctc act gat ccc tcc     15495
Pro Glu Pro Asp Val Ala Val Leu Thr Ser Met Leu Thr Asp Pro Ser
    925                 930                 935 cat ata aca gca gag gcg gcc ggg cga agg ttg gcg agg gga tca ccc     15543
His Ile Thr Ala Glu Ala Ala Gly Arg Arg Leu Ala Arg Gly Ser Pro
940                 945                 950                 955 ccc tct gtg gcc agc tcc tcg gct agc cag cta tcc gct cca tct ctc     15591
Pro Ser Val Ala Ser Ser Ser Ala Ser Gln Leu Ser Ala Pro Ser Leu
                960                 965                 970 aag gca act tgc acc gct aac cat gac tcc cct gat gct gag ctc ata     15639
Lys Ala Thr Cys Thr Ala Asn His Asp Ser Pro Asp Ala Glu Leu Ile
            975                 980                 985 gag gcc aac ctc cta tgg agg cag gag atg ggc ggc aac atc acc agg     15687
Glu Ala Asn Leu Leu Trp Arg Gln Glu Met Gly Gly Asn Ile Thr Arg
        990                 995                 1000 gtt gag tca gaa aac aaa gtg gtg att ctg gac tcc ttc gat ccg ctt     15735
Val Glu Ser Glu Asn Lys Val Val Ile Leu Asp Ser Phe Asp Pro Leu
    1005                1010                1015 gtg gcg gag gag gac gag cgg gag atc tcc gta ccc gca gaa atc ctg     15783
Val Ala Glu Glu Asp Glu Arg Glu Ile Ser Val Pro Ala Glu Ile Leu
1020                1025                1030                1035 cgg aag tct cgg aga ttc gcc cag gcc ctg ccc gtt tgg gcg cgg ccg     15831
Arg Lys Ser Arg Arg Phe Ala Gln Ala Leu Pro Val Trp Ala Arg Pro
                1040                1045                1050 gac tat aac ccc ccg cta gtg gag acg tgg aaa aag ccc gac tac gaa     15879
Asp Tyr Asn Pro Pro Leu Val Glu Thr Trp Lys Lys Pro Asp Tyr Glu
            1055                1060                1065 cca cct gtg gtc cat ggc tgc ccg ctt cca cct cca aag tcc cct cct     15927
Pro Pro Val Val His Gly Cys Pro Leu Pro Pro Pro Lys Ser Pro Pro
        1070                1075                1080
```

```
gtg cct ccg cct cgg aag aag cgg acg gtg gtc ctc act gaa tca acc     15975
Val Pro Pro Pro Arg Lys Lys Arg Thr Val Val Leu Thr Glu Ser Thr
    1085                1090                1095 cta tct act gcc ttg gcc gag ctc gcc acc aga agc ttt ggc agc tcc     16023
Leu Ser Thr Ala Leu Ala Glu Leu Ala Thr Arg Ser Phe Gly Ser Ser
1100                1105                1110                1115 tca act tcc ggc att acg ggc gac aat acg aca aca tcc tct gag ccc     16071
Ser Thr Ser Gly Ile Thr Gly Asp Asn Thr Thr Thr Ser Ser Glu Pro
                1120                1125                1130 gcc cct tct ggc tgc ccc ccc gac tcc gac gct gag tcc tat tcc tcc     16119
Ala Pro Ser Gly Cys Pro Pro Asp Ser Asp Ala Glu Ser Tyr Ser Ser
        1135                1140                1145 atg ccc ccc ctg gag ggg gag cct ggg gat ccg gat ctt agc gac ggg     16167
Met Pro Pro Leu Glu Gly Glu Pro Gly Asp Pro Asp Leu Ser Asp Gly
    1150                1155                1160 tca tgg tca acg gtc agt agt gag gcc aac gcg gag gat gtc gtg tgc     16215
Ser Trp Ser Thr Val Ser Ser Glu Ala Asn Ala Glu Asp Val Val Cys
1165                1170                1175 tgc tca atg tct tac tct tgg aca ggc gca ctc gtc acc ccg tgc gcc     16263
Cys Ser Met Ser Tyr Ser Trp Thr Gly Ala Leu Val Thr Pro Cys Ala
1180                1185                1190                1195 gcg gaa gaa cag aaa ctg ccc atc aat gca cta agc aac tcg ttg cta     16311
Ala Glu Glu Gln Lys Leu Pro Ile Asn Ala Leu Ser Asn Ser Leu Leu
                1200                1205                1210 cgt cac cac aat ttg gtg tat tcc acc acc tca cgc agt gct tgc caa     16359
Arg His His Asn Leu Val Tyr Ser Thr Thr Ser Arg Ser Ala Cys Gln
        1215                1220                1225 agg cag aag aaa gtc aca ttt gac aga ctg caa gtt ctg gac agc cat     16407
Arg Gln Lys Lys Val Thr Phe Asp Arg Leu Gln Val Leu Asp Ser His
    1230                1235                1240 tac cag gac gta ctc aag gag gtt aaa gca gcg gcg tca aaa gtg aag     16455
Tyr Gln Asp Val Leu Lys Glu Val Lys Ala Ala Ala Ser Lys Val Lys
    1245                1250                1255 gct aac ttg cta tcc gta gag gaa gct tgc agc ctg acg ccc cca cac     16503
Ala Asn Leu Leu Ser Val Glu Glu Ala Cys Ser Leu Thr Pro Pro His
1260                1265                1270                1275 tca gcc aaa tcc aag ttt ggt tat ggg gca aaa gac gtc cgt tgc cat     16551
Ser Ala Lys Ser Lys Phe Gly Tyr Gly Ala Lys Asp Val Arg Cys His
                1280                1285                1290 gcc aga aag gcc gta acc cac atc aac tcc gtg tgg aaa gac ctt ctg     16599
Ala Arg Lys Ala Val Thr His Ile Asn Ser Val Trp Lys Asp Leu Leu
        1295                1300                1305 gaa gac aat gta aca cca ata gac act acc atc atg gct aag aac gag     16647
Glu Asp Asn Val Thr Pro Ile Asp Thr Thr Ile Met Ala Lys Asn Glu
    1310                1315                1320 gtt ttc tgc gtt cag cct gag aag ggg ggt cgt aag cca gct cgt ctc     16695
Val Phe Cys Val Gln Pro Glu Lys Gly Gly Arg Lys Pro Ala Arg Leu
    1325                1330                1335 atc gtg ttc ccc gat ctg ggc gtg cgc gtg tgc gaa aag atg gct ttg     16743
Ile Val Phe Pro Asp Leu Gly Val Arg Val Cys Glu Lys Met Ala Leu
1340                1345                1350                1355 tac gac gtg gtt aca aag ctc ccc ttg gcc gtg atg gga agc tcc tac     16791
Tyr Asp Val Val Thr Lys Leu Pro Leu Ala Val Met Gly Ser Ser Tyr
                1360                1365                1370 gga ttc caa tac tca cca gga cag cgg gtt gaa ttc ctc gtg caa gcg     16839
Gly Phe Gln Tyr Ser Pro Gly Gln Arg Val Glu Phe Leu Val Gln Ala
        1375                1380                1385 tgg aag tcc aag aaa acc cca atg ggg ttc tcg tat gat acc cgc tgc     16887
Trp Lys Ser Lys Lys Thr Pro Met Gly Phe Ser Tyr Asp Thr Arg Cys
    1390                1395                1400
```

```
ttt gac tcc aca gtc act gag agc gac atc cgt acg gag gag gca atc      16935
Phe Asp Ser Thr Val Thr Glu Ser Asp Ile Arg Thr Glu Glu Ala Ile
    1405                1410                1415 tac caa tgt tgt gac ctc gac ccc caa gcc cgc gtg gcc atc aag tcc      16983
Tyr Gln Cys Cys Asp Leu Asp Pro Gln Ala Arg Val Ala Ile Lys Ser
1420                1425                1430                1435 ctc acc gag agg ctt tat gtt ggg ggc cct ctt acc aat tca agg ggg      17031
Leu Thr Glu Arg Leu Tyr Val Gly Gly Pro Leu Thr Asn Ser Arg Gly
                1440                1445                1450 gag aac tgc ggc tat cgc agg tgc cgc gcg agc ggc gta ctg aca act      17079
Glu Asn Cys Gly Tyr Arg Arg Cys Arg Ala Ser Gly Val Leu Thr Thr
    1455                1460                1465 agc tgt ggt aac acc ctc act tgc tac atc aag gcc cgg gca gcc tgt      17127
Ser Cys Gly Asn Thr Leu Thr Cys Tyr Ile Lys Ala Arg Ala Ala Cys
        1470                1475                1480 cga gcc gca ggg ctc cag gac tgc acc atg ctc gtg tgt ggc gac gac      17175
Arg Ala Ala Gly Leu Gln Asp Cys Thr Met Leu Val Cys Gly Asp Asp
    1485                1490                1495 tta gtc gtt atc tgt gaa agc gcg ggg gtc cag gag gac gcg gcg agc      17223
Leu Val Val Ile Cys Glu Ser Ala Gly Val Gln Glu Asp Ala Ala Ser
1500                1505                1510                1515 ctg aga gcc ttc acg gag gct atg acc agg tac tcc gcc ccc cct ggg      17271
Leu Arg Ala Phe Thr Glu Ala Met Thr Arg Tyr Ser Ala Pro Pro Gly
                1520                1525                1530 gac ccc cca caa cca gaa tac gac ttg gag ctc ata aca tca tgc tcc      17319
Asp Pro Pro Gln Pro Glu Tyr Asp Leu Glu Leu Ile Thr Ser Cys Ser
    1535                1540                1545 tcc aac gtg tca gtc gcc cac gac ggc gct gga aag agg gtc tac tac      17367
Ser Asn Val Ser Val Ala His Asp Gly Ala Gly Lys Arg Val Tyr Tyr
        1550                1555                1560 ctc acc cgt gac cct aca acc ccc ctc gcg aga gct gcg tgg gag aca      17415
Leu Thr Arg Asp Pro Thr Thr Pro Leu Ala Arg Ala Ala Trp Glu Thr
    1565                1570                1575 gca aga cac act cca gtc aat tcc tgg cta ggc aac ata atc atg ttt      17463
Ala Arg His Thr Pro Val Asn Ser Trp Leu Gly Asn Ile Ile Met Phe
1580                1585                1590                1595 gcc ccc aca ctg tgg gcg agg atg ata ctg atg acc cat ttc ttt agc      17511
Ala Pro Thr Leu Trp Ala Arg Met Ile Leu Met Thr His Phe Phe Ser
                1600                1605                1610 gtc ctt ata gcc agg gac cag ctt gaa cag gcc ctc gat tgc gag atc      17559
Val Leu Ile Ala Arg Asp Gln Leu Glu Gln Ala Leu Asp Cys Glu Ile
    1615                1620                1625 tac ggg gcc tgc tac tcc ata gaa cca ctg gat cta cct cca atc att      17607
Tyr Gly Ala Cys Tyr Ser Ile Glu Pro Leu Asp Leu Pro Pro Ile Ile
        1630                1635                1640 caa aga ctc cat ggc ctc agc gca ttt tca ctc cac agt tac tct cca      17655
Gln Arg Leu His Gly Leu Ser Ala Phe Ser Leu His Ser Tyr Ser Pro
    1645                1650                1655 ggt gaa atc aat agg gtg gcc gca tgc ctc aga aaa ctt ggg gta ccg      17703
Gly Glu Ile Asn Arg Val Ala Ala Cys Leu Arg Lys Leu Gly Val Pro
1660                1665                1670                1675 ccc ttg cga gct tgg aga cac cgg gcc cgg agc gtc cgc gct agg ctt      17751
Pro Leu Arg Ala Trp Arg His Arg Ala Arg Ser Val Arg Ala Arg Leu
                1680                1685                1690 ctg gcc aga gga ggc agg gct gcc ata tgt ggc aag tac ctc ttc aac      17799
Leu Ala Arg Gly Gly Arg Ala Ala Ile Cys Gly Lys Tyr Leu Phe Asn
    1695                1700                1705 tgg gca gta aga aca aag ctc aaa ctc act cca ata gcg gcc gct ggc      17847
Trp Ala Val Arg Thr Lys Leu Lys Leu Thr Pro Ile Ala Ala Ala Gly
```

```
       1710               1715               1720
cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
    1725               1730               1735 att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740               1745               1750               1755 cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
                    1760               1765               1770 tgaatagtcg actttgttcc cactgtactt ttagctcgta caaaatacaa tatacttttc   18051
atttctccgt aaacaacatg tttccccatg taatatcctt ttctattttt cgttccgtta   18111
ccaactttac atacttta tatagctatt cacttctata cactaaaaaa ctaagacaat    18171
tttaattttg ctgcctgcca tatttcaatt tgttataaat tcctataatt tatcctatta   18231
gtagctaaaa aaagatgaat gtgaatcgaa tcctaagaga attggatctg atccacagga   18291
cgggtgtggt cgccatgatc gcgtagtcga tagtggctcc aagtagcgaa gcgagcagga   18351
ctgggcggcg gccaaagcgg tcggacagtg ctccgagaac gggtgcgcat agaaattgca   18411
tcaacgcata tagcgctagc agcacgccat agtgactggc gatgctgtcg aatggacga    18471 tatcccgcaa gaggcccggc agtaccggca taaccaagcc tatgcctaca gcatccaggg   18531
tgacggtgcc gaggatgacg atgagcgcat tgttagattt catacacggt gcctgactgc   18591
gttagcaatt taactgtgat aaactaccgc attaaagctt tttctttcca attttttttt   18651
tttcgtcatt ataaaaatca ttacgaccga gattcccggg taataactga tataattaaa   18711
ttgaagctct aatttgtgag tttagtatac atgcatttac ttataataca gttttttagt   18771
tttgctggcc gcatcttctc aaatatgctt cccagcctgc ttttctgtaa cgttcaccct   18831
ctaccttagc atcccttccc tttgcaaata gtcctcttcc aacaataata atgtcagatc   18891
ctgtagagac cacatcatcc acggttctat actgttgacc caatgcgtct cccttgtcat   18951
ctaaacccac accgggtgtc ataatcaacc aatcgtaacc ttcatctctt ccacccatgt   19011
ctctttgagc aataaagccg ataacaaaat ctttgtcgct cttcgcaatg tcaacagtac   19071
ccttagtata ttctccagta gatagggagc ccttgcatga caattctgct aacatcaaaa   19131
ggcctctagg ttccttttgtt acttcttctg ccgcctgctt caaaccgcta acaatacctg   19191
ggcccaccac accgtgtgca ttcgtaatgt ctgcccattc tgctattctg tatacacccg   19251
cagagtactg caatttgact gtattaccaa tgtcagcaaa ttttctgtct tcgaagagta   19311
aaaaattgta cttggcggat aatgcctta gcggcttaac tgtgccctcc atggaaaaat   19371
cagtcaagat atccacatgt gtttttagta aacaaatttt gggacctaat gcttcaacta   19431
actccagtaa ttccttggtg gtacgaacat ccaatgaagc acacaagttt gtttgctttt   19491
cgtgcatgat attaaatagc ttggcagcaa caggactagg atgagtagca gcacgttcct   19551
tatatgtagc tttcgacatg atttatcttc gtttcctgca ggtttttgtt ctgtgcagtt   19611
gggttaagaa tactgggcaa tttcatgttt cttcaacact acatatgcgt atatatacca   19671
atctaagtct gtgctccttc cttcgttctt ccttctgttc ggagattacc gaatcaaaaa   19731
aatttcaagg aaaccgaaat caaaaaaaag aataaaaaaa aaatgatgaa ttgaaaagct   19791
tatcgat                                                            19798
```

<210> SEQ ID NO 11
<211> LENGTH: 1771

```
<212> TYPE: PRT
<213> ORGANISM: Artificial Sequence
<220> FEATURE:
<223> OTHER INFORMATION: Description of Artificial Sequence:
      pd.deltaNS3NS5.pj

<400> SEQUENCE: 11

Met Ala Ala Tyr Ala Ala Gln Gly Tyr Lys Val Leu Val Leu Asn Pro
 1               5                  10                  15

Ser Val Ala Ala Thr Leu Gly Phe Gly Ala Tyr Met Ser Lys Ala His
                20                  25                  30

Gly Ile Asp Pro Asn Ile Arg Thr Gly Val Arg Thr Ile Thr Thr Gly
            35                  40                  45

Ser Pro Ile Thr Tyr Ser Thr Tyr Gly Lys Phe Leu Ala Asp Gly Gly
        50                  55                  60

Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                85                  90                  95

Glu Thr Ala Gly Ala Arg Leu Val Val Leu Ala Thr Ala Thr Pro Pro
            100                 105                 110

Gly Ser Val Thr Val Pro His Pro Asn Ile Glu Glu Val Ala Leu Ser
        115                 120                 125

Thr Thr Gly Glu Ile Pro Phe Tyr Gly Lys Ala Ile Pro Leu Glu Val
130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
370                 375                 380
```

```
Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
            435                 440                 445

Ser Gly Lys Pro Ala Ile Ile Pro Asp Arg Glu Val Leu Tyr Arg Glu
        450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
770                 775                 780

Met His Thr Arg Cys His Cys Gly Ala Glu Ile Thr Gly His Val Lys
785                 790                 795                 800
```

-continued

```
Asn Gly Thr Met Arg Ile Val Gly Pro Arg Thr Cys Arg Asn Met Trp
                805                 810                 815
Ser Gly Thr Phe Pro Ile Asn Ala Tyr Thr Thr Gly Pro Cys Thr Pro
                820                 825                 830
Leu Pro Ala Pro Asn Tyr Thr Phe Ala Leu Trp Arg Val Ser Ala Glu
                835                 840                 845
Glu Tyr Val Glu Ile Arg Gln Val Gly Asp Phe His Tyr Val Thr Gly
                850                 855                 860
Met Thr Thr Asp Asn Leu Lys Cys Pro Cys Gln Val Pro Ser Pro Glu
865                 870                 875                 880
Phe Phe Thr Glu Leu Asp Gly Val Arg Leu His Arg Phe Ala Pro Pro
                885                 890                 895
Cys Lys Pro Leu Leu Arg Glu Glu Val Ser Phe Arg Val Gly Leu His
                900                 905                 910
Glu Tyr Pro Val Gly Ser Gln Leu Pro Cys Glu Pro Glu Pro Asp Val
                915                 920                 925
Ala Val Leu Thr Ser Met Leu Thr Asp Pro Ser His Ile Thr Ala Glu
                930                 935                 940
Ala Ala Gly Arg Arg Leu Ala Arg Gly Ser Pro Pro Ser Val Ala Ser
945                 950                 955                 960
Ser Ser Ala Ser Gln Leu Ser Ala Pro Ser Leu Lys Ala Thr Cys Thr
                965                 970                 975
Ala Asn His Asp Ser Pro Asp Ala Glu Leu Ile Glu Ala Asn Leu Leu
                980                 985                 990
Trp Arg Gln Glu Met Gly Gly Asn Ile Thr Arg Val Glu Ser Glu Asn
                995                 1000                1005
Lys Val Val Ile Leu Asp Ser Phe Asp Pro Leu Val Ala Glu Glu Asp
    1010                1015                1020
Glu Arg Glu Ile Ser Val Pro Ala Glu Ile Leu Arg Lys Ser Arg Arg
1025                1030                1035                1040
Phe Ala Gln Ala Leu Pro Val Trp Ala Arg Pro Asp Tyr Asn Pro Pro
                1045                1050                1055
Leu Val Glu Thr Trp Lys Lys Pro Asp Tyr Glu Pro Pro Val Val His
                1060                1065                1070
Gly Cys Pro Leu Pro Pro Pro Lys Ser Pro Pro Val Pro Pro Pro Arg
                1075                1080                1085
Lys Lys Arg Thr Val Val Leu Thr Glu Ser Thr Leu Ser Thr Ala Leu
    1090                1095                1100
Ala Glu Leu Ala Thr Arg Ser Phe Gly Ser Ser Ser Thr Ser Gly Ile
1105                1110                1115                1120
Thr Gly Asp Asn Thr Thr Thr Ser Ser Glu Pro Ala Pro Ser Gly Cys
                1125                1130                1135
Pro Pro Asp Ser Asp Ala Glu Ser Tyr Ser Ser Met Pro Pro Leu Glu
                1140                1145                1150
Gly Glu Pro Gly Asp Pro Asp Leu Ser Asp Gly Ser Trp Ser Thr Val
                1155                1160                1165
Ser Ser Glu Ala Asn Ala Glu Asp Val Val Cys Cys Ser Met Ser Tyr
                1170                1175                1180
Ser Trp Thr Gly Ala Leu Val Thr Pro Cys Ala Ala Glu Glu Gln Lys
1185                1190                1195                1200
Leu Pro Ile Asn Ala Leu Ser Asn Ser Leu Leu Arg His His Asn Leu
                1205                1210                1215
Val Tyr Ser Thr Thr Ser Arg Ser Ala Cys Gln Arg Gln Lys Lys Val
```

-continued

```
                1220                1225                1230
Thr Phe Asp  Arg Leu Gln Val Leu  Asp Ser His Tyr Gln  Asp Val Leu
             1235                1240                1245
Lys Glu  Val Lys Ala Ala  Ser Lys Val Lys  Ala Asn Leu Leu Ser
        1250                1255                1260
Val Glu Glu Ala Cys  Ser Leu Thr Pro Pro  His Ser Ala Lys Ser  Lys
1265                1270                1275                1280
Phe Gly Tyr Gly Ala  Lys Asp Val Arg Cys  His Ala Arg Lys Ala  Val
                1285                1290                1295
Thr His Ile Asn  Ser Val Trp Lys Asp  Leu Leu Glu Asp Asn  Val Thr
             1300                1305                1310
Pro Ile Asp  Thr Thr Ile Met Ala  Lys Asn Glu Val Phe  Cys Val Gln
             1315                1320                1325
Pro Glu  Lys Gly Gly Arg Lys  Pro Ala Arg Leu Ile  Val Phe Pro Asp
        1330                1335                1340
Leu Gly Val Arg Val  Cys Glu Lys Met Ala  Leu Tyr Asp Val Val  Thr
1345                1350                1355                1360
Lys Leu Pro Leu Ala  Val Met Gly Ser Ser  Tyr Gly Phe Gln Tyr  Ser
                1365                1370                1375
Pro Gly Gln Arg  Val Glu Phe Leu Val  Gln Ala Trp Lys Ser  Lys Lys
             1380                1385                1390
Thr Pro Met  Gly Phe Ser Tyr Asp  Thr Arg Cys Phe Asp  Ser Thr Val
             1395                1400                1405
Thr Glu  Ser Asp Ile Arg Thr  Glu Glu Ala Ile Tyr  Gln Cys Cys Asp
        1410                1415                1420
Leu  Asp Pro Gln Ala Arg  Val Ala Ile Lys Ser  Leu Thr Glu Arg  Leu
1425                1430                1435                1440
Tyr Val Gly Gly Pro  Leu Thr Asn Ser Arg  Gly Glu Asn Cys Gly  Tyr
                1445                1450                1455
Arg Arg Cys Arg  Ala Ser Gly Val Leu  Thr Thr Ser Cys Gly  Asn Thr
             1460                1465                1470
Leu Thr Cys  Tyr Ile Lys Ala Arg  Ala Ala Cys Arg Ala  Ala Gly Leu
             1475                1480                1485
Gln Asp Cys Thr Met  Leu Val Cys Gly Asp  Asp Leu Val Val Ile  Cys
1490                1495                1500
Glu  Ser Ala Gly Val Gln  Glu Asp Ala Ala Ser  Leu Arg Ala Phe  Thr
1505                1510                1515                1520
Glu Ala Met Thr Arg  Tyr Ser Ala Pro Pro  Gly Asp Pro Pro Gln  Pro
                1525                1530                1535
Glu Tyr Asp Leu  Glu Leu Ile Thr Ser  Cys Ser Ser Asn Val  Ser Val
             1540                1545                1550
Ala His Asp  Gly Ala Gly Lys Arg  Val Tyr Tyr Leu Thr  Arg Asp Pro
             1555                1560                1565
Thr Thr  Pro Leu Ala Arg Ala  Ala Trp Glu Thr Ala  Arg His Thr Pro
        1570                1575                1580
Val Asn Ser Trp Leu  Gly Asn Ile Ile Met  Phe Ala Pro Thr Leu  Trp
1585                1590                1595                1600
Ala Arg Met Ile Leu  Met Thr His Phe Phe  Ser Val Leu Ile Ala  Arg
                1605                1610                1615
Asp Gln Leu Glu  Gln Ala Leu Asp Cys  Glu Ile Tyr Gly Ala  Cys Tyr
             1620                1625                1630
Ser Ile Glu  Pro Leu Asp Leu Pro  Pro Ile Ile Gln Arg  Leu His Gly
             1635                1640                1645
```

-continued

```
Leu Ser Ala Phe Ser Leu His Ser Tyr Ser Pro Gly Glu Ile Asn Arg
    1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
            1685                1690                1695

Arg Ala Ala Ile Cys Gly Lys Tyr Leu Phe Asn Trp Ala Val Arg Thr
        1700                1705                1710

Lys Leu Lys Leu Thr Pro Ile Ala Ala Ala Gly Gln Leu Asp Leu Ser
    1715                1720                1725

Gly Trp Phe Thr Ala Gly Tyr Ser Gly Gly Asp Ile Tyr His Ser Val
1730                1735                1740

Ser His Ala Arg Pro Arg Trp Ile Trp Phe Cys Leu Leu Leu Leu Ala
1745                1750                1755                1760

Ala Gly Val Gly Ile Tyr Leu Leu Pro Asn Arg
            1765                1770

<210> SEQ ID NO 12
<211> LENGTH: 20160
<212> TYPE: DNA
<213> ORGANISM: Artificial Sequence
<220> FEATURE:
<223> OTHER INFORMATION: Description of Artificial Sequence:
      pd.delta.NS3NS5.pj.core121
<220> FEATURE:
<221> NAME/KEY: CDS
<222> LOCATION: (12679)..(18354)

<400> SEQUENCE: 12
atcgatccta ccccttgcgc taaagaagta tatgtgccta ctaacgcttg tctttgtctc      60
tgtcactaaa cactggatta ttactcccag atacttattt tggactaatt taaatgattt    120
cggatcaacg ttcttaatat cgctgaatct tccacaattg atgaaagtag ctaggaagag    180
gaattggtat aaagttttg tttttgtaaa tctcgaagta tactcaaacg aatttagtat     240
tttctcagtg atctcccaga tgctttcacc ctcacttaga agtgctttaa gcattttttt    300
actgtggcta tttcccttat ctgcttcttc cgatgattcg aactgtaatt gcaaactact    360
tacaatatca gtgatatcag attgatgttt tgtccatag taaggaataa ttgtaaattc     420
ccaagcagga atcaatttct ttaatgaggc ttccagaatt gttgcttttt gcgtcttgta    480
tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta attttagac     960 ggcccgcagg ttcgttttgc ggtactatct tgtgataaaa agttgttttg acatgtgatc   1020
tgcacagatt ttataatgta ataagcaaga atacattatc aaacgaacaa tactggtaaa   1080
agaaaaccaa aatggacgac attgaaacag ccaagaatct gacggtaaaa gcacgtacag   1140
cttatagcgt ctgggatgta tgtcggctgt ttattgaaat gattgctcct gatgtagata   1200
```

```
ttgatataga gagtaaacgt aagtctgatg agctactctt tccaggatat gtcataaggc   1260
ccatggaatc tctcacaacc ggtaggccgt atggtcttga ttctagcgca aagattcca    1320
gcgtatcttc tgactccagt gctgaggtaa ttttgcctgc tgcgaagatg gttaaggaaa   1380
ggtttgattc gattggaaat ggtatgctct cttcacaaga agcaagtcag gctgccatag   1440
atttgatgct acagaataac aagctgttag acaatagaaa gcaactatac aaatctattg   1500
ctataataat aggaagattg cccgagaaag acaagaagag agctaccgaa atgctcatga   1560
gaaaaatgga ttgtacacag ttattagtcc caccagctcc aacggaagaa gatgttatga   1620
agctcgtaag cgtcgttacc caattgctta ctttagttcc accagatcgt caagctgctt   1680
taataggtga tttattcatc ccggaatctc taaaggatat attcaatagt ttcaatgaac   1740
tggcggcaga gaatcgttta cagcaaaaaa agagtgagtt ggaaggaagg actgaagtga   1800
accatgctaa tacaaatgaa gaagttccct ccaggcgaac aagaagtaga gacacaaatg   1860
caagaggagc atataaatta caaaacacca tcactgaggg ccctaaagcg gttcccacga   1920
aaaaaggag agtagcaacg agggtaaggg gcagaaaatc acgtaatact tctagggtat    1980
gatccaatat caaggaaat gatagcattg aaggatgaga ctaatccaat tgaggagtgg    2040
cagcatatag aacagctaaa gggtagtgct gaaggaagca tacgataccc cgcatggaat   2100
gggataatat cacaggaggt actagactac ctttcatcct acataaatag acgcatataa   2160
gtacgcattt aagcataaac acgcactatg ccgttcttct catgtatata tatatacagg   2220
caacacgcag atataggtgc gacgtgaaca gtgagctgta tgtgcgcagc tcgcgttgca   2280
ttttcggaag cgctcgtttt cggaaacgct ttgaagttcc tattccgaag ttcctattct   2340
ctagaaagta taggaacttc agagcgcttt tgaaaaccaa aagcgctctg aagacgcact   2400
ttcaaaaaac caaaaacgca ccggactgta acagctact aaaatattgc gaataccgct    2460
tccacaaaca ttgctcaaaa gtatctcttt gctatatatc tctgtgctat atccctatat   2520
aacctaccca tccacctttc gctccttgaa cttgcatcta aactcgacct ctacatcaac   2580
aggcttccaa tgctcttcaa attttactgt caagtagacc catacggctg taatatgctg   2640
ctcttcataa tgtaagctta tctttatcga atcgtgtgaa aaactactac cgcgataaac   2700
ctttacggtt ccctgagatt gaattagttc ctttagtata tgatacaaga cactttgaa    2760
ctttgtacga cgaattttga ggttcgccat cctctggcta tttccaatta tcctgtcggc   2820
tattatctcc gcctcagttt gatcttccgc ttcagactgc cattttttcac ataatgaatc   2880
tatttcaccc cacaatcctt catccgcctc cgcatcttgt tccgttaaac tattgacttc   2940
atgttgtaca ttgtttagtt cacgagaagg gtcctcttca ggcggtagct cctgatctcc   3000
tatatgacct ttatcctgtt ctctttccac aaacttagaa atgtattcat gaattatgga   3060
gcacctaata acattcttca aggcggagaa gtttgggcca gatgcccaat atgcttgaca   3120
tgaaaacgtg agaatgaatt tagtattatt gtgatattct gaggcaattt tattataatc   3180
tcgaagataa gagaagaatg cagtgacctt tgtattgaca aatggagatt ccatgtatct   3240
aaaaaatacg cctttaggcc ttctgatacc ctttcccctg cggtttagcg tgcctttac    3300
attaatatct aaaccctctc cgatggtggc ctttaactga ctaataaatg caaccgatat   3360
aaactgtgat aattctgggt gatttatgat tcgatcgaca attgtattgt acactagtgc   3420
aggatcaggc caatccagtt cttttttcaat taccggtgtg tcgtctgtat tcagtacatg   3480
tccaacaaat gcaaatgcta acgttttgta tttcttataa ttgtcaggaa ctggaaaagt   3540
cccccttgtc gtctcgatta cacacctact ttcatcgtac accataggtt ggaagtgctg   3600
```

-continued

| | | | | | |
|---|---|---|---|---|---|
| cataatacat | tgcttaatac | aagcaagcag | tctctcgcca | ttcatatttc | agttattttc | 3660 |
| cattacagct | gatgtcattg | tatatcagcg | ctgtaaaaat | ctatctgtta | cagaaggttt | 3720 |
| tcgcggtttt | tataaacaaa | actttcgtta | cgaaatcgag | caatcacccc | agctgcgtat | 3780 |
| ttggaaattc | gggaaaaagt | agagcaacgc | gagttgcatt | ttttacacca | taatgcatga | 3840 |
| ttaacttcga | gaagggatta | aggctaattt | cactagtatg | tttcaaaaac | ctcaatctgt | 3900 |
| ccattgaatg | ccttataaaa | cagctataga | ttgcatagaa | gagttagcta | ctcaatgctt | 3960 |
| tttgtcaaag | cttactgatg | atgatgtgtc | tactttcagg | cgggtctgta | gtaaggagaa | 4020 |
| tgacattata | aagctggcac | ttagaattcc | acggactata | gactatacta | gtatactccg | 4080 |
| tctactgtac | gatacacttc | cgctcaggtc | cttgtccttt | aacgaggcct | taccactctt | 4140 |
| ttgttactct | attgatccag | ctcagcaaag | gcagtgtgat | ctaagattct | atcttcgcga | 4200 |
| tgtagtaaaa | ctagctagac | cgagaaagag | actagaaatg | caaaaggcac | ttctacaatg | 4260 |
| gctgccatca | ttattatccg | atgtgacgct | gcatttttt | tttttttttt | tttttttttt | 4320 |
| tttttttttt | tttttttttt | tttttggta | caaatatcat | aaaaaaagag | aatcttttta | 4380 |
| agcaaggatt | ttcttaactt | cttcggcgac | agcatcaccg | acttcggtgg | tactgttgga | 4440 |
| accacctaaa | tcaccagttc | tgatacctgc | atccaaaacc | tttttaactg | catcttcaat | 4500 |
| ggctttacct | tcttcaggca | agttcaatga | caatttcaac | atcattgcag | cagacaagat | 4560 |
| agtggcgata | gggttgacct | tattctttgg | caaatctgga | gcggaaccat | ggcatggttc | 4620 |
| gtacaaacca | aatgcggtgt | tcttgtctgg | caaagaggcc | aaggacgcag | atggcaacaa | 4680 |
| acccaaggag | cctgggataa | cggaggcttc | atcggagatg | atatcaccaa | acatgttgct | 4740 |
| ggtgattata | ataccattta | ggtgggttgg | gttcttaact | aggatcatgg | cggcagaatc | 4800 |
| aatcaattga | tgttgaactt | tcaatgtagg | gaattcgttc | ttgatggttt | cctccacagt | 4860 |
| ttttctccat | aatcttgaag | aggccaaaac | attagcttta | tccaaggacc | aaataggcaa | 4920 |
| tggtggctca | tgttgtaggg | ccatgaaagc | ggccattctt | gtgattcttt | gcacttctgg | 4980 |
| aacggtgtat | tgttcactat | cccaagcgac | accatcacca | tcgtcttcct | ttctcttacc | 5040 |
| aaagtaaata | cctcccacta | attctctaac | aacaacgaag | tcagtacctt | tagcaaattg | 5100 |
| tggcttgatt | ggagataagt | ctaaaagaga | gtcggatgca | aagttacatg | gtcttaagtt | 5160 |
| ggcgtacaat | tgaagttctt | tacggatttt | tagtaaacct | tgttcaggtc | taacactacc | 5220 |
| ggtaccccat | ttaggaccac | ccacagcacc | taacaaaacg | gcatcagcct | tcttggaggc | 5280 |
| ttccagcgcc | tcatctggaa | gtggaacacc | tgtagcatcg | atagcagcac | caccaattaa | 5340 |
| atgattttcg | aaatcgaact | tgacattgga | acgaacatca | gaaatagctt | taagaacctt | 5400 |
| aatggcttcg | gctgtgattt | cttgaccaac | gtggtcacct | ggcaaaacga | cgatcttctt | 5460 |
| aggggcagac | attacaatgg | tatatccttg | aaatatatat | aaaaaaaaaa | aaaaaaaaa | 5520 |
| aaaaaaaaa | atgcagcttc | tcaatgatat | tcgaatacgc | tttgaggaga | tacagcctaa | 5580 |
| tatccgacaa | actgttttac | agatttacga | tcgtacttgt | tacccatcat | tgaattttga | 5640 |
| acatccgaac | ctgggagttt | tccctgaaac | agatagtata | tttgaacctg | tataataata | 5700 |
| tatagtctag | cgcttacgg | aagacaatgt | atgtatttcg | gttcctggag | aaactattgc | 5760 |
| atctattgca | taggtaatct | tgcacgtcgc | atccccggtt | cattttctgc | gtttccatct | 5820 |
| tgcacttcaa | tagcatatct | ttgttaacga | agcatctgtg | cttcattttg | tagaacaaaa | 5880 |
| atgcaacgcg | agagcgctaa | tttttcaaac | aaagaatctg | agctgcattt | ttacagaaca | 5940 |

```
gaaatgcaac gcgaaagcgc tattttacca acgaagaatc tgtgcttcat ttttgtaaaa    6000
caaaaatgca acgcgagagc gctaatttt caaacaaaga atctgagctg cattttaca    6060 gaacagaaat gcaacgcgag agcgctattt taccaacaaa gaatctatac ttcttttttg    6120
ttctacaaaa atgcatcccg agagcgctat ttttctaaca aagcatctta gattactttt    6180
tttctccttt gtgcgctcta taatgcagtc tcttgataac ttttttgcact gtaggtccgt    6240 taaggttaga agaaggctac tttggtgtct attttctctt ccataaaaaa agcctgactc    6300
cacttcccgc gtttactgat tactagcgaa gctgcgggtg cattttttca agataaaggc    6360
atccccgatt atattctata ccgatgtgga ttgcgcatac tttgtgaaca gaaagtgata    6420
gcgttgatga ttcttcattg gtcagaaaat tatgaacggt ttcttctatt ttgtctctat    6480
atactacgta taggaaatgt ttacattttc gtattgtttt cgattcactc tatgaatagt    6540
tcttactaca attttttgt ctaaagagta atactagaga taaacataaa aaatgtagag    6600
gtcgagttta gatgcaagtt caaggagcga aggtggatg ggtaggttat atagggatat    6660
agcacagaga tatatagcaa agagatactt ttgagcaatg tttgtggaag cggtattcgc    6720
aatattttag tagctcgtta cagtccggtg cgttttggt tttttgaaag tgcgtcttca    6780
gagcgctttt ggttttcaaa agcgctctga agttcctata ctttctagag aataggaact    6840
tcggaatagg aacttcaaag cgtttccgaa aacgagcgct tccgaaaatg caacgcgagc    6900
tgcgcacata cagctcactg ttcacgtcgc acctatatct gcgtgttgcc tgtatatata    6960
tatacatgag aagaacggca tagtgcgtgt ttatgcttaa atgcgtactt atatgcgtct    7020
atttatgtag gatgaaaggt agtctagtac ctcctgtgat attatcccat tccatgcggg    7080
gtatcgtatg cttccttcag cactacccctt tagctgttct atatgctgcc actcctcaat    7140
tggattagtc tcatccttca atgctatcat ttcctttgat attggatcat atgcatagta    7200
ccgagaaact agtgcgaagt agtgatcagg tattgctgtt atctgatgag tatacgttgt    7260
cctggccacg gcagaagcac gcttatcgct ccaattccc acaacattag tcaactccgt    7320
taggcccttc attgaaagaa atgaggtcat caaatgtctt ccaatgtgag attttgggcc    7380
attttttata gcaaagattg aataaggcgc attttcttc aaagctttat tgtacgatct    7440
gactaagtta tcttttaata attggtattc ctgtttattg cttgaagaat tgccggtcct    7500
atttactcgt tttaggactg gttcagaatt cctcaaaaat tcatccaaat atacaagtgg    7560
atcgatgata agctgtcaaa catgagaatt cttgaagacg aaagggcctc gtgatacgcc    7620
tatttttata ggttaatgtc atgataataa tggtttctta gacgtcaggt ggcacttttc    7680
ggggaaatgt gcgcggaacc cctatttgtt tattttccta aatacattca aatatgtatc    7740
cgctcatgag acaataaccc tgataaatgc ttcaataata ttgaaaaagg aagagtatga    7800
gtattcaaca tttccgtgtc gcccttattc ccttttttgc ggcattttgc cttcctgttt    7860
ttgctcaccc agaaacgctg gtgaaagtaa aagatgctga agatcagttg ggtgcacgag    7920
tgggttacat cgaactggat ctcaacagcg gtaagatcct tgagagtttt cgccccgaag    7980
aacgttttcc aatgatgagc acttttaaag ttctgctatg tggcgcggta ttatcccgtt    8040
ttgacgccgg gcaagagcaa ctcggtcgcc gcatacacta ttctcagaat gacttggttg    8100
agtactcacc agtcacagaa aagcatctta cggatggcat gacagtaaga gaattatgca    8160
gtgctgccat aaccatgagt gataacactg cggccaactt acttctgaca acgatcggag    8220
gaccgaagga gctaaccgct tttttgcaca acatggggga tcatgtaact cgccttgatc    8280
gttgggaacc ggagctgaat gaagccatac caaacgacga gcgtgacacc acgatgcctg    8340
```

```
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata aatctggagc cggtgagcgt gggtctcgcg   8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct ccaggggga aacgcctggt atctttatag tcctgtcggg tttcgccacc   9360
tctgacttga gcgtcgattt tgtgatgct cgtcaggggg gcggagccta tggaaaaacg   9420
ccagcaacgc ggccttttta cggttcctgg ccttttgctg gccttttgct cacatgttct   9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg ccatgttaa gggcggtttt  10020 ttcctgtttg gtcactgatg cctccgtgta agggggattt ctgttcatgg gggtaatgat  10080
accgatgaaa cgagagagga tgctcacgat acgggttact gatgatgaac atgcccggtt  10140
actggaacgt tgtgagggta aacaactggc ggtatggatg cggcgggacc agagaaaaat  10200
cactcagggt caatgccagc gcttcgttaa tacagatgta ggtgttccac agggtagcca  10260
gcagcatcct gcgatgcaga tccggaacat aatggtgcag ggcgctgact ccgcgtttc  10320 cagactttac gaaacacgga aaccgaagac cattcatgtt gttgctcagg tcgcagacgt  10380
tttgcagcag cagtcgcttc acgttcgctc gcgtatcggt gattcattct gctaaccagt  10440
aaggcaaccc cgccagccta gccgggtcct caacgacagg agcacgatca tgcgcacccg  10500
tggccaggac ccaacgctgc ccgagatgcg ccgcgtgcgg ctgctggaga tggcggacgc  10560
gatggatatg ttctgccaag ggttggtttg cgcattcaca gttctccgca agaattgatt  10620
ggctccaatt cttggagtgg tgaatccgtt agcgaggtgc cgccggcttc cattcaggtc  10680
```

```
gaggtggccc ggctccatgc accgcgacgc aacgcgggga ggcagacaag gtataggggcg    10740 gcgcctacaa tccatgccaa cccgttccat gtgctcgccg aggcggcata aatcgccgtg    10800
acgatcagcg gtccaatgat cgaagttagg ctggtaagag ccgcgagcga tccttgaagc    10860
tgtccctgat ggtcgtcatc tacctgcctg acacgcatgg cctgcaacgc gggcatcccg    10920
atgccgccgg aagcgagaag aatcataatg gggaaggcca tccagcctcg cgtcgcgaac    10980
gccagcaaga cgtagcccag cgcgtcggcc gccatgccgg cgataatggc ctgcttctcg    11040
ccgaaacgtt tggtggcggg accagtgacg aaggcttgag cgagggcgtg caagattccg    11100
aataccgcaa cgacaggcc gatcatcgtc gcgctccagc gaaagcggtc ctcgccgaaa    11160
atgacccaga gcgctgccgg cacctgtcct acgagttgca tgataaagaa gacagtcata    11220
agtgcggcga cgatagtcat gccccgcgcc caccggaagg agctgactgg gttgaaggct    11280
ctcaagggca tcggtcgagg atccttcaat atgcgcacat acgctgttat gttcaaggtc    11340
ccttcgttta agaacgaaag cggtcttcct tttgagggat gtttcaagtt gttcaaatct    11400
atcaaatttg caaatcccca gtctgtatct agagcgttga atcggtgatg cgatttgtta    11460
attaaattga tggtgtcacc attaccaggt ctagatatac caatggcaaa ctgagcacaa    11520
caataccagt ccggatcaac tggcaccatc tctcccgtag tctcatctaa ttttcttcc     11580 ggatgaggtt ccagatatac cgcaacacct ttattatggt ttccctgagg gaataataga    11640
atgtcccatt cgaaatcacc aattctaaac ctgggcgaat tgtatttcgg gtttgttaac    11700
tcgttccagt caggaatgtt ccacgtgaag ctatcttcca gcaaagtctc cacttcttca    11760
tcaaattgtg gagaatactc ccaatgctct tatctatggg acttccggga aacacagtac    11820
cgatacttcc caattcgtct tcagagctca ttgtttgttt gaagagacta atcaaagaat    11880
cgttttctca aaaaaattaa tatcttaact gatagtttga tcaaaggggc aaaacgtagg    11940
ggcaaacaaa cggaaaaatc gtttctcaaa ttttctgatg ccaagaactc taaccagtct    12000
tatctaaaaa ttgccttatg atccgtctct ccggttacag cctgtgtaac tgattaatcc    12060
tgcctttcta atcaccattc taatgtttta attaagggat tttgtcttca ttaacggctt    12120
tcgctcataa aaatgttatg acgttttgcc cgcaggcggg aaaccatcca cttcacgaga    12180
ctgatctcct ctgccggaac accgggcatc tccaacttat aagttggaga ataagagaa    12240 tttcagattg agagaatgaa aaaaaaaaac ccttagttca taggtccatt ctcttagcgc    12300
aactacagag aacaggggca caaacaggca aaaacgggc acaacctcaa tggagtgatg    12360
caacctgcct ggagtaaatg atgacacaag gcaattgacc cacgcatgta tctatctcat    12420
tttcttacac cttctattac cttctgctct ctctgatttg gaaaagctg aaaaaaaagg    12480 ttgaaaccag ttccctgaaa ttattcccct acttgactaa taagtatata aagacggtag    12540
gtattgattg taattctgta aatctatttc ttaaacttct taaattctac ttttatagtt    12600 agtcttttt ttagttttaa aacaccaaga acttagtttc gaataaacac acataaacaa     12660
acaagcttac aaaacaaa atg gct gca tat gca gct cag ggc tat aag gtg       12711
                    Met Ala Ala Tyr Ala Ala Gln Gly Tyr Lys Val
                     1               5                  10 cta gta ctc aac ccc tct gtt gct gca aca ctg ggc ttt ggt gct tac       12759
Leu Val Leu Asn Pro Ser Val Ala Ala Thr Leu Gly Phe Gly Ala Tyr
            15                  20                  25 atg tcc aag gct cat ggg atc gat cct aac atc agg acc ggg gtg aga       12807
Met Ser Lys Ala His Gly Ile Asp Pro Asn Ile Arg Thr Gly Val Arg
        30                  35                  40 aca att acc act ggc agc ccc atc acg tac tcc acc tac ggc aag ttc       12855
```

```
Thr Ile Thr Thr Gly Ser Pro Ile Thr Tyr Ser Thr Tyr Gly Lys Phe
    45                  50                  55 ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
 60                  65                  70                  75 gac gag tgc cac tcc acg gat gcc aca tcc atc ttg ggc att ggc act    12951
Asp Glu Cys His Ser Thr Asp Ala Thr Ser Ile Leu Gly Ile Gly Thr
                 80                  85                  90 gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
             95                 100                 105 acc gcc acc cct ccg ggc tcc gtc act gtg ccc cat ccc aac atc gag    13047
Thr Ala Thr Pro Pro Gly Ser Val Thr Val Pro His Pro Asn Ile Glu
            110                 115                 120 gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
        125                 130                 135 atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155 tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170 atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185 acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200 tat acc ggc gac ttc gac tcg gtg ata gac tgc aat acg tgt gtc acc    13335
Tyr Thr Gly Asp Phe Asp Ser Val Ile Asp Cys Asn Thr Cys Val Thr
    205                 210                 215 cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235 acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250 ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265 ccc tcc ggc atg ttc gac tcg tcc gtc ctc tgt gag tgc tat gac gca    13527
Pro Ser Gly Met Phe Asp Ser Ser Val Leu Cys Glu Cys Tyr Asp Ala
        270                 275                 280 ggc tgt gct tgg tat gag ctc acg ccc gcc gag act aca gtt agg cta    13575
Gly Cys Ala Trp Tyr Glu Leu Thr Pro Ala Glu Thr Thr Val Arg Leu
    285                 290                 295 cga gcg tac atg aac acc ccg ggg ctt ccc gtg tgc cag gac cat ctt    13623
Arg Ala Tyr Met Asn Thr Pro Gly Leu Pro Val Cys Gln Asp His Leu
300                 305                 310                 315 gaa ttt tgg gag ggc gtc ttt aca ggc ctc act cat ata gat gcc cac    13671
Glu Phe Trp Glu Gly Val Phe Thr Gly Leu Thr His Ile Asp Ala His
                320                 325                 330 ttt cta tcc cag aca aag cag agt ggg gag aac ctt cct tac ctg gta    13719
Phe Leu Ser Gln Thr Lys Gln Ser Gly Glu Asn Leu Pro Tyr Leu Val
            335                 340                 345 gcg tac caa gcc acc gtg tgc gct agg gct caa gcc cct ccc cca tcg    13767
Ala Tyr Gln Ala Thr Val Cys Ala Arg Ala Gln Ala Pro Pro Pro Ser
        350                 355                 360
```

| | | |
|---|---|---|
| tgg gac cag atg tgg aag tgt ttg att cgc ctc aag ccc acc ctc cat<br>Trp Asp Gln Met Trp Lys Cys Leu Ile Arg Leu Lys Pro Thr Leu His<br>365                           370                       375 | | 13815 |
| ggg cca aca ccc ctg cta tac aga ctg ggc gct gtt cag aat gaa atc<br>Gly Pro Thr Pro Leu Leu Tyr Arg Leu Gly Ala Val Gln Asn Glu Ile<br>380                       385                       390                     395 | | 13863 |
| acc ctg acg cac cca gtc acc aaa tac atc atg aca tgc atg tcg gcc<br>Thr Leu Thr His Pro Val Thr Lys Tyr Ile Met Thr Cys Met Ser Ala<br>                     400                       405                     410 | | 13911 |
| gac ctg gag gtc gtc acg agc acc tgg gtg ctc gtt ggc ggc gtc ctg<br>Asp Leu Glu Val Val Thr Ser Thr Trp Val Leu Val Gly Gly Val Leu<br>415                           420                       425 | | 13959 |
| gct gct ttg gcc gcg tat tgc ctg tca aca ggc tgc gtg gtc ata gtg<br>Ala Ala Leu Ala Ala Tyr Cys Leu Ser Thr Gly Cys Val Val Ile Val<br>                     430                       435                     440 | | 14007 |
| ggc agg gtc gtc ttg tcc ggg aag ccg gca atc ata cct gac agg gaa<br>Gly Arg Val Val Leu Ser Gly Lys Pro Ala Ile Ile Pro Asp Arg Glu<br>445                           450                       455 | | 14055 |
| gtc ctc tac cga gag ttc gat gag atg gaa gag tgc tct cag cac tta<br>Val Leu Tyr Arg Glu Phe Asp Glu Met Glu Glu Cys Ser Gln His Leu<br>460                           465                       470                     475 | | 14103 |
| ccg tac atc gag caa ggg atg atg ctc gcc gag cag ttc aag cag aag<br>Pro Tyr Ile Glu Gln Gly Met Met Leu Ala Glu Gln Phe Lys Gln Lys<br>                     480                       485                     490 | | 14151 |
| gcc ctc ggc ctc ctg cag acc gcg tcc cgt cag gca gag gtt atc gcc<br>Ala Leu Gly Leu Leu Gln Thr Ala Ser Arg Gln Ala Glu Val Ile Ala<br>                 495                       500                     505 | | 14199 |
| cct gct gtc cag acc aac tgg caa aaa ctc gag acc ttc tgg gcg aag<br>Pro Ala Val Gln Thr Asn Trp Gln Lys Leu Glu Thr Phe Trp Ala Lys<br>510                           515                       520 | | 14247 |
| cat atg tgg aac ttc atc agt ggg ata caa tac ttg gcg ggc ttg tca<br>His Met Trp Asn Phe Ile Ser Gly Ile Gln Tyr Leu Ala Gly Leu Ser<br>525                           530                       535 | | 14295 |
| acg ctg cct ggt aac ccc gcc att gct tca ttg atg gct ttt aca gct<br>Thr Leu Pro Gly Asn Pro Ala Ile Ala Ser Leu Met Ala Phe Thr Ala<br>540                           545                       550                     555 | | 14343 |
| gct gtc acc agc cca cta acc act agc caa acc ctc ctc ttc aac ata<br>Ala Val Thr Ser Pro Leu Thr Thr Ser Gln Thr Leu Leu Phe Asn Ile<br>                     560                       565                     570 | | 14391 |
| ttg ggg ggg tgg gtg gct gcc cag ctc gcc gcc ccc ggt gcc gct act<br>Leu Gly Gly Trp Val Ala Ala Gln Leu Ala Ala Pro Gly Ala Ala Thr<br>                 575                       580                     585 | | 14439 |
| gcc ttt gtg ggc gct ggc tta gct ggc gcc gcc atc ggc agt gtt gga<br>Ala Phe Val Gly Ala Gly Leu Ala Gly Ala Ala Ile Gly Ser Val Gly<br>                 590                       595                     600 | | 14487 |
| ctg ggg aag gtc ctc ata gac atc ctt gca ggg tat ggc gcg ggc gtg<br>Leu Gly Lys Val Leu Ile Asp Ile Leu Ala Gly Tyr Gly Ala Gly Val<br>605                           610                       615 | | 14535 |
| gcg gga gct ctt gtg gca ttc aag atc atg agc ggt gag gtc ccc tcc<br>Ala Gly Ala Leu Val Ala Phe Lys Ile Met Ser Gly Glu Val Pro Ser<br>620                           625                       630                     635 | | 14583 |
| acg gag gac ctg gtc aat cta ctg ccc gcc atc ctc tcg ccc gga gcc<br>Thr Glu Asp Leu Val Asn Leu Leu Pro Ala Ile Leu Ser Pro Gly Ala<br>                     640                       645                     650 | | 14631 |
| ctc gta gtc ggc gtg gtc tgt gca gca ata ctg cgc cgg cac gtt ggc<br>Leu Val Val Gly Val Val Cys Ala Ala Ile Leu Arg Arg His Val Gly<br>                     655                       660                     665 | | 14679 |
| ccg ggc gag ggg gca gtg cag tgg atg aac cgg ctg ata gcc ttc gcc<br>Pro Gly Glu Gly Ala Val Gln Trp Met Asn Arg Leu Ile Ala Phe Ala<br>                 670                       675                     680 | | 14727 |

```
tcc cgg ggg aac cat gtt tcc ccc acg cac tac gtg ccg gag agc gat    14775
Ser Arg Gly Asn His Val Ser Pro Thr His Tyr Val Pro Glu Ser Asp
        685                 690                 695 gca gct gcc cgc gtc act gcc ata ctc agc agc ctc act gta acc cag    14823
Ala Ala Ala Arg Val Thr Ala Ile Leu Ser Ser Leu Thr Val Thr Gln
700                 705                 710                 715 ctc ctg agg cga ctg cac cag tgg ata agc tcg gag tgt acc act cca    14871
Leu Leu Arg Arg Leu His Gln Trp Ile Ser Ser Glu Cys Thr Thr Pro
                720                 725                 730 tgc tcc ggt tcc tgg cta agg gac atc tgg gac tgg ata tgc gag gtg    14919
Cys Ser Gly Ser Trp Leu Arg Asp Ile Trp Asp Trp Ile Cys Glu Val
            735                 740                 745 ttg agc gac ttt aag acc tgg cta aaa gct aag ctc atg cca cag ctg    14967
Leu Ser Asp Phe Lys Thr Trp Leu Lys Ala Lys Leu Met Pro Gln Leu
        750                 755                 760 cct ggg atc ccc ttt gtg tcc tgc cag cgc ggg tat aag ggg gtc tgg    15015
Pro Gly Ile Pro Phe Val Ser Cys Gln Arg Gly Tyr Lys Gly Val Trp
765                 770                 775 cga ggg gac ggc atc atg cac act cgc tgc cac tgt gga gct gag atc    15063
Arg Gly Asp Gly Ile Met His Thr Arg Cys His Cys Gly Ala Glu Ile
780                 785                 790                 795 act gga cat gtc aaa aac ggg acg atg agg atc gtc ggt cct agg acc    15111
Thr Gly His Val Lys Asn Gly Thr Met Arg Ile Val Gly Pro Arg Thr
                800                 805                 810 tgc agg aac atg tgg agt ggg acc ttc ccc att aat gcc tac acc acg    15159
Cys Arg Asn Met Trp Ser Gly Thr Phe Pro Ile Asn Ala Tyr Thr Thr
            815                 820                 825 ggc ccc tgt acc ccc ctt cct gcg ccg aac tac acg ttc gcg cta tgg    15207
Gly Pro Cys Thr Pro Leu Pro Ala Pro Asn Tyr Thr Phe Ala Leu Trp
        830                 835                 840 agg gtg tct gca gag gaa tac gtg gag ata agg cag gtg ggg gac ttc    15255
Arg Val Ser Ala Glu Glu Tyr Val Glu Ile Arg Gln Val Gly Asp Phe
845                 850                 855 cac tac gtg acg ggt atg act act gac aat ctt aaa tgc ccg tgc cag    15303
His Tyr Val Thr Gly Met Thr Thr Asp Asn Leu Lys Cys Pro Cys Gln
860                 865                 870                 875 gtc cca tcg ccc gaa ttt ttc aca gaa ttg gac ggg gtg cgc cta cat    15351
Val Pro Ser Pro Glu Phe Phe Thr Glu Leu Asp Gly Val Arg Leu His
                880                 885                 890 agg ttt gcg ccc ccc tgc aag ccc ttg ctg cgg gag gag gta tca ttc    15399
Arg Phe Ala Pro Pro Cys Lys Pro Leu Leu Arg Glu Glu Val Ser Phe
            895                 900                 905 aga gta gga ctc cac gaa tac ccg gta ggg tcg caa tta cct tgc gag    15447
Arg Val Gly Leu His Glu Tyr Pro Val Gly Ser Gln Leu Pro Cys Glu
        910                 915                 920 ccc gaa ccg gac gtg gcc gtg ttg acg tcc atg ctc act gat ccc tcc    15495
Pro Glu Pro Asp Val Ala Val Leu Thr Ser Met Leu Thr Asp Pro Ser
925                 930                 935 cat ata aca gca gag gcg gcc ggg cga agg ttg gcg agg gga tca ccc    15543
His Ile Thr Ala Glu Ala Ala Gly Arg Arg Leu Ala Arg Gly Ser Pro
940                 945                 950                 955 ccc tct gtg gcc agc tcc tcg gct agc cag cta tcc gct cca tct ctc    15591
Pro Ser Val Ala Ser Ser Ser Ala Ser Gln Leu Ser Ala Pro Ser Leu
                960                 965                 970 aag gca act tgc acc gct aac cat gac tcc cct gat gct gag ctc ata    15639
Lys Ala Thr Cys Thr Ala Asn His Asp Ser Pro Asp Ala Glu Leu Ile
            975                 980                 985 gag gcc aac ctc cta tgg agg cag gag atg ggc ggc aac atc acc agg    15687
Glu Ala Asn Leu Leu Trp Arg Gln Glu Met Gly Gly Asn Ile Thr Arg
```

```
                990               995              1000
gtt gag tca gaa aac aaa gtg gtg att ctg gac tcc ttc gat ccg ctt    15735
Val Glu Ser Glu Asn Lys Val Val Ile Leu Asp Ser Phe Asp Pro Leu
        1005             1010             1015 gtg gcg gag gag gac gag cgg gag atc tcc gta ccc gca gaa atc ctg    15783
Val Ala Glu Glu Asp Glu Arg Glu Ile Ser Val Pro Ala Glu Ile Leu
1020             1025             1030             1035 cgg aag tct cgg aga ttc gcc cag gcc ctg ccc gtt tgg gcg cgg ccg    15831
Arg Lys Ser Arg Arg Phe Ala Gln Ala Leu Pro Val Trp Ala Arg Pro
            1040             1045             1050 gac tat aac ccc ccg cta gtg gag acg tgg aaa aag ccc gac tac gaa    15879
Asp Tyr Asn Pro Pro Leu Val Glu Thr Trp Lys Lys Pro Asp Tyr Glu
                1055             1060             1065 cca cct gtg gtc cat ggc tgc ccg ctt cca cct cca aag tcc cct cct    15927
Pro Pro Val Val His Gly Cys Pro Leu Pro Pro Pro Lys Ser Pro Pro
        1070             1075             1080 gtg cct ccg cct cgg aag aag cgg acg gtg gtc ctc act gaa tca acc    15975
Val Pro Pro Pro Arg Lys Lys Arg Thr Val Val Leu Thr Glu Ser Thr
    1085             1090             1095 cta tct act gcc ttg gcc gag ctc gcc acc aga agc ttt ggc agc tcc    16023
Leu Ser Thr Ala Leu Ala Glu Leu Ala Thr Arg Ser Phe Gly Ser Ser
1100             1105             1110             1115 tca act tcc ggc att acg ggc gac aat acg aca aca tcc tct gag ccc    16071
Ser Thr Ser Gly Ile Thr Gly Asp Asn Thr Thr Thr Ser Ser Glu Pro
            1120             1125             1130 gcc cct tct ggc tgc ccc ccc gac tcc gac gct gag tcc tat tcc tcc    16119
Ala Pro Ser Gly Cys Pro Pro Asp Ser Asp Ala Glu Ser Tyr Ser Ser
                1135             1140             1145 atg ccc ccc ctg gag ggg gag cct ggg gat ccg gat ctt agc gac ggg    16167
Met Pro Pro Leu Glu Gly Glu Pro Gly Asp Pro Asp Leu Ser Asp Gly
        1150             1155             1160 tca tgg tca acg gtc agt agt gag gcc aac gcg gag gat gtc gtg tgc    16215
Ser Trp Ser Thr Val Ser Ser Glu Ala Asn Ala Glu Asp Val Val Cys
    1165             1170             1175 tgc tca atg tct tac tct tgg aca ggc gca ctc gtc acc ccg tgc gcc    16263
Cys Ser Met Ser Tyr Ser Trp Thr Gly Ala Leu Val Thr Pro Cys Ala
1180             1185             1190             1195 gcg gaa gaa cag aaa ctg ccc atc aat gca cta agc aac tcg ttg cta    16311
Ala Glu Glu Gln Lys Leu Pro Ile Asn Ala Leu Ser Asn Ser Leu Leu
            1200             1205             1210 cgt cac cac aat ttg gtg tat tcc acc acc tca cgc agt gct tgc caa    16359
Arg His His Asn Leu Val Tyr Ser Thr Thr Ser Arg Ser Ala Cys Gln
                1215             1220             1225 agg cag aag aaa gtc aca ttt gac aga ctg caa gtt ctg gac agc cat    16407
Arg Gln Lys Lys Val Thr Phe Asp Arg Leu Gln Val Leu Asp Ser His
        1230             1235             1240 tac cag gac gta ctc aag gag gtt aaa gca gcg gcg tca aaa gtg aag    16455
Tyr Gln Asp Val Leu Lys Glu Val Lys Ala Ala Ala Ser Lys Val Lys
    1245             1250             1255 gct aac ttg cta tcc gta gag gaa gct tgc agc ctg acg ccc cca cac    16503
Ala Asn Leu Leu Ser Val Glu Glu Ala Cys Ser Leu Thr Pro Pro His
1260             1265             1270             1275 tca gcc aaa tcc aag ttt ggt tat ggg gca aaa gac gtc cgt tgc cat    16551
Ser Ala Lys Ser Lys Phe Gly Tyr Gly Ala Lys Asp Val Arg Cys His
            1280             1285             1290 gcc aga aag gcc gta acc cac atc aac tcc gtg tgg aaa gac ctt ctg    16599
Ala Arg Lys Ala Val Thr His Ile Asn Ser Val Trp Lys Asp Leu Leu
                1295             1300             1305 gaa gac aat gta aca cca ata gac act acc atc atg gct aag aac gag    16647
```

-continued

```
Glu Asp Asn Val Thr Pro Ile Asp Thr Thr Ile Met Ala Lys Asn Glu
    1310                1315                1320 gtt ttc tgc gtt cag cct gag aag ggg ggt cgt aag cca gct cgt ctc      16695
Val Phe Cys Val Gln Pro Glu Lys Gly Gly Arg Lys Pro Ala Arg Leu
        1325                1330                1335 atc gtg ttc ccc gat ctg ggc gtg cgc gtg tgc gaa aag atg gct ttg      16743
Ile Val Phe Pro Asp Leu Gly Val Arg Val Cys Glu Lys Met Ala Leu
1340                1345                1350                1355 tac gac gtg gtt aca aag ctc ccc ttg gcc gtg atg gga agc tcc tac      16791
Tyr Asp Val Val Thr Lys Leu Pro Leu Ala Val Met Gly Ser Ser Tyr
            1360                1365                1370 gga ttc caa tac tca cca gga cag cgg gtt gaa ttc ctc gtg caa gcg      16839
Gly Phe Gln Tyr Ser Pro Gly Gln Arg Val Glu Phe Leu Val Gln Ala
        1375                1380                1385 tgg aag tcc aag aaa acc cca atg ggg ttc tcg tat gat acc cgc tgc      16887
Trp Lys Ser Lys Lys Thr Pro Met Gly Phe Ser Tyr Asp Thr Arg Cys
    1390                1395                1400 ttt gac tcc aca gtc act gag agc gac atc cgt acg gag gag gca atc      16935
Phe Asp Ser Thr Val Thr Glu Ser Asp Ile Arg Thr Glu Glu Ala Ile
    1405                1410                1415 tac caa tgt tgt gac ctc gac ccc caa gcc cgc gtg gcc atc aag tcc      16983
Tyr Gln Cys Cys Asp Leu Asp Pro Gln Ala Arg Val Ala Ile Lys Ser
1420                1425                1430                1435 ctc acc gag agg ctt tat gtt ggg ggc cct ctt acc aat tca agg ggg      17031
Leu Thr Glu Arg Leu Tyr Val Gly Gly Pro Leu Thr Asn Ser Arg Gly
            1440                1445                1450 gag aac tgc ggc tat cgc agg tgc cgc gcg agc ggc gta ctg aca act      17079
Glu Asn Cys Gly Tyr Arg Arg Cys Arg Ala Ser Gly Val Leu Thr Thr
        1455                1460                1465 agc tgt ggt aac acc ctc act tgc tac atc aag gcc cgg gca gcc tgt      17127
Ser Cys Gly Asn Thr Leu Thr Cys Tyr Ile Lys Ala Arg Ala Ala Cys
    1470                1475                1480 cga gcc gca ggg ctc cag gac tgc acc atg ctc gtg tgt ggc gac gac      17175
Arg Ala Ala Gly Leu Gln Asp Cys Thr Met Leu Val Cys Gly Asp Asp
        1485                1490                1495 tta gtc gtt atc tgt gaa agc gcg ggg gtc cag gag gac gcg gcg agc      17223
Leu Val Val Ile Cys Glu Ser Ala Gly Val Gln Glu Asp Ala Ala Ser
1500                1505                1510                1515 ctg aga gcc ttc acg gag gct atg acc agg tac tcc gcc ccc cct ggg      17271
Leu Arg Ala Phe Thr Glu Ala Met Thr Arg Tyr Ser Ala Pro Pro Gly
            1520                1525                1530 gac ccc cca caa cca gaa tac gac ttg gag ctc ata aca tca tgc tcc      17319
Asp Pro Pro Gln Pro Glu Tyr Asp Leu Glu Leu Ile Thr Ser Cys Ser
        1535                1540                1545 tcc aac gtg tca gtc gcc cac gac ggc gct gga aag agg gtc tac tac      17367
Ser Asn Val Ser Val Ala His Asp Gly Ala Gly Lys Arg Val Tyr Tyr
    1550                1555                1560 ctc acc cgt gac cct aca acc ccc ctc gcg aga gct gcg tgg gag aca      17415
Leu Thr Arg Asp Pro Thr Thr Pro Leu Ala Arg Ala Ala Trp Glu Thr
1565                1570                1575 gca aga cac act cca gtc aat tcc tgg cta ggc aac ata atc atg ttt      17463
Ala Arg His Thr Pro Val Asn Ser Trp Leu Gly Asn Ile Ile Met Phe
1580                1585                1590                1595 gcc ccc aca ctg tgg gcg agg atg ata ctg atg acc cat ttc ttt agc      17511
Ala Pro Thr Leu Trp Ala Arg Met Ile Leu Met Thr His Phe Phe Ser
            1600                1605                1610 gtc ctt ata gcc agg gac cag ctt gaa cag gcc ctc gat tgc gag atc      17559
Val Leu Ile Ala Arg Asp Gln Leu Glu Gln Ala Leu Asp Cys Glu Ile
        1615                1620                1625
```

```
tac ggg gcc tgc tac tcc ata gaa cca ctg gat cta cct cca atc att      17607
Tyr Gly Ala Cys Tyr Ser Ile Glu Pro Leu Asp Leu Pro Pro Ile Ile
         1630                1635                1640 caa aga ctc cat ggc ctc agc gca ttt tca ctc cac agt tac tct cca      17655
Gln Arg Leu His Gly Leu Ser Ala Phe Ser Leu His Ser Tyr Ser Pro
     1645                1650                1655 ggt gaa atc aat agg gtg gcc gca tgc ctc aga aaa ctt ggg gta ccg      17703
Gly Glu Ile Asn Arg Val Ala Ala Cys Leu Arg Lys Leu Gly Val Pro
 1660                1665                1670                1675 ccc ttg cga gct tgg aga cac cgg gcc cgg agc gtc cgc gct agg ctt      17751
Pro Leu Arg Ala Trp Arg His Arg Ala Arg Ser Val Arg Ala Arg Leu
             1680                1685                1690 ctg gcc aga gga ggc agg gct gcc ata tgt ggc aag tac ctc ttc aac      17799
Leu Ala Arg Gly Gly Arg Ala Ala Ile Cys Gly Lys Tyr Leu Phe Asn
         1695                1700                1705 tgg gca gta aga aca aag ctc aaa ctc act cca ata gcg gcc gct ggc      17847
Trp Ala Val Arg Thr Lys Leu Lys Leu Thr Pro Ile Ala Ala Ala Gly
     1710                1715                1720 cag ctg gac ttg tcc ggc tgg ttc acg gct ggc tac agc ggg gga gac      17895
Gln Leu Asp Leu Ser Gly Trp Phe Thr Ala Gly Tyr Ser Gly Gly Asp
 1725                1730                1735 att tat cac agc gtg tct cat gcc cgg ccc cgc tgg atc tgg ttt tgc      17943
Ile Tyr His Ser Val Ser His Ala Arg Pro Arg Trp Ile Trp Phe Cys
1740                1745                1750                1755 cta ctc ctg ctt gct gca ggg gta ggc atc tac ctc ctc ccc aac cga      17991
Leu Leu Leu Leu Ala Ala Gly Val Gly Ile Tyr Leu Leu Pro Asn Arg
             1760                1765                1770 atg agc acg aat cct aaa cct caa aga aag acc aaa cgt aac acc aac      18039
Met Ser Thr Asn Pro Lys Pro Gln Arg Lys Thr Lys Arg Asn Thr Asn
         1775                1780                1785 cgg cgg ccg cag gac gtc aag ttc ccg ggt ggc ggt cag atc gtt ggt      18087
Arg Arg Pro Gln Asp Val Lys Phe Pro Gly Gly Gly Gln Ile Val Gly
     1790                1795                1800 gga gtt tac ttg ttg ccg cgc agg ggc cct aga ttg ggt gtg cgc gcg      18135
Gly Val Tyr Leu Leu Pro Arg Arg Gly Pro Arg Leu Gly Val Arg Ala
 1805                1810                1815 acg aga aag act tcc gag cgg tcg caa cct cga ggt aga cgt cag cct      18183
Thr Arg Lys Thr Ser Glu Arg Ser Gln Pro Arg Gly Arg Arg Gln Pro
1820                1825                1830                1835 atc ccc aag gct cgt cgg ccc gag ggc agg acc tgg gct cag ccc ggg      18231
Ile Pro Lys Ala Arg Arg Pro Glu Gly Arg Thr Trp Ala Gln Pro Gly
             1840                1845                1850 tac cct tgg ccc ctc tat ggc aat gag ggc tgc ggg tgg gcg gga tgg      18279
Tyr Pro Trp Pro Leu Tyr Gly Asn Glu Gly Cys Gly Trp Ala Gly Trp
         1855                1860                1865 ctc ctg tct ccc cgt ggc tct cgg cct agc tgg ggc ccc aca gac ccc      18327
Leu Leu Ser Pro Arg Gly Ser Arg Pro Ser Trp Gly Pro Thr Asp Pro
     1870                1875                1880 cgg cgt agg tcg cgc aat ttg ggt aag taatagtcga ctttgttccc            18374
Arg Arg Arg Ser Arg Asn Leu Gly Lys
 1885                1890 actgtacttt tagctcgtac aaaatacaat atacttttca tttctccgta aacaacatgt    18434
tttcccatgt aatatccttt tctatttttc gttccgttac caactttaca catactttat    18494
atagctattc acttctatac actaaaaaac taagacaatt ttaattttgc tgcctgccat    18554
atttcaattt gttataaatt cctataattt atcctattag tagctaaaaa aagatgaatg    18614
tgaatcgaat cctaagagaa ttggatctga tccacaggac gggtgtggtc gccatgatcg    18674
cgtagtcgat agtggctcca agtagcgaag cgagcaggac tgggcggcgg ccaaagcggt    18734
```

-continued

| | | | | |
|---|---|---|---|---|
| cggacagtgc | tccgagaacg | ggtgcgcata | gaaattgcat | caacgcatat agcgctagca | 18794 |
| gcacgccata | gtgactggcg | atgctgtcgg | aatggacgat | atcccgcaag aggcccggca | 18854 |
| gtaccggcat | aaccaagcct | atgcctacag | catccaggt | gacggtgccg aggatgacga | 18914 |
| tgagcgcatt | gttagatttc | atacacggtg | cctgactgcg | ttagcaattt aactgtgata | 18974 |
| aactaccgca | ttaaagcttt | ttcttt ccaa | ttttttttt | ttcgtcatta taaaaatcat | 19034 |
| tacgaccgag | attcccgggt | aataactgat | ataattaaat | tgaagctcta atttgtgagt | 19094 |
| ttagtataca | tgcatttact | tataatacag | ttttttagtt | ttgctggccg catcttctca | 19154 |
| aatatgcttc | ccagcctgct | tttctgtaac | gttcaccctc | taccttagca tcccttccct | 19214 |
| ttgcaaatag | tcctcttcca | acaataataa | tgtcagatcc | tgtagagacc acatcatcca | 19274 |
| cggttctata | ctgttgaccc | aatgcgtctc | ccttgtcatc | taaacccaca ccgggtgtca | 19334 |
| taatcaacca | atcgtaacct | tcatctcttc | cacccatgtc | tctttgagca ataaagccga | 19394 |
| taacaaaatc | tttgtcgctc | ttcgcaatgt | caacagtacc | cttagtatat tctccagtag | 19454 |
| atagggagcc | cttgcatgac | aattctgcta | acatcaaaag | gcctctaggt tcctttgtta | 19514 |
| cttcttctgc | cgcctgcttc | aaaccgctaa | caatacctgg | gcccaccaca ccgtgtgcat | 19574 |
| tcgtaatgtc | tgcccattct | gctattctgt | atacacccgc | agagtactgc aatttgactg | 19634 |
| tattaccaat | gtcagcaaat | tttctgtctt | cgaagagtaa | aaaattgtac ttggcggata | 19694 |
| atgcctttag | cggcttaact | gtgccctcca | tggaaaaatc | agtcaagata tccacatgtg | 19754 |
| tttttagtaa | acaaattttg | ggacctaatg | cttcaactaa | ctccagtaat tccttggtgg | 19814 |
| tacgaacatc | caatgaagca | cacaagtttg | tttgcttttc | gtgcatgata ttaaatagct | 19874 |
| tggcagcaac | aggactagga | tgagtagcag | cacgttcctt | atatgtagct ttcgacatga | 19934 |
| tttatcttcg | tttcctgcag | gttttgttc | tgtgcagttg | ggttaagaat actgggcaat | 19994 |
| ttcatgtttc | ttcaacacta | catatgcgta | tataccaa | tctaagtctg tgctccttcc | 20054 |
| ttcgttcttc | cttctgttcg | gagattaccg | aatcaaaaaa | atttcaagga aaccgaaatc | 20114 |
| aaaaaaaaga | ataaaaaaaa | aatgatgaat | tgaaaagctt | atcgat | 20160 |

<210> SEQ ID NO 13
<211> LENGTH: 1892
<212> TYPE: PRT
<213> ORGANISM: Artificial Sequence
<220> FEATURE:
<223> OTHER INFORMATION: Description of Artificial Sequence:
      pd.delta.NS3NS5.pj.core121

<400> SEQUENCE: 13

Met Ala Ala Tyr Ala Ala Gln Gly Tyr Lys Val Leu Val Leu Asn Pro
 1               5                   10                  15

Ser Val Ala Ala Thr Leu Gly Phe Gly Ala Tyr Met Ser Lys Ala His
                20                  25                  30

Gly Ile Asp Pro Asn Ile Arg Thr Gly Val Arg Thr Ile Thr Thr Gly
            35                  40                  45

Ser Pro Ile Thr Tyr Ser Thr Tyr Gly Lys Phe Leu Ala Asp Gly Gly
        50                  55                  60

Cys Ser Gly Gly Ala Tyr Asp Ile Ile Ile Cys Asp Glu Cys His Ser
    65                  70                  75                  80

Thr Asp Ala Thr Ser Ile Leu Gly Ile Gly Thr Val Leu Asp Gln Ala
                85                  90                  95

Glu Thr Ala Gly Ala Arg Leu Val Val Leu Ala Thr Ala Thr Pro Pro

-continued

```
                100                 105                 110
Gly Ser Val Thr Val Pro His Pro Asn Ile Glu Glu Val Ala Leu Ser
            115                 120                 125

Thr Thr Gly Glu Ile Pro Phe Tyr Gly Lys Ala Ile Pro Leu Glu Val
130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
            195                 200                 205

Asp Ser Val Ile Asp Cys Asn Thr Cys Val Thr Gln Thr Val Asp Phe
            210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
            275                 280                 285

Glu Leu Thr Pro Ala Glu Thr Thr Val Arg Leu Arg Ala Tyr Met Asn
            290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
            355                 360                 365

Lys Cys Leu Ile Arg Leu Lys Pro Thr Leu His Gly Pro Thr Pro Leu
            370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
            435                 440                 445

Ser Gly Lys Pro Ala Ile Ile Pro Asp Arg Glu Val Leu Tyr Arg Glu
            450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
            515                 520                 525
```

```
Ile Ser Gly Ile Gln Tyr Leu Ala Gly Leu Ser Thr Leu Pro Gly Asn
        530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
            820                 825                 830

Leu Pro Ala Pro Asn Tyr Thr Phe Ala Leu Trp Arg Val Ser Ala Glu
        835                 840                 845

Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895

Cys Lys Pro Leu Leu Arg Glu Glu Val Ser Phe Arg Val Gly Leu His
            900                 905                 910

Glu Tyr Pro Val Gly Ser Gln Leu Pro Cys Glu Pro Glu Pro Asp Val
        915                 920                 925

Ala Val Leu Thr Ser Met Leu Thr Asp Pro Ser His Ile Thr Ala Glu
    930                 935                 940
```

```
Ala Ala Gly Arg Arg Leu Ala Arg Gly Ser Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
        995                 1000                1005

Lys Val Val Ile Leu Asp Ser Phe Asp Pro Leu Val Ala Glu Glu Asp
    1010                1015                1020

Glu Arg Glu Ile Ser Val Pro Ala Glu Ile Leu Arg Lys Ser Arg Arg
1025                1030                1035                1040

Phe Ala Gln Ala Leu Pro Val Trp Ala Arg Pro Asp Tyr Asn Pro Pro
                1045                1050                1055

Leu Val Glu Thr Trp Lys Lys Pro Asp Tyr Glu Pro Pro Val Val His
            1060                1065                1070

Gly Cys Pro Leu Pro Pro Lys Ser Pro Pro Val Pro Pro Pro Arg
        1075                1080                1085

Lys Lys Arg Thr Val Val Leu Thr Glu Ser Thr Leu Ser Thr Ala Leu
1090                1095                1100

Ala Glu Leu Ala Thr Arg Ser Phe Gly Ser Ser Ser Thr Ser Gly Ile
1105                1110                1115                1120

Thr Gly Asp Asn Thr Thr Thr Ser Ser Glu Pro Ala Pro Ser Gly Cys
                1125                1130                1135

Pro Pro Asp Ser Asp Ala Glu Ser Tyr Ser Ser Met Pro Pro Leu Glu
                1140                1145                1150

Gly Glu Pro Gly Asp Pro Asp Leu Ser Asp Gly Ser Trp Ser Thr Val
            1155                1160                1165

Ser Ser Glu Ala Asn Ala Glu Asp Val Val Cys Cys Ser Met Ser Tyr
1170                1175                1180

Ser Trp Thr Gly Ala Leu Val Thr Pro Cys Ala Ala Glu Glu Gln Lys
1185                1190                1195                1200

Leu Pro Ile Asn Ala Leu Ser Asn Ser Leu Leu Arg His His Asn Leu
                1205                1210                1215

Val Tyr Ser Thr Thr Ser Arg Ser Ala Cys Gln Arg Gln Lys Lys Val
            1220                1225                1230

Thr Phe Asp Arg Leu Gln Val Leu Asp Ser His Tyr Gln Asp Val Leu
            1235                1240                1245

Lys Glu Val Lys Ala Ala Ala Ser Lys Val Lys Ala Asn Leu Leu Ser
1250                1255                1260

Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
                1285                1290                1295

Thr His Ile Asn Ser Val Trp Lys Asp Leu Leu Glu Asp Asn Val Thr
            1300                1305                1310

Pro Ile Asp Thr Thr Ile Met Ala Lys Asn Glu Val Phe Cys Val Gln
        1315                1320                1325

Pro Glu Lys Gly Gly Arg Lys Pro Ala Arg Leu Ile Val Phe Pro Asp
    1330                1335                1340

Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
```

-continued

```
            1365                1370                1375
Pro Gly Gln Arg  Val Glu Phe Leu  Val Gln Ala Trp  Lys Ser Lys Lys
            1380                1385                1390

Thr Pro Met  Gly Phe Ser Tyr Asp  Thr Arg Cys Phe Asp  Ser Thr Val
        1395                1400                1405

Thr Glu  Ser Asp Ile Arg Thr  Glu Ala Ile  Tyr Gln Cys Cys Asp
        1410                1415                1420

Leu Asp Pro Gln Ala Arg  Val Ala Ile Lys Ser  Leu Thr Glu Arg Leu
1425                1430                1435                1440

Tyr Val Gly Gly Pro  Leu Thr Asn Ser Arg  Gly Glu Asn Cys Gly  Tyr
                1445                1450                1455

Arg Arg Cys Arg  Ala Ser Gly Val Leu  Thr Thr Ser Cys Gly  Asn Thr
                1460                1465                1470

Leu Thr Cys  Tyr Ile Lys Ala Arg  Ala Ala Cys Arg Ala  Ala Gly Leu
        1475                1480                1485

Gln Asp  Cys Thr Met Leu Val  Cys Gly Asp Asp Leu  Val Val Ile Cys
        1490                1495                1500

Glu  Ser Ala Gly Val Gln  Glu Asp Ala Ala Ser  Leu Arg Ala Phe  Thr
1505                1510                1515                1520

Glu Ala Met Thr Arg  Tyr Ser Ala Pro Pro  Gly Asp Pro Pro Gln  Pro
                1525                1530                1535

Glu Tyr Asp Leu  Glu Leu Ile Thr Ser  Cys Ser Ser Asn Val  Ser Val
                1540                1545                1550

Ala His Asp  Gly Ala Gly Lys Arg  Val Tyr Tyr Leu Thr  Arg Asp Pro
        1555                1560                1565

Thr Thr  Pro Leu Ala Arg Ala  Ala Trp Glu Thr Ala  Arg His Thr Pro
        1570                1575                1580

Val  Asn Ser Trp Leu Gly  Asn Ile Ile Met Phe  Ala Pro Thr Leu  Trp
1585                1590                1595                1600

Ala Arg Met Ile Leu  Met Thr His Phe Phe  Ser Val Leu Ile Ala  Arg
                1605                1610                1615

Asp Gln Leu Glu  Gln Ala Leu Asp Cys  Glu Ile Tyr Gly Ala  Cys Tyr
                1620                1625                1630

Ser Ile Glu  Pro Leu Asp Leu Pro  Pro Ile Ile Gln Arg  Leu His Gly
        1635                1640                1645

Leu Ser  Ala Phe Ser Leu His  Ser Tyr Ser Pro Gly  Glu Ile Asn Arg
        1650                1655                1660

Val  Ala Ala Cys Leu Arg  Lys Leu Gly Val Pro  Pro Leu Arg Ala  Trp
1665                1670                1675                1680

Arg His Arg Ala Arg  Ser Val Arg Ala Arg  Leu Leu Ala Arg Gly  Gly
                1685                1690                1695

Arg Ala Ala Ile  Cys Gly Lys Tyr Leu  Phe Asn Trp Ala Val  Arg Thr
                1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
        1730                1735                1740

Ser  His Ala Arg Pro Arg  Trp Ile Trp Phe Cys  Leu Leu Leu Leu Ala
1745                1750                1755                1760

Ala Gly Val Gly Ile  Tyr Leu Leu Pro Asn  Arg Met Ser Thr Asn  Pro
                1765                1770                1775

Lys Pro Gln Arg  Lys Thr Lys Arg Asn  Thr Asn Arg Arg Pro  Gln Asp
                1780                1785                1790
```

```
Val Lys Phe Pro Gly Gly Gln Ile Val Gly Val Tyr Leu Leu
        1795                1800                1805

Pro Arg Arg Gly Pro Arg Leu Gly Val Arg Ala Thr Arg Lys Thr Ser
    1810                1815                1820

Glu Arg Ser Gln Pro Arg Gly Arg Arg Gln Pro Ile Pro Lys Ala Arg
1825                1830                1835                1840

Arg Pro Glu Gly Arg Thr Trp Ala Gln Pro Gly Tyr Pro Trp Pro Leu
                1845                1850                1855

Tyr Gly Asn Glu Gly Cys Gly Trp Ala Gly Trp Leu Leu Ser Pro Arg
            1860                1865                1870

Gly Ser Arg Pro Ser Trp Gly Pro Thr Asp Pro Arg Arg Ser Arg
        1875                1880                1885

Asn Leu Gly Lys
    1890

<210> SEQ ID NO 14
<211> LENGTH: 20316
<212> TYPE: DNA
<213> ORGANISM: Artificial Sequence
<220> FEATURE:
<223> OTHER INFORMATION: Description of Artificial Sequence:
      pd.delta.NS3NS5.pj.core173
<220> FEATURE:
<221> NAME/KEY: CDS
<222> LOCATION: (12679)..(18510)

<400> SEQUENCE: 14
```

| | | |
|---|---|---|
| atcgatccta cccttgcgc taaagaagta tatgtgccta ctaacgcttg tctttgtctc | 60 |
| tgtcactaaa cactggatta ttactcccag atacttattt tggactaatt taaatgattt | 120 |
| cggatcaacg ttcttaatat cgctgaatct tccacaattg atgaaagtag ctaggaagag | 180 |
| gaattggtat aaagtttttg tttttgtaaa tctcgaagta tactcaaacg aatttagtat | 240 |
| tttctcagtg atctcccaga tgctttcacc ctcacttaga agtgctttaa gcattttttt | 300 |
| actgtggcta tttcccttat ctgcttcttc cgatgattcg aactgtaatt gcaaactact | 360 |
| tacaatatca gtgatatcag attgatgttt ttgtccatag taaggaataa ttgtaaattc | 420 |
| ccaagcagga atcaatttct ttaatgaggc ttccagaatt gttgcttttt gcgtcttgta | 480 |
| tttaaactgg agtgatttat tgacaatatc gaaactcagc gaattgctta tgatagtatt | 540 |
| atagctcatg aatgtggctc tcttgattgc tgttccgtta tgtgtaatca tccaacataa | 600 |
| ataggttagt tcagcagcac ataatgctat tttctcacct gaaggtcttt caaacctttc | 660 |
| cacaaactga cgaacaagca ccttaggtgg tgttttacat aatatatcaa attgtggcat | 720 |
| gcttagcgcc gatcttgtgt gcaattgata tctagtttca actactctat ttatcttgta | 780 |
| tcttgcagta ttcaaacacg ctaactcgaa aaactaactt taattgtcct gtttgtctcg | 840 |
| cgttctttcg aaaaatgcac cggccgcgca ttatttgtac tgcgaaaata attggtactg | 900 |
| cggtatcttc atttcatatt ttaaaaatgc acctttgctg cttttccttg atttttagac | 960 |
| ggcccgcagg ttcgttttgc ggtactatct tgtgataaaa agttgttttg acatgtgatc | 1020 |
| tgcacagatt ttataatgta ataagcaaga atacattatc aaacgaacaa tactggtaaa | 1080 |
| agaaaaccaa aatggacgac attgaaacag ccaagaatct gacggtaaaa gcacgtacag | 1140 |
| cttatagcgt ctgggatgta tgtcggctgt ttattgaaat gattgctcct gatgtagata | 1200 |
| ttgatataga gagtaaacgt aagtctgatg agctactctt tccaggatat gtcataaggc | 1260 |
| ccatggaatc tctcacaacc ggtaggccgt atggtcttga ttctagcgca gaagattcca | 1320 |

```
gcgtatcttc tgactccagt gctgaggtaa ttttgcctgc tgcgaagatg gttaaggaaa    1380
ggtttgattc gattggaaat ggtatgctct cttcacaaga agcaagtcag gctgccatag    1440
atttgatgct acagaataac aagctgttag acaatagaaa gcaactatac aaatctattg    1500
ctataataat aggaagattg cccgagaaag acaagaagag agctaccgaa atgctcatga    1560
gaaaaatgga ttgtacacag ttattagtcc caccagctcc aacggaagaa gatgttatga    1620
agctcgtaag cgtcgttacc caattgctta ctttagttcc accagatcgt caagctgctt    1680
taataggtga tttattcatc ccggaatctc taaaggatat attcaatagt ttcaatgaac    1740
tggcggcaga gaatcgttta cagcaaaaaa agagtgagtt ggaaggaagg actgaagtga    1800
accatgctaa tacaaatgaa gaagttccct ccaggcgaac aagaagtaga cacacaaatg    1860
caagaggagc atataaatta caaaacacca tcactgaggg ccctaaagcg gttcccacga    1920
aaaaaaggag agtagcaacg agggtaaggg gcagaaaatc acgtaatact tctagggtat    1980
gatccaatat caaaggaaat gatagcattg aaggatgaga ctaatccaat tgaggagtgg    2040
cagcatatag aacagctaaa gggtagtgct gaaggaagca tacgataccc cgcatggaat    2100
gggataatat cacaggaggt actagactac cttttcatcct acataaatag acgcatataa    2160
gtacgcattt aagcataaac acgcactatg ccgttcttct catgtatata tatatacagg    2220
caacacgcag ataggtgc gacgtgaaca gtgagctgta tgtgcgcagc tcgcgttgca    2280
ttttcggaag cgctcgtttt cggaaacgct ttgaagttcc tattccgaag ttcctattct    2340
ctagaaagta taggaacttc agagcgcttt tgaaaaccaa aagcgctctg aagacgcact    2400
ttcaaaaaac caaaaacgca ccggactgta acgagctact aaaatattgc gaataccgct    2460
tccacaaaca ttgctcaaaa gtatctcttt gctatatatc tctgtgctat atccctatat    2520
aacctaccca tccacctttc gctccttgaa cttgcatcta aactcgacct ctacatcaac    2580
aggcttccaa tgctcttcaa attttactgt caagtagacc catacggctg taatatgctg    2640
ctcttcataa tgtaagctta tctttatcga atcgtgtgaa aaactactac cgcgataaac    2700
ctttacggtt ccctgagatt gaattagttc ctttagtata tgatacaaga cacttttgaa    2760
ctttgtacga cgaattttga ggttcgccat cctctggcta tttccaatta tcctgtcggc    2820
tattatctcc gcctcagttt gatcttccgc ttcagactgc catttttcac ataatgaatc    2880
tatttcaccc cacaatcctt catccgcctc cgcatcttgt tccgttaaac tattgacttc    2940
atgttgtaca ttgtttagtt cacgagaagg gtcctcttca ggcggtagct cctgatctcc    3000
tatatgacct ttatcctgtt ctctttccac aaacttagaa atgtattcat gaattatgga    3060
gcacctaata acattcttca aggcggagaa gtttgggcca gatgcccaat atgcttgaca    3120
tgaaaacgtg agaatgaatt tagtattatt gtgatattct gaggcaattt tattataatc    3180
tcgaagataa gagaagaatg cagtgacctt tgtattgaca aatggagatt ccatgtatct    3240
aaaaaatacg cctttaggcc ttctgatacc ctttcccctg cggtttagcg tgccttttac    3300
attaatatct aaaccctctc cgatggtggc ctttaactga ctaataaatg caaccgatat    3360
aaactgtgat aattctgggt gatttatgat tcgatcgaca attgtattgt acactagtgc    3420
aggatcaggc caatccagtt cttttttcaat taccggtgtg tcgtctgtat tcagtacatg    3480
tccaacaaat gcaaatgcta acgttttgta tttcttataa ttgtcaggaa ctggaaaagt    3540 ccccccttgtc gtctcgatta cacacctact ttcatcgtac accataggtt ggaagtgctg    3600
cataatacat tgcttaatac aagcaagcag tctctcgcca ttcatatttc agttattttc    3660
```

```
cattacagct gatgtcattg tatatcagcg ctgtaaaaat ctatctgtta cagaaggttt    3720
tcgcggtttt tataaacaaa actttcgtta cgaaatcgag caatcacccc agctgcgtat    3780
ttggaaattc gggaaaaagt agagcaacgc gagttgcatt ttttacacca taatgcatga    3840
ttaacttcga gaagggatta aggctaattt cactagtatg tttcaaaaac ctcaatctgt    3900
ccattgaatg ccttataaaa cagctataga ttgcatagaa gagttagcta ctcaatgctt    3960
tttgtcaaag cttactgatg atgatgtgtc tactttcagg cgggtctgta gtaaggagaa    4020
tgacattata aagctggcac ttagaattcc acggactata gactatacta gtatactccg    4080
tctactgtac gatacacttc cgctcaggtc cttgtccttt aacgaggcct taccactctt    4140
ttgttactct attgatccag ctcagcaaag gcagtgtgat ctaagattct atcttcgcga    4200
tgtagtaaaa ctagctagac cgagaaagag actagaaatg caaaaggcac ttctacaatg    4260
gctgccatca ttattatccg atgtgacgct gcatttttt tttttttttt ttttttttt    4320 tttttttttt tttttttttt ttttttggta caaatatcat aaaaaagag aatcttttta    4380 agcaaggatt ttcttaactt cttcggcgac agcatcaccg acttcggtgg tactgttgga    4440
accacctaaa tcaccagttc tgatacctgc atccaaaacc ttttttaactg catcttcaat    4500 ggctttacct tcttcaggca agttcaatga caatttcaac atcattgcag cagacaagat    4560
agtggcgata gggttgacct tattctttgg caaatctgga gcggaaccat ggcatggttc    4620
gtacaaacca aatgcggtgt tcttgtctgg caaagaggcc aaggacgcag atggcaacaa    4680
acccaaggag cctgggataa cggaggcttc atcggagatg atatcaccaa acatgttgct    4740
ggtgattata ataccattta ggtgggttgg gttcttaact aggatcatgg cggcagaatc    4800
aatcaattga tgttgaactt tcaatgtagg gaattcgttc ttgatggttt cctccacagt    4860
ttttctccat aatcttgaag aggccaaaac attagcttta tccaaggacc aaataggcaa    4920
tggtggctca tgttgtaggg ccatgaaagc ggccattctt tgtgattcttt gcacttctgg    4980 aacggtgtat tgttcactat cccaagcgac accatcacca tcgtcttcct ttctcttacc    5040
aaagtaaata cctcccacta attctctaac aacaacgaag tcagtacctt tagcaaattg    5100
tggcttgatt ggagataagt ctaaaagaga gtcggatgca aagttacatg gtcttaagtt    5160
ggcgtacaat tgaagttctt tacggatttt tagtaaacct tgttcaggtc taacactacc    5220
ggtaccccat ttaggaccac ccacagcacc taacaaaacg gcatcagcct tcttggaggc    5280
ttccagcgcc tcatctggaa gtggaacacc tgtagcatcg atagcagcac caccaattaa    5340
atgattttcg aaatcgaact tgacattgga acgaacatca gaaatagctt taagaacctt    5400
aatggcttcg gctgtgattt cttgaccaac gtggtcacct ggcaaaacga cgatcttctt    5460
aggggcagac attacaatgg tatatccttg aaatatatat aaaaaaaaa aaaaaaaaaa    5520 aaaaaaaaaa atgcagcttc tcaatgatat tcgaatacgc tttgaggaga tacagcctaa    5580
tatccgacaa actgttttac agatttacga tcgtacttgt tacccatcat gaattttga    5640 acatccgaac ctgggagttt tccctgaaac agatagtata tttgaacctg tataataata    5700
tatagtctag cgctttacgg aagacaatgt atgtatttcg gttcctggag aaactattgc    5760
atctattgca taggtaatct tgcacgtcgc atccccggtt cattttctgc gtttccatct    5820
tgcacttcaa tagcatatct ttgttaacga agcatctgtg cttcattttg tagaacaaaa    5880
atgcaacgcg agagcgctaa ttttcaaac aaagaatctg agctgcattt ttacagaaca    5940
gaaatgcaac gcgaaagcgc tattttacca acgaagaatc tgtgcttcat ttttgtaaaa    6000
caaaaatgca acgcgagagc gctaattttt caaacaaaga atctgagctg cattttcaca    6060
```

-continued

```
gaacagaaat gcaacgcgag agcgctattt taccaacaaa gaatctatac ttctttttg    6120 ttctacaaaa atgcatcccg agagcgctat ttttctaaca aagcatctta gattactttt    6180
tttctccttt gtgcgctcta taatgcagtc tcttgataac tttttgcact gtaggtccgt    6240
taaggttaga agaaggctac tttggtgtct attttctctt ccataaaaaa agcctgactc    6300
cacttcccgc gtttactgat tactagcgaa gctgcgggtg catttttca agataaaggc     6360 atccccgatt atattctata ccgatgtgga ttgcgcatac tttgtgaaca gaaagtgata    6420
gcgttgatga ttcttcattg gtcagaaaat tatgaacggt ttcttctatt ttgtctctat    6480
atactacgta taggaaatgt ttacattttc gtattgtttt cgattcactc tatgaatagt    6540
tcttactaca atttttttgt ctaaagagta atactagaga taaacataaa aaatgtagag    6600
gtcgagttta gatgcaagtt caaggagcga aggtggatg ggtaggttat atagggatat    6660
agcacagaga tatatagcaa agagatactt tgagcaatg tttgtggaag cggtattcgc     6720
aatattttag tagctcgtta cagtccggtg cgttttggt ttttgaaag tgcgtcttca     6780 gagcgctttt ggttttcaaa agcgctctga agttcctata cttctagag aataggaact    6840 tcggaatagg aacttcaaag cgtttccgaa aacgagcgct tccgaaaatg caacgcgagc    6900
tgcgcacata cagctcactg ttcacgtcgc acctatatct gcgtgttgcc tgtatatata    6960
tatacatgag aagaacggca tagtgcgtgt ttatgcttaa atgcgtactt atatgcgtct    7020
atttatgtag gatgaaaggt agtctagtac ctcctgtgat attatcccat tccatgcggg    7080
gtatcgtatg cttccttcag cactacccctt tagctgttct atatgctgcc actcctcaat    7140
tggattagtc tcatccttca atgctatcat ttcctttgat attggatcat atgcatagta    7200
ccgagaaact agtgcgaagt agtgatcagg tattgctgtt atctgatgag tatacgttgt    7260
cctggccacg gcagaagcac gcttatcgct ccaatttccc acaacattag tcaactccgt    7320
taggcccttc attgaaagaa atgaggtcat caaatgtctt ccaatgtgag attttgggcc    7380
attttttata gcaaagattg aataaggcgc attttttcttc aaagctttat tgtacgatct    7440
gactaagtta tcttttaata attggtattc ctgtttattg cttgaagaat tgccggtcct    7500
atttactcgt tttaggactg gttcagaatt cctcaaaaat tcatccaaat atacaagtgg    7560
atcgatgata agctgtcaaa catgagaatt cttgaagacg aaagggcctc gtgatacgcc    7620 tattttata ggttaatgtc atgataataa tggttctta gacgtcaggt ggcactttc     7680 ggggaaatgt gcgcggaacc cctatttgtt tatttttcta aatacattca aatatgtatc    7740
cgctcatgag acaataaccc tgataaatgc ttcaataata ttgaaaaagg aagagtatga    7800
gtattcaaca tttccgtgtc gcccttattc ccttttttgc ggcattttgc cttcctgttt    7860
ttgctcaccc agaaacgctg gtgaaagtaa aagatgctga agatcagttg ggtgcacgag    7920
tgggttacat cgaactggat ctcaacagcg gtaagatcct tgagagtttt cgccccgaag    7980
aacgttttcc aatgatgagc acttttaaag ttctgctatg tggcgcggta ttatcccgtg    8040
ttgacgccgg gcaagagcaa ctcggtcgcc gcatacacta ttctcagaat gacttggttg    8100
agtactcacc agtcacagaa aagcatctta cggatggcat gacagtaaga gaattatgca    8160
gtgctgccat aaccatgagt gataacactg cggccaactt acttctgaca acgatcggag    8220
gaccgaagga gctaaccgct tttttgcaca acatggggga tcatgtaact cgccttgatc    8280
gttgggaacc ggagctgaat gaagccatac caaacgacga gcgtgacacc acgatgcctg    8340
cagcaatggc aacaacgttg cgcaaactat taactggcga actacttact ctagcttccc    8400
```

```
ggcaacaatt aatagactgg atggaggcgg ataaagttgc aggaccactt ctgcgctcgg   8460
cccttccggc tggctggttt attgctgata atctggagc cggtgagcgt gggtctcgcg    8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaattttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactctttt ccgaaggtaa    8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt tgtgatgct cgtcaggggg cggagccta tggaaaaacg     9420
ccagcaacgc ggcctttttta cggttcctgg ccttttgctg ccttttgct cacatgttct    9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg ccatgttaa gggcggtttt   10020
ttcctgtttg gtcactgatg cctccgtgta agggggattt ctgttcatgg ggtaatgat   10080
accgatgaaa cgagagagga tgctcacgat acgggttact gatgatgaac atgcccggtt  10140
actggaacgt tgtgagggta acaactggc ggtatggatg cggcgggacc agagaaaaat   10200
cactcagggt caatgccagc gcttcgttaa tacagatgta ggtgttccac agggtagcca   10260
gcagcatcct gcgatgcaga tccggaacat aatggtgcag ggcgctgact tccgcgtttc   10320
cagactttac gaaacacgga aaccgaagac cattcatgtt gttgctcagg tcgcagacgt   10380
tttgcagcag cagtcgcttc acgttcgctc gcgtatcggt gattcattct gctaaccagt   10440
aaggcaaccc cgccagccta gccgggtcct caacgacagg agcacgatca tgcgcacccg   10500
tggccaggac ccaacgctgc ccgagatgcg ccgcgtgcgg ctgctggaga tggcggacgc   10560
gatggatatg ttctgccaag ggttggtttg cgcattcaca gttctccgca agaattgatt  10620
ggctccaatt cttggagtgg tgaatccgtt agcgaggtgc cgccggcttc cattcaggtc   10680
gaggtggccc ggctccatgc accgcgacgc aacgcgggga ggcagacaag gtataggcg   10740
gcgcctacaa tccatgccaa cccgttccat gtgctcgccg aggcggcata aatcgccgtg   10800
```

-continued

```
acgatcagcg gtccaatgat cgaagttagg ctggtaagag ccgcgagcga tccttgaagc   10860
tgtccctgat ggtcgtcatc tacctgcctg acagcatgg cctgcaacgc gggcatcccg    10920
atgccgccgg aagcgagaag aatcataatg gggaaggcca tccagcctcg cgtcgcgaac   10980
gccagcaaga cgtagcccag cgcgtcggcc gccatgccgg cgataatggc ctgcttctcg   11040
ccgaaacgtt tggtggcggg accagtgacg aaggcttgag cgagggcgtg caagattccg   11100
aataccgcaa gcgacaggcc gatcatcgtc gcgctccagc gaaagcggtc ctcgccgaaa   11160
atgacccaga gcgctgccgg cacctgtcct acgagttgca tgataaagaa gacagtcata   11220
agtgcggcga cgatagtcat gccccgcgcc caccggaagg agctgactgg gttgaaggct   11280
ctcaagggca tcggtcgagg atccttcaat atgcgcacat acgctgttat gttcaaggtc   11340
ccttcgttta agaacgaaag cggtcttcct tttgagggat gtttcaagtt gttcaaatct   11400
atcaaatttg caaatcccca gtctgtatct agagcgttga atcggtgatg cgatttgtta   11460
attaaattga tggtgtcacc attaccaggt ctagatatac caatggcaaa ctgagcacaa   11520
caataccagt ccggatcaac tggcaccatc tctcccgtag tctcatctaa ttttttcttcc  11580
ggatgaggtt ccagatatac cgcaacacct ttattatggt ttccctgagg gaataataga   11640
atgtcccatt cgaaatcacc aattctaaac ctgggcgaat tgtatttcgg gtttgttaac   11700
tcgttccagt caggaatgtt ccacgtgaag ctatcttcca gcaaagtctc cacttcttca   11760
tcaaattgtg gagaatactc ccaatgctct tatctatggg acttccggga aacacagtac   11820
cgatacttcc caattcgtct tcagagctca ttgtttgttt gaagagacta atcaaagaat   11880
cgttttctca aaaaaattaa tatcttaact gatagtttga tcaaaggggc aaaacgtagg   11940
ggcaaacaaa cggaaaaatc gtttctcaaa ttttctgatg ccaagaactc taaccagtct   12000
tatctaaaaa ttgccttatg atccgtctct ccggttacag cctgtgtaac tgattaatcc   12060
tgcctttcta atcaccattc taatgttta attaagggat tttgtcttca ttaacggctt    12120
tcgctcataa aaatgttatg acgttttgcc cgcaggcggg aaaccatcca cttcacgaga   12180
ctgatctcct ctgccggaac accgggcatc tccaacttat aagttggaga ataagagaa    12240
tttcagattg agagaatgaa aaaaaaaaac ccttagttca taggtccatt ctcttagcgc   12300
aactacagag aacaggggca caaacaggca aaaacgggc acaacctcaa tggagtgatg    12360
caacctgcct ggagtaaatg atgacacaag gcaattgacc cacgcatgta tctatctcat   12420
tttcttacac cttctattac cttctgctct ctctgatttg gaaaaagctg aaaaaaaagg   12480
ttgaaaccag ttccctgaaa ttattcccct acttgactaa taagtatata aagacggtag   12540
gtattgattg taattctgta aatctatttc ttaaacttct taaattctac ttttatagtt   12600
agtctttttt ttagttttaa aacaccaaga acttagtttc gaataaacac acataaacaa   12660
```

| | | | | |
|---|---|---|---|---|
| acaagcttac aaaacaaa | atg gct gca tat gca gct cag ggc tat aag gtg | | | 12711 |
| | Met Ala Ala Tyr Ala Ala Gln Gly Tyr Lys Val | | | |
| | 1 5 10 | | | |

| | | |
|---|---|---|
| cta gta ctc aac ccc tct gtt gct gca aca ctg ggc ttt ggt gct tac | | 12759 |
| Leu Val Leu Asn Pro Ser Val Ala Ala Thr Leu Gly Phe Gly Ala Tyr | | |
| 15 20 25 | | |

| | | |
|---|---|---|
| atg tcc aag gct cat ggg atc gat cct aac atc agg acc ggg gtg aga | | 12807 |
| Met Ser Lys Ala His Gly Ile Asp Pro Asn Ile Arg Thr Gly Val Arg | | |
| 30 35 40 | | |

| | | |
|---|---|---|
| aca att acc act ggc agc ccc atc acg tac tcc acc tac ggc aag ttc | | 12855 |
| Thr Ile Thr Thr Gly Ser Pro Ile Thr Tyr Ser Thr Tyr Gly Lys Phe | | |
| 45 50 55 | | |

```
ctt gcc gac ggc ggg tgc tcg ggg ggc gct tat gac ata ata att tgt      12903
Leu Ala Asp Gly Gly Cys Ser Gly Gly Ala Tyr Asp Ile Ile Ile Cys
 60                  65                  70                  75 gac gag tgc cac tcc acg gat gcc aca tcc atc ttg ggc att ggc act      12951
Asp Glu Cys His Ser Thr Asp Ala Thr Ser Ile Leu Gly Ile Gly Thr
             80                  85                  90 gtc ctt gac caa gca gag act gcg ggg gcg aga ctg gtt gtg ctc gcc      12999
Val Leu Asp Gln Ala Glu Thr Ala Gly Ala Arg Leu Val Val Leu Ala
         95                 100                 105 acc gcc acc cct ccg ggc tcc gtc act gtg ccc cat ccc aac atc gag      13047
Thr Ala Thr Pro Pro Gly Ser Val Thr Val Pro His Pro Asn Ile Glu
     110                 115                 120 gag gtt gct ctg tcc acc acc gga gag atc cct ttt tac ggc aag gct      13095
Glu Val Ala Leu Ser Thr Thr Gly Glu Ile Pro Phe Tyr Gly Lys Ala
 125                 130                 135 atc ccc ctc gaa gta atc aag ggg ggg aga cat ctc atc ttc tgt cat      13143
Ile Pro Leu Glu Val Ile Lys Gly Gly Arg His Leu Ile Phe Cys His
140                 145                 150                 155 tca aag aag aag tgc gac gaa ctc gcc gca aag ctg gtc gca ttg ggc      13191
Ser Lys Lys Lys Cys Asp Glu Leu Ala Ala Lys Leu Val Ala Leu Gly
             160                 165                 170 atc aat gcc gtg gcc tac tac cgc ggt ctt gac gtg tcc gtc atc ccg      13239
Ile Asn Ala Val Ala Tyr Tyr Arg Gly Leu Asp Val Ser Val Ile Pro
         175                 180                 185 acc agc ggc gat gtt gtc gtc gtg gca acc gat gcc ctc atg acc ggc      13287
Thr Ser Gly Asp Val Val Val Val Ala Thr Asp Ala Leu Met Thr Gly
     190                 195                 200 tat acc ggc gac ttc gac tcg gtg ata gac tgc aat acg tgt gtc acc      13335
Tyr Thr Gly Asp Phe Asp Ser Val Ile Asp Cys Asn Thr Cys Val Thr
 205                 210                 215 cag aca gtc gat ttc agc ctt gac cct acc ttc acc att gag aca atc      13383
Gln Thr Val Asp Phe Ser Leu Asp Pro Thr Phe Thr Ile Glu Thr Ile
220                 225                 230                 235 acg ctc ccc caa gat gct gtc tcc cgc act caa cgt cgg ggc agg act      13431
Thr Leu Pro Gln Asp Ala Val Ser Arg Thr Gln Arg Arg Gly Arg Thr
             240                 245                 250 ggc agg ggg aag cca ggc atc tac aga ttt gtg gca ccg ggg gag cgc      13479
Gly Arg Gly Lys Pro Gly Ile Tyr Arg Phe Val Ala Pro Gly Glu Arg
         255                 260                 265 ccc tcc ggc atg ttc gac tcg tcc gtc ctc tgt gag tgc tat gac gca      13527
Pro Ser Gly Met Phe Asp Ser Ser Val Leu Cys Glu Cys Tyr Asp Ala
     270                 275                 280 ggc tgt gct tgg tat gag ctc acg ccc gcc gag act aca gtt agg cta      13575
Gly Cys Ala Trp Tyr Glu Leu Thr Pro Ala Glu Thr Thr Val Arg Leu
 285                 290                 295 cga gcg tac atg aac acc ccg ggg ctt ccc gtg tgc cag gac cat ctt      13623
Arg Ala Tyr Met Asn Thr Pro Gly Leu Pro Val Cys Gln Asp His Leu
300                 305                 310                 315 gaa ttt tgg gag ggc gtc ttt aca ggc ctc act cat ata gat gcc cac      13671
Glu Phe Trp Glu Gly Val Phe Thr Gly Leu Thr His Ile Asp Ala His
             320                 325                 330 ttt cta tcc cag aca aag cag agt ggg gag aac ctt cct tac ctg gta      13719
Phe Leu Ser Gln Thr Lys Gln Ser Gly Glu Asn Leu Pro Tyr Leu Val
         335                 340                 345 gcg tac caa gcc acc gtg tgc gct agg gct caa gcc cct ccc cca tcg      13767
Ala Tyr Gln Ala Thr Val Cys Ala Arg Ala Gln Ala Pro Pro Pro Ser
     350                 355                 360 tgg gac cag atg tgg aag tgt ttg att cgc ctc aag ccc acc ctc cat      13815
Trp Asp Gln Met Trp Lys Cys Leu Ile Arg Leu Lys Pro Thr Leu His
 365                 370                 375
```

| | |
|---|---|
| ggg cca aca ccc ctg cta tac aga ctg ggc gct gtt cag aat gaa atc<br>Gly Pro Thr Pro Leu Leu Tyr Arg Leu Gly Ala Val Gln Asn Glu Ile<br>380                      385                      390                      395 | 13863 |
| acc ctg acg cac cca gtc acc aaa tac atc atg aca tgc atg tcg gcc<br>Thr Leu Thr His Pro Val Thr Lys Tyr Ile Met Thr Cys Met Ser Ala<br>                      400                      405                      410 | 13911 |
| gac ctg gag gtc gtc acg agc acc tgg gtg ctc gtt ggc ggc gtc ctg<br>Asp Leu Glu Val Val Thr Ser Thr Trp Val Leu Val Gly Gly Val Leu<br>                415                      420                      425 | 13959 |
| gct gct ttg gcc gcg tat tgc ctg tca aca ggc tgc gtg gtc ata gtg<br>Ala Ala Leu Ala Ala Tyr Cys Leu Ser Thr Gly Cys Val Val Ile Val<br>            430                      435                      440 | 14007 |
| ggc agg gtc gtc ttg tcc ggg aag ccg gca atc ata cct gac agg gaa<br>Gly Arg Val Val Leu Ser Gly Lys Pro Ala Ile Ile Pro Asp Arg Glu<br>445                      450                      455 | 14055 |
| gtc ctc tac cga gag ttc gat gag atg gaa gag tgc tct cag cac tta<br>Val Leu Tyr Arg Glu Phe Asp Glu Met Glu Glu Cys Ser Gln His Leu<br>460                      465                      470                      475 | 14103 |
| ccg tac atc gag caa ggg atg atg ctc gcc gag cag ttc aag cag aag<br>Pro Tyr Ile Glu Gln Gly Met Met Leu Ala Glu Gln Phe Lys Gln Lys<br>                      480                      485                      490 | 14151 |
| gcc ctc ggc ctc ctg cag acc gcg tcc cgt cag gca gag gtt atc gcc<br>Ala Leu Gly Leu Leu Gln Thr Ala Ser Arg Gln Ala Glu Val Ile Ala<br>            495                      500                      505 | 14199 |
| cct gct gtc cag acc aac tgg caa aaa ctc gag acc ttc tgg gcg aag<br>Pro Ala Val Gln Thr Asn Trp Gln Lys Leu Glu Thr Phe Trp Ala Lys<br>                510                      515                      520 | 14247 |
| cat atg tgg aac ttc atc agt ggg ata caa tac ttg gcg ggc ttg tca<br>His Met Trp Asn Phe Ile Ser Gly Ile Gln Tyr Leu Ala Gly Leu Ser<br>525                      530                      535 | 14295 |
| acg ctg cct ggt aac ccc gcc att gct tca ttg atg gct ttt aca gct<br>Thr Leu Pro Gly Asn Pro Ala Ile Ala Ser Leu Met Ala Phe Thr Ala<br>540                      545                      550                      555 | 14343 |
| gct gtc acc agc cca cta acc act agc caa acc ctc ctc ttc aac ata<br>Ala Val Thr Ser Pro Leu Thr Thr Ser Gln Thr Leu Leu Phe Asn Ile<br>            560                      565                      570 | 14391 |
| ttg ggg ggg tgg gtg gct gcc cag ctc gcc gcc ccc ggt gcc gct act<br>Leu Gly Gly Trp Val Ala Ala Gln Leu Ala Ala Pro Gly Ala Ala Thr<br>                575                      580                      585 | 14439 |
| gcc ttt gtg ggc gct ggc tta gct ggc gcc gcc atc ggc agt gtt gga<br>Ala Phe Val Gly Ala Gly Leu Ala Gly Ala Ala Ile Gly Ser Val Gly<br>            590                      595                      600 | 14487 |
| ctg ggg aag gtc ctc ata gac atc ctt gca ggg tat ggc gcg ggc gtg<br>Leu Gly Lys Val Leu Ile Asp Ile Leu Ala Gly Tyr Gly Ala Gly Val<br>605                      610                      615 | 14535 |
| gcg gga gct ctt gtg gca ttc aag atc atg agc ggt gag gtc ccc tcc<br>Ala Gly Ala Leu Val Ala Phe Lys Ile Met Ser Gly Glu Val Pro Ser<br>620                      625                      630                      635 | 14583 |
| acg gag gac ctg gtc aat cta ctg ccc gcc atc ctc tcg ccc gga gcc<br>Thr Glu Asp Leu Val Asn Leu Leu Pro Ala Ile Leu Ser Pro Gly Ala<br>                640                      645                      650 | 14631 |
| ctc gta gtc ggc gtg gtc tgt gca gca ata ctg cgc cgg cac gtt ggc<br>Leu Val Val Gly Val Val Cys Ala Ala Ile Leu Arg Arg His Val Gly<br>            655                      660                      665 | 14679 |
| ccg ggc gag ggg gca gtg cag tgg atg aac cgg ctg ata gcc ttc gcc<br>Pro Gly Glu Gly Ala Val Gln Trp Met Asn Arg Leu Ile Ala Phe Ala<br>            670                      675                      680 | 14727 |
| tcc cgg ggg aac cat gtt tcc ccc acg cac tac gtg ccg gag agc gat<br>Ser Arg Gly Asn His Val Ser Pro Thr His Tyr Val Pro Glu Ser Asp | 14775 |

```
                685                 690                 695
gca gct gcc cgc gtc act gcc ata ctc agc agc ctc act gta acc cag    14823
Ala Ala Ala Arg Val Thr Ala Ile Leu Ser Ser Leu Thr Val Thr Gln
700                 705                 710                 715 ctc ctg agg cga ctg cac cag tgg ata agc tcg gag tgt acc act cca    14871
Leu Leu Arg Arg Leu His Gln Trp Ile Ser Ser Glu Cys Thr Thr Pro
                720                 725                 730 tgc tcc ggt tcc tgg cta agg gac atc tgg gac tgg ata tgc gag gtg    14919
Cys Ser Gly Ser Trp Leu Arg Asp Ile Trp Asp Trp Ile Cys Glu Val
            735                 740                 745 ttg agc gac ttt aag acc tgg cta aaa gct aag ctc atg cca cag ctg    14967
Leu Ser Asp Phe Lys Thr Trp Leu Lys Ala Lys Leu Met Pro Gln Leu
        750                 755                 760 cct ggg atc ccc ttt gtg tcc tgc cag cgc ggg tat aag ggg gtc tgg    15015
Pro Gly Ile Pro Phe Val Ser Cys Gln Arg Gly Tyr Lys Gly Val Trp
    765                 770                 775 cga ggg gac ggc atc atg cac act cgc tgc cac tgt gga gct gag atc    15063
Arg Gly Asp Gly Ile Met His Thr Arg Cys His Cys Gly Ala Glu Ile
780                 785                 790                 795 act gga cat gtc aaa aac ggg acg atg agg atc gtc ggt cct agg acc    15111
Thr Gly His Val Lys Asn Gly Thr Met Arg Ile Val Gly Pro Arg Thr
                800                 805                 810 tgc agg aac atg tgg agt ggg acc ttc ccc att aat gcc tac acc acg    15159
Cys Arg Asn Met Trp Ser Gly Thr Phe Pro Ile Asn Ala Tyr Thr Thr
            815                 820                 825 ggc ccc tgt acc ccc ctt cct gcg ccg aac tac acg ttc gcg cta tgg    15207
Gly Pro Cys Thr Pro Leu Pro Ala Pro Asn Tyr Thr Phe Ala Leu Trp
        830                 835                 840 agg gtg tct gca gag gaa tac gtg gag ata agg cag gtg ggg gac ttc    15255
Arg Val Ser Ala Glu Glu Tyr Val Glu Ile Arg Gln Val Gly Asp Phe
    845                 850                 855 cac tac gtg acg ggt atg act act gac aat ctt aaa tgc ccg tgc cag    15303
His Tyr Val Thr Gly Met Thr Thr Asp Asn Leu Lys Cys Pro Cys Gln
860                 865                 870                 875 gtc cca tcg ccc gaa ttt ttc aca gaa ttg gac ggg gtg cgc cta cat    15351
Val Pro Ser Pro Glu Phe Phe Thr Glu Leu Asp Gly Val Arg Leu His
                880                 885                 890 agg ttt gcg ccc ccc tgc aag ccc ttg ctg cgg gag gag gta tca ttc    15399
Arg Phe Ala Pro Pro Cys Lys Pro Leu Leu Arg Glu Glu Val Ser Phe
            895                 900                 905 aga gta gga ctc cac gaa tac ccg gta ggg tcg caa tta cct tgc gag    15447
Arg Val Gly Leu His Glu Tyr Pro Val Gly Ser Gln Leu Pro Cys Glu
        910                 915                 920 ccc gaa ccg gac gtg gcc gtg ttg acg tcc atg ctc act gat ccc tcc    15495
Pro Glu Pro Asp Val Ala Val Leu Thr Ser Met Leu Thr Asp Pro Ser
    925                 930                 935 cat ata aca gca gag gcg gcc ggg cga agg ttg gcg agg gga tca ccc    15543
His Ile Thr Ala Glu Ala Ala Gly Arg Arg Leu Ala Arg Gly Ser Pro
940                 945                 950                 955 ccc tct gtg gcc agc tcc tcg gct agc cag cta tcc gct cca tct ctc    15591
Pro Ser Val Ala Ser Ser Ser Ala Ser Gln Leu Ser Ala Pro Ser Leu
                960                 965                 970 aag gca act tgc acc gct aac cat gac tcc cct gat gct gag ctc ata    15639
Lys Ala Thr Cys Thr Ala Asn His Asp Ser Pro Asp Ala Glu Leu Ile
            975                 980                 985 gag gcc aac ctc cta tgg agg cag gag atg ggc ggc aac atc acc agg    15687
Glu Ala Asn Leu Leu Trp Arg Gln Glu Met Gly Gly Asn Ile Thr Arg
        990                 995                 1000 gtt gag tca gaa aac aaa gtg gtg att ctg gac tcc ttc gat ccg ctt    15735
```

```
Val Glu Ser Glu Asn Lys Val Val Ile Leu Asp Ser Phe Asp Pro Leu
    1005                1010                1015 gtg gcg gag gag gac gag cgg gag atc tcc gta ccc gca gaa atc ctg       15783
Val Ala Glu Glu Asp Glu Arg Glu Ile Ser Val Pro Ala Glu Ile Leu
1020                1025                1030                1035 cgg aag tct cgg aga ttc gcc cag gcc ctg ccc gtt tgg gcg cgg ccg       15831
Arg Lys Ser Arg Arg Phe Ala Gln Ala Leu Pro Val Trp Ala Arg Pro
                1040                1045                1050 gac tat aac ccc ccg cta gtg gag acg tgg aaa aag ccc gac tac gaa       15879
Asp Tyr Asn Pro Pro Leu Val Glu Thr Trp Lys Lys Pro Asp Tyr Glu
    1055                1060                1065 cca cct gtg gtc cat ggc tgc ccg ctt cca cct cca aag tcc cct cct       15927
Pro Pro Val Val His Gly Cys Pro Leu Pro Pro Pro Lys Ser Pro Pro
        1070                1075                1080 gtg cct ccg cct cgg aag aag cgg acg gtg gtc ctc act gaa tca acc       15975
Val Pro Pro Pro Arg Lys Lys Arg Thr Val Val Leu Thr Glu Ser Thr
    1085                1090                1095 cta tct act gcc ttg gcc gag ctc gcc acc aga agc ttt ggc agc tcc       16023
Leu Ser Thr Ala Leu Ala Glu Leu Ala Thr Arg Ser Phe Gly Ser Ser
1100                1105                1110                1115 tca act tcc ggc att acg ggc gac aat acg aca aca tcc tct gag ccc       16071
Ser Thr Ser Gly Ile Thr Gly Asp Asn Thr Thr Thr Ser Ser Glu Pro
                1120                1125                1130 gcc cct tct ggc tgc ccc ccc gac tcc gac gct gag tcc tat tcc tcc       16119
Ala Pro Ser Gly Cys Pro Pro Asp Ser Asp Ala Glu Ser Tyr Ser Ser
            1135                1140                1145 atg ccc ccc ctg gag ggg gag cct ggg gat ccg gat ctt agc gac ggg       16167
Met Pro Pro Leu Glu Gly Glu Pro Gly Asp Pro Asp Leu Ser Asp Gly
        1150                1155                1160 tca tgg tca acg gtc agt agt gag gcc aac gcg gag gat gtc gtg tgc       16215
Ser Trp Ser Thr Val Ser Ser Glu Ala Asn Ala Glu Asp Val Val Cys
    1165                1170                1175 tgc tca atg tct tac tct tgg aca ggc gca ctc gtc acc ccg tgc gcc       16263
Cys Ser Met Ser Tyr Ser Trp Thr Gly Ala Leu Val Thr Pro Cys Ala
1180                1185                1190                1195 gcg gaa gaa cag aaa ctg ccc atc aat gca cta agc aac tcg ttg cta       16311
Ala Glu Glu Gln Lys Leu Pro Ile Asn Ala Leu Ser Asn Ser Leu Leu
                1200                1205                1210 cgt cac cac aat ttg gtg tat tcc acc acc tca cgc agt gct tgc caa       16359
Arg His His Asn Leu Val Tyr Ser Thr Thr Ser Arg Ser Ala Cys Gln
            1215                1220                1225 agg cag aag aaa gtc aca ttt gac aga ctg caa gtt ctg gac agc cat       16407
Arg Gln Lys Lys Val Thr Phe Asp Arg Leu Gln Val Leu Asp Ser His
        1230                1235                1240 tac cag gac gta ctc aag gag gtt aaa gca gcg gcg tca aaa gtg aag       16455
Tyr Gln Asp Val Leu Lys Glu Val Lys Ala Ala Ala Ser Lys Val Lys
    1245                1250                1255 gct aac ttg cta tcc gta gag gaa gct tgc agc ctg acg ccc cca cac       16503
Ala Asn Leu Leu Ser Val Glu Glu Ala Cys Ser Leu Thr Pro Pro His
1260                1265                1270                1275 tca gcc aaa tcc aag ttt ggt tat ggg gca aaa gac gtc cgt tgc cat       16551
Ser Ala Lys Ser Lys Phe Gly Tyr Gly Ala Lys Asp Val Arg Cys His
                1280                1285                1290 gcc aga aag gcc gta acc cac atc aac tcc gtg tgg aaa gac ctt ctg       16599
Ala Arg Lys Ala Val Thr His Ile Asn Ser Val Trp Lys Asp Leu Leu
            1295                1300                1305 gaa gac aat gta aca cca ata gac act acc atc atg gct aag aac gag       16647
Glu Asp Asn Val Thr Pro Ile Asp Thr Thr Ile Met Ala Lys Asn Glu
        1310                1315                1320
```

-continued

| | |
|---|---|
| gtt ttc tgc gtt cag cct gag aag ggg ggt cgt aag cca gct cgt ctc<br>Val Phe Cys Val Gln Pro Glu Lys Gly Gly Arg Lys Pro Ala Arg Leu<br>1325                    1330                    1335 | 16695 |
| atc gtg ttc ccc gat ctg ggc gtg cgc gtg tgc gaa aag atg gct ttg<br>Ile Val Phe Pro Asp Leu Gly Val Arg Val Cys Glu Lys Met Ala Leu<br>1340                    1345                    1350                    1355 | 16743 |
| tac gac gtg gtt aca aag ctc ccc ttg gcc gtg atg gga agc tcc tac<br>Tyr Asp Val Val Thr Lys Leu Pro Leu Ala Val Met Gly Ser Ser Tyr<br>                1360                    1365                    1370 | 16791 |
| gga ttc caa tac tca cca gga cag cgg gtt gaa ttc ctc gtg caa gcg<br>Gly Phe Gln Tyr Ser Pro Gly Gln Arg Val Glu Phe Leu Val Gln Ala<br>                    1375                    1380                    1385 | 16839 |
| tgg aag tcc aag aaa acc cca atg ggg ttc tcg tat gat acc cgc tgc<br>Trp Lys Ser Lys Lys Thr Pro Met Gly Phe Ser Tyr Asp Thr Arg Cys<br>1390                    1395                    1400 | 16887 |
| ttt gac tcc aca gtc act gag agc gac atc cgt acg gag gag gca atc<br>Phe Asp Ser Thr Val Thr Glu Ser Asp Ile Arg Thr Glu Glu Ala Ile<br>1405                    1410                    1415 | 16935 |
| tac caa tgt tgt gac ctc gac ccc caa gcc cgc gtg gcc atc aag tcc<br>Tyr Gln Cys Cys Asp Leu Asp Pro Gln Ala Arg Val Ala Ile Lys Ser<br>1420                    1425                    1430                    1435 | 16983 |
| ctc acc gag agg ctt tat gtt ggg ggc cct ctt acc aat tca agg ggg<br>Leu Thr Glu Arg Leu Tyr Val Gly Gly Pro Leu Thr Asn Ser Arg Gly<br>                    1440                    1445                    1450 | 17031 |
| gag aac tgc ggc tat cgc agg tgc cgc gcg agc ggc gta ctg aca act<br>Glu Asn Cys Gly Tyr Arg Arg Cys Arg Ala Ser Gly Val Leu Thr Thr<br>                    1455                    1460                    1465 | 17079 |
| agc tgt ggt aac acc ctc act tgc tac atc aag gcc cgg gca gcc tgt<br>Ser Cys Gly Asn Thr Leu Thr Cys Tyr Ile Lys Ala Arg Ala Ala Cys<br>1470                    1475                    1480 | 17127 |
| cga gcc gca ggg ctc cag gac tgc acc atg ctc gtg tgt ggc gac gac<br>Arg Ala Ala Gly Leu Gln Asp Cys Thr Met Leu Val Cys Gly Asp Asp<br>                    1485                    1490                    1495 | 17175 |
| tta gtc gtt atc tgt gaa agc gcg ggg gtc cag gag gac gcg gcg agc<br>Leu Val Val Ile Cys Glu Ser Ala Gly Val Gln Glu Asp Ala Ala Ser<br>1500                    1505                    1510                    1515 | 17223 |
| ctg aga gcc ttc acg gag gct atg acc agg tac tcc gcc ccc cct ggg<br>Leu Arg Ala Phe Thr Glu Ala Met Thr Arg Tyr Ser Ala Pro Pro Gly<br>                    1520                    1525                    1530 | 17271 |
| gac ccc cca caa cca gaa tac gac ttg gag ctc ata aca tca tgc tcc<br>Asp Pro Pro Gln Pro Glu Tyr Asp Leu Glu Leu Ile Thr Ser Cys Ser<br>                    1535                    1540                    1545 | 17319 |
| tcc aac gtg tca gtc gcc cac gac ggc gct gga aag agg gtc tac tac<br>Ser Asn Val Ser Val Ala His Asp Gly Ala Gly Lys Arg Val Tyr Tyr<br>1550                    1555                    1560 | 17367 |
| ctc acc cgt gac cct aca acc ccc ctc gcg aga gct gcg tgg gag aca<br>Leu Thr Arg Asp Pro Thr Thr Pro Leu Ala Arg Ala Ala Trp Glu Thr<br>1565                    1570                    1575 | 17415 |
| gca aga cac act cca gtc aat tcc tgg cta ggc aac ata atc atg ttt<br>Ala Arg His Thr Pro Val Asn Ser Trp Leu Gly Asn Ile Ile Met Phe<br>1580                    1585                    1590                    1595 | 17463 |
| gcc ccc aca ctg tgg gcg agg atg ata ctg atg acc cat ttc ttt agc<br>Ala Pro Thr Leu Trp Ala Arg Met Ile Leu Met Thr His Phe Phe Ser<br>                    1600                    1605                    1610 | 17511 |
| gtc ctt ata gcc agg gac cag ctt gaa cag gcc ctc gat tgc gag atc<br>Val Leu Ile Ala Arg Asp Gln Leu Glu Gln Ala Leu Asp Cys Glu Ile<br>                    1615                    1620                    1625 | 17559 |
| tac ggg gcc tgc tac tcc ata gaa cca ctg gat cta cct cca atc att<br>Tyr Gly Ala Cys Tyr Ser Ile Glu Pro Leu Asp Leu Pro Pro Ile Ile<br>                    1630                    1635                    1640 | 17607 |

```
caa aga ctc cat ggc ctc agc gca ttt tca ctc cac agt tac tct cca    17655
Gln Arg Leu His Gly Leu Ser Ala Phe Ser Leu His Ser Tyr Ser Pro
    1645                1650                1655 ggt gaa atc aat agg gtg gcc gca tgc ctc aga aaa ctt ggg gta ccg    17703
Gly Glu Ile Asn Arg Val Ala Ala Cys Leu Arg Lys Leu Gly Val Pro
1660                1665                1670                1675 ccc ttg cga gct tgg aga cac cgg gcc cgg agc gtc cgc gct agg ctt    17751
Pro Leu Arg Ala Trp Arg His Arg Ala Arg Ser Val Arg Ala Arg Leu
            1680                1685                1690 ctg gcc aga gga ggc agg gct gcc ata tgt ggc aag tac ctc ttc aac    17799
Leu Ala Arg Gly Gly Arg Ala Ala Ile Cys Gly Lys Tyr Leu Phe Asn
        1695                1700                1705 tgg gca gta aga aca aag ctc aaa ctc act cca ata gcg gcc gct ggc    17847
Trp Ala Val Arg Thr Lys Leu Lys Leu Thr Pro Ile Ala Ala Ala Gly
    1710                1715                1720 cag ctg gac ttg tcc ggc tgg ttc acg gct ggc tac agc ggg gga gac    17895
Gln Leu Asp Leu Ser Gly Trp Phe Thr Ala Gly Tyr Ser Gly Gly Asp
1725                1730                1735 att tat cac agc gtg tct cat gcc cgg ccc cgc tgg atc tgg ttt tgc    17943
Ile Tyr His Ser Val Ser His Ala Arg Pro Arg Trp Ile Trp Phe Cys
1740                1745                1750                1755 cta ctc ctg ctt gct gca ggg gta ggc atc tac ctc ctc ccc aac cga    17991
Leu Leu Leu Leu Ala Ala Gly Val Gly Ile Tyr Leu Leu Pro Asn Arg
            1760                1765                1770 atg agc acg aat cct aaa cct caa aga aag acc aaa cgt aac acc aac    18039
Met Ser Thr Asn Pro Lys Pro Gln Arg Lys Thr Lys Arg Asn Thr Asn
        1775                1780                1785 cgg cgg ccg cag gac gtc aag ttc ccg ggt ggc ggt cag atc gtt ggt    18087
Arg Arg Pro Gln Asp Val Lys Phe Pro Gly Gly Gly Gln Ile Val Gly
    1790                1795                1800 gga gtt tac ttg ttg ccg cgc agg ggc cct aga ttg ggt gtg cgc gcg    18135
Gly Val Tyr Leu Leu Pro Arg Arg Gly Pro Arg Leu Gly Val Arg Ala
1805                1810                1815 acg aga aag act tcc gag cgg tcg caa cct cga ggt aga cgt cag cct    18183
Thr Arg Lys Thr Ser Glu Arg Ser Gln Pro Arg Gly Arg Arg Gln Pro
1820                1825                1830                1835 atc ccc aag gct cgt cgg ccc gag ggc agg acc tgg gct cag ccc ggg    18231
Ile Pro Lys Ala Arg Arg Pro Glu Gly Arg Thr Trp Ala Gln Pro Gly
            1840                1845                1850 tac cct tgg ccc ctc tat ggc aat gag ggc tgc ggg tgg gcg gga tgg    18279
Tyr Pro Trp Pro Leu Tyr Gly Asn Glu Gly Cys Gly Trp Ala Gly Trp
        1855                1860                1865 ctc ctg tct ccc cgt ggc tct cgg cct agc tgg ggc ccc aca gac ccc    18327
Leu Leu Ser Pro Arg Gly Ser Arg Pro Ser Trp Gly Pro Thr Asp Pro
    1870                1875                1880 cgg cgt agg tcg cgc aat ttg ggt aag gtc atc gat acc ctt acg tgc    18375
Arg Arg Arg Ser Arg Asn Leu Gly Lys Val Ile Asp Thr Leu Thr Cys
1885                1890                1895 ggc ttc gcc gac ctc atg ggg tac ata ccg ctc gtc ggc gcc cct ctt    18423
Gly Phe Ala Asp Leu Met Gly Tyr Ile Pro Leu Val Gly Ala Pro Leu
1900                1905                1910                1915 gga ggc gct gcc agg gcc ctg gcg cat ggc gtc cgg gtt ctg gaa gac    18471
Gly Gly Ala Ala Arg Ala Leu Ala His Gly Val Arg Val Leu Glu Asp
            1920                1925                1930 ggc gtg aac tat gca aca ggg aac ctt cct ggt tgc tct taatagtcga    18520
Gly Val Asn Tyr Ala Thr Gly Asn Leu Pro Gly Cys Ser
        1935                1940 ctttgttccc actgtacttt tagctcgtac aaaatacaat atactttca tttctccgta   18580
```

-continued

```
aacaacatgt tttcccatgt aatatccttt tctattttc gttccgttac caactttaca  18640
catactttat atagctattc acttctatac actaaaaaac taagacaatt ttaattttgc  18700
tgcctgccat atttcaattt gttataaatt cctataattt atcctattag tagctaaaaa  18760
aagatgaatg tgaatcgaat cctaagagaa ttggatctga tccacaggac gggtgtggtc  18820
gccatgatcg cgtagtcgat agtggctcca agtagcgaag cgagcaggac tgggcggcgg  18880
ccaaagcggt cggacagtgc tccgagaacg ggtgcgcata gaaattgcat caacgcatat  18940
agcgctagca gcacgccata gtgactggcg atgctgtcgg aatggacgat atcccgcaag  19000
aggcccggca gtaccggcat aaccaagcct atgcctacag catccagggt gacggtgccg  19060
aggatgacga tgagcgcatt gttagatttc atacacggtg cctgactgcg ttagcaattt  19120
aactgtgata aactaccgca ttaaagcttt tcctttccaa tttttttttt ttcgtcatta  19180
taaaaatcat tacgaccgag attcccgggt aataactgat ataattaaat tgaagctcta  19240
atttgtgagt ttagtataca tgcatttact tataatacag tttttttagtt ttgctggccg  19300 catcttctca aatatgcttc ccagcctgct tttctgtaac gttcaccctc taccttagca  19360
tcccttccct ttgcaaatag tcctcttcca acaataataa tgtcagatcc tgtagagacc  19420
acatcatcca cggttctata ctgttgaccc aatgcgtctc ccttgtcatc taaacccaca  19480
ccgggtgtca taatcaacca atcgtaacct tcatctcttc cacccatgtc tctttgagca  19540
ataaagccga taacaaaatc tttgtcgctc ttcgcaatgt caacagtacc cttagtatat  19600
tctccagtag atagggagcc cttgcatgac aattctgcta acatcaaaag gcctctaggt  19660
tcctttgtta cttcttctgc cgcctgcttc aaaccgctaa caatacctgg gcccaccaca  19720
ccgtgtgcat tcgtaatgtc tgcccattct gctattctgt atacacccgc agagtactgc  19780
aatttgactg tattaccaat gtcagcaaat tttctgtctt cgaagagtaa aaaattgtac  19840
ttggcggata atgcctttag cggcttaact gtgccctcca tggaaaaatc agtcaagata  19900
tccacatgtg tttttagtaa acaaattttg ggacctaatg cttcaactaa ctccagtaat  19960
tccttggtgg tacgaacatc caatgaagca cacaagtttg tttgcttttc gtgcatgata  20020
ttaaatagct tggcagcaac aggactagga tgagtagcag cacgttcctt atatgtagct  20080
ttcgacatga tttatcttcg tttcctgcag gttttttgttc tgtgcagttg ggttaagaat  20140
actgggcaat ttcatgtttc ttcaacacta catatgcgta tatataccaa tctaagtctg  20200
tgctccttcc ttcgttcttc cttctgttcg gagattaccg aatcaaaaaa atttcaagga  20260
aaccgaaatc aaaaaaaaga ataaaaaaaa aatgatgaat tgaaaagctt atcgat       20316
```

<210> SEQ ID NO 15
<211> LENGTH: 1944
<212> TYPE: PRT
<213> ORGANISM: Artificial Sequence
<220> FEATURE:
<223> OTHER INFORMATION: Description of Artificial Sequence:
      pd.delta.NS3NS5.pj.core173

<400> SEQUENCE: 15

Met Ala Ala Tyr Ala Ala Gln Gly Tyr Lys Val Leu Val Leu Asn Pro
1               5                   10                  15

Ser Val Ala Ala Thr Leu Gly Phe Gly Ala Tyr Met Ser Lys Ala His
                20                  25                  30

Gly Ile Asp Pro Asn Ile Arg Thr Gly Val Arg Thr Ile Thr Thr Gly
            35                  40                  45

Ser Pro Ile Thr Tyr Ser Thr Tyr Gly Lys Phe Leu Ala Asp Gly Gly

-continued

```
              50                  55                  60
Cys Ser Gly Gly Ala Tyr Asp Ile Ile Ile Cys Asp Glu Cys His Ser
 65                  70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
             100                 105                 110

Gly Ser Val Thr Val Pro His Pro Asn Ile Glu Val Ala Leu Ser
             115                 120                 125

Thr Thr Gly Glu Ile Pro Phe Tyr Gly Lys Ala Ile Pro Leu Glu Val
130                 135                 140

Ile Lys Gly Gly Arg His Leu Ile Phe Cys His Ser Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
                180                 185                 190

Val Val Val Ala Thr Asp Ala Leu Met Thr Gly Tyr Thr Gly Asp Phe
            195                 200                 205

Asp Ser Val Ile Asp Cys Asn Thr Cys Val Thr Gln Thr Val Asp Phe
210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
            275                 280                 285

Glu Leu Thr Pro Ala Glu Thr Thr Val Arg Leu Arg Ala Tyr Met Asn
290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Ser Trp Asp Gln Met Trp
            355                 360                 365

Lys Cys Leu Ile Arg Leu Lys Pro Thr Leu His Gly Pro Thr Pro Leu
370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
            420                 425                 430

Tyr Cys Leu Ser Thr Gly Cys Val Val Ile Val Gly Arg Val Val Leu
            435                 440                 445

Ser Gly Lys Pro Ala Ile Ile Pro Asp Arg Glu Val Leu Tyr Arg Glu
            450                 455                 460

Phe Asp Glu Met Glu Glu Cys Ser Gln His Leu Pro Tyr Ile Glu Gln
465                 470                 475                 480
```

```
Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
            515                 520                 525

Ile Ser Gly Ile Gln Tyr Leu Ala Gly Leu Ser Thr Leu Pro Gly Asn
            530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Thr Ala Phe Val Gly Ala
                580                 585                 590

Gly Leu Ala Gly Ala Ala Ile Gly Ser Val Gly Leu Gly Lys Val Leu
                595                 600                 605

Ile Asp Ile Leu Ala Gly Tyr Gly Ala Gly Val Ala Gly Ala Leu Val
                610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
                660                 665                 670

Val Gln Trp Met Asn Arg Leu Ile Ala Phe Ala Ser Arg Gly Asn His
                675                 680                 685

Val Ser Pro Thr His Tyr Val Pro Glu Ser Asp Ala Ala Ala Arg Val
                690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
                740                 745                 750

Thr Trp Leu Lys Ala Lys Leu Met Pro Gln Leu Pro Gly Ile Pro Phe
                755                 760                 765

Val Ser Cys Gln Arg Gly Tyr Lys Gly Val Trp Arg Gly Asp Gly Ile
                770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
                805                 810                 815

Ser Gly Thr Phe Pro Ile Asn Ala Tyr Thr Thr Gly Pro Cys Thr Pro
                820                 825                 830

Leu Pro Ala Pro Asn Tyr Thr Phe Ala Leu Trp Arg Val Ser Ala Glu
                835                 840                 845

Glu Tyr Val Glu Ile Arg Gln Val Gly Asp Phe His Tyr Val Thr Gly
                850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
                885                 890                 895
```

```
Cys Lys Pro Leu Leu Arg Glu Glu Val Ser Phe Arg Val Gly Leu His
            900                 905                 910
Glu Tyr Pro Val Gly Ser Gln Leu Pro Cys Glu Pro Glu Pro Asp Val
            915                 920                 925
Ala Val Leu Thr Ser Met Leu Thr Asp Pro Ser His Ile Thr Ala Glu
            930                 935                 940
Ala Ala Gly Arg Arg Leu Ala Arg Gly Ser Pro Pro Ser Val Ala Ser
945                 950                 955                 960
Ser Ser Ala Ser Gln Leu Ser Ala Pro Ser Leu Lys Ala Thr Cys Thr
                965                 970                 975
Ala Asn His Asp Ser Pro Asp Ala Glu Leu Ile Glu Ala Asn Leu Leu
            980                 985                 990
Trp Arg Gln Glu Met Gly Gly Asn Ile Thr Arg Val Glu Ser Glu Asn
            995                 1000                1005
Lys Val Val Ile Leu Asp Ser Phe Asp Pro Leu Val Ala Glu Glu Asp
       1010                 1015                1020
Glu Arg Glu Ile Ser Val Pro Ala Glu Ile Leu Arg Lys Ser Arg Arg
1025                1030                1035                1040
Phe Ala Gln Ala Leu Pro Val Trp Ala Arg Pro Asp Tyr Asn Pro Pro
                1045                1050                1055
Leu Val Glu Thr Trp Lys Lys Pro Asp Tyr Glu Pro Pro Val Val His
            1060                1065                1070
Gly Cys Pro Leu Pro Pro Pro Lys Ser Pro Pro Val Pro Pro Pro Arg
            1075                1080                1085
Lys Lys Arg Thr Val Val Leu Thr Glu Ser Thr Leu Ser Thr Ala Leu
    1090                1095                1100
Ala Glu Leu Ala Thr Arg Ser Phe Gly Ser Ser Ser Thr Ser Gly Ile
1105                1110                1115                1120
Thr Gly Asp Asn Thr Thr Thr Ser Ser Glu Pro Ala Pro Ser Gly Cys
                1125                1130                1135
Pro Pro Asp Ser Asp Ala Glu Ser Tyr Ser Ser Met Pro Pro Leu Glu
            1140                1145                1150
Gly Glu Pro Gly Asp Pro Asp Leu Ser Asp Gly Ser Trp Ser Thr Val
            1155                1160                1165
Ser Ser Glu Ala Asn Ala Glu Asp Val Val Cys Cys Ser Met Ser Tyr
            1170                1175                1180
Ser Trp Thr Gly Ala Leu Val Thr Pro Cys Ala Ala Glu Glu Gln Lys
1185                1190                1195                1200
Leu Pro Ile Asn Ala Leu Ser Asn Ser Leu Leu Arg His His Asn Leu
                1205                1210                1215
Val Tyr Ser Thr Thr Ser Arg Ser Ala Cys Gln Arg Gln Lys Lys Val
            1220                1225                1230
Thr Phe Asp Arg Leu Gln Val Leu Asp Ser His Tyr Gln Asp Val Leu
            1235                1240                1245
Lys Glu Val Lys Ala Ala Ala Ser Lys Val Lys Ala Asn Leu Leu Ser
    1250                1255                1260
Val Glu Glu Ala Cys Ser Leu Thr Pro Pro His Ser Ala Lys Ser Lys
1265                1270                1275                1280
Phe Gly Tyr Gly Ala Lys Asp Val Arg Cys His Ala Arg Lys Ala Val
                1285                1290                1295
Thr His Ile Asn Ser Val Trp Lys Asp Leu Leu Glu Asp Asn Val Thr
            1300                1305                1310
Pro Ile Asp Thr Thr Ile Met Ala Lys Asn Glu Val Phe Cys Val Gln
```

-continued

```
           1315                1320                1325
Pro Glu  Lys Gly Gly Arg  Lys Pro Ala Arg  Leu Ile  Val Phe Pro Asp
   1330                1335                1340

Leu  Gly Val Arg Val  Cys Glu Lys Met Ala  Leu  Tyr Asp Val Val  Thr
1345                1350                1355                1360

Lys Leu Pro Leu Ala  Val Met Gly Ser Ser  Tyr Gly Phe Gln Tyr  Ser
            1365                1370                1375

Pro Gly Gln Arg  Val Glu Phe Leu Val  Gln Ala Trp Lys Ser  Lys Lys
            1380                1385                1390

Thr Pro Met  Gly Phe Ser Tyr Asp  Thr Arg Cys Phe Asp  Ser Thr Val
        1395                1400                1405

Thr Glu  Ser Asp Ile Arg  Thr Glu Glu Ala Ile  Tyr  Gln Cys Cys Asp
    1410                1415                1420

Leu  Asp Pro Gln Ala  Arg  Val Ala Ile Lys Ser  Leu Thr Glu Arg  Leu
1425                1430                1435                1440

Tyr Val Gly Gly Pro  Leu Thr Asn Ser Arg  Gly Glu Asn Cys Gly  Tyr
            1445                1450                1455

Arg Arg Cys Arg  Ala Ser Gly Val Leu  Thr Thr Ser Cys Gly  Asn Thr
            1460                1465                1470

Leu Thr Cys  Tyr Ile Lys Ala Arg  Ala Ala Cys Arg Ala  Ala Gly Leu
        1475                1480                1485

Gln Asp  Cys Thr Met Leu Val  Cys Gly Asp Asp Leu  Val Val Ile  Cys
    1490                1495                1500

Glu  Ser Ala Gly Val  Gln Glu Asp Ala Ala  Ser  Leu Arg Ala Phe  Thr
1505                1510                1515                1520

Glu Ala Met Thr Arg  Tyr Ser Ala Pro Pro  Gly Asp Pro Pro Gln  Pro
            1525                1530                1535

Glu Tyr Asp Leu  Glu Leu Ile Thr Ser  Cys Ser Ser Asn Val  Ser Val
            1540                1545                1550

Ala His Asp  Gly Ala Gly Lys Arg  Val Tyr Tyr Leu Thr  Arg Asp Pro
        1555                1560                1565

Thr Thr  Pro Leu Ala Arg Ala  Ala Trp Glu Thr Ala  Arg His Thr Pro
    1570                1575                1580

Val  Asn Ser Trp Leu  Gly Asn Ile Ile Met  Phe Ala Pro Thr Leu  Trp
1585                1590                1595                1600

Ala Arg Met Ile Leu  Met Thr His Phe Phe  Ser Val Leu Ile Ala  Arg
            1605                1610                1615

Asp Gln Leu Glu  Gln Ala Leu Asp Cys  Glu Ile Tyr Gly Ala  Cys Tyr
            1620                1625                1630

Ser Ile Glu  Pro Leu Asp Leu Pro  Pro Ile Ile Gln Arg  Leu His Gly
        1635                1640                1645

Leu Ser  Ala Phe Ser Leu His  Ser Tyr Ser Pro Gly  Glu Ile Asn Arg
    1650                1655                1660

Val  Ala Ala Cys Leu  Arg Lys Leu Gly Val  Pro  Pro Leu Arg Ala  Trp
1665                1670                1675                1680

Arg His Arg Ala Arg  Ser Val Arg Ala Arg  Leu Leu Ala Arg Gly  Gly
            1685                1690                1695

Arg Ala Ala Ile  Cys Gly Lys Tyr Leu  Phe Asn Trp Ala Val  Arg Thr
            1700                1705                1710

Lys Leu Lys  Leu Thr Pro Ile Ala  Ala Ala Gly Gln Leu  Asp Leu Ser
        1715                1720                1725

Gly Trp  Phe Thr Ala Gly Tyr  Ser Gly Gly Asp Ile  Tyr His Ser Val
    1730                1735                1740
```

| | | | | | | | | | | | | | | |
|---|---|---|---|---|---|---|---|---|---|---|---|---|---|---|
| Ser | His | Ala | Arg | Pro | Arg | Trp | Ile | Trp | Phe | Cys | Leu | Leu | Leu | Ala |
| 1745 | | | | 1750 | | | | 1755 | | | | 1760 | | |
| Ala | Gly | Val | Gly | Ile | Tyr | Leu | Leu | Pro | Asn | Arg | Met | Ser | Thr | Asn | Pro |
| | | | 1765 | | | | | 1770 | | | | | 1775 | |
| Lys | Pro | Gln | Arg | Lys | Thr | Lys | Arg | Asn | Thr | Asn | Arg | Arg | Pro | Gln | Asp |
| | | | 1780 | | | | | 1785 | | | | | 1790 | |
| Val | Lys | Phe | Pro | Gly | Gly | Gln | Ile | Val | Gly | Val | Tyr | Leu | Leu |
| | | | 1795 | | | | 1800 | | | | | 1805 | |
| Pro | Arg | Arg | Gly | Pro | Arg | Leu | Gly | Val | Arg | Ala | Thr | Arg | Lys | Thr | Ser |
| | 1810 | | | | 1815 | | | | | 1820 | | | | |
| Glu | Arg | Ser | Gln | Pro | Arg | Gly | Arg | Arg | Gln | Pro | Ile | Pro | Lys | Ala | Arg |
| 1825 | | | | | 1830 | | | | | 1835 | | | | 1840 | |
| Arg | Pro | Glu | Gly | Arg | Thr | Trp | Ala | Gln | Pro | Gly | Tyr | Pro | Trp | Pro | Leu |
| | | | | 1845 | | | | | 1850 | | | | | 1855 | |
| Tyr | Gly | Asn | Glu | Gly | Cys | Gly | Trp | Ala | Gly | Trp | Leu | Leu | Ser | Pro | Arg |
| | | | 1860 | | | | | 1865 | | | | | 1870 | | |
| Gly | Ser | Arg | Pro | Ser | Trp | Gly | Pro | Thr | Asp | Pro | Arg | Arg | Arg | Ser | Arg |
| | | 1875 | | | | | 1880 | | | | | 1885 | | |
| Asn | Leu | Gly | Lys | Val | Ile | Asp | Thr | Leu | Thr | Cys | Gly | Phe | Ala | Asp | Leu |
| | | 1890 | | | | | 1895 | | | | | 1900 | | |
| Met | Gly | Tyr | Ile | Pro | Leu | Val | Gly | Ala | Pro | Leu | Gly | Gly | Ala | Ala | Arg |
| 1905 | | | | | 1910 | | | | | 1915 | | | | 1920 | |
| Ala | Leu | Ala | His | Gly | Val | Arg | Val | Leu | Glu | Asp | Gly | Val | Asn | Tyr | Ala |
| | | | | 1925 | | | | | 1930 | | | | | 1935 | |
| Thr | Gly | Asn | Leu | Pro | Gly | Cys | Ser |
| | | | | 1940 | | | |

<210> SEQ ID NO 16
<211> LENGTH: 20217
<212> TYPE: DNA
<213> ORGANISM: Artificial Sequence
<220> FEATURE:
<223> OTHER INFORMATION: Description of Artificial Sequence:
    pd.delta.NS3NS5.pj.core140
<220> FEATURE:
<221> NAME/KEY: CDS
<222> LOCATION: (12679)..(18411)

<400> SEQUENCE: 16

```
atcgatccta ccccttgcgc taaagaagta tatgtgccta ctaacgcttg tctttgtctc      60
tgtcactaaa cactggatta ttactcccag atacttattt tggactaatt taaatgattt    120
cggatcaacg ttcttaatat cgctgaatct tccacaattg atgaaagtag ctaggaagag    180
gaattggtat aaagttttg tttttgtaaa tctcgaagta tactcaaacg aatttagtat     240
tttctcagtg atctcccaga tgctttcacc ctcacttaga agtgctttaa gcattttttt    300
actgtggcta tttcccttat ctgcttcttc cgatgattcg aactgtaatt gcaaactact    360
tacaatatca gtgatatcag attgatgttt ttgtccatag taaggaataa ttgtaaattc    420
ccaagcagga atcaatttct ttaatgaggc ttccagaatt gttgcttttt gcgtcttgta    480
tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
cacaaactga cgaacaagca ccttaggtgg tgttttacat aatatatcaa attgtggcat    720
gcttagcgcc gatcttgtgt gcaattgata tctagtttca actactctat ttatcttgta    780
```

-continued

```
tcttgcagta ttcaaacacg ctaactcgaa aaactaactt taattgtcct gtttgtctcg    840
cgttctttcg aaaaatgcac cggccgcgca ttatttgtac tgcgaaaata attggtactg    900
cggtatcttc atttcatatt ttaaaaatgc acctttgctg cttttcctta attttagac    960 ggcccgcagg ttcgttttgc ggtactatct tgtgataaaa agttgttttg acatgtgatc    1020
tgcacagatt ttataatgta ataagcaaga atacattatc aaacgaacaa tactggtaaa    1080
agaaaaccaa aatggacgac attgaaacag ccaagaatct gacggtaaaa gcacgtacag    1140
cttatagcgt ctgggatgta tgtcggctgt ttattgaaat gattgctcct gatgtagata    1200
ttgatataga gagtaaacgt aagtctgatg agctactctt tccaggatat gtcataaggc    1260
ccatggaatc tctcacaacc ggtaggccgt atggtcttga ttctagcgca gaagattcca    1320
gcgtatcttc tgactccagt gctgaggtaa ttttgcctgc tgcgaagatg gttaaggaaa    1380
ggtttgattc gattggaaat ggtatgctct cttcacaaga agcaagtcag gctgccatag    1440
atttgatgct acagaataac aagctgttag acaatagaaa gcaactatac aaatctattg    1500
ctataataat aggaagattg cccgagaaag acaagaagag agctaccgaa atgctcatga    1560
gaaaaatgga ttgtacacag ttattagtcc caccagctcc aacggaagaa gatgttatga    1620
agctcgtaag cgtcgttacc caattgctta ctttagttcc accagatcgt caagctgctt    1680
taataggtga tttattcatc ccggaatctc taaaggatat attcaatagt ttcaatgaac    1740
tggcggcaga gaatcgttta cagcaaaaaa agagtgagtt ggaaggaagg actgaagtga    1800
accatgctaa tacaaatgaa gaagttccct ccaggcgaac aagaagtaga gacacaaatg    1860
caagaggagc atataaatta caaaacacca tcactgaggg ccctaaagcg gttcccacga    1920
aaaaaaggag agtagcaacg agggtaaggg gcagaaaatc acgtaatact tctagggtat    1980
gatccaatat caaaggaaat gatagcattg aaggatgaga ctaatccaat tgaggagtgg    2040
cagcatatag aacagctaaa gggtagtgct gaaggaagca tacgataccc cgcatggaat    2100
gggataatat cacaggaggt actagactac ctttcatcct acataaatag acgcatataa    2160
gtacgcattt aagcataaac acgcactatg ccgttcttct catgtatata tatatacagg    2220
caacacgcag atataggtgc gacgtgaaca gtgagctgta tgtgcgcagc tcgcgttgca    2280
ttttcggaag cgctcgtttt cggaaacgct ttgaagttcc tattccgaag ttcctattct    2340
ctagaaagta taggaacttc agagcgcttt tgaaaaccaa aagcgctctg aagacgcact    2400
ttcaaaaaac caaaaacgca ccggactgta acgagctact aaaatattgc gaataccgct    2460
tccacaaaca ttgctcaaaa gtatctcttt gctatatatc tctgtgctat atccctatat    2520
aacctaccca tccaccttc gctccttgaa cttgcatcta aactcgacct ctacatcaac    2580
aggcttccaa tgctcttcaa atttactgt caagtagacc catacggctg taatatgctg    2640
ctcttcataa tgtaagctta tctttatcga atcgtgtgaa aaactactac cgcgataaac    2700
ctttacggtt ccctgagatt gaattagttc ctttagtata tgatacaaga cacttttgaa    2760
ctttgtacga cgaattttga ggttcgccat cctctggcta tttccaatta tcctgtcggc    2820
tattatctcc gcctcagttt gatcttccgc ttcagactgc cattttcac ataatgaatc    2880 tatttcaccc cacaatcctt catccgcctc cgcatcttgt tccgttaaac tattgacttc    2940
atgttgtaca ttgtttagtt cacgagaagg gtcctcttca ggcggtagct cctgatctcc    3000
tatatgacct ttatcctgtt ctcttttccac aaacttagaa atgtattcat gaattatgga    3060
gcacctaata acattcttca aggcggagaa gtttgggcca gatgcccaat atgcttgaca    3120
```

```
tgaaaacgtg agaatgaatt tagtattatt gtgatattct gaggcaattt tattataatc    3180
tcgaagataa gagaagaatg cagtgacctt tgtattgaca aatggagatt ccatgtatct    3240
aaaaaatacg cctttaggcc ttctgatacc ctttcccctg cggtttagcg tgccttttac    3300
attaatatct aaaccctctc cgatggtggc ctttaactga ctaataaatg caaccgatat    3360
aaactgtgat aattctgggt gatttatgat tcgatcgaca attgtattgt acactagtgc    3420
aggatcaggc caatccagtt cttttcaat taccggtgtg tcgtctgtat tcagtacatg     3480
tccaacaaat gcaaatgcta acgttttgta tttcttataa ttgtcaggaa ctggaaaagt    3540
cccccttgtc gtctcgatta cacacctact ttcatcgtac accataggtt ggaagtgctg    3600
cataatacat tgcttaatac aagcaagcag tctctcgcca ttcatatttc agttattttc    3660
cattacagct gatgtcattg tatatcagcg ctgtaaaaat ctatctgtta cagaaggttt    3720
tcgcggtttt tataaacaaa actttcgtta cgaaatcgag caatcacccc agctgcgtat    3780
ttggaaattc gggaaaaagt agagcaacgc gagttgcatt ttttacacca taatgcatga    3840
ttaacttcga gaagggatta aggctaattt cactagtatg tttcaaaaac ctcaatctgt    3900
ccattgaatg cctataaaa cagctataga ttgcatagaa gagttagcta ctcaatgctt     3960
tttgtcaaag cttactgatg atgatgtgtc tactttcagg cgggtctgta gtaaggagaa    4020
tgacattata aagctggcac ttagaattcc acgactata gactatacta gtatactccg      4080
tctactgtac gatacacttc cgctcaggtc cttgtccttt aacgaggcct taccactctt    4140
ttgttactct attgatccag ctcagcaaag gcagtgtgat ctaagattct atcttcgcga    4200
tgtagtaaaa ctagctagac cgagaaagag actagaaatg caaaaggcac ttctacaatg    4260
gctgccatca ttattatccg atgtgacgct gcatttttt tttttttttt ttttttttt     4320
ttttttttt tttttttt tttttggta caaatatcat aaaaaaagag aatcttttta       4380
agcaaggatt tcttaacttc cttcggcgac agcatcaccg acttcggtgg tactgttgga    4440
accacctaaa tcaccagttc tgatacctgc atccaaaacc tttttaactg catcttcaat    4500
ggctttacct tcttcaggca agttcaatga caatttcaac atcattgcag cagacaagat    4560
agtggcgata gggttgacct tattctttgg caaatctgga gcggaaccat ggcatggttc    4620
gtacaaacca aatgcggtgt tcttgtctgg caaagaggcc aaggacgcag atggcaacaa    4680
acccaaggag cctgggataa cggaggcttc atcggagatg atatcaccaa acatgttgct    4740
ggtgattata ataccattta ggtgggttgg gttcttaact aggatcatgg cggcagaatc    4800
aatcaattga tgttgaactt tcaatgtagg gaattcgttc ttgatggttt cctccacagt    4860
ttttctccat aatcttgaag aggccaaaac attagcttta tccaaggacc aaataggcaa    4920
tggtggctca tgttgtaggg ccatgaaagc ggccattctt tgattctttt gcacttctgg    4980
aacggtgtat tgttcactat cccaagcgac accatcacca tcgtcttcct ttctcttacc    5040
aaagtaaata cctcccacta attctctaac aacaacgaag tcagtacctt tagcaaattg    5100
tggcttgatt ggagataagt ctaaaagaga gtcggatgca agttacatg tcttaagtt     5160
ggcgtacaat tgaagttctt tacggatttt tagtaaacct tgttcaggtc taacactacc    5220
ggtaccccat ttaggaccac ccacagcacc taacaaaacg gcatcagcct tcttggaggc    5280
ttccagcgcc tcatctggaa gtggaacacc tgtagcatcg atagcagcac caccaattaa    5340
atgattttcg aaatcgaact tgacattgga acgaacatca gaaatagctt taagaacctt    5400
aatggcttcg gctgtgattt cttgaccaac gtggtcacct ggcaaaacga cgatcttctt    5460
aggggcagac attacaatgg tatatccttg aaatatatat aaaaaaaaaa aaaaaaaaaa    5520
```

```
aaaaaaaaaa atgcagcttc tcaatgatat tcgaatacgc tttgaggaga tacagcctaa    5580
tatccgacaa actgttttac agatttacga tcgtacttgt tacccatcat tgaattttga    5640
acatccgaac ctgggagttt tccctgaaac agatagtata tttgaacctg tataataata    5700
tatagtctag cgctttacgg aagacaatgt atgtatttcg gttcctggag aaactattgc    5760
atctattgca taggtaatct tgcacgtcgc atccccggtt cattttctgc gtttccatct    5820
tgcacttcaa tagcatatct ttgttaacga agcatctgtg cttcattttg tagaacaaaa    5880
atgcaacgcg agagcgctaa tttttcaaac aaagaatctg agctgcattt ttacagaaca    5940
gaaatgcaac gcgaaagcgc tattttacca acgaagaatc tgtgcttcat ttttgtaaaa    6000
caaaaatgca acgcgagagc gctaattttt caaacaaaga atctgagctg cattttttaca   6060
gaacagaaat gcaacgcgag agcgctattt taccaacaaa gaatctatac ttcttttttg    6120
ttctacaaaa atgcatcccg agagcgctat ttttctaaca aagcatctta gattactttt    6180
tttctccttt gtgcgctcta taatgcagtc tcttgataac ttttttgcact gtaggtccgt    6240
taaggttaga agaaggctac tttggtgtct attttctctt ccataaaaaa agcctgactc    6300
cacttcccgc gtttactgat tactagcgaa gctgcgggtg catttttttca agataaaggc    6360
atccccgatt atattctata ccgatgtgga ttgcgcatac tttgtgaaca gaaagtgata    6420
gcgttgatga ttcttcattg gtcagaaaat tatgaacggt ttcttctatt tgtctctat    6480
atactacgta taggaaatgt ttacatttc gtattgtttt cgattcactc tatgaatagt    6540
tcttactaca atttttttgt ctaaagagta atactagaga taaacataaa aaatgtagag    6600
gtcgagttta gatgcaagtt caaggagcga aaggtggatg ggtaggttat atagggatat    6660
agcacagaga tatatagcaa agagatactt ttgagcaatg tttgtggaag cggtattcgc    6720
aatattttag tagctcgtta cagtccggtg cgttttggt tttttgaaag tgcgtcttca    6780
gagcgctttt ggttttcaaa agcgctctga agttcctata ctttctagag aataggaact    6840
tcggaatagg aacttcaaag cgtttccgaa aacgagcgct tccgaaaatg caacgcgagc    6900
tgcgcacata cagctcactg ttcacgtcgc acctatatct gcgtgttgcc tgtatatata    6960
tatacatgag aagaacggca tagtgcgtgt ttatgcttaa atgcgtactt atatgcgtct    7020
atttatgtag gatgaaaggt agtctagtac ctcctgtgat attatcccat tccatgcggg    7080
gtatcgtatg cttccttcag cactacccett tagctgttct atatgctgcc actcctcaat    7140
tggattagtc tcatccttca atgctatcat ttcctttgat attggatcat atgcatagta    7200
ccgagaaact agtgcgaagt agtgatcagg tattgctgtt atctgatgag tatacgttgt    7260
cctggccacg gcagaagcac gcttatcgct ccaatttccc acaacattag tcaactccgt    7320
taggcccttc attgaaagaa atgaggtcat caaatgtctt ccaatgtgag attttgggcc    7380
atttttata gcaaagattg aataaggcgc atttttcttc aaagctttat tgtacgatct    7440
gactaagtta tcttttaata attggtattc ctgtttattg cttgaagaat tgccggtcct    7500
atttactcgt tttaggactg gttcagaatt cctcaaaaat tcatccaaat atacaagtgg    7560
atcgatgata agctgtcaaa catgagaatt cttgaagacg aaagggcctc gtgatacgcc    7620
tatttttata ggttaatgtc atgataataa tggtttctta cgtcaggt ggcacttttc     7680
ggggaaatgt gcgcggaacc cctatttgtt tatttttcta aatacattca aatatgtatc    7740
cgctcatgag acaataaccc tgataaatgc ttcaataata ttgaaaaagg aagagtatga    7800
gtattcaaca tttccgtgtc gcccttattc ccttttttgc ggcattttgc cttcctgttt    7860
```

```
ttgctcaccc agaaacgctg gtgaaagtaa aagatgctga agatcagttg ggtgcacgag   7920
tgggttacat cgaactggat ctcaacagcg gtaagatcct tgagagtttt cgccccgaag   7980
aacgttttcc aatgatgagc acttttaaag ttctgctatg tggcgcggta ttatcccgtg   8040
ttgacgccgg gcaagagcaa ctcggtcgcc gcatacacta ttctcagaat gacttggttg   8100
agtactcacc agtcacagaa aagcatctta cggatggcat gacagtaaga gaattatgca   8160
gtgctgccat aaccatgagt gataacactg cggccaactt acttctgaca acgatcggag   8220
gaccgaagga gctaaccgct tttttgcaca catggggga tcatgtaact cgccttgatc     8280
gttgggaacc ggagctgaat gaagccatac caaacgacga gcgtgacacc acgatgcctg   8340
cagcaatggc aacaacgttg cgcaaactat taactggcga actacttact ctagcttccc   8400
ggcaacaatt aatagactgg atggaggcgg ataaagttgc aggaccactt ctgcgctcgg   8460
cccttccggc tggctggttt attgctgata atctggagc cggtgagcgt gggtctcgcg    8520
gtatcattgc agcactgggg ccagatggta agccctcccg tatcgtagtt atctacacga   8580
cggggagtca ggcaactatg gatgaacgaa atagacagat cgctgagata ggtgcctcac   8640
tgattaagca ttggtaactg tcagaccaag tttactcata tatactttag attgatttaa   8700
aacttcattt ttaatttaaa aggatctagg tgaagatcct ttttgataat ctcatgacca   8760
aaatccctta acgtgagttt tcgttccact gagcgtcaga ccccgtagaa aagatcaaag   8820
gatcttcttg agatcctttt tttctgcgcg taatctgctg cttgcaaaca aaaaaaccac   8880
cgctaccagc ggtggtttgt ttgccggatc aagagctacc aactcttttt ccgaaggtaa   8940
ctggcttcag cagagcgcag ataccaaata ctgtccttct agtgtagccg tagttaggcc   9000
accacttcaa gaactctgta gcaccgccta catacctcgc tctgctaatc ctgttaccag   9060
tggctgctgc cagtggcgat aagtcgtgtc ttaccgggtt ggactcaaga cgatagttac   9120
cggataaggc gcagcggtcg ggctgaacgg ggggttcgtg cacacagccc agcttggagc   9180
gaacgaccta caccgaactg agatacctac agcgtgagct atgagaaagc gccacgcttc   9240
ccgaagggag aaaggcggac aggtatccgg taagcggcag ggtcggaaca ggagagcgca   9300
cgagggagct tccaggggga aacgcctggt atctttatag tcctgtcggg tttcgccacc   9360
tctgacttga gcgtcgattt ttgtgatgct cgtcaggggg gcggagccta tggaaaaacg   9420
ccagcaacgc ggcctttta cggttcctgg ccttttgctg gccttttgct cacatgttct    9480
ttcctgcgtt atcccctgat tctgtggata accgtattac cgcctttgag tgagctgata   9540
ccgctcgccg cagccgaacg accgagcgca gcgagtcagt gagcgaggaa gcggaagagc   9600
gcctgatgcg gtattttctc cttacgcatc tgtgcggtat ttcacaccgc atatggtgca   9660
ctctcagtac aatctgctct gatgccgcat agttaagcca gtatacactc cgctatcgct   9720
acgtgactgg gtcatggctg cgccccgaca cccgccaaca cccgctgacg cgccctgacg   9780
ggcttgtctg ctcccggcat ccgcttacag acaagctgtg accgtctccg ggagctgcat   9840
gtgtcagagg ttttcaccgt catcaccgaa acgcgcgagg cagctgcggt aaagctcatc   9900
agcgtggtcg tgaagcgatt cacagatgtc tgcctgttca tccgcgtcca gctcgttgag   9960
tttctccaga agcgttaatg tctggcttct gataaagcgg ccatgttaa gggcggtttt   10020
ttcctgtttg gtcactgatg cctccgtgta agggggattt ctgttcatgg ggtaatgat   10080
accgatgaaa cgagagagga tgctcacgat acgggttact gatgatgaac atgcccggtt   10140
actggaacgt tgtgagggta aacaactggc ggtatggatg cggcgggacc agagaaaaat   10200
cactcagggt caatgccagc gcttcgttaa tacagatgta ggtgttccac agggtagcca   10260
```

```
gcagcatcct gcgatgcaga tccggaacat aatggtgcag ggcgctgact tccgcgtttc    10320
cagactttac gaaacacgga aaccgaagac cattcatgtt gttgctcagg tcgcagacgt    10380
tttgcagcag cagtcgcttc acgttcgctc gcgtatcgt  gattcattct gctaaccagt    10440
aaggcaaccc cgccagccta gccgggtcct caacgacagg agcacgatca tgcgcacccg    10500
tggccaggac ccaacgctgc ccgagatgcg ccgcgtgcgg ctgctggaga tggcggacgc    10560
gatggatatg ttctgccaag ggttggtttg cgcattcaca gttctccgca agaattgatt    10620
ggctccaatt cttggagtgg tgaatccgtt agcgaggtgc cgccggcttc cattcaggtc    10680
gaggtggccc ggctccatgc accgcgacgc aacgcgggga ggcagacaag gtatagggcg    10740
gcgcctacaa tccatgccaa cccgttccat gtgctcgccg aggcggcata atcgccgtg    10800 acgatcagcg gtccaatgat cgaagttagg ctggtaagag ccgcgagcga tccttgaagc    10860
tgtccctgat ggtcgtcatc tacctgcctg acagcatgg  cctgcaacgc gggcatcccg    10920
atgccgccgg aagcgagaag aatcataatg gggaaggcca tccagcctcg cgtcgcgaac    10980
gccagcaaga cgtagcccag cgcgtcggcc gccatgccgg cgataatggc ctgcttctcg    11040
ccgaaacgtt tggtggcggg accagtgacg aaggcttgag cgagggcgtg caagattccg    11100
aataccgcaa cgacaggcc  gatcatcgtc gcgctccagc gaaagcggtc ctcgccgaaa    11160
atgacccaga gcgctgccgg cacctgtcct acagagttgca tgataaagaa gacagtcata    11220
agtgcggcga cgatagtcat gccccgcgcc caccggaagg agctgactgg gttgaaggct    11280
ctcaagggca tcggtcgagg atccttcaat atgcgcacat acgctgttat gttcaaggtc    11340
ccttcgttta agaacgaaag cggtcttcct tttgagggat gtttcaagtt gttcaaatct    11400
atcaaatttg caaatcccca gtctgtatct agagcgttga atcggtgatg cgatttgtta    11460
attaaattga tggtgtcacc attaccaggt ctagatatac caatggcaaa ctgagcacaa    11520
caataccagt ccggatcaac tggcaccatc tctcccgtag tctcatctaa tttttcttcc    11580
ggatgaggtt ccagatatac cgcaacacct ttattatggt ttccctgagg gaataataga    11640
atgtcccatt cgaaatcacc aattctaaac ctgggcgaat tgtatttcgg gtttgttaac    11700
tcgttccagt caggaatgtt ccacgtgaag ctatcttcca gcaaagtctc cacttcttca    11760
tcaaattgtg gagaatactc ccaatgctct tatctatggg acttccggga aacacagtac    11820
cgatacttcc caattcgtct tcagagctca ttgtttgttt gaagagacta atcaaagaat    11880
cgttttctca aaaaaattaa tatcttaact gatagtttga tcaaagggggc aaaacgtagg    11940 ggcaaacaaa cggaaaaatc gtttctcaaa ttttctgatg ccaagaactc taaccagtct    12000
tatctaaaaa ttgccttatg atccgtctct ccggttacag cctgtgtaac tgattaatcc    12060
tgcctttcta atcaccattc taatgtttta attaagggat tttgtcttca ttaacggctt    12120
tcgctcataa aaatgttatg acgttttgcc cgcaggcggg aaaccatcca cttcacgaga    12180
ctgatctcct ctgccggaac accgggcatc tccaacttat aagttggaga ataagagaa    12240 tttcagattg agagaatgaa aaaaaaaaac ccttagttca taggtccatt ctcttagcgc    12300
aactacagag aacaggggca caaacaggca aaaacgggc  acaacctcaa tggagtgatg    12360
caacctgcct ggagtaaatg atgacacaag gcaattgacc cacgcatgta tctatctcat    12420
tttcttacac cttctattac cttctgctct ctctgatttg gaaaagctg  aaaaaaaagg    12480 ttgaaaccag ttccctgaaa ttattcccct acttgactaa taagtatata aagacggtag    12540
gtattgattg taattctgta aatctatttc ttaaacttct taaattctac ttttatagtt    12600
```

```
-continued agtcttttt ttagttttaa aacaccaaga acttagtttc gaataaacac acataaacaa    12660
acaagcttac aaaacaaa atg gct gca tat gca gct cag ggc tat aag gtg    12711
                    Met Ala Ala Tyr Ala Ala Gln Gly Tyr Lys Val
                     1               5                  10 cta gta ctc aac ccc tct gtt gct gca aca ctg ggc ttt ggt gct tac    12759
Leu Val Leu Asn Pro Ser Val Ala Ala Thr Leu Gly Phe Gly Ala Tyr
            15                  20                  25 atg tcc aag gct cat ggg atc gat cct aac atc agg acc ggg gtg aga    12807
Met Ser Lys Ala His Gly Ile Asp Pro Asn Ile Arg Thr Gly Val Arg
        30                  35                  40 aca att acc act ggc agc ccc atc acg tac tcc acc tac ggc aag ttc    12855
Thr Ile Thr Thr Gly Ser Pro Ile Thr Tyr Ser Thr Tyr Gly Lys Phe
    45                  50                  55 ctt gcc gac ggc ggg tgc tcg ggg ggc gct tat gac ata ata att tgt    12903
Leu Ala Asp Gly Gly Cys Ser Gly Gly Ala Tyr Asp Ile Ile Ile Cys
60                  65                  70                  75 gac gag tgc cac tcc acg gat gcc aca tcc atc ttg ggc att ggc act    12951
Asp Glu Cys His Ser Thr Asp Ala Thr Ser Ile Leu Gly Ile Gly Thr
                80                  85                  90 gtc ctt gac caa gca gag act gcg ggg gcg aga ctg gtt gtg ctc gcc    12999
Val Leu Asp Gln Ala Glu Thr Ala Gly Ala Arg Leu Val Val Leu Ala
            95                 100                 105 acc gcc acc cct ccg ggc tcc gtc act gtg ccc cat ccc aac atc gag    13047
Thr Ala Thr Pro Pro Gly Ser Val Thr Val Pro His Pro Asn Ile Glu
        110                 115                 120 gag gtt gct ctg tcc acc acc gga gag atc cct ttt tac ggc aag gct    13095
Glu Val Ala Leu Ser Thr Thr Gly Glu Ile Pro Phe Tyr Gly Lys Ala
    125                 130                 135 atc ccc ctc gaa gta atc aag ggg ggg aga cat ctc atc ttc tgt cat    13143
Ile Pro Leu Glu Val Ile Lys Gly Gly Arg His Leu Ile Phe Cys His
140                 145                 150                 155 tca aag aag aag tgc gac gaa ctc gcc gca aag ctg gtc gca ttg ggc    13191
Ser Lys Lys Lys Cys Asp Glu Leu Ala Ala Lys Leu Val Ala Leu Gly
                160                 165                 170 atc aat gcc gtg gcc tac tac cgc ggt ctt gac gtg tcc gtc atc ccg    13239
Ile Asn Ala Val Ala Tyr Tyr Arg Gly Leu Asp Val Ser Val Ile Pro
            175                 180                 185 acc agc ggc gat gtt gtc gtc gtg gca acc gat gcc ctc atg acc ggc    13287
Thr Ser Gly Asp Val Val Val Val Ala Thr Asp Ala Leu Met Thr Gly
        190                 195                 200 tat acc ggc gac ttc gac tcg gtg ata gac tgc aat acg tgt gtc acc    13335
Tyr Thr Gly Asp Phe Asp Ser Val Ile Asp Cys Asn Thr Cys Val Thr
    205                 210                 215 cag aca gtc gat ttc agc ctt gac cct acc ttc acc att gag aca atc    13383
Gln Thr Val Asp Phe Ser Leu Asp Pro Thr Phe Thr Ile Glu Thr Ile
220                 225                 230                 235 acg ctc ccc caa gat gct gtc tcc cgc act caa cgt cgg ggc agg act    13431
Thr Leu Pro Gln Asp Ala Val Ser Arg Thr Gln Arg Arg Gly Arg Thr
                240                 245                 250 ggc agg ggg aag cca ggc atc tac aga ttt gtg gca ccg ggg gag cgc    13479
Gly Arg Gly Lys Pro Gly Ile Tyr Arg Phe Val Ala Pro Gly Glu Arg
            255                 260                 265 ccc tcc ggc atg ttc gac tcg tcc gtc ctc tgt gag tgc tat gac gca    13527
Pro Ser Gly Met Phe Asp Ser Ser Val Leu Cys Glu Cys Tyr Asp Ala
        270                 275                 280 ggc tgt gct tgg tat gag ctc acg ccc gcc gag act aca gtt agg cta    13575
Gly Cys Ala Trp Tyr Glu Leu Thr Pro Ala Glu Thr Thr Val Arg Leu
    285                 290                 295 cga gcg tac atg aac acc ccg ggg ctt ccc gtg tgc cag gac cat ctt    13623
```

```
Arg Ala Tyr Met Asn Thr Pro Gly Leu Pro Val Cys Gln Asp His Leu
300                 305                 310                 315 gaa ttt tgg gag ggc gtc ttt aca ggc ctc act cat ata gat gcc cac      13671
Glu Phe Trp Glu Gly Val Phe Thr Gly Leu Thr His Ile Asp Ala His
                320                 325                 330 ttt cta tcc cag aca aag cag agt ggg gag aac ctt cct tac ctg gta      13719
Phe Leu Ser Gln Thr Lys Gln Ser Gly Glu Asn Leu Pro Tyr Leu Val
            335                 340                 345 gcg tac caa gcc acc gtg tgc gct agg gct caa gcc cct ccc cca tcg      13767
Ala Tyr Gln Ala Thr Val Cys Ala Arg Ala Gln Ala Pro Pro Pro Ser
        350                 355                 360 tgg gac cag atg tgg aag tgt ttg att cgc ctc aag ccc acc ctc cat      13815
Trp Asp Gln Met Trp Lys Cys Leu Ile Arg Leu Lys Pro Thr Leu His
    365                 370                 375 ggg cca aca ccc ctg cta tac aga ctg ggc gct gtt cag aat gaa atc      13863
Gly Pro Thr Pro Leu Leu Tyr Arg Leu Gly Ala Val Gln Asn Glu Ile
380                 385                 390                 395 acc ctg acg cac cca gtc acc aaa tac atc atg aca tgc atg tcg gcc      13911
Thr Leu Thr His Pro Val Thr Lys Tyr Ile Met Thr Cys Met Ser Ala
                400                 405                 410 gac ctg gag gtc gtc acg agc acc tgg gtg ctc gtt ggc ggc gtc ctg      13959
Asp Leu Glu Val Val Thr Ser Thr Trp Val Leu Val Gly Gly Val Leu
            415                 420                 425 gct gct ttg gcc gcg tat tgc ctg tca aca ggc tgc gtg gtc ata gtg      14007
Ala Ala Leu Ala Ala Tyr Cys Leu Ser Thr Gly Cys Val Val Ile Val
        430                 435                 440 ggc agg gtc gtc ttg tcc ggg aag ccg gca atc ata cct gac agg gaa      14055
Gly Arg Val Val Leu Ser Gly Lys Pro Ala Ile Ile Pro Asp Arg Glu
    445                 450                 455 gtc ctc tac cga gag ttc gat gag atg gaa gag tgc tct cag cac tta      14103
Val Leu Tyr Arg Glu Phe Asp Glu Met Glu Glu Cys Ser Gln His Leu
460                 465                 470                 475 ccg tac atc gag caa ggg atg atg ctc gcc gag cag ttc aag cag aag      14151
Pro Tyr Ile Glu Gln Gly Met Met Leu Ala Glu Gln Phe Lys Gln Lys
                480                 485                 490 gcc ctc ggc ctc ctg cag acc gcg tcc cgt cag gca gag gtt atc gcc      14199
Ala Leu Gly Leu Leu Gln Thr Ala Ser Arg Gln Ala Glu Val Ile Ala
            495                 500                 505 cct gct gtc cag acc aac tgg caa aaa ctc gag acc ttc tgg gcg aag      14247
Pro Ala Val Gln Thr Asn Trp Gln Lys Leu Glu Thr Phe Trp Ala Lys
        510                 515                 520 cat atg tgg aac ttc atc agt ggg ata caa tac ttg gcg ggc ttg tca      14295
His Met Trp Asn Phe Ile Ser Gly Ile Gln Tyr Leu Ala Gly Leu Ser
    525                 530                 535 acg ctg cct ggt aac ccc gcc att gct tca ttg atg gct ttt aca gct      14343
Thr Leu Pro Gly Asn Pro Ala Ile Ala Ser Leu Met Ala Phe Thr Ala
540                 545                 550                 555 gct gtc acc agc cca cta acc act agc caa acc ctc ctc ttc aac ata      14391
Ala Val Thr Ser Pro Leu Thr Thr Ser Gln Thr Leu Leu Phe Asn Ile
                560                 565                 570 ttg ggg ggg tgg gtg gct gcc cag ctc gcc gcc ccc ggt gcc gct act      14439
Leu Gly Gly Trp Val Ala Ala Gln Leu Ala Ala Pro Gly Ala Ala Thr
            575                 580                 585 gcc ttt gtg ggc gct ggc tta gct ggc gcc gcc atc ggc agt gtt gga      14487
Ala Phe Val Gly Ala Gly Leu Ala Gly Ala Ala Ile Gly Ser Val Gly
        590                 595                 600 ctg ggg aag gtc ctc ata gac atc ctt gca ggg tat ggc gcg ggc gtg      14535
Leu Gly Lys Val Leu Ile Asp Ile Leu Ala Gly Tyr Gly Ala Gly Val
    605                 610                 615
```

| | | | | | | | | | | | | | | | |
|---|---|---|---|---|---|---|---|---|---|---|---|---|---|---|---|
| gcg | gga | gct | ctt | gtg | gca | ttc | aag | atc | atg | agc | ggt | gag | gtc | ccc | tcc | 14583 |
| Ala | Gly | Ala | Leu | Val | Ala | Phe | Lys | Ile | Met | Ser | Gly | Glu | Val | Pro | Ser | |
| 620 | | | | 625 | | | | | 630 | | | | | 635 | | |
| acg | gag | gac | ctg | gtc | aat | cta | ctg | ccc | gcc | atc | ctc | tcg | ccc | gga | gcc | 14631 |
| Thr | Glu | Asp | Leu | Val | Asn | Leu | Leu | Pro | Ala | Ile | Leu | Ser | Pro | Gly | Ala | |
| | | | 640 | | | | | 645 | | | | | 650 | | | |
| ctc | gta | gtc | ggc | gtg | gtc | tgt | gca | gca | ata | ctg | cgc | cgg | cac | gtt | ggc | 14679 |
| Leu | Val | Val | Gly | Val | Val | Cys | Ala | Ala | Ile | Leu | Arg | Arg | His | Val | Gly | |
| | | | 655 | | | | | 660 | | | | | 665 | | | |
| ccg | ggc | gag | ggg | gca | gtg | cag | tgg | atg | aac | cgg | ctg | ata | gcc | ttc | gcc | 14727 |
| Pro | Gly | Glu | Gly | Ala | Val | Gln | Trp | Met | Asn | Arg | Leu | Ile | Ala | Phe | Ala | |
| 670 | | | | 675 | | | | | 680 | | | | | | | |
| tcc | cgg | ggg | aac | cat | gtt | tcc | ccc | acg | cac | tac | gtg | ccg | gag | agc | gat | 14775 |
| Ser | Arg | Gly | Asn | His | Val | Ser | Pro | Thr | His | Tyr | Val | Pro | Glu | Ser | Asp | |
| | 685 | | | | 690 | | | | | 695 | | | | | | |
| gca | gct | gcc | cgc | gtc | act | gcc | ata | ctc | agc | agc | ctc | act | gta | acc | cag | 14823 |
| Ala | Ala | Ala | Arg | Val | Thr | Ala | Ile | Leu | Ser | Ser | Leu | Thr | Val | Thr | Gln | |
| 700 | | | | 705 | | | | | 710 | | | | | 715 | | |
| ctc | ctg | agg | cga | ctg | cac | cag | tgg | ata | agc | tcg | gag | tgt | acc | act | cca | 14871 |
| Leu | Leu | Arg | Arg | Leu | His | Gln | Trp | Ile | Ser | Ser | Glu | Cys | Thr | Thr | Pro | |
| | | | | 720 | | | | | 725 | | | | | 730 | | |
| tgc | tcc | ggt | tcc | tgg | cta | agg | gac | atc | tgg | gac | tgg | ata | tgc | gag | gtg | 14919 |
| Cys | Ser | Gly | Ser | Trp | Leu | Arg | Asp | Ile | Trp | Asp | Trp | Ile | Cys | Glu | Val | |
| | | | 735 | | | | | 740 | | | | | 745 | | | |
| ttg | agc | gac | ttt | aag | acc | tgg | cta | aaa | gct | aag | ctc | atg | cca | cag | ctg | 14967 |
| Leu | Ser | Asp | Phe | Lys | Thr | Trp | Leu | Lys | Ala | Lys | Leu | Met | Pro | Gln | Leu | |
| | | 750 | | | | | 755 | | | | | 760 | | | | |
| cct | ggg | atc | ccc | ttt | gtg | tcc | tgc | cag | cgc | ggg | tat | aag | ggg | gtc | tgg | 15015 |
| Pro | Gly | Ile | Pro | Phe | Val | Ser | Cys | Gln | Arg | Gly | Tyr | Lys | Gly | Val | Trp | |
| | 765 | | | | 770 | | | | | 775 | | | | | | |
| cga | ggg | gac | ggc | atc | atg | cac | act | cgc | tgc | cac | tgt | gga | gct | gag | atc | 15063 |
| Arg | Gly | Asp | Gly | Ile | Met | His | Thr | Arg | Cys | His | Cys | Gly | Ala | Glu | Ile | |
| 780 | | | | 785 | | | | | 790 | | | | | 795 | | |
| act | gga | cat | gtc | aaa | aac | ggg | acg | atg | agg | atc | gtc | ggt | cct | agg | acc | 15111 |
| Thr | Gly | His | Val | Lys | Asn | Gly | Thr | Met | Arg | Ile | Val | Gly | Pro | Arg | Thr | |
| | | | | 800 | | | | | 805 | | | | | 810 | | |
| tgc | agg | aac | atg | tgg | agt | ggg | acc | ttc | ccc | att | aat | gcc | tac | acc | acg | 15159 |
| Cys | Arg | Asn | Met | Trp | Ser | Gly | Thr | Phe | Pro | Ile | Asn | Ala | Tyr | Thr | Thr | |
| | | | 815 | | | | | 820 | | | | | 825 | | | |
| ggc | ccc | tgt | acc | ccc | ctt | cct | gcg | ccg | aac | tac | acg | ttc | gcg | cta | tgg | 15207 |
| Gly | Pro | Cys | Thr | Pro | Leu | Pro | Ala | Pro | Asn | Tyr | Thr | Phe | Ala | Leu | Trp | |
| | | 830 | | | | | 835 | | | | | 840 | | | | |
| agg | gtg | tct | gca | gag | gaa | tac | gtg | gag | ata | agg | cag | gtg | ggg | gac | ttc | 15255 |
| Arg | Val | Ser | Ala | Glu | Glu | Tyr | Val | Glu | Ile | Arg | Gln | Val | Gly | Asp | Phe | |
| | 845 | | | | 850 | | | | | 855 | | | | | | |
| cac | tac | gtg | acg | ggt | atg | act | act | gac | aat | ctt | aaa | tgc | ccg | tgc | cag | 15303 |
| His | Tyr | Val | Thr | Gly | Met | Thr | Thr | Asp | Asn | Leu | Lys | Cys | Pro | Cys | Gln | |
| 860 | | | | 865 | | | | | 870 | | | | | 875 | | |
| gtc | cca | tcg | ccc | gaa | ttt | ttc | aca | gaa | ttg | gac | ggg | gtg | cgc | cta | cat | 15351 |
| Val | Pro | Ser | Pro | Glu | Phe | Phe | Thr | Glu | Leu | Asp | Gly | Val | Arg | Leu | His | |
| | | | | 880 | | | | | 885 | | | | | 890 | | |
| agg | ttt | gcg | ccc | ccc | tgc | aag | ccc | ttg | ctg | cgg | gag | gag | gta | tca | ttc | 15399 |
| Arg | Phe | Ala | Pro | Pro | Cys | Lys | Pro | Leu | Leu | Arg | Glu | Glu | Val | Ser | Phe | |
| | | | 895 | | | | | 900 | | | | | 905 | | | |
| aga | gta | gga | ctc | cac | gaa | tac | ccg | gta | ggg | tcg | caa | tta | cct | tgc | gag | 15447 |
| Arg | Val | Gly | Leu | His | Glu | Tyr | Pro | Val | Gly | Ser | Gln | Leu | Pro | Cys | Glu | |
| | | 910 | | | | | 915 | | | | | 920 | | | | |
| ccc | gaa | ccg | gac | gtg | gcc | gtg | ttg | acg | tcc | atg | ctc | act | gat | ccc | tcc | 15495 |
| Pro | Glu | Pro | Asp | Val | Ala | Val | Leu | Thr | Ser | Met | Leu | Thr | Asp | Pro | Ser | |
| 925 | | | | 930 | | | | | 935 | | | | | | | |

-continued

```
cat ata aca gca gag gcg gcc ggg cga agg ttg gcg agg gga tca ccc      15543
His Ile Thr Ala Glu Ala Ala Gly Arg Arg Leu Ala Arg Gly Ser Pro
940                 945                 950                 955 ccc tct gtg gcc agc tcc tcg gct agc cag cta tcc gct cca tct ctc      15591
Pro Ser Val Ala Ser Ser Ser Ala Ser Gln Leu Ser Ala Pro Ser Leu
                960                 965                 970 aag gca act tgc acc gct aac cat gac tcc cct gat gct gag ctc ata      15639
Lys Ala Thr Cys Thr Ala Asn His Asp Ser Pro Asp Ala Glu Leu Ile
            975                 980                 985 gag gcc aac ctc cta tgg agg cag gag atg ggc ggc aac atc acc agg      15687
Glu Ala Asn Leu Leu Trp Arg Gln Glu Met Gly Gly Asn Ile Thr Arg
        990                 995                 1000 gtt gag tca gaa aac aaa gtg gtg att ctg gac tcc ttc gat ccg ctt      15735
Val Glu Ser Glu Asn Lys Val Val Ile Leu Asp Ser Phe Asp Pro Leu
    1005                1010                1015 gtg gcg gag gag gac gag cgg gag atc tcc gta ccc gca gaa atc ctg      15783
Val Ala Glu Glu Asp Glu Arg Glu Ile Ser Val Pro Ala Glu Ile Leu
1020                1025                1030                1035 cgg aag tct cgg aga ttc gcc cag gcc ctg ccc gtt tgg gcg cgg ccg      15831
Arg Lys Ser Arg Arg Phe Ala Gln Ala Leu Pro Val Trp Ala Arg Pro
                1040                1045                1050 gac tat aac ccc ccg cta gtg gag acg tgg aaa aag ccc gac tac gaa      15879
Asp Tyr Asn Pro Pro Leu Val Glu Thr Trp Lys Lys Pro Asp Tyr Glu
                1055                1060                1065 cca cct gtg gtc cat ggc tgc ccg ctt cca cct cca aag tcc cct cct      15927
Pro Pro Val Val His Gly Cys Pro Leu Pro Pro Pro Lys Ser Pro Pro
        1070                1075                1080 gtg cct ccg cct cgg aag aag cgg acg gtg gtc ctc act gaa tca acc      15975
Val Pro Pro Pro Arg Lys Lys Arg Thr Val Val Leu Thr Glu Ser Thr
    1085                1090                1095 cta tct act gcc ttg gcc gag ctc gcc acc aga agc ttt ggc agc tcc      16023
Leu Ser Thr Ala Leu Ala Glu Leu Ala Thr Arg Ser Phe Gly Ser Ser
1100                1105                1110                1115 tca act tcc ggc att acg ggc gac aat acg aca aca tcc tct gag ccc      16071
Ser Thr Ser Gly Ile Thr Gly Asp Asn Thr Thr Thr Ser Ser Glu Pro
                1120                1125                1130 gcc cct tct ggc tgc ccc ccc gac tcc gac gct gag tcc tat tcc tcc      16119
Ala Pro Ser Gly Cys Pro Pro Asp Ser Asp Ala Glu Ser Tyr Ser Ser
                1135                1140                1145 atg ccc ccc ctg gag ggg gag cct ggg gat ccg gat ctt agc gac ggg      16167
Met Pro Pro Leu Glu Gly Glu Pro Gly Asp Pro Asp Leu Ser Asp Gly
        1150                1155                1160 tca tgg tca acg gtc agt agt gag gcc aac gcg gag gat gtc gtg tgc      16215
Ser Trp Ser Thr Val Ser Ser Glu Ala Asn Ala Glu Asp Val Val Cys
    1165                1170                1175 tgc tca atg tct tac tct tgg aca ggc gca ctc gtc acc ccg tgc gcc      16263
Cys Ser Met Ser Tyr Ser Trp Thr Gly Ala Leu Val Thr Pro Cys Ala
1180                1185                1190                1195 gcg gaa gaa cag aaa ctg ccc atc aat gca cta agc aac tcg ttg cta      16311
Ala Glu Glu Gln Lys Leu Pro Ile Asn Ala Leu Ser Asn Ser Leu Leu
                1200                1205                1210 cgt cac cac aat ttg gtg tat tcc acc acc tca cgc agt gct tgc caa      16359
Arg His His Asn Leu Val Tyr Ser Thr Thr Ser Arg Ser Ala Cys Gln
            1215                1220                1225 agg cag aag aaa gtc aca ttt gac aga ctg caa gtt ctg gac agc cat      16407
Arg Gln Lys Lys Val Thr Phe Asp Arg Leu Gln Val Leu Asp Ser His
        1230                1235                1240 tac cag gac gta ctc aag gag gtt aaa gca gcg gcg tca aaa gtg aag      16455
Tyr Gln Asp Val Leu Lys Glu Val Lys Ala Ala Ala Ser Lys Val Lys
```

```
                    -continued
     1245               1250              1255 gct aac ttg cta tcc gta gag gaa gct tgc agc ctg acg ccc cca cac     16503
Ala Asn Leu Leu Ser Val Glu Glu Ala Cys Ser Leu Thr Pro Pro His
1260                1265              1270              1275 tca gcc aaa tcc aag ttt ggt tat ggg gca aaa gac gtc cgt tgc cat     16551
Ser Ala Lys Ser Lys Phe Gly Tyr Gly Ala Lys Asp Val Arg Cys His
         1280              1285              1290 gcc aga aag gcc gta acc cac atc aac tcc gtg tgg aaa gac ctt ctg     16599
Ala Arg Lys Ala Val Thr His Ile Asn Ser Val Trp Lys Asp Leu Leu
             1295              1300              1305 gaa gac aat gta aca cca ata gac act acc atc atg gct aag aac gag     16647
Glu Asp Asn Val Thr Pro Ile Asp Thr Thr Ile Met Ala Lys Asn Glu
     1310              1315              1320 gtt ttc tgc gtt cag cct gag aag ggg ggt cgt aag cca gct cgt ctc     16695
Val Phe Cys Val Gln Pro Glu Lys Gly Gly Arg Lys Pro Ala Arg Leu
1325                1330              1335 atc gtg ttc ccc gat ctg ggc gtg cgc gtg tgc gaa aag atg gct ttg     16743
Ile Val Phe Pro Asp Leu Gly Val Arg Val Cys Glu Lys Met Ala Leu
1340                1345              1350              1355 tac gac gtg gtt aca aag ctc ccc ttg gcc gtg atg gga agc tcc tac     16791
Tyr Asp Val Val Thr Lys Leu Pro Leu Ala Val Met Gly Ser Ser Tyr
         1360              1365              1370 gga ttc caa tac tca cca gga cag cgg gtt gaa ttc ctc gtg caa gcg     16839
Gly Phe Gln Tyr Ser Pro Gly Gln Arg Val Glu Phe Leu Val Gln Ala
             1375              1380              1385 tgg aag tcc aag aaa acc cca atg ggg ttc tcg tat gat acc cgc tgc     16887
Trp Lys Ser Lys Lys Thr Pro Met Gly Phe Ser Tyr Asp Thr Arg Cys
     1390              1395              1400 ttt gac tcc aca gtc act gag agc gac atc cgt acg gag gag gca atc     16935
Phe Asp Ser Thr Val Thr Glu Ser Asp Ile Arg Thr Glu Glu Ala Ile
1405                1410              1415 tac caa tgt tgt gac ctc gac ccc caa gcc cgc gtg gcc atc aag tcc     16983
Tyr Gln Cys Cys Asp Leu Asp Pro Gln Ala Arg Val Ala Ile Lys Ser
1420                1425              1430              1435 ctc acc gag agg ctt tat gtt ggg ggc cct ctt acc aat tca agg ggg     17031
Leu Thr Glu Arg Leu Tyr Val Gly Gly Pro Leu Thr Asn Ser Arg Gly
         1440              1445              1450 gag aac tgc ggc tat cgc agg tgc cgc gcg agc ggc gta ctg aca act     17079
Glu Asn Cys Gly Tyr Arg Arg Cys Arg Ala Ser Gly Val Leu Thr Thr
             1455              1460              1465 agc tgt ggt aac acc ctc act tgc tac atc aag gcc cgg gca gcc tgt     17127
Ser Cys Gly Asn Thr Leu Thr Cys Tyr Ile Lys Ala Arg Ala Ala Cys
     1470              1475              1480 cga gcc gca ggg ctc cag gac tgc acc atg ctc gtg tgt ggc gac gac     17175
Arg Ala Ala Gly Leu Gln Asp Cys Thr Met Leu Val Cys Gly Asp Asp
1485                1490              1495 tta gtc gtt atc tgt gaa agc gcg ggg gtc cag gag gac gcg gcg agc     17223
Leu Val Val Ile Cys Glu Ser Ala Gly Val Gln Glu Asp Ala Ala Ser
1500                1505              1510              1515 ctg aga gcc ttc acg gag gct atg acc agg tac tcc gcc ccc cct ggg     17271
Leu Arg Ala Phe Thr Glu Ala Met Thr Arg Tyr Ser Ala Pro Pro Gly
         1520              1525              1530 gac ccc cca caa cca gaa tac gac ttg gag ctc ata aca tca tgc tcc     17319
Asp Pro Pro Gln Pro Glu Tyr Asp Leu Glu Leu Ile Thr Ser Cys Ser
             1535              1540              1545 tcc aac gtg tca gtc gcc cac gac ggc gct gga aag agg gtc tac tac     17367
Ser Asn Val Ser Val Ala His Asp Gly Ala Gly Lys Arg Val Tyr Tyr
     1550              1555              1560 ctc acc cgt gac cct aca acc ccc ctc gcg aga gct gcg tgg gag aca     17415
```

```
Leu Thr Arg Asp Pro Thr Thr Pro Leu Ala Arg Ala Ala Trp Glu Thr
    1565                1570                1575 gca aga cac act cca gtc aat tcc tgg cta ggc aac ata atc atg ttt         17463
Ala Arg His Thr Pro Val Asn Ser Trp Leu Gly Asn Ile Ile Met Phe
1580                1585                1590                1595 gcc ccc aca ctg tgg gcg agg atg ata ctg atg acc cat ttc ttt agc         17511
Ala Pro Thr Leu Trp Ala Arg Met Ile Leu Met Thr His Phe Phe Ser
                1600                1605                1610 gtc ctt ata gcc agg gac cag ctt gaa cag gcc ctc gat tgc gag atc         17559
Val Leu Ile Ala Arg Asp Gln Leu Glu Gln Ala Leu Asp Cys Glu Ile
            1615                1620                1625 tac ggg gcc tgc tac tcc ata gaa cca ctg gat cta cct cca atc att         17607
Tyr Gly Ala Cys Tyr Ser Ile Glu Pro Leu Asp Leu Pro Pro Ile Ile
        1630                1635                1640 caa aga ctc cat ggc ctc agc gca ttt tca ctc cac agt tac tct cca         17655
Gln Arg Leu His Gly Leu Ser Ala Phe Ser Leu His Ser Tyr Ser Pro
    1645                1650                1655 ggt gaa atc aat agg gtg gcc gca tgc ctc aga aaa ctt ggg gta ccg         17703
Gly Glu Ile Asn Arg Val Ala Ala Cys Leu Arg Lys Leu Gly Val Pro
1660                1665                1670                1675 ccc ttg cga gct tgg aga cac cgg gcc cgg agc gtc cgc gct agg ctt         17751
Pro Leu Arg Ala Trp Arg His Arg Ala Arg Ser Val Arg Ala Arg Leu
                1680                1685                1690 ctg gcc aga gga ggc agg gct gcc ata tgt ggc aag tac ctc ttc aac         17799
Leu Ala Arg Gly Gly Arg Ala Ala Ile Cys Gly Lys Tyr Leu Phe Asn
            1695                1700                1705 tgg gca gta aga aca aag ctc aaa ctc act cca ata gcg gcc gct ggc         17847
Trp Ala Val Arg Thr Lys Leu Lys Leu Thr Pro Ile Ala Ala Ala Gly
        1710                1715                1720 cag ctg gac ttg tcc ggc tgg ttc acg gct ggc tac agc ggg gga gac         17895
Gln Leu Asp Leu Ser Gly Trp Phe Thr Ala Gly Tyr Ser Gly Gly Asp
    1725                1730                1735 att tat cac agc gtg tct cat gcc cgg ccc cgc tgg atc tgg ttt tgc         17943
Ile Tyr His Ser Val Ser His Ala Arg Pro Arg Trp Ile Trp Phe Cys
1740                1745                1750                1755 cta ctc ctg ctt gct gca ggg gta ggc atc tac ctc ctc ccc aac cga         17991
Leu Leu Leu Leu Ala Ala Gly Val Gly Ile Tyr Leu Leu Pro Asn Arg
                1760                1765                1770 atg agc acg aat cct aaa cct caa aga aag acc aaa cgt aac acc aac         18039
Met Ser Thr Asn Pro Lys Pro Gln Arg Lys Thr Lys Arg Asn Thr Asn
            1775                1780                1785 cgg cgg ccg cag gac gtc aag ttc ccg ggt ggc ggt cag atc gtt ggt         18087
Arg Arg Pro Gln Asp Val Lys Phe Pro Gly Gly Gly Gln Ile Val Gly
        1790                1795                1800 gga gtt tac ttg ttg ccg cgc agg ggc cct aga ttg ggt gtg cgc gcg         18135
Gly Val Tyr Leu Leu Pro Arg Arg Gly Pro Arg Leu Gly Val Arg Ala
    1805                1810                1815 acg aga aag act tcc gag cgg tcg caa cct cga ggt aga cgt cag cct         18183
Thr Arg Lys Thr Ser Glu Arg Ser Gln Pro Arg Gly Arg Arg Gln Pro
1820                1825                1830                1835 atc ccc aag gct cgt cgg ccc gag ggc agg acc tgg gct cag ccc ggg         18231
Ile Pro Lys Ala Arg Arg Pro Glu Gly Arg Thr Trp Ala Gln Pro Gly
                1840                1845                1850 tac cct tgg ccc ctc tat ggc aat gag ggc tgc ggg tgg gcg gga tgg         18279
Tyr Pro Trp Pro Leu Tyr Gly Asn Glu Gly Cys Gly Trp Ala Gly Trp
            1855                1860                1865 ctc ctg tct ccc cgt ggc tct cgg cct agc tgg ggc ccc aca gac ccc         18327
Leu Leu Ser Pro Arg Gly Ser Arg Pro Ser Trp Gly Pro Thr Asp Pro
        1870                1875                1880
```

-continued

| | | |
|---|---|---|
| cgg cgt agg tcg cgc aat ttg ggt aag gtc atc gat acc ctt acg tgc<br>Arg Arg Arg Ser Arg Asn Leu Gly Lys Val Ile Asp Thr Leu Thr Cys<br>1885                    1890                    1895 | 18375 |
| ggc ttc gcc gac ctc atg ggg tac ata ccg ctc gtc taatagtcga<br>Gly Phe Ala Asp Leu Met Gly Tyr Ile Pro Leu Val<br>1900                    1905                    1910 | 18421 |
| ctttgttccc actgtacttt tagctcgtac aaaatacaat atacttttca tttctccgta | 18481 |
| aacaacatgt tttcccatgt aatatccttt tctattttc gttccgttac caactttaca | 18541 |
| catactttat atagctattc acttctatac actaaaaaac taagacaatt ttaattttgc | 18601 |
| tgcctgccat atttcaattt gttataaatt cctataattt atcctattag tagctaaaaa | 18661 |
| aagatgaatg tgaatcgaat cctaagagaa ttggatctga tccacaggac gggtgtggtc | 18721 |
| gccatgatcg cgtagtcgat agtggctcca agtagcgaag cgagcaggac tgggcggcgg | 18781 |
| ccaaagcggt cggacagtgc tccgagaacg ggtgcgcata gaaattgcat caacgcatat | 18841 |
| agcgctagca gcacgccata gtgactggcg atgctgtcgg aatggacgat atcccgcaag | 18901 |
| aggcccggca gtaccggcat aaccaagcct atgcctacag catccagggt gacggtgccg | 18961 |
| aggatgacga tgagcgcatt gttagatttc atacacggtg cctgactgcg ttagcaattt | 19021 |
| aactgtgata aactaccgca ttaaagcttt ttctttccaa ttttttttt ttcgtcatta | 19081 |
| taaaaatcat tacgaccgag attcccgggt aataactgat ataattaaat tgaagctcta | 19141 |
| atttgtgagt ttagtataca tgcatttact tataatacag ttttttagtt ttgctggccg | 19201 |
| catcttctca aatatgcttc ccagcctgct tttctgtaac gttcaccctc taccttagca | 19261 |
| tcccttccct ttgcaaatag tcctcttcca acaataataa tgtcagatcc tgtagagacc | 19321 |
| acatcatcca cggttctata ctgttgaccc aatgcgtctc ccttgtcatc taaacccaca | 19381 |
| ccgggtgtca taatcaacca atcgtaacct tcatctcttc cacccatgtc tctttgagca | 19441 |
| ataaagccga taacaaaatc tttgtcgctc ttcgcaatgt caacagtacc cttagtatat | 19501 |
| tctccagtag atagggagcc cttgcatgac aattctgcta acatcaaaag gcctctaggt | 19561 |
| tcctttgtta cttcttctgc cgcctgcttc aaaccgctaa caatacctgg gcccaccaca | 19621 |
| ccgtgtgcat tcgtaatgtc tgcccattct gctattctgt atacaccgc agagtactgc | 19681 |
| aatttgactg tattaccaat gtcagcaaat tttctgtctt cgaagagtaa aaaattgtac | 19741 |
| ttggcggata atgcctttag cggcttaact gtgccctcca tggaaaaatc agtcaagata | 19801 |
| tccacatgtg ttttagtaa acaaattttg ggacctaatg cttcaactaa ctccagtaat | 19861 |
| tccttggtgg tacgaacatc caatgaagca cacaagtttg tttgcttttc gtgcatgata | 19921 |
| ttaaatagct tggcagcaac aggactagga tgagtagcag cacgttcctt atatgtagct | 19981 |
| ttcgacatga tttatcttcg tttcctgcag gttttgttc tgtgcagttg ggttaagaat | 20041 |
| actgggcaat ttcatgtttc ttcaacacta catatgcgta tatataccaa tctaagtctg | 20101 |
| tgctccttcc ttcgttcttc cttctgttcg gagattaccg aatcaaaaaa atttcaagga | 20161 |
| aaccgaaatc aaaaaaaaga ataaaaaaaa aatgatgaat tgaaaagctt atcgat | 20217 |

<210> SEQ ID NO 17
<211> LENGTH: 1911
<212> TYPE: PRT
<213> ORGANISM: Artificial Sequence
<220> FEATURE:
<223> OTHER INFORMATION: Description of Artificial Sequence:
    pd.delta.NS3NS5.pj.core140

<400> SEQUENCE: 17

```
Met Ala Ala Tyr Ala Ala Gln Gly Tyr Lys Val Leu Val Leu Asn Pro
  1               5                  10                  15

Ser Val Ala Ala Thr Leu Gly Phe Gly Ala Tyr Met Ser Lys Ala His
             20                  25                  30

Gly Ile Asp Pro Asn Ile Arg Thr Gly Val Arg Thr Ile Thr Thr Gly
         35                  40                  45

Ser Pro Ile Thr Tyr Ser Thr Tyr Gly Lys Phe Leu Ala Asp Gly Gly
     50                  55                  60

Cys Ser Gly Gly Ala Tyr Asp Ile Ile Ile Cys Asp Glu Cys His Ser
 65              70                  75                  80

Thr Asp Ala Thr Ser Ile Leu Gly Ile Gly Thr Val Leu Asp Gln Ala
                 85                  90                  95

Glu Thr Ala Gly Ala Arg Leu Val Val Leu Ala Thr Ala Thr Pro Pro
                100                 105                 110

Gly Ser Val Thr Val Pro His Pro Asn Ile Glu Glu Val Ala Leu Ser
            115                 120                 125

Thr Thr Gly Glu Ile Pro Phe Tyr Gly Lys Ala Ile Pro Leu Glu Val
    130                 135                 140

Ile Lys Gly Gly Arg His Leu Ile Phe Cys His Ser Lys Lys Lys Cys
145                 150                 155                 160

Asp Glu Leu Ala Ala Lys Leu Val Ala Leu Gly Ile Asn Ala Val Ala
                165                 170                 175

Tyr Tyr Arg Gly Leu Asp Val Ser Val Ile Pro Thr Ser Gly Asp Val
            180                 185                 190

Val Val Val Ala Thr Asp Ala Leu Met Thr Gly Tyr Thr Gly Asp Phe
        195                 200                 205

Asp Ser Val Ile Asp Cys Asn Thr Cys Val Thr Gln Thr Val Asp Phe
    210                 215                 220

Ser Leu Asp Pro Thr Phe Thr Ile Glu Thr Ile Thr Leu Pro Gln Asp
225                 230                 235                 240

Ala Val Ser Arg Thr Gln Arg Arg Gly Arg Thr Gly Arg Gly Lys Pro
                245                 250                 255

Gly Ile Tyr Arg Phe Val Ala Pro Gly Glu Arg Pro Ser Gly Met Phe
            260                 265                 270

Asp Ser Ser Val Leu Cys Glu Cys Tyr Asp Ala Gly Cys Ala Trp Tyr
        275                 280                 285

Glu Leu Thr Pro Ala Glu Thr Thr Val Arg Leu Arg Ala Tyr Met Asn
    290                 295                 300

Thr Pro Gly Leu Pro Val Cys Gln Asp His Leu Glu Phe Trp Glu Gly
305                 310                 315                 320

Val Phe Thr Gly Leu Thr His Ile Asp Ala His Phe Leu Ser Gln Thr
                325                 330                 335

Lys Gln Ser Gly Glu Asn Leu Pro Tyr Leu Val Ala Tyr Gln Ala Thr
            340                 345                 350

Val Cys Ala Arg Ala Gln Ala Pro Pro Pro Ser Trp Asp Gln Met Trp
        355                 360                 365

Lys Cys Leu Ile Arg Leu Lys Pro Thr Leu His Gly Pro Thr Pro Leu
    370                 375                 380

Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
                405                 410                 415

Thr Ser Thr Trp Val Leu Val Gly Gly Val Leu Ala Ala Leu Ala Ala
```

-continued

```
                420                 425                 430
Tyr Cys Leu Ser Thr Gly Cys Val Val Ile Val Gly Arg Val Val Leu
            435                 440                 445
Ser Gly Lys Pro Ala Ile Ile Pro Asp Arg Glu Val Leu Tyr Arg Glu
450                 455                 460
Phe Asp Glu Met Glu Glu Cys Ser Gln His Leu Pro Tyr Ile Glu Gln
465                 470                 475                 480
Gly Met Met Leu Ala Glu Gln Phe Lys Gln Lys Ala Leu Gly Leu Leu
                485                 490                 495
Gln Thr Ala Ser Arg Gln Ala Glu Val Ile Ala Pro Ala Val Gln Thr
                500                 505                 510
Asn Trp Gln Lys Leu Glu Thr Phe Trp Ala Lys His Met Trp Asn Phe
                515                 520                 525
Ile Ser Gly Ile Gln Tyr Leu Ala Gly Leu Ser Thr Leu Pro Gly Asn
                530                 535                 540
Pro Ala Ile Ala Ser Leu Met Ala Phe Thr Ala Ala Val Thr Ser Pro
545                 550                 555                 560
Leu Thr Thr Ser Gln Thr Leu Leu Phe Asn Ile Leu Gly Gly Trp Val
                565                 570                 575
Ala Ala Gln Leu Ala Ala Pro Gly Ala Ala Thr Ala Phe Val Gly Ala
                580                 585                 590
Gly Leu Ala Gly Ala Ala Ile Gly Ser Val Gly Leu Gly Lys Val Leu
                595                 600                 605
Ile Asp Ile Leu Ala Gly Tyr Gly Ala Gly Val Ala Gly Ala Leu Val
                610                 615                 620
Ala Phe Lys Ile Met Ser Gly Glu Val Pro Ser Thr Glu Asp Leu Val
625                 630                 635                 640
Asn Leu Leu Pro Ala Ile Leu Ser Pro Gly Ala Leu Val Val Gly Val
                645                 650                 655
Val Cys Ala Ala Ile Leu Arg Arg His Val Gly Pro Gly Glu Gly Ala
                660                 665                 670
Val Gln Trp Met Asn Arg Leu Ile Ala Phe Ala Ser Arg Gly Asn His
                675                 680                 685
Val Ser Pro Thr His Tyr Val Pro Glu Ser Asp Ala Ala Ala Arg Val
                690                 695                 700
Thr Ala Ile Leu Ser Ser Leu Thr Val Thr Gln Leu Leu Arg Arg Leu
705                 710                 715                 720
His Gln Trp Ile Ser Ser Glu Cys Thr Thr Pro Cys Ser Gly Ser Trp
                725                 730                 735
Leu Arg Asp Ile Trp Asp Trp Ile Cys Glu Val Leu Ser Asp Phe Lys
                740                 745                 750
Thr Trp Leu Lys Ala Lys Leu Met Pro Gln Leu Pro Gly Ile Pro Phe
                755                 760                 765
Val Ser Cys Gln Arg Gly Tyr Lys Gly Val Trp Arg Gly Asp Gly Ile
                770                 775                 780
Met His Thr Arg Cys His Cys Gly Ala Glu Ile Thr Gly His Val Lys
785                 790                 795                 800
Asn Gly Thr Met Arg Ile Val Gly Pro Arg Thr Cys Arg Asn Met Trp
                805                 810                 815
Ser Gly Thr Phe Pro Ile Asn Ala Tyr Thr Thr Gly Pro Cys Thr Pro
                820                 825                 830
Leu Pro Ala Pro Asn Tyr Thr Phe Ala Leu Trp Arg Val Ser Ala Glu
                835                 840                 845
```

```
Glu Tyr Val Glu Ile Arg Gln Val Gly Asp Phe His Tyr Val Thr Gly
    850                 855                 860

Met Thr Thr Asp Asn Leu Lys Cys Pro Cys Gln Val Pro Ser Pro Glu
865                 870                 875                 880

Phe Phe Thr Glu Leu Asp Gly Val Arg Leu His Arg Phe Ala Pro Pro
            885                 890                 895

Cys Lys Pro Leu Leu Arg Glu Glu Val Ser Phe Arg Val Gly Leu His
                900                 905                 910

Glu Tyr Pro Val Gly Ser Gln Leu Pro Cys Glu Pro Glu Pro Asp Val
            915                 920                 925

Ala Val Leu Thr Ser Met Leu Thr Asp Pro Ser His Ile Thr Ala Glu
930                 935                 940

Ala Ala Gly Arg Arg Leu Ala Arg Gly Ser Pro Ser Val Ala Ser
945                 950                 955                 960

Ser Ser Ala Ser Gln Leu Ser Ala Pro Ser Leu Lys Ala Thr Cys Thr
                965                 970                 975

Ala Asn His Asp Ser Pro Asp Ala Glu Leu Ile Glu Ala Asn Leu Leu
            980                 985                 990

Trp Arg Gln Glu Met Gly Gly Asn Ile Thr Arg Val Glu Ser Glu Asn
                995                 1000                1005

Lys Val Val Ile Leu Asp Ser Phe Asp Pro Leu Val Ala Glu Glu Asp
    1010                1015                1020

Glu Arg Glu Ile Ser Val Pro Ala Glu Ile Leu Arg Lys Ser Arg Arg
1025                1030                1035                1040

Phe Ala Gln Ala Leu Pro Val Trp Ala Arg Pro Asp Tyr Asn Pro Pro
                1045                1050                1055

Leu Val Glu Thr Trp Lys Lys Pro Asp Tyr Glu Pro Pro Val Val His
                1060                1065                1070

Gly Cys Pro Leu Pro Pro Pro Lys Ser Pro Pro Val Pro Pro Pro Arg
            1075                1080                1085

Lys Lys Arg Thr Val Val Leu Thr Glu Ser Thr Leu Ser Thr Ala Leu
    1090                1095                1100

Ala Glu Leu Ala Thr Arg Ser Phe Gly Ser Ser Ser Thr Ser Gly Ile
1105                1110                1115                1120

Thr Gly Asp Asn Thr Thr Thr Ser Ser Glu Pro Ala Pro Ser Gly Cys
                1125                1130                1135

Pro Pro Asp Ser Asp Ala Glu Ser Tyr Ser Ser Met Pro Pro Leu Glu
            1140                1145                1150

Gly Glu Pro Gly Asp Pro Asp Leu Ser Asp Gly Ser Trp Ser Thr Val
            1155                1160                1165

Ser Ser Glu Ala Asn Ala Glu Asp Val Val Cys Cys Ser Met Ser Tyr
    1170                1175                1180

Ser Trp Thr Gly Ala Leu Val Thr Pro Cys Ala Ala Glu Glu Gln Lys
1185                1190                1195                1200

Leu Pro Ile Asn Ala Leu Ser Asn Ser Leu Leu Arg His His Asn Leu
                1205                1210                1215

Val Tyr Ser Thr Thr Ser Arg Ser Ala Cys Gln Arg Gln Lys Lys Val
            1220                1225                1230

Thr Phe Asp Arg Leu Gln Val Leu Asp Ser His Tyr Gln Asp Val Leu
            1235                1240                1245

Lys Glu Val Lys Ala Ala Ala Ser Lys Val Lys Ala Asn Leu Leu Ser
    1250                1255                1260
```

-continued

```
Val Glu Glu Ala Cys Ser Leu Thr Pro Pro His Ser Ala Lys Ser Lys
1265                1270                1275                1280

Phe Gly Tyr Gly Ala Lys Asp Val Arg Cys His Ala Arg Lys Ala Val
            1285                1290                1295

Thr His Ile Asn Ser Val Trp Lys Asp Leu Leu Glu Asp Asn Val Thr
        1300                1305                1310

Pro Ile Asp Thr Thr Ile Met Ala Lys Asn Glu Val Phe Cys Val Gln
    1315                1320                1325

Pro Glu Lys Gly Gly Arg Lys Pro Ala Arg Leu Ile Val Phe Pro Asp
1330                1335                1340

Leu Gly Val Arg Val Cys Glu Lys Met Ala Leu Tyr Asp Val Val Thr
1345                1350                1355                1360

Lys Leu Pro Leu Ala Val Met Gly Ser Ser Tyr Gly Phe Gln Tyr Ser
            1365                1370                1375

Pro Gly Gln Arg Val Glu Phe Leu Val Gln Ala Trp Lys Ser Lys Lys
        1380                1385                1390

Thr Pro Met Gly Phe Ser Tyr Asp Thr Arg Cys Phe Asp Ser Thr Val
    1395                1400                1405

Thr Glu Ser Asp Ile Arg Thr Glu Glu Ala Ile Tyr Gln Cys Cys Asp
    1410                1415                1420

Leu Asp Pro Gln Ala Arg Val Ala Ile Lys Ser Leu Thr Glu Arg Leu
1425                1430                1435                1440

Tyr Val Gly Gly Pro Leu Thr Asn Ser Arg Gly Glu Asn Cys Gly Tyr
            1445                1450                1455

Arg Arg Cys Arg Ala Ser Gly Val Leu Thr Thr Ser Cys Gly Asn Thr
        1460                1465                1470

Leu Thr Cys Tyr Ile Lys Ala Arg Ala Ala Cys Arg Ala Ala Gly Leu
    1475                1480                1485

Gln Asp Cys Thr Met Leu Val Cys Gly Asp Asp Leu Val Val Ile Cys
    1490                1495                1500

Glu Ser Ala Gly Val Gln Glu Asp Ala Ala Ser Leu Arg Ala Phe Thr
1505                1510                1515                1520

Glu Ala Met Thr Arg Tyr Ser Ala Pro Pro Gly Asp Pro Pro Gln Pro
            1525                1530                1535

Glu Tyr Asp Leu Glu Leu Ile Thr Ser Cys Ser Ser Asn Val Ser Val
        1540                1545                1550

Ala His Asp Gly Ala Gly Lys Arg Val Tyr Tyr Leu Thr Arg Asp Pro
    1555                1560                1565

Thr Thr Pro Leu Ala Arg Ala Ala Trp Glu Thr Ala Arg His Thr Pro
    1570                1575                1580

Val Asn Ser Trp Leu Gly Asn Ile Ile Met Phe Ala Pro Thr Leu Trp
1585                1590                1595                1600

Ala Arg Met Ile Leu Met Thr His Phe Phe Ser Val Leu Ile Ala Arg
            1605                1610                1615

Asp Gln Leu Glu Gln Ala Leu Asp Cys Glu Ile Tyr Gly Ala Cys Tyr
        1620                1625                1630

Ser Ile Glu Pro Leu Asp Leu Pro Ile Ile Gln Arg Leu His Gly
    1635                1640                1645

Leu Ser Ala Phe Ser Leu His Ser Tyr Ser Pro Gly Glu Ile Asn Arg
    1650                1655                1660

Val Ala Ala Cys Leu Arg Lys Leu Gly Val Pro Pro Leu Arg Ala Trp
1665                1670                1675                1680

Arg His Arg Ala Arg Ser Val Arg Ala Arg Leu Leu Ala Arg Gly Gly
```

-continued

```
                    1685                1690                 1695
Arg Ala Ala Ile  Cys Gly Lys Tyr  Leu Phe Asn Trp  Ala Val Arg Thr
                1700                1705                 1710

Lys Leu Lys Leu  Thr Pro Ile Ala  Ala Ala Gly Gln  Leu Asp Leu Ser
            1715                 1720                1725

Gly Trp Phe Thr  Ala Gly Tyr Ser  Gly Gly Asp Ile  Tyr His Ser Val
            1730                 1735                1740

Ser His Ala Arg  Pro Arg Trp Ile  Trp Phe Cys Leu  Leu Leu Leu Ala
1745                 1750                1755                1760

Ala Gly Val Gly  Ile Tyr Leu Leu  Pro Asn Arg Met  Ser Thr Asn Pro
                1765                1770                 1775

Lys Pro Gln Arg  Lys Thr Lys Arg  Asn Thr Asn Arg  Arg Pro Gln Asp
            1780                1785                 1790

Val Lys Phe Pro  Gly Gly Gly Gln  Ile Val Gly Gly  Val Tyr Leu Leu
            1795                 1800                1805

Pro Arg Arg Gly  Pro Arg Leu Gly  Val Arg Ala Thr  Arg Lys Thr Ser
            1810                 1815                1820

Glu Arg Ser Gln  Pro Arg Gly Arg  Arg Gln Pro Ile  Pro Lys Ala Arg
1825                 1830                1835                1840

Arg Pro Glu Gly  Arg Thr Trp Ala  Gln Pro Gly Tyr  Pro Trp Pro Leu
                1845                1850                 1855

Tyr Gly Asn Glu  Gly Cys Gly Trp  Ala Gly Trp Leu  Leu Ser Pro Arg
                1860                1865                 1870

Gly Ser Arg Pro  Ser Trp Gly Pro  Thr Asp Pro Arg  Arg Arg Ser Arg
            1875                 1880                1885

Asn Leu Gly Lys  Val Ile Asp Thr  Leu Thr Cys Gly  Phe Ala Asp Leu
    1890                1895                 1900

Met Gly Tyr Ile  Pro Leu Val
1905                 1910

<210> SEQ ID NO 18
<211> LENGTH: 20247
<212> TYPE: DNA
<213> ORGANISM: Artificial Sequence
<220> FEATURE:
<223> OTHER INFORMATION: Description of Artificial Sequence:
      pd.delta.NS3NS5.pj.core150
<220> FEATURE:
<221> NAME/KEY: CDS
<222> LOCATION: (12679)..(18441)

<400> SEQUENCE: 18
atcgatccta ccccttgcgc taaagaagta tatgtgccta ctaacgcttg tctttgtctc      60
tgtcactaaa cactggatta ttactcccag atacttattt tggactaatt taaatgattt    120
cggatcaacg ttcttaatat cgctgaatct tccacaattg atgaaagtag ctaggaagag    180
gaattggtat aaagttttg tttttgtaaa tctcgaagta tactcaaacg aatttagtat     240
tttctcagtg atctcccaga tgctttcacc ctcacttaga agtgctttaa gcatttttt     300 actgtggcta tttcccttat ctgcttcttc cgatgattcg aactgtaatt gcaaactact    360
tacaatatca gtgatatcag attgatgttt ttgtccatag taaggaataa ttgtaaattc    420
ccaagcagga atcaatttct ttaatgaggc ttccagaatt gttgcttttt gcgtcttgta    480
tttaaactgg agtgatttat tgacaatatc gaaactcagc gaattgctta tgatagtatt    540
atagctcatg aatgtggctc tcttgattgc tgttccgtta tgtgtaatca tccaacataa    600
ataggttagt tcagcagcac ataatgctat tttctcacct gaaggtcttt caaacctttc    660
```

```
cacaaactga cgaacaagca ccttaggtgg tgttttacat aatatatcaa attgtggcat     720
gcttagcgcc gatcttgtgt gcaattgata tctagtttca actactctat ttatcttgta     780
tcttgcagta ttcaaacacg ctaactcgaa aaactaactt taattgtcct gtttgtctcg     840
cgttctttcg aaaaatgcac cggccgcgca ttatttgtac tgcgaaaata attggtactg     900
cggtatcttc atttcatatt ttaaaaatgc acctttgctg cttttcctta attttagac     960 ggcccgcagg ttcgttttgc ggtactatct tgtgataaaa agttgttttg acatgtgatc    1020
tgcacagatt ttataatgta ataagcaaga atacattatc aaacgaacaa tactggtaaa    1080
agaaaaccaa aatggacgac attgaaacag ccaagaatct gacggtaaaa gcacgtacag    1140
cttatagcgt ctgggatgta tgtcggctgt ttattgaaat gattgctcct gatgtagata    1200
ttgatataga gagtaaacgt aagtctgatg agctactctt tccaggatat gtcataaggc    1260
ccatggaatc tctcacaacc ggtaggccgt atggtcttga ttctagcgca gaagattcca    1320
gcgtatcttc tgactccagt gctgaggtaa ttttgcctgc tgcgaagatg gttaaggaaa    1380
ggtttgattc gattggaaat ggtatgctct cttcacaaga agcaagtcag gctgccatag    1440
atttgatgct acagaataac aagctgttag acaatagaaa gcaactatac aaatctattg    1500
ctataataat aggaagattg cccgagaaag acaagaagag agctaccgaa atgctcatga    1560
gaaaaatgga ttgtacacag ttattagtcc caccagctcc aacggaagaa gatgttatga    1620
agctcgtaag cgtcgttacc caattgctta ctttagttcc accagatcgt caagctgctt    1680
taataggtga tttattcatc ccggaatctc taaaggatat attcaatagt ttcaatgaac    1740
tggcggcaga gaatcgttta cagcaaaaaa agagtgagtt ggaaggaagg actgaagtga    1800
accatgctaa tacaaatgaa gaagttccct ccaggcgaac aagaagtaga gacacaaatg    1860
caagaggagc atataaatta caaaacacca tcactgaggg ccctaaagcg gttcccacga    1920
aaaaaaggag agtagcaacg agggtaaggg gcagaaaatc acgtaatact tctagggtat    1980
gatccaatat caaaggaaat gatagcattg aaggatgaga ctaatccaat tgaggagtgg    2040
cagcatatag aacagctaaa gggtagtgct gaaggaagca tacgataccc cgcatggaat    2100
gggataatat cacaggaggt actagactac ctttcatcct acataaatag acgcatataa    2160
gtacgcattt aagcataaac acgcactatg ccgttcttct catgtatata tatatacagg    2220
caacacgcag atataggtgc gacgtgaaca gtgagctgta tgtgcgcagc tcgcgttgca    2280
ttttcggaag cgctcgtttt cggaaacgct ttgaagttcc tattccgaag ttcctattct    2340
ctagaaagta taggaacttc agagcgcttt tgaaaaccaa aagcgctctg aagacgcact    2400
ttcaaaaaac caaaaacgca ccggactgta acgagctact aaaatattgc gaataccgct    2460
tccacaaaca ttgctcaaaa gtatctcttt gctatatatc tctgtgctat atccctatat    2520
aacctaccca tccaccttc gctccttgaa cttgcatcta aactcgacct ctacatcaac     2580
aggcttccaa tgctcttcaa attttactgt caagtagacc catacggctg taatatgctg    2640
ctcttcataa tgtaagctta tctttatcga atcgtgtgaa aaactactac cgcgataaac    2700
ctttacggtt ccctgagatt gaattagttc ctttagtata tgatacaaga cacttttgaa    2760
ctttgtacga cgaattttga ggttcgccat cctctggcta tttccaatta tcctgtcggc    2820
tattatctcc gcctcagttt gatcttccgc ttcagactgc cattttcac ataatgaatc     2880 tatttcaccc cacaatcctt catccgcctc cgcatcttgt tccgttaaac tattgacttc    2940
atgttgtaca ttgtttagtt cacgagaagg gtcctcttca ggcggtagct cctgatctcc    3000
```

```
tatatgacct ttatcctgtt ctctttccac aaacttagaa atgtattcat gaattatgga    3060
gcacctaata acattcttca aggcggagaa gtttgggcca gatgcccaat atgcttgaca    3120
tgaaaacgtg agaatgaatt tagtattatt gtgatattct gaggcaattt tattataatc    3180
tcgaagataa gagaagaatg cagtgacctt tgtattgaca aatggagatt ccatgtatct    3240
aaaaaatacg cctttaggcc ttctgatacc ctttcccctg cggtttagcg tgccttttac    3300
attaatatct aaaccctctc cgatggtggc ctttaactga ctaataaatg caaccgatat    3360
aaactgtgat aattctgggt gatttatgat tcgatcgaca attgtattgt acactagtgc    3420
aggatcaggc caatccagtt cttttcaat taccggtgtg tcgtctgtat tcagtacatg    3480
tccaacaaat gcaaatgcta acgttttgta tttcttataa ttgtcaggaa ctggaaaagt    3540
ccccttgtc gtctcgatta cacacctact ttcatcgtac accataggtt ggaagtgctg     3600
cataatacat tgcttaatac aagcaagcag tctctcgcca ttcatatttc agttattttc    3660
cattacagct gatgtcattg tatatcagcg ctgtaaaaat ctatctgtta cagaaggttt    3720
tcgcggtttt tataaacaaa actttcgtta cgaaatcgag caatcacccc agctgcgtat    3780
ttggaaattc gggaaaaagt agagcaacgc gagttgcatt ttttacacca taatgcatga    3840
ttaacttcga gaagggatta aggctaattt cactagtatg tttcaaaaac ctcaatctgt    3900
ccattgaatg ccttataaaa cagctataga ttgcatagaa gagttagcta ctcaatgctt    3960
tttgtcaaag cttactgatg atgatgtgtc tactttcagg cgggtctgta gtaaggagaa    4020
tgacattata aagctggcac ttagaattcc acggactata gactatacta gtatactccg    4080
tctactgtac gatacacttc cgctcaggtc cttgtccttt aacgaggcct taccactctt    4140
ttgttactct attgatccag ctcagcaaag gcagtgtgat ctaagattct atcttcgcga    4200
tgtagtaaaa ctagctagac cgagaaagag actagaaatg caaaaggcac ttctacaatg    4260
gctgccatca ttattatccg atgtgacgct gcattttttt tttttttttt tttttttttt    4320
tttttttttt tttttttttt tttttggta caaatatcat aaaaaaagag aatcttttta    4380
agcaaggatt ttcttaactt cttcggcgac agcatcaccg acttcggtgg tactgttgga    4440
accacctaaa tcaccagttc tgatacctgc atccaaaacc tttttaactg catcttcaat    4500
ggctttacct tcttcaggca agttcaatga caatttcaac atcattgcag cagacaagat    4560
agtggcgata gggttgacct tattctttgg caaatctgga gcggaaccat ggcatggttc    4620
gtacaaacca aatgcggtgt tcttgtctgg caaagaggcc aaggacgcag atggcaacaa    4680
acccaaggag cctgggataa cggaggcttc atcggagatg atatcaccaa acatgttgct    4740
ggtgattata ataccatta ggtggttgg gttcttaact aggatcatgg cggcagaatc      4800
aatcaattga tgttgaactt tcaatgtagg gaattcgttc ttgatggttt cctccacagt    4860
ttttctccat aatcttgaag aggccaaaac attagcttta tccaaggacc aaataggcaa    4920
tggtggctca tgttgtaggg ccatgaaagc ggccattctt tgattctttg cacttctgg     4980
aacggtgtat tgttcactat cccaagcgac accatcacca tcgtcttcct ttctcttacc    5040
aaagtaaata cctcccacta attctctaac aacaacgaag tcagtacctt tagcaaattg    5100
tggcttgatt ggagataagt ctaaaagaga gtcggatgca agttacatg tcttaagtt      5160
ggcgtacaat tgaagttctt tacgattttt tagtaaacct tgttcaggtc taacactacc    5220
ggtaccccat ttaggaccac ccacagcacc taacaaaacg gcatcagcct tcttggaggc    5280
ttccagcgcc tcatctggaa gtggaacacc tgtagcatcg atagcagcac caccaattaa    5340
atgattttcg aaatcgaact tgacattgga acgaacatca gaaatagctt taagaacctt    5400
```

```
aatggcttcg gctgtgattt cttgaccaac gtggtcacct ggcaaaacga cgatcttctt    5460
aggggcagac attacaatgg tatatccttg aaatatatat aaaaaaaaaa aaaaaaaaa     5520 aaaaaaaaaa atgcagcttc tcaatgatat tcgaatacgc tttgaggaga tacagcctaa    5580
tatccgacaa actgttttac agatttacga tcgtacttgt tacccatcat tgaattttga    5640
acatccgaac ctgggagttt tccctgaaac agatagtata tttgaacctg tataataata    5700
tatagtctag cgctttacgg aagacaatgt atgtatttcg gttcctggag aaactattgc    5760
atctattgca taggtaatct tgcacgtcgc atccccggtt cattttctgc gtttccatct    5820
tgcacttcaa tagcatatct ttgttaacga agcatctgtg cttcattttg tagaacaaaa    5880
atgcaacgcg agagcgctaa tttttcaaac aaagaatctg agctgcattt ttacagaaca    5940
gaaatgcaac gcgaaagcgc tattttacca acgaagaatc tgtgcttcat ttttgtaaaa    6000
caaaaatgca acgcgagagc gctaattttt caaacaaaga atctgagctg catttttaca    6060
gaacagaaat gcaacgcgag agcgctattt taccaacaaa gaatctatac ttcttttttg    6120
ttctacaaaa atgcatcccg agagcgctat ttttctaaca aagcatctta gattactttt    6180
tttctccttt gtgcgctcta taatgcagtc tcttgataac ttttttgcact gtaggtccgt    6240 taaggttaga agaaggctac tttggtgtct atttttctctt ccataaaaaa agcctgactc    6300
cacttcccgc gtttactgat tactagcgaa gctgcgggtg catttttca agataaaggc    6360 atccccgatt atattctata ccgatgtgga ttgcgcatac tttgtgaaca gaaagtgata    6420
gcgttgatga ttcttcattg gtcagaaaat tatgaacggt ttcttctatt ttgtctctat    6480
atactacgta taggaaatgt ttacattttc gtattgtttt cgattcactc tatgaatagt    6540
tcttactaca atttttttgt ctaaagagta atactagaga taaacataaa aaatgtagag    6600
gtcgagttta gatgcaagtt caaggagcga aaggtggatg ggtaggttat atagggatat    6660
agcacagaga tatatagcaa agagatactt ttgagcaatg tttgtggaag cggtattcgc    6720
aatattttag tagctcgtta cagtccggtg cgttttttggt tttttgaaag tgcgtcttca    6780
gagcgctttt ggttttcaaa agcgctctga agttcctata cttctagag aataggaact    6840 tcggaatagg aacttcaaag cgtttccgaa aacgagcgct tccgaaaatg caacgcgagc    6900
tgcgcacata cagctcactg ttcacgtcgc acctatatct gcgtgttgcc tgtatatata    6960
tatacatgag aagaacggca tagtgcgtgt ttatgcttaa atgcgtactt atatgcgtct    7020
atttatgtag gatgaaaggt agtctagtac ctcctgtgat attatcccat tccatgcggg    7080
gtatcgtatg cttccttcag cactacccctt tagctgttct atatgctgcc actcctcaat    7140
tggattagtc tcatccttca atgctatcat ttcctttgat attggatcat atgcatagta    7200
ccgagaaact agtgcgaagt agtgatcagg tattgctgtt atctgatgag tatacgttgt    7260
cctggccacg gcagaagcac gcttatcgct ccaatttccc acaacattag tcaactccgt    7320
taggcccttc attgaaagaa atgaggtcat caaatgtctt ccaatgtgag attttgggcc    7380 atttttata gcaaagattg aataaggcgc attttttcttc aaagctttat tgtacgatct    7440
gactaagtta tctttaata attggtattc ctgtttattg cttgaagaat tgccggtcct    7500
atttactcgt tttaggactg gttcagaatt cctcaaaaat tcatccaaat atacaagtgg    7560
atcgatgata agctgtcaaa catgagaatt cttgaagacg aaagggcctc gtgatacgcc    7620
tatttttata ggttaatgtc atgataataa tggtttctta cgtgtcaggt ggcactttc    7680 ggggaaatgt gcgcggaacc cctatttgtt tattttttcta aatacattca aatatgtatc    7740
```

-continued

```
cgctcatgag acaataaccc tgataaatgc ttcaataata ttgaaaaagg aagagtatga     7800
gtattcaaca tttccgtgtc gcccttattc ccttttttgc ggcattttgc cttcctgttt     7860
ttgctcaccc agaaacgctg gtgaaagtaa aagatgctga agatcagttg ggtgcacgag     7920
tgggttacat cgaactggat ctcaacagcg gtaagatcct tgagagtttt cgccccgaag     7980
aacgttttcc aatgatgagc acttttaaag ttctgctatg tggcgcggta ttatcccgtg     8040
ttgacgccgg gcaagagcaa ctcggtcgcc gcatacacta ttctcagaat gacttggttg     8100
agtactcacc agtcacagaa aagcatctta cggatggcat gacagtaaga gaattatgca     8160
gtgctgccat aaccatgagt gataacactg cggccaactt acttctgaca acgatcgag     8220
gaccgaagga gctaaccgct tttttgcaca acatggggga tcatgtaact cgccttgatc     8280
gttgggaacc ggagctgaat gaagccatac caaacgacga gcgtgacacc acgatgcctg     8340
cagcaatggc aacaacgttg cgcaaactat taactggcga actacttact ctagcttccc     8400
ggcaacaatt aatagactgg atggaggcgg ataaagttgc aggaccactt ctgcgctcgg     8460
cccttccggc tggctggttt attgctgata atctggagcc ggtgagcgt gggtctcgcg     8520
gtatcattgc agcactgggg ccagatggta agccctcccg tatcgtagtt atctacacga     8580
cggggagtca ggcaactatg gatgaacgaa atagacagat cgctgagata ggtgcctcac     8640
tgattaagca ttggtaactg tcagaccaag tttactcata tatactttag attgatttaa     8700
aacttcattt ttaatttaaa aggatctagg tgaagatcct ttttgataat ctcatgacca     8760
aaatccctta acgtgagttt tcgttccact gagcgtcaga ccccgtagaa aagatcaaag     8820
gatcttcttg agatcctttt tttctgcgcg taatctgctg cttgcaaaca aaaaaaccac     8880
cgctaccagc ggtggttttgt tgccggatc aagagctacc aactctttttt ccgaaggtaa     8940
ctggcttcag cagagcgcag ataccaaata ctgtccttct agtgtagccg tagttaggcc     9000
accacttcaa gaactctgta gcaccgccta catacctcgc tctgctaatc ctgttaccag     9060
tggctgctgc cagtggcgat aagtcgtgtc ttaccgggtt ggactcaaga cgatagttac     9120
cggataaggc gcagcggtcg ggctgaacgg ggggttcgtg cacacagccc agcttggagc     9180
gaacgaccta caccgaactg agatacctac agcgtgagct atgagaaagc gccacgcttc     9240
ccgaagggag aaaggcggac aggtatccgg taagcggcag ggtcggaaca ggagagcgca     9300
cgagggagct tccaggggga aacgcctggt atctttatag tcctgtcggg tttcgccacc     9360
tctgacttga gcgtcgattt ttgtgatgct cgtcagggg gcggagccta tggaaaaacg     9420
ccagcaacgc ggcctttta cggttcctgg ccttttgctg gccttttgct cacatgttct     9480
ttcctgcgtt atcccctgat tctgtggata accgtattac cgcctttgag tgagctgata     9540
ccgctcgccg cagccgaacg accgagcgca gcgagtcagt gagcgaggaa gcggaagagc     9600
gcctgatgcg gtattttctc cttacgcatc tgtgcggtat ttcacaccgc atatggtgca     9660
ctctcagtac aatctgctct gatgccgcat agttaagcca gtatacactc cgctatcgct     9720
acgtgactgg gtcatggctg cgccccgaca cccgccaaca cccgctgacg cgccctgacg     9780
ggcttgtctg ctcccggcat ccgcttacag acaagctgtg accgtctccg ggagctgcat     9840
gtgtcagagg ttttcaccgt catcaccgaa acgcgcgagg cagctgcggt aaagctcatc     9900
agcgtggtcg tgaagcgatt cacagatgtc tgcctgttca tccgcgtcca gctcgttgag     9960
tttctccaga agcgttaatg tctggcttct gataaagcgg ccatgttaa gggcggtttt    10020
ttcctgtttg gtcactgatg cctccgtgta agggggattt ctgttcatgg ggtaatgat    10080
accgatgaaa cgagagagga tgctcacgat acgggttact gatgatgaac atgcccggtt    10140
```

```
actggaacgt tgtgagggta acaactggc ggtatggatg cggcgggacc agagaaaaat    10200
cactcagggt caatgccagc gcttcgttaa tacagatgta ggtgttccac agggtagcca    10260
gcagcatcct gcgatgcaga tccggaacat aatggtgcag ggcgctgact tccgcgtttc    10320
cagactttac gaaacacgga aaccgaagac cattcatgtt gttgctcagg tcgcagacgt    10380
tttgcagcag cagtcgcttc acgttcgctc gcgtatcgt gattcattct gctaaccagt    10440
aaggcaaccc cgccagccta gccgggtcct caacgacagg agcacgatca tgcgcacccg    10500
tggccaggac ccaacgctgc ccgagatgcg ccgcgtgcgg ctgctggaga tggcggacgc    10560
gatggatatg ttctgccaag ggttggtttg cgcattcaca gttctccgca agaattgatt    10620
ggctccaatt cttggagtgg tgaatccgtt agcgaggtgc cgccggcttc cattcaggtc    10680
gaggtggccc ggctccatgc accgcgacgc aacgcgggga ggcagacaag gtatagggcg    10740
gcgcctacaa tccatgccaa cccgttccat gtgctcgccg aggcggcata atcgccgtg    10800
acgatcagcg gtccaatgat cgaagttagg ctggtaagag ccgcgagcga tccttgaagc    10860
tgtccctgat ggtcgtcatc tacctgcctg acagcatgg cctgcaacgc gggcatcccg    10920
atgccgccgg aagcgagaag aatcataatg gggaaggcca tccagcctcg cgtcgcgaac    10980
gccagcaaga cgtagcccag cgcgtcggcc gccatgccgg cgataatggc ctgcttctcg    11040
ccgaaacgtt tggtggcggg accagtgacg aaggcttgag cgagggcgtg caagattccg    11100
aataccgcaa gcgacaggcc gatcatcgtc gcgctccagc gaaagcggtc ctcgccgaaa    11160
atgacccaga gcgctgccgg cacctgtcct acgagttgca tgataaagaa gacagtcata    11220
agtgcggcga cgatagtcat gccccgcgcc caccggaagg agctgactgg gttgaaggct    11280
ctcaagggca tcggtcgagg atccttcaat atgcgcacat acgctgttat gttcaaggtc    11340
ccttcgttta agaacgaaag cggtcttcct tttgagggat gtttcaagtt gttcaaatct    11400
atcaaatttg caaatcccca gtctgtatct agagcgttga atcggtgatg cgatttgtta    11460
attaaattga tggtgtcacc attaccaggt ctagatatac caatggcaaa ctgagcacaa    11520
caataccagt ccggatcaac tggcaccatc tctcccgtag tctcatctaa ttttctttcc    11580
ggatgaggtt ccagatatac cgcaacacct ttattatggt ttccctgagg gaataataga    11640
atgtcccatt cgaaatcacc aattctaaac ctgggcgaat tgtatttcgg gtttgttaac    11700
tcgttccagt caggaatgtt ccacgtgaag ctatcttcca gcaaagtctc cacttcttca    11760
tcaaattgtg gagaatactc ccaatgctct tatctatggg acttccggga aacacagtac    11820
cgatacttcc caattcgtct tcagagctca ttgtttgttt gaagagacta atcaaagaat    11880
cgttttctca aaaaaattaa tatcttaact gatagtttga tcaaaggggc aaaacgtagg    11940
ggcaaacaaa cggaaaaatc gtttctcaaa ttttctgatg ccaagaactc taaccagtct    12000
tatctaaaaa ttgccttatg atccgtctct ccggttacag cctgtgtaac tgattaatcc    12060
tgcctttcta atcaccattc taatgttta attaagggat tttgtcttca ttaacggctt    12120
tcgctcataa aaatgttatg acgttttgcc cgcaggcggg aaaccatcca cttcacgaga    12180
ctgatctcct ctgccggaac accgggcatc tccaacttat aagttggaga aataagagaa    12240
tttcagattg agagaatgaa aaaaaaaaac ccttagttca taggtccatt ctcttagcgc    12300
aactacagag aacaggggca caaacaggca aaaacgggc acaacctcaa tggagtgatg    12360
caacctgcct ggagtaaatg atgacacaag gcaattgacc cacgcatgta tctatctcat    12420
tttcttacac cttctattac cttctgctct ctctgatttg gaaaaagctg aaaaaaaagg    12480
```

-continued

```
ttgaaaccag ttccctgaaa ttattccct acttgactaa taagtatata aagacggtag    12540
gtattgattg taattctgta aatctatttc ttaaacttct taaattctac ttttatagtt    12600 agtcttttt ttagttta aacaccaaga acttagttc gaataaacac acataaacaa       12660
```

| acaagcttac aaaacaaa atg gct gca tat gca gct cag ggc tat aag gtg | 12711 |
|---|---|
| Met Ala Ala Tyr Ala Ala Gln Gly Tyr Lys Val | |
| 1 5 10 | |

| cta gta ctc aac ccc tct gtt gct gca aca ctg ggc ttt ggt gct tac | 12759 |
|---|---|
| Leu Val Leu Asn Pro Ser Val Ala Ala Thr Leu Gly Phe Gly Ala Tyr | |
| 15 20 25 | |

| atg tcc aag gct cat ggg atc gat cct aac atc agg acc ggg gtg aga | 12807 |
|---|---|
| Met Ser Lys Ala His Gly Ile Asp Pro Asn Ile Arg Thr Gly Val Arg | |
| 30 35 40 | |

| aca att acc act ggc agc ccc atc acg tac tcc acc tac ggc aag ttc | 12855 |
|---|---|
| Thr Ile Thr Thr Gly Ser Pro Ile Thr Tyr Ser Thr Tyr Gly Lys Phe | |
| 45 50 55 | |

| ctt gcc gac ggc ggg tgc tcg ggg ggc gct tat gac ata ata att tgt | 12903 |
|---|---|
| Leu Ala Asp Gly Gly Cys Ser Gly Gly Ala Tyr Asp Ile Ile Ile Cys | |
| 60 65 70 75 | |

| gac gag tgc cac tcc acg gat gcc aca tcc atc ttg ggc att ggc act | 12951 |
|---|---|
| Asp Glu Cys His Ser Thr Asp Ala Thr Ser Ile Leu Gly Ile Gly Thr | |
| 80 85 90 | |

| gtc ctt gac caa gca gag act gcg ggg gcg aga ctg gtt gtg ctc gcc | 12999 |
|---|---|
| Val Leu Asp Gln Ala Glu Thr Ala Gly Ala Arg Leu Val Val Leu Ala | |
| 95 100 105 | |

| acc gcc acc cct ccg ggc tcc gtc act gtg ccc cat ccc aac atc gag | 13047 |
|---|---|
| Thr Ala Thr Pro Pro Gly Ser Val Thr Val Pro His Pro Asn Ile Glu | |
| 110 115 120 | |

| gag gtt gct ctg tcc acc acc gga gag atc cct ttt tac ggc aag gct | 13095 |
|---|---|
| Glu Val Ala Leu Ser Thr Thr Gly Glu Ile Pro Phe Tyr Gly Lys Ala | |
| 125 130 135 | |

| atc ccc ctc gaa gta atc aag ggg gga aga cat ctc atc ttc tgt cat | 13143 |
|---|---|
| Ile Pro Leu Glu Val Ile Lys Gly Gly Arg His Leu Ile Phe Cys His | |
| 140 145 150 155 | |

| tca aag aag aag tgc gac gaa ctc gcc gca aag ctg gtc gca ttg ggc | 13191 |
|---|---|
| Ser Lys Lys Lys Cys Asp Glu Leu Ala Ala Lys Leu Val Ala Leu Gly | |
| 160 165 170 | |

| atc aat gcc gtg gcc tac tac cgc ggt ctt gac gtg tcc gtc atc ccg | 13239 |
|---|---|
| Ile Asn Ala Val Ala Tyr Tyr Arg Gly Leu Asp Val Ser Val Ile Pro | |
| 175 180 185 | |

| acc agc ggc gat gtt gtc gtc gtg gca acc gat gcc ctc atg acc ggc | 13287 |
|---|---|
| Thr Ser Gly Asp Val Val Val Val Ala Thr Asp Ala Leu Met Thr Gly | |
| 190 195 200 | |

| tat acc ggc gac ttc gac tcg gtg ata gac tgc aat acg tgt gtc acc | 13335 |
|---|---|
| Tyr Thr Gly Asp Phe Asp Ser Val Ile Asp Cys Asn Thr Cys Val Thr | |
| 205 210 215 | |

| cag aca gtc gat ttc agc ctt gac cct acc ttc acc att gag aca atc | 13383 |
|---|---|
| Gln Thr Val Asp Phe Ser Leu Asp Pro Thr Phe Thr Ile Glu Thr Ile | |
| 220 225 230 235 | |

| acg ctc ccc caa gat gct gtc tcc cgc act caa cgt cgg ggc agg act | 13431 |
|---|---|
| Thr Leu Pro Gln Asp Ala Val Ser Arg Thr Gln Arg Arg Gly Arg Thr | |
| 240 245 250 | |

| ggc agg ggg aag cca ggc atc tac aga ttt gtg gca ccg ggg gag cgc | 13479 |
|---|---|
| Gly Arg Gly Lys Pro Gly Ile Tyr Arg Phe Val Ala Pro Gly Glu Arg | |
| 255 260 265 | |

| ccc tcc ggc atg ttc gac tcg tcc gtc ctc tgt gag tgc tat gac gca | 13527 |
|---|---|
| Pro Ser Gly Met Phe Asp Ser Ser Val Leu Cys Glu Cys Tyr Asp Ala | |
| 270 275 280 | |

| ggc tgt gct tgg tat gag ctc acg ccc gcc gag act aca gtt agg cta | 13575 |
|---|---|

```
                Gly Cys Ala Trp Tyr Glu Leu Thr Pro Ala Glu Thr Thr Val Arg Leu
                    285                 290                 295 cga gcg tac atg aac acc ccg ggg ctt ccc gtg tgc cag gac cat ctt        13623
Arg Ala Tyr Met Asn Thr Pro Gly Leu Pro Val Cys Gln Asp His Leu
300                 305                 310                 315 gaa ttt tgg gag ggc gtc ttt aca ggc ctc act cat ata gat gcc cac        13671
Glu Phe Trp Glu Gly Val Phe Thr Gly Leu Thr His Ile Asp Ala His
                320                 325                 330 ttt cta tcc cag aca aag cag agt ggg gag aac ctt cct tac ctg gta        13719
Phe Leu Ser Gln Thr Lys Gln Ser Gly Glu Asn Leu Pro Tyr Leu Val
            335                 340                 345 gcg tac caa gcc acc gtg tgc gct agg gct caa gcc cct ccc cca tcg        13767
Ala Tyr Gln Ala Thr Val Cys Ala Arg Ala Gln Ala Pro Pro Pro Ser
        350                 355                 360 tgg gac cag atg tgg aag tgt ttg att cgc ctc aag ccc acc ctc cat        13815
Trp Asp Gln Met Trp Lys Cys Leu Ile Arg Leu Lys Pro Thr Leu His
    365                 370                 375 ggg cca aca ccc ctg cta tac aga ctg ggc gct gtt cag aat gaa atc        13863
Gly Pro Thr Pro Leu Leu Tyr Arg Leu Gly Ala Val Gln Asn Glu Ile
380                 385                 390                 395 acc ctg acg cac cca gtc acc aaa tac atc atg aca tgc atg tcg gcc        13911
Thr Leu Thr His Pro Val Thr Lys Tyr Ile Met Thr Cys Met Ser Ala
                400                 405                 410 gac ctg gag gtc gtc acg agc acc tgg gtg ctc gtt ggc ggc gtc ctg        13959
Asp Leu Glu Val Val Thr Ser Thr Trp Val Leu Val Gly Gly Val Leu
                415                 420                 425 gct gct ttg gcc gcg tat tgc ctg tca aca ggc tgc gtg gtc ata gtg        14007
Ala Ala Leu Ala Ala Tyr Cys Leu Ser Thr Gly Cys Val Val Ile Val
            430                 435                 440 ggc agg gtc gtc ttg tcc ggg aag ccg gca atc ata cct gac agg gaa        14055
Gly Arg Val Val Leu Ser Gly Lys Pro Ala Ile Ile Pro Asp Arg Glu
        445                 450                 455 gtc ctc tac cga gag ttc gat gag atg gaa gag tgc tct cag cac tta        14103
Val Leu Tyr Arg Glu Phe Asp Glu Met Glu Glu Cys Ser Gln His Leu
    460                 465                 470                 475 ccg tac atc gag caa ggg atg atg ctc gcc gag cag ttc aag cag aag        14151
Pro Tyr Ile Glu Gln Gly Met Met Leu Ala Glu Gln Phe Lys Gln Lys
                480                 485                 490 gcc ctc ggc ctc ctg cag acc gcg tcc cgt cag gca gag gtt atc gcc        14199
Ala Leu Gly Leu Leu Gln Thr Ala Ser Arg Gln Ala Glu Val Ile Ala
            495                 500                 505 cct gct gtc cag acc aac tgg caa aaa ctc gag acc ttc tgg gcg aag        14247
Pro Ala Val Gln Thr Asn Trp Gln Lys Leu Glu Thr Phe Trp Ala Lys
        510                 515                 520 cat atg tgg aac ttc atc agt ggg ata caa tac ttg gcg ggc ttg tca        14295
His Met Trp Asn Phe Ile Ser Gly Ile Gln Tyr Leu Ala Gly Leu Ser
    525                 530                 535 acg ctg cct ggt aac ccc gcc att gct tca ttg atg gct ttt aca gct        14343
Thr Leu Pro Gly Asn Pro Ala Ile Ala Ser Leu Met Ala Phe Thr Ala
540                 545                 550                 555 gct gtc acc agc cca cta acc act agc caa acc ctc ctc ttc aac ata        14391
Ala Val Thr Ser Pro Leu Thr Thr Ser Gln Thr Leu Leu Phe Asn Ile
                560                 565                 570 ttg ggg ggg tgg gtg gct gcc cag ctc gcc gcc ccc ggt gcc gct act        14439
Leu Gly Gly Trp Val Ala Ala Gln Leu Ala Ala Pro Gly Ala Ala Thr
                575                 580                 585 gcc ttt gtg ggc gct ggc tta gct ggc gcc gcc atc ggc agt gtt gga        14487
Ala Phe Val Gly Ala Gly Leu Ala Gly Ala Ala Ile Gly Ser Val Gly
            590                 595                 600
```

```
ctg ggg aag gtc ctc ata gac atc ctt gca ggg tat ggc gcg ggc gtg        14535
Leu Gly Lys Val Leu Ile Asp Ile Leu Ala Gly Tyr Gly Ala Gly Val
    605                 610                 615 gcg gga gct ctt gtg gca ttc aag atc atg agc ggt gag gtc ccc tcc        14583
Ala Gly Ala Leu Val Ala Phe Lys Ile Met Ser Gly Glu Val Pro Ser
620                 625                 630                 635 acg gag gac ctg gtc aat cta ctg ccc gcc atc ctc tcg ccc gga gcc        14631
Thr Glu Asp Leu Val Asn Leu Leu Pro Ala Ile Leu Ser Pro Gly Ala
                640                 645                 650 ctc gta gtc ggc gtg gtc tgt gca gca ata ctg cgc cgg cac gtt ggc        14679
Leu Val Val Gly Val Val Cys Ala Ala Ile Leu Arg Arg His Val Gly
            655                 660                 665 ccg ggc gag ggg gca gtg cag tgg atg aac cgg ctg ata gcc ttc gcc        14727
Pro Gly Glu Gly Ala Val Gln Trp Met Asn Arg Leu Ile Ala Phe Ala
        670                 675                 680 tcc cgg ggg aac cat gtt tcc ccc acg cac tac gtg ccg gag agc gat        14775
Ser Arg Gly Asn His Val Ser Pro Thr His Tyr Val Pro Glu Ser Asp
    685                 690                 695 gca gct gcc cgc gtc act gcc ata ctc agc agc ctc act gta acc cag        14823
Ala Ala Ala Arg Val Thr Ala Ile Leu Ser Ser Leu Thr Val Thr Gln
700                 705                 710                 715 ctc ctg agg cga ctg cac cag tgg ata agc tcg gag tgt acc act cca        14871
Leu Leu Arg Arg Leu His Gln Trp Ile Ser Ser Glu Cys Thr Thr Pro
                720                 725                 730 tgc tcc ggt tcc tgg cta agg gac atc tgg gac tgg ata tgc gag gtg        14919
Cys Ser Gly Ser Trp Leu Arg Asp Ile Trp Asp Trp Ile Cys Glu Val
            735                 740                 745 ttg agc gac ttt aag acc tgg cta aaa gct aag ctc atg cca cag ctg        14967
Leu Ser Asp Phe Lys Thr Trp Leu Lys Ala Lys Leu Met Pro Gln Leu
        750                 755                 760 cct ggg atc ccc ttt gtg tcc tgc cag cgc ggg tat aag ggg gtc tgg        15015
Pro Gly Ile Pro Phe Val Ser Cys Gln Arg Gly Tyr Lys Gly Val Trp
    765                 770                 775 cga ggg gac ggc atc atg cac act cgc tgc cac tgt gga gct gag atc        15063
Arg Gly Asp Gly Ile Met His Thr Arg Cys His Cys Gly Ala Glu Ile
780                 785                 790                 795 act gga cat gtc aaa aac ggg acg atg agg atc gtc ggt cct agg acc        15111
Thr Gly His Val Lys Asn Gly Thr Met Arg Ile Val Gly Pro Arg Thr
                800                 805                 810 tgc agg aac atg tgg agt ggg acc ttc ccc att aat gcc tac acc acg        15159
Cys Arg Asn Met Trp Ser Gly Thr Phe Pro Ile Asn Ala Tyr Thr Thr
            815                 820                 825 ggc ccc tgt acc ccc ctt cct gcg ccg aac tac acg ttc gcg cta tgg        15207
Gly Pro Cys Thr Pro Leu Pro Ala Pro Asn Tyr Thr Phe Ala Leu Trp
        830                 835                 840 agg gtg tct gca gag gaa tac gtg gag ata agg cag gtg ggg gac ttc        15255
Arg Val Ser Ala Glu Glu Tyr Val Glu Ile Arg Gln Val Gly Asp Phe
    845                 850                 855 cac tac gtg acg ggt atg act act gac aat ctt aaa tgc ccg tgc cag        15303
His Tyr Val Thr Gly Met Thr Thr Asp Asn Leu Lys Cys Pro Cys Gln
860                 865                 870                 875 gtc cca tcg ccc gaa ttt ttc aca gaa ttg gac ggg gtg cgc cta cat        15351
Val Pro Ser Pro Glu Phe Phe Thr Glu Leu Asp Gly Val Arg Leu His
                880                 885                 890 agg ttt gcg ccc ccc tgc aag ccc ttg ctg cgg gag gag gta tca ttc        15399
Arg Phe Ala Pro Pro Cys Lys Pro Leu Leu Arg Glu Glu Val Ser Phe
            895                 900                 905 aga gta gga ctc cac gaa tac ccg gta ggg tcg caa tta cct tgc gag        15447
Arg Val Gly Leu His Glu Tyr Pro Val Gly Ser Gln Leu Pro Cys Glu
        910                 915                 920
```

-continued

| | |
|---|---|
| ccc gaa ccg gac gtg gcc gtg ttg acg tcc atg ctc act gat ccc tcc<br>Pro Glu Pro Asp Val Ala Val Leu Thr Ser Met Leu Thr Asp Pro Ser<br>925     930     935 | 15495 |
| cat ata aca gca gag gcg gcc ggg cga agg ttg gcg agg gga tca ccc<br>His Ile Thr Ala Glu Ala Ala Gly Arg Arg Leu Ala Arg Gly Ser Pro<br>940     945     950     955 | 15543 |
| ccc tct gtg gcc agc tcc tcg gct agc cag cta tcc gct cca tct ctc<br>Pro Ser Val Ala Ser Ser Ser Ala Ser Gln Leu Ser Ala Pro Ser Leu<br>     960     965     970 | 15591 |
| aag gca act tgc acc gct aac cat gac tcc cct gat gct gag ctc ata<br>Lys Ala Thr Cys Thr Ala Asn His Asp Ser Pro Asp Ala Glu Leu Ile<br>975     980     985 | 15639 |
| gag gcc aac ctc cta tgg agg cag gag atg ggc ggc aac atc acc agg<br>Glu Ala Asn Leu Leu Trp Arg Gln Glu Met Gly Gly Asn Ile Thr Arg<br>990     995     1000 | 15687 |
| gtt gag tca gaa aac aaa gtg gtg att ctg gac tcc ttc gat ccg ctt<br>Val Glu Ser Glu Asn Lys Val Val Ile Leu Asp Ser Phe Asp Pro Leu<br>1005     1010     1015 | 15735 |
| gtg gcg gag gag gac gag cgg gag atc tcc gta ccc gca gaa atc ctg<br>Val Ala Glu Glu Asp Glu Arg Glu Ile Ser Val Pro Ala Glu Ile Leu<br>1020     1025     1030     1035 | 15783 |
| cgg aag tct cgg aga ttc gcc cag gcc ctg ccc gtt tgg gcg cgg ccg<br>Arg Lys Ser Arg Arg Phe Ala Gln Ala Leu Pro Val Trp Ala Arg Pro<br>     1040     1045     1050 | 15831 |
| gac tat aac ccc ccg cta gtg gag acg tgg aaa aag ccc gac tac gaa<br>Asp Tyr Asn Pro Pro Leu Val Glu Thr Trp Lys Lys Pro Asp Tyr Glu<br>     1055     1060     1065 | 15879 |
| cca cct gtg gtc cat ggc tgc ccg ctt cca cct cca aag tcc cct cct<br>Pro Pro Val Val His Gly Cys Pro Leu Pro Pro Pro Lys Ser Pro Pro<br>1070     1075     1080 | 15927 |
| gtg cct ccg cct cgg aag aag cgg acg gtg gtc ctc act gaa tca acc<br>Val Pro Pro Pro Arg Lys Lys Arg Thr Val Val Leu Thr Glu Ser Thr<br>1085     1090     1095 | 15975 |
| cta tct act gcc ttg gcc gag ctc gcc acc aga agc ttt ggc agc tcc<br>Leu Ser Thr Ala Leu Ala Glu Leu Ala Thr Arg Ser Phe Gly Ser Ser<br>1100     1105     1110     1115 | 16023 |
| tca act tcc ggc att acg ggc gac aat acg aca aca tcc tct gag ccc<br>Ser Thr Ser Gly Ile Thr Gly Asp Asn Thr Thr Thr Ser Ser Glu Pro<br>     1120     1125     1130 | 16071 |
| gcc cct tct ggc tgc ccc ccc gac tcc gac gct gag tcc tat tcc tcc<br>Ala Pro Ser Gly Cys Pro Pro Asp Ser Asp Ala Glu Ser Tyr Ser Ser<br>     1135     1140     1145 | 16119 |
| atg ccc ccc ctg gag ggg gag cct ggg gat ccg gat ctt agc gac ggg<br>Met Pro Pro Leu Glu Gly Glu Pro Gly Asp Pro Asp Leu Ser Asp Gly<br>1150     1155     1160 | 16167 |
| tca tgg tca acg gtc agt agt gag gcc aac gcg gag gat gtc gtg tgc<br>Ser Trp Ser Thr Val Ser Ser Glu Ala Asn Ala Glu Asp Val Val Cys<br>1165     1170     1175 | 16215 |
| tgc tca atg tct tac tct tgg aca ggc gca ctc gtc acc ccg tgc gcc<br>Cys Ser Met Ser Tyr Ser Trp Thr Gly Ala Leu Val Thr Pro Cys Ala<br>1180     1185     1190     1195 | 16263 |
| gcg gaa gaa cag aaa ctg ccc atc aat gca cta agc aac tcg ttg cta<br>Ala Glu Glu Gln Lys Leu Pro Ile Asn Ala Leu Ser Asn Ser Leu Leu<br>     1200     1205     1210 | 16311 |
| cgt cac cac aat ttg gtg tat tcc acc acc tca cgc agt gct tgc caa<br>Arg His His Asn Leu Val Tyr Ser Thr Thr Ser Arg Ser Ala Cys Gln<br>     1215     1220     1225 | 16359 |
| agg cag aag aaa gtc aca ttt gac aga ctg caa gtt ctg gac agc cat<br>Arg Gln Lys Lys Val Thr Phe Asp Arg Leu Gln Val Leu Asp Ser His | 16407 |

-continued

```
           1230                1235                1240
tac cag gac gta ctc aag gag gtt aaa gca gcg gcg tca aaa gtg aag      16455
Tyr Gln Asp Val Leu Lys Glu Val Lys Ala Ala Ala Ser Lys Val Lys
        1245                1250                1255 gct aac ttg cta tcc gta gag gaa gct tgc agc ctg acg ccc cac          16503
Ala Asn Leu Leu Ser Val Glu Glu Ala Cys Ser Leu Thr Pro Pro His
1260                1265                1270                1275 tca gcc aaa tcc aag ttt ggt tat ggg gca aaa gac gtc cgt tgc cat      16551
Ser Ala Lys Ser Lys Phe Gly Tyr Gly Ala Lys Asp Val Arg Cys His
                1280                1285                1290 gcc aga aag gcc gta acc cac atc aac tcc gtg tgg aaa gac ctt ctg      16599
Ala Arg Lys Ala Val Thr His Ile Asn Ser Val Trp Lys Asp Leu Leu
        1295                1300                1305 gaa gac aat gta aca cca ata gac act acc atc atg gct aag aac gag      16647
Glu Asp Asn Val Thr Pro Ile Asp Thr Thr Ile Met Ala Lys Asn Glu
1310                1315                1320 gtt ttc tgc gtt cag cct gag aag ggg ggt cgt aag cca gct cgt ctc      16695
Val Phe Cys Val Gln Pro Glu Lys Gly Gly Arg Lys Pro Ala Arg Leu
        1325                1330                1335 atc gtg ttc ccc gat ctg ggc gtg cgc gtg tgc gaa aag atg gct ttg      16743
Ile Val Phe Pro Asp Leu Gly Val Arg Val Cys Glu Lys Met Ala Leu
1340                1345                1350                1355 tac gac gtg gtt aca aag ctc ccc ttg gcc gtg atg gga agc tcc tac      16791
Tyr Asp Val Val Thr Lys Leu Pro Leu Ala Val Met Gly Ser Ser Tyr
                1360                1365                1370 gga ttc caa tac tca cca gga cag cgg gtt gaa ttc ctc gtg caa gcg      16839
Gly Phe Gln Tyr Ser Pro Gly Gln Arg Val Glu Phe Leu Val Gln Ala
        1375                1380                1385 tgg aag tcc aag aaa acc cca atg ggg ttc tcg tat gat acc cgc tgc      16887
Trp Lys Ser Lys Lys Thr Pro Met Gly Phe Ser Tyr Asp Thr Arg Cys
1390                1395                1400 ttt gac tcc aca gtc act gag agc gac atc cgt acg gag gag gca atc      16935
Phe Asp Ser Thr Val Thr Glu Ser Asp Ile Arg Thr Glu Glu Ala Ile
        1405                1410                1415 tac caa tgt tgt gac ctc gac ccc caa gcc cgc gtg gcc atc aag tcc      16983
Tyr Gln Cys Cys Asp Leu Asp Pro Gln Ala Arg Val Ala Ile Lys Ser
1420                1425                1430                1435 ctc acc gag agg ctt tat gtt ggg ggc cct ctt acc aat tca agg ggg      17031
Leu Thr Glu Arg Leu Tyr Val Gly Gly Pro Leu Thr Asn Ser Arg Gly
                1440                1445                1450 gag aac tgc ggc tat cgc agg tgc cgc gcg agc ggc gta ctg aca act      17079
Glu Asn Cys Gly Tyr Arg Arg Cys Arg Ala Ser Gly Val Leu Thr Thr
        1455                1460                1465 agc tgt ggt aac acc ctc act tgc tac atc aag gcc cgg gca gcc tgt      17127
Ser Cys Gly Asn Thr Leu Thr Cys Tyr Ile Lys Ala Arg Ala Ala Cys
1470                1475                1480 cga gcc gca ggg ctc cag gac tgc acc atg ctc gtg tgt ggc gac gac      17175
Arg Ala Ala Gly Leu Gln Asp Cys Thr Met Leu Val Cys Gly Asp Asp
        1485                1490                1495 tta gtc gtt atc tgt gaa agc gcg ggg gtc cag gag gac gcg gcg agc      17223
Leu Val Val Ile Cys Glu Ser Ala Gly Val Gln Glu Asp Ala Ala Ser
1500                1505                1510                1515 ctg aga gcc ttc acg gag gct atg acc agg tac tcc gcc ccc cct ggg      17271
Leu Arg Ala Phe Thr Glu Ala Met Thr Arg Tyr Ser Ala Pro Pro Gly
                1520                1525                1530 gac ccc cca caa cca gaa tac gac ttg gag ctc ata aca tca tgc tcc      17319
Asp Pro Pro Gln Pro Glu Tyr Asp Leu Glu Leu Ile Thr Ser Cys Ser
        1535                1540                1545 tcc aac gtg tca gtc gcc cac gac ggc gct gga aag agg gtc tac tac      17367
```

```
Ser Asn Val Ser Val Ala His Asp Gly Ala Gly Lys Arg Val Tyr Tyr
         1550                1555                1560 ctc acc cgt gac cct aca acc ccc ctc gcg aga gct gcg tgg gag aca     17415
Leu Thr Arg Asp Pro Thr Thr Pro Leu Ala Arg Ala Ala Trp Glu Thr
    1565                1570                1575 gca aga cac act cca gtc aat tcc tgg cta ggc aac ata atc atg ttt     17463
Ala Arg His Thr Pro Val Asn Ser Trp Leu Gly Asn Ile Ile Met Phe
1580                1585                1590                1595 gcc ccc aca ctg tgg gcg agg atg ata ctg atg acc cat ttc ttt agc     17511
Ala Pro Thr Leu Trp Ala Arg Met Ile Leu Met Thr His Phe Phe Ser
            1600                1605                1610 gtc ctt ata gcc agg gac cag ctt gaa cag gcc ctc gat tgc gag atc     17559
Val Leu Ile Ala Arg Asp Gln Leu Glu Gln Ala Leu Asp Cys Glu Ile
        1615                1620                1625 tac ggg gcc tgc tac tcc ata gaa cca ctg gat cta cct cca atc att     17607
Tyr Gly Ala Cys Tyr Ser Ile Glu Pro Leu Asp Leu Pro Pro Ile Ile
    1630                1635                1640 caa aga ctc cat ggc ctc agc gca ttt tca ctc cac agt tac tct cca     17655
Gln Arg Leu His Gly Leu Ser Ala Phe Ser Leu His Ser Tyr Ser Pro
1645                1650                1655 ggt gaa atc aat agg gtg gcc gca tgc ctc aga aaa ctt ggg gta ccg     17703
Gly Glu Ile Asn Arg Val Ala Ala Cys Leu Arg Lys Leu Gly Val Pro
            1660                1665                1670                1675 ccc ttg cga gct tgg aga cac cgg gcc cgg agc gtc cgc gct agg ctt     17751
Pro Leu Arg Ala Trp Arg His Arg Ala Arg Ser Val Arg Ala Arg Leu
                1680                1685                1690 ctg gcc aga gga ggc agg gct gcc ata tgt ggc aag tac ctc ttc aac     17799
Leu Ala Arg Gly Gly Arg Ala Ala Ile Cys Gly Lys Tyr Leu Phe Asn
            1695                1700                1705 tgg gca gta aga aca aag ctc aaa ctc act cca ata gcg gcc gct ggc     17847
Trp Ala Val Arg Thr Lys Leu Lys Leu Thr Pro Ile Ala Ala Ala Gly
    1710                1715                1720 cag ctg gac ttg tcc ggc tgg ttc acg gct ggc tac agc ggg gga gac     17895
Gln Leu Asp Leu Ser Gly Trp Phe Thr Ala Gly Tyr Ser Gly Gly Asp
1725                1730                1735 att tat cac agc gtg tct cat gcc cgg ccc cgc tgg atc tgg ttt tgc     17943
Ile Tyr His Ser Val Ser His Ala Arg Pro Arg Trp Ile Trp Phe Cys
1740                1745                1750                1755 cta ctc ctg ctt gct gca ggg gta ggc atc tac ctc ctc ccc aac cga     17991
Leu Leu Leu Leu Ala Ala Gly Val Gly Ile Tyr Leu Leu Pro Asn Arg
                1760                1765                1770 atg agc acg aat cct aaa cct caa aga aag acc aaa cgt aac acc aac     18039
Met Ser Thr Asn Pro Lys Pro Gln Arg Lys Thr Lys Arg Asn Thr Asn
            1775                1780                1785 cgg cgg ccg cag gac gtc aag ttc ccg ggt ggc ggt cag atc gtt ggt     18087
Arg Arg Pro Gln Asp Val Lys Phe Pro Gly Gly Gly Gln Ile Val Gly
    1790                1795                1800 gga gtt tac ttg ttg ccg cgc agg ggc cct aga ttg ggt gtg cgc gcg     18135
Gly Val Tyr Leu Leu Pro Arg Arg Gly Pro Arg Leu Gly Val Arg Ala
1805                1810                1815 acg aga aag act tcc gag cgg tcg caa cct cga ggt aga cgt cag cct     18183
Thr Arg Lys Thr Ser Glu Arg Ser Gln Pro Arg Gly Arg Arg Gln Pro
1820                1825                1830                1835 atc ccc aag gct cgt cgg ccc gag ggc agg acc tgg gct cag ccc ggg     18231
Ile Pro Lys Ala Arg Arg Pro Glu Gly Arg Thr Trp Ala Gln Pro Gly
            1840                1845                1850 tac cct tgg ccc ctc tat ggc aat gag ggc tgc ggg tgg gcg gga tgg     18279
Tyr Pro Trp Pro Leu Tyr Gly Asn Glu Gly Cys Gly Trp Ala Gly Trp
    1855                1860                1865
```

```
ctc ctg tct ccc cgt ggc tct cgg cct agc tgg ggc ccc aca gac ccc     18327
Leu Leu Ser Pro Arg Gly Ser Arg Pro Ser Trp Gly Pro Thr Asp Pro
        1870                1875                1880 cgg cgt agg tcg cgc aat ttg ggt aag gtc atc gat acc ctt acg tgc     18375
Arg Arg Arg Ser Arg Asn Leu Gly Lys Val Ile Asp Thr Leu Thr Cys
    1885                1890                1895 ggc ttc gcc gac ctc atg ggg tac ata ccg ctc gtc ggc gcc cct ctt     18423
Gly Phe Ala Asp Leu Met Gly Tyr Ile Pro Leu Val Gly Ala Pro Leu
1900                1905                1910                1915 gga ggc gct gcc agg gcc taatagtcga ctttgttccc actgtacttt            18471
Gly Gly Ala Ala Arg Ala
                1920 tagctcgtac aaaatacaat atactttca tttctccgta acaacatgt tttcccatgt     18531
aatatccttt tctatttttc gttccgttac caacttaca catactttat atagctattc    18591
acttctatac actaaaaac taagacaatt ttaattttgc tgcctgccat atttcaattt    18651
gttataaatt cctataattt atcctattag tagctaaaaa aagatgaatg tgaatcgaat   18711
cctaagagaa ttggatctga tccacaggac gggtgtggtc gccatgatcg cgtagtcgat   18771
agtggctcca gtagcgaag cgagcaggac tgggcggcgg ccaaagcggt cggacagtgc    18831
tccgagaacg ggtgcgcata gaaattgcat caacgcatat agcgctagca gcacgccata   18891
gtgactggcg atgctgtcgg aatggacgat atcccgcaag aggcccggca gtaccggcat   18951
aaccaagcct atgcctacag catccagggt gacggtgccg aggatgacga tgagcgcatt   19011
gttagatttc atacacggtg cctgactgcg ttagcaattt aactgtgata aactaccgca   19071
ttaaagcttt ttcttttccaa ttttttttttt ttcgtcatta taaaaatcat tacgaccgag  19131
attcccgggt aataactgat ataattaaat tgaagctcta atttgtgagt ttagtataca   19191
tgcatttact tataatacag ttttttagtt ttgctggccg catcttctca aatatgcttc   19251
ccagcctgct tttctgtaac gttcaccctc taccttagca tcccttccct ttgcaaatag   19311
tcctcttcca acaataataa tgtcagatcc tgtagagacc acatcatcca cggttctata   19371
ctgttgaccc aatgcgtctc ccttgtcatc taaacccaca ccgggtgtca taatcaacca   19431
atcgtaacct tcatctcttc cacccatgtc tctttgagca ataaagccga taacaaaatc   19491
tttgtcgctc ttcgcaatgt caacagtacc cttagtatat tctccagtag atagggagcc   19551
cttgcatgac aattctgcta acatcaaaag gcctctaggt tcctttgtta cttcttctgc   19611
cgcctgcttc aaaccgctaa caatacctgg gcccaccaca ccgtgtgcat tcgtaatgtc   19671
tgcccattct gctattctgt atacacccgc agagtactgc aatttgactg tattaccaat   19731
gtcagcaaat tttctgtctt cgaagagtaa aaaattgtac ttggcggata atgcctttag   19791
cggcttaact gtgccctcca tggaaaaatc agtcaagata tccacatgtg tttttagtaa   19851
acaaattttg ggacctaatg cttcaactaa ctccagtaat tccttggtgg tacgaacatc   19911
caatgaagca cacaagtttg tttgcttttc gtgcatgata ttaaatagct tggcagcaac   19971
aggactagga tgagtagcag cacgttcctt atatgtagct ttcgacatga tttatcttcg   20031
tttcctgcag gtttttgttc tgtgcagttg ggttaagaat actgggcaat tcatgtttc    20091
ttcaacacta catatgcgta tatataccaa tctaagtctg tgctccttcc ttcgttcttc   20151
cttctgttcg gagattaccg aatcaaaaaa atttcaagga aaccgaaatc aaaaaaaaga   20211
ataaaaaaaa aatgatgaat tgaaaagctt atcgat                             20247
```

<210> SEQ ID NO 19
<211> LENGTH: 1921

```
<212> TYPE: PRT
<213> ORGANISM: Artificial Sequence
<220> FEATURE:
<223> OTHER INFORMATION: Description of Artificial Sequence:
      pd.delta.NS3NS5.pj.core150

<400> SEQUENCE: 19
```

| | | | | | | | | | | | | | | | |
|---|---|---|---|---|---|---|---|---|---|---|---|---|---|---|---|
| Met | Ala | Tyr | Ala | Ala | Gln | Gly | Tyr | Lys | Val | Leu | Val | Leu | Asn | Pro | |
| 1 | | | | 5 | | | | | 10 | | | | | 15 | |
| Ser | Val | Ala | Ala | Thr | Leu | Gly | Phe | Gly | Ala | Tyr | Met | Ser | Lys | Ala | His |
| | | | 20 | | | | | 25 | | | | | 30 | | |
| Gly | Ile | Asp | Pro | Asn | Ile | Arg | Thr | Gly | Val | Arg | Thr | Ile | Thr | Thr | Gly |
| | | 35 | | | | | 40 | | | | | 45 | | | |
| Ser | Pro | Ile | Thr | Tyr | Ser | Thr | Tyr | Gly | Lys | Phe | Leu | Ala | Asp | Gly | Gly |
| | 50 | | | | | 55 | | | | | 60 | | | | |
| Cys | Ser | Gly | Gly | Ala | Tyr | Asp | Ile | Ile | Ile | Cys | Asp | Glu | Cys | His | Ser |
| 65 | | | | | 70 | | | | 75 | | | | | | 80 |
| Thr | Asp | Ala | Thr | Ser | Ile | Leu | Gly | Ile | Gly | Thr | Val | Leu | Asp | Gln | Ala |
| | | | | 85 | | | | | 90 | | | | | 95 | |
| Glu | Thr | Ala | Gly | Ala | Arg | Leu | Val | Val | Leu | Ala | Thr | Ala | Thr | Pro | Pro |
| | | | 100 | | | | | 105 | | | | | 110 | | |
| Gly | Ser | Val | Thr | Val | Pro | His | Pro | Asn | Ile | Glu | Glu | Val | Ala | Leu | Ser |
| | | 115 | | | | | 120 | | | | | 125 | | | |
| Thr | Thr | Gly | Glu | Ile | Pro | Phe | Tyr | Gly | Lys | Ala | Ile | Pro | Leu | Glu | Val |
| 130 | | | | | 135 | | | | | 140 | | | | | |
| Ile | Lys | Gly | Gly | Arg | His | Leu | Ile | Phe | Cys | His | Ser | Lys | Lys | Lys | Cys |
| 145 | | | | | 150 | | | | | 155 | | | | | 160 |
| Asp | Glu | Leu | Ala | Ala | Lys | Leu | Val | Ala | Leu | Gly | Ile | Asn | Ala | Val | Ala |
| | | | | 165 | | | | | 170 | | | | | 175 | |
| Tyr | Tyr | Arg | Gly | Leu | Asp | Val | Ser | Val | Ile | Pro | Thr | Ser | Gly | Asp | Val |
| | | | 180 | | | | | 185 | | | | | 190 | | |
| Val | Val | Val | Ala | Thr | Asp | Ala | Leu | Met | Thr | Gly | Tyr | Thr | Gly | Asp | Phe |
| | | 195 | | | | | 200 | | | | | 205 | | | |
| Asp | Ser | Val | Ile | Asp | Cys | Asn | Thr | Cys | Val | Thr | Gln | Thr | Val | Asp | Phe |
| 210 | | | | | 215 | | | | | 220 | | | | | |
| Ser | Leu | Asp | Pro | Thr | Phe | Thr | Ile | Glu | Thr | Ile | Thr | Leu | Pro | Gln | Asp |
| 225 | | | | | 230 | | | | | 235 | | | | | 240 |
| Ala | Val | Ser | Arg | Thr | Gln | Arg | Arg | Gly | Arg | Thr | Gly | Arg | Gly | Lys | Pro |
| | | | | 245 | | | | | 250 | | | | | 255 | |
| Gly | Ile | Tyr | Arg | Phe | Val | Ala | Pro | Gly | Glu | Arg | Pro | Ser | Gly | Met | Phe |
| | | | 260 | | | | | 265 | | | | | 270 | | |
| Asp | Ser | Ser | Val | Leu | Cys | Glu | Cys | Tyr | Asp | Ala | Gly | Cys | Ala | Trp | Tyr |
| | | 275 | | | | | 280 | | | | | 285 | | | |
| Glu | Leu | Thr | Pro | Ala | Glu | Thr | Thr | Val | Arg | Leu | Arg | Ala | Tyr | Met | Asn |
| | 290 | | | | | 295 | | | | | 300 | | | | |
| Thr | Pro | Gly | Leu | Pro | Val | Cys | Gln | Asp | His | Leu | Glu | Phe | Trp | Glu | Gly |
| 305 | | | | | 310 | | | | | 315 | | | | | 320 |
| Val | Phe | Thr | Gly | Leu | Thr | His | Ile | Asp | Ala | His | Phe | Leu | Ser | Gln | Thr |
| | | | | 325 | | | | | 330 | | | | | 335 | |
| Lys | Gln | Ser | Gly | Glu | Asn | Leu | Pro | Tyr | Leu | Val | Ala | Tyr | Gln | Ala | Thr |
| | | | 340 | | | | | 345 | | | | | 350 | | |
| Val | Cys | Ala | Arg | Ala | Gln | Ala | Pro | Pro | Ser | Trp | Asp | Gln | Met | Trp | |
| | | 355 | | | | | 360 | | | | | 365 | | | |
| Lys | Cys | Leu | Ile | Arg | Leu | Lys | Pro | Thr | Leu | His | Gly | Pro | Thr | Pro | Leu |
| 370 | | | | | 375 | | | | | 380 | | | | | |

```
Leu Tyr Arg Leu Gly Ala Val Gln Asn Glu Ile Thr Leu Thr His Pro
385                 390                 395                 400

Val Thr Lys Tyr Ile Met Thr Cys Met Ser Ala Asp Leu Glu Val Val
            405                 410                 415

Thr Ser Thr Trp Val Leu Val Gly Gly Val Leu Ala Ala Leu Ala Ala
                420                 425                 430

Tyr Cys Leu Ser Thr Gly Cys Val Val Ile Val Gly Arg Val Val Leu
            435                 440                 445

Ser Gly Lys Pro Ala Ile Ile Pro Asp Arg Glu Val Leu Tyr Arg Glu
    450                 455                 460

Phe Asp Glu Met Glu Glu Cys Ser Gln His Leu Pro Tyr Ile Glu Gln
465                 470                 475                 480

Gly Met Met Leu Ala Glu Gln Phe Lys Gln Lys Ala Leu Gly Leu Leu
                485                 490                 495

Gln Thr Ala Ser Arg Gln Ala Glu Val Ile Ala Pro Ala Val Gln Thr
            500                 505                 510

Asn Trp Gln Lys Leu Glu Thr Phe Trp Ala Lys His Met Trp Asn Phe
        515                 520                 525

Ile Ser Gly Ile Gln Tyr Leu Ala Gly Leu Ser Thr Leu Pro Gly Asn
    530                 535                 540

Pro Ala Ile Ala Ser Leu Met Ala Phe Thr Ala Ala Val Thr Ser Pro
545                 550                 555                 560

Leu Thr Thr Ser Gln Thr Leu Leu Phe Asn Ile Leu Gly Gly Trp Val
                565                 570                 575

Ala Ala Gln Leu Ala Ala Pro Gly Ala Ala Thr Ala Phe Val Gly Ala
            580                 585                 590

Gly Leu Ala Gly Ala Ala Ile Gly Ser Val Gly Leu Gly Lys Val Leu
        595                 600                 605

Ile Asp Ile Leu Ala Gly Tyr Gly Ala Gly Val Ala Gly Ala Leu Val
    610                 615                 620

Ala Phe Lys Ile Met Ser Gly Glu Val Pro Ser Thr Glu Asp Leu Val
625                 630                 635                 640

Asn Leu Leu Pro Ala Ile Leu Ser Pro Gly Ala Leu Val Val Gly Val
                645                 650                 655

Val Cys Ala Ala Ile Leu Arg Arg His Val Gly Pro Gly Glu Gly Ala
            660                 665                 670

Val Gln Trp Met Asn Arg Leu Ile Ala Phe Ala Ser Arg Gly Asn His
        675                 680                 685

Val Ser Pro Thr His Tyr Val Pro Glu Ser Asp Ala Ala Ala Arg Val
    690                 695                 700

Thr Ala Ile Leu Ser Ser Leu Thr Val Thr Gln Leu Leu Arg Arg Leu
705                 710                 715                 720

His Gln Trp Ile Ser Ser Glu Cys Thr Thr Pro Cys Ser Gly Ser Trp
                725                 730                 735

Leu Arg Asp Ile Trp Asp Trp Ile Cys Glu Val Leu Ser Asp Phe Lys
            740                 745                 750

Thr Trp Leu Lys Ala Lys Leu Met Pro Gln Leu Pro Gly Ile Pro Phe
        755                 760                 765

Val Ser Cys Gln Arg Gly Tyr Lys Gly Val Trp Arg Gly Asp Gly Ile
    770                 775                 780

Met His Thr Arg Cys His Cys Gly Ala Glu Ile Thr Gly His Val Lys
785                 790                 795                 800

Asn Gly Thr Met Arg Ile Val Gly Pro Arg Thr Cys Arg Asn Met Trp
```

-continued

```
                805                 810                 815
Ser Gly Thr Phe Pro Ile Asn Ala Tyr Thr Thr Gly Pro Cys Thr Pro
            820                 825                 830
Leu Pro Ala Pro Asn Tyr Thr Phe Ala Leu Trp Arg Val Ser Ala Glu
            835                 840                 845
Glu Tyr Val Glu Ile Arg Gln Val Gly Asp Phe His Tyr Val Thr Gly
            850                 855                 860
Met Thr Thr Asp Asn Leu Lys Cys Pro Cys Gln Val Pro Ser Pro Glu
865                 870                 875                 880
Phe Phe Thr Glu Leu Asp Gly Val Arg Leu His Arg Phe Ala Pro Pro
                885                 890                 895
Cys Lys Pro Leu Leu Arg Glu Glu Val Ser Phe Arg Val Gly Leu His
                900                 905                 910
Glu Tyr Pro Val Gly Ser Gln Leu Pro Cys Glu Pro Glu Pro Asp Val
                915                 920                 925
Ala Val Leu Thr Ser Met Leu Thr Asp Pro Ser His Ile Thr Ala Glu
                930                 935                 940
Ala Ala Gly Arg Arg Leu Ala Arg Gly Ser Pro Pro Ser Val Ala Ser
945                 950                 955                 960
Ser Ser Ala Ser Gln Leu Ser Ala Pro Ser Leu Lys Ala Thr Cys Thr
                965                 970                 975
Ala Asn His Asp Ser Pro Asp Ala Glu Leu Ile Glu Ala Asn Leu Leu
                980                 985                 990
Trp Arg Gln Glu Met Gly Gly Asn Ile Thr Arg Val Glu Ser Glu Asn
                995                 1000                1005
Lys Val Val Ile Leu Asp Ser Phe Asp Pro Leu Val Ala Glu Glu Asp
    1010                1015                1020
Glu Arg Glu Ile Ser Val Pro Ala Glu Ile Leu Arg Lys Ser Arg Arg
1025                1030                1035                1040
Phe Ala Gln Ala Leu Pro Val Trp Ala Arg Pro Asp Tyr Asn Pro Pro
                    1045                1050                1055
Leu Val Glu Thr Trp Lys Lys Pro Asp Tyr Glu Pro Pro Val Val His
                1060                1065                1070
Gly Cys Pro Leu Pro Pro Pro Lys Ser Pro Pro Val Pro Pro Pro Arg
                1075                1080                1085
Lys Lys Arg Thr Val Val Leu Thr Glu Ser Thr Leu Ser Thr Ala Leu
    1090                1095                1100
Ala Glu Leu Ala Thr Arg Ser Phe Gly Ser Ser Ser Thr Ser Gly Ile
1105                1110                1115                1120
Thr Gly Asp Asn Thr Thr Thr Ser Ser Glu Pro Ala Pro Ser Gly Cys
                1125                1130                1135
Pro Pro Asp Ser Asp Ala Glu Ser Tyr Ser Ser Met Pro Pro Leu Glu
            1140                1145                1150
Gly Glu Pro Gly Asp Pro Asp Leu Ser Asp Gly Ser Trp Ser Thr Val
                1155                1160                1165
Ser Ser Glu Ala Asn Ala Glu Asp Val Val Cys Cys Ser Met Ser Tyr
                1170                1175                1180
Ser Trp Thr Gly Ala Leu Val Thr Pro Cys Ala Ala Glu Glu Gln Lys
1185                1190                1195                1200
Leu Pro Ile Asn Ala Leu Ser Asn Ser Leu Leu Arg His His Asn Leu
                1205                1210                1215
Val Tyr Ser Thr Thr Ser Arg Ser Ala Cys Gln Arg Gln Lys Lys Val
            1220                1225                1230
```

-continued

```
Thr Phe Asp  Arg Leu Gln Val Leu Asp Ser His Tyr Gln  Asp Val Leu
         1235              1240              1245

Lys Glu  Val Lys Ala Ala  Ala  Ser Lys Val Lys Ala  Asn Leu Leu Ser
    1250              1255              1260

Val  Glu Glu Ala Cys Ser Leu Thr Pro Pro His  Ser Ala Lys Ser Lys
1265              1270              1275              1280

Phe Gly Tyr Gly Ala  Lys Asp Val Arg Cys  His Ala Arg Lys Ala  Val
             1285              1290              1295

Thr His Ile Asn  Ser Val Trp Lys Asp  Leu Leu Glu Asp Asn  Val Thr
             1300              1305              1310

Pro Ile Asp  Thr Thr  Ile Met Ala  Lys Asn Glu Val Phe  Cys Val Gln
         1315              1320              1325

Pro Glu  Lys Gly Gly Arg Lys  Pro Ala Arg Leu Ile  Val Phe Pro Asp
     1330              1335              1340

Leu  Gly Val Arg Val  Cys  Glu Lys Met Ala Leu  Tyr Asp Val Val  Thr
1345              1350              1355              1360

Lys Leu Pro Leu Ala  Val Met Gly Ser Ser  Tyr Gly Phe Gln Tyr   Ser
             1365              1370              1375

Pro Gly Gln Arg  Val Glu Phe Leu Val  Gln Ala Trp Lys Ser  Lys Lys
         1380              1385              1390

Thr Pro Met  Gly Phe Ser Tyr Asp  Thr Arg Cys Phe Asp  Ser Thr Val
         1395              1400              1405

Thr Glu  Ser Asp Ile Arg Thr   Glu Glu Ala Ile Tyr  Gln Cys Cys Asp
     1410              1415              1420

Leu  Asp Pro Gln Ala Arg  Val Ala Ile Lys Ser  Leu Thr Glu Arg  Leu
1425              1430              1435              1440

Tyr Val Gly Gly Pro  Leu Thr Asn Ser Arg  Gly Glu Asn Cys Gly  Tyr
             1445              1450              1455

Arg Arg Cys Arg  Ala Ser Gly Val Leu  Thr Thr Ser Cys Gly  Asn Thr
         1460              1465              1470

Leu Thr Cys  Tyr Ile Lys Ala Arg  Ala Ala Cys Arg Ala  Ala Gly Leu
         1475              1480              1485

Gln Asp  Cys Thr Met Leu Val  Cys Gly Asp Asp Leu  Val Val Ile Cys
     1490              1495              1500

Glu  Ser Ala Gly Val  Gln  Glu Asp Ala Ala Ser  Leu Arg Ala Phe  Thr
1505              1510              1515              1520

Glu Ala Met Thr Arg  Tyr Ser Ala Pro Pro  Gly Asp Pro Pro Gln  Pro
             1525              1530              1535

Glu Tyr Asp Leu  Glu Leu Ile Thr Ser  Cys Ser Ser Asn Val  Ser Val
         1540              1545              1550

Ala His Asp  Gly Ala Gly Lys Arg  Val Tyr Tyr Leu Thr  Arg Asp Pro
         1555              1560              1565

Thr Thr  Pro Leu Ala Arg Ala  Ala Trp Glu Thr Ala  Arg His Thr Pro
     1570              1575              1580

Val  Asn Ser Trp Leu  Gly Asn Ile Ile Met  Phe Ala Pro Thr Leu  Trp
1585              1590              1595              1600

Ala Arg Met Ile Leu  Met Thr His Phe Phe  Ser Val Leu Ile Ala  Arg
             1605              1610              1615

Asp Gln Leu Glu  Gln Ala Leu Asp Cys  Glu Ile Tyr Gly Ala  Cys Tyr
         1620              1625              1630

Ser Ile Glu  Pro Leu Asp Leu Pro  Pro Ile Ile Gln Arg  Leu His Gly
         1635              1640              1645
```

```
-continued

Leu Ser  Ala Phe Ser Leu His  Ser Tyr Ser Pro Gly  Glu Ile Asn Arg
    1650             1655             1660

Val Ala Ala Cys Leu Arg  Lys Leu Gly Val Pro  Pro Leu Arg Ala Trp
1665            1670             1675                         1680

Arg His Arg Ala Arg  Ser Val Arg Ala Arg  Leu Leu Ala Arg Gly  Gly
            1685                 1690                     1695

Arg Ala Ala Ile  Cys Gly Lys Tyr Leu  Phe Asn Trp Ala Val  Arg Thr
            1700                 1705                 1710

Lys Leu Lys  Leu Thr Pro Ile Ala  Ala Ala Gly Gln Leu  Asp Leu Ser
            1715                 1720                 1725

Gly Trp  Phe Thr Ala Gly Tyr  Ser Gly Gly Asp Ile  Tyr His Ser Val
    1730                 1735                 1740

Ser His Ala Arg Pro  Arg Trp Ile Trp Phe  Cys Leu Leu Leu Leu  Ala
1745                 1750                 1755                  1760

Ala Gly Val Gly Ile  Tyr Leu Leu Pro Asn  Arg Met Ser Thr Asn  Pro
                1765                 1770                 1775

Lys Pro Gln Arg  Lys Thr Lys Arg Asn  Thr Asn Arg Arg Pro  Gln Asp
            1780                 1785                 1790

Val Lys Phe  Pro Gly Gly Gln  Ile Val Gly Gly Val  Tyr Leu Leu
            1795             1800                 1805

Pro Arg  Arg Gly Pro Arg Leu  Gly Val Arg Ala Thr  Arg Lys Thr Ser
    1810                 1815                 1820

Glu  Arg Ser Gln Pro Arg  Gly Arg Arg Gln Pro  Ile Pro Lys Ala Arg
1825                 1830                 1835                 1840

Arg Pro Glu Gly Arg  Thr Trp Ala Gln Pro  Gly Tyr Pro Trp Pro  Leu
                1845                 1850                 1855

Tyr Gly Asn Glu  Gly Cys Gly Trp Ala  Gly Trp Leu Leu Ser  Pro Arg
            1860                 1865                 1870

Gly Ser Arg  Pro Ser Trp Gly Pro  Thr Asp Pro Arg Arg  Arg Ser Arg
            1875                 1880                 1885

Asn Leu Gly Lys Val Ile Asp  Thr Leu Thr Cys Gly  Phe Ala Asp Leu
            1890                 1895                 1900

Met Gly Tyr Ile Pro Leu  Val Gly Ala Pro Leu  Gly Gly Ala Ala Arg
1905                 1910                 1915                 1920

Ala
```

What is claimed is:

1. A method of eliciting an immune response in a subject, comprising the step of administering to the subject a mutant non-structural (NS) HCV polypeptide, wherein the NS polypeptide comprises a mutant NS3 polypeptide, an NS4 polypeptide and an NS5 polypeptide, wherein the mutant NS3 polypeptide has an N-terminal deletion that functionally disrupts the catalytic domain of NS3 and further wherein said mutant NS3 polypeptide has an N-terminus at an amino acid corresponding to amino acid 1242 of HCV-1 and comprises an amino acid sequence corresponding to amino acids 1242-1657 of HCV-1.

2. The method of claim 1, wherein said NS polypeptide consists of said mutant NS3 polypeptide, NS4 and NS5.

3. The method of claim 1, wherein said NS5 polypeptide consists of NS5a.

4. The method of claim 1, wherein said NS5 polypeptide consists of NS5b.

5. The method of claim 1, wherein said NS4 polypeptide consists of NS4a.

6. The method of claim 1, wherein said NS4 polypeptide consists of NS4b.

7. The method of claim 1, wherein said NS polypeptide further comprises a second viral polypeptide that is not NS3, NS4 or NS5 of HCV.

8. The method of claim 7, wherein the second viral polypeptide comprises an HCV Core polypeptide ("C") or immunogenic fragment thereof.

9. The method of claim 8, wherein the C polypeptide is truncated.

10. The method of claim 9, wherein the truncation is at amino acid 121.

11. The method of claim 7, wherein the polypeptide further comprises an HCV envelope protein ("E").

12. The method of claim 11, wherein the E is E1.

13. The method of claim 11, wherein the E is E2.

* * * * *